United States Patent
Bartels et al.

(10) Patent No.: US 11,319,314 B2
(45) Date of Patent: May 3, 2022

(54) PHENOXYTRIAZOLES

(71) Applicant: Hoffmann-La Roche Inc., Little Falls, NJ (US)

(72) Inventors: Bjoern Bartels, Basel (CH); Stefan Berchtold, Basel (CH); Guido Galley, Basel (CH); Annick Goergler, Basel (CH); Roland Jakob-Roetne, Basel (CH); Daniela Krummenacher, Basel (CH); Anja Limberg, Basel (CH); Werner Neidhart, Basel (CH); Hasane Ratni, Basel (CH); Michael Reutlinger, Basel (CH); Rosa Maria Rodriguez Sarmiento, Basel (CH); Christian Schnider, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 399 days.

(21) Appl. No.: 16/348,322

(22) PCT Filed: Nov. 6, 2017

(86) PCT No.: PCT/EP2017/078260
§ 371 (c)(1),
(2) Date: May 8, 2019

(87) PCT Pub. No.: WO2018/087018
PCT Pub. Date: May 17, 2018

(65) Prior Publication Data
US 2021/0309653 A1    Oct. 7, 2021

(30) Foreign Application Priority Data
Nov. 8, 2016    (EP) .................................... 16197660

(51) Int. Cl.
*C07D 401/14*    (2006.01)
*C07D 413/14*    (2006.01)
(Continued)

(52) U.S. Cl.
CPC ......... *C07D 417/14* (2013.01); *C07D 401/14* (2013.01); *C07D 403/14* (2013.01); *C07D 413/14* (2013.01); *C07B 2200/05* (2013.01)

(58) Field of Classification Search
CPC .. C07D 401/14; C07D 413/14; C07D 403/14; C07D 417/14; A61K 31/431;
(Continued)

(56) References Cited

U.S. PATENT DOCUMENTS

| 6,432,985 B2 | 8/2002 | Alanine et al. |
| 8,703,763 B2 | 4/2014 | Baumann et al. |
| 2005/0277664 A1 | 12/2005 | Bornemann et al. |

FOREIGN PATENT DOCUMENTS

| WO | 01/081309 A2 | 11/2001 |
| WO | 2005/117874 A1 | 12/2005 |

(Continued)

OTHER PUBLICATIONS

Aiwale, S., et al., "Efficient Synthesis of 3,7-Diaryl-1,4-dihydro[1,2,4]triazolo[5,1-c][1,2,4]triazines" Synthesis (Stuttgart) 44(19):3055-3058 (Oct. 1, 2012).
(Continued)

*Primary Examiner* — Bruck Kifle
(74) *Attorney, Agent, or Firm* — Genentech, Inc.; Richard G. A. Bone

(57) ABSTRACT

The present invention relates to a compound of formula I, HetAr is a five or six membered heteroaryl group, selected from wherein $R^1$ is hydrogen, halogen, lower alkyl, lower alkoxy or lower alkyl substituted by halogen, and may be the same or different, if two $R^1$ occur; $R^2$ is lower alkyl or a mono- or polydeutered derivative thereof, lower alkyl substituted by halogen or lower alkoxy, lower alkenyl unsubstituted or substituted by halogen, cycloalkyl or $CH_2$-cycloalkyl unsubstituted or substituted by halogen, heterocycloalkyl or $CH_2$-heterocycloalkyl unsubstituted or substituted by lower alkyl; $R^3$ is halogen, lower alkyl, lower alkyl substituted by halogen, lower alkoxy substituted by halogen or $S(O)_2$-lower alkyl; n is 1, 2 or 3; if n is >1, then $R^3$ may be the same or different; or to a pharmaceutically active acid addition salt thereof, to a racemic mixture or to its corresponding enantiomer and/or an optical isomer and/or stereoisomer thereof. The compounds may be used for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome.

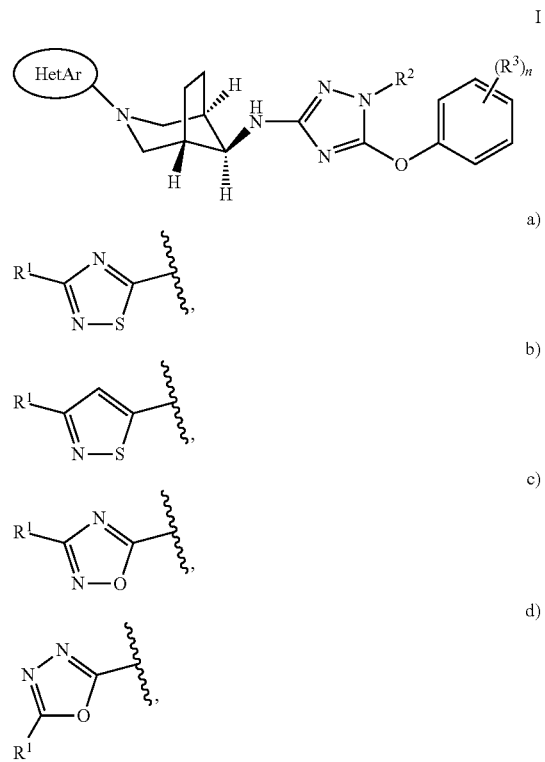

(Continued)

-continued

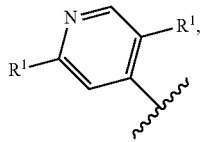

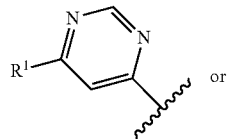 or

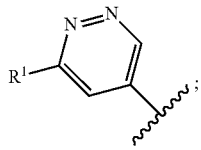

;

19 Claims, No Drawings

(51) Int. Cl.
*C07D 403/14* (2006.01)
*C07D 417/14* (2006.01)
*A61K 31/431* (2006.01)
*A61K 31/4245* (2006.01)
*A61K 31/435* (2006.01)
*A61K 31/44* (2006.01)
*A61K 31/497* (2006.01)
*A61P 25/00* (2006.01)

(58) Field of Classification Search
CPC .. A61K 31/4245; A61K 31/435; A61K 31/44; A61K 31/497; A61P 25/00
See application file for complete search history.

(56) References Cited

FOREIGN PATENT DOCUMENTS

| WO | 2010/114958 A1 | 10/2010 |
| WO | 2011/006903 A1 | 1/2011 |
| WO | 2011/086098 A1 | 7/2011 |
| WO | 2012/116965 A1 | 9/2012 |

OTHER PUBLICATIONS

"International Preliminary Report on Patentability—PCT/EP2017/078260" (dated May 14, 2019, Chapter I),:pp. 1-7 (dated May 23, 2019).

"International Search Report—PCT/EP2017/078260":pp. 1-5 (dated Jan. 24, 2018).

PHENOXYTRIAZOLES

The present invention relates to a compound of formula I,

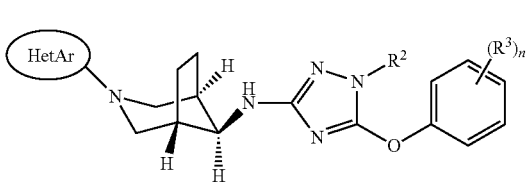

wherein
HetAr is a five or six membered heteroaryl group, selected from a) 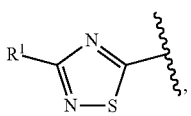

b) 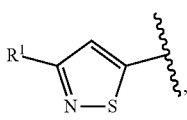

c) 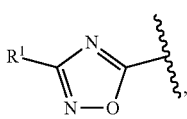

d) 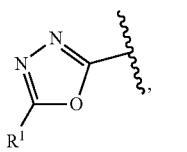

e) 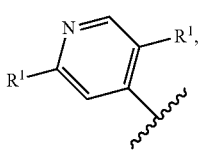

f) 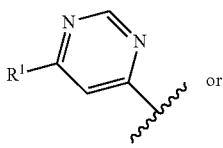 or g) 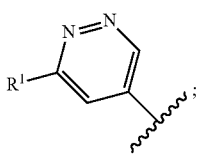

wherein
$R^1$ is hydrogen, halogen, lower alkyl, lower alkoxy or lower alkyl substituted by halogen, and may be the same or different, if two $R^1$ occur;
$R^2$ is lower alkyl or a mono- or polydeutered derivative thereof,
lower alkyl substituted by halogen or lower alkoxy,
lower alkenyl unsubstituted or substituted by halogen,
cycloalkyl or $CH_2$-cycloalkyl unsubstituted or substituted by halogen,
heterocycloalkyl or $CH_2$-heterocycloalkyl unsubstituted or substituted by lower alkyl;
$R^3$ is halogen, lower alkyl, lower alkyl substituted by halogen, lower alkoxy substituted by halogen or $S(O)_2$-lower alkyl;
n is 1, 2 or 3; if n is >1, then $R^3$ may be the same or different;
or to a pharmaceutically active acid addition salt thereof, to a racemic mixture or to its corresponding enantiomer and/or an optical isomer and/or stereoisomer thereof.

Now it has been found that the present compounds of formula I are modulators of γ-secretase, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, 525, pages 212-217). The presenilins are bearing the catalytic site and represent a group of atypical aspartyl proteases which cleave their substrates within the TM of and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease. Therefore, it was believed that selective and potent inhibition of γ-secretase might be useful for the prevention and treatment of AD.

An alternative mode of treatment is the modulation of the γ-secretase activity which results in a selective reduction of the Aβ42 production. This will lead in an increase of shorter Aβ isoforms, such as Aβ38, Aβ37 or others, which have no or reduced capability for aggregation and plaque formation, and are not or less neurotoxic. Compounds which show this effect on modulating γ-secretase activity include certain non-steroidal anti-inflammatory drugs (NSAIDs) and related analogues (Weggen et al., Nature, 414 (2001) 212-16).

Thus, the compounds of this invention will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Numerous documents describe the current knowledge on γ-secretase modulation, for example the following publications:
Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem., 279 (2004) 43419-26
Lleo et al, Nature Med., 10 (2004) 1065-6
Kukar et al, Nature Med., 11 (2005) 545-50
Perretto et al, J. Med. Chem. 48 (2005) 5705-20
Clarke et al, J. Biol. Chem., 281 (2006) 31279-89
Stock et al, Bioorg. Med. Chem. Lett. 16 (2006) 2219-2223
Narlawar et al, J. Med. Chem. 49 (2006) 7588-91
Ebke et al, J. Biol. Chem., 286 (2011) 37181-86
Oehlich, Gijsen et al, J. Med. Chem., 54 (2011), 669-698
Li et al., Biochemistry, 52 (2013), 3197-3216
Hall et al, Progress in Med. Chem., 53 (2014) 101-145
Bursavich et al, J. Med. Chem., 59 (2016) 7389-7409
The following definitions for compounds of formula I are used:

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by halogen" denotes an alkyl group as defined above, wherein at least one hydrogen atom is replaced by halogen, for example $CF_3$, $CHF_2$, $CH_2F$, $CHFCF_3$, $CH_2CHF_2$, $CH_2CH_2F$, $CH_2C(CH_3)_2CF_3$, $CH_2CF_2CF_3$, $CH(CF_3)_2$, $CH_2CF_3$, $(CH_2)_2CF_3$, $(CH_2)_3CF_3$, $CH(CH_3)CF_3$, $CF_2CF_3$, and the like. The preferred group is $CF_3$.

The term "lower alkoxy" denotes a lower alkyl group as defined above, which group is connected via an O atom.

The term "halogen" denotes chlorine, iodine, fluorine and bromine.

The term "cycloalkyl" denotes a saturated carbon ring, containing 3 to 6 carbon atoms, for example cyclopropyl, cyclobutyl, cyclopentyl and cyclohexyl.

The term "heterocycloalkyl" denotes a cycloalkyl group as described above, wherein at least one carbon ring atom is replaced by a heteroatom, selected from O, N or S. Preferred heterocycloalkyl groups are oxetan- or oxolan groups.

The term "mono- or polydeutered derivative of lower alkyl" denotes a lower alkyl group as described above, wherein at least one hydrogen atom is replaced by deuterium, for example $CH(CD_3)_2$, $CD(CD_3)_2$, $CD_3$ or $CH(D_2)CD_3$.

The term "lower alkenyl" denotes a carbon chain with 2 to 4 carbon atoms, wherein at least one single bond is replaced by a double bond.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Objects of the present invention are compounds of formula I, the use of such compounds for the preparation of medicaments for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, their manufacture and medicaments based on a compound of formula I in accordance with the invention.

Further objects of the present invention are all forms of optically pure enantiomers, racemates or diastereometric mixtures for compounds of formula I.

One object of the present invention is a compound of formula I-a,

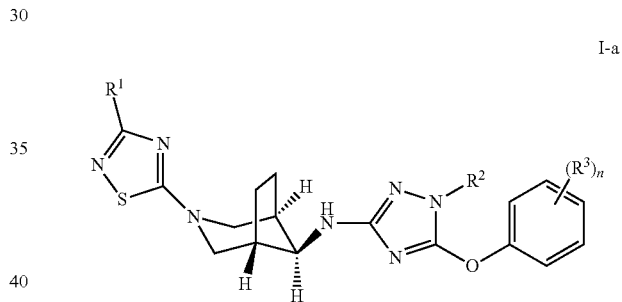

I-a wherein
$R^1$ is hydrogen, halogen, lower alkyl, lower alkoxy or lower alkyl substituted by halogen;
$R^2$ is lower alkyl or a mono- or polydeutered derivative thereof,
  lower alkyl substituted by halogen or lower alkoxy,
  lower alkenyl unsubstituted or substituted by halogen,
  cycloalkyl or $CH_2$-cycloalkyl unsubstituted or substituted by halogen,
  heterocycloalkyl or $CH_2$-heterocycloalkyl unsubstituted or substituted by lower alkyl;
$R^3$ is halogen, lower alkyl, lower alkyl substituted by halogen, lower alkoxy substituted by halogen or $S(O)_2$-lower alkyl;
n is 1, 2 or 3; if n is >1, then $R^3$ may be the same or different;
or a pharmaceutically active acid addition salt thereof, a racemic mixture or its corresponding enantiomer and/or an optical isomer and/or stereoisomer thereof, for example the following compound
(1R,5S,8s)-N-(5-(2-Chlorophenoxy)-1-(propan-2-yl)-1H-1, 2,4-triazol-3-yl)-3-(3-methyl-1,2,4-thiadiazol-5-yl)-3-azabicyclo[3.2.1]octan-8-amine.

One further object of the present invention is a compound of formula I-b,

I-b

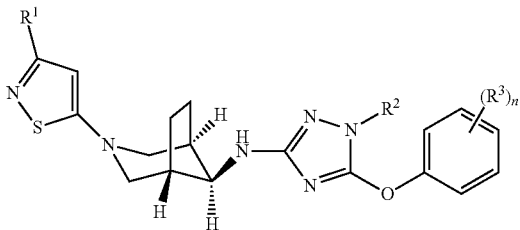

wherein
R¹ is hydrogen, halogen, lower alkyl, lower alkoxy or lower alkyl substituted by halogen;
R² is lower alkyl or a mono- or polydeutered derivative thereof,
lower alkyl substituted by halogen or lower alkoxy,
lower alkenyl unsubstituted or substituted by halogen,
cycloalkyl or CH₂-cycloalkyl unsubstituted or substituted by halogen,
heterocycloalkyl or CH₂-heterocycloalkyl unsubstituted or substituted by lower alkyl;
R³ is halogen, lower alkyl, lower alkyl substituted by halogen, lower alkoxy substituted by halogen or S(O)₂-lower alkyl;
n is 1, 2 or 3; if n is >1, then R³ may be the same or different;
or a pharmaceutically active acid addition salt thereof, a racemic mixture or its corresponding enantiomer and/or an optical isomer and/or stereoisomer thereof, for example the following compounds
(1R,5S,8s)-N-(5-(2-Chlorophenoxy)-1-(propan-2-yl)-1H-1,2,4-triazol-3-yl)-3-(3-methylisothiazol-5-yl)-3-azabicyclo[3.2.1]octan-8-amine
(1R,5S,8s)-N-(5-(3-Fluorophenoxy)-1-(propan-2-yl)-1H-1,2,4-triazol-3-yl)-3-(3-methylisothiazol-5-yl)-3-azabicyclo[3.2.1]octan-8-amine
(1R,5S,8s)-N-(5-(4-Fluoro-3-(trifluoromethyl)phenoxy)-1-(propan-2-yl)-1H-1,2,4-triazol-3-yl)-3-(3-methylisothiazol-5-yl)-3-azabicyclo[3.2.1]octan-8-amine
(1R,5S,8s)-N-(1-(Propan-2-yl)-5-(2-(trifluoromethoxy)phenoxy)-1H-1,2,4-triazol-3-yl)-3-(3-methylisothiazol-5-yl)-3-azabicyclo[3.2.1]octan-8-amine
(1R,5S,8s)-N-(5-(2-Fluorophenoxy)-1-(propan-2-yl)-1H-1,2,4-triazol-3-yl)-3-(3-methylisothiazol-5-yl)-3-azabicyclo[3.2.1]octan-8-amine
(1R,5S,8s)-3-(3-Methyl-1,2-thiazol-5-yl)-N-[1-(propan-2-yl)-5-[4-(trifluoromethoxy)phenoxy]-1H-1,2,4-triazol-3-yl]-3-azabicyclo[3.2.1]octan-8-amine
(1R,5S,8s)-N-[5-(4-Fluorophenoxy)-1-(propan-2-yl)-1H-1,2,4-triazol-3-yl]-3-(3-methyl-1,2-thiazol-5-yl)-3-azabicyclo[3.2.1]octan-8-amine
(1R,5S,8s)-N-{5-[3-Fluoro-5-(trifluoromethyl)phenoxy]-1-(propan-2-yl)-1H-1,2,4-triazol-3-yl}-3-(3-methyl-1,2-thiazol-5-yl)-3-azabicyclo[3.2.1]octan-8-amine
(1R,5S,8s)-3-(3-Methyl-1,2-thiazol-5-yl)-N-[1-(propan-2-yl)-5-[3-(trifluoromethyl)phenoxy]-1H-1,2,4-triazol-3-yl]-3-azabicyclo[3.2.1]octan-8-amine
(1R,5S,8s)-N-[5-(3,5-Difluorophenoxy)-1-(propan-2-yl)-1H-1,2,4-triazol-3-yl]-3-(3-methyl-1,2-thiazol-5-yl)-3-azabicyclo[3.2.1]octan-8-amine
(1R,5S,8s)-N-[5-(4-Methanesulfonylphenoxy)-1-(propan-2-yl)-1H-1,2,4-triazol-3-yl]-3-(3-methyl-1,2-thiazol-5-yl)-3-azabicyclo[3.2.1]octan-8-amine or
(1R,5S,8s)-N-[5-(3-Methanesulfonylphenoxy)-1-(propan-2-yl)-1H-1,2,4-triazol-3-yl]-3-(3-methyl-1,2-thiazol-5-yl)-3-azabicyclo[3.2.1]octan-8-amine.

One object of the present invention is a compound of formula I-c,

I-c

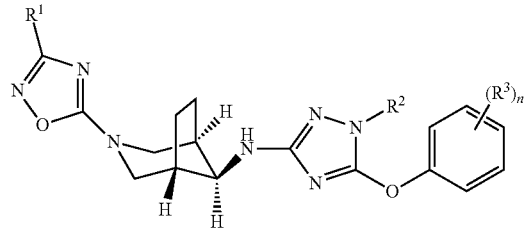

wherein
R¹ is hydrogen, halogen, lower alkyl, lower alkoxy or lower alkyl substituted by halogen;
R² is lower alkyl or a mono- or polydeutered derivative thereof,
lower alkyl substituted by halogen or lower alkoxy,
lower alkenyl unsubstituted or substituted by halogen,
cycloalkyl or CH₂-cycloalkyl unsubstituted or substituted by halogen,
heterocycloalkyl or CH₂-heterocycloalkyl unsubstituted or substituted by lower alkyl;
R³ is halogen, lower alkyl, lower alkyl substituted by halogen, lower alkoxy substituted by halogen or S(O)₂-lower alkyl;
n is 1, 2 or 3; if n is >1, then R³ may be the same or different;
or a pharmaceutically active acid addition salt thereof, a racemic mixture or its corresponding enantiomer and/or an optical isomer and/or stereoisomer thereof, for example the following compounds
(1R,5S,8s)-N-{5-[4-Fluoro-3-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine
(1R,5S,8s)-N-(1-(Propan-2-yl)-5-(2-(trifluoromethoxy)phenoxy)-1H-1,2,4-triazol-3-yl)-3-(3-methyl-1,2,4-oxadiazol-5-yl)-3-azabicyclo[3.2.1]octan-8-amine
(1R,5S,8s)-3-(3-Methyl-1,2,4-oxadiazol-5-yl)-N-[1-(propan-2-yl)-5-[3-(trifluoromethoxy)phenoxy]-1H-1,2,4-triazol-3-yl]-3-azabicyclo[3.2.1]octan-8-amine
(1R,5S,8s)-3-(3-Methyl-1,2,4-oxadiazol-5-yl)-N-[1-(propan-2-yl)-5-[4-(trifluoromethoxy)phenoxy]-1H-1,2,4-triazol-3-yl]-3-azabicyclo[3.2.1]octan-8-amine
(1R,5S,8s)-N-[5-(3-Fluorophenoxy)-1-(propan-2-yl)-1H-1,2,4-triazol-3-yl]-3-(3-methyl-1,2,4-oxadiazol-5-yl)-3-azabicyclo[3.2.1]octan-8-amine
(1R,5S,8s)-3-(3-Methyl-1,2,4-oxadiazol-5-yl)-N-[1-(propan-2-yl)-5-[3-(trifluoromethyl)phenoxy]-1H-1,2,4-triazol-3-yl]-3-azabicyclo[3.2.1]octan-8-amine
(1R,5S,8s)-N-(5-(3-Fluorophenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine
(1R,5S,8s)-N-(5-(4-Fluoro-3-(trifluoromethyl)phenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine
(1R,5S,8s)-N-(5-(4-Fluoro-3-(trifluoromethyl)phenoxy)-1-methyl-1H-1,2,4-triazol-3-yl)-3-(3-methyl-1,2,4-oxadiazol-5-yl)-3-azabicyclo[3.2.1]octan-8-amine (1R,5S,8s)-3-(3-Methyl-1,2,4-oxadiazol-5-yl)-N-[1-(propan-2-yl)-5-[2-fluoro-3-(trifluoromethyl)phenoxy]-1H-1,2,4-triazol-3-yl]-3-azabicyclo[3.2.1]octan-8-amine (1R,5S,8s)-N-{5-[2-Fluoro-5-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine (1R,5S,8s)-N-{5-[3-Fluoro-4-(trifluoromethoxy)phenoxy]-1-(propan-2-yl)-1H-1,2,4-triazol-3-yl}-3-(3-methyl-1,2,4-oxadiazol-5-yl)-3-azabicyclo[3.2.1]octan-8-amine (1R,5S,8s)-3-(3-Methyl-1,2,4-oxadiazol-5-yl)-N-(1-(2,2,2-trifluoroethyl)-5-(3-(trifluoromethyl)phenoxy)-1H-1,2,4-triazol-3-yl)-3-azabicyclo[3.2.1]octan-8-amine (1R,5S,8s)-3-(3-Methyl-1,2,4-oxadiazol-5-yl)-N-(1-(2,2,2-trifluoroethyl)-5-(4-(trifluoromethyl)phenoxy)-1H-1,2,4-triazol-3-yl)-3-azabicyclo[3.2.1]octan-8-amine (1R,5S,8s)-3-(3-Methyl-1,2,4-oxadiazol-5-yl)-N-{5-[3-methyl-5-(trifluoromethyl)phenoxy]-1-(propan-2-yl)-1H-1,2,4-triazol-3-yl}-3-azabicyclo[3.2.1]octan-8-amine (1R,5S,8s)-N-{5-[4-Fluoro-3-methyl-5-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine (1R,5S,8s)-N-{5-[3-Chloro-5-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine (1R,5S,8s)-N-(5-(3-Chlorophenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine (1R,5S,8s)-N-{5-[4-Methyl-3-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine (1R,5S,8s)-N-{5-[4-Chloro-3-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine (1R,5S,8s)(1R,5S,8s)-N-[1-(Propan-2-yl)-5-[4-(trifluoromethoxy)-3-(trifluoromethyl)phenoxy]-1,2,4-triazol-3-yl]-3-(3-methyl-1,2,4-oxadiazol-5-yl)-3-azabicyclo[3.2.1]octan-8-amine (1R,5S,8s)-N-{5-[3,5-Bis (trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine (1R,5S,8s)-N-[5-(3-Chlorophenoxy)-1-(propan-2-yl)-1H-1,2,4-triazol-3-yl]-3-(3-methyl-1,2,4-oxadiazol-5-yl)-3-azabicyclo[3.2.1]octan-8-amine (1R,5S,8s)-N-[5-(3-Chloro-4-methylphenoxy)-1-(propan-2-yl)-1H-1,2,4-triazol-3-yl]-3-(3-methyl-1,2,4-oxadiazol-5-yl)-3-azabicyclo[3.2.1]octan-8-amine (1R,5S,8s)-N-[5-(3-Chloro-2-methylphenoxy)-1-(propan-2-yl)-1H-1,2,4-triazol-3-yl]-3-(3-methyl-1,2,4-oxadiazol-5-yl)-3-azabicyclo[3.2.1]octan-8-amine (1R,5S,8s)-N-[5-(3-Chloro-5-methylphenoxy)-1-(propan-2-yl)-1H-1,2,4-triazol-3-yl]-3-(3-methyl-1,2,4-oxadiazol-5-yl)-3-azabicyclo[3.2.1]octan-8-amine (1R,5S,8s)-N-(5-(3-Chloro-5-fluorophenoxy)-1-(propan-2-yl)-1H-1,2,4-triazol-3-yl)-3-(3-methyl-1,2,4-oxadiazol-5-yl)-3-azabicyclo[3.2.1]octan-8-amine (1R,5S,8s)-N-[5-(3-Chloro-4-fluorophenoxy)-1-methyl-1,2,4-triazol-3-yl]-3-(3-methyl-1,2,4-oxadiazol-5-yl)-3-azabicyclo[3.2.1]octan-8-amine or (1R,5S,8s)-N-[5-(3-Chloro-4-fluorophenoxy)-1-(1,1,1,2,3,3,3-heptadeuteriopropan-2-yl)-1,2,4-triazol-3-yl]-3-(3-methyl-1,2,4-oxadiazol-5-yl)-3-azabicyclo[3.2.1]octan-8-amine.

One object of the present invention is a compound of formula I-d,

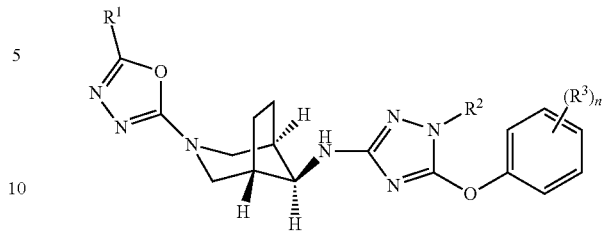

wherein
$R^1$ is hydrogen, halogen, lower alkyl, lower alkoxy or lower alkyl substituted by halogen;
$R^2$ is lower alkyl or a mono- or polydeutered derivative thereof,
lower alkyl substituted by halogen or lower alkoxy,
lower alkenyl unsubstituted or substituted by halogen,
cycloalkyl or $CH_2$-cycloalkyl unsubstituted or substituted by halogen,
heterocycloalkyl or $CH_2$-heterocycloalkyl unsubstituted or substituted by lower alkyl;
$R^3$ is halogen, lower alkyl, lower alkyl substituted by halogen, lower alkoxy substituted by halogen or $S(O)_2$-lower alkyl;
n is 1, 2 or 3; if n is >1, then $R^3$ may be the same or different;
or a pharmaceutically active acid addition salt thereof, a racemic mixture or its corresponding enantiomer and/or an optical isomer and/or stereoisomer thereof, for example the following compounds (1R,5S,8s)-N-(5-(3-Fluorophenoxy)-1-(2,2,2-trifluoroethyl)-1H-1,2,4-triazol-3-yl)-3-(5-methyl-1,3,4-oxadiazol-2-yl)-3-azabicyclo[3.2.1]octan-8-amine (1R,5S,8s)-N-(5-(4-Fluoro-3-(trifluoromethyl)phenoxy)-1-(2,2,2-trifluoroethyl)-1H-1,2,4-triazol-3-yl)-3-(5-methyl-1,3,4-oxadiazol-2-yl)-3-azabicyclo[3.2.1]octan-8-amine (1R,5S,8s)-N-(5-(3-Chlorophenoxy)-1-(2,2,2-trifluoroethyl)-1H-1,2,4-triazol-3-yl)-3-(5-methyl-1,3,4-oxadiazol-2-yl)-3-azabicyclo[3.2.1]octan-8-amine (1R,5S,8s)-3-(5-Methyl-1,3,4-oxadiazol-2-yl)-N-(1-(2,2,2-trifluoroethyl)-5-(4-(trifluoromethyl)phenoxy)-1H-1,2,4-triazol-3-yl)-3-azabicyclo[3.2.1]octan-8-amine (1R,5S,8s)-3-(5-Methyl-1,3,4-oxadiazol-2-yl)-N-(1-(2,2,2-trifluoroethyl)-5-(3-(trifluoromethoxy)phenoxy)-1H-1,2,4-triazol-3-yl)-3-azabicyclo[3.2.1]octan-8-amine (1R,5S,8s)-3-(5-Methyl-1,3,4-oxadiazol-2-yl)-N-(1-(2,2,2-trifluoroethyl)-5-(3-(trifluoromethyl)phenoxy)-1H-1,2,4-triazol-3-yl)-3-azabicyclo[3.2.1]octan-8-amine (1R,5S,8s)-3-(5-Methyl-1,3,4-oxadiazol-2-yl)-N-[1-(propan-2-yl)-5-[4-(trifluoromethoxy)phenoxy]-1H-1,2,4-triazol-3-yl]-3-azabicyclo[3.2.1]octan-8-amine (1R,5S,8s)-3-(5-Methyl-1,3,4-oxadiazol-2-yl)-N-[1-(propan-2-yl)-5-[3-(trifluoromethyl)phenoxy]-1H-1,2,4-triazol-3-yl]-3-azabicyclo[3.2.1]octan-8-amine (1R,5S,8s)-3-(5-Methyl-1,3,4-oxadiazol-2-yl)-N-[1-(propan-2-yl)-5-[4-fluoro-3-(trifluoromethyl)phenoxy]-1H-1,2,4-triazol-3-yl]-3-azabicyclo[3.2.1]octan-8-amine (1R,5S,8s)-N-(5-(3-Chlorophenoxy)-1-(2,2,3,3,3-pentafluoropropyl)-1H-1,2,4-triazol-3-yl)-3-(5-methyl-1,3,4-oxadiazol-2-yl)-3-azabicyclo[3.2.1]octan-8-amine (1R,5S,8s)-3-(3-Methyl-1,2,4-oxadiazol-5-yl)-N-[1-(propan-2-yl)-5-[2-fluoro-5-(trifluoromethyl)phenoxy]-1H-1,2,4-triazol-3-yl]-3-azabicyclo[3.2.1]octan-8-amine (1R,5S,8s)-N-{5-[2-Fluoro-3-(trifluoromethyl)phenoxy]-1-(propan-2-yl)-1H-1,2,4-triazol-3-yl}-3-(5-methyl-1,3,4-oxadiazol-2-yl)-3-azabicyclo[3.2.1]octan-8-amine (1R,5S,8s)-3-(5-Methyl-1,3,4-oxadiazol-2-yl)-N-{5-[4-methyl-3-(trifluoromethyl)phenoxy]-1-(propan-2-yl)-1H-1,2,4-triazol-3-yl}-3-azabicyclo[3.2.1]octan-8-amine (1R,5S,8s)-3-(5-Methyl-1,3,4-oxadiazol-2-yl)-N-{5-[3-methyl-5-(trifluoromethyl)phenoxy]-1-(propan-2-yl)-1H-1,2,4-triazol-3-yl}-3-azabicyclo[3.2.1]octan-8-amine (1R,5S,8s)-3-(5-Methyl-1,3,4-oxadiazol-2-yl)-N-[1-(propan-2-yl)-5-[4-(trifluoromethoxy)-3-(trifluoromethyl)phenoxy]-1H-1,2,4-triazol-3-yl]-3-azabicyclo[3.2.1]octan-8-amine (1R,5S,8s)-N-{5-[3,5-Bis(trifluoromethyl)phenoxy]-1-(propan-2-yl)-1H-1,2,4-triazol-3-yl}-3-(5-methyl-1,3,4-oxadiazol-2-yl)-3-azabicyclo[3.2.1]octan-8-amine (1R,5S,8s)-N-(5-(3-Chloro-5-methylphenoxy)-1-methyl-1H-1,2,4-triazol-3-yl)-3-(5-methyl-1,3,4-oxadiazol-2-yl)-3-azabicyclo[3.2.1]octan-8-amine (1R,5S,8s)-N-(5-(3-Chlorophenoxy)-1-ethyl-1H-1,2,4-triazol-3-yl)-3-(5-methyl-1,3,4-oxadiazol-2-yl)-3-azabicyclo[3.2.1]octan-8-amine (1R,5S,8s)-N-(5-(3-Chlorophenoxy)-1-propyl-1H-1,2,4-triazol-3-yl)-3-(5-methyl-1,3,4-oxadiazol-2-yl)-3-azabicyclo[3.2.1]octan-8-amine (1R,5S,8s)-N-[5-(3-Chlorophenoxy)-1-(propan-2-yl)-1H-1,2,4-triazol-3-yl]-3-(5-methyl-1,3,4-oxadiazol-2-yl)-3-azabicyclo[3.2.1]octan-8-amine (1R,5S,8s)-N-(5-(3-Chloro-5-fluorophenoxy)-1-(propan-2-yl)-1H-1,2,4-triazol-3-yl)-3-(5-methyl-1,3,4-oxadiazol-2-yl)-3-azabicyclo[3.2.1]octan-8-amine (1R,5S,8s)-N-(5-(3-Chloro-4-fluorophenoxy)-1-propyl-1H-1,2,4-triazol-3-yl)-3-(5-methyl-1,3,4-oxadiazol-2-yl)-3-azabicyclo[3.2.1]octan-8-amine or (1R,5S,8s)-N-[5-(3-Chloro-4-fluorophenoxy)-1-(1,1,1,2,3,3,3-heptadeuteriopropan-2-yl)-1,2,4-triazol-3-yl]-3-(5-methyl-1,3,4-oxadiazol-2-yl)-3-azabicyclo[3.2.1]octan-8-amine.

One object of the present invention is a compound of formula I-e,

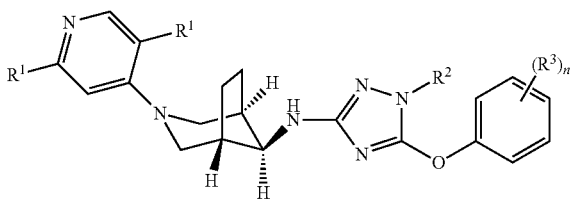

I-e wherein
$R^1$ is hydrogen, halogen, lower alkyl, lower alkoxy or lower alkyl substituted by halogen, and may be the same or different;

$R^2$ is lower alkyl or a mono- or polydeutered derivative thereof,
lower alkyl substituted by halogen or lower alkoxy,
lower alkenyl unsubstituted or substituted by halogen,
cycloalkyl or $CH_2$-cycloalkyl unsubstituted or substituted by halogen,
heterocycloalkyl or $CH_2$-heterocycloalkyl unsubstituted or substituted by lower alkyl;

$R^3$ is halogen, lower alkyl, lower alkyl substituted by halogen, lower alkoxy substituted by halogen or $S(O)_2$-lower alkyl;

n is 1, 2 or 3; if n is >1, then $R^3$ may be the same or different;
or a pharmaceutically active acid addition salt thereof, a racemic mixture or its corresponding enantiomer and/or an optical isomer and/or stereoisomer thereof, for example the following compounds (1R,5S,8s)-N-{5-[4-Fluoro-3-(trifluoromethyl)phenoxy]-1-(propan-2-yl)-1H-1,2,4-triazol-3-yl}-3-[2-(trifluoromethyl)pyridin-4-yl]-3-azabicyclo[3.2.1]octan-8-amine (1R,5S,8s)-N-[5-(3,5-Difluorophenoxy)-1-(propan-2-yl)-1H-1,2,4-triazol-3-yl]-3-[2-(trifluoromethyl)pyridin-4-yl]-3-azabicyclo[3.2.1]octan-8-amine (1R,5S,8s)-N-(5-(2-Fluorophenoxy)-1-(2,2,2-trifluoroethyl)-1H-1,2,4-triazol-3-yl)-3-(2-[trifluoromethyl)pyridin-4-yl]-3-azabicyclo[3.2.1]octan-8-amine (1R,5S,8s)-N-[1-(Propan-2-yl)-5-[3-(trifluoromethyl)phenoxy]-1H-1,2,4-triazol-3-yl]-3-[2-(trifluoromethyl)pyridin-4-yl]-3-azabicyclo[3.2.1]octan-8-amine (1R,5S,8s)-N-[5-(3-Fluorophenoxy)-1-(propan-2-yl)-1H-1,2,4-triazol-3-yl]-3-[2-(trifluoromethyl)pyridin-4-yl]-3-azabicyclo[3.2.1]octan-8-amine (1R,5S,8s)-N-(5-(3-Fluorophenoxy)-1-(2,2,2-trifluoroethyl)-1H-1,2,4-triazol-3-yl)-3-(2-(trifluoromethyl)pyridin-4-yl)-3-azabicyclo[3.2.1]octan-8-amine (1R,5S,8s)-N-(5-(3-Fluorophenoxy)-1-methyl-1H-1,2,4-triazol-3-yl)-3-(2-(trifluoromethyl)pyridin-4-yl)-3-azabicyclo[3.2.1]octan-8-amine (1R,5S,8s)-3-(2-Chloropyridin-4-yl)-N-(5-(4-fluoro-3-(trifluoromethyl)phenoxy)-1-methyl-1H-1,2,4-triazol-3-yl)-3-azabicyclo[3.2.1]octan-8-amine (1R,5S,8s)-3-(2-Chloropyridin-4-yl)-N-(5-(3-fluorophenoxy)-1-(2,2,2-trifluoroethyl)-1H-1,2,4-triazol-3-yl)-3-azabicyclo[3.2.1]octan-8-amine (1R,5S,8s)-N-(5-(3-Chlorophenoxy)-1-methyl-1H-1,2,4-triazol-3-yl)-3-(5-fluoro-2-methylpyridin-4-yl)-3-azabicyclo[3.2.1]octan-8-amine (1R,5S,8s)-N-(5-(3-Chlorophenoxy)-1-methyl-1H-1,2,4-triazol-3-yl)-3-(2-methoxypyridin-4-yl)-3-azabicyclo[3.2.1]octan-8-amine (1R,5S,8s)-N-(5-(3-Chlorophenoxy)-1-methyl-1H-1,2,4-triazol-3-yl)-3-(2-chloropyridin-4-yl)-3-azabicyclo[3.2.1]octan-8-amine (1R,5S,8s)-N-(5-(3-Chlorophenoxy)-1-ethyl-1H-1,2,4-triazol-3-yl)-3-(2-methoxypyridin-4-yl)-3-azabicyclo[3.2.1]octan-8-amine (1R,5S,8s)-N-(5-(3-Chlorophenoxy)-1-(2,2,2-trifluoroethyl)-1H-1,2,4-triazol-3-yl)-3-(2-methoxypyridin-4-yl)-3-azabicyclo[3.2.1]octan-8-amine (1R,5S,8s)-N-(5-(3-Chlorophenoxy)-1-ethyl-1H-1,2,4-triazol-3-yl)-3-(2-chloropyridin-4-yl)-3-azabicyclo[3.2.1]octan-8-amine (1R,5S,8s)-N-(5-(3-Chlorophenoxy)-1-propyl-1H-1,2,4-triazol-3-yl)-3-(2-methoxypyridin-4-yl)-3-azabicyclo[3.2.1]octan-8-amine (1R,5S,8s)-N-(5-(3-Chlorophenoxy)-1-propyl-1H-1,2,4-triazol-3-yl)-3-(2-chloropyridin-4-yl)-3-azabicyclo[3.2.1]octan-8-amine (1R,5S,8s)-N-(5-(3-Chloro-5-methylphenoxy)-1-methyl-1H-1,2,4-triazol-3-yl)-3-(2-chloropyridin-4-yl)-3-azabicyclo[3.2.1]octan-8-amine (1R,5S,8s)-N-(5-(3-Fluoro-5-methylphenoxy)-1-methyl-1H-1,2,4-triazol-3-yl)-3-(2-chloropyridin-4-yl)-3-azabicyclo[3.2.1]octan-8-amine (1R,5S,8s)-N-[5-(3-Chlorophenoxy)-1-(propan-2-yl)-1H-1,2,4-triazol-3-yl]-3-(2-methoxy-4-pyridyl)-3-azabicyclo[3.2.1]octan-8-amine (1R,5S,8s)-N-[5-(3,4-Difluorophenoxy)-1-(propan-2-yl)-1H-1,2,4-triazol-3-yl]-3-(2-methoxypyridin-4-yl)-3-azabicyclo[3.2.1]octan-8-amine (1R,5S,8s)-N-(5-(3,4-Difluorophenoxy)-1-(2,2,2-trifluoroethyl)-1H-1,2,4-triazol-3-yl)-3-(2-methoxypyridin-4-yl)-3-azabicyclo[3.2.1]octan-8-amine (1R,5S,8s)-N-(5-(3-Fluorophenoxy)-1-(propan-2-yl)-1H-1,2,4-triazol-3-yl)-3-(2-methoxypyridin-4-yl)-3-azabicyclo[3.2.1]octan-8-amine (1R,5S,8s)-N-[5-(2,3-Difluorophenoxy)-1-(propan-2-yl)-1H-1,2,4-triazol-3-yl]-3-(2-methoxypyridin-4-yl)-3-azabicyclo[3.2.1]octan-8-amine (1R,5S,8s)-N-[5-(3,5-Difluorophenoxy)-1-(propan-2-yl)-1H-1,2,4-triazol-3-yl]-3-(2-methoxypyridin-4-yl)-3-azabicyclo[3.2.1]octan-8-amine (1R,5S,8s)-N-(5-(3-Chloro-4-fluorophenoxy)-1-(propan-2-yl)-1H-1,2,4-triazol-3-yl)-3-(2-methoxypyridin-4-yl)-3-azabicyclo[3.2.1]octan-8-amine (1R,5S,8s)-N-(5-(3,5-Difluorophenoxy)-1-(2,2,2-trifluoroethyl)-1H-1,2,4-triazol-3-yl)-3-(2-methoxypyridin-4-yl)-3-azabicyclo[3.2.1]octan-8-amine (1R,5S,8s)-N-(5-(2,3-Difluorophenoxy)-1-(2,2,2-trifluoroethyl)-1H-1,2,4-triazol-3-yl)-3-(2-methoxypyridin-4-yl)-3-azabicyclo[3.2.1]octan-8-amine (1R,5S,8s)-N-(5-(3-Chloro-4-fluorophenoxy)-1-(2,2,2-trifluoroethyl)-1H-1,2,4-triazol-3-yl)-3-(2-methoxypyridin-4-yl)-3-azabicyclo[3.2.1]octan-8-amine (1R,5S,8s)-N-[5-(3-Chloro-5-fluorophenoxy)-1-(propan-2-yl)-1H-1,2,4-triazol-3-yl]-3-(2-methoxypyridin-4-yl)-3-azabicyclo[3.2.1]octan-8-amine (1R,5S,8s)-N-(5-(3-Fluorophenoxy)-1-(2,2,2-trifluoroethyl)-1H-1,2,4-triazol-3-yl)-3-(2-methoxypyridin-4-yl)-3-azabicyclo[3.2.1]octan-8-amine (1R,5S)—N-[5-(3-Chloro-2-fluoro-phenoxy)-1-isopropyl-1,2,4-triazol-3-yl]-3-(2-methoxy-4-pyridyl)-3-azabicyclo[3.2.1]octan-8-amine (1R,5S,8s)-N-[5-(2-Chlorophenoxy)-1-(propan-2-yl)-1H-1,2,4-triazol-3-yl]-3-(2-methoxypyridin-4-yl)-3-azabicyclo[3.2.1]octan-8-amine (1R,5S,8s)-N-(5-(2-Chlorophenoxy)-1-(2,2,2-trifluoroethyl)-1H-1,2,4-triazol-3-yl)-3-(2-methoxypyridin-4-yl)-3-azabicyclo[3.2.1]octan-8-amine (1R,5S,8s)-N-[5-(3-Chloro-2-fluoro-phenoxy)-1-(2,2,2-trifluoroethyl)-1,2,4-triazol-3-yl]-3-(2-methoxy-4-pyridyl)-3-azabicyclo[3.2.1]octan-8-amine (1R,5S,8s)-N-(5-(3-Chloro-5-fluorophenoxy)-1-methyl-1,2,4-triazol-3-yl)-3-(2-methoxypyridin-4-yl)-3-azabicyclo[3.2.1]octan-8-amine (1R,5S,8s)-N-(5-(3-Chloro-4-fluorophenoxy)-1-ethyl-1H-1,2,4-triazol-3-yl)-3-(2-methoxypyridin-4-yl)-3-azabicyclo[3.2.1]octan-8-amine (1R,5S,8s)-N-(5-(3-Chloro-4-fluorophenoxy)-1-propyl-1H-1,2,4-triazol-3-yl)-3-(2-methoxypyridin-4-yl)-3-azabicyclo[3.2.1]octan-8-amine (1R,5S,8s)-N-(5-(3-Chloro-4-fluorophenoxy)-1-isobutyl-1H-1,2,4-triazol-3-yl)-3-(2-methoxypyridin-4-yl)-3-azabicyclo[3.2.1]octan-8-amine (1R,5S,8s)-N-(5-(3-Chloro-4-fluorophenoxy)-1-((3,3-difluorocyclobutyl)methyl)-1H-1,2,4-triazol-3-yl)-3-(2-methoxypyridin-4-yl)-3-azabicyclo[3.2.1]octan-8-amine (1R,5S,8s)-N-[5-(3-Chloro-4-fluorophenoxy)-1-(1,1,1,2,3,3,3-heptadeuteriopropan-2-yl)-1,2,4-triazol-3-yl]-3-(2-methoxypyridin-4-yl)-3-azabicyclo[3.2.1]octan-8-amine (1R,5S,8s)-N-[5-(3-Chloro-4-fluorophenoxy)-1-(trideuteriomethyl)-1H-1,2,4-triazol-3-yl]-3-(2-methoxypyridin-4-yl)-3-azabicyclo[3.2.1]octan-8-amine (1R,5S,8s)-N-[5-(3-Chloro-4-fluorophenoxy)-1-(1,1,2,2,2-pentadeuterioethyl)-1,2,4-triazol-3-yl]-3-(2-methoxy-pyridin-4-yl)-3-azabicyclo[3.2.1]octan-8-amine or (1R,5S,8s)-N-(5-(3-Chloro-5-fluorophenoxy)-1-(2,2,2-trifluoroethyl)-1H-1,2,4-triazol-3-yl)-3-(2-methoxypyridin-4-yl)-3-azabicyclo[3.2.1]octan-8-amine.

One object of the present invention is a compound of formula I-f,

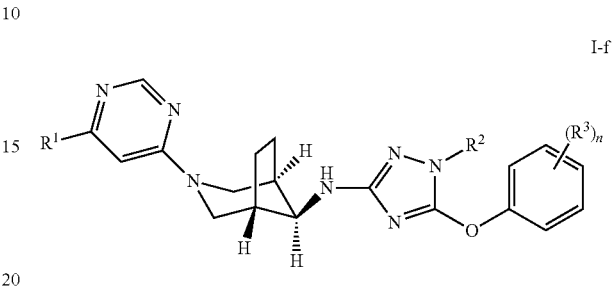

I-f wherein
R¹ is hydrogen, halogen, lower alkyl, lower alkoxy or lower alkyl substituted by halogen;
R² is lower alkyl or a mono- or polydeutered derivative thereof,
lower alkyl substituted by halogen or lower alkoxy,
lower alkenyl unsubstituted or substituted by halogen,
cycloalkyl or CH₂-cycloalkyl unsubstituted or substituted by halogen,
heterocycloalkyl or CH₂-heterocycloalkyl unsubstituted or substituted by lower alkyl;
R³ is halogen, lower alkyl, lower alkyl substituted by halogen, lower alkoxy substituted by halogen or S(O)₂-lower alkyl;
n is 1, 2 or 3; if n is >1, then R³ may be the same or different;
or a pharmaceutically active acid addition salt thereof, a racemic mixture or its corresponding enantiomer and/or an optical isomer and/or stereoisomer thereof, for example the following compounds (1R,5S,8s)-N-(5-(4-Fluoro-3-(trifluoromethyl)phenoxy)-1-methyl-1H-1,2,4-triazol-3-yl)-3-(6-methylpyrimidin-4-yl)-3-azabicyclo[3.2.1]octan-8-amine (1R,5S,8s)-N-(5-(4-Fluoro-3-(trifluoromethyl)phenoxy)-1-(2,2,2-trifluoroethyl)-1H-1,2,4-triazol-3-yl)-3-(6-methylpyrimidin-4-yl)-3-azabicyclo[3.2.1]octan-8-amine ((1R,5S,8s)-N-(5-(3-Fluorophenoxy)-1-(2,2,2-trifluoroethyl)-1H-1,2,4-triazol-3-yl)-3-(6-methylpyrimidin-4-yl)-3-azabicyclo[3.2.1]octan-8-amine (1R,5S,8s)-N-(5-(3-Chlorophenoxy)-1-methyl-1H-1,2,4-triazol-3-yl)-3-(6-methylpyrimidin-4-yl)-3-azabicyclo[3.2.1]octan-8-amine (1R,5S,8s)-N-(1-Methyl-5-(3-(trifluoromethoxy)phenoxy)-1H-1,2,4-triazol-3-yl)-3-(6-methylpyrimidin-4-yl)-3-azabicyclo[3.2.1]octan-8-amine (1R,5S,8s)-N-(5-(3-Chlorophenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine (1R,5S,8s)-3-(6-Chloropyrimidin-4-yl)-N-[1-(propan-2-yl)-5-[3-(trifluoromethyl)phenoxy]-1H-1,2,4-triazol-3-yl]-3-azabicyclo[3.2.1]octan-8-amine (1R,5S,8s)-N-(5-(3-Chlorophenoxy)-1-methyl-1H-1,2,4-triazol-3-yl)-3-(6-methoxypyrimidin-4-yl)-3-azabicyclo[3.2.1]octan-8-amine (1R,5S,8s)-N-[5-(3-Chlorophenoxy)-1-(propan-2-yl)-1H-1,2,4-triazol-3-yl]-3-(6-chloropyrimidin-4-yl)-3-azabicyclo[3.2.1]octan-8-amine (1R,5S,8s)-3-(6-Chloropyrimidin-4-yl)-N-[5-(3-fluorophenoxy)-1-(propan-2-yl)-1H-1,2,4-triazol-3-yl]-3-azabicyclo[3.2.1]octan-8-amine (1R,5S,8s)-N-(5-(3-Chlorophenoxy)-1-ethyl-1H-1,2,4-triazol-3-yl)-3-(6-methylpyrimidin-4-yl)-3-azabicyclo[3.2.1]octan-8-amine (1R,5S,8s)-N-(5-(3-Chlorophenoxy)-1-ethyl-1H-1,2,4-triazol-3-yl)-3-(6-chloropyrimidin-4-yl)-3-azabicyclo[3.2.1]octan-8-amine (1R,5S,8s)-N-(5-(3-Chlorophenoxy)-1-propyl-1H-1,2,4-triazol-3-yl)-3-(6-methylpyrimidin-4-yl)-3-azabicyclo[3.2.1]octan-8-amine (1R,5S,8s)-N-(5-(3-Chlorophenoxy)-1-(2,2,2-trifluoroethyl)-1H-1,2,4-triazol-3-yl)-3-(6-methylpyrimidin-4-yl)-3-azabicyclo[3.2.1]octan-8-amine (1R,5S,8s)-N-(5-(3-Chlorophenoxy)-1-propyl-1H-1,2,4-triazol-3-yl)-3-(6-chloropyrimidin-4-yl)-3-azabicyclo[3.2.1]octan-8-amine (1R,5S,8s)-N-(5-(3-Chlorophenoxy)-1-(2,2,2-trifluoroethyl)-1H-1,2,4-triazol-3-yl)-3-(6-chloropyrimidin-4-yl)-3-azabicyclo[3.2.1]octan-8-amine (1R,5S,8s)-N-(5-(3-Fluoro-5-methylphenoxy)-1-methyl-1H-1,2,4-triazol-3-yl)-3-(6-chloropyrimidin-4-yl)-3-azabicyclo[3.2.1]octan-8-amine (1R,5S,8s)-N-(5-(3-Chloro-5-methylphenoxy)-1-methyl-1H-1,2,4-triazol-3-yl)-3-(6-methylpyrimidin-4-yl)-3-azabicyclo[3.2.1]octan-8-amine (1R,5S,8s)-N-(5-(3-Fluoro-5-methylphenoxy)-1-methyl-1H-1,2,4-triazol-3-yl)-3-(6-methylpyrimidin-4-yl)-3-azabicyclo[3.2.1]octan-8-amine (1R,5S,8s)-N-[5-(3-Chlorophenoxy)-1-(propan-2-yl)-1H-1,2,4-triazol-3-yl]-3-(6-methylpyrimidin-4-yl)-3-azabicyclo[3.2.1]octan-8-amine (1R,5S,8s)-N-(1-Cyclopropyl-5-(3,4-difluorophenoxy)-1H-1,2,4-triazol-3-yl)-3-(6-methylpyrimidin-4-yl)-3-azabicyclo[3.2.1]octan-8-amine (1R,5S,8s)-N-[5-(3,4-Difluorophenoxy)-1-(propan-2-yl)-1H-1,2,4-triazol-3-yl]-3-(6-methylpyrimidin-4-yl)-3-azabicyclo[3.2.1]octan-8-amine (1R,5S,8s)-N-(5-(3,4-Difluorophenoxy)-1-(2,2,2-trifluoroethyl)-1H-1,2,4-triazol-3-yl)-3-(6-methylpyrimidin-4-yl)-3-azabicyclo[3.2.1]octan-8-amine (1R,5S,8s)-N-[5-(3,5-Difluorophenoxy)-1-(propan-2-yl)-1H-1,2,4-triazol-3-yl]-3-(6-methylpyrimidin-4-yl)-3-azabicyclo[3.2.1]octan-8-amine (1R,5S,8s)-N-[5-(2,3-Difluorophenoxy)-1-(propan-2-yl)-1H-1,2,4-triazol-3-yl]-3-(6-methylpyrimidin-4-yl)-3-azabicyclo[3.2.1]octan-8-amine (1R,5S,8s)-N-(5-(3-Chloro-4-fluorophenoxy)-1-isopropyl-1H-1,2,4-triazol-3-yl)-3-(6-methylpyrimidin-4-yl)-3-azabicyclo[3.2.1]octan-8-amine (1R,5S,8s)-N-[5-(4-Fluorophenoxy)-1-(propan-2-yl)-1H-1,2,4-triazol-3-yl]-3-(6-methylpyrimidin-4-yl)-3-azabicyclo[3.2.1]octan-8-amine (1R,5S,8s)-N-[5-(3-Fluorophenoxy)-1-(propan-2-yl)-1H-1,2,4-triazol-3-yl]-3-(6-methylpyrimidin-4-yl)-3-azabicyclo[3.2.1]octan-8-amine (1R,5S,8s)-N-[5-(3-Chloro-5-fluorophenoxy)-1-(propan-2-yl)-1H-1,2,4-triazol-3-yl]-3-(6-methylpyrimidin-4-yl)-3-azabicyclo[3.2.1]octan-8-amine (1R,5S,8s)-N-(5-(3,5-Difluorophenoxy)-1-(2,2,2-trifluoroethyl)-1H-1,2,4-triazol-3-yl)-3-(6-methylpyrimidin-4-yl)-3-azabicyclo[3.2.1]octan-8-amine (1R,5S)—N-[5-(5-Chloro-2-fluoro-phenoxy)-1-isopropyl-1,2,4-triazol-3-yl]-3-(6-methylpyrimidin-4-yl)-3-azabicyclo[3.2.1]octan-8-amine (1R,5S,8s)-N-[5-(3-Chloro-2-fluoro-phenoxy)-1-isopropyl-1,2,4-triazol-3-yl]-3-(6-methylpyrimidin-4-yl)-3-azabicyclo[3.2.1]octan-8-amine (1R,5S,8s)-N-(5-(2,3-Difluorophenoxy)-1-(2,2,2-trifluoroethyl)-1H-1,2,4-triazol-3-yl)-3-(6-methylpyrimidin-4-yl)-3-azabicyclo[3.2.1]octan-8-amine (1R,5S,8s)-N-(5-(3-Chloro-4-fluorophenoxy)-1-(2,2,2-trifluoroethyl)-1H-1,2,4-triazol-3-yl)-3-(6-methylpyrimidin-4-yl)-3-azabicyclo[3.2.1]octan-8-amine (1R,5S,8s)-N-[5-(2-Chlorophenoxy)-1-(propan-2-yl)-1H-1,2,4-triazol-3-yl]-3-(6-methylpyrimidin-4-yl)-3-azabicyclo[3.2.1]octan-8-amine (1R,5S,8s)-N-(5-(3-Chloro-4-fluorophenoxy)-1-(2,2-difluoroethyl)-1H-1,2,4-triazol-3-yl)-3-(6-methylpyrimidin-4-yl)-3-azabicyclo[3.2.1]octan-8-amine (1R,5S,8s)-N-(5-(3-Chloro-4-fluorophenoxy)-1-(2-fluorovinyl)-1H-1,2,4-triazol-3-yl)-3-(6-methylpyrimidin-4-yl)-3-azabicyclo[3.2.1]octan-8-amine (1R,5S,8s)-N-(5-(3-Chloro-5-fluorophenoxy)-1-(2,2-difluoroethyl)-1H-1,2,4-triazol-3-yl)-3-(6-methylpyrimidin-4-yl)-3-azabicyclo[3.2.1]octan-8-amine (1R,5S,8s)-N-(5-(3-Chloro-5-fluorophenoxy)-1-(2-fluorovinyl)-1H-1,2,4-triazol-3-yl)-3-(6-methylpyrimidin-4-yl)-3-azabicyclo[3.2.1]octan-8-amine (1R,5S,8s)-N-(5-(3,5-Difluorophenoxy)-1-(2,2-difluoroethyl)-1H-1,2,4-triazol-3-yl)-3-(6-methylpyrimidin-4-yl)-3-azabicyclo[3.2.1]octan-8-amine (1R,5S,8s)-N-(5-(3,5-Difluorophenoxy)-1-(2-fluorovinyl)-1H-1,2,4-triazol-3-yl)-3-(6-methylpyrimidin-4-yl)-3-azabicyclo[3.2.1]octan-8-amine (1R,5S,8s)-N-(5-(3-Chloro-4-fluorophenoxy)-1-(2-fluoroethyl)-1H-1,2,4-triazol-3-yl)-3-(6-methylpyrimidin-4-yl)-3-azabicyclo[3.2.1]octan-8-amine (1R,5S,8s)-N-(5-(3-Chloro-4-fluorophenoxy)-1-vinyl-1H-1,2,4-triazol-3-yl)-3-(6-methylpyrimidin-4-yl)-3-azabicyclo[3.2.1]octan-8-amine (1R,5S,8s)-N-(5-(3-Chloro-5-fluorophenoxy)-1-(2-fluoroethyl)-1H-1,2,4-triazol-3-yl)-3-(6-methylpyrimidin-4-yl)-3-azabicyclo[3.2.1]octan-8-amine (1R,5S,8s)-N-(5-(3-Chloro-5-fluorophenoxy)-1-vinyl-1H-1,2,4-triazol-3-yl)-3-(6-methylpyrimidin-4-yl)-3-azabicyclo[3.2.1]octan-8-amine (1R,5S,8s)-N-(5-(3-Chloro-5-fluorophenoxy)-1-(2-methoxyethyl)-1H-1,2,4-triazol-3-yl)-3-(6-methylpyrimidin-4-yl)-3-azabicyclo[3.2.1]octan-8-amine (1R,5S,8s)-N-(5-(3-Chloro-4-fluorophenoxy)-1-(2-methoxyethyl)-1H-1,2,4-triazol-3-yl)-3-(6-methylpyrimidin-4-yl)-3-azabicyclo[3.2.1]octan-8-amine (1R,5S,8s)-N-(5-(3-Chlorophenoxy)-1-(2,2-difluoroethyl)-1H-1,2,4-triazol-3-yl)-3-(6-methylpyrimidin-4-yl)-3-azabicyclo[3.2.1]octan-8-amine (1R,5S,8s)-N-(5-(3-Chlorophenoxy)-1-(2-fluorovinyl)-1H-1,2,4-triazol-3-yl)-3-(6-methylpyrimidin-4-yl)-3-azabicyclo[3.2.1]octan-8-amine (1R,5S,8s)-N-(5-(3,5-Difluorophenoxy)-1-(2-fluoroethyl)-1H-1,2,4-triazol-3-yl)-3-(6-methylpyrimidin-4-yl)-3-azabicyclo[3.2.1]octan-8-amine (1R,5S,8s)-N-(5-(3,5-Difluorophenoxy)-1-vinyl-1H-1,2,4-triazol-3-yl)-3-(6-methylpyrimidin-4-yl)-3-azabicyclo[3.2.1]octan-8-amine (1R,5S,8s)-N-(5-(2-Chlorophenoxy)-1-(2,2,2-trifluoroethyl)-1H-1,2,4-triazol-3-yl)-3-(6-methylpyrimidin-4-yl)-3-azabicyclo[3.2.1]octan-8-amine (1R,5S)—N-[5-(3-Chloro-2-fluoro-phenoxy)-1-(2,2,2-trifluoroethyl)-1,2,4-triazol-3-yl]-3-(6-methylpyrimidin-4-yl)-3-azabicyclo[3.2.1]octan-8-amine (1R,5S,8s)-N-(5-(2-Chlorophenoxy)-1-(2,2-difluoroethyl)-1H-1,2,4-triazol-3-yl)-3-(6-methylpyrimidin-4-yl)-3-azabicyclo[3.2.1]octan-8-amine
(1R,5S,8s)-N-(5-(2-Chlorophenoxy)-1-(2-fluorovinyl)-1H-1,2,4-triazol-3-yl)-3-(6-methylpyrimidin-4-yl)-3-azabicyclo[3.2.1]octan-8-amine
(1R,5S,8s)-N-(5-(3-Chloro-5-fluorophenoxy)-1-(methoxymethyl)-1H-1,2,4-triazol-3-yl)-3-(6-methylpyrimidin-4-yl)-3-azabicyclo[3.2.1]octan-8-amine
(1R,5S,8s)-N-[5-(4-Chlorophenoxy)-1-(propan-2-yl)-1H-1,2,4-triazol-3-yl]-3-(6-methylpyrimidin-4-yl)-3-azabicyclo[3.2.1]octan-8-amine
(1R,5S,8s)-N-(5-(3-Chloro-2-fluorophenoxy)-1-(2,2-difluoroethyl)-1H-1,2,4-triazol-3-yl)-3-(6-methylpyrimidin-4-yl)-3-azabicyclo[3.2.1]octan-8-amine
(1R,5S,8s)-N-(5-(3-Chloro-2-fluorophenoxy)-1-(2-fluorovinyl)-1H-1,2,4-triazol-3-yl)-3-(6-methylpyrimidin-4-yl)-3-azabicyclo[3.2.1]octan-8-amine
(1R,5S,8s)-N-(5-(2-Chlorophenoxy)-1-(2-fluoroethyl)-1H-1,2,4-triazol-3-yl)-3-(6-methylpyrimidin-4-yl)-3-azabicyclo[3.2.1]octan-8-amine
(1R,5S,8s)-N-(5-(3-Chloro-2-fluorophenoxy)-1-(2-fluoroethyl)-1H-1,2,4-triazol-3-yl)-3-(6-methylpyrimidin-4-yl)-3-azabicyclo[3.2.1]octan-8-amine
(1R,5S,8s)-N-(5-(3-Chloro-2-fluorophenoxy)-1-vinyl-1H-1,2,4-triazol-3-yl)-3-(6-methylpyrimidin-4-yl)-3-azabicyclo[3.2.1]octan-8-amine
(1R,5S,8s)-N-(5-(2-Chloro-3-fluorophenoxy)-1-isopropyl-1H-1,2,4-triazol-3-yl)-3-(6-methylpyrimidin-4-yl)-3-azabicyclo[3.2.1]octan-8-amine
(1R,5S,8s)-N-(5-(3,5-Difluorophenoxy)-1-isopropyl-1H-1,2,4-triazol-3-yl)-3-(6-methylpyrimidin-4-yl)-3-azabicyclo[3.2.1]octan-8-amine
(1S,5R.8s)-N-[5-(3-Chloro-5-fluorophenoxy)-1-methyl-1,2,4-triazol-3-yl]-3-(6-methylpyrimidin-4-yl)-3-azabicyclo[3.2.1]octan-8-amine
(1R,5S,8s)-N-[5-(4-Chlorophenoxy)-1-methyl-1H-1,2,4-triazol-3-yl]-3-(6-methylpyrimidin-4-yl)-3-azabicyclo[3.2.1]octan-8-amine
(1R,5S,8s)-N-[5-(3-Chloro-4-fluorophenoxy)-1-methyl-1,2,4-triazol-3-yl]-3-(6-methylpyrimidin-4-yl)-3-azabicyclo[3.2.1]octan-8-amine
(1S,5R.8s)-N-[5-(3-Chloro-2-fluorophenoxy)-1-methyl-1,2,4-triazol-3-yl]-3-(6-methylpyrimidin-4-yl)-3-azabicyclo[3.2.1]octan-8-amine
(1S,5R.8s)-N-[5-(2-Chloro-3-fluorophenoxy)-1-methyl-1,2,4-triazol-3-yl]-3-(6-methylpyrimidin-4-yl)-3-azabicyclo[3.2.1]octan-8-amine
(1R,5S,8s)-N-[5-(3-Chloro-5-fluorophenoxy)-1-ethyl-1,2,4-triazol-3-yl]-3-(6-methylpyrimidin-4-yl)-3-azabicyclo[3.2.1]octan-8-amine
(1R,5S,8s)-N-[5-(3,5-Difluorophenoxy)-1-ethyl-1,2,4-triazol-3-yl]-3-(6-methylpyrimidin-4-yl)-3-azabicyclo[3.2.1]octan-8-amine
(1R,5S,8s)-N-(5-(2-Chlorophenoxy)-1-ethyl-1H-1,2,4-triazol-3-yl)-3-(6-methylpyrimidin-4-yl)-3-azabicyclo[3.2.1]octan-8-amine
(1R,5S)—N-[5-(3-Chloro-4-fluorophenoxy)-1-ethyl-1,2,4-triazol-3-yl]-3-(6-methylpyrimidin-4-yl)-3-azabicyclo[3.2.1]octan-8-amine
(1R,5S,8s)-N-[5-(3-Chloro-5-fluorophenoxy)-1-propyl-1,2,4-triazol-3-yl]-3-(6-methylpyrimidin-4-yl)-3-azabicyclo[3.2.1]octan-8-amine
(1R,5S,8s)-N-[5-(3,5-Difluorophenoxy)-1-propyl-1,2,4-triazol-3-yl]-3-(6-methylpyrimidin-4-yl)-3-azabicyclo[3.2.1]octan-8-amine
(1R,5S,8s)-N-(5-(2-Chlorophenoxy)-1-propyl-1H-1,2,4-triazol-3-yl)-3-(6-methylpyrimidin-4-yl)-3-azabicyclo[3.2.1]octan-8-amine
(1R,5S,8s)-N-[5-(3-Chloro-4-fluorophenoxy)-1-propyl-1,2,4-triazol-3-yl]-3-(6-methylpyrimidin-4-yl)-3-azabicyclo[3.2.1]octan-8-amine
(1R,5S,8s)-N-[5-(3-Chloro-5-fluorophenoxy)-1-(2-methylpropyl)-1,2,4-triazol-3-yl]-3-(6-methylpyrimidin-4-yl)-3-azabicyclo[3.2.1]octan-8-amine
(1R,5S,8s)-N-(5-(2-Chlorophenoxy)-1-isobutyl-1H-1,2,4-triazol-3-yl)-3-(6-methylpyrimidin-4-yl)-3-azabicyclo[3.2.1]octan-8-amine
(1R,5S,8s)-N-(5-(3-Chloro-4-fluorophenoxy)-1-isobutyl-1H-1,2,4-triazol-3-yl)-3-(6-methylpyrimidin-4-yl)-3-azabicyclo[3.2.1]octan-8-amine
(1R,5S,8s)-N-[5-(3-Chloro-5-fluorophenoxy)-1-[(3-methyloxetan-3-yl)methyl]-1,2,4-triazol-3-yl]-3-(6-methylpyrimidin-4-yl)-3-azabicyclo[3.2.1]octan-8-amine
(1R,5S,8s)-N-[5-(3-Chloro-4-fluorophenoxy)-1-[(3-methyloxetan-3-yl)methyl]-1,2,4-triazol-3-yl]-3-(6-methylpyrimidin-4-yl)-3-azabicyclo[3.2.1]octan-8-amine
(1R,5S,8s)-N-[5-(3-Chloro-5-fluorophenoxy)-1-[2-methoxypropyl]-1,2,4-triazol-3-yl]-3-(6-methylpyrimidin-4-yl)-3-azabicyclo[3.2.1]octan-8-amine
(1R,5S,8s)-N-[5-(3-Chloro-5-fluorophenoxy)-1-(3,3,3-trifluoropropyl)-1,2,4-triazol-3-yl]-3-(6-methylpyrimidin-4-yl)-3-azabicyclo[3.2.1]octan-8-amine
(1R,5S,8s)-N-(5-(3-Chloro-5-fluorophenoxy)-1-((3,3-difluorocyclobutyl)methyl)-1H-1,2,4-triazol-3-yl)-3-(6-methylpyrimidin-4-yl)-3-azabicyclo[3.2.1]octan-8-amine
(1R,5S,8s)-N-(5-(3-Chloro-4-fluorophenoxy)-1-((3,3-difluorocyclobutyl)methyl)-1H-1,2,4-triazol-3-yl)-3-(6-methylpyrimidin-4-yl)-3-azabicyclo[3.2.1]octan-8-amine
(1R,5S,8s)-N-[5-(3-Chloro-5-fluorophenoxy)-1-(oxetan-3-yl)-1,2,4-triazol-3-yl]-3-(6-methylpyrimidin-4-yl)-3-azabicyclo[3.2.1]octan-8-amine
(1R,5S,8s)-N-[5-(3-Chloro-4-fluorophenoxy)-1-(oxetan-3-yl)-1,2,4-triazol-3-yl]-3-(6-methylpyrimidin-4-yl)-3-azabicyclo[3.2.1]octan-8-amine
(1R,5S,8s)-N-[5-(3-Chloro-5-fluorophenoxy)-1-(oxolan-3-yl)-1,2,4-triazol-3-yl]-3-(6-methylpyrimidin-4-yl)-3-azabicyclo[3.2.1]octan-8-amine
(1R,5S,8s)-N-[5-(3-Chloro-4-fluorophenoxy)-1-(oxolan-3-yl)-1,2,4-triazol-3-yl]-3-(6-methylpyrimidin-4-yl)-3-azabicyclo[3.2.1]octan-8-amine
(1R,5S,8s)-N-(5-(3-Chloro-5-fluorophenoxy)-1-cyclobutyl-1H-1,2,4-triazol-3-yl)-3-(6-methylpyrimidin-4-yl)-3-azabicyclo[3.2.1]octan-8-amine
(1R,5S,8s)-N-(5-(3-Chloro-4-fluorophenoxy)-1-cyclobutyl-1H-1,2,4-triazol-3-yl)-3-(6-methylpyrimidin-4-yl)-3-azabicyclo[3.2.1]octan-8-amine
(1R,5S,8s)-N-[5-(3-Chloro-5-fluorophenoxy)-1-(1,1,1,3,3,3-hexadeuteriopropan-2-yl)-1,2,4-triazol-3-yl]-3-(6-methylpyrimidin-4-yl)-3-azabicyclo[3.2.1]octan-8-amine
(1R,5S,8s)-N-[5-(3-Chloro-5-fluorophenoxy)-1-(1,1,1,2,3,3,3-heptadeuteriopropan-2-yl)-1,2,4-triazol-3-yl]-3-(6-methylpyrimidin-4-yl)-3-azabicyclo[3.2.1]octan-8-amine
(1R,5S,8s)-N-[5-(3-Chloro-4-fluorophenoxy)-1-(1,1,1,2,3,3,3-heptadeuteriopropan-2-yl)-1,2,4-triazol-3-yl]-3-(6-methylpyrimidin-4-yl)-3-azabicyclo[3.2.1]octan-8-amine
(1R,5S,8s)-N-[5-(3-Chloro-5-fluorophenoxy)-1-(trideuteriomethyl)-1,2,4-triazol-3-yl]-3-(6-methylpyrimidin-4-yl)-3-azabicyclo[3.2.1]octan-8-amine
(1R,5S,8s)-N-[5-(3-Chloro-4-fluorophenoxy)-1-(trideuteriomethyl)-1,2,4-triazol-3-yl]-3-(6-methylpyrimidin-4-yl)-3-azabicyclo[3.2.1]octan-8-amine (1R,5S,8s)-N-[5-(3-Chloro-5-fluorophenoxy)-1-(1,1,2,2,2-pentadeuterioethyl)-1,2,4-triazol-3-yl]-3-(6-methylpyrimidin-4-yl)-3-azabicyclo[3.2.1]octan-8-amine (1R,5S,8s)-N-[5-(3-Chloro-4-fluorophenoxy)-1-(1,1,2,2,2-pentadeuterioethyl)-1,2,4-triazol-3-yl]-3-(6-methylpyrimidin-4-yl)-3-azabicyclo[3.2.1]octan-8-amine (1R,5S,8s)-N-(5-(3-Chloro-5-fluorophenoxy)-1-(2,2,2-trifluoroethyl)-1H-1,2,4-triazol-3-yl)-3-(6-methylpyrimidin-4-yl)-3-azabicyclo[3.2.1]octan-8-amine or (1R,5S,8s)-N-(5-(3-Chlorophenoxy)-1-(2-fluoroethyl)-1H-1,2,4-triazol-3-yl)-3-(6-methylpyrimidin-4-yl)-3-azabicyclo[3.2.1]octan-8-amine.

One object of the present invention is a compound of formula I-g,

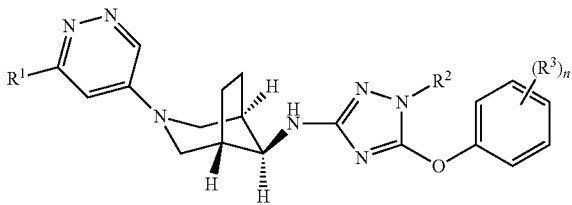

I-g wherein
R¹ is hydrogen, halogen, lower alkyl, lower alkoxy or lower alkyl substituted by halogen;
R² is lower alkyl or a mono- or polydeutered derivative thereof,
 lower alkyl substituted by halogen or lower alkoxy,
 lower alkenyl unsubstituted or substituted by halogen,
 cycloalkyl or CH₂-cycloalkyl unsubstituted or substituted by halogen,
 heterocycloalkyl or CH₂-heterocycloalkyl unsubstituted or substituted by lower alkyl;
R³ is halogen, lower alkyl, lower alkyl substituted by halogen, lower alkoxy substituted by halogen or S(O)₂-lower alkyl;
n is 1, 2 or 3; if n is >1, then R³ may be the same or different;
or a pharmaceutically active acid addition salt thereof, a racemic mixture or its corresponding enantiomer and/or an optical isomer and/or stereoisomer thereof, for example the following compounds (1R,5S,8s)-N-(5-(3-Chlorophenoxy)-1-methyl-1H-1,2,4-triazol-3-yl)-3-(6-chloropyridazin-4-yl)-3-azabicyclo[3.2.1]octan-8-amine (1R,5S,8s)-N-(5-(3-Chloro-5-methylphenoxy)-1-methyl-1H-1,2,4-triazol-3-yl)-3-(6-chloropyridazin-4-yl)-3-azabicyclo[3.2.1]octan-8-amine (1R,5S,8s)-N-(5-(3-Chlorophenoxy)-1-ethyl-1H-1,2,4-triazol-3-yl)-3-(6-methoxypyridazin-4-yl)-3-azabicyclo[3.2.1]octan-8-amine (1R,5S,8s)-N-(5-(3-Chlorophenoxy)-1-propyl-1H-1,2,4-triazol-3-yl)-3-(6-methoxypyridazin-4-yl)-3-azabicyclo[3.2.1]octan-8-amine (1R,5S,8s)-N-(5-(3-Chlorophenoxy)-1-propyl-1H-1,2,4-triazol-3-yl)-3-(6-chloropyridazin-4-yl)-3-azabicyclo[3.2.1]octan-8-amine (1R,5S,8s)-N-(5-(3-Chloro-5-methylphenoxy)-1-methyl-1H-1,2,4-triazol-3-yl)-3-(6-methoxypyridazin-4-yl)-3-azabicyclo[3.2.1]octan-8-amine (1R,5S,8s)-N-(5-(3-Chlorophenoxy)-1-methyl-1H-1,2,4-triazol-3-yl)-3-(6-methoxypyridazin-4-yl)-3-azabicyclo[3.2.1]octan-8-amine (1R,5S,8s)-N-(5-(3-Chlorophenoxy)-1-ethyl-1H-1,2,4-triazol-3-yl)-3-(6-chloropyridazin-4-yl)-3-azabicyclo[3.2.1]octan-8-amine (1R,5S,8s)-N-(5-(3-Chlorophenoxy)-1-(2,2,2-trifluoroethyl)-1H-1,2,4-triazol-3-yl)-3-(6-chloropyridazin-4-yl)-3-azabicyclo[3.2.1]octan-8-amine (1R,5S,8s)-N-(5-(3-Fluoro-5-methylphenoxy)-1-methyl-1H-1,2,4-triazol-3-yl)-3-(6-chloropyridazin-4-yl)-3-azabicyclo[3.2.1]octan-8-amine (1R,5S,8s)-N-(5-(3-Chlorophenoxy)-1-(2,2-difluoroethyl)-1H-1,2,4-triazol-3-yl)-3-(6-chloropyridazin-4-yl)-3-azabicyclo[3.2.1]octan-8-amine (1R,5S,8s)-N-(5-(3-Chlorophenoxy)-1-(2-fluoroethyl)-1H-1,2,4-triazol-3-yl)-3-(6-chloropyridazin-4-yl)-3-azabicyclo[3.2.1]octan-8-amine (1R,5S,8s)-N-(5-(3-Chlorophenoxy)-1-(2,2-difluoroethyl)-1H-1,2,4-triazol-3-yl)-3-(6-methoxypyridazin-4-yl)-3-azabicyclo[3.2.1]octan-8-amine (1R,5S,8s)-N-(5-(3-Chlorophenoxy)-1-(2-fluoroethyl)-1H-1,2,4-triazol-3-yl)-3-(6-methoxypyridazin-4-yl)-3-azabicyclo[3.2.1]octan-8-amine (1R,5S,8s)-N-[5-(3,4-Difluorophenoxy)-1-(propan-2-yl)-1H-1,2,4-triazol-3-yl]-3-(6-methoxypyridazin-4-yl)-3-azabicyclo[3.2.1]octan-8-amine (1R,5S,8s)-N-[5-(3-Fluorophenoxy)-1-(propan-2-yl)-1H-1,2,4-triazol-3-yl]-3-(6-methoxypyridazin-4-yl)-3-azabicyclo[3.2.1]octan-8-amine (1R,5S,8s)-N-(5-(2,3-Difluorophenoxy)-1-(propan-2-yl)-1H-1,2,4-triazol-3-yl)-3-(6-methoxypyridazin-4-yl)-3-azabicyclo[3.2.1]octan-8-amine (1R,5S,8s)-N-(5-(3,5-Difluorophenoxy)-1-(propan-2-yl)-1H-1,2,4-triazol-3-yl)-3-(6-methoxypyridazin-4-yl)-3-azabicyclo[3.2.1]octan-8-amine (1R,5S,8s)-N-(5-(3-Chloro-4-fluorophenoxy)-1-(propan-2-yl)-1H-1,2,4-triazol-3-yl)-3-(6-methoxypyridazin-4-yl)-3-azabicyclo[3.2.1]octan-8-amine (1R,5S,8s)-N-(5-(3-Chloro-5-fluorophenoxy)-1-(propan-2-yl)-1H-1,2,4-triazol-3-yl)-3-(6-methoxypyridazin-4-yl)-3-azabicyclo[3.2.1]octan-8-amine (1R,5S)—N-[5-(3-Chloro-2-fluoro-phenoxy)-1-isopropyl-1,2,4-triazol-3-yl]-3-(6-methoxypyridazin-4-yl)-3-azabicyclo[3.2.1]octan-8-amine (1R,5S,8s)-N-[5-(3-Chloro-5-fluorophenoxy)-1-methyl-1,2,4-triazol-3-yl]-3-(6-methoxypyridazin-4-yl)-3-azabicyclo[3.2.1]octan-8-amine (1R,5S,8s)-N-[5-(3-Chloro-4-fluorophenoxy)-1-ethyl-1H-1,2,4-triazol-3-yl]-3-(6-methoxypyridazin-4-yl)-3-azabicyclo[3.2.1]octan-8-amine (1R,5S,8s)-N-(5-(3-Chloro-4-fluorophenoxy)-1-propyl-1H-1,2,4-triazol-3-yl)-3-(6-methoxypyridazin-4-yl)-3-azabicyclo[3.2.1]octan-8-amine (1R,5S,8s)-N-(5-(3-Chloro-4-fluorophenoxy)-1-isobutyl-1H-1,2,4-triazol-3-yl)-3-(6-methoxypyridazin-4-yl)-3-azabicyclo[3.2.1]octan-8-amine (1R,5S,8s)-N-(5-(3-Chloro-4-fluorophenoxy)-1-((3,3-difluorocyclobutyl)methyl)-1H-1,2,4-triazol-3-yl)-3-(6-methoxypyridazin-4-yl)-3-azabicyclo[3.2.1]octan-8-amine (1R,5S,8s)-N-[5-(3-Chloro-4-fluorophenoxy)-1-(1,1,1,2,3,3,3-heptadeuteriopropan-2-yl)-1,2,4-triazol-3-yl]-3-(6-methoxypyridazin-4-yl)-3-azabicyclo[3.2.1]octan-8-amine (1R,5S,8s)-N-[5-(3-Chloro-4-fluorophenoxy)-1-(trideuteriomethyl)-1,2,4-triazol-3-yl]-3-(6-methoxypyridazin-4-yl)-3-azabicyclo[3.2.1]octan-8-amine or (1R,5S,8s)-N-[5-(3-Chloro-4-fluorophenoxy)-1-(1,1,2,2,2-pentadeuterioethyl)-1,2,4-triazol-3-yl]-3-(6-methoxy-pyridazin-4-yl)-3-azabicyclo[3.2.1]octan-8-amine.

The present compounds of formula I and their pharmaceutically acceptable salts can be prepared by methods known in the art, for example, by processes described below, which processes comprise a) reacting a compound of formula II

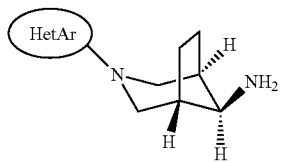

with a compound of formula III

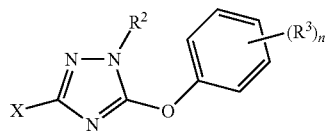

to a compound of formula I

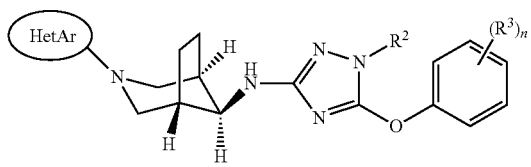

wherein the substituents have the meaning as described above, and X is halogen, and, if desired, converting the compounds obtained into pharmaceutically acceptable acid addition salts;

or b) reacting a compound of formula VI

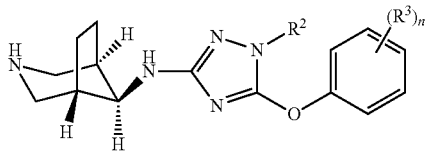

with a compound of formula

HetAr-X to a compound of formula

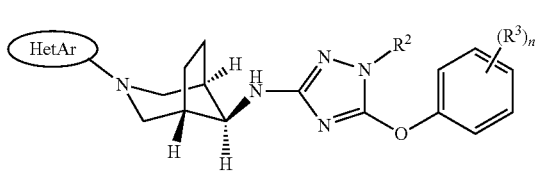

I wherein the groups have the meaning as described above, and X is halogen, or if desired converting the compounds obtained into pharmaceutically acceptable acid addition salts.

In more detail, compounds of formula I and their intermediates may be prepared by schemes 1-7 and by the description of 239 specific examples.

Scheme 1

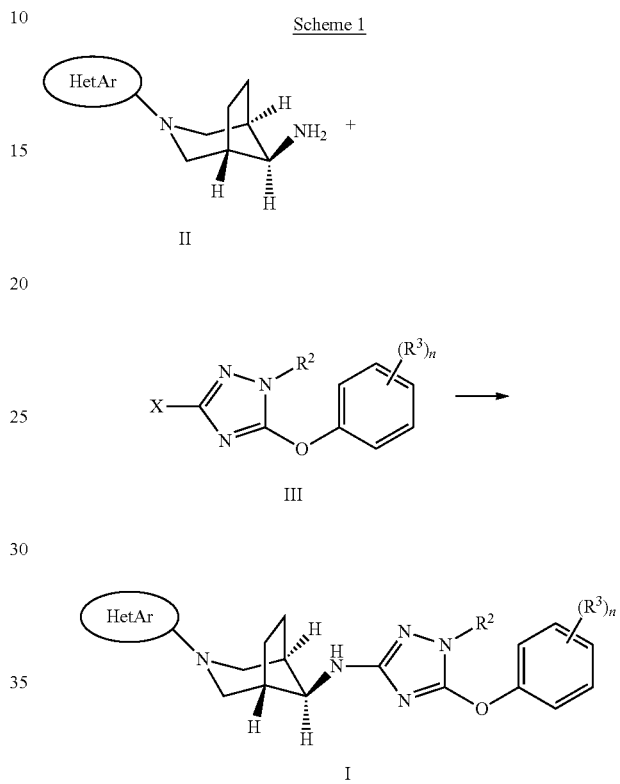

An intermediate of formula II, wherein the heteroaromatic ring HetAr is as defined above, is reacted with a compound of formula III, wherein n, $R^2$ and $R^3$ are as defined above, and X is halogen, preferably bromine, as shown in Scheme 1. The reaction can be carried out in the presence of catalytic or stoichiometric amounts of a suitable transition metal complex, e.g. tris(dibenzylideneacetone)dipalladium(0), optionally as solvent adduct, or chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9]) and, respectively, catalytic or stoichiometric amounts of a suitable phosphine ligand, e.g. 4,5-bis(diphenylphosphino)-9,9-dimethylxanthene ("xantphos", CAS [161265-03-8]), 1,2,3,4,5-pentaphenyl-1'-(di-tert-butylphosphino)ferrocene ("Q-phos", CAS [312959-24-3]), 2-dicyclohexylphosphino-2',6'-diisopropoxybiphenyl ("Ruphos", CAS [787618-22-8]) or di-tert-butyl(2',4',6'-triisopropylbiphenyl-2-yl)phosphine ("tBuXPhos", CAS [564483-19-8]) and, furthermore, in the presence of a suitable base, e.g. alkali tertbutoxide, alkali carbonate, or alkaliphosphate, e.g. sodium tertbutoxide. The reaction can be carried out in a polar, aprotic solvent, e.g. 1,4-dioxane, tetrahydrofuran or 2-methyltetrahydrofuran, at temperatures between 100° C. and 170° C., preferably between 110° C. and 140° C., optionally under microwave radiation in a closed vial.

Scheme 2

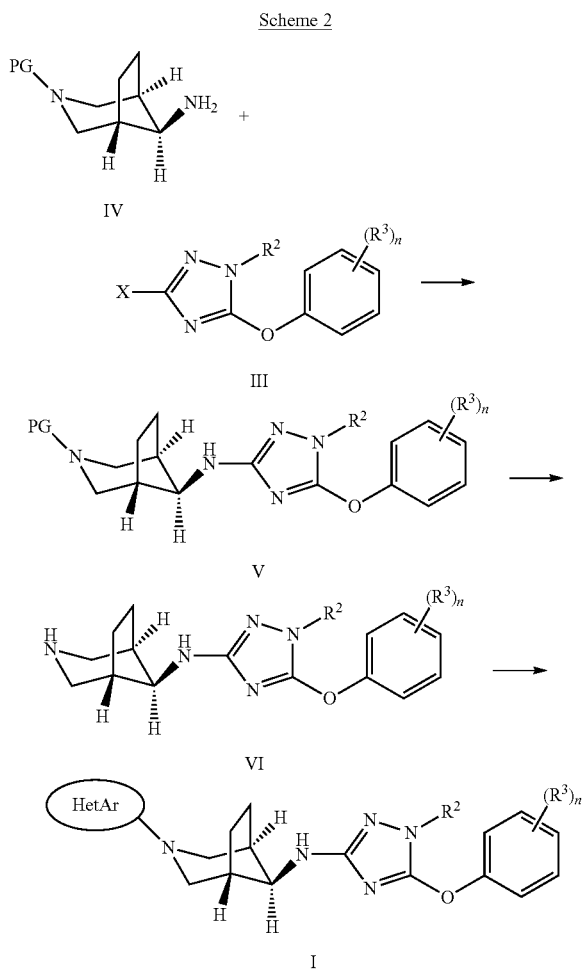

Alternatively, compounds of formula I, wherein HetAr, n, $R^2$ and $R^3$ are as defined above, can be accessed as outlined in Scheme 2. In analogy to the reaction depicted in Scheme 1, an intermediate of formula III, wherein n, $R^2$, $R^3$ are as defined above and X is halogen, preferably bromine, can be reacted with a compound of formula IV, wherein PG is a suitabale protecting group, e.g. tert-butoxycarbonyl (Boc) in the presence of catalytic or stoichiometric amounts of a suitable transition metal complex, e.g. tris(dibenzylideneacetone)dipalladium(0), optionally as solvent adduct, or chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9]) and, respectively, catalytic or stoichiometric amounts of a suitable phosphine ligand, e.g. 4,5-bis(diphenylphosphino)-9,9-dimethylxanthene ("Xantphos", CAS [161265-03-8]), 1,2,3,4,5-pentaphenyl-1'-(di-tert-butylphosphino)ferrocene ("Q-phos", CAS [312959-24-3]), 2-dicyclohexylphosphino-2',6'-diisopropoxybiphenyl ("Ruphos", CAS [787618-22-8]) or di-tert-butyl(2',4',6'-triisopropylbiphenyl-2-yl)phosphine ("tBuXPhos", CAS [564483-19-8]) and, furthermore, in the presence of a suitable base, e.g. alkali tertbutoxide, alkali carbonate, or alkaliphosphate, e.g. sodium tertbutoxide. The reaction can be carried out in a polar, aprotic solvent, e.g. 1,4-dioxane, tetrahydrofuran or 2-methyltetrahydrofuran, at temperatures between 100° C. and 170° C., preferably between 110° C. and 140° C., optionally under microwave radiation in a closed vial.

Next, the protecting group PG can be cleaved using methods known in the art. In case PG is Boc, the deprotection can be achieved by stirring the intermediate of formula V in the presence of a strong acid, such as triflouroacetic acid (TFA) or hydrochloric acid (HCl), e.g. as solution in dioxane, methanol or water, optionally in the presence of a suitable solvent, e.g. dichloromethane. The resulting intermediate of formula VI can be transformed into a compound of formula I by reaction with a heterorayl halide HetAr-Y, wherein HetAr is as defined above and Y is halogen, preferably chlorine or bromine, in the presence of a suitable base, such as a trialkyl amine, e.g. triethyl amine, in an appropriate polar protic or aprotic solvent, e.g. ethanol, at temperatures between 50° C. and 130° C., preferably 70° C. to 100° C.

Compounds of formula I-c, wherein $R^1$, $R^2$, $R^3$ and n are as defined above, represent a subgroup of compounds of formula I, as defined above. This subgroup of compounds can be synthesized using the sequence depicted in Scheme 3.

Scheme 3

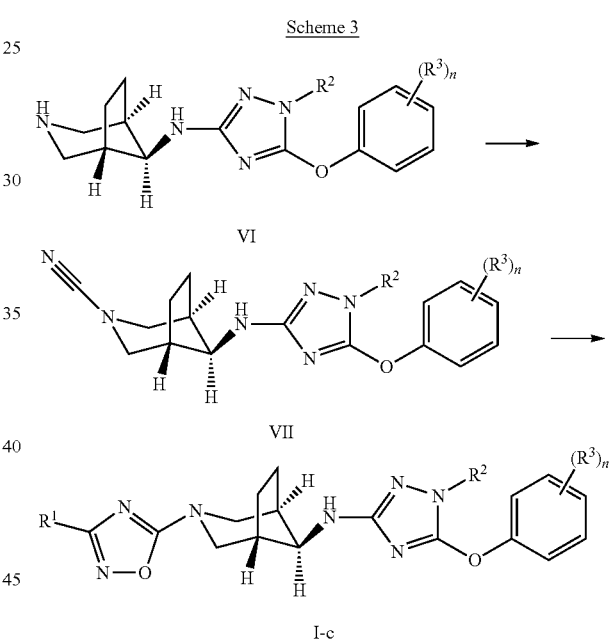

A compound of formula VI, wherein $R^2$, $R^3$ and n are as defined above, can be reacted with cyanogen bromide in the presence of a suitable base, e.g. sodium hydrogencarbonate, in an appropriate solvent, such as dichloromethane or ethanol, optionally in the presence of water. The reaction can be carried out at temperatures of 0° C. to 70° C., preferably at 20° C. to 30° C. Next, the resulting compounds of formula VII can be reacted in a [3+2] dipolar cycloaddition with an appropriate hydroxyalkanimidamide, e.g. hydroxyethanimidamide for $R^1$=Me, in the presence of catalytic or stoichiometric amounts of a strong acid, such as p-toluenesulfonic acid, and catalytic or stoichiometric amounts of a Lewis acid, e.g. zinc(II) chloride, in a suitable solvent, e.d. N,N-dimethylformamide or N-methyl-2-pyrrolidinone, at elevated temperatures of 50° C. to 100° C., preferably 70° C. to 90° C.

Scheme 4

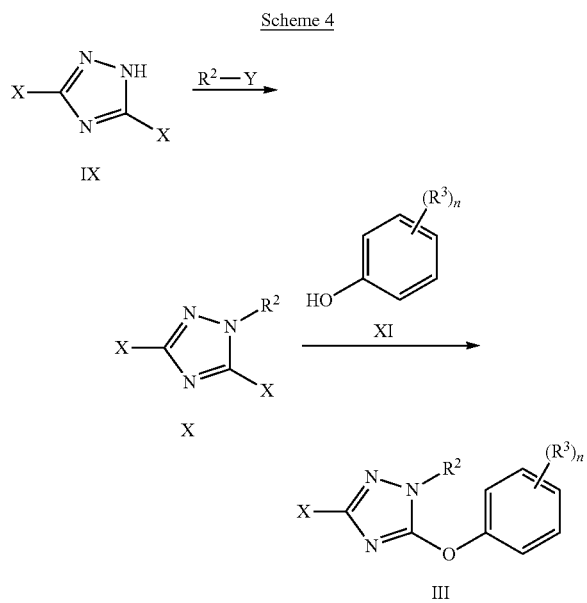

Scheme 5

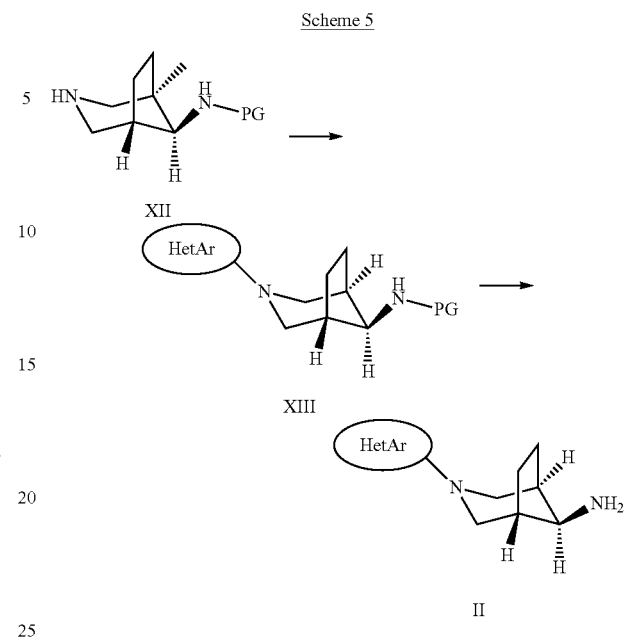

Building blocks of formula III can be synthesized following the route shown in Scheme 4. In the first step, an intermediate of formula IX, wherein X is each independently selected from halogen, preferably bromine, is reacted with a compound of formula $R^2$—Y, wherein $R^2$ is as defined above, and Y is selected from arenesulfonoyl, e.g. p-toluenesulfonoyl, alkanesulfonoyl, e.g. methanesulfonoyl or triflouromethanesulfonoyl, or halogen, e.g. bromine or iodine, in the presence of a suitable base, e.g. sodium hydride or potassium carbonate, in a polar aprotic solvent, e.g. N,N-dimethylformamide or N-methyl-2-pyrrolidinone.

In order to access intermediates of formula X and III, containing a mono- or polydeuterated substituent $R^2$, the triazole of formula IX can be reacted under similar conditions as described above with the respective building blocks $R^2$-Y, wherein $R^2$ is mono- or polydeuterated lower alkyl, and Y is selected from p-toluenesulfonoyl, alkanesulfonoyl, e.g. methanesulfonoyl or triflouromethanesulfonoyl, or halogen, e.g. bromine or iodine. The building blocks $R^2$-Y are commercially available or can be prepared by methods known in the art.

Alternatively, the intermediate of formula IX can be reacted in a Chan-Lam coupling with a boron containing compound of formula $R^2$—Y, wherein $R^2$ is as defined above, and Y is $B(OH)_2$, B(pin) or $BF_4K$, preferably $B(OH)_2$, in the presence of a Cu(I) or Cu(II) salt, e.g. copper(II) acetate, and a suitable ligand, such as 2,2'-bipyridine, moreover in the presence of an appropriate base, e.g. sodium carbonate, in a suitable solvent, e.g. 1,2-dichloroethane or dioxane, at temperatures of 20° C. to 100° C., preferably 50° C. to 80° C.

The second step, reaction of intermediate X with a phenol of formula XI, can be carried out in presence of a suitable base, e.g. potassium carbonate or 1,8-diazabicyclo[5.4.0]undec-7-ene ("DBU"), in an appropriate polar aprotic solvent, e.g. N,N-dimethylformamide or N-methyl-2-pyrrolidinone, at elevated temperatures of 80° C. to 150° C., preferably 90° C. to 130° C., optionally under microwave radiation in a closed vial.

Intermediates of formula II, wherein HetAr is as defined above, are either commercially available or can be synthesized by methods known in the art, e.g. as described in WO2012116965. Alternatively, they can be accessed according to the general route depicted in Scheme 5. A compound of formula XII, wherein PG is a suitable protecting group, e.g. tertbutoxycarbonyl (Boc), and that can be synthesized (for PG=Boc) according to procedures described in WO2012116965, can be reacted with a reagent of formula HetAr-X, wherein HetAr is as defined above and X is halogen, preferably chlorine or bromine, in the presence of a suitable base, such as a trialkyl amine, e.g. triethyl amine, in an appropriate polar protic or aprotic solvent, e.g. ethanol, at temperatures between 50° C. and 130° C., preferably 70° C. to 100° C.

Alternatively, compounds of formula XII can be reacted with heteroaryl halides of formula HetAr-X, wherein HetAr is as defined above and X is halogen, preferably chlorine or bromine, in the presence of catalytic or stoichiometric amounts of a suitable transition metal complex, e.g. bis(dibenzylideneacetone)palladium(0) or tris(dibenzylideneacetone)di-palladium(0), or palladium(II)acetate and, respectively, catalytic or stoichiometric amounts of a suitable phosphine ligand, e.g. dicyclohexyl[2',4',6'-tris(1-methylethyl)[1,1'-biphenyl]-2-yl] phosphine ("X-Phos") or 2,2'-bis(diphenylphosphanyl)-1,1'-binaphthyl ("BINAP"), and, furthermore, in the presence of a suitable base, e.g. alkali carbonate, alkali tertbutoxide, or alkaliphosphate, e.g. cesium carbonate or sodium tertbutoxide. The reaction can be carried out in an aprotic solvent, e.g. N-methylpyrrolidinone, 1,4-dioxane or toluene, at temperatures between 80° C. and 130° C., preferably between 90° C. and 120° C., optionally under microwave radiation in a closed vial.

Next the protecting group can be cleaved to give the desired compounds of formula II using methods known in the art. In case PG is Boc, this transformation can be achieved by reaction with an excess of a strong acid, e.g. trifluoroacetic acid (TFA) or hydrochloric acid in a suitable solvent, e.g. dichloromethane, ethanol, or water, or mixtures thereof.

The heteroaryl halides of formula HetAr-X are either commercially available, known in the literature so they can be prepared by methods known in the art.

Scheme 6

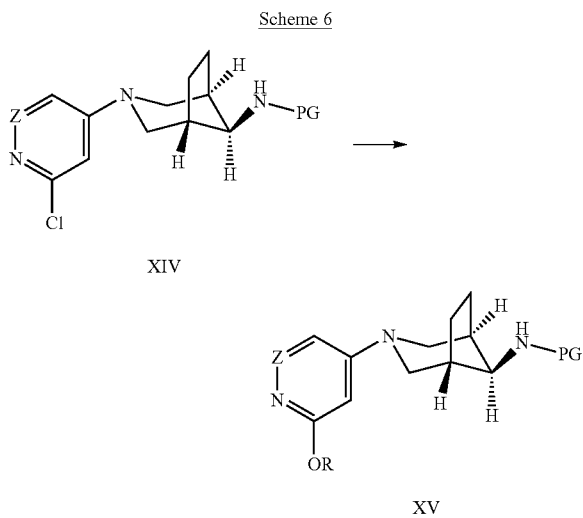

Alternatively, certain compounds of formula II can be synthesized via intermediates depicted in Scheme 6. Likewise, a compound of formula XIV, wherein PG is a suitable protecting group, e.g. Boc, and Z is N or CH, that is a special case of a compound of formula XIII and that can be prepared according to the reaction shown in Scheme 5, can be reacted with alkoxides of formula MOR, wherein M is an alkali metal, e.g. sodium, and R is lower alkyl, e.g. methyl, in a suitable polar solvent, such as N-methylpyrrolidinone or an alcohol, preferably ROH, wherein R is the same as in the reagent MOR, at elevated temperatures of 50° C. to 120° C., preferably 80° C. to 90° C. The resulting intermediate of formula XV is again a special case of the intermediate of formula XIII and can be deprotected to give compounds of formula II, as outlined in Scheme 5.

Scheme 7

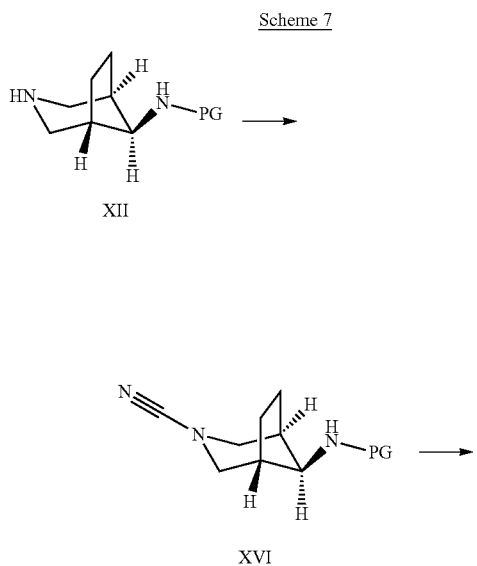

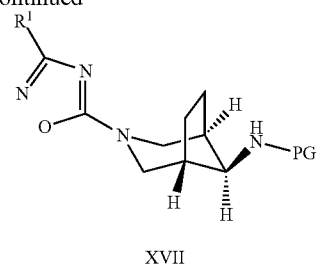

Alternatively, certain compounds of formula II can be synthesized via intermediates depicted in Scheme 7. Likewise, a compound of formula XII, wherein PG is a suitable protecting group, e.g. Boc, can be reacted with cyanogen bromide in the presence of a suitable base, e.g. sodium hydrogencarbonate, in an appropriate solvent, such as dichloromethane or ethanol, optionally in the presence of water. The reaction can be carried out at temperatures of 0° C. to 70° C., preferably at 20° C. to 30° C. Next, the resulting compounds of formula XVI can be reacted in a [3+2] dipolar cycloaddition with an appropriate hydroxyalkanimidamide, e.g. hydroxyethanimidamide for $R^1$=Me, in the presence of catalytic or stoichiometric amounts of a strong acid, such as p-toluenesulfonic acid, and catalytic or stoichiometric amounts of a Lewis acid, e.g. zinc(II) chloride, in a suitable solvent, e.g. N,N-dimethylformamide or N-methyl-2-pyrrolidinone, at elevated temperatures of 50° C. to 100° C., preferably 70° C. to 90° C. The resulting intermediate of formula XVII is a special case of the intermediate of formula XIII and can be deprotected to give compounds of formula II, as outlined in Scheme 5.

The compounds were investigated in accordance with the test given hereinafter.

Description of γ-Secretase Assay

Cellular γ-Secretase Assay

Human neuroglioma H4 cells overexpressing human APP695 with the Swedish double mutation (K595N/M596L) were plated at 30,000 cells/well/100 µl in 96-well plates in IMDM media containing 10% FCS, 0.2 mg/l Hygromycin B and incubated at 37° C., 5% $CO_2$.

3-4 hr post plating, compounds are a diluted in media and 50 µl is added as 1.5-fold concentrate to achieve the final concentration. Compound incubation is performed for 24 hr. Final doses typically range from 4 µM down to 0.0013 µM in half-log steps resulting in a eight point dose response curve.

Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa assay kit (Human Amyloid beta 1-42 Kit: Cat #AL203C, Perkin Elmer). 20 µl of the cell culture supernatant was transferred to an assay plate. Then 10 µl of a mixture of the AlphaLisa coupled capture antibody and the biotinylated detection antibody was added and incubated for 3 hours at room temperature while softly shaking the assay plate. After a further addition of 20 µl of the Donor beads the assay plate was incubated for 30 min at room temperature and constant shaking without exposure to direct light. The assay plate was then read on a Paradigm AlphaLisa Reader using the build-in program with excitation at 680 nm and emission at 570 nm.
The measured signals were then used to calculate $IC_{50}$ values for inhibition of Aβ42 secretion by nonlinear regression fit analysis using XLfit 5.3 software (IDBS).

The table below shows the data for all compounds for the inhibition of Aβ42 secretion (nM):

| Example No. | $EC_{50}$ Aβ42 (nM) | Example No. | $EC_{50}$ Aβ42 (nM) |
|---|---|---|---|
| 1 | 17 | 2 | 9 |
| 3 | 12 | 4 | 4 |
| 5 | 6 | 6 | 8 |
| 7 | 3 | 8 | 3 |
| 9 | 6 | 10 | 4 |
| 11 | 5 | 12 | 59 |
| 13 | 25 | 14 | 80 |
| 15 | 90 | 16 | 87 |
| 17 | 59 | 18 | 98 |
| 19 | 22 | 20 | 69 |
| 21 | 79 | 22 | 37 |
| 23 | 97 | 24 | 29 |
| 25 | 75 | 26 | 53 |
| 27 | 38 | 28 | 16 |
| 29 | 18 | 30 | 28 |
| 31 | 19 | 32 | 24 |
| 33 | 11 | 34 | 8 |
| 35 | 43 | 36 | 31 |
| 37 | 76 | 38 | 35 |
| 39 | 52 | 40 | 43 |
| 41 | 42 | 42 | 45 |
| 43 | 16 | 44 | 44 |
| 45 | 43 | 46 | 15 |
| 47 | 22 | 48 | 70 |
| 49 | 75 | 50 | 67 |
| 51 | 30 | 52 | 58 |
| 53 | 83 | 54 | 51 |
| 55 | 47 | 56 | 31 |
| 57 | 16 | 58 | 32 |
| 59 | 33 | 60 | 46 |
| 61 | 31 | 62 | 35 |
| 63 | 88 | 64 | 42 |
| 65 | 87 | 66 | 46 |
| 67 | 78 | 68 | 16 |
| 69 | 33 | 70 | 23 |
| 71 | 8 | 72 | 69 |
| 73 | 19 | 74 | 25 |
| 75 | 25 | 76 | 22 |
| 77 | 16 | 78 | 54 |
| 79 | 50 | 80 | 69 |
| 81 | 17 | 82 | 18 |
| 83 | 12 | 84 | 53 |
| 85 | 29 | 86 | 18 |
| 87 | 17 | 88 | 44 |
| 89 | 30 | 90 | 14 |
| 91 | 15 | 92 | 11 |
| 93 | 11 | 94 | 12 |
| 95 | 32 | 96 | 13 |
| 97 | 27 | 98 | 56 |
| 99 | 17 | 100 | 34 |
| 101 | 12 | 102 | 15 |
| 103 | 12 | 104 | 61 |
| 105 | 10 | 106 | 13 |
| 107 | 16 | 108 | 21 |
| 109 | 46 | 110 | 17 |
| 111 | 24 | 112 | 14 |
| 113 | 27 | 114 | 18 |
| 115 | 15 | 116 | 18 |
| 117 | 41 | 118 | 16 |
| 119 | 22 | 120 | 15 |
| 121 | 14 | 122 | 9 |
| 123 | 27 | 124 | 22 |
| 125 | 18 | 126 | 19 |
| 127 | 10 | 128 | 21 |
| 129 | 21 | 130 | 12 |
| 131 | 12 | 132 | 18 |
| 133 | 26 | 134 | 16 |
| 135 | 12 | 136 | 10 |
| 137 | 14 | 138 | 12 |
| 139 | 12 | 140 | 15 |
| 141 | 14 | 142 | 9 |
| 143 | 15 | 144 | 15 |
| 145 | 10 | 146 | 5 |
| 147 | 10 | 148 | 10 |
| 149 | 11 | 150 | 12 |
| 151 | 20 | 152 | 24 |
| 153 | 18 | 154 | 16 |
| 155 | 14 | 156 | 16 |
| 157 | 21 | 158 | 27 |
| 159 | 20 | 160 | 19 |
| 161 | 14 | 162 | 15 |
| 163 | 18 | 164 | 22 |
| 165 | 21 | 166 | 12 |
| 167 | 10 | 168 | 24 |
| 169 | 17 | 170 | 39 |
| 171 | 18 | 172 | 41 |
| 173 | 10 | 174 | 14 |
| 175 | 15 | 176 | 28 |
| 177 | 15 | 178 | 10 |
| 179 | 12 | 180 | 27 |
| 181 | 63 | 182 | 19 |
| 183 | 30 | 184 | 34 |
| 185 | 32 | 186 | 17 |
| 187 | 42 | 188 | 17 |
| 189 | 66 | 190 | 15 |
| 191 | 25 | 192 | 26 |
| 193 | 12 | 194 | 9 |
| 195 | 17 | 196 | 13 |
| 197 | 18 | 198 | 21 |
| 199 | 11 | 200 | 10 |
| 201 | 17 | 202 | 30 |
| 203 | 14 | 204 | 13 |
| 205 | 6 | 206 | 17 |
| 207 | 13 | 208 | 48 |
| 209 | 32 | 210 | 23 |
| 211 | 23 | 212 | 16 |
| 213 | 23 | 214 | 14 |
| 215 | 19 | 216 | 64 |
| 217 | 36 | 218 | 32 |
| 219 | 23 | 220 | 12 |
| 221 | 10 | 222 | 11 |
| 223 | 13 | 224 | 11 |
| 225 | 27 | 226 | 14 |
| 227 | 42 | 228 | 37 |
| 229 | 29 | 230 | 12 |
| 231 | 16 | 232 | 19 |
| 233 | 18 | 234 | 9 |
| 235 | 11 | 236 | 16 |
| 237 | 9 | 238 | 11 |
| 239 | 15 | | |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions. The administration can also be effected topically, e.g. transdermal administration, or in form of eye drops or ear drops.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, drag-es and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXPERIMENTAL PART

The following examples are provided for illustration of the invention. They should not be considered as limiting the scope of the invention, but merely as being representative thereof.

General

Analytical Methods

HPLC (method LCMS_fastgradient)

Column: Agilent Zorbax Eclipse Plus C18, Rapid Resolution HT, 2.1×30 mm, 1.8 μm, Part. no. 959731-902

Solvent A: Water 0.01% Formic Acid; Solvent B: acetonitrile (MeCN)

Gradients:

| Time [min] | Flow Rate [ml/min] | % A | % B |
|---|---|---|---|
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

1H NMR

1H NMR data are given in the following format: chemical shift in ppm (multiplet, coupling constants if applicable, integral). Abbreviations for multiplets: s, singlet; d, dublet; t, triplet; q, quartet; hept, heptet; m, multiplet. The chemical shifts are referenced to the respective deuterated solvent, CDCl3 (7.27 ppm) or d6-DMSO (2.50 ppm).

Abbreviations

The following abbreviations were used in the experimental part:

THF=tetrahydrofuran;

MTBE=methyl-tert-butylether;

DMF=dimethylformamide;

TLC=thin layer chromatography;

rt=room temperature, 20-25° C.

Starting Materials

Basic chemicals and solvents were purchased and used as is without further purification. Intermediates Int-1, Int-17, Int-94 are commercially available, or they can be synthesized, e.g. as described in Synthesis 2012, 44, pages 3055-

3058 (Int-1), WO2010114958 (Int-17), or WO2012116965 (Int-94). Int-132 can be synthesized using procedures published in WO2012116965.

INTERMEDIATES

Int-3

3-Bromo-5-(3-fluorophenoxy)-1-(propan-2-yl)-1H-1,2,4-triazole

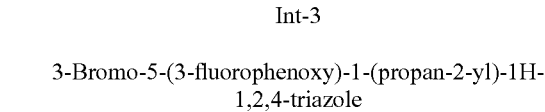

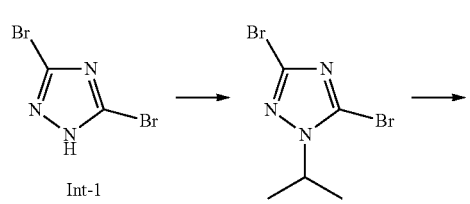

Step 1: 3,5-Dibromo-1-(propan-2-yl)-1H-1,2,4-triazole (Int-2)

To a solution of 3,5-dibromo-1H-1,2,4-triazole (Int-1, 5.0 g, 22.0 mmol) in DMF (70 mL) was added sodium hydride (793 mg, 33.1 mmol) at 0° C. under argon atmosphere. After complete addition reaction was allowed to stir at 25° C. for 30 min. Then 2-iodopropane (2.6 mL, 26.4 mmol) was added followed by stirring at 40° C. for 4 h. After complete consumption of starting material (as monitored by TLC) reaction mixture was poured into ice-water followed by extraction with MTBE. The organic layer was separated and dried over sodium sulphate. Solvent was evaporated under reduced pressure to afford the title compound as yellow liquid (5.4 g, crude) which was sufficiently pure for use in next step. $^1$H NMR (DMSO-d6, 400 MHz): 1.39 (d, J=6.6 Hz, 6H), 4.64-4.71 (m, 1H). MS (ES+) m/z 270.0 [M+H].

Step 2: 3-Bromo-5-(3-fluorophenoxy)-1-(propan-2-yl)-1H-1,2,4-triazole (Int-3)

To a solution of 3,5-dibromo-1-(propan-2-yl)-1H-1,2,4-triazole (Int-2, 300 mg, 1.1 mmol) and 3-fluorophenol (125 mg, 1.1 mmol) in DMF (4 mL) was added K$_2$CO$_3$ (308 mg, 2.2 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (120 mg, 36%). $^1$H NMR (DMSO-d6, 400 MHz): 1.41 (d, J=6.6 Hz, 6H), 4.62 (p, J=6.4 Hz, 1H), 7.13-7.20 (m, 1H), 7.23 (dd, J=8.4, 2.1 Hz, 1H), 7.37 (dt, J=10.0, 2.3 Hz, 1H), 7.48-7.55 (m, 1H). MS (ES+) m/z 302.0 [M+H].

Int-4

3-Bromo-5-(2-chlorophenoxy)-1-(propan-2-yl)-1H-1,2,4-triazole

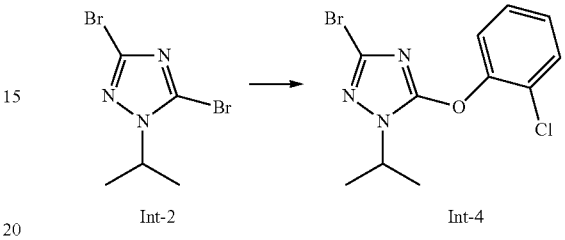

In an 8 mL microwave vial, 3,5-dibromo-1-(propan-2-yl)-1H-1,2,4-triazole (Int-2, 300 mg, 1.12 mmol) was dissolved in DMF (4.5 mL) and 2-chlorophenol (143 mg, 1.12 mmol) was added, followed by potassium carbonate (308 mg, 2.23 mmol). The reaction mixture was heated under microwave irradiation at 160° C. for 45 min. After cooling, the mixture was poured onto water (20 mL), and extracted with MTBE (3×20 mL). The combined organics were dried (magnesium sulfate) and concentrated in vacuo. The resulting crude product was triturated with a mixture of MTBE/n-heptane, ca. 1:1 v/v, ca. 10 mL). The remaining solid was dried in vacuo to afford the title compound as white crystalline solid (210 mg, 59%). HPLC (method LCMS_fastgradient) t$_R$=1.35 min. $^1$H NMR (CDCl$_3$, 300 MHz): δ 1.56 (d, J=6.7 Hz, 6H), 4.70 (hept, J=6.8 Hz, 1H), 7.20-7.26 (m, 1H), 7.31-7.37 (m, 1H), 7.45 (dd, J=1.8, 3.6 Hz, 1H), 7.48 (dd, J=1.6, 3.6 Hz, 1H). MS (ES+) m/z 318.1 [M+H].

Int-5

3-Bromo-5-[4-fluoro-3-(trifluoromethyl)phenoxy]-1-(propan-2-yl)-1H-1,2,4-triazole

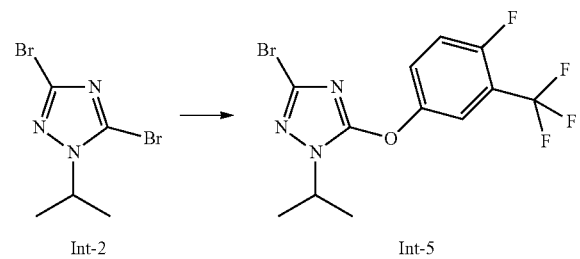

To a solution of 3,5-dibromo-1-(propan-2-yl)-1H-1,2,4-triazole (Int-2, 400 mg, 1.5 mmol) and 4-fluoro-3-(trifluoromethyl)phenol (267.9 mg, 1.5 mmol) in DMF (4 mL) was added K$_2$CO$_3$ (411 mg, 2.9 mmol). The stirring was continued in a microwave at 145° C. for 1 h. After complete consumption of starting material (as monitored by TLC) the reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 3:97 v/v) to afford the title compound as white solid (320 mg, 59%). ¹H NMR (DMSO-d6, 400 MHz): 1.43 (d, J=6.6 Hz, 6H), 4.63 (p, J=6.6 Hz, 1H), 7.65 (t, J=9.7 Hz, 1H), 7.84 (dt, J=7.1, 3.5 Hz, 1H), 7.97 (dd, J=5.8, 3.0 Hz, 1H). MS (ES+) m/z 370.0 [M+H].

Int-6

3-Bromo-1-(propan-2-yl)-5-[2-(trifluoromethoxy)phenoxy]-1H-1,2,4-triazole

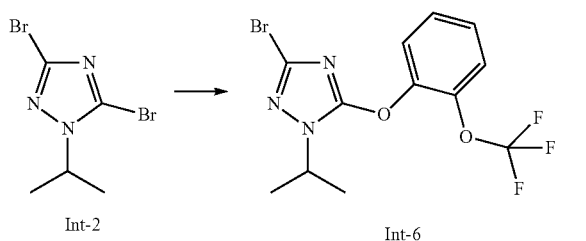

To a solution of 3,5-dibromo-1-(propan-2-yl)-1H-1,2,4-triazole (Int-2, 400 mg, 1.5 mmol) and 2-(trifluoromethoxy)phenol (264.9 mg, 1.5 mmol) in DMF (4 mL) was added K₂CO₃ (411 mg, 2.9 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (480 mg, 88%). ¹H NMR (DMSO-d6, 400 MHz): 1.43 (d, J=6.6 Hz, 6H), 4.63 (p, J=6.7 Hz, 1H), 7.47 (td, J=7.8, 1.5 Hz, 1H), 7.53 (td, J=7.9, 1.5 Hz, 1H), 7.60 (d, J=8.0 Hz, 1H), 7.68 (dd, J=8.1, 1.5 Hz, 1H). MS (ES+) m/z 368.0 [M+H].

Int-7

3-Bromo-5-(2-fluorophenoxy)-1-(propan-2-yl)-1H-1,2,4-triazole

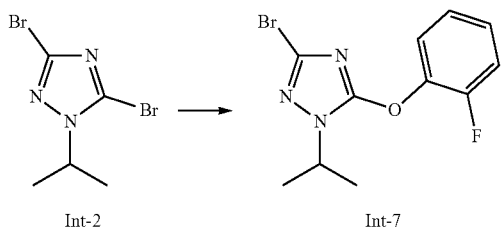

To a solution of 3,5-dibromo-1-(propan-2-yl)-1H-1,2,4-triazole (Int-2, 400 mg, 1.5 mmol) and 2-fluorophenol (0.1 mL, 1.5 mmol) in DMF (4 mL) was added K₂CO₃ (411 mg, 2.9 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (320 mg, 72%). ¹H NMR (DMSO-d6, 400 MHz): 1.43 (d, J=6.6 Hz, 6H), 4.66 (p, J=6.6 Hz, 1 H), 7.30 (t, J=7.8 Hz, 1H), 7.34-7.41 (m, 1H), 7.42-7.48 (m, 1H), 7.57 (td, J=8.1, 1.5 Hz, 1H). MS (ES+) m/z 302.2 [M+H].

Int-8

3-Bromo-1-(propan-2-yl)-5-[2-(trifluoromethoxy)phenoxy]-1H-1,2,4-triazole

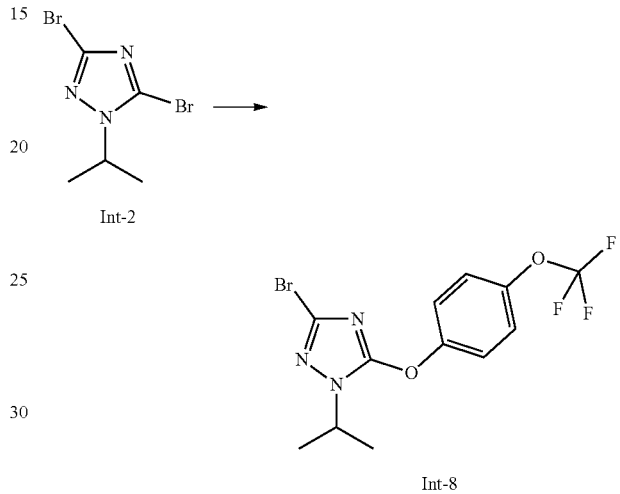

To a solution of 3,5-dibromo-1-(propan-2-yl)-1H-1,2,4-triazole (Int-2, 400 mg, 1.5 mmol) and 4-(trifluoromethoxy)phenol (0.2 mL, 1.5 mmol) in DMF (4 mL) was added K₂CO₃ (411 mg, 2.9 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (325 mg, 60%). ¹H NMR (DMSO-d6, 400 MHz): 1.42 (d, J=6.6 Hz, 6H), 4.63 (p, J=6.6 Hz, 1H), 7.50 (q, J=9.1 Hz, 4H). MS (ES+) m/z 365.8 [M+H].

Int-9

3-Bromo-5-(4-fluorophenoxy)-1-(propan-2-yl)-1H-1,2,4-triazole

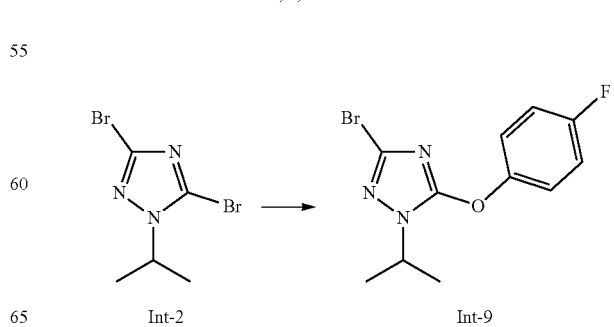

To a solution of 3,5-dibromo-1-(propan-2-yl)-1H-1,2,4-triazole (Int-2, 400 mg, 1.5 mmol) and 4-fluorophenol (166.7 mg, 1.5 mmol) in DMF (4 mL) was added K$_2$CO$_3$ (411 mg, 2.9 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (220 mg, 49%). $^1$H NMR (DMSO-d6, 400 MHz): 1.40 (d, J=6.7 Hz, 6H), 4.58-4.66 (m, 1H), 7.30 (t, J=8.7 Hz, 2H), 7.36-7.48 (m, 2H). MS (ES+) m/z 302.1 [M+H].

Int-10

3-Bromo-5-[3-fluoro-5-(trifluoromethyl)phenoxy]-1-(propan-2-yl)-1H-1,2,4-triazole Int-2

Int-10

To a solution of 3,5-dibromo-1-(propan-2-yl)-1H-1,2,4-triazole (Int-2, 500 mg, 1.9 mmol) and 3-fluoro-5-(trifluoromethyl)phenol (334.8 mg, 1.9 mmol) in DMF (4 mL) was added K$_2$CO$_3$ (513.8 mg, 3.7 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (400 mg, 58%). $^1$H NMR (DMSO-d6, 400 MHz): 1.42 (d, J=6.6 Hz, 6H), 4.64 (p, J=6.6 Hz, 1H), 7.71 (d, J=8.5 Hz, 1H), 7.80 (s, 1H), 7.83 (d, J=1.9 Hz, 1H). MS (ES+) m/z 368.0 [M+H].

Int-11

3-Bromo-1-(propan-2-yl)-5-[3-(trifluoromethyl)phenoxy]-1H-1,2,4-triazole

Int-2

Int-11

To a solution of 3,5-dibromo-1-(propan-2-yl)-1H-1,2,4-triazole (Int-2, 500 mg, 1.9 mmol) and 3-(trifluoromethyl)phenol (0.4 mL, 3.2 mmol) in DMF (4 mL) was added 1,8-diazabicyclo[5.4.0]undec-7-ene ("DBU", 0.6 mL, 3.7 mmol). The stirring was continued in microwave at 100° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 3:97 v/v) to afford the title compound as white solid (220 mg, 34%). $^1$H NMR (DMSO-d6, 400 MHz): 1.43 (d, J=6.6 Hz, 6H), 4.65 (hept, J=6.7, 6.0 Hz, 1H), 7.71-7.72 (m, 3H), 7.87 (s, 1H). MS (ES+) m/z 352.1 [M+H].

Int-13

3-Bromo-5-(2-fluorophenoxy)-1-(2,2,2-trifluoroethyl)-1H-1,2,4-triazole

Int-1

Int-12

-continued

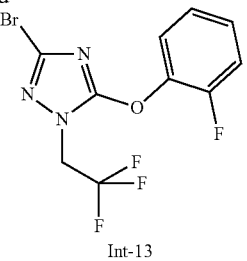

Int-13

-continued

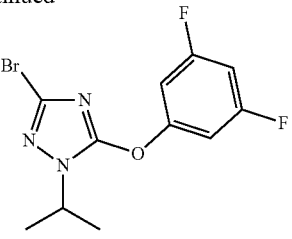

Int-14

Step 1: 3,5-Dibromo-1-(2,2,2-trifluoroethyl)-1H-1,2,4-triazole (Int-12)

In a 250 mL round bottomed flask, 3,5-dibromo-1H-1,2,4-triazole (Int-1, 2.00 g, 8.82 mmol) was dissolved in DMF (60 mL) and potassium carbonate (2.72 g, 19.5 mmol) was added. After stirring for 20 min at room temperature, 2,2,2-trifluoroethyl trifluoromethanesulfonate (2.32 g, 1.36 mL, 9.70 mmol) was added and the reaction mixture was stirred for 20 h at room temperature. After that, it was concentrated in vacuo, combined with ice-water (200 mL) and extracted with MTBE (3×200 mL). The combined organic layers were washed with water (2×200 mL) and brine (200 mL), dried (sodium sulfate) and concentrated in vacuo to yield the title compound as yellow liquid (2.71 g, 99%) which was used in the next step without further purification. $^1$H NMR (DMSO-d6, 300 MHz): 5.31 (q, J=8.8 Hz, 2H). MS (ES+) m/z 307.9, 309.9, 311.9 [M+H, 2 Br isotopes].

Step 2: 3-Bromo-5-(3-fluorophenoxy)-1-(propan-2-yl)-1H-1,2,4-triazole (Int-13)

In a 5 mL round bottomed flask, 3,5-dibromo-1-(2,2,2-trifluoroethyl)-1H-1,2,4-triazole (Int-12, 265 mg, 858 µmol) was dissolved in DMF (1 mL) and potassium carbonate (182 mg, 1.32 mmol), followed by 2-fluorophenol (75.5 mg, 660 µmol) were added. The reaction mixture was stirred for 20 h at 100° C. After cooling, it was concentrated in vacuo, the residue was dissolved in dichloromethane (10 mL) and saturated aqueous solution of sodium carbonate (10 mL). Phases were separated, the aqueous layer was extracted with dichloromethane (2×10 mL), the combined organic layers were dried (sodium sulfate) and concentrated in vacuo. The crude product was purified by column chromatography (silica gel, 70 g, eluting with ethyl acetate/n-heptane gradient 0:100 to 25:75 v/v) to afford the title compound as white solid (215 mg, 96%). HPLC (method LCMS_fastgradient) $t_R$=1.19 min. $^1$H NMR (CDCl$_3$, 300 MHz): δ 4.70 (q, J=8.0 Hz, 2H), 7.18-7.34 (m, 3H), 7.39-7.46 (m, 1H). MS (ES+) m/z 340.0, 342.0 [M+H, Br isotopes].

Int-14

3-Bromo-5-(3,5-difluorophenoxy)-1-(propan-2-yl)-1H-1,2,4-triazole

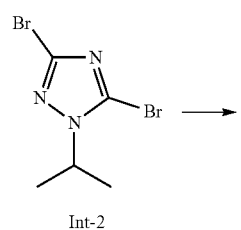

Int-2

To a solution of 3,5-dibromo-1-(propan-2-yl)-1H-1,2,4-triazole (Int-2, 500 mg, 1.9 mmol) and 3,5-difluorophenol (242 mg, 1.9 mmol) in DMF (4 mL) was added 1,8-diazabicyclo[5.4.0]undec-7-ene ("DBU", 0.6 mL, 3.7 mmol). The stirring was continued in microwave at 100° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 3:97 v/v) to afford the title compound as off-white solid (400 mg, 68%). $^1$H NMR (DMSO-d6, 400 MHz): 1.41 (d, J=6.6 Hz, 6H), 4.55-4.66 (m, 1H), 7.21-7.35 (m, 3H). MS (ES+) m/z 320.2 [M+H].

Int-15

3-Bromo-5-(4-methanesulfonylphenoxy)-1-(propan-2-yl)-1H-1,2,4-triazole

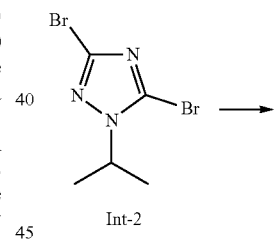

Int-2

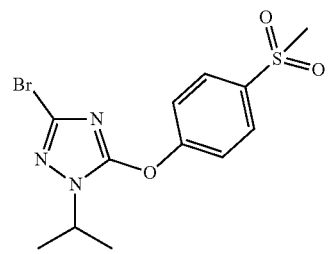

Int-15

To a solution of 3,5-dibromo-1-(propan-2-yl)-1H-1,2,4-triazole (Int-2, 500 mg, 1.9 mmol) and 4-methanesulfonylphenol (0.4 mL, 3.2 mmol) in DMF (4 mL) was added 1,8-diazabicyclo[5.4.0]undec-7-ene ("DBU", 0.5 mL, 3.7 mmol). The stirring was continued in microwave at 100° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as light brown solid (420 mg, 63%). ¹H NMR (DMSO-d6, 400 MHz): 1.42 (d, J=6.6 Hz, 6H), 3.26 (s, 3H), 4.59-4.71 (m, 1H), 7.65 (d, J=8.7 Hz, 2H), 8.03 (d, J=8.7 Hz, 2H). MS (ES+) m/z 362.1 [M+H].

Int-16

3-Bromo-5-(3-methanesulfonylphenoxy)-1-(propan-2-yl)-1H-1,2,4-triazole

To a solution of 3,5-dibromo-1-(propan-2-yl)-1H-1,2,4-triazole (Int-2, 500 mg, 1.9 mmol) and 3-methanesulfonylphenol (320 mg, 1.9 mmol) in DMF (4 mL) was added 1,8-diazabicyclo[5.4.0]undec-7-ene ("DBU", 0.5 mL, 3.7 mmol). The stirring was continued in microwave at 100° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (508 mg, 76%). ¹H NMR (DMSO-d6, 400 MHz): 1.43 (d, J=6.6 Hz, 6H), 3.29 (s, 3H), 4.65 (p, J=6.5 Hz, 1H), 7.76-7.77 (m, 2H), 7.86-7.88 (m, 1H), 7.99 (s, 1H).

Int-20

(1R,5S,8s)-tert-Butyl 8-amino-3-azabicyclo[3.2.1]octane-3-carboxylate

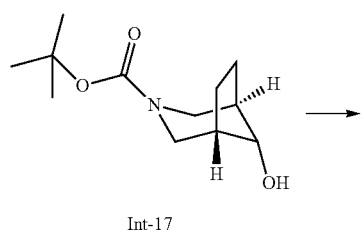

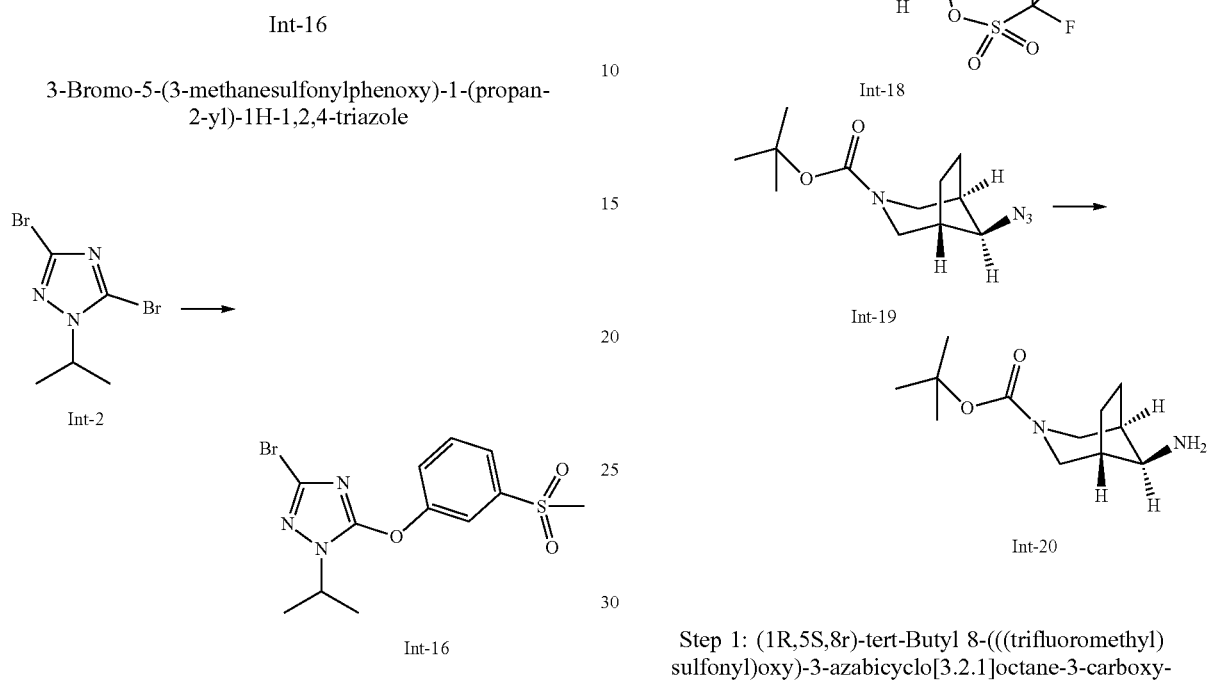

Step 1: (1R,5S,8r)-tert-Butyl 8-(((trifluoromethyl)sulfonyl)oxy)-3-azabicyclo[3.2.1]octane-3-carboxylate (Int-18)

In a dry, 250 mL round bottomed flask, (1R,5S,8r)-tert-butyl 8-hydroxy-3-azabicyclo[3.2.1]octane-3-carboxylate (Int-17, 2.283 g, 10.0 mmol) was dissolved in dichloromethane (70 mL) and pyridine (7.15 g, 7.27 mL, 90.4 mmol) was added. The solution was cooled to −78° C.−−74° C. (dry ice/acetone bath) and trifluoromethanesulfonic anhydride (6.36 g, 3.74 mL, 22.1 mmol) was added dropwise. The reaction mixture was stirred for 1 h at 0-5° C. (ice bath). Then, it was poured into a saturated aqueous solution of sodium hydrogen-carbonate (50 mL), stirred for 5 min at room temperature. The aqueous phase was extracted with dichloromethane (2×30 mL), the combined organic layers were dried (sodium sulfate) and concentrated in vacuo. The crude product was purified by column chromatography (silica gel, 100 g, eluting with ethyl acetate/n-heptane gradient 0:100 to 32:68 v/v) to yield the title compound as light yellow viscous oil (3.44 g, 95%). ¹H NMR (CDCl₃, 300 MHz): 1.48 (s, 9H), 1.64-1.83 (m, 4H), 2.29-2.44 (m, 2H), 3.16-3.37 (m, 2H), 3.66-3.91 (m, 2H), 5.04 (t, J=5.2 Hz, 1H). MS (ES+) m/z 304.0, 345.0.

Step 2: (1R,5S,8s)-tert-Butyl 8-azido-3-azabicyclo[3.2.1]octane-3-carboxylate (Int-19)

In a 100 mL round bottomed flask, (1R,5S,8r)-tert-butyl 8-(((trifluoromethyl)sulfonyl)oxy)-3-azabicyclo[3.2.1]octane-3-carboxylate (Int-18, 3.37 g, 9.38 mmol) was dissolved in dry N,N-dimethylformamide (20 mL) and sodium azide (1.23 g, 18.8 mmol) was added. The reaction mixture was stirred for 1 h at 80° C. Then, after cooling to room temperature, the mixture was poured into water (25 mL), extracted with ethyl acetate (3×50 mL), the combined organics were dried (sodium sulfate) and concentrated in vacuo. The crude product was purified by column chromatography (silica gel, 100 g, eluting with ethyl acetate/n-heptane gradient 0:100 to 10:90 v/v) to yield the title compound as white solid (1.417 g, 60%). $^1$H NMR (CDCl$_3$, 300 MHz): 1.48 (s, 9H), 1.51-1.64 (m, 2H), 1.76-1.89 (m, 2H), 2.16-2.33 (m, 2H), 2.76-2.97 (m, 2H), 3.69 (s, 1H), 3.79-4.07 (m, 2H). MS (ES+) m/z 197.1, 238.1.

Step 3: (1R,5S,8s)-tert-Butyl 8-amino-3-azabicyclo[3.2.1]octane-3-carboxylate (Int-20)

To a suspension of (1R,5S,8s)-tert-butyl 8-azido-3-azabicyclo[3.2.1]octane-3-carboxylate (Int-19, 1.425 g, 5.65 mmol) in methanol (25 mL) was added palladium on charcoal (10% w/w, 134 mg, 126 µmol). The mixture was stirred under a hydrogen atmosphere (balloon) at room temperature for 5 h. After that, the mixture was filtered through a plug of Celite, and washed thoroughly with methanol. The combined filtrate was concentrated in vacuo to afford the title compound as light yellow viscous oil (1.10 g, 86%). MS (ES+) m/z 227.2 [M+H].

Int-23

(1R,5S,8s)-8-({5-[4-Fluoro-3-(trifluoromethyl)phenoxy]-1-(propan-2-yl)-1H-1,2,4-triazol-3-yl}amino)-3-azabicyclo[3.2.1]octane-3-carbonitrile

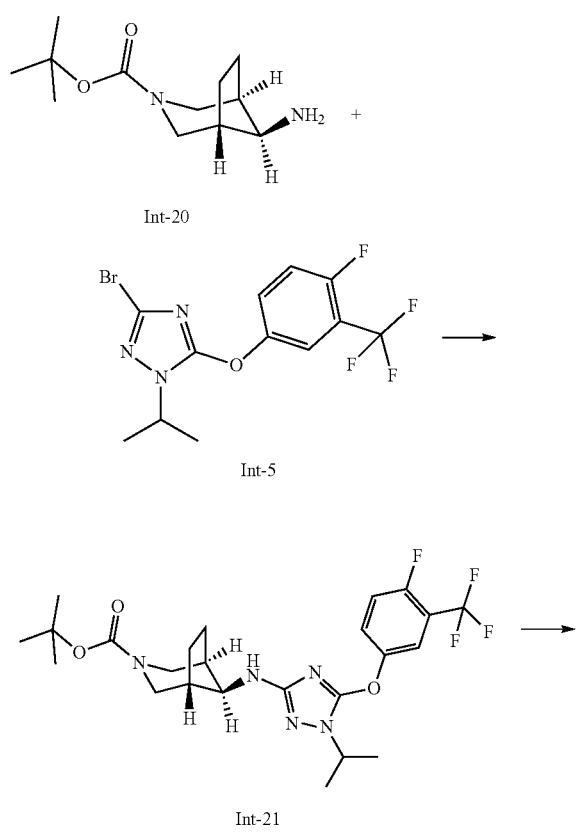

Int-20

Int-5

Int-21

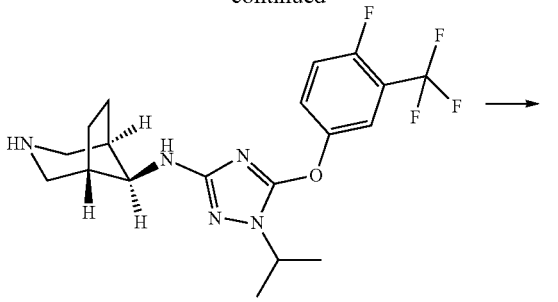

Int-22

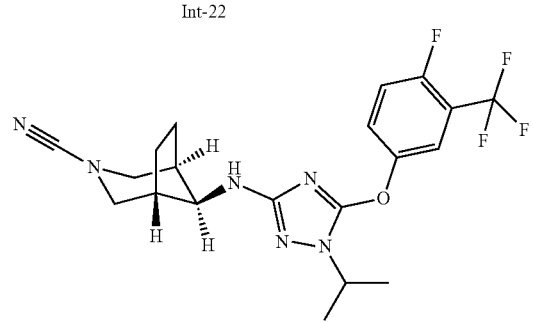

Int-23

Step 1: tert-Butyl (1R,5S,8s)-8-({5-[4-fluoro-3-(trifluoromethyl)phenoxy]-1-(propan-2-yl)-1H-1,2,4-triazol-3-yl}amino)-3-azabicyclo[3.2.1]octane-3-carboxylate (Int-21)

To a solution of (1R,5S,8s)-tert-butyl 8-amino-3-azabicyclo[3.2.1]octane-3-carboxylate (Int-20, 400 mg, 1.8 mmol) and 3-bromo-5-[4-fluoro-3-(trifluoromethyl)phenoxy]-1-(propan-2-yl)-1H-1,2,4-triazole (Int-5, 976 mg, 2.7 mmol) in dry 1,4-dioxane (3 mL) in sealed tube was added 2-dicyclohexylphosphino-2',6'-diisopropoxybiphenyl ("Ruphos", CAS [787618-22-8], 165 mg, 0.3 mmol). The reaction mixture was degassed with argon over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 282.3 mg, 0.3 mmol). The reaction mixture was again degassed with argon for 10 min followed by addition of sodium tertbutoxide (678.6 mg, 7.0 mmol). The reaction mixture was stirred at 130° C. for 4 h. Reaction mixture was then concentrated under reduced pressure to get crude which was purified by column chromatography (amino modified silica gel, eluting with EtOAc/n-hexane 40:60 v/v) to yield the title compound as white solid (450 mg, 50%). MS (ES+) m/z 514.1 [M+H].

Step 2: (1R,5S,8s)-N-{5-[4-Fluoro-3-(trifluoromethyl)phenoxy]-1-(propan-2-yl)-1H-1,2,4-triazol-3-yl}-3-azabicyclo[3.2.1]octan-8-amine (Int-22)

To a solution of tert-butyl (1R,5S,8s)-8-({5-[4-fluoro-3-(trifluoromethyl)phenoxy]-1-(propan-2-yl)-1H-1,2,4-triazol-3-yl}amino)-3-azabicyclo[3.2.1]octane-3-carboxylate (Int-21, 170 mg, 0.3 mmol) in dichloromethane (3 mL) was added trifluoroacetic acid (0.3 mL, 3.3 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the title compound as white solid (160 mg, crude). MS (ES+) m/z 414.0 [M+H].

Step 3: (1R,5S,8s)-8-({5-[4-Fluoro-3-(trifluoromethyl)phenoxy]-1-(propan-2-yl)-1H-1,2,4-triazol-3-yl}amino)-3-azabicyclo[3.2.1]octane-3-carbonitrile (Int-23)

To a solution of (1R,5S,8s)-N-{5-[4-fluoro-3-(trifluoromethyl)phenoxy]-1-(propan-2-yl)-1H-1,2,4-triazol-3-yl}-3-azabicyclo[3.2.1]octan-8-amine (Int-22, 150 mg, 0.4 mmol) in dichloromethane (2 mL) was added NaHCO₃ (91.4 mg, 1.1 mmol) dissolved in H₂O (1.5 mL) under ice cold condition. To it BrCN (48.2 mg, 0.5 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to afford the title compound as white solid (170 mg, crude). MS (ES+) m/z 439.3.

Int-26

(1R,5S,8s)-8-{[1-(Propan-2-yl)-5-[2-(trifluoromethoxy)phenoxy]-1H-1,2,4-triazol-3-yl]amino}-3-azabicyclo[3.2.1]octane-3-carbonitrile

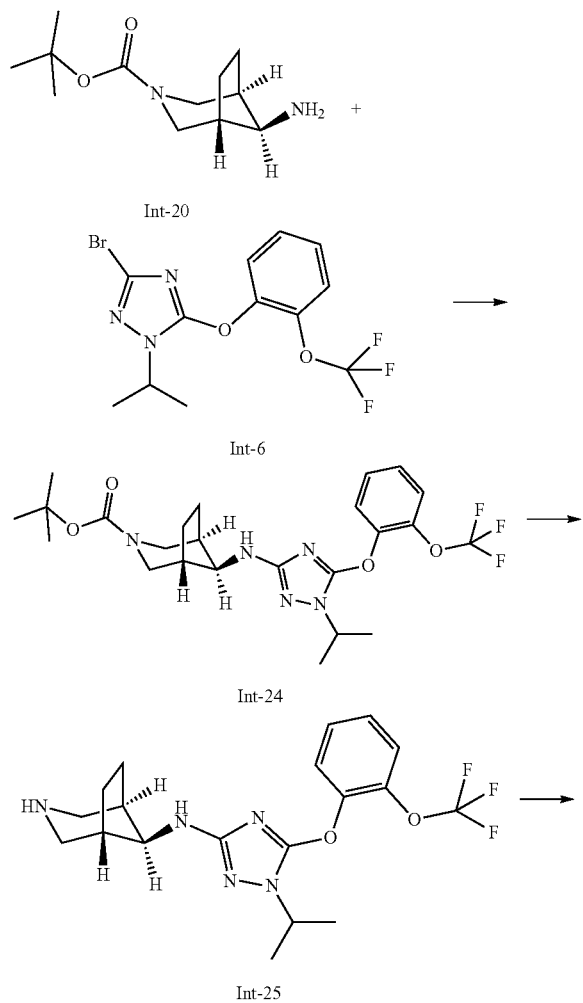

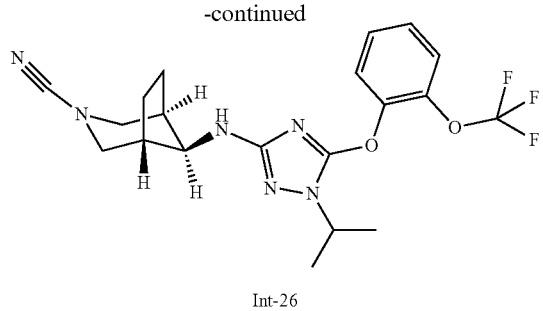

Int-26

Step 1: tert-Butyl (1R,5S,8s)-8-{[1-(propan-2-yl)-5-[2-(trifluoromethoxy)phenoxy]-1H-1,2,4-triazol-3-yl]amino}-3-azabicyclo[3.2.1]octane-3-carboxylate (Int-24)

To a solution of (1R,5S,8s)-tert-butyl 8-amino-3-azabicyclo[3.2.1]octane-3-carboxylate (Int-20, 200 mg, 0.9 mmol) and 3-bromo-1-(propan-2-yl)-5-[2-(trifluoromethoxy)phenoxy]-1H-1,2,4-triazole (Int-6, 485 mg, 1.3 mmol) in dry 1,4-dioxane (2 mL) in sealed tube was added 2-dicyclohexylphosphino-2',6'-diisopropoxybiphenyl ("Ruphos", CAS [787618-22-8], 82.5 mg, 0.2 mmol). The reaction mixture was degassed with argon over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 141.2 mg, 0.2 mmol). The reaction mixture was again degassed with argon for 10 min followed by addition of sodium tertbutoxide (339.3 mg, 3.5 mmol). The reaction mixture was stirred at 130° C. for 4 h. Reaction mixture was then concentrated under reduced pressure to get crude which was purified by column chromatography (amino modified silica gel, eluting with EtOAc/n-hexane 5:95 v/v) to yield the title compound as white solid (210 mg, 46%). MS (ES+) m/z 511.6 [M+H].

Step 2: (1R,5S,8s)-N-[1-(Propan-2-yl)-5-[2-(trifluoromethoxy)phenoxy]-1H-1,2,4-triazol-3-yl]-3-azabicyclo[3.2.1]octan-8-amine (Int-25)

To a solution of tert-butyl (1R,5S,8s)-8-{[1-(propan-2-yl)-5-[2-(trifluoromethoxy)phenoxy]-1H-1,2,4-triazol-3-yl]amino}-3-azabicyclo[3.2.1]octane-3-carboxylate (Int-24, 240 mg, 0.5 mmol) in dichloromethane (3 mL) was added trifluoroacetic acid (0.4 mL, 4.8 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the title compound as white solid (150 mg, crude). MS (ES+) m/z 412.2 [M+H].

Step 3: (1R,5S,8s)-8-{[1-(Propan-2-yl)-5-[2-(trifluoromethoxy)phenoxy]-1H-1,2,4-triazol-3-yl]amino}-3-azabicyclo[3.2.1]octane-3-carbonitrile (Int-26)

To a solution of (1R,5S,8s)-N-[1-(propan-2-yl)-5-[2-(trifluoromethoxy)phenoxy]-1H-1,2,4-triazol-3-yl]-3-azabicyclo[3.2.1]octan-8-amine (Int-25, 150 mg, 0.4 mmol) in dichloromethane (2.5 mL) was added a solution of NaHCO₃ (92 mg, 1.1 mmol) in H₂O (1.5 mL) under ice cold condition. To it BrCN (46 mg, 0.4 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to afford the title compound as white solid (170 mg, crude). MS (ES+) m/z 437.3 [M+H].

Int-27

3-Bromo-1-(propan-2-yl)-5-[3-(trifluoromethoxy)phenoxy]-1,2,4-triazole

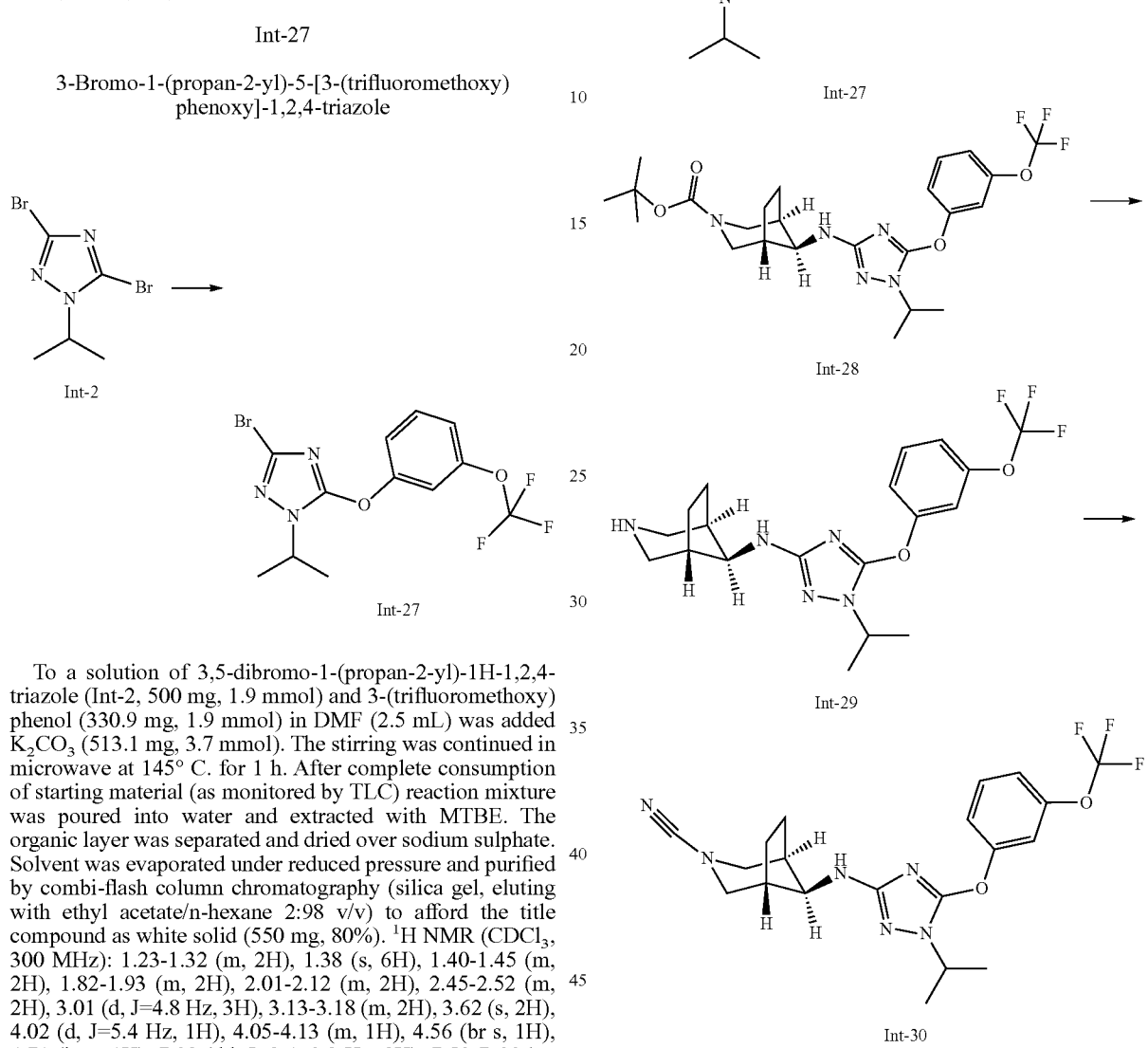

To a solution of 3,5-dibromo-1-(propan-2-yl)-1H-1,2,4-triazole (Int-2, 500 mg, 1.9 mmol) and 3-(trifluoromethoxy)phenol (330.9 mg, 1.9 mmol) in DMF (2.5 mL) was added $K_2CO_3$ (513.1 mg, 3.7 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (550 mg, 80%). $^1$H NMR (CDCl$_3$, 300 MHz): 1.23-1.32 (m, 2H), 1.38 (s, 6H), 1.40-1.45 (m, 2H), 1.82-1.93 (m, 2H), 2.01-2.12 (m, 2H), 2.45-2.52 (m, 2H), 3.01 (d, J=4.8 Hz, 3H), 3.13-3.18 (m, 2H), 3.62 (s, 2H), 4.02 (d, J=5.4 Hz, 1H), 4.05-4.13 (m, 1H), 4.56 (br s, 1H), 4.71 (br s, 1H), 7.02 (dd, J=8.4, 9.2 Hz, 2H), 7.59-7.66 (m, 2H). MS (ES+) m/z 397.3 [M+H].

Int-30

(1R,5S,8s)-8-{[1-(Propan-2-yl)-5-[3-(trifluoromethoxy)phenoxy]-1H-1,2,4-triazol-3-yl]amino}-3-azabicyclo[3.2.1]octane-3-carbonitrile Step 1: tert-Butyl (1R,5S,8s)-8-{[1-(propan-2-yl)-5-[3-(trifluoromethoxy)phenoxy]-1H-1,2,4-triazol-3-yl]amino}-3-azabicyclo[3.2.1]octane-3-carboxylate (Int-28)

To a solution of (1R,5S,8s)-tert-butyl 8-amino-3-azabicyclo[3.2.1]octane-3-carboxylate (Int-20, 200 mg, 0.9 mmol) and 3-bromo-1-(propan-2-yl)-5-[3-(trifluoromethoxy)phenoxy]-1H-1,2,4-triazole (Int-27, 485 mg, 1.3 mmol) in dry 1,4-dioxane (2 mL) in sealed tube was added 2-dicyclohexylphosphino-2',6'-diisopropoxybiphenyl ("Ruphos", CAS [787618-22-8], 82.5 mg, 0.2 mmol). The reaction mixture was degassed with argon over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 141.2 mg, 0.2 mmol). The reaction mixture was again degassed with argon for 10 min followed by addition of sodium tertbutoxide (339.3 mg, 3.5 mmol). The reaction mixture was stirred at 130° C. for 4 h. Reaction mixture was then concentrated under reduced pressure to get crude which was purified by column chromatography (amino modified silica gel, 12 g, eluting with EtOAc/n-hexane 5:95 v/v) to yield the title compound as white solid (270 mg, 60%). MS (ES+) m/z 512.3 [M+H].

Step 2: (1R,5S,8s)-N-[1-(Propan-2-yl)-5-[3-(trifluoromethoxy)phenoxy]-1H-1,2,4-triazol-3-yl]-3-azabicyclo[3.2.1]octan-8-amine (Int-29)

To a solution of tert-butyl (1R,5S,8s)-8-{[1-(propan-2-yl)-5-[3-(trifluoromethoxy)phenoxy]-1H-1,2,4-triazol-3-yl]amino}-3-azabicyclo[3.2.1]octane-3-carboxylate (Int-28, 240 mg, 0.5 mmol) in dichloromethane (3 mL) was added trifluoroacetic acid (0.4 mL, 4.8 mmol) at 0° C. After 5 min reaction mixture was allowed to warm to 25° C. and the stirring was continued at the same temperature for 2 h. The resulting mixture was concentrated under reduced pressure followed by azeotrope with toluene (3×5 mL) to afford the title compound as white solid (150 mg, crude). MS (ES+) m/z 411.8 [M+H].

Step 3: (1R,5S,8s)-8-{[1-(Propan-2-yl)-5-[3-(trifluoromethoxy)phenoxy]-1H-1,2,4-triazol-3-yl]amino}-3-azabicyclo[3.2.1]octane-3-carbonitrile (Int-30)

To a solution of (1R,5S,8s)-N-[1-(propan-2-yl)-5-[3-(trifluoromethoxy)phenoxy]-1H-1,2,4-triazol-3-yl]-3-azabicyclo[3.2.1]octan-8-amine (Int-29, 150 mg, 0.4 mmol) in dichloromethane (2.5 mL) was added NaHCO$_3$ (92 mg, 1.1 mmol) dissolved in H$_2$O (1.5 mL) under ice cold condition. To it BrCN (46 mg, 0.4 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to afford the title compound as white solid (170 mg, crude). MS (ES+) m/z 437.4 [M+H].

Int-33

(1R,5S,8s)-8-{[1-(Propan-2-yl)-5-[4-(trifluoromethoxy)phenoxy]-1H-1,2,4-triazol-3-yl]amino}-3-azabicyclo[3.2.1]octane-3-carbonitrile

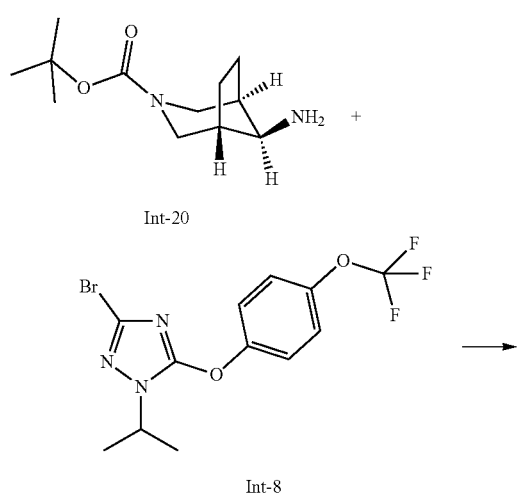

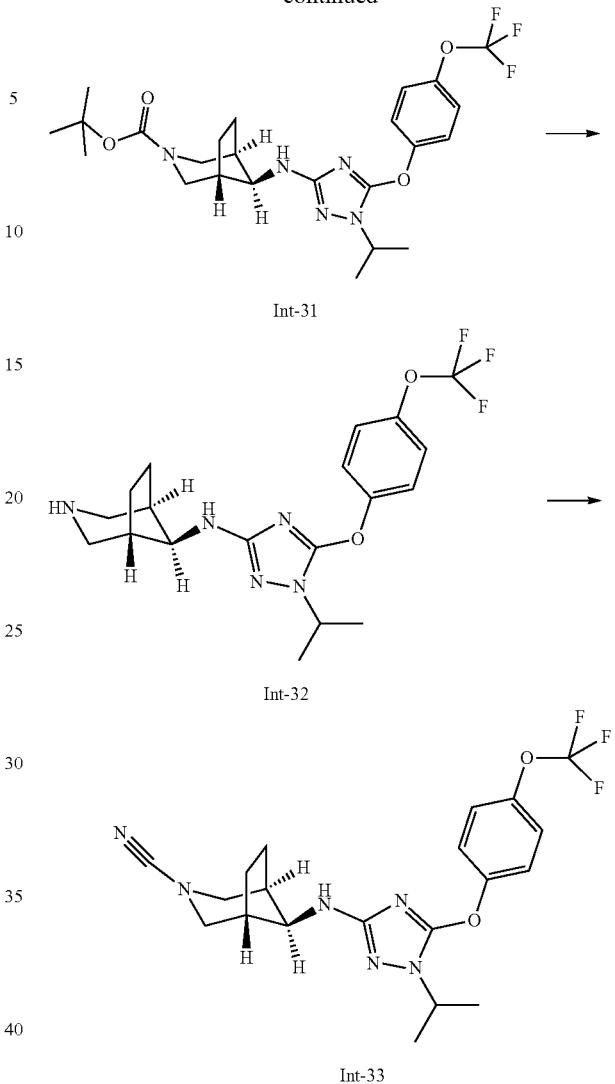

Step 1: tert-Butyl (1R,5S,8s)-8-{[1-(propan-2-yl)-5-[4-(trifluoromethoxy)phenoxy]-1H-1,2,4-triazol-3-yl]amino}-3-azabicyclo[3.2.1]octane-3-carboxylate (Int-31)

To a solution of (1R,5S,8s)-tert-butyl 8-amino-3-azabicyclo[3.2.1]octane-3-carboxylate (Int-20, 200 mg, 0.9 mmol) and 3-bromo-5-(4-(trifluoromethoxy)phenoxy)-1-(propan-2-yl)-1H-1,2,4-triazole (Int-8, 485 mg, 1.3 mmol) in dry 1,4-dioxane (2 mL) in sealed tube was added 2-dicyclohexylphosphino-2',6'-diisopropoxybiphenyl ("Ruphos", CAS [787618-22-8], 82.5 mg, 0.2 mmol). The reaction mixture was degassed with argon over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 141.2 mg, 0.2 mmol). The reaction mixture was again degassed with argon for 10 min followed by addition of sodium tertbutoxide (339.3 mg, 3.5 mmol). The reaction mixture was stirred at 130° C. for 4 h. Reaction mixture was then concentrated under reduced pressure to get crude which was purified by column chromatography (amino modified silica gel, 12 g, eluting with EtOAc/n-hexane 5:95 v/v) to yield the title compound as white solid (260 mg, 58%). MS (ES+) m/z 511.7 [M+H].

Step 2: (1R,5S,8s)-N-[1-(Propan-2-yl)-5-[4-(trifluoromethoxy)phenoxy]-1H-1,2,4-triazol-3-yl]-3-azabicyclo[3.2.1]octan-8-amine (Int-32)

To a solution of tert-butyl (1R,5S,8s)-8-{[1-(propan-2-yl)-5-[4-(trifluoromethoxy)phenoxy]-1H-1,2,4-triazol-3-yl]amino}-3-azabicyclo[3.2.1]octane-3-carboxylate (Int-31, 240 mg, 0.5 mmol) in dichloromethane (3 mL) was added trifluoroacetic acid (0.4 mL, 4.8 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the title compound as white solid (150 mg, crude). MS (ES+) m/z 411.6 [M+H].

Step 3: (1R,5S,8s)-8-{[1-(Propan-2-yl)-5-[4-(trifluoromethoxy)phenoxy]-1H-1,2,4-triazol-3-yl]amino}-3-azabicyclo[3.2.1]octane-3-carbonitrile (Int-33)

To a solution of (1R,5S,8s)-N-[1-(propan-2-yl)-5-[4-(trifluoromethoxy)phenoxy]-1H-1,2,4-triazol-3-yl]-3-azabicyclo[3.2.1]octan-8-amine (Int-32, 150 mg, 0.4 mmol) in dichloromethane (2.5 mL) was added NaHCO₃ (92 mg, 1.1 mmol) dissolved in H₂O (1.5 mL) under ice cold condition. To it BrCN (46 mg, 0.4 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to afford the title compound as white solid (170 mg, crude). MS (ES+) m/z 437.0 [M+H].

Int-36

(1R,5S,8s)-8-{[5-(3-Fluorophenoxy)-1-(propan-2-yl)-1H-1,2,4-triazol-3-yl]amino}-3-azabicyclo[3.2.1]octane-3-carbonitrile

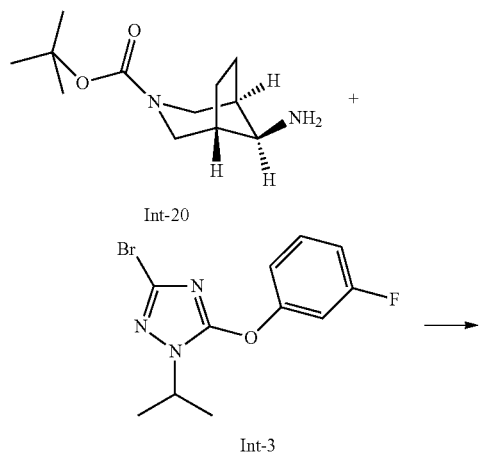

Int-20

Int-3

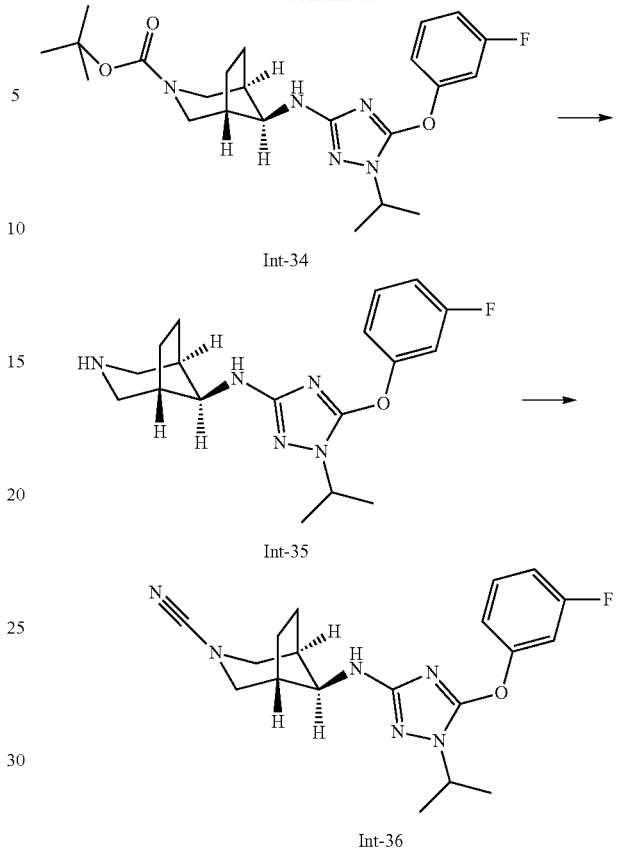

Int-34

Int-35

Int-36

Step 1: tert-Butyl (1R,5S,8s)-8-{[5-(3-fluorophenoxy)-1-(propan-2-yl)-1H-1,2,4-triazol-3-yl]amino}-3-azabicyclo[3.2.1]octane-3-carboxylate (Int-34)

To a solution of (1R,5S,8s)-tert-butyl 8-amino-3-azabicyclo[3.2.1]octane-3-carboxylate (Int-20, 200 mg, 0.9 mmol) and 3-bromo-5-(3-fluorophenoxy)-1-(propan-2-yl)-1H-1,2,4-triazole (Int-3, 397.6 mg, 1.3 mmol) in dry 1,4-dioxane (2 mL) in sealed tube was added 2-dicyclohexylphosphino-2',6'-diisopropoxybiphenyl ("Ruphos", CAS [787618-22-8], 82.5 mg, 0.2 mmol). The reaction mixture was degassed with argon over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 141.2 mg, 0.2 mmol). The reaction mixture was again degassed with argon for 10 min followed by addition of sodium tertbutoxide (339.3 mg, 3.5 mmol). The reaction mixture was stirred at 130° C. for 4 h. Reaction mixture was then concentrated under reduced pressure to get crude which was purified by column chromatography (amino modified silica gel, 12 g, eluting with EtOAc/n-hexane 5:95 v/v) to yield the title compound as white solid (133 mg, 34%). MS (ES+) m/z 446.3 [M+H].

Step 2: (1R,5S,8s)-N-[5-(3-Fluorophenoxy)-1-(propan-2-yl)-1H-1,2,4-triazol-3-yl]-3-azabicyclo[3.2.1]octan-8-amine (Int-35)

To a solution of tert-butyl (1R,5S,8s)-8-{[5-(3-fluorophenoxy)-1-(propan-2-yl)-1H-1,2,4-triazol-3-yl]amino}-3- azabicyclo[3.2.1]octane-3-carboxylate (Int-34, 130 mg, 0.3 mmol) in dichloromethane (2 mL) was added trifluoroacetic acid (0.2 mL, 3.0 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the title compound as white solid (90 mg, crude). MS (ES+) m/z 346.0 [M+H].

Step 3: (1R,5S,8s)-8-{[5-(3-Fluorophenoxy)-1-(propan-2-yl)-1H-1,2,4-triazol-3-yl]amino}-3-azabicyclo[3.2.1]octane-3-carbonitrile (Int-36)

To a solution of (1R,5S,8s)-N-[5-(3-Fluorophenoxy)-1-(propan-2-yl)-1H-1,2,4-triazol-3-yl]-3-azabicyclo[3.2.1]octan-8-amine (Int-35, 90 mg, 0.3 mmol) in dichloromethane (2.0 mL) was added NaHCO₃ (66 mg, 0.8 mmol) dissolved in H₂O (1.0 mL) under ice cold condition. To it BrCN (33 mg, 0.3 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to afford the title compound as white solid (85 mg, crude). MS (ES+) m/z 371.1 [M+H].

Int-39

(1R,5S,8s)-8-{[1-(Propan-2-yl)-5-[3-(trifluoromethyl)phenoxy]-1H-1,2,4-triazol-3-yl]amino}-3-azabicyclo[3.2.1]octane-3-carbonitrile

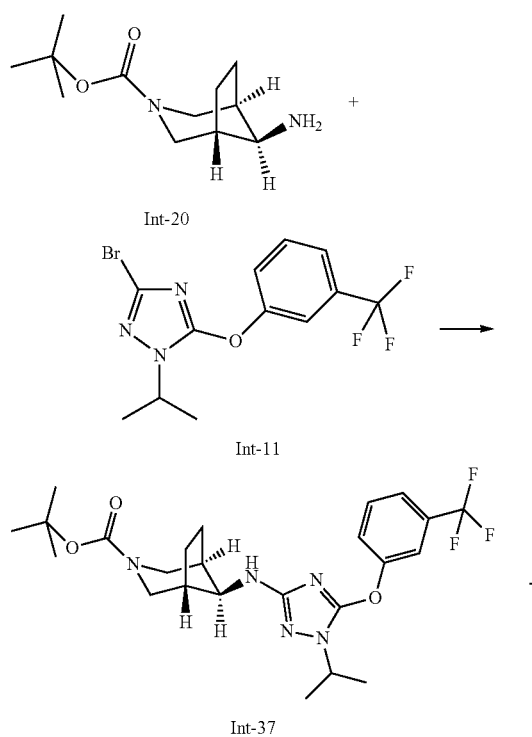

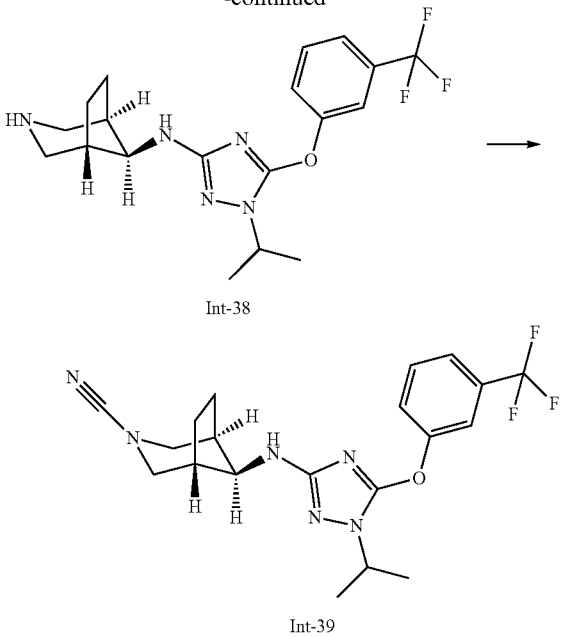

Step 1: tert-Butyl-(1R,5S,8s)-8-{[1-(propan-2-yl)-5-[3-(trifluoromethyl)phenoxy]-1H-1,2,4-triazol-3-yl]amino}-3-azabicyclo[3.2.1]octane-3-carboxylate (Int-37)

To a solution of (1R,5S,8s)-tert-butyl 8-amino-3-azabicyclo[3.2.1]octane-3-carboxylate (Int-20, 200 mg, 0.9 mmol) and 3-bromo-1-(propan-2-yl)-5-[3-(trifluoromethyl)phenoxy]-1H-1,2,4-triazole (Int-11, 463.9 mg, 1.3 mmol) in dry 1,4-dioxane (2 mL) in sealed tube was added 2-dicyclohexylphosphino-2',6'-diisopropoxybiphenyl ("Ruphos", CAS [787618-22-8], 82.5 mg, 0.2 mmol). The reaction mixture was degassed with argon over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 141.2 mg, 0.2 mmol). The reaction mixture was again degassed with argon for 10 min followed by addition of sodium tertbutoxide (339.3 mg, 3.5 mmol). The reaction mixture was stirred at 110° C. for 8 h. Reaction mixture was then concentrated under reduced pressure to get crude which was purified by column chromatography (amino modified silica gel, 12 g, eluting with EtOAc/n-hexane 5:95 v/v) to yield the title compound as off-white solid (370 mg, 85%). MS (ES+) m/z 496.1 [M+H].

Step 2: (1R,5S,8s)-N-[1-(Propan-2-yl)-5-[3-(trifluoromethyl)phenoxy]-1H-1,2,4-triazol-3-yl]-3-azabicyclo[3.2.1]octan-8-amine (Int-38)

To a solution of tert-butyl-(1R,5S,8s)-8-{[1-(propan-2-yl)-5-[3-(trifluoromethyl)phenoxy]-1H-1,2,4-triazol-3-yl]amino}-3-azabicyclo[3.2.1]octane-3-carboxylate (Int-37, 240 mg, 0.5 mmol) in dichloromethane (2 mL) was added trifluoroacetic acid (0.4 mL, 4.8 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the title compound as white solid (150 mg, crude). MS (ES+) m/z 395.9 [M+H].

Step 3: (1R,5S,8s)-8-{[1-(Propan-2-yl)-5-[3-(trifluoromethyl)phenoxy]-1H-1,2,4-triazol-3-yl]amino}-3-azabicyclo[3.2.1]octane-3-carbonitrile (Int-39)

To a solution of (1R,5S,8s)-N-[1-(propan-2-yl)-5-[3-(trifluoromethyl)phenoxy]-1H-1,2,4-triazol-3-yl]-3-azabicyclo[3.2.1]octan-8-amine (Int-38, 150 mg, 0.4 mmol) in dichloromethane (2.5 mL) was added NaHCO$_3$ (95.6 mg, 1.1 mmol) dissolved in H$_2$O (1.5 mL) under ice cold condition. To it BrCN (48.2 mg, 0.5 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to afford the title compound as white solid (150 mg, crude). MS (ES+) m/z 421.2 [M+H].

Int-40

3-Bromo-5-(3-fluorophenoxy)-1-(2,2,2-trifluoroethyl)-1H-1,2,4-triazole

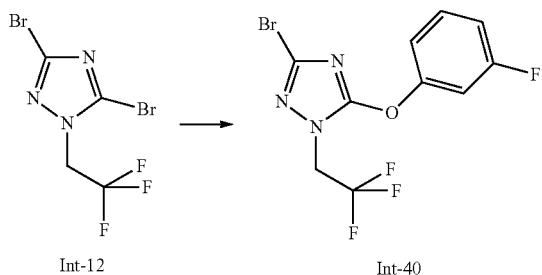 [SMILES: FC(F)(F)Cn1nc(Br)nc1Br ; Fc1cccc(Oc2nc(Br)nn2CC(F)(F)F)c1]

In a 10 mL round bottomed flask, 3,5-dibromo-1-(2,2,2-trifluoroethyl)-1H-1,2,4-triazole (Int-12, 700 mg, 2.27 mmol) was dissolved in DMF (3 mL) and potassium carbonate (626 mg, 4.53 mmol), followed by 3-fluorophenol (262 mg, 210 µL, 2.27 mmol) were added. The reaction mixture was stirred for 20 h at 100° C. After cooling, it was concentrated in vacuo, the residue was dissolved in dichloromethane (10 mL) and saturated aqueous solution of sodium carbonate (10 mL). Phases were separated, the aqueous layer was extracted with dichloromethane (2×10 mL), the combined organic layers were dried (sodium sulfate) and concentrated in vacuo. The crude product was purified by column chromatography (silica gel, 70 g, eluting with ethyl acetate/n-heptane, gradient 0:100 to 25:75 v/v) to afford the title compound as white solid (498 mg, 65%). HPLC (method LCMS_fastgradient) t$_R$=1.22 min. $^1$H NMR (DMSO-d6, 300 MHz): δ 5.21 (q, J=8.9 Hz, 2H), 7.18-7.29 (m, 2H), 7.39 (ddd, J=2.4, 2.4, 9.9 Hz, 1H), 7.54 (ddd, J=6.7, 8.3, 8.3 Hz, 1H). MS (ES+) m/z 340.0, 342.0 [M+H, Br isotopes].

Int-42

3-Bromo-5-(3-fluorophenoxy)-1-methyl-1H-1,2,4-triazole

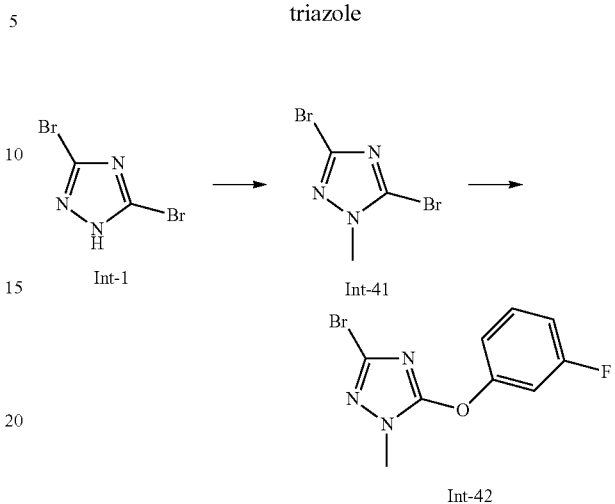

Step 1: 3,5-Dibromo-1-methyl-1H-1,2,4-triazole (Int-41)

In a 250 mL round bottomed flask, 3,5-dibromo-1H-1,2,4-triazole (Int-1, 8.00 g, 35.3 mmol) was dissolved in DMF (80 mL) and the solution was cooled to 0-5° C. (ice bath). Sodium hydride (60% dispersion in mineral oil, 1.69 g, 42.3 mmol) was added in portions and the resulting mixture was stirred for 45 min at 0-5° C. and for 15 min at room temperature. After that, iodomethane (10.0 g, 4.41 mL, 70.5 mmol) was added dropwise at 0-5° C. (ice bath). The resulting mixture was stirred for 18 h at room temperature. After that, it was concentrated in vacuo, the residue was diluted with ethyl acetate (200 mL) and water (200 mL), the aqueous phase was extracted with ethyl acetate (2×200 mL). The combined organic layers were dried (sodium sulfate) and concentrated in vacuo to yield the title compound as light yellow solid (8.15 g, 96%). $^1$H NMR (CDCl$_3$, 300 MHz): δ 3.89 (3H). MS (ES+) m/z 240.0, 242.0, 244.0 [M+H, 2 Br isotopes].

Step 2: 3-Bromo-5-(3-fluorophenoxy)-1-methyl-1H-1,2,4-triazole (Int-42)

In a 25 mL round bottomed flask, 3,5-dibromo-1-methyl-1H-1,2,4-triazole (Int-41, 442 mg, 1.84 mmol) was dissolved in DMF (4 mL) and potassium carbonate (483 mg, 3.5 mmol), followed by 3-fluorophenol (200 mg, 1.75 mmol) were added. The reaction mixture was stirred for 18 h at 100° C. After cooling, it was concentrated in vacuo, the residue was purified directly by column chromatography (silica gel, 70 g, eluting with ethyl acetate/n-heptane, gradient 0:100 to 20:80 v/v) to afford the title compound as white solid (397 mg, 83%). HPLC (method LCMS_fastgradient) t$_R$=1.05 min. $^1$H NMR (CDCl$_3$, 300 MHz): δ 3.78 (s, 3H), 6.94-7.02 (m, 1H), 7.06-7.14 (2H), 7.34-7.43 (m, 1H). MS (ES+) m/z 272.1, 274.1 [M+H, Br isotopes].

Int-43

3-Bromo-5-(4-fluoro-3-(trifluoromethyl)phenoxy)-1-methyl-1H-1,2,4-triazole

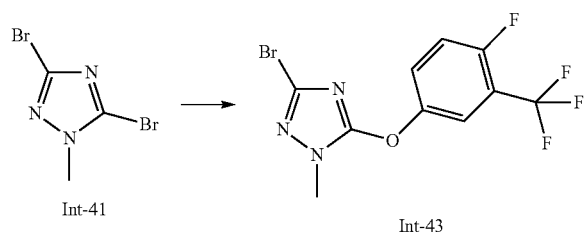

Int-41 → Int-43

In a 25 mL round bottomed flask, 3,5-dibromo-1-methyl-1H-1,2,4-triazole (Int-41, 536 mg, 2.23 mmol) was dissolved in DMF (4 mL) and potassium carbonate (615 mg, 4.45 mmol), followed by 4-fluoro-3-(trifluoromethyl)phenol (401 mg, 350 µL, 2.23 mmol) were added. The reaction mixture was stirred for 18 h at 100° C. After cooling, it was concentrated in vacuo, the residue was dissolved in dichloromethane (15 mL) and saturated aqueous solution of sodium carbonate (15 mL). Phases were separated, the aqueous layer was extracted with dichloromethane (2×15 mL), the combined organic layers were dried (sodium sulfate) and concentrated in vacuo. The crude product was purified by column chromatography (silica gel, 20 g, eluting with ethyl acetate/n-heptane, gradient 0:100 to 50:50 v/v) to afford the title compound as white solid (737 mg, 97%). HPLC (method LCMS_fastgradient) $t_R$=1.28 min. $^1$H NMR (CDCl$_3$, 300 MHz): δ 3.80 (s, 3H), 7.23-7.31 (m, 1H), 7.53-7.61 (m, 2H). MS (ES+) m/z 340.0, 342.0 [M+H, Br isotopes].

Int-44

3-Bromo-5-(4-fluoro-3-(trifluoromethyl)phenoxy)-1-(2,2,2-trifluoroethyl)-1H-1,2,4-triazole

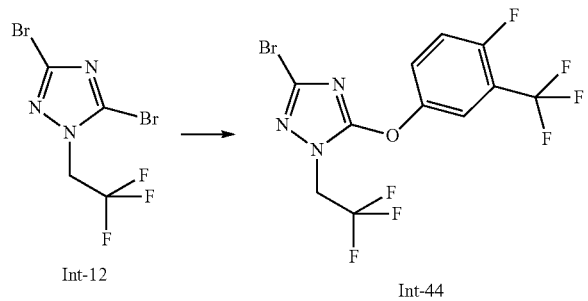 [SMILES: FC(F)(F)Cn1nc(Br)nc1Br ; Fc1ccc(Oc2nc(Br)nn2CC(F)(F)F)cc1C(F)(F)F]

Int-12 → Int-44

In a 50 mL round bottomed flask, 3,5-dibromo-1-(2,2,2-trifluoroethyl)-1H-1,2,4-triazole (Int-12, 2.42 g, 7.84 mmol) was dissolved in DMF (14 mL) and potassium carbonate (1.67 g, 12.1 mmol), followed by 4-fluoro-3-(trifluoromethyl)phenol (1.12 g, 978 µL, 6.03 mmol) were added. The reaction mixture was stirred for 20 h at 100° C. After cooling, it was concentrated in vacuo, the residue was dissolved in dichloromethane (30 mL) and saturated aqueous solution of sodium carbonate (30 mL). Phases were separated, the aqueous layer was extracted with dichloromethane (2×30 mL), the combined organic layers were dried (sodium sulfate) and concentrated in vacuo. The crude product was purified by column chromatography (silica gel, 70 g, eluting with ethyl acetate/n-heptane, gradient 0:100 to 20:80 v/v) to afford the title compound as white solid (2.46 g, quant.). HPLC (method LCMS_fastgradient) $t_R$=1.34 min. $^1$H NMR (CDCl$_3$, 300 MHz): δ 4.68 (q, J=8.0 Hz, 2H), 7.26-7.34 (m, 1H), 7.54-7.61 (m, 2H). MS (ES+) m/z 408.0, 410.0 [M+H, Br isotopes].

Int-45

3-Bromo-5-(3-chlorophenoxy)-1-(2,2,2-trifluoroethyl)-1H-1,2,4-triazole

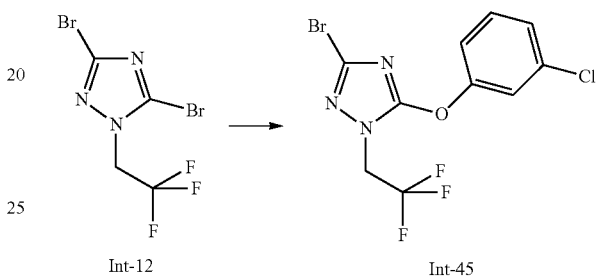

Int-12 → Int-45

In a 25 mL round bottomed flask, 3,5-dibromo-1-(2,2,2-trifluoroethyl)-1H-1,2,4-triazole (Int-12, 1.19 g, 3.84 mmol) was dissolved in DMF (6 mL) and potassium carbonate (817 mg, 5.91 mmol), followed by 3-chlorophenol (384 mg, 308 µL, 2.96 mmol) were added. The reaction mixture was stirred for 20 h at 100° C. After cooling, it was concentrated in vacuo, the residue was purified directly by column chromatography (amino modified silica gel, 50 g, eluting with ethyl acetate/n-heptane, gradient 0:100 to 1:6 v/v) to afford the title compound as light yellow solid (1.02 g, 97%). HPLC (method LCMS_fastgradient) $t_R$=1.35 min. $^1$H NMR (DMSO-d6, 300 MHz): δ 5.20 (q, J=9.0 Hz, 2H), 7.37-7.46 (m, 2H), 7.53 (t, J=8.1 Hz, 1H), 7.59 (t, J=2.0 Hz, 1H). MS (ES+) m/z 356.0, 357.9, 360.0 [M+H, Br, Cl isotopes].

Int-46

3-Bromo-5-(4-(trifluoro methyl)phenoxy)-1-(2,2,2-trifluoroethyl)-1H-1,2,4-triazole

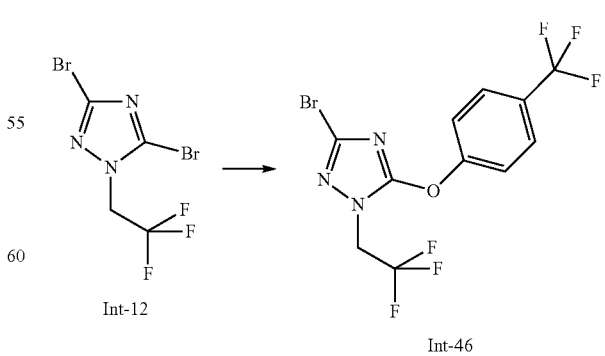

Int-12 → Int-46

In a 10 mL round bottomed flask, 3,5-dibromo-1-(2,2,2-trifluoroethyl)-1H-1,2,4-triazole (Int-12, 421 mg, 1.36 mmol) was dissolved in DMF (1.9 mL) and potassium carbonate (290 mg, 2.1 mmol), followed by 4-(trifluoromethyl)phenol (170 mg, 1.05 mmol) were added. The reaction mixture was stirred for 15 h at 100° C. After cooling, it was concentrated in vacuo, the residue was dissolved in dichloromethane (15 mL) and saturated aqueous solution of sodium carbonate (15 mL). Phases were separated, the aqueous layer was extracted with dichloromethane (3×15 mL), the combined organic layers were dried (sodium sulfate) and concentrated in vacuo. The crude product was purified by column chromatography (silica gel, 20 g, eluting with ethyl acetate/n-heptane, gradient 0:100 to 33:67 v/v) to yield the title compound as white solid (310 mg, 76%). HPLC (method LCMS_fastgradient) $t_R$=1.33 min. $^1$H NMR (CDCl$_3$, 300 MHz): δ 4.70 (q, J=8.0 Hz, 2H), 7.53 (d, J=8.5 Hz, 2H), 7.73 (d, J=8.5 Hz, 2H). MS (ES+) m/z 390.1, 392.1 [M+H, Br isotopes].

Int-47

3-Bromo-1-(2,2,2-trifluoroethyl)-5-(3-(trifluoromethoxy)phenoxy)-1H-1,2,4-triazole

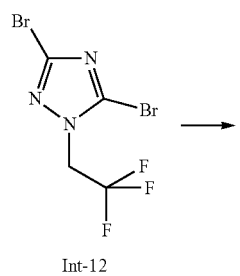

Int-12

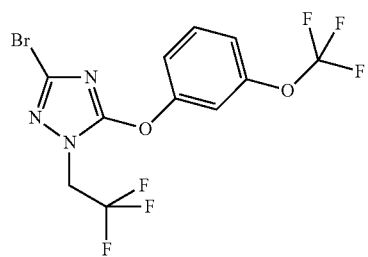

Int-47

In a 5 mL round bottomed flask, 3,5-dibromo-1-(2,2,2-trifluoroethyl)-1H-1,2,4-triazole (Int-12, 225 mg, 730 µmol) was dissolved in DMF (1 mL) and potassium carbonate (155 mg, 1.12 mmol), followed by 3-(trifluoromethoxy)phenol (100 mg, 72.5 µL, 561 µmol) were added. The reaction mixture was stirred for 18 h at 100° C. After cooling, it was concentrated in vacuo, the residue was dissolved in dichloromethane (10 mL) and saturated aqueous solution of sodium carbonate (10 mL). Phases were separated, the aqueous layer was extracted with dichloromethane (2×10 mL), the combined organic layers were dried (sodium sulfate) and concentrated in vacuo. The crude product was purified by column chromatography (silica gel, 20 g, eluting with ethyl acetate/n-heptane, gradient 0:100 to 33:67 v/v) to afford the title compound as colorless, viscous oil (138 mg, 60%). HPLC (method LCMS_fastgradient) $t_R$=1.36 min. $^1$H NMR (CDCl$_3$, 300 MHz): δ 4.68 (q, J=8.0 Hz, 2H), 7.15-7.21 (m, 1H), 7.22-7.25 (m, 1H), 7.30-7.34 (m, 1H), 7.48 (t, J=8.3 Hz, 1H). MS (ES+) m/z 406.1, 408.1 [M+H, Br isotopes].

Int-48

3-Bromo-1-(2,2,2-trifluoroethyl)-5-(3-(trifluoromethyl)phenoxy)-1H-1,2,4-triazole

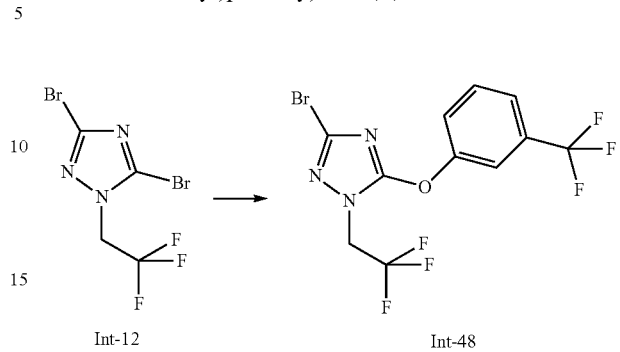

In a 10 mL round bottomed flask, 3,5-dibromo-1-(2,2,2-trifluoroethyl)-1H-1,2,4-triazole (Int-12, 421 mg, 1.36 mmol) was dissolved in DMF (1.9 mL) and potassium carbonate (290 mg, 2.1 mmol), followed by 3-(trifluoromethyl)phenol (170 mg, 1.05 mmol) were added. The reaction mixture was stirred for 16 h at 100° C. After cooling, it was concentrated in vacuo, the residue was dissolved in dichloromethane (15 mL) and saturated aqueous solution of sodium carbonate (15 mL). Phases were separated, the aqueous layer was extracted with dichloromethane (3×15 mL), the combined organic layers were dried (sodium sulfate) and concentrated in vacuo. The crude product was purified by column chromatography (silica gel, 20 g, eluting with ethyl acetate/n-heptane, gradient 0:100 to 33:67 v/v) to yield the title compound as white solid (350 mg, 86%). HPLC (method LCMS_fastgradient) $t_R$=1.38 min. $^1$H NMR (CDCl$_3$, 300 MHz): δ 4.69 (q, J=8.0 Hz, 2H), 7.57-7.60 (m, 4H). MS (ES+) m/z 390.1, 392.1 [M+H, Br isotopes].

Int-49

3-Bromo-5-[2-fluoro-3-(trifluoromethyl)phenoxy]-1-(propan-2-yl)-1,2,4-triazole

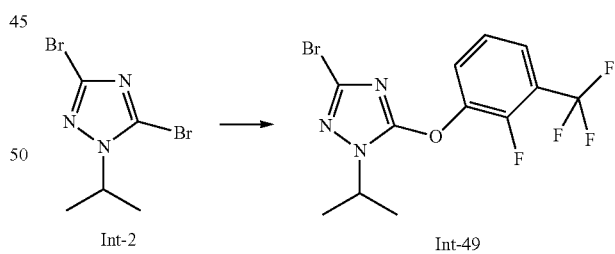

To a solution of 3,5-dibromo-1-(propan-2-yl)-1H-1,2,4-triazole (Int-2, 500 mg, 1.9 mmol) and 2-fluoro-3-(trifluoromethyl)phenol (334.8 mg, 1.9 mmol) in DMF (5.0 mL) was added K$_2$CO$_3$ (513.8 mg, 3.7 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as colorless liquid (375 mg, 55%). ¹H NMR (DMSO-d6, 400 MHz): 1.44 (d, J=6.6 Hz, 6H), 4.68 (p, J=6.4 Hz, 1H), 7.54 (t, J=8.0 Hz, 1H), 7.78 (t, J=6.8 Hz, 1H), 8.00 (t, J=7.7 Hz, 1H). MS (ES+) m/z 367.8 [M+H].

Int-52

(1R,5S,8s)-8-({5-[2-Fluoro-3-(trifluoromethyl)phenoxy]-1-(propan-2-yl)-1H-1,2,4-triazol-3-yl}amino)-3-azabicyclo[3.2.1]octane-3-carbonitrile

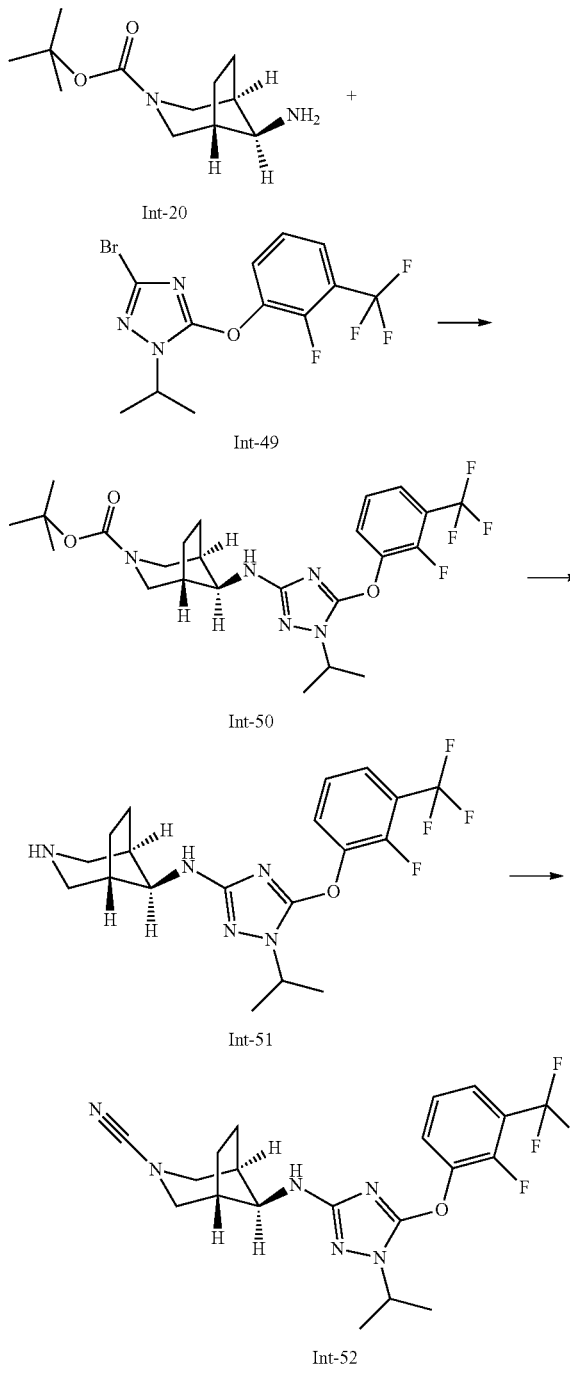

Step 1: tert-Butyl (1R,5S,8s)-8-({5-[2-fluoro-3-(trifluoromethyl)phenoxy]-1-(propan-2-yl)-1H-1,2,4-triazol-3-yl}amino)-3-azabicyclo[3.2.1]octane-3-carboxylate (Int-50)

To a solution of tert-butyl (1R,5S,8s)-8-amino-3-azabicyclo[3.2.1]octane-3-carboxylate (Int-20, 200 mg, 0.9 mmol) and 3-bromo-5-[2-fluoro-3-(trifluoromethyl)phenoxy]-1-(propan-2-yl)-1H-1,2,4-triazole (Int-49, 487.9 mg, 1.3 mmol) in dry 1,4-dioxane (3 mL) in sealed tube was added 2-dicyclohexylphosphino-2',6'-diisopropoxybiphenyl ("Ruphos", CAS [787618-22-8], 82.5 mg, 0.2 mmol). The reaction mixture was degassed with argon over a period of 15 min. To it then added chloro[2-(dicyclohexylphosphino)-3,6-dimethoxy-2',4',6'-triisopropyl-1,1'-biphenyl] [2-(2-aminoethyl)phenyl]palladium(II) ("Brettphos palladacycle", CAS [1148148-01-9], 141.2 mg, 0.2 mmol). The reaction mixture was again degassed with argon for 10 min followed by addition of sodium tertbutoxide (339.3 mg, 3.5 mmol). The reaction mixture was stirred at 130° C. for 4 h. Reaction mixture was then concentrated under reduced pressure to get crude which was purified by column chromatography (amino modified silica gel, 12 g, eluting with EtOAc/n-hexane 5:95 v/v) to yield the title compound as white solid (450 mg, 99%). MS (ES+) m/z 514.0 [M+H].

Step 2: (1R,5S,8s)-N-{5-[2-Fluoro-3-(trifluoromethyl)phenoxy]-1-(propan-2-yl)-1H-1,2,4-triazol-3-yl}-3-azabicyclo[3.2.1]octan-8-amine (Int-51)

To a solution of tert-butyl (1R,5S,8s)-8-({5-[2-fluoro-3-(trifluoromethyl)phenoxy]-1-(propan-2-yl)-1H-1,2,4-triazol-3-yl}amino)-3-azabicyclo[3.2.1]octane-3-carboxylate (Int-50, 450 mg, 0.9 mmol) in dichloromethane (6 mL) was added trifluoroacetic acid (0.7 mL, 8.7 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the title compound as white solid (360 mg, crude). MS (ES+) m/z 413.9 [M+H].

Step 3: (1R,5S,8s)-8-({5-[2-Fluoro-3-(trifluoromethyl)phenoxy]-1-(propan-2-yl)-1H-1,2,4-triazol-3-yl}amino)-3-azabicyclo[3.2.1]octane-3-carbonitrile (Int-52)

To a solution of (1R,5S,8s)-N-{5-[2-fluoro-3-(trifluoromethyl)phenoxy]-1-(propan-2-yl)-1H-1,2,4-triazol-3-yl}-3-azabicyclo[3.2.1]octan-8-amine (Int-51, 360 mg, 0.9 mmol) in dichloromethane (4.5 mL) was added NaHCO₃ (219.5 mg, 2.6 mmol) dissolved in H₂O (2.5 mL) under ice cold condition. To it BrCN (110.6 mg, 1.0 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to afford the title compound as white solid (380 mg, crude). MS (ES+) m/z 439.4 [M+H].

Int-53

3-Bromo-5-[2-fluoro-5-(trifluoromethyl)phenoxy]-1-(propan-2-yl)-1H-1,2,4-triazole

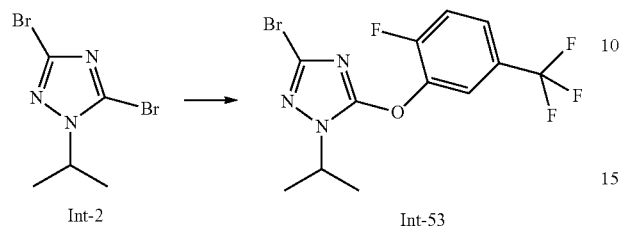

To a solution of 3,5-dibromo-1-(propan-2-yl)-1H-1,2,4-triazole (Int-2, 1.0 g, 3.7 mmol) and 2-fluoro-5-(trifluoromethyl)phenol (670 mg, 3.7 mmol) in DMF (10 mL) was added 1,8-diazabicyclo[5.4.0]undec-7-ene ("DBU", 1.1 mL, 7.4 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (450 mg, 33%). $^1$H NMR (DMSO-d6, 400 MHz): 1.44 (d, J=6.6 Hz, 6H), 4.67 (p, J=6.6 Hz, 1H), 7.73 (t, J=9.5 Hz, 1H), 7.78-7.87 (m, 1H), 8.19 (d, J=5.5 Hz, 1H). MS (ES+) m/z 370.0 [M+H].

Int-56

(1R,5S,8s)-8-({5-[2-Fluoro-5-(trifluoromethyl)phenoxy]-1-(propan-2-yl)-1H-1,2,4-triazol-3-yl}amino)-3-azabicyclo[3.2.1]octane-3-carbonitrile

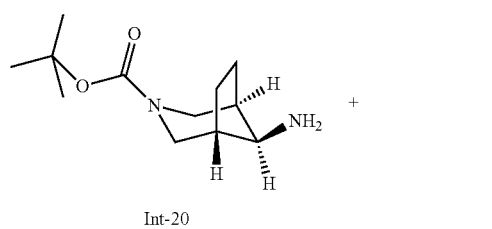

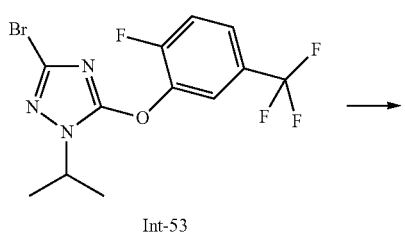

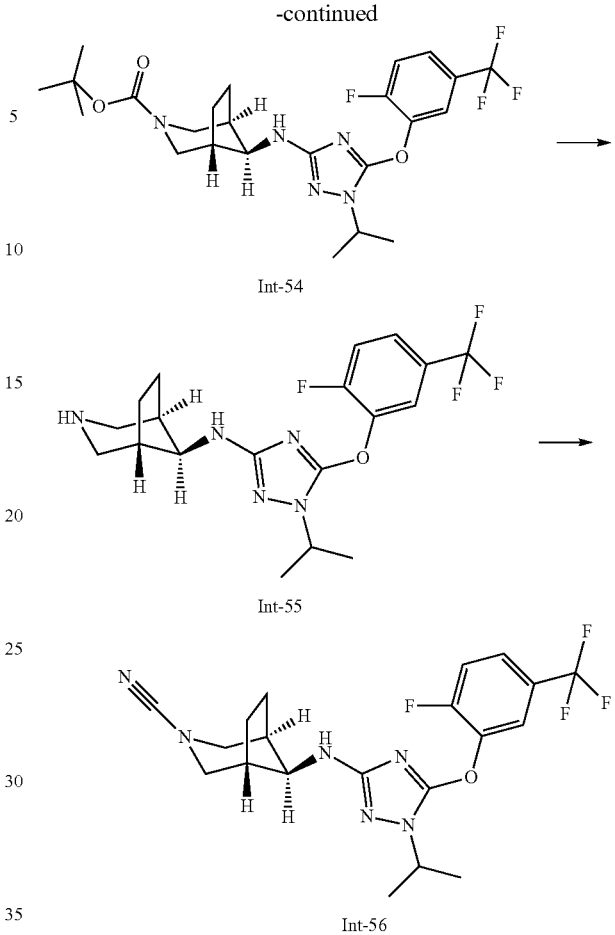

Step 1: tert-Butyl (1R,5S,8s)-8-({5-[2-fluoro-5-(trifluoromethyl)phenoxy]-1-(propan-2-yl)-1H-1,2,4-triazol-3-yl}amino)-3-azabicyclo[3.2.1]octane-3-carboxylate (Int-54)

To a solution of tert-butyl (1R,5S,8s)-8-amino-3-azabicyclo[3.2.1]octane-3-carboxylate (Int-20, 200 mg, 0.9 mmol) and 3-bromo-5-[2-fluoro-5-(trifluoromethyl)phenoxy]-1-(propan-2-yl)-1H-1,2,4-triazole (Int-53, 487.9 mg, 1.3 mmol) in dry 1,4-dioxane (3 mL) in sealed tube was added 2-dicyclohexylphosphino-2',6'-diisopropoxybiphenyl ("Ruphos", CAS [787618-22-8], 82.5 mg, 0.2 mmol). The reaction mixture was degassed with argon over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 141.2 mg, 0.2 mmol). The reaction mixture was again degassed with argon for 10 min followed by addition of sodium tertbutoxide (339.3 mg, 3.5 mmol). The reaction mixture was stirred at 130° C. for 4 h. Reaction mixture was then concentrated under reduced pressure to get crude which was purified by column chromatography (amino modified silica gel, eluting with EtOAc/n-hexane 5:95 v/v) to yield the title compound as sticky yellow liquid (250 mg, 55%). MS (ES+) m/z 513.8 [M+H].

Step 2: (1R,5S,8s)-N-{5-[2-Fluoro-5-(trifluoromethyl)phenoxy]-1-(propan-2-yl)-1H-1,2,4-triazol-3-yl}-3-azabicyclo[3.2.1]octan-8-amine (Int-55)

To a solution of tert-butyl (1R,5S,8s)-8-({5-[2-fluoro-5-(trifluoromethyl)phenoxy]-1-(propan-2-yl)-1H-1,2,4-triazol-3-yl}amino)-3-azabicyclo[3.2.1]octane-3-carboxylate (Int-54, 250 mg, 0.5 mmol) in dichloromethane (6 mL) was added trifluoroacetic acid (0.4 mL, 5.0 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the title compound as sticky solid (200 mg, crude). MS (ES+) m/z 414.0 [M+H].

Step 3: (1R,5S,8s)-8-({5-[2-Fluoro-5-(trifluoromethyl)phenoxy]-1-(propan-2-yl)-1H-1,2,4-triazol-3-yl}amino)-3-azabicyclo[3.2.1]octane-3-carbonitrile (Int-56)

To a solution of (1R,5S,8s)-N-{5-[2-fluoro-5-(trifluoromethyl)phenoxy]-1-(propan-2-yl)-1H-1,2,4-triazol-3-yl}-3-azabicyclo[3.2.1]octan-8-amine (Int-55, 200 mg, 0.5 mmol) in dichloromethane (3.0 mL) was added NaHCO₃ (122 mg, 1.5 mmol) dissolved in H₂O (1.5 mL) under ice cold condition. To it BrCN (61.5 mg, 0.5 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to afford the title compound as white solid (210 mg, crude). MS (ES+) m/z 439.3 [M+H].

Int-57

3-Bromo-5-[3-fluoro-4-(trifluoromethoxy)phenoxy]-1-(propan-2-yl)-1,2,4-triazole

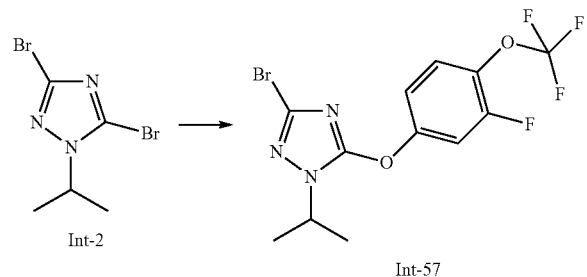

To a solution of 3,5-dibromo-1-(propan-2-yl)-1H-1,2,4-triazole (Int-2, 500 mg, 1.9 mmol) and 3-fluoro-4-(trifluoromethoxy)phenol (364.6 mg, 1.9 mmol) in DMF (5.0 mL) was added K₂CO₃ (513.8 mg, 3.7 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (500 mg, 70%). ¹H NMR (DMSO-d6, 400 MHz): 1.42 (d, J=6.6 Hz, 6H), 4.62 (hept, J=6.4 Hz, 1H), 7.36-7.43 (m, 1H), 7.66-7.80 (m, 2H). MS (ES+) m/z 384.0 [M+H].

Int-60

(1R,5S,8s)-8-({5-[3-Fluoro-4-(trifluoromethoxy)phenoxy]-1-(propan-2-yl)-1H-1,2,4-triazol-3-yl}amino)-3-azabicyclo[3.2.1]octane-3-carbonitrile

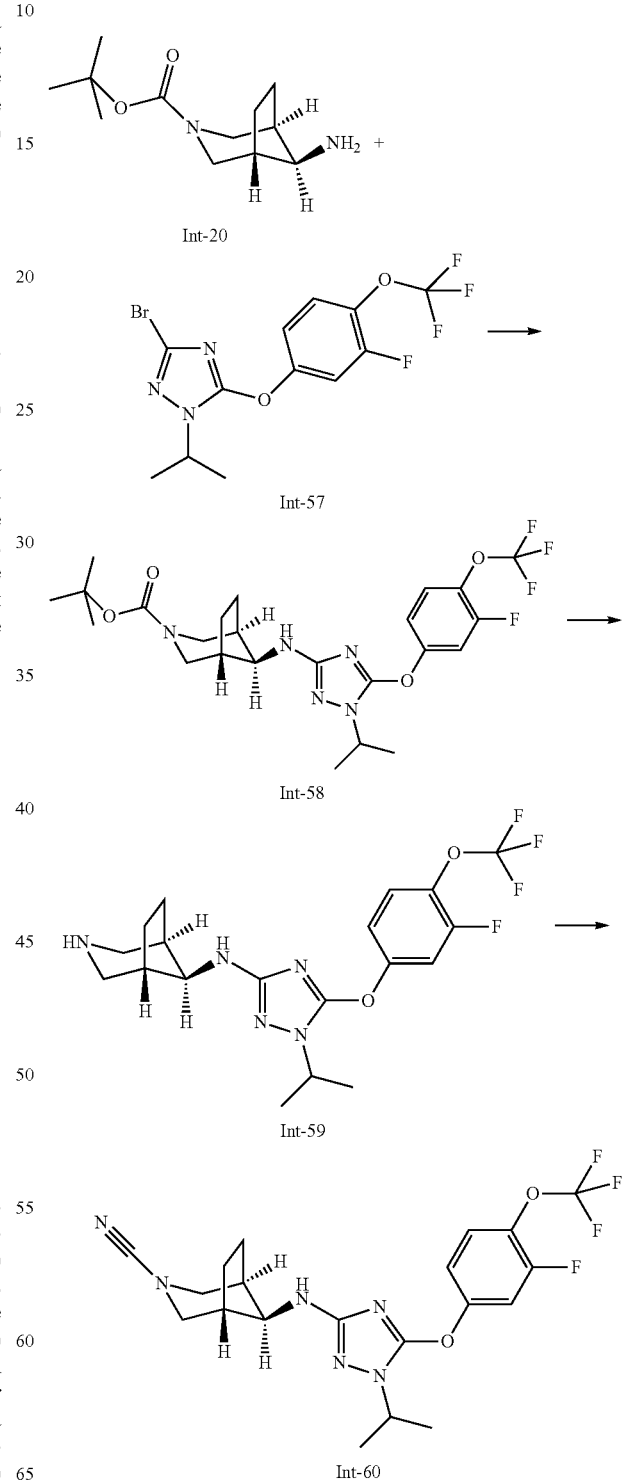

Step 1: tert-Butyl (1R,5S,8s)-8-({5-[3-fluoro-4-(trifluoromethoxy)phenoxy]-1-(propan-2-yl)-1H-1,2,4-triazol-3-yl}amino)-3-azabicyclo[3.2.1]octane-3-carboxylate (Int-58)

To a solution of tert-butyl (1R,5S,8s)-8-amino-3-azabicyclo[3.2.1]octane-3-carboxylate (Int-20, 200 mg, 0.9 mmol) and 3-bromo-5-[3-fluoro-4-(trifluoromethoxy)phenoxy]-1-(propan-2-yl)-1,2,4-triazole (Int-57, 509.2 mg, 1.3 mmol) in dry 1,4-dioxane (3 mL) in sealed tube was added 2-dicyclohexylphosphino-2',6'-diisopropoxybiphenyl ("Ruphos", CAS [787618-22-8], 82.5 mg, 0.2 mmol). The reaction mixture was degassed with argon over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 141.2 mg, 0.2 mmol). The reaction mixture was again degassed with argon for 10 min followed by addition of sodium tertbutoxide (339.3 mg, 3.5 mmol). The reaction mixture was stirred at 130° C. for 4 h. Reaction mixture was then concentrated under reduced pressure to get crude which was purified by column chromatography (amino modified silica gel, eluting with EtOAc/n-hexane 5:95 v/v) to yield the title compound as sticky yellow liquid (400 mg, 85%). MS (ES+) m/z 529.9 [M+H].

Step 2: (1R,5S,8s)-N-{5-[3-Fluoro-4-(trifluoromethoxy)phenoxy]-1-(propan-2-yl)-1H-1,2,4-triazol-3-yl}-3-azabicyclo[3.2.1]octan-8-amine (Int-59)

To a solution of tert-butyl (1R,5S,8s)-8-({5-[3-fluoro-4-(trifluoromethoxy)phenoxy]-1-(propan-2-yl)-1H-1,2,4-triazol-3-yl}amino)-3-azabicyclo[3.2.1]octane-3-carboxylate (Int-58, 400 mg, 0.8 mmol) in dichloromethane (6 mL) was added trifluoroacetic acid (0.6 mL, 8.0 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the title compound as sticky solid (330 mg, crude). MS (ES+) m/z 429.8.

Step 3: (1R,5S,8s)-N-{5-[3-Fluoro-4-(trifluoromethoxy)phenoxy]-1-(propan-2-yl)-1H-1,2,4-triazol-3-yl}-3-azabicyclo[3.2.1]octan-8-amine (Int-60)

To a solution of (1R,5S,8s)-N-{5-[3-fluoro-4-(trifluoromethoxy)phenoxy]-1-(propan-2-yl)-1H-1,2,4-triazol-3-yl}-3-azabicyclo[3.2.1]octan-8-amine (Int-59, 300 mg, 0.7 mmol) in dichloromethane (4.5 mL) was added NaHCO3 (183 mg, 2.1 mmol) dissolved in H2O (2.5 mL) under ice cold condition. To it BrCN (92.2 mg, 0.9 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to afford the title compound as white solid (320 mg, crude). MS (ES+) m/z 454.9 [M+H].

Int-61

3-Bromo-5-(3-chlorophenoxy)-1-methyl-1H-1,2,4-triazole

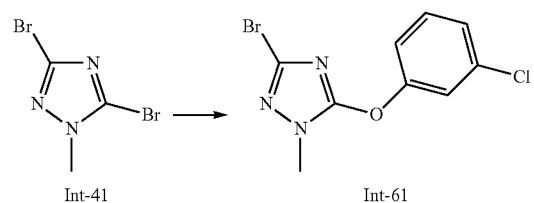

In a 25 mL pressure vial, 3,5-dibromo-1-methyl-1H-1,2,4-triazole (Int-41, 424 mg, 1.76 mmol) was dissolved in DMF (5 mL) and potassium carbonate (375 mg, 2.71 mmol), followed by 3-chlorophenol (176 mg, 141 μL, 1.36 mmol) were added. The vial was sealed, the reaction mixture was stirred for 15 h at 100° C. After cooling, it was concentrated in vacuo, the residue was purified by column chromatography (silica gel, 70 g, eluting with ethyl acetate/n-heptane, gradient 0:100 to 30:70 v/v) to yield the title compound as white solid (388 mg, 99%). $^1$H NMR (CDCl3, 300 MHz): δ 3.78 (s, 3H), 7.21-7.28 (m, 2H), 7.32-7.39 (m, 2H). MS (ES+) m/z 288.0, 290.0, 292.0 [M+H, Br & Cl isotopes].

Int-62

3-Bromo-5-(3-(trifluoromethoxy)phenoxy)-1-methyl-1H-1,2,4-triazole

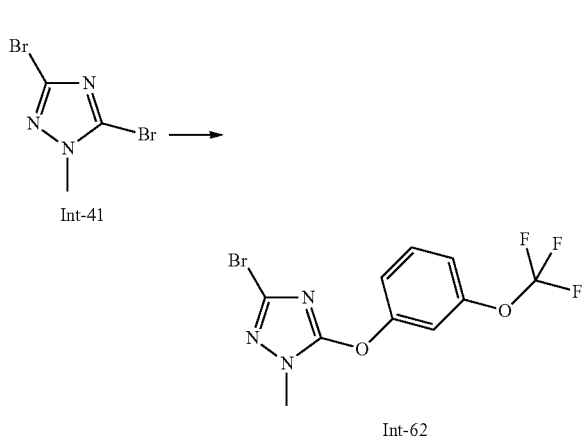

In a 10 mL pressure vial, 3,5-dibromo-1-methyl-1H-1,2,4-triazole (Int-41, 181 mg, 752 μmol) was dissolved in DMF (2 mL) and potassium carbonate (160 mg, 1.16 mmol), followed by 3-(trifluoromethoxy)phenol (103 mg, 74.7 μL, 578 μmol) were added. The vial was sealed, the reaction mixture was stirred for 18 h at 100° C. After cooling, it was concentrated in vacuo, the residue was purified by column chromatography (silica gel, 70 g, eluting with ethyl acetate/n-heptane, gradient 0:100 to 20:80 v/v) to yield the title compound as colorless liquid (187 mg, 95%). HPLC (method LCMS_fastgradient) $t_R$=1.28 min. $^1$H NMR (CDCl3, 300 MHz): δ 3.79 (s, 3H), 7.11-7.16 (m, 1H), 7.20-7.24 (m, 1H), 7.29-7.33 (m, 1H), 7.45 (t, J=8.3 Hz, 1H). MS (ES+) m/z 338.1, 340.1 [M+H, Br isotopes].

Int-63

3-Bromo-5-[3-methyl-5-(trifluoromethyl)phenoxy]-1-(propan-2-yl)-1H-1,2,4-triazole

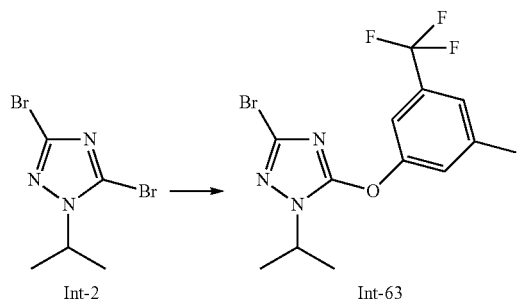

To a solution of 3,5-dibromo-1-(propan-2-yl)-1H-1,2,4-triazole (Int-2, 500 mg, 1.9 mmol) and 3-methyl-5-(trifluoromethyl)phenol (327.2 mg, 1.9 mmol) in DMF (5.0 mL) was added $Cs_2CO_3$ (1211.5 mg, 3.7 mmol). The stirring was continued in microwave at 110° C. for 40 min. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (436 mg, 64%). MS (ES+) m/z 364.0 [M+H].

Int-66

(1R,5S,8s)-8-({5-[3-Methyl-5-(trifluoromethyl)phenoxy]-1-(propan-2-yl)-1H-1,2,4-triazol-3-yl}amino)-3-azabicyclo[3.2.1]octane-3-carbonitrile

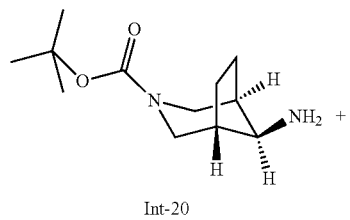

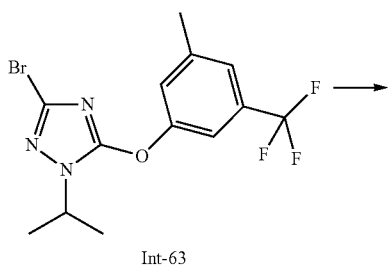

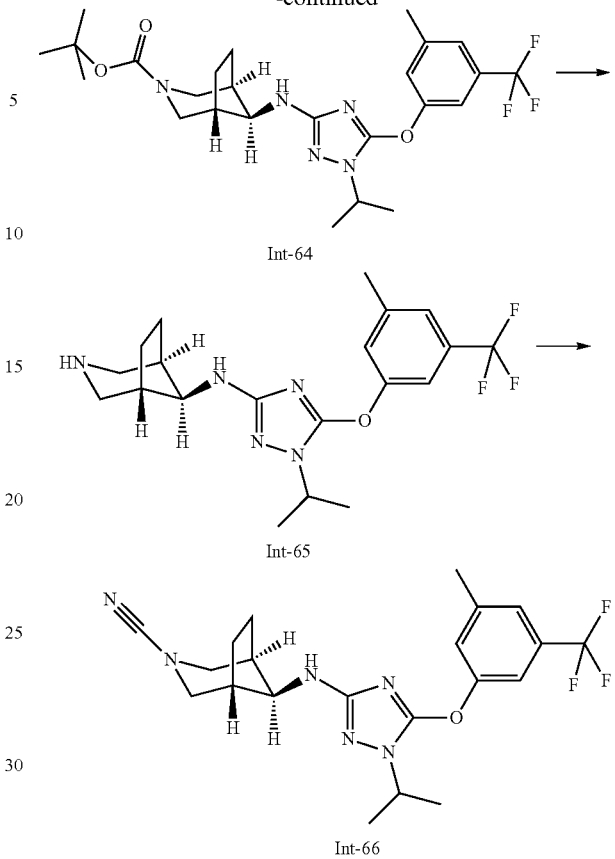

Step 1: tert-Butyl (1R,5S,8s)-8-({5-[3-methyl-5-(trifluoromethyl)phenoxy]-1-(propan-2-yl)-1H-1,2,4-triazol-3-yl}amino)-3-azabicyclo[3.2.1]octane-3-carboxylate (Int-64)

To a solution of tert-butyl (1R,5S,8s)-8-amino-3-azabicyclo[3.2.1]octane-3-carboxylate (Int-20, 150 mg, 0.6 mmol) and 3-bromo-5-[3-methyl-5-(trifluoromethyl)phenoxy]-1-(propan-2-yl)-1H-1,2,4-triazole (Int-63, 362 mg, 0.9 mmol) in dry 1,4-dioxane (3 mL) in sealed tube was added 2-dicyclohexylphosphino-2',6'-diisopropoxybiphenyl ("Ruphos", CAS [787618-22-8], 62 mg, 0.1 mmol). The reaction mixture was degassed with argon over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 105.8 mg, 0.1 mmol). The reaction mixture was again degassed with argon for 10 min followed by addition of sodium tertbutoxide (254.5 mg, 2.6 mmol). The reaction mixture was stirred at 130° C. for 4 h. Reaction mixture was then concentrated under reduced pressure to get crude which was purified by column chromatography (amino modified silica gel, eluting with EtOAc/n-hexane 5:95 v/v) to yield the title compound as off-white solid (280 mg, 83%). MS (ES+) m/z 509.8 [M+H].

Step 2: (1R,5S,8s)-N-{5-[3-Methyl-5-(trifluoromethyl)phenoxy]-1-(propan-2-yl)-1H-1,2,4-triazol-3-yl}-3-azabicyclo[3.2.1]octan-8-amine (Int-65)

To a solution of tert-butyl (1R,5S,8s)-8-({5-[3-methyl-5-(trifluoromethyl)phenoxy]-1-(propan-2-yl)-1H-1,2,4-triazol-3-yl}amino)-3-azabicyclo[3.2.1]octane-3-carboxylate (Int-64, 280 mg, 0.6 mmol) in dichloromethane (3.5 mL) was added trifluoroacetic acid (0.4 mL, 5.6 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the title compound as off white solid (200 mg, crude). MS (ES+) m/z 410.0 [M+H].

Step 3: (1R,5S,8s)-8-({5-[3-Methyl-5-(trifluoromethyl)phenoxy]-1-(propan-2-yl)-1H-1,2,4-triazol-3-yl}amino)-3-azabicyclo[3.2.1]octane-3-carbonitrile (Int-66)

To a solution of (1R,5S,8s)-N-{5-[3-methyl-5-(trifluoromethyl)phenoxy]-1-(propan-2-yl)-1H-1,2,4-triazol-3-yl}-3-azabicyclo[3.2.1]octan-8-amine (Int-65, 200 mg, 0.5 mmol) in dichloromethane (3.0 mL) was added NaHCO₃ (123.1 mg, 1.4 mmol) dissolved in H₂O (1.5 mL) under ice cold condition. To it BrCN (62.1 mg, 0.6 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to afford the title compound as white solid (170 mg, crude). MS (ES+) m/z 434.8 [M+H].

Int-68

3-Bromo-5-(3-chlorophenoxy)-1-(2,2,3,3,3-pentafluoropropyl)-1H-1,2,4-triazole

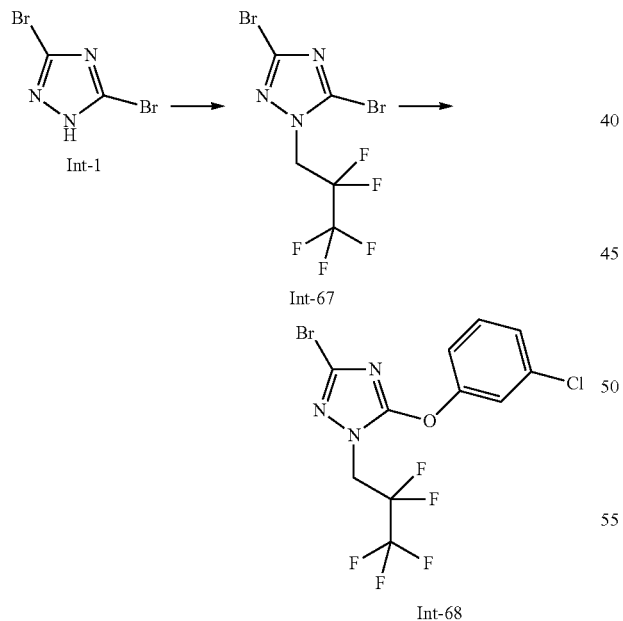

Step 1: 3,5-Dibromo-1-(2,2,3,3,3-pentafluoropropyl)-1H-1,2,4-triazole (Int-67)

In a 50 mL round bottomed flask, 3,5-dibromo-1H-1,2,4-triazole (Int-1, 500 mg, 2.2 mmol) was dissolved in DMF (8 mL) and potassium carbonate (680 mg, 4.87 mmol) was added. After stirring for 20 min at room temperature, 2,2,3,3,3-pentafluoropropyl trifluoromethanesulfonate (705 mg, 414 µL, 2.42 mmol) was added and the reaction mixture was stirred for 20 h at room temperature. After that, it was concentrated in vacuo, the residue was purified by column chromatography (silica gel, 50 g, eluting with ethyl acetate/n-heptane, gradient 20:80 to 50:50 v/v) to yield the title compound as white solid (409 mg, 52%). HPLC (method LCMS_fastgradient) $t_R$=1.11 min. ¹H NMR (CDCl₃, 300 MHz): δ 4.78 (t, J=13.4 Hz, 2H). MS (ES+) m/z 357.9, 359.9, 361.9 [M+H, 2 Br isotopes].

Step 2: 3-Bromo-5-(3-chlorophenoxy)-1-(2,2,3,3,3-pentafluoropropyl)-1H-1,2,4-triazole (Int-68)

In a 25 mL round bottomed flask, 3,5-dibromo-1-(2,2,3,3,3-pentafluoropropyl)-1H-1,2,4-triazole (Int-67, 374 mg, 1.04 mmol) was dissolved in DMF (4 mL) and potassium carbonate (234 mg, 1.69 mmol), followed by 3-chlorophenol (110 mg, 847 µmol) were added. The reaction mixture was stirred for 16 h at 100° C. After cooling, it was concentrated in vacuo, the residue was purified by column chromatography (silica gel, 100 g, eluting with ethyl acetate/n-heptane, gradient 0:100 to 20:80 v/v) to afford the title compound as white solid (159 mg, 46%). HPLC (method LCMS_fastgradient) $t_R$=1.46 min. ¹H NMR (CDCl₃, 300 MHz): δ 4.70 (t, J=13.4 Hz, 2H), 7.22-7.42 (m, 4H). MS (ES+) m/z 406.0, 408.0, 410.0 [M+H, Br & Cl isotopes].

Int-69

3-Bromo-5-[3-chloro-5-(trifluoromethyl)phenoxy]-1-(propan-2-yl)-1H-1,2,4-triazole

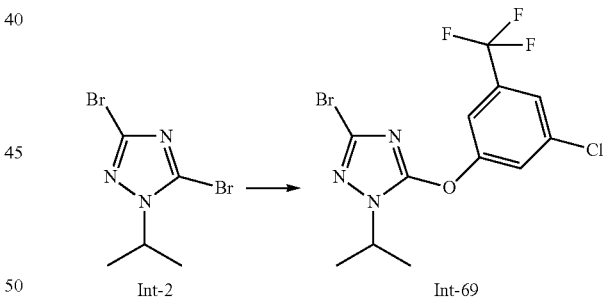

To a solution of 3,5-dibromo-1-(propan-2-yl)-1H-1,2,4-triazole (Int-2, 1.0 g, 3.7 mmol) and 3-chloro-5-hydroxybenzotrifluoride (731 mg, 3.7 mmol) in DMF (10.0 mL) was added K₂CO₃ (1.0 g, 7.4 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (600 mg, 42%). ¹H NMR (DMSO-d6, 400 MHz): 1.43 (d, J=6.6 Hz, 6H), 4.63 (p, J=6.6 Hz, 1H), 7.87 (s, 1H), 7.93 (s, 1H), 8.01 (s, 1H). MS (ES+) m/z 385.8 [M+H].

Int-70

3-Bromo-5-[4-methyl-3-(trifluoromethyl)phenoxy]-1-(propan-2-yl)-1H-1,2,4-triazole

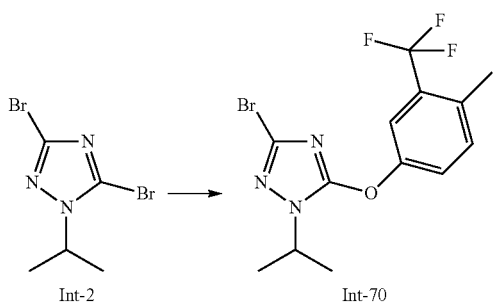

To a solution of 3,5-dibromo-1-(propan-2-yl)-1H-1,2,4-triazole (Int-2, 500 mg, 1.9 mmol) and 4-methyl-3-(trifluoromethyl)phenol (327.2 mg, 1.9 mmol) in DMF (5.0 mL) was added Cs$_2$CO$_3$ (1211.5 mg, 3.7 mmol). The stirring was continued in microwave at 150° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (400 mg, 59%). MS (ES+) m/z 363.8 [M+H].

Int-71

3-Bromo-5-[4-chloro-3-(trifluoromethyl)phenoxy]-1-(propan-2-yl)-1H-1,2,4-triazole

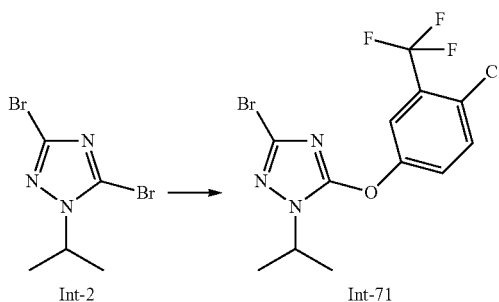

To a solution of 3,5-dibromo-1-(propan-2-yl)-1H-1,2,4-triazole (Int-2, 500 mg, 1.9 mmol) and 2-chloro-5-hydroxybenzotrifluoride (365.4 mg, 1.9 mmol) in DMF (5.0 mL) was added Cs$_2$CO$_3$ (1211.5 mg, 3.7 mmol). The stirring was continued in microwave at 150° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (350 mg, 49%).

$^1$H NMR (DMSO-d6, 400 MHz): 1.42 (d, J=6.3 Hz, 6H), 4.62-4.65 (m, 1H), 7.79-7.86 (m, 2H), 8.02 (s, 1H).

Int-72

3-Bromo-5-(4-fluoro-3-methyl-5-(trifluoromethyl)phenoxy)-1-propan-2-yl-1H-1,2,4-triazole

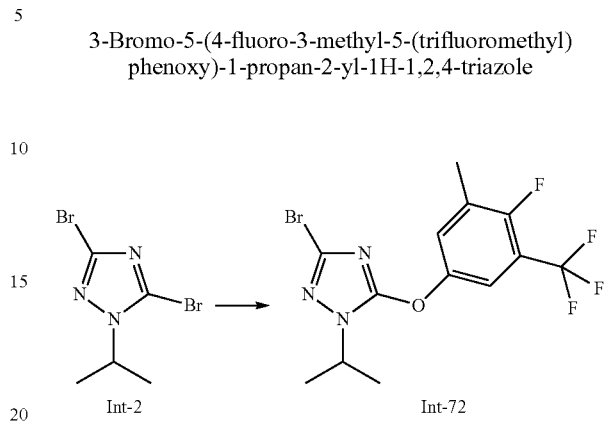

To a solution of 3,5-dibromo-1-(propan-2-yl)-1H-1,2,4-triazole (Int-2, 1.0 g, 3.7 mmol) and 2-fluoro-5-hydroxy-3-methylbenzotrifluoride (722 mg, 3.2 mmol) in DMF (10 mL) was added 1,8-diazabicyclo[5.4.0]undec-7-ene ("DBU", 1.1 mL, 7.4 mmol). The stirring was continued in microwave at 100° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (450 mg, 32%). MS (ES+) m/z 384.0 [M+H].

Int-73

5-[3,5-B is (trifluoromethyl)phenoxy]-3-bromo-1-(propan-2-yl)-1H-1,2,4-triazole

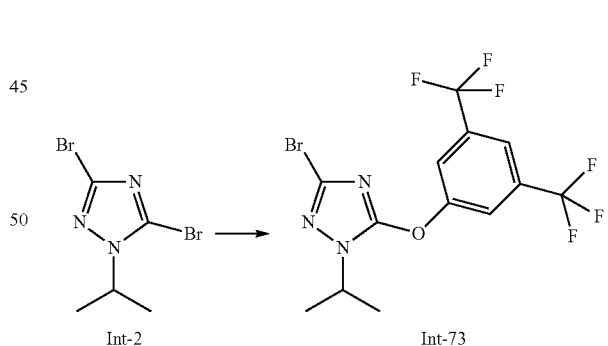

To a solution of 3,5-dibromo-1-(propan-2-yl)-1H-1,2,4-triazole (Int-2, 500 mg, 1.9 mmol) and 3,5-bis(trifluoromethyl)phenol (0.5 mL, 3.2 mmol) in DMF (5 mL) was added 1,8-diazabicyclo[5.4.0]undec-7-ene ("DBU", 0.6 mL, 3.7 mmol). The stirring was continued in microwave at 100° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-

Int-74

3-Bromo-1-(propan-2-yl)-5-[4-(trifluoromethoxy)-3-(trifluoromethyl)phenoxy]-1H-1,2,4-triazole

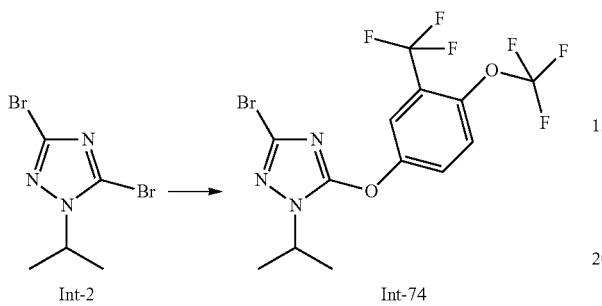

To a solution of 3,5-dibromo-1-(propan-2-yl)-1H-1,2,4-triazole (Int-2, 500 mg, 1.9 mmol) and 4-(trifluoromethoxy)-3-(trifluoromethyl)phenol (457.3 mg, 1.9 mmol) in DMF (5.0 mL) was added K$_2$CO$_3$ (513.1 mg, 3.7 mmol). The stirring was continued in microwave at 145° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 3:97 v/v) to afford the title compound as white solid (280 mg, 46%). MS (ES+) m/z 435.8 [M+H].

Int-75

3-Bromo-5-(3-chlorophenoxy)-1-(propan-2-yl)-1H-1,2,4-triazole

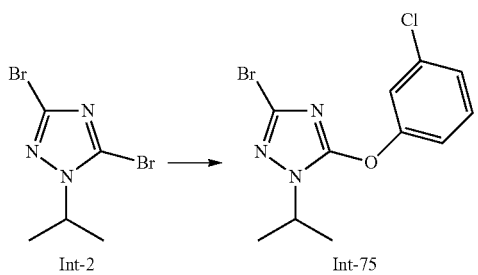

To a solution of 3,5-dibromo-1-(propan-2-yl)-1H-1,2,4-triazole (Int-2, 500 mg, 1.9 mmol) and 3-chlorophenol (237.9 mg, 1.9 mmol) in DMF (5.0 mL) was added K$_2$CO$_3$ (513.7 mg, 3.7 mmol). The stirring was continued in microwave at 140° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (300 mg, 51%). $^1$H NMR (DMSO-d6, 400 MHz): 1.41 (d, J=6.6 Hz, 6H), 4.58-4.64 (m, 1H), 7.38 (t, J=9.1 Hz, 2H), 7.50 (t, J=8.1 Hz, 1H), 7.59 (s, 1H). MS (ES+) m/z 317.9 [M+H].

Int-76

3-Bromo-5-(3-chloro-4-methyl-phenoxy)-1-(propan-2-yl)-1H-1,2,4-triazole

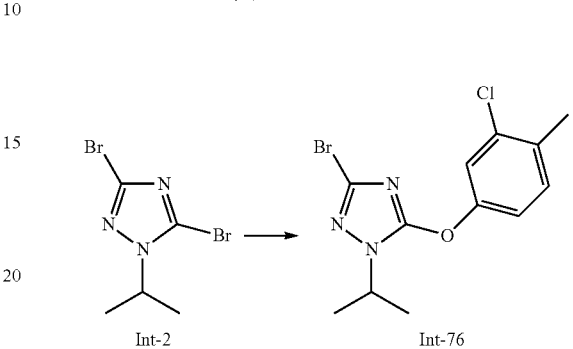

To a solution of 3,5-dibromo-1-(propan-2-yl)-1H-1,2,4-triazole (Int-2, 500 mg, 1.9 mmol) and 3-chloro-4-methyl-phenol (264.1 mg, 1.9 mmol) in DMSO (5.0 mL) was added Cs$_2$CO$_3$ (1211.3 mg, 3.7 mmol). The stirring was continued in microwave at 120° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (280 mg, 46%). $^1$H NMR (DMSO-d6, 400 MHz): 1.41 (d, J=6.8 Hz, 6H), 2.34 (s, 3H), 4.61 (p, J=6.7 Hz, 1H), 7.27 (dd, J=8.4, 2.4 Hz, 1H), 7.44 (d, J=8.4 Hz, 1H), 7.55 (d, J=2.4 Hz, 1H). MS (ES+) m/z 332.3 [M+H].

Int-77

3-Bromo-5-(3-chloro-2-methyl-phenoxy)-1-(propan-2-yl)-1H-1,2,4-triazole

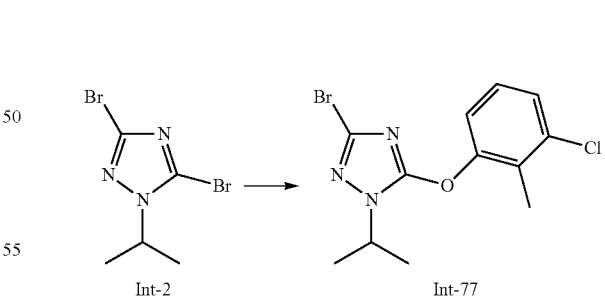

To a solution of 3,5-dibromo-1-(propan-2-yl)-1H-1,2,4-triazole (Int-2, 500 mg, 1.9 mmol) and 3-chloro-2-methylphenol (291.5 mg, 2.0 mmol) in DMSO (2.0 mL) was added Cs$_2$CO$_3$ (1211.3 mg, 3.7 mmol). The stirring was continued in microwave at 120° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (350 mg, 57%). MS (ES+) m/z 330.0 [M+H].

Int-78

3-Bromo-5-(3-chloro-5-methyl-phenoxy)-1-(propan-2-yl)-1H-1,2,4-triazole

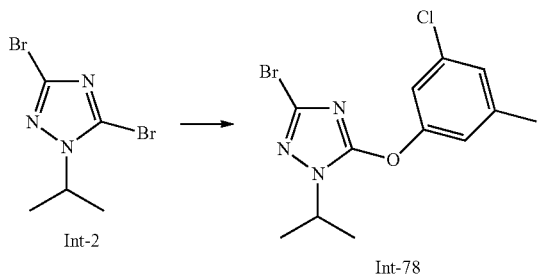

To a solution of 3,5-dibromo-1-(propan-2-yl)-1H-1,2,4-triazole (Int-2, 500 mg, 1.9 mmol) and 3-chloro-5-methyl-phenol (290.5 mg, 2.0 mmol) in DMSO (5.0 mL) was added $Cs_2CO_3$ (1211.3 mg, 3.7 mmol). The stirring was continued in microwave at 120° C. for 1 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, eluting with ethyl acetate/n-hexane 2:98 v/v) to afford the title compound as white solid (280 mg, 46%). $^1$H NMR (DMSO-d6, 400 MHz): 1.41 (d, J=6.6 Hz, 6H), 2.34 (s, 3H), 4.60 (hept, J=6.6 Hz, 1H), 7.19 (s, 1H), 7.24 (s, 1H), 7.36 (s, 1H). MS (ES+) m/z 332.2 [M+H].

Int-79

3-Bromo-5-(3-chloro-5-methylphenoxy)-1-methyl-1H-1,2,4-triazole

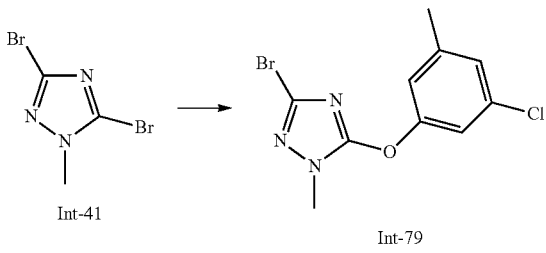

In a 50 mL pressure vial, 3,5-dibromo-1-methyl-1H-1,2,4-triazole (Int-41, 1.42 g, 5.89 mmol) was dissolved in DMF (12 mL) and potassium carbonate (1.36 mg, 9.82 mmol), followed by 3-chloro-5-methylphenol (700 mg, 4.91 mmol) were added. The vial was sealed, the reaction mixture was stirred for 15 h at 100° C. After cooling, it was concentrated in vacuo, the residue was purified by column chromatography (silica gel, 70 g, eluting with ethyl acetate/n-heptane, gradient 0:100 to 25:75 v/v) to yield the title compound as white solid (1.37 g, 92%). $^1$H NMR (CDCl$_3$, 300 MHz): δ 2.37 (s, 3H), 3.77 (s, 3H), 6.99-7.02 (m, 1H), 7.06-7.08 (m, 1H), 7.11-7.14 (m, 1H). MS (ES+) m/z 302.0, 304.0, 306.0 [M+H, Br & Cl isotopes].

Int-81

3-Bromo-5-(3-chlorophenoxy)-1-ethyl-1H-1,2,4-triazole

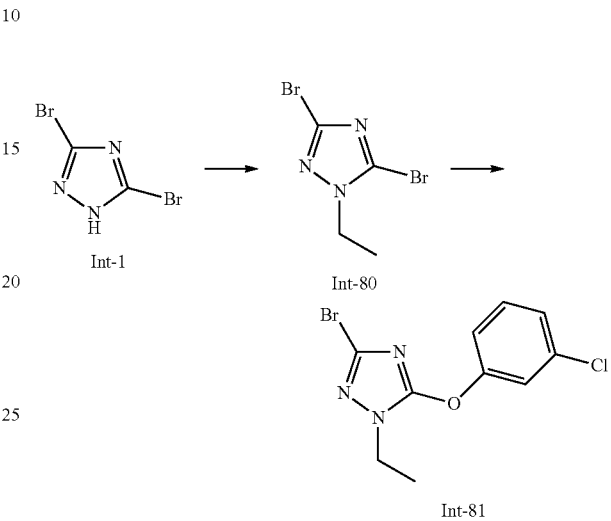

Step 1: 3,5-Dibromo-1-ethyl-1H-1,2,4-triazole (Int-80)

In a 100 mL round bottomed flask, 3,5-dibromo-1H-1,2,4-triazole (Int-1, 2.50 g, 11 mmol) was dissolved in DMF (32 mL) and the solution was cooled to 0-5° C. (ice bath). Sodium hydride (55% dispersion in mineral oil, 577 mg, 13.2 mmol) was added in portions and the resulting mixture was stirred for 5 min at 0-5° C. and for 15 min at room temperature. After that, ethyl methanesulfonate (2.74 g, 2.27 mL, 22 mmol) was added dropwise at room temperature. The resulting mixture was stirred for 1.5 h at 100° C., and 16 h at room temperature. After that, it was concentrated in vacuo, the residue was diluted with ethyl acetate (100 mL) and water (100 mL), the aqueous phase was extracted with ethyl acetate (3×100 mL). The combined organic layers were dried (sodium sulfate) and concentrated in vacuo, the residue was purified by column chromatography (silica gel, 70 g, eluting with ethyl acetate/n-heptane, gradient 0:100 to 22:78 v/v) to yield the title compound as white solid (1.98 g, 70%). HPLC (method LCMS_fastgradient) $t_R$=0.88 min. $^1$H NMR (CDCl$_3$, 300 MHz): δ 1.49 (t, J=7.2 Hz, 3H), 4.21 (q, J=7.2 Hz, 2H). MS (ES+) m/z 253.9, 255.9, 258.0 [M+H, 2 Br isotopes].

Step 2: 3-Bromo-5-(3-chlorophenoxy)-1-ethyl-1H-1,2,4-triazole (Int-81)

In a 100 mL round bottomed flask, 3,5-dibromo-1-ethyl-1H-1,2,4-triazole (Int-80, 1.98 g, 7.77 mmol) was dissolved in DMF (30 mL) and potassium carbonate (1.65 g, 12 mmol), followed by 3-chlorophenol (776 mg, 5.98 mmol) were added. The reaction mixture was stirred for 18 h at 100° C. After cooling, it was concentrated in vacuo, the residue was purified by column chromatography (silica gel, 100 g, eluting with ethyl acetate/n-heptane, gradient 0:100 to 26:74 v/v) to yield the title compound as white solid (1.61 g, 89%). HPLC (method LCMS_fastgradient) $t_R$=1.30 min. $^1$H NMR (CDCl$_3$, 300 MHz): δ 1.49 (t, J=7.3 Hz, 3H), 4.12 (q, J=7.2 Hz, 2H), 7.20-7.27 (m, 2H), 7.31-7.38 (m, 2H). MS (ES+) m/z 302.0, 304.0, 306.0 [M+H, Br & Cl isotopes].

Int-83

3-Bromo-5-(3-chlorophenoxy)-1-propyl-1H-1,2,4-triazole

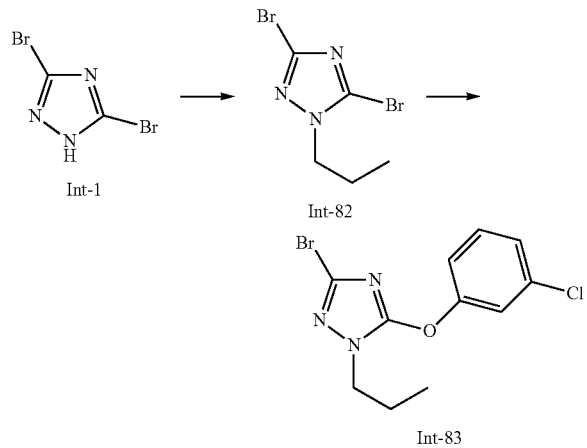

Step 1: 3,5-Dibromo-1-propyl-1H-1,2,4-triazole (Int-82)

In a 50 mL round bottomed flask, 3,5-dibromo-1H-1,2,4-triazole (Int-1, 1.00 g, 4.41 mmol) was dissolved in DMF (13 mL) and the solution was cooled to 0-5° C. (ice bath). Sodium hydride (55% dispersion in mineral oil, 231 mg, 5.29 mmol) was added in portions and the resulting mixture was stirred for 5 min at 0-5° C. and for 15 min at room temperature. After that, propyl methanesulfonate (1.24 g, 1.08 mL, 8.82 mmol) was added dropwise at room temperature. The resulting mixture was stirred for 15 h at room temperature, followed by 1 h at 100° C. After that, it was concentrated in vacuo, the residue was diluted with ethyl acetate (50 mL) and water (50 mL), the aqueous phase was extracted with ethyl acetate (3×50 mL). The combined organic layers were dried (sodium sulfate) and concentrated in vacuo, the residue was purified by column chromatography (silica gel, 70 g, eluting with ethyl acetate/n-heptane, gradient 0:100 to 28:72 v/v) to yield the title compound as colorless oil (672 mg, 57%). $^1$H NMR (CDCl$_3$, 300 MHz): δ 0.97 (t, J=7.4 Hz, 3H), 1.85-1.98 (m, 2H), 4.12 (q, J=7.0 Hz, 2H). MS (ES+) m/z 267.9, 270.0, 271.9 [M+H, 2 Br isotopes].

Step 2: 3-Bromo-5-(3-chlorophenoxy)-1-propyl-1H-1,2,4-triazole (Int-83)

In a 100 mL round bottomed flask, 3,5-dibromo-1-propyl-1H-1,2,4-triazole (Int-82, 668 mg, 2.48 mmol) was dissolved in DMF (11 mL) and potassium carbonate (528 mg, 3.82 mmol), followed by 3-chlorophenol (248 mg, 1.91 mmol) were added. The reaction mixture was stirred for 14 h at 100° C. After cooling, it was concentrated in vacuo, the residue was purified by column chromatography (silica gel, 100 g, eluting with ethyl acetate/n-heptane, gradient 0:100 to 22:78 v/v) to yield the title compound as colorless oil (496 mg, 82%). HPLC (method LCMS_fastgradient) $t_R$=1.37 min. $^1$H NMR (CDCl$_3$, 300 MHz): δ 0.99 (t, J=7.4 Hz, 3H), 1.84-1.97 (m, 2H), 4.03 (t, J=7.0 Hz, 2H), 7.19-7.27 (m, 2H), 7.31-7.39 (m, 2H). MS (ES+) m/z 316.0, 318.0, 320.0 [M+H, Br & Cl isotopes].

Int-84

3-Bromo-5-(3-fluoro-5-methylphenoxy)-1-methyl-1H-1,2,4-triazole

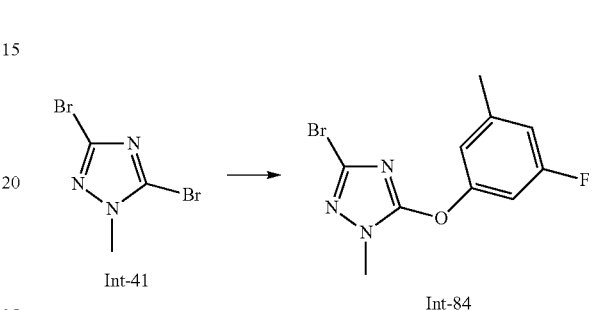

In a 50 mL pressure vial, 3,5-dibromo-1-methyl-1H-1,2,4-triazole (Int-41, 1.47 g, 6.1 mmol) was dissolved in DMF (13 mL) and potassium carbonate (1.53 mg, 11.1 mmol), followed by 3-fluoro-5-methylphenol (700 mg, 5.55 mmol) were added. The vial was sealed, the reaction mixture was stirred for 15 h at 100° C. After cooling, it was concentrated in vacuo, the residue was purified by column chromatography (silica gel, 70 g, eluting with ethyl acetate/n-heptane, gradient 0:100 to 25:75 v/v) to yield the title compound as light yellow solid (1.23 g, 75%). $^1$H NMR (CDCl$_3$, 300 MHz): δ 2.38 (s, 3H), 3.77 (s, 3H), 6.76-6.82 (m, 1H), 6.84-6.91 (m, 2H). MS (ES+) m/z 286.0, 288.0 [M+H, Br isotopes].

Int-86

(1R,5S,8s)-N-[5-(3-Chlorophenoxy)-1-(propan-2-yl)-1H-1,2,4-triazol-3-yl]-3-azabicyclo[3.2.1]octan-8-amine

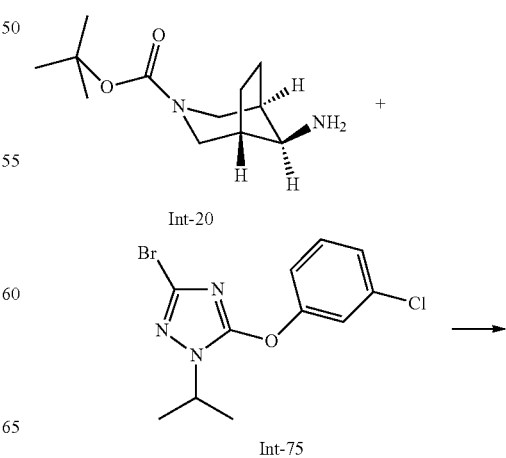

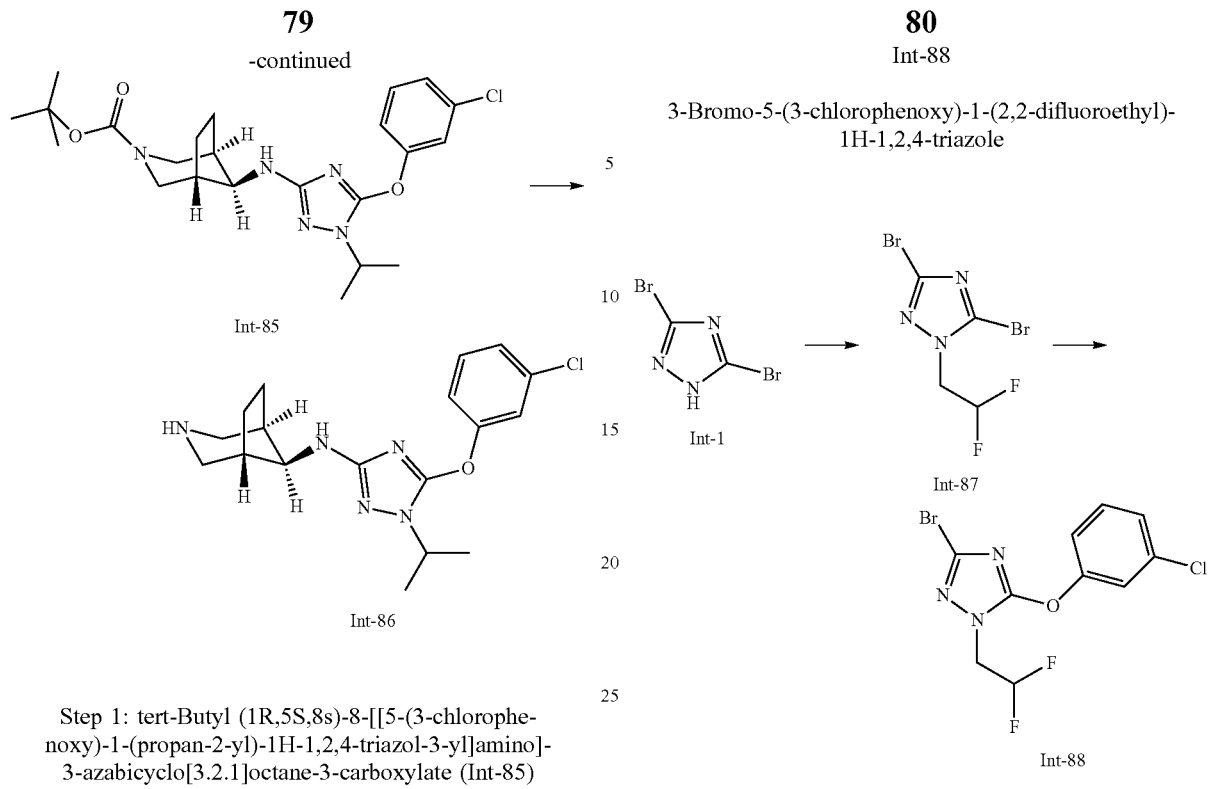

Int-85

Int-86

Step 1: tert-Butyl (1R,5S,8s)-8-[[5-(3-chlorophenoxy)-1-(propan-2-yl)-1H-1,2,4-triazol-3-yl]amino]-3-azabicyclo[3.2.1]octane-3-carboxylate (Int-85)

To a solution of tert-butyl (1R,5S,8s)-8-amino-3-azabicyclo[3.2.1]octane-3-carboxylate (Int-20, 800 mg, 3.5 mmol) and 3-bromo-5-(3-chlorophenoxy)-1-(propan-2-yl)-1H-1,2,4-triazole (Int-75, 1.1 g, 3.1 mmol) in dry 1,4-dioxane (12 mL) in sealed tube was added 2-dicyclohexylphosphino-2',6'-diisopropoxybiphenyl ("Ruphos", CAS [787618-22-8], 329.4 mg, 0.7 mmol). The reaction mixture was degassed with argon over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 940.2 mg, 1.1 mmol). The reaction mixture was again degassed with argon for 10 min followed by addition of sodium tertbutoxide (678.5 mg, 7.0 mmol). The reaction mixture was stirred at 120° C. for 4 h. Reaction mixture was then concentrated under reduced pressure to get crude which was purified by column chromatography (silica gel, 20 g, eluting with EtOAc/n-hexane 20:80 v/v) to yield the title compound as yellow semi-solid (400 mg, 25%). MS (ES+) m/z 461.8 [M+H].

Step 2: (1R,5S,8s)-N-[5-(3-Chlorophenoxy)-1-(propan-2-yl)-1H-1,2,4-triazol-3-yl]-3-azabicyclo[3.2.1]octan-8-amine (Int-86)

To a solution of tert-butyl (1R,5S,8s)-8-[[5-(3-chlorophenoxy)-1-(propan-2-yl)-1H-1,2,4-triazol-3-yl]amino]-3-azabicyclo[3.2.1]octane-3-carboxylate (Int-85, 450 mg, 0.4 mmol) in dichloromethane (6.0 mL) was added trifluoroacetic acid (0.5 mL, 0.4 mmol) at 0° C. After 5 min reaction mixture was allowed to warm to 25° C. and continued the stirring at the same temperature for 16 h. The resulting mixture was concentrated under reduced pressure followed by azeotrope with toluene (3×5 mL) to afford the crude which was purified by column chromatography (amino modified silica gel, 12 g, eluting with MeOH/dichloromethane 5:90 v/v) title compound as off-white solid (60 mg, 40%). MS (ES+) m/z 361.9 [M+H].

Int-88

3-Bromo-5-(3-chlorophenoxy)-1-(2,2-difluoroethyl)-1H-1,2,4-triazole

Int-1

Int-87

Int-88

Step 1: 3,5-Dibromo-1-(2,2-difluoroethyl)-1H-1,2,4-triazole (Int-87)

In a 250 mL round bottomed flask, 3,5-dibromo-1H-1,2,4-triazole (Int-1, 2.00 g, 8.82 mmol) was dissolved in DMF (60 mL) and potassium carbonate (2.72 g, 19.5 mmol) was added. The resulting suspension was stirred for 20 min at room temperature. Then, 2,2-difluoroethyl trifluoromethanesulfonate (2.08 g, 1.29 mL, 9.7 mmol) was added and the reaction mixture was stirred for 6 h at room temperature. After that, it was concentrated in vacuo, the residue was diluted with MTBE (100 mL) and ice water (100 mL), the aqueous phase was extracted with MTBE (3×100 mL). The combined organic layers were washed with water (2×100 mL) and brine (1×100 mL), dried (sodium sulfate) and concentrated in vacuo. The resulting crude product, a white solid, was used in the next step without further purification (2.402 g, 94%). HPLC (method LCMS_fastgradient) $t_R$=0.88 min. $^1$H NMR (CDCl$_3$, 300 MHz): δ 4.52 (dt, J=4.2, 12.6 Hz, 2H), 6.16 (tt, J=4.2, 54.8 Hz, 1H). MS (ES+) m/z 289.9, 291.9, 293.9 [M+H, 2 Br isotopes].

Step 2: 3-Bromo-5-(3-chlorophenoxy)-1-(2,2-difluoroethyl)-1H-1,2,4-triazole (Int-88)

In a 25 mL round bottomed flask, 3,5-dibromo-1-(2,2-difluoroethyl)-1H-1,2,4-triazole (Int-87, 582 mg, 2.00 mmol) was dissolved in DMF (5 mL) and potassium carbonate (426 mg, 3.08 mmol), followed by 3-chlorophenol (200 mg, 161 μL-1.54 mmol) were added. The reaction mixture was stirred for 18 h at 100° C. After cooling, it was concentrated in vacuo, the residue was purified by column chromatography (amino modified silica gel, 50 g, eluting with ethyl acetate/n-heptane, gradient 0:100 to 1:6 v/v) to yield the title compound as colorless viscous oil (516 mg, 99%). HPLC (method LCMS_fastgradient) $t_R$=1.30 min. $^1$H NMR (CDCl$_3$, 300 MHz): δ 4.43 (dt, J=4.2, 13.0 Hz, 2H), 6.17 (tt, J=4.2, 55.0 Hz, 1H), 7.21-7.30 (m, 2H), 7.33-7.40 (m, 2H). MS (ES+) m/z 338.0, 340.0, 342.0 [M+H, Br & Cl isotopes].

Int-90

3-Bromo-5-(3-chlorophenoxy)-1-(2-fluoroethyl)-1H-1,2,4-triazole

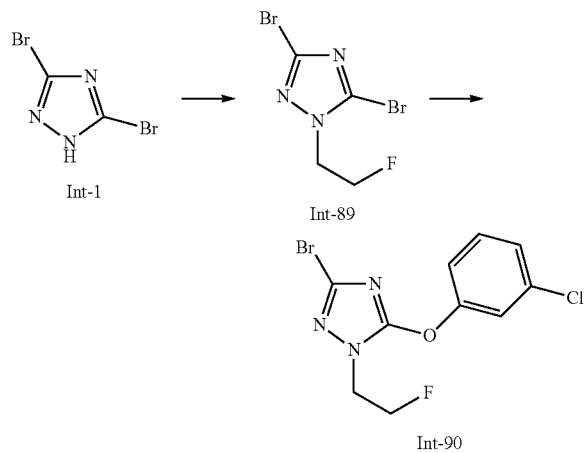

Int-92

3-Bromo-1-cyclopropyl-5-(3,4-difluorophenoxy)-1H-1,2,4-triazole

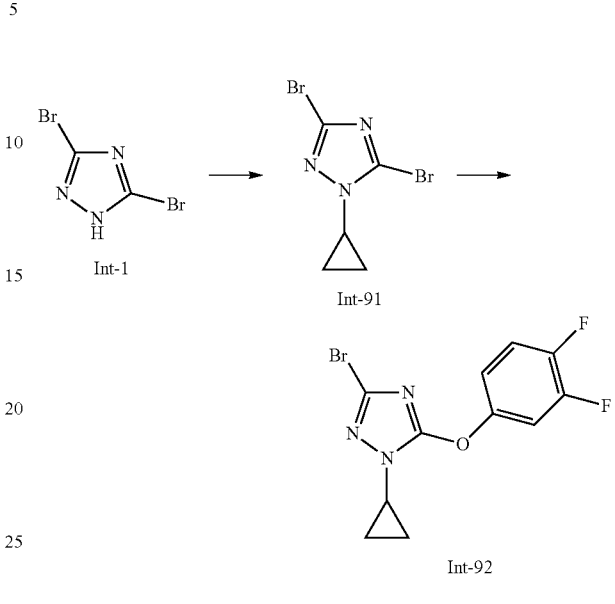

Step 1: 3,5-Dibromo-1-(2-fluoroethyl)-1H-1,2,4-triazole (Int-89)

In a 50 mL round bottomed flask, 3,5-dibromo-1H-1,2,4-triazole (Int-1, 1.50 g, 6.61 mmol) was dissolved in DMF (15 mL) and the solution was cooled to 0-5° C. (ice bath). Sodium hydride (55% dispersion in mineral oil, 317 mg, 7.93 mmol) was added in portions and the resulting mixture was stirred for 30 min at 0-5° C. and for 15 min at room temperature. After that, 1-fluoro-2-iodoethane (1.15 g, 537 µL, 6.61 mmol) was added dropwise at room temperature. The resulting mixture was stirred for 18 h at room temperature. After that, it was concentrated in vacuo, the residue was purified by column chromatography (silica gel, 70 g, eluting with ethyl acetate/n-heptane, gradient 0:100 to 40:60 v/v) to yield the title compound as yellow oil (1.51 g, 84%). $^1$H NMR (CDCl$_3$, 300 MHz): δ 4.46 (td, J=4.7, 24.2 Hz, 2H), 4.80 (td, J=4.7, 46.3 Hz, 2H). MS (ES+) m/z 271.9, 273.9, 275.9 [M+H, 2 Br isotopes].

Step 2: 3-Bromo-5-(3-chlorophenoxy)-1-(2-fluoroethyl)-1H-1,2,4-triazole (Int-90)

In a 50 mL pressure vial, 3,5-dibromo-1-(2-fluoroethyl)-1H-1,2,4-triazole (Int-89, 1.51 g, 5.53 mmol) was dissolved in DMF (12 mL) and potassium carbonate (1.53 g, 11.1 mmol), followed by 3-chlorophenol (719 mg, 579 µL, 5.53 mmol) were added. The tube was sealed, the yellow reaction mixture was stirred for 15 h at 100° C. After cooling, it was concentrated in vacuo, the residue was purified by column chromatography (silica gel, 70 g, eluting with ethyl acetate/n-heptane, gradient 0:100 to 30:70 v/v) to yield the title compound as colorless oil (719 mg, 39%). HPLC (method LCMS_fastgradient) t$_R$=1.26 min. $^1$H NMR (CDCl$_3$, 300 MHz): δ 4.37 (td, J=4.8, 24.8 Hz, 2H), 4.80 (td, J=4.8, 46.5 Hz, 2H), 7.20-7.28 (m, 2H), 7.32-7.39 (m, 2H). MS (ES+) m/z 319.9, 321.9, 323.9 [M+H, Br & Cl isotopes].

Step 1: 3,5-Dibromo-1-cyclopropyl-1H-1,2,4-triazole (Int-91)

In a 500 mL round bottomed flask, 3,5-dibromo-1H-1,2,4-triazole (Int-1, 3.00 g, 13.2 mmol) was dissolved in 1,2-dichloroethane (100 mL), and cyclopropylboronic acid (2.84 g, 33.1 mmol), sodium carbonate (3.50 g, 33.1 mmol), copper(II) acetate (2.94 g, 15.9 mmol) and 2,2'-bipyridine (2.50 g, 15.9 mmol) were added. The reaction mixture was stirred for 3 h at 75° C. After that, it was diluted with dichloromethane (100 mL) and washed with saturated aqueous solution of ammonium chloride (100 mL) and brine (100 mL), dried (sodium sulfate) and concentrated in vacuo. The crude product was purified by column chromatography (silica gel, 80 g, eluting with dichloromethane/methanol, gradient 100:0 to 95:5 v/v) to afford the title compound as colorless oil (660 mg, 13%). HPLC (method LCMS_fastgradient) t$_R$=1.00 min. $^1$H NMR (CDCl$_3$, 300 MHz): δ1.12-1.31 (m, 4H), 3.45-3.54 (m, 1H). MS (ES+) m/z 265.8, 267.7, 269.8 [M+H, 2 Br isotopes].

Step 2: 3-Bromo-1-cyclopropyl-5-(3,4-difluorophenoxy)-1H-1,2,4-triazole (Int-92)

In a 10 mL pressure vial, 3,5-dibromo-1-cyclopropyl-1H-1,2,4-triazole (Int-91, 215 mg, 807 µmol) was dissolved in DMF (2 mL) and potassium carbonate (212 mg, 1.54 mmol), followed by 3,4-difluorophenol (100 mg, 769 µmol) were added. The tube was sealed, the reaction mixture was stirred for 16 h at 100° C. After cooling, it was diluted with MTBE (50 mL), washed with brine (3×10 mL), dried (sodium sulfate) and concentrated in vacuo. The crude product was purified by column chromatography (silica gel, 12 g, eluting with ethyl acetate/n-heptane, gradient 0:100 to 50:50 v/v) to yield the title compound as colorless oil (188 mg, 77%). HPLC (method LCMS_fastgradient) t$_R$=1.29 min. $^1$H NMR (CDCl₃, 300 MHz): δ 1.07-1.28 (m, 4H), 3.39-3.47 (m, 1H), 7.04-7.12 (m, 1H), 7.16-7.27 (m, 2H). MS (ES+) m/z 315.9, 317.9 [M+H, Br isotopes].

Int-96

(1R,5S,8s)-3-(3-Methylisothiazol-5-yl)-3-azabicyclo[3.2.1]octan-8-amine

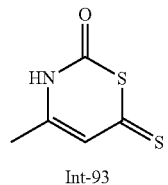
Int-93

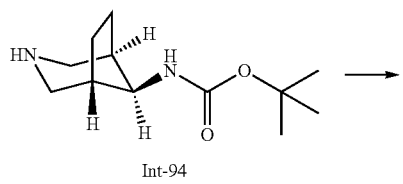
Int-94

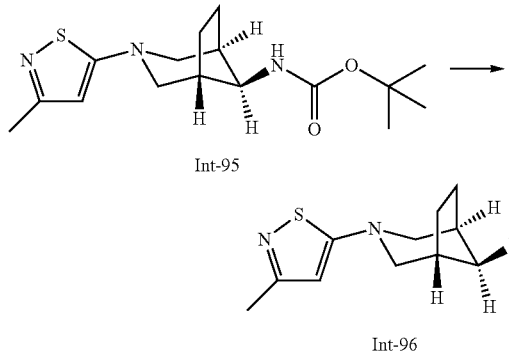
Int-95

Int-96

Step 1: tert-Butyl 41R,5S,8s)-3-(3-methylisothiazol-5-yl)-3-azabicyclo[3.2.1]octan-8-yl)carbamate (Int-95)

To a solution of 4-methyl-6-sulfanylidene-3,6-dihydro-2H-1,3-thiazin-2-one (Int-93, 500 mg, 3.1 mmol), tert-butyl (1R,5S,8s)-3-azabicyclo[3.2.1]octan-8-ylcarbamate (Int-94, 754.7 mg, 3.1 mmol), 4-methylmorpholine (1.0 mL, 9.4 mmol) and 4-dimethylaminopyridine (3.8 mg, 0.03 mmol) in 1,4-dioxane (17 mL) were combined to give a light brown solution. This reaction mixture was heated at 80° C. with stirring for a period of 16 h. After cooling DIPEA (2.1 mL, 4.0 mmol) was added and the reaction mixture was cooled in ice bath. Then iodine (1.5 g, 6.3 mmol) in 1,4-dioxane (2 mL) was added and the reaction was continued in the up-heating ice bath for a period of 16 h. The crude reaction mixture was concentrated under reduced pressure and purified by column chromatography (amino modified silica gel, eluting with ethyl acetate/n-hexane 30:70 v/v) to afford the title compound as off white solid (550 mg, 54%). ¹H NMR (DMSO-d6, 400 MHz): 1.39 (s, 9H), 1.44 (s, 2H), 1.83-1.87 (m, 2H), 2.19 (s, 3H), 2.24 (s, 2H), 3.07 (d, J=11.0 Hz, 2H), 3.18 (d, J=9.6 Hz, 2H), 3.53 (s, 1H), 6.07 (s, 1H), 6.82 (s, 1H). MS (ES+) m/z 324.1 [M+H].

Step 2: (1R,5S,8s)-3-(3-Methylisothiazol-5-yl)-3-azabicyclo[3.2.1]octan-8-amine (Int-96)

To a solution of tert-butyl ((1R,5S,8s)-3-(3-methylisothiazol-5-yl)-3-azabicyclo[3.2.1]octan-8-yl)carbamate (Int-95, 550 mg, 1.7 mmol) in dichloromethane (10 mL) was added trifluoroacetic acid (0.9 mL, 11.9 mmol) at 0° C. After 5 min reaction mixture was allowed to warm to 25° C. and continued at the same temperature for 6 h. The resulting mixture was concentrated under reduced pressure followed by azeotrope with toluene (3×5 mL). This crude was purified by column chromatography (amino modified silica gel, eluting with MeOH/dichloromethane 10:90 v/v) to afford the title compound as off white solid (265 mg, 70%). ¹H NMR (DMSO-d6, 400 MHz): 1.39 (d, J=7.6 Hz, 2H), 1.52 (s, 2H), 1.88-1.93 (m, 2H), 1.99 (s, 2H), 2.18 (s, 3H), 3.00-3.02 (m, 2H), 3.13-3.17 (m, 2H), 6.04 (s, 1H). MS (ES+) m/z 224.4 [M+H].

Int-99

(1R,5S,8s)-3-(2-(Trifluoromethyl)pyridin-4-yl)-3-azabicyclo[3.2.1]octan-8-amine

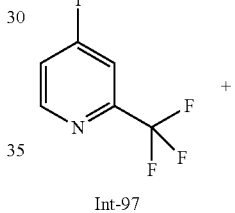
Int-97

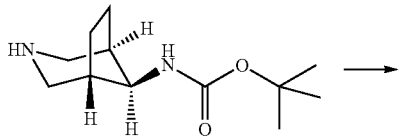
Int-94

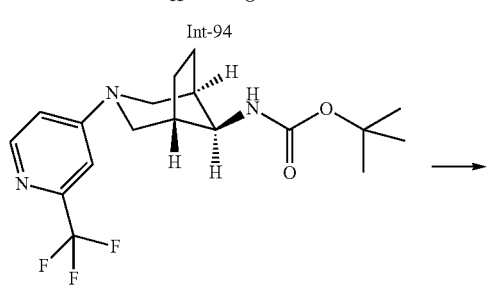
Int-98

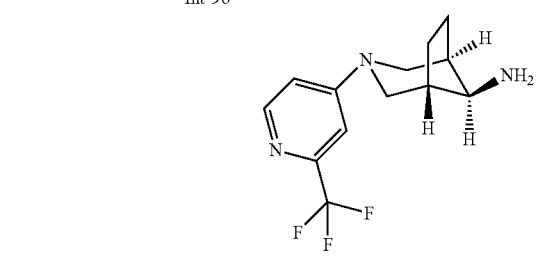
Int-99

Step 1: tert-Butyl N-[(1R,5S,8s)-3-[2-(trifluoromethyl)pyridin-4-yl]-3-azabicyclo[3.2.1]octan-8-yl]carbamate (Int-98)

To a solution of 4-iodo-2-(trifluoromethyl)pyridine (Int-97, 1.0 g, 3.7 mmol) and tert-butyl N-[(1R,5S,8s)-3-azabicyclo[3.2.1]octan-8-yl]carbamate (Int-94, 1.1 g, 4.8 mmol) in N-methyl-2-pyrrolidone (7 mL) was added diisopropylethylamine (0.9 mL, 5.1 mmol). The reaction mixture was degassed with argon and then stirred at 150° C. for 6 h. The reaction mixture was poured into water (100 mL) and extracted with EtOAc (300 mL). The organic layer was separated and dried over sodium sulphate. Solvent was evaporated under reduced pressure followed by purification by combi-flash column chromatography (silica gel, eluting with ethyl acetate/n-hexane 20:80 v/v) to afford the title compound as off white solid (900 mg, 66%). $^1$H NMR (DMSO-d6, 400 MHz): 1.40 (s, 9H), 1.75-1.93 (m, 2H), 2.31 (s, 2H), 2.97 (d, J=11.5 Hz, 2H), 3.52-3.58 (m, 1H), 3.71 (d, J=9.5 Hz, 2H), 6.82 (s, 1H), 6.93 (dd, J=5.9, 2.2 Hz, 1H), 7.09 (d, J=2.2 Hz, 1H), 8.24 (d, J=5.9 Hz, 1H). MS (ES+) m/z 371.8 [M+H].

Step 2: (1R,5S,8s)-3-(2-(Trifluoromethyl)pyridin-4-yl)-3-azabicyclo[3.2.1]octan-8-amine (Int-99)

To a solution of tert-butyl N-[(1R,5S,8s)-3-[2-(trifluoromethyl)pyridin-4-yl]-3-azabicyclo[3.2.1]octan-8-yl]carbamate (Int-98, 900 mg, 2.4 mmol) in dichloromethane (5 mL) was added trifluoroacetic acid (1.9 mL, 24.2 mmol) at 0° C. After 5 min reaction mixture was allowed to warm to 25° C. and stirring continued at the same temperature for 2h. The resulting crude was concentrated under reduced pressure followed by azeotrope with toluene (3×5 mL). This crude was further purified by column chromatography (amino modified silica gel, eluting with MeOH/dichloromethane 10:90 v/v) to afford the title compound as light yellow solid (600 mg, 91%). $^1$H NMR (400 MHz, DMSO-d6) δ 1.47 (d, J=7.8 Hz, 2H), 1.85-1.93 (m, 2H), 2.24 (s, 2H), 2.97 (d, J=11.4 Hz, 2H), 3.26 (s, 1H), 3.73 (d, J=9.8 Hz, 2H), 5.17-5.22 (br s, 2H), 6.93 (d, J=3.5 Hz, 1H), 7.09 (s, 1H), 8.25 (d, J=5.7 Hz, 1H). MS (ES+) m/z 271.7 [M+H].

Int-102

(1R,5S,8s)-3-(3-Methyl-1,2,4-oxadiazol-5-yl)-3-azabicyclo[3.2.1]octan-8-amine

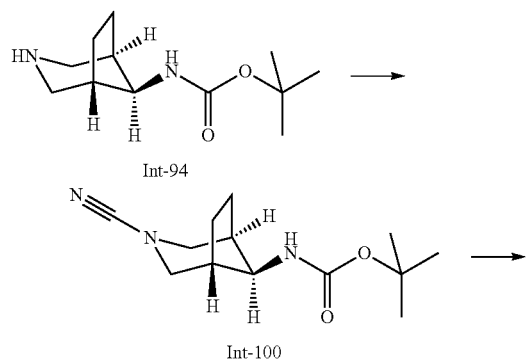

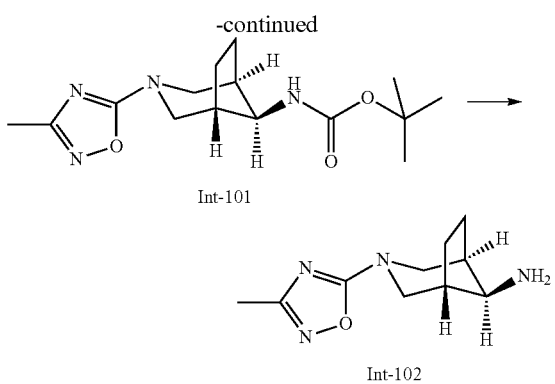

Step 1: tert-Butyl N-[(1R,5S,8s)-3-cyano-3-azabicyclo[3.2.1]octan-8-yl]carbamate (Int-100)

To a solution of (tert-butyl N-[(1R,5S,8s)-3-azabicyclo[3.2.1]octan-8-yl]carbamate (Int-94, 2.0 g, 8.0 mmol) in dichloromethane (28 mL) in was added NaHCO$_3$ (2.2 g, 26.5 mmol) in H$_2$O (8 mL) under ice cold condition. To it BrCN (1.1 g, 10.6 mmol) was added and allowed to attain at 25° C. followed by stirring at same temperature for a period of 5 h. The reaction mixture was diluted with water and extracted with dichloromethane. The organic layer was dried followed by evaporation of solvent under reduced pressure to title compound as white solid (2.0 g, crude). MS (ES+) m/z 252.0 [M+H].

Step 2: tert-Butyl N-[(1R,5S,8s)-3-(3-methyl-1,2,4-oxadiazol-5-yl)-3-azabicyclo[3.2.1]octan-8-yl]carbamate (Int-101)

To a solution of tert-butyl N-[(1R,5S,8s)-3-cyano-3-azabicyclo[3.2.1]octan-8-yl]carbamate (Int-100, 2.0 g, 8.0 mmol) and N-hydroxyethanimidamide (590 mg, 8.0 mmol) in DMF (30 mL) was added p-toluenesulfonic acid (303 mg, 1.6 mmol) and solid ZnCl$_2$ (217 mg, 1.6 mmol). The reaction mixture was heated at 80° C. for a period of 5 h. Then, ice-water was added and the reaction mixture was extracted with EtOAc (3×20 mL). The organic layer was dried and concentrated under reduced pressure to afford the crude which was purified by column chromatography (silica gel, eluting with EtOAc/n-hexane 60:40 v/v) to yield the title compound as white solid (1.5 g, 61%). $^1$H NMR (DMSO-d6, 400 MHz): 1.36-1.38 (m, 2H), 1.39 (s, 9H), 1.80-1.87 (m, 2H), 2.08 (s, 3H), 2.23 (s, 2H), 3.25 (d, J=12.2 Hz, 2H), 3.55 (d, J=3.3 Hz, 1H), 3.66 (d, J=9.9 Hz, 2H), 6.83 (d, J=5.7 Hz, 1H). MS (ES+) m/z 309.3 [M+H].

Step 3: (1R,5S,8s)-3-(3-Methyl-1,2,4-oxadiazol-5-yl)-3-azabicyclo[3.2.1]octan-8-amine (Int-102)

To a solution of tert-butyl N-[(1R,5S,8s)-3-(3-methyl-1,2,4-oxadiazol-5-yl)-3-azabicyclo[3.2.1]octan-8-yl]carbamate (Int-101, 1.5 g, 4.8 mmol) in dichloromethane (20 mL) was added trifluoroacetic acid (3.7 mL, 48.6 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford crude which was purified by column chromatography (amino modified silica gel, eluting with MeOH/dichloromethane 5:95 v/v) to yield the title compound as off-white solid (700 mg, 69%). MS (ES+) m/z 209.1 [M+H].

Int-105

(1R,5S,8s)-3-(5-Methyl-1,3,4-oxadiazol-2-yl)-3-azabicyclo[3.2.1]octan-8-amine

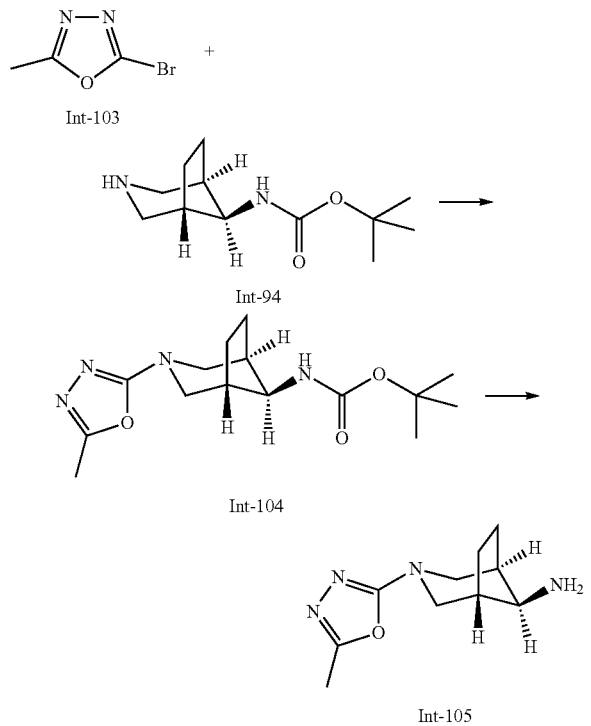

Step 1: tert-Butyl N-[(1R,5S,8s)-3-(5-methyl-1,3,4-oxadiazol-2-yl)-3-azabicyclo[3.2.1]octan-8-yl]carbamate (Int-104)

To a solution of tert-butyl N-[(1R,5S,8s)-3-azabicyclo[3.2.1]octan-8-yl]carbamate (Int-94, 50 mg, 0.2 mmol) in MeOH (1.3 mL) was added 2-bromo-5-methyl-1,3,4-oxadiazole (Int-103, 72 mg, 0.4 mmol) and triethylamine (0.1 ml, 0.8 mmol) in a sealed tube. The reaction was stirred at 130° C. for 16 h. After complete consumption of starting material (as monitored by TLC) reaction mixture was concentrated in vacuo followed by column chromatography (silica gel, eluting with EtOAc/n-hexane 60:40 v/v) to yield the title compound as white solid (50 mg, 73%). ¹H NMR (DMSO-d6, 400 MHz): 1.39 (s, 10H), 1.79-1.87 (m, 2H), 2.22 (s, 2H), 2.31 (s, 3H), 3.14 (d, J=11.5 Hz, 2H), 3.47-3.52 (m, 3H), 6.81 (br s, 1H). MS (ES+) m/z 309.0 [M+H].

Step 2: (1R,5S,8s)-3-(5-Methyl-1,3,4-oxadiazol-2-yl)-3-azabicyclo[3.2.1]octan-8-amine (Int-105)

To a solution of tert-butyl N-[(1R,5S,8s)-3-(5-methyl-1,3,4-oxadiazol-2-yl)-3-azabicyclo[3.2.1]octan-8-yl]carbamate (Int-104, 500 mg, 1.6 mmol) in dichloromethane (10 mL) was added trifluoroacetic acid (1.2 mL, 16.2 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the crude which was purified by column chromatography (amino modified silica gel, eluting with MeOH/dichloromethane 10:90 v/v) to yield the title compound as off-white solid (250 mg, 73%). ¹H NMR (DMSO-d6, 400 MHz): 1.37 (d, J=7.6 Hz, 2H), 1.87-1.89 (m, 2H), 1.97 (s, 2H), 2.30 (s, 3H), 2.99 (s, 1H), 3.07 (d, J=11.5 Hz, 2H), 3.47 (d, J=11.5 Hz, 2H). MS (ES+) m/z 209.1 [M+H].

Int-108

(1R,5S,8s)-3-(6-Chloropyrimidin-4-yl)-3-azabicyclo[3.2.1]octan-8-amine

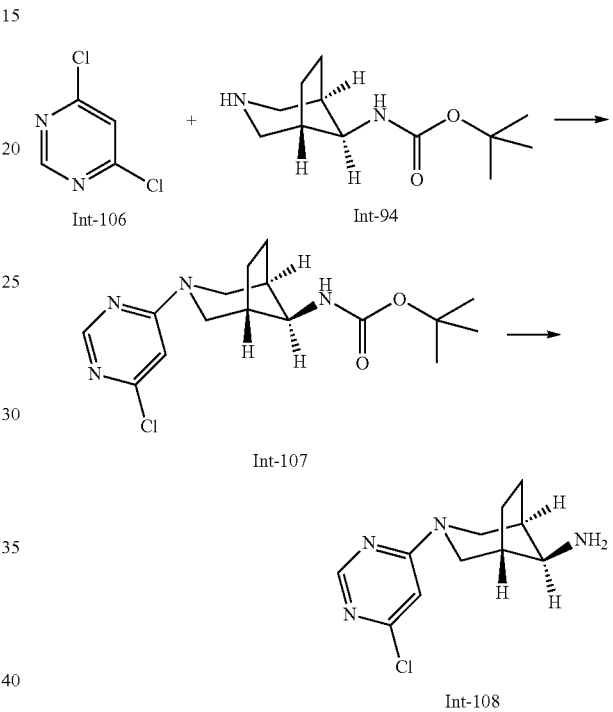

Step 1: tert-Butyl N-[(1R,5S,8s)-3-(6-chloropyrimidin-4-yl)-3-azabicyclo[3.2.1]octan-8-yl]carbamate (Int-107)

To a solution of 4,6-dichloropyrimidine (Int-106, 329.6 g, 3.7 mmol) and tert-butyl N-[(1R,5S,8s)-3-azabicyclo[3.2.1]octan-8-yl]carbamate (Int-94, 500.0 g, 2.2 mmol) in dry ethanol (81 mL) was added triethylamine (1.5 mL, 11.0 mmol). The reaction mixture was degassed with argon and then stirred at 130° C. for 6 h. After completion of reaction, as monitored by thin layer chromatography, solvent was evaporated under reduced pressure to obtain the crude which was purified by combi-flash chromatography (silica gel, 10 g, eluting with ethyl acetate/n-hexane 40:60 v/v) to afford the title compound as white solid (400 mg, 53%). ¹H NMR (DMSO-d6, 400 MHz): 1.28 (d, J=7.7 Hz, 2H), 1.39 (s, 9H), 1.78-1.80 (m, 2H), 2.25 (br s, 2H), 2.97-3.00 (m, 2H), 3.57 (s, 1H), 6.79 (br s, 1H), 6.85 (s, 1H), 8.30 (s, 1H). MS (ES+) m/z 339.1 [M+H].

Step 2: (1R,5S,8s)-3-(6-Chloropyrimidin-4-yl)-3-azabicyclo[3.2.1]octan-8-amine (Int-108)

To a solution of tert-butyl N-[(1R,5S,8s)-3-(6-chloropyrimidin-4-yl)-3-azabicyclo[3.2.1]octan-8-yl]carbamate (Int- 107, 400 mg, 1.2 mmol) in dichloromethane (5 mL) was added trifluoroacetic acid (0.9 mL, 11.0 mmol) at 0° C. After 5 min reaction mixture was allowed to warm to 25° C. and stirring continued at the same temperature for 4 h. The resulting crude was concentrated under reduced pressure followed by azeotrope with toluene (3×5 mL). This crude was further purified by column chromatography (amino modified silica gel, eluting with MeOH/dichloromethane 10:90 v/v) to afford the title compound as white solid (240 mg, 85%). $^1$H (DMSO-d6, 400 MHz): 1.23-1.26 (m, 2H), 1.55 (br s, 2H), 1.84-1.86 (m, 2H), 2.00 (s, 2H), 2.93 (br s, 2H), 3.06 (s, 1H), 6.83 (s, 1H), 8.29 (s, 1H). MS (ES+) m/z 239.2 [M+H].

Int-111

(1R,5S,8s)-3-(2-Methoxy-4-pyridyl)-3-azabicyclo[3.2.1]octan-8-amine

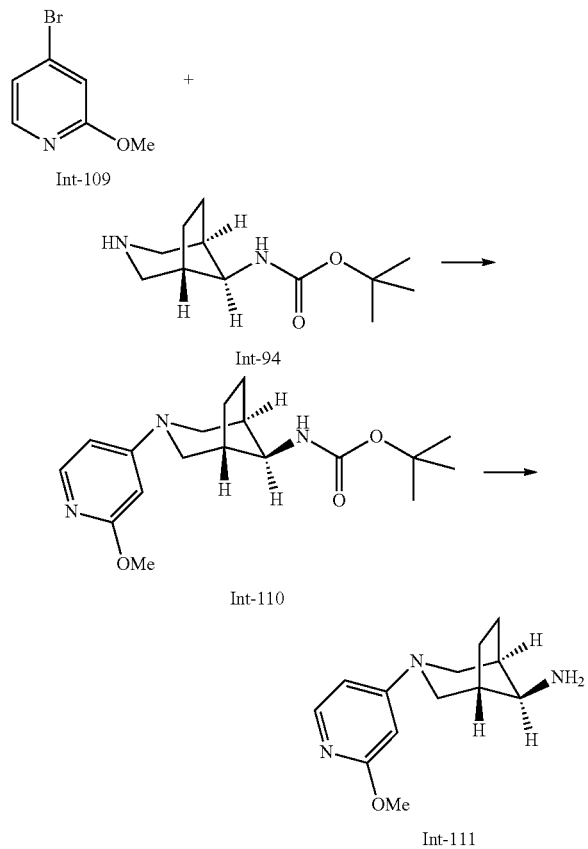

Step 1: tert-Butyl N-[(1R,5S,8s)-3-(2-methoxy-4-pyridyl)-3-azabicyclo[3.2.1]octan-8-yl]carbamate (Int-110)

To a solution of tert-butyl N-[(1R,5S,8s)-3-azabicyclo[3.2.1]octan-8-yl]carbamate (Int-94, 50 mg, 0.2 mmol) and 4-bromo-2-methoxypyridine (Int-109, 41 mg, 0.2 mmol) in dry toluene (2.5 mL) in sealed tube was degassed with argon over a period of 5 min. To it then added sodium tertbutoxide (63.7 mg, 0.7 mmol) and 4,5-bis(diphenylphosphino)-9,9-dimethylxanthene ("Xantphos", CAS [161265-03-8], 1.3 mg, 2.2 µmol). The reaction mixture was again degassed with argon for 5 min followed by addition of tris(dibenzylideneacetone)dipalladium(0) ("Pd$_2$(dba)$_3$", CAS [51364-51-3], 4.0 mg, 4.4 µmol). The reaction mixture was stirred at 100° C. for 16 h. Reaction mixture was then concentrated under reduced pressure to get crude which was purified by column chromatography (silica gel, eluting with EtOAc/n-hexane 10:90 v/v) to yield the title compound as off white solid (30 mg, 40%). $^1$H NMR (DMSO-d6, 400 MHz): 1.39 (s, 9H), 1.81 (s, 2H), 2.26 (br s, 2H), 2.84 (d, J=11.2 Hz, 2H), 3.48 (br s, 1H), 3.56 (d, J=10.4 Hz, 2H), 3.74 (s, 3H), 5.97 (s, 1H), 6.45 (d, J=4.2 Hz, 1H), 6.79 (s, 1H), 7.74 (d, J=5.8 Hz, 1H). MS (ES+) m/z 334.2 [M+H].

Step 2: (1R,5S,8s)-3-(2-Methoxy-4-pyridyl)-3-azabicyclo[3.2.1]octan-8-amine (Int-111)

To a solution of tert-butyl N-[(1R,5S,8s)-3-(2-methoxy-4-pyridyl)-3-azabicyclo[3.2.1]octan-8-yl]carbamate (Int-110, 100 mg, 0.3 mmol) in dichloromethane (5.0 mL) was added trifluoroacetic acid (0.2 mL, 3.0 mmol) at 0° C. After 5 min reaction mixture was allowed to warm to 25° C. and continued the stirring at the same temperature for 4 h. The resulting mixture was concentrated under reduced pressure followed by dilution with saturated potassium carbonate solution (10 mL) and extraction with 10% MeOH in dichloromethane (6×20 mL). After drying the separated organic part, the solvent was evaporated to afford the title compound as yellow semi-solid (50 mg, crude). MS (ES+) m/z 234.3 [M+H].

Int-114

(1R,5S,8s)-3-(6-Methylpyrimidin-4-yl)-3-azabicyclo[3.2.1]octan-8-amine

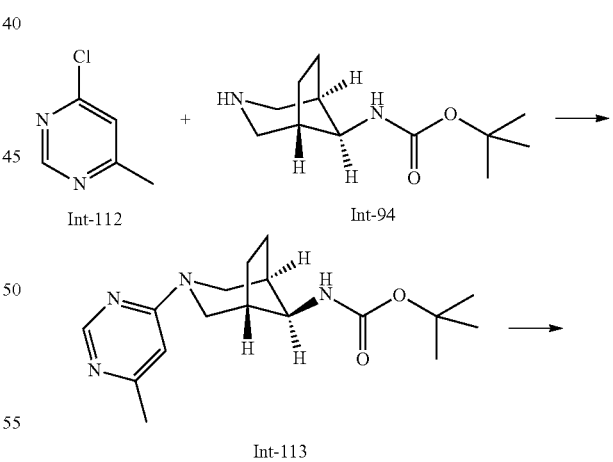

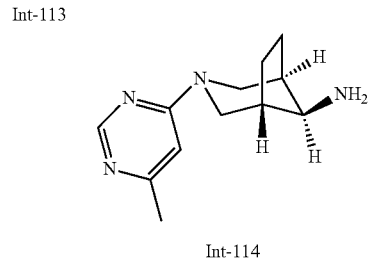

Step 1: tert-Butyl N-[(1R,5S,8s)-3-(6-methylpyrimidin-4-yl)-3-azabicyclo[3.2.1]octan-8-yl]carbamate (Int-113)

In a sealed tube tert-butyl N-[(1R,5S,8s)-3-azabicyclo[3.2.1]octan-8-yl]carbamate (Int-94, 500 mg, 2.21 mmol) was dissolved in EtOH (10 mL) and 4-chloro-6-methylpyrimidine (869 mg, 6.63 mmol) was added followed by triethylamine (894 mg, 1.23 mL, 8.84 mmol). The reaction mixture was stirred at 130° C. overnight. The crude reaction mixture was concentrated in vacuum. The residue was diluted with 20 mL of CH$_2$Cl$_2$ and 20 mL of water. The organic phase was extracted with CH$_2$Cl$_2$ (3×20 mL), dried over MgSO$_4$ and concentrated in vacuum. The crude material was purified by flash chromatography (0% to 100% EtOAc in heptane) to afford the title compound as a yellow solid (496 mg, 71% yield). MS (ES+) m/z: 319.2 [M+H].

Step 2: (1R,5S,8s)-3-(6-Methylpyrimidin-4-yl)-3-azabicyclo[3.2.1]octan-8-amine (Int-114)

To a light yellow solution of tert-butyl N-[(1R,5S,8s)-3-(6-methylpyrimidin-4-yl)-3-azabicyclo[3.2.1]octan-8-yl]carbamate (Int-113, 260 mg, 817 μmol) in CH$_2$Cl$_2$ (8 mL) was added TFA (931 mg, 629 μl, 8.17 mmol). The reaction mixture was stirred at room temperature over night and concentrated in vacuum. The crude material was purified by Ion-exchange column (Si-SCX-2, 10 g, washed with MeOH and liberated with MeOH (NH$_3$ 2 M)) to afford the title compound (195 mg, 804 μmol, 98.5% yield) that was used in the next step without further purification. MS (ES+) m/z: 219.2 [M+H].

Int-117

(1R,5S,8s)-3-(5-Fluoro-2-methyl-pyridin-4-yl)-3-azabicyclo[3.2.1]octan-8-amine

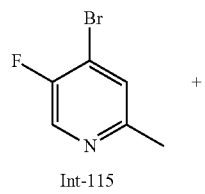

Int-115

+

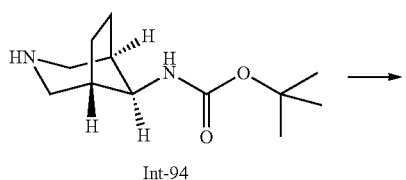

Int-94

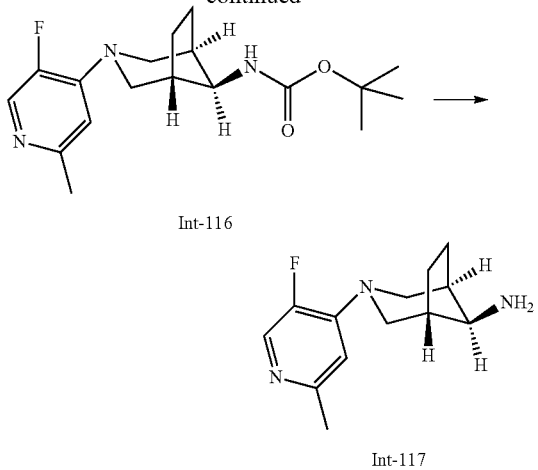

Int-116

Int-117

Step 1: tert-Butyl N-[(1R,5S,8s)-3-(5-fluoro-2-methyl-pyridin-4-yl)-3-azabicyclo[3.2.1]octan-8-yl]carbamate (Int-116)

In a 5 mL pressure vial, tert-butyl N-[(1R,5S,8s)-3-azabicyclo[3.2.1]octan-8-yl]carbamate (Int-94, 50 mg, 221 μmol) was dissolved in NMP (1 mL), diisopropylethylamine (57.1 mg, 442 μmol) and 4-bromo-5-fluoro-2-methylpyridine (Int-115, 63 mg, 331 μmol) were added. The vial was closed under argon and the reaction mixture was stirred for 18 h at 150° C. After that, the mixture was diluted with water (15 mL) and extracted with dichloromethane (3×15 mL). The combined organic layers were dried (magnesium sulfate) and concentrated in vacuo. The crude product was purified by column chromatography (silica gel, 12 g, eluting with EtOAc/n-heptane, gradient 0:100 to 80:20 v/v) to afford the title compound as white powder (39 mg, 53%). HPLC (method LCMS_fastgradient) t$_R$=0.82 min. $^1$H NMR (CDCl$_3$, 300 MHz): δ 1.47 (s, 9H), 1.74-1.82 (m, 4H), 2.28-2.35 (m, 2H), 2.43 (s, 3H), 2.97-3.04 (m, 2H), 3.50-3.59 (m, 2H), 3.67-3.75 (m, 1H), 4.41-4.50 (m, 1H), 6.50 (d, J=7.7 Hz, 1H), 8.06 (d, J=6.0 Hz, 1H). MS (ES+) m/z 336.2 [M+H].

Step 2: (1R,5S,8s)-3-(5-Fluoro-2-methyl-pyridin-4-yl)-3-azabicyclo[3.2.1]octan-8-amine (Int-117)

In a 50 mL flask, tert-butyl N-[(1R,5S,8s)-3-(5-fluoro-2-methyl-pyridin-4-yl)-3-azabicyclo[3.2.1]octan-8-yl]carbamate (Int-116, 126 mg, 376 μmol) was dissolved in dichloromethane (1.8 mL), and concentrated hydrochloric acid (37% m/m, 222 mg, 185 μl, 2.25 mmol) was added. The reaction mixture was stirred for 2 h at room temperature. Then, saturated aqueous sodium hydrogencarbonate solution (10 mL) was added, the mixture was extracted with dichloromethane (6×15 mL). The combined organic layers were dried (magnesium sulfate) and concentrated in vacuo to yield the title compound (81 mg, 92%) as a white powder, which was used in the next step without further purification. HPLC (method LCMS_fastgradient) t$_R$=0.13 min. $^1$H NMR (CDCl$_3$, 300 MHz): δ1.65-1.76 (m, 2H), 1.87-1.98 (m, 2H), 2.06-2.14 (m, 2H), 2.42 (d, J=0.6 Hz, 3H), 2.90-2.97 (m, 2H), 3.06 (s, 1H), 3.52-3.59 (m, 2H), 6.50 (d, J=7.7 Hz, 1H), 8.05 (d, J=6.0 Hz, 1H). MS (ES+) m/z 236.2 [M+H].

Int-120

(1R,5S,8s)-3-(6-Methoxypyrimidin-4-yl)-3-azabicyclo[3.2.1]octan-8-amine

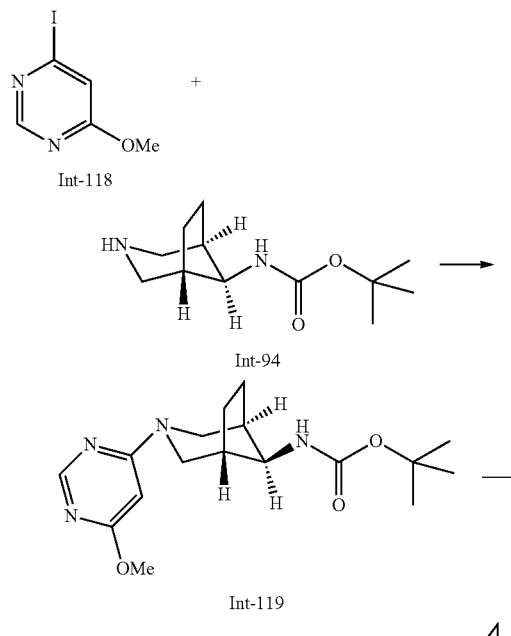

Step 1: tert-Butyl N-[(1R,5S,8s)-3-(6-methoxypyrimidin-4-yl)-3-azabicyclo[3.2.1]octan-8-yl]carbamate (Int-119)

In analogy to the preparation of the intermediate Int-113 from tert-butyl N-[(1R,5S,8s)-3-azabicyclo[3.2.1]octan-8-yl]carbamate (Int-94, 250 mg, 1.1 mmol) and 4-iodo-6-methoxypyrimidine (Int-118, 391 mg, 1.66 mmol) in a sealed tube at 100° C. using DMF as solvent in the presence of $K_2CO_3$ (458 mg, 3.31 mmol), the title compound (315 mg, 85% yield) was obtained as a white solid. MS (ES+) m/z: 335.2 [M+H].

Step 2: (1R,5S,8s)-3-(6-Methoxypyrimidin-4-yl)-3-azabicyclo[3.2.1]octan-8-amine (Int-120)

In analogy to the preparation of intermediate Int-114 from tert-butyl N-[(1R,5S,8s)-3-(6-methoxypyrimidin-4-yl)-3-azabicyclo[3.2.1]octan-8-yl]carbamate (Int-119, 330 mg, 987 μmol) in $CH_2Cl_2$ in the presence of TFA (1.13 g, 760 μl, 9.87 mmol), the title compound (222 mg, 96% yield) was obtained as a white solid and used directly in the next step without further purification. MS (ES+) m/z: 235.2 [M+H].

Int-123

(1R,5S,8s)-3-(2-Chloro-4-pyridyl)-3-azabicyclo[3.2.1]octan-8-amine

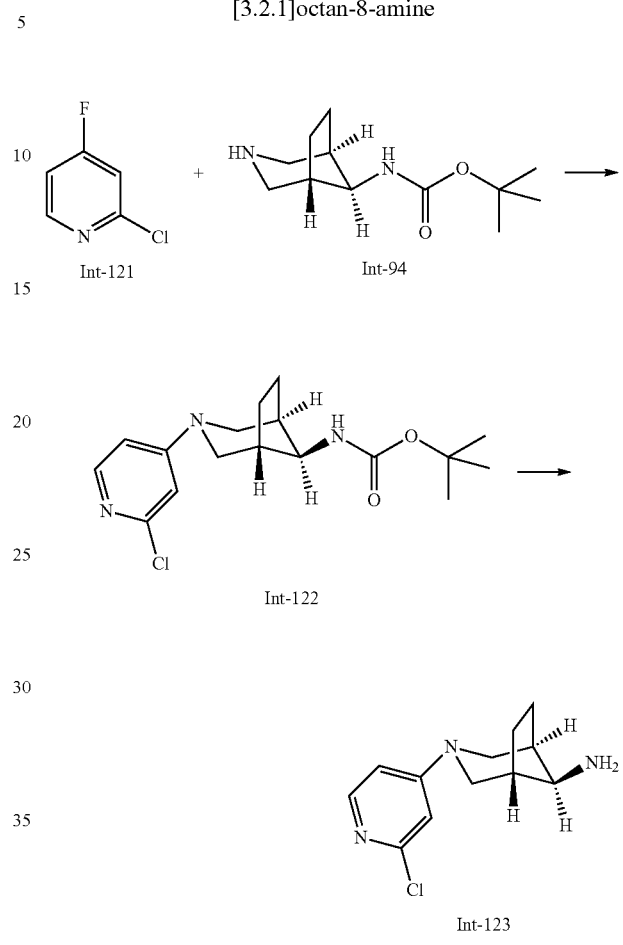

Step 1: tert-Butyl N-[(1R,5S,8s)-3-(2-chloro-4-pyridyl)-3-azabicyclo[3.2.1]octan-8-yl]carbamate (Int-122)

In analogy to the preparation of the intermediate Int-113 from tert-butyl N-[(1R,5S,8s)-3-azabicyclo[3.2.1]octan-8-yl]carbamate (Int-94, 120 mg, 0.53 mmol) and 2-chloro-4-fluoro-pyridine (Int-121, 76 mg, 0.58 mmol) in a sealed tube at 150° C. using NMP as solvent in the presence of DIPEA (137 mg, 0.185 ml, 1.06 mmol), the title compound (150 mg, 82% yield) was obtained as a white solid. MS (ES+) m/z: 338.2 [M+H].

Step 2: (1R,5S,8s)-3-(2-Chloro-4-pyridyl)-3-azabicyclo[3.2.1]octan-8-amine (Int-123)

In analogy to the preparation of intermediate Int-114 from tert-butyl N-[(1R,5S,8s)-3-[2-(trifluoromethyl)-4-pyridyl]-3-azabicyclo[3.2.1]octan-8-yl]carbamate (Int-122, 147 mg, 435 μmol) in $CH_2Cl_2$ in the presence of HCl 37% (257 mg, 214 μl, 2.61 mmol), the title compound (90 mg, 87% yield) was obtained as a white solid and used directly in the next step without further purification. MS (ES+) m/z: 238.1 [M+H].

Int-126

(1R,5S,8s)-3-(6-Chloropyridazin-4-yl)-3-azabicyclo[3.2.1]octan-8-amine

Int-128

(1R,5S,8s)-3-(6-Methoxypyridazin-4-yl)-3-azabicyclo[3.2.1]octan-8-amine

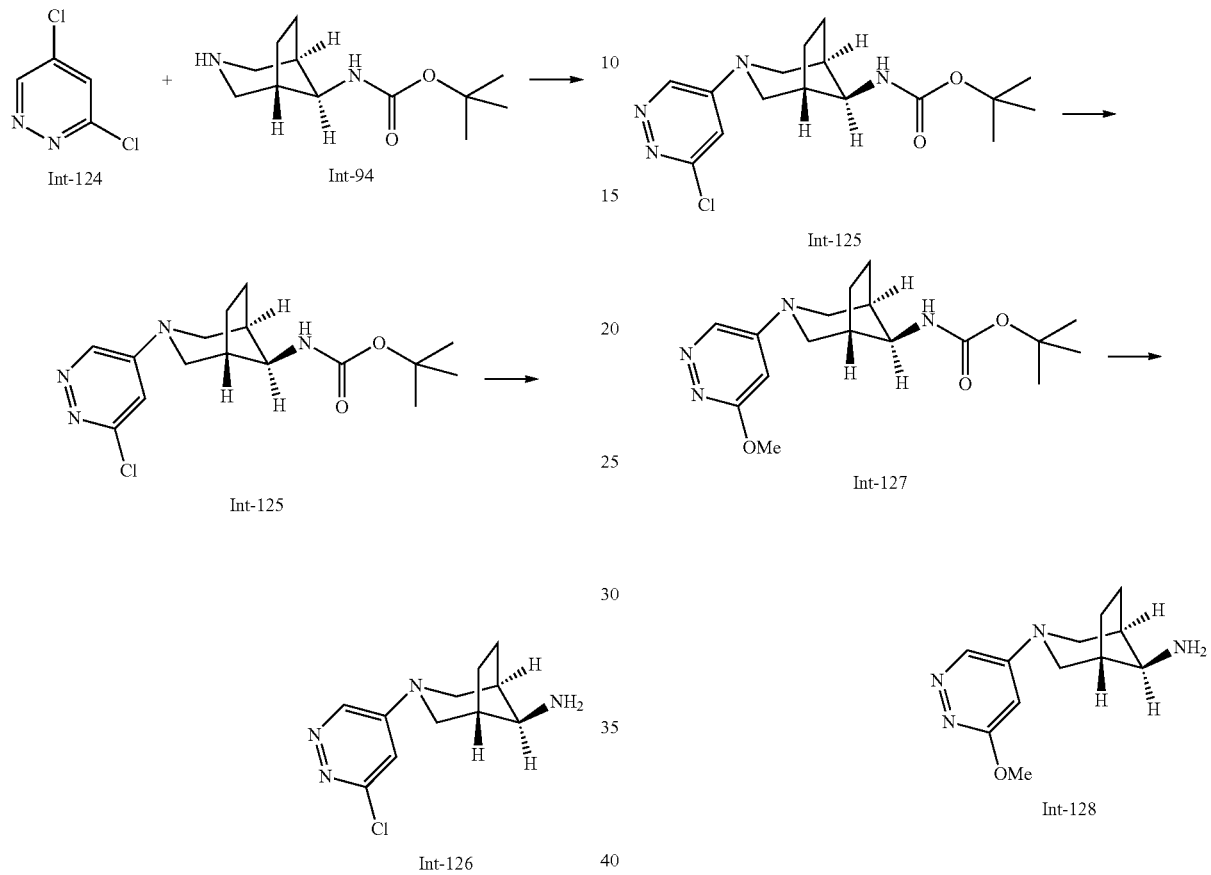

Step 1: tert-Butyl N-[(1R,5S,8s)-3-(6-chloropyridazin-4-yl)-3-azabicyclo[3.2.1]octan-8-yl]carbamate (Int-125)

In analogy to the preparation of the intermediate Int-113 from tert-butyl N-[(1R,5S,8s)-3-azabicyclo[3.2.1]octan-8-yl]carbamate (Int-94, 2.00 g, 8.84 mmol) and 3,5-dichloropyridazine (Int-124, 2.0 g, 13.4 mmol) in a sealed tube at 90° C. using EtOH as solvent in the presence of Et$_3$N (3.63 g, 5.0 mL, 35.9 mmol), the title compound (1.71 g, 54%) was obtained as a white solid. MS (ES+) m/z: 339.2 [M+H].

Step 2: (1R,5S,8s)-3-(6-Chloropyridazin-4-yl)-3-azabicyclo[3.2.1]octan-8-amine (Int-126)

In analogy to the preparation of intermediate Int-114 from tert-butyl N-[(1R,5S,8s)-3-(6-chloropyridazin-4-yl)-3-azabicyclo[3.2.1]octan-8-yl]carbamate (Int-125, 0.93 g, 2.72 mmol) in CH$_2$Cl$_2$ in the presence of HCl 37% (1.61 g, 1.34 mL, 16.3 mmol), the title compound (0.65 g, 100%) was obtained as a white solid and used directly in the next step without further purification. MS (ES+) m/z: 239.1 [M+H].

Step 1: tert-Butyl N-[(1R,5S,8s)-3-(6-methoxypyridazin-4-yl)-3-azabicyclo[3.2.1]octan-8-yl]carbamate (Int-127)

To a solution of tert-butyl N-[(1R,5S,8s)-3-(6-chloropyridazin-4-yl)-3-azabicyclo[3.2.1]octan-8-yl]carbamate (Int-125, 963 mg, 2.70 mmol) in MeOH (22 mL) in a sealed tube was added a solution of NaOMe in methanol (25%, 1.9 mL, 8.3 mmol). The reaction mixture was heated at 85° C. over night. The reaction mixture was adsorbed on Isolute HM-N and a column chromatography gave the title compound (362 mg, 38%) as a white solid. MS (ES+) m/z: 335.2 [M+H].

Step 2: (1R,5S,8s)-3-(6-Methoxypyridazin-4-yl)-3-azabicyclo[3.2.1]octan-8-amine (Int-128)

In analogy to the preparation of intermediate Int-114 from tert-butyl N-[(1R,5S,8s)-3-(6-methoxypyridazin-4-yl)-3-azabicyclo[3.2.1]octan-8-yl]carbamate (Int-127, 0.93 g, 2.72 mmol) in CH$_2$Cl$_2$ in the presence of TFA (1.12 g, 0.76 mL, 9.86 mmol), the title compound (225 mg, 96%) was obtained as a white solid and used directly in the next step without further purification. MS (ES+) m/z: 235.2 [M+H].

Int-131

(1R,5S,8s)-8-((5-(3-Fluorophenoxy)-1-(2,2,2-trifluoroethyl)-1H-1,2,4-triazol-3-yl)amino)-3-azabicyclo[3.2.1]octane-3-carbonitrile

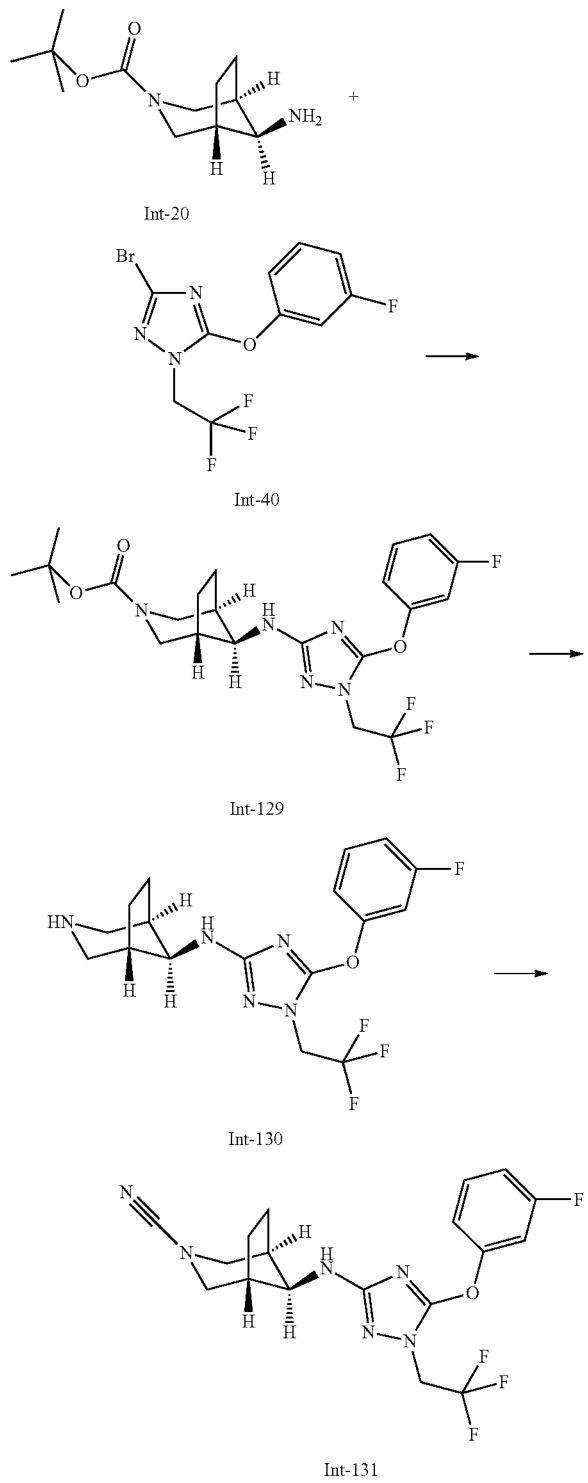

Step 1: (1R,5S,8s)-tert-Butyl 8-((5-(3-fluorophenoxy)-1-(2,2,2-trifluoroethyl)-1H-1,2,4-triazol-3-yl)amino)-3-azabicyclo[3.2.1]octane-3-carboxylate (Int-129)

In an 8 mL microwave vial, (1R,5S,8s)-tert-butyl 8-amino-3-azabicyclo[3.2.1]octane-3-carboxylate (Int-20, 75 mg, 331 µmol) was dissolved in dry 1,4-dioxane (4 mL) and 3-bromo-5-(3-fluorophenoxy)-1-(2,2,2-trifluoroethyl)-1H-1,2,4-triazole (Int-40, 124 mg, 365 µmol), sodium tert-butoxide (127 mg, 1.33 mmol), 2-dicyclohexylphosphino-2',6'-diisopropoxybiphenyl ("Ruphos", CAS [787618-22-8], 32.6 mg, 66.3 µmol) and chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 52.9 mg, 66.3 µmol) were added. The reaction mixture was degassed with argon for 10 min, the vial was capped and the mixture was stirred for 18 h at 120° C. Then, it was concentrated under reduced pressure and the resulting crude product was purified by column chromatography (silica gel, 70 g, eluting with ethyl acetate/n-heptane, gradient 0:100 to 67:33 v/v) to afford the title compound as white foam (36 mg, 22%). HPLC (method LCMS_fastgradient) $t_R$=1.38 min. $^1$H NMR (CDCl$_3$, 300 MHz): δ 1.46 (s, 9H), 1.51-1.61 (m, 2H), 1.71-1.80 (m, 2H), 2.24-2.33 (m, 2H), 2.87-3.07 (m, 2H), 3.60 (d, J=6.1 Hz, 1H), 3.77-4.02 (m, 2H), 3.95 (d, J=6.1 Hz, 1H), 4.51 (q, J=8.2 Hz, 2H), 6.94-7.02 (m, 1H), 7.05-7.12 (m, 2H), 7.33-7.43 (m, 1H). MS (ES+) m/z 430.3 [M+H—CH$_2$=CMe$_2$].

Step 2: (1R,5S,8s)-N-(5-(3-Fluorophenoxy)-1-(2,2,2-trifluoroethyl)-1H-1,2,4-triazol-3-yl)-3-azabicyclo[3.2.1]octan-8-amine (Int-130)

In a 5 mL round bottomed flask, (1R,5S,8s)-tert-butyl 8-((5-(3-fluorophenoxy)-1-(2,2,2-trifluoroethyl)-1H-1,2,4-triazol-3-yl)amino)-3-azabicyclo[3.2.1]octane-3-carboxylate (Int-129, 36 mg, 74.2 µmol) was dissolved in dichloromethane (1 mL) and trifluoroacetic acid (84.6 mg, 57 µL, 742 µmol) was added. The mixture was stirred for 17 h at room temperature. After that, it was concentrated in vacuo, the residue was redissolved in dichloromethane (1 mL) and saturated aqueous solution of sodium hydrogencarbonate (2 mL). The aqueous layer was extracted with dichloromethane (3×10 mL), the combined organic extracts were dried (sodium sulfate) and concentrated in vacuo to yield the crude product as light yellow solid, which was used without further purification in the next step (28.5 mg, 99%). HPLC (method LCMS_fastgradient) $t_R$=0.88 min. $^1$H NMR (CDCl$_3$, 300 MHz): δ1.55-1.64 (m, 2H), 1.76-1.85 (m, 2H), 2.19-2.27 (m, 2H), 2.78 (dd, J=3.2, 12.9 Hz, 2H), 2.91 (d, J=12.5 Hz, 2H), 3.59 (d, J=6.3 Hz, 1H), 3.95 (d, J=6.5 Hz, 1H), 4.51 (q, J=8.1 Hz, 2H), 6.94-7.02 (m, 1H), 7.05-7.12 (m, 2H), 7.33-7.43 (m, 1H). MS (ES+) m/z 386.2 [M+H].

Step 3: (1R,5S,8s)-8-((5-(3-Fluorophenoxy)-1-(2,2,2-trifluoroethyl)-1H-1,2,4-triazol-3-yl)amino)-3-azabicyclo[3.2.1]octane-3-carbonitrile (Int-131)

In a 10 mL round bottomed flask, (1R,5S,8s)-N-(5-(3-fluorophenoxy)-1-(2,2,2-trifluoroethyl)-1H-1,2,4-triazol-3-yl)-3-azabicyclo[3.2.1]octan-8-amine (Int-130, 28 mg, 73

μmol) was dissolved in ethanol (1 mL) and sodium hydrogencarbonate (6.7 mg, 80 μmol), followed by cyanogen bromide (8.7 mg, 80 μmol) were added. The reaction mixture was stirred for 42 h at room temperature. After that, additional sodium hydrogencarbonate (2.4 mg, 22 μmol) and cyanogen bromide (1.8 mg, 21 μmol) were added, the mixture was stirred for 1 h at room temperature, and 4.5 h at 50° C. Then, it was concentrated in vacuo, the resulting crude product was purified by column chromatography (silica gel, 20 g, eluting with ethyl acetate/n-heptane, gradient 0:100 to 50:50 v/v) to yield the title compound as white solid (22 mg, 75%). HPLC (method LCMS_fastgradient) $t_R$=1.14 min. $^1$H NMR (CDCl$_3$, 300 MHz): δ 1.79-1.94 (m, 4H), 2.33-2.39 (m, 2H), 3.23 (dd, J=3.2, 12.1 Hz, 2H), 3.38 (d, J=11.9 Hz, 2H), 3.56 (d, J=6.1 Hz, 1H), 3.95 (d, J=6.1 Hz, 1H), 4.51 (q, J=8.1 Hz, 2H), 6.95-7.03 (m, 1H), 7.04-7.10 (m, 2H), 7.33-7.43 (m, 1H). MS (ES+) m/z 411.2 [M+H].

Int-132

3-Bromo-5-(3,4-difluorophenoxy)-1-isopropyl-1H-1,2,4-triazole

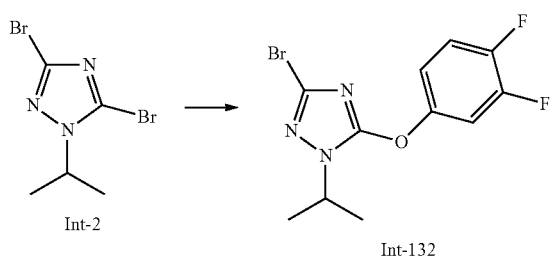

3,5-Dibromo-1-isopropyl-1,2,4-triazole (Int-2, 1.06 g, 3.94 mmol) was dissolved in DMF (8 mL) and 3,4-difluorophenol (769 mg, 5.91 mmol) was added, followed by potassium carbonate (1.36 g, 9.85 mmol). The reaction mixture was stirred for 20 h at 110° C. in a sealed tube. After cooling to room temperature, the reaction mixture was poured into water (30 mL) and extracted with MTBE (2×150 mL). The combined organic layers were washed with 0.5 N sodium hydroxide solution (50 mL), water (50 mL) and brine (50 mL), dried over sodium sulphate and concentrated in vacuo to give the crude product, that was sufficiently pure, as off-white solid (1.21 g, 96%). No further purification. HPLC (method LCMS_fastgradient) $t_R$=1.32 min. $^1$H NMR (d6-DMSO, 300 MHz): 1.41 (d, J=6.6 Hz, 6H), 4.61 (hept, J=6.6 Hz, 1H), 7.26-7.33 (m, 1H), 7.50-7.62 (m, 1H), 7.64-7.73 (m, 1H). MS (ES+) m/z 318.3, 320.3 [M+H, Br isotopes].

Int-133

3-Bromo-5-(3,4-difluorophenoxy)-1-(2,2,2-trifluoroethyl)-1H-1,2,4-triazole

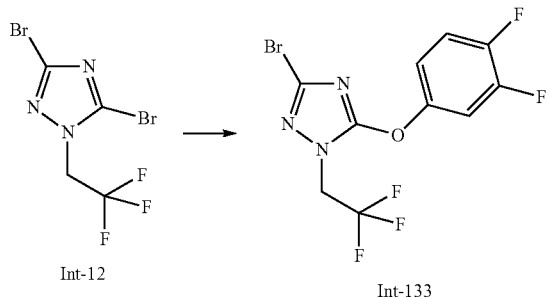 [SMILES: FC(F)(F)Cn1nc(Br)nc1Br ; Fc1ccc(Oc2nc(Br)nn2CC(F)(F)F)cc1F]

3,5-Dibromo-1-(2,2,2-trifluoroethyl)-1H-1,2,4-triazole (Int-12, 1.00 g, 3.24 mmol) was dissolved in DMF (8 mL) and 3,4-difluorophenol (632 mg, 4.86 mmol) was added, followed by potassium carbonate (1.12 g, 8.09 mmol). The reaction mixture was stirred for 20 h at 110° C. in a sealed tube. After cooling to room temperature, the reaction mixture was poured into water (30 mL) and extracted with MTBE (2×150 mL). The combined organic layers were washed with 0.5 N sodium hydroxide solution (50 mL), water (50 mL) and brine (50 mL), dried over sodium sulphate and concentrated in vacuo. The crude product was purified by column chromatography (silica gel, 25 g, eluting with ethyl acetate/n-heptane, gradient 0:100 to 20:80 v/v), to yield the title compound as a colorless oil (440 mg, 38%). HPLC (method LCMS_fastgradient) $t_R$=1.29 min. $^1$H NMR (CDCl$_3$, 300 MHz): 4.67 (q, J=8.0 Hz, 2H), 7.06-7.13 (m, 1H), 7.19-7.29 (m, 2H). MS (ES+) m/z 358.3, 360.3 [M+H, Br isotopes].

Int-134

3-Bromo-5-(2,3-difluorophenoxy)-1-isopropyl-1H-1,2,4-triazole

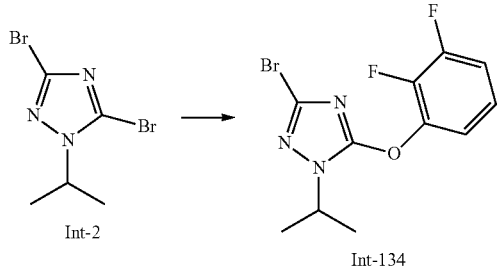

3,5-Dibromo-1-isopropyl-1,2,4-triazole (Int-2, 1.14 g, 4.26 mmol) was dissolved in DMF (8 mL) and 2,3-difluorophenol (831 mg, 6.39 mmol) was added, followed by potassium carbonate (1.47 g, 10.6 mmol). The reaction mixture was stirred for 20 h at 110° C. in a sealed tube. After cooling to room temperature, the reaction mixture was poured into water (30 mL) and extracted with MTBE (2×150 mL). The combined organic layers were washed with 0.5 N sodium hydroxide solution (50 mL), water (50 mL) and brine (50 mL), dried over sodium sulphate and concentrated in vacuo to give the crude product, that was sufficiently pure, as a light brown solid (1.31 g, 97%). No further purification. ¹H NMR (CDCl₃, 300 MHz): 1.54 (d, J=6.6 Hz, 6H), 4.66 (hept, J=6.7 Hz, 1H), 7.05-7.18 (m, 2H), 7.21-7.28 (m, 1H). MS (ES+) m/z 318.3, 320.3 [M+H, Br isotopes].

Int-135

3-Bromo-5-(3-chloro-4-fluorophenoxy)-1-isopropyl-1H-1,2,4-triazole

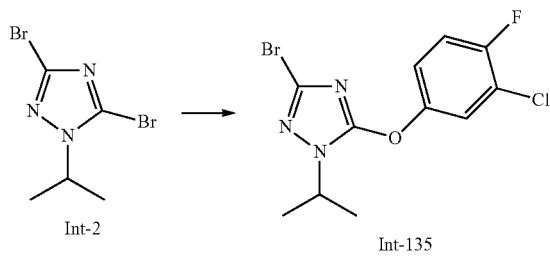

3,5-Dibromo-1-isopropyl-1,2,4-triazole (Int-2, 903 mg, 3.36 mmol) was dissolved in DMF (8 mL) and 3-chloro-4-fluorophenol (738 mg, 5.04 mmol) was added, followed by potassium carbonate (1.16 g, 8.39 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo to give the crude product, that was sufficiently pure, as a light brown solid (1.16 g, 93%). No further purification. HPLC (method LCMS_fastgradient) $t_R$=1.38 min. ¹H NMR (CDCl₃, 300 MHz): 1.52 (d, J=6.8 Hz, 6H), 4.60 (hept, J=6.6 Hz, 1H), 7.14-7.25 (m, 2H), 7.37-7.42 (m, 1H). MS (ES+) m/z 334.3, 336.3, 338.3 [M+H, Br & Cl isotopes].

Int-136

3-Bromo-5-(3-chloro-5-fluorophenoxy)-1-isopropyl-1H-1,2,4-triazole

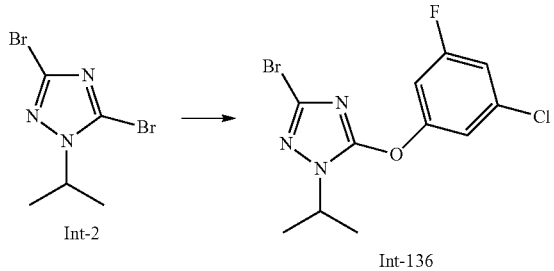

3,5-Dibromo-1-isopropyl-1,2,4-triazole (Int-2, 1.13 g, 4.2 mmol) was dissolved in DMF (8 mL) and 3-chloro-5-fluorophenol (924 mg, 6.3 mmol) was added, followed by potassium carbonate (1.45 g, 10.5 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo to give the crude product, that was sufficiently pure, as a light brown solid (1.55 g, 99%). No further purification. HPLC (method LCMS_fastgradient) $t_R$=1.47 min. ¹H NMR (CDCl₃, 300 MHz): 1.52 (d, J=6.8 Hz, 6H), 4.59 (hept, J=6.6 Hz, 1H), 6.98-7.06 (m, 2H), 7.13-7.16 (m, 1H). MS (ES+) m/z 334.3, 336.3, 338.3 [M+H, Br & Cl isotopes].

Int-137

3-Bromo-5-(3,5-difluorophenoxy)-1-(2,2,2-trifluoro-ethyl)-1H-1,2,4-triazole

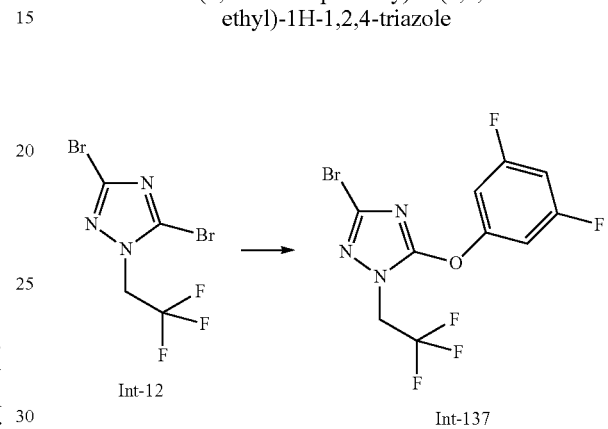

3,5-Dibromo-1-(2,2,2-trifluoroethyl)-1H-1,2,4-triazole (Int-12, 1.42 g, 4.6 mmol) was dissolved in DMF (6 mL) and 3,5-difluorophenol (897 mg, 6.9 mmol) was added, followed by potassium carbonate (1.59 g, 11.5 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a white solid (833 mg, 51%). HPLC (method LCMS_fastgradient) $t_R$=1.36 min. ¹H NMR (CDCl₃, 300 MHz): 4.67 (q, J=8.0 Hz, 2H), 6.73-6.83 (m, 1H), 6.93-7.00 (m, 2H). MS (ES+) m/z 358.3, 360.3 [M+H, Br isotopes].

Int-138

3-Bromo-5-(5-chloro-2-fluoro-phenoxy)-1-isopropyl-1,2,4-triazole

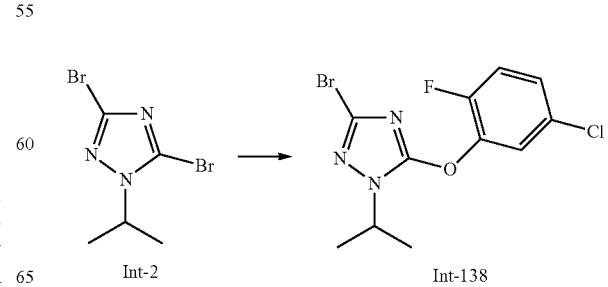

To a solution of 3,5-dibromo-1-isopropyl-1,2,4-triazole (Int-2, 800.0 mg, 3.0 mmol) in DMF (8 mL) was added 5-chloro-2-fluoro-phenol (436.0 mg, 3.0 mmol) followed by DBU (0.9 mL, 5.9 mmol) under argon atmosphere. After complete addition, reaction was allowed to irradiate at 145° C. for 1 h in microwave. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel, 10 g, eluting with ethyl acetate/n-hexane 30:70 v/v) to afford the title compound as white solid (370 mg, 37%). $^1$H NMR (CDCl$_3$, 400 MHz): 1.52 (d, J=6.7 Hz, 6H), 4.62 (dt, J=13.2, 6.6 Hz, 1H), 7.13 (t, J=9.3 Hz, 1H), 7.16-7.25 (m, 1H), 7.45 (dd, J=6.7, 2.3 Hz, 1H). MS (ES+) m/z 336.2 [M+H].

Int-139

3-Bromo-5-(2,3-difluorophenoxy)-1-(2,2,2-trifluoroethyl)-1H-1,2,4-triazole

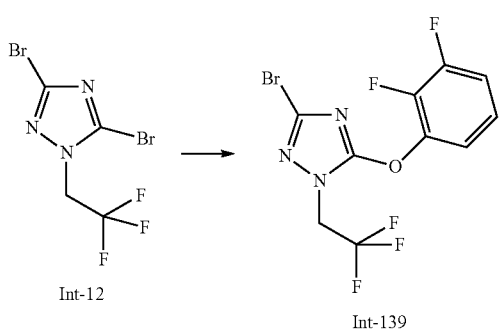 [SMILES: FC(F)(F)Cn1nc(Br)nc1Br ; Fc1cccc(Oc2nc(Br)nn2CC(F)(F)F)c1F]

3,5-Dibromo-1-(2,2,2-trifluoroethyl)-1H-1,2,4-triazole (Int-12, 1.38 g, 4.47 mmol) was dissolved in DMF (6 mL) and 2,3-difluorophenol (872 mg, 6.7 mmol) was added, followed by potassium carbonate (1.54 g, 11.2 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a white solid (880 mg, 55%). HPLC (method LCMS_fastgradient) t$_R$=1.32 min. $^1$H NMR (CDCl$_3$, 300 MHz): 4.71 (q, J=8.0 Hz, 2H), 7.13-7.20 (m, 2H), 7.21-7.27 (m, 1H). MS (ES+) m/z 358.3, 360.3 [M+H, Br isotopes].

Int-140

3-Bromo-5-(3-chloro-4-fluorophenoxy)-1-(2,2,2-trifluoroethyl)-1H-1,2,4-triazole

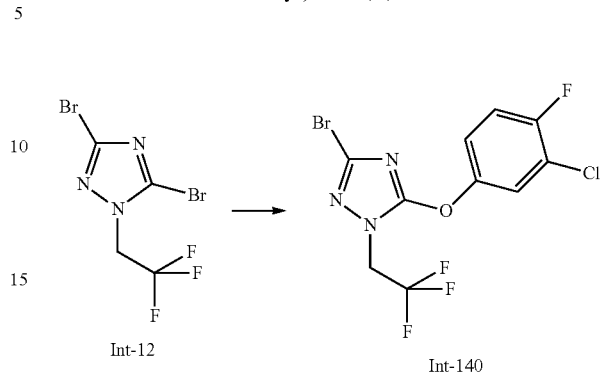

3,5-Dibromo-1-(2,2,2-trifluoroethyl)-1H-1,2,4-triazole (Int-12, 1.31 g, 4.24 mmol) was dissolved in DMF (6 mL) and 3-chloro-4-fluorophenol (932 mg, 6.36 mmol) was added, followed by potassium carbonate (1.47 g, 10.6 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 20:80 v/v), followed by preparative HPLC (YMC-Actus Triart C18, 100×30 mm×5 µm, eluting with acetonitrile/(water+0.1% triethylamine), gradient 20:80 to 98:2 v/v), to yield the title compound as a white solid (530 mg, 33%). HPLC (method LCMS_fastgradient) t$_R$=1.40 min. $^1$H NMR (CDCl$_3$, 300 MHz): 4.67 (q, J=8.0 Hz, 2H), 7.17-7.26 (m, 2H), 7.40-7.45 (m, 1H). MS (ES+) m/z 374.3, 376.3, 378.3 [M+H, Br & Cl isotopes].

Int-141

3-Bromo-5-(3-chloro-4-fluorophenoxy)-1-(2,2-difluoroethyl)-1H-1,2,4-triazole

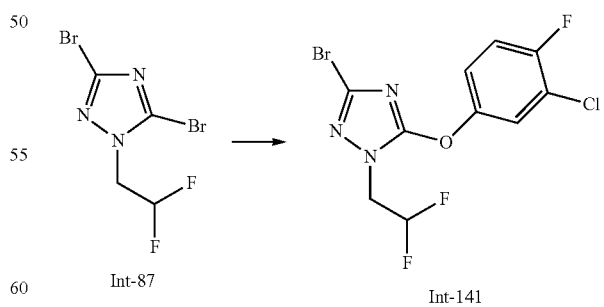

3,5-Dibromo-1-(2,2-difluoroethyl)-1H-1,2,4-triazole (Int-87, 523 mg, 1.8 mmol) was dissolved in DMF (5 mL) and 3-chloro-4-fluorophenol (343 mg, 2.34 mmol) was added, followed by potassium carbonate (621 mg, 4.49 mmol). The reaction mixture was stirred for 20 h at 110° C. in a sealed

Int-142

3-Bromo-5-(3-chloro-5-fluorophenoxy)-1-(2,2-difluoroethyl)-1H-1,2,4-triazole

3,5-Dibromo-1-(2,2-difluoroethyl)-1H-1,2,4-triazole (Int-87, 474 mg, 1.63 mmol) was dissolved in DMF (5 mL) and 3-chloro-5-fluorophenol (310 mg, 2.12 mmol) was added, followed by potassium carbonate (563 mg, 4.07 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a colorless oil (480 mg, 83%). HPLC (method LCMS_fastgradient) $t_R$=1.35 min. $^1$H NMR (CDCl$_3$, 300 MHz): 4.43 (dt, J=4.2, 13.0 Hz, 2H), 6.16 (tt, J=4.2, 55.0 Hz, 1H), 7.02-7.09 (m, 2H), 7.17-7.20 (m, 1H). MS (ES+) m/z 356.3, 358.3, 360.3 [M+H, Br & Cl isotopes].

Int-143

3-Bromo-1-(2,2-difluoroethyl)-5-(3,5-difluorophenoxy)-1H-1,2,4-triazole

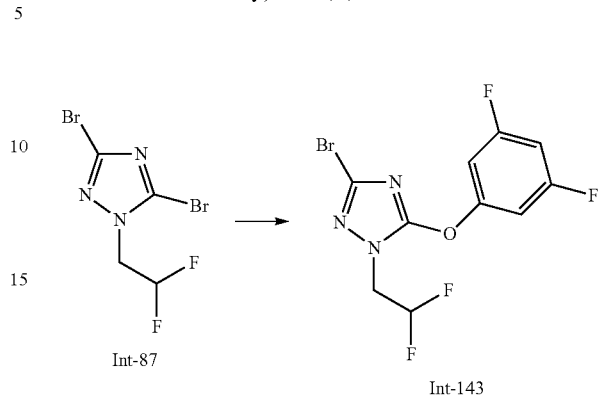

3,5-Dibromo-1-(2,2-difluoroethyl)-1H-1,2,4-triazole (Int-87, 461 mg, 1.58 mmol) was dissolved in DMF (5 mL) and 3,5-difluorophenol (268 mg, 2.06 mmol) was added, followed by potassium carbonate (548 mg, 3.96 mmol). The reaction mixture was stirred for 20 h at 110° C. in a sealed tube. After cooling to room temperature, the reaction mixture was poured into brine (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a colorless oil (492 mg, 91%). HPLC (method LCMS_fastgradient) $t_R$=1.26 min. $^1$H NMR (CDCl$_3$, 300 MHz): 4.43 (dt, J=4.2, 13.0 Hz, 2H), 6.16 (tt, J=4.2, 55.0 Hz, 1 H), 6.77 (tt, J=2.2, 8.8 Hz, 1H), 6.91-7.00 (m, 2H). MS (ES+) m/z 339.8, 341.8 [M+H, Br isotopes].

Int-144

3-Bromo-5-(3-chloro-4-fluorophenoxy)-1-(2-fluoroethyl)-1H-1,2,4-triazole

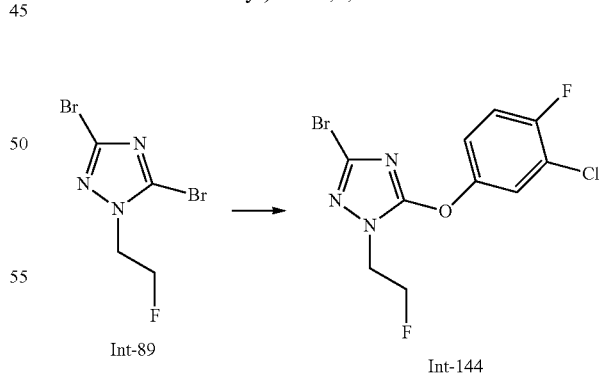

3,5-Dibromo-1-(2-fluoroethyl)-1H-1,2,4-triazole (Int-89, 700 mg, 2.57 mmol) was dissolved in DMF (8 mL) and 3-chloro-4-fluorophenol (489 mg, 3.33 mmol) was added, followed by potassium carbonate (886 mg, 6.41 mmol). The reaction mixture was stirred for 20 h at 110° C. in a sealed tube. After cooling to room temperature, the reaction mixture was poured into water (50 mL) and extracted with Int-145

3-Bromo-5-(3-chloro-5-fluorophenoxy)-1-(2-fluoroethyl)-1H-1,2,4-triazole

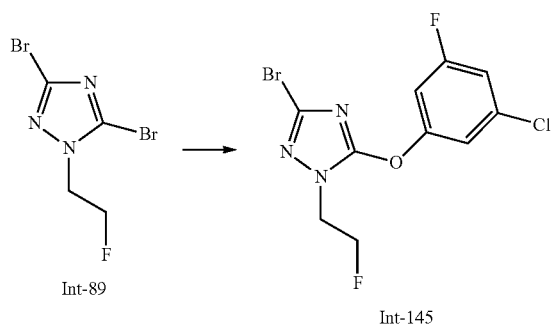 [SMILES: FCCn1nc(Br)nc1Br ; FCCn1nc(Br)nc1Oc1cc(F)cc(Cl)c1]

3,5-Dibromo-1-(2-fluoroethyl)-1H-1,2,4-triazole (Int-89, 771 mg, 2.83 mmol) was dissolved in DMF (8 mL) and 3-chloro-5-fluorophenol (538 mg, 3.67 mmol) was added, followed by potassium carbonate (976 mg, 7.06 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a colorless oil (405 mg, 44%). HPLC (method LCMS_fastgradient) $t_R$=1.26 min. $^1$H NMR (CDCl$_3$, 300 MHz): 4.37 (td, J=4.8, 25.0 Hz, 2H), 4.80 (td, J=4.7, 46.7 Hz, 2H), 7.15-7.26 (m, 2H), 7.39-7.43 (m, 1H). MS (ES+) m/z 338.0, 340.0, 342.0 [M+H, Br & Cl isotopes].

Int-147

3-Bromo-5-(3-chloro-5-fluorophenoxy)-1-(2-methoxyethyl)-1H-1,2,4-triazole

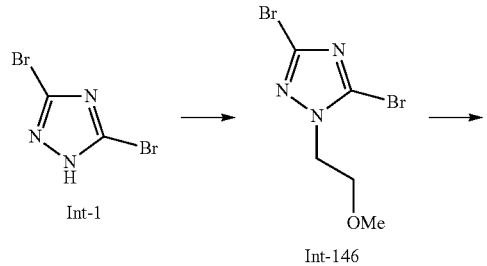

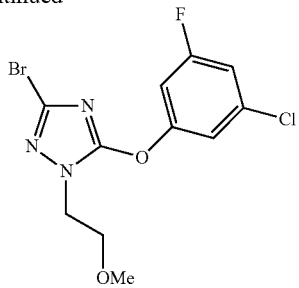

Step 1: 3,5-Dibromo-1-(2-methoxyethyl)-1,2,4-triazole (Int-146)

In a 100 mL round bottomed flask, 3,5-dibromo-1H-1,2,4-triazole (Int-1, 500.0 mg, 2.2 mmol) was dissolved in DMF (32 mL) and the solution was cooled to 0-5° C. (ice bath). Sodium hydride (55% dispersion in mineral oil, 106 mg, 2.64 mmol) was added in portions and the resulting mixture was stirred for 5 min at 0-5° C. and for 15 min at room temperature. After that, 2-methoxyethyl methanesulfonate (815.5 mg, 5.29 mmol) was added dropwise at room temperature. The resulting mixture was stirred for 15 h at room temperature. After that, it was diluted with ethyl acetate (20 mL) and water (20 mL), the aqueous phase was extracted with ethyl acetate (3×30 mL). The combined organic layers were dried (sodium sulfate) and concentrated in vacuo, the residue was purified by column chromatography (silica gel, 30 g, eluting with ethyl acetate/n-heptane, gradient 0:100 to 20:80 v/v) to yield the title compound as colorless oil (362 mg, 58%). $^1$H NMR (CDCl$_3$, 300 MHz): 3.33 (s, 3H), 3.76 (t, J=5.3 Hz, 2H), 4.29 (t, J=5.3 Hz, 2H). MS (ES+) m/z 285.8.

Step 2: 3-Bromo-5-(3-chloro-5-fluorophenoxy)-1-(2-methoxyethyl)-1H-1,2,4-triazole (Int-147)

3,5-Dibromo-1-(2-methoxyethyl)-1,2,4-triazole (Int-146, 579 mg, 2.03 mmol) was dissolved in DMF (8 mL) and 3-chloro-5-fluorophenol (387 mg, 2.64 mmol) was added, followed by potassium carbonate (702 mg, 5.08 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a colorless oil (523 mg, 73%). HPLC (method LCMS_fastgradient) $t_R$=1.33 min. $^1$H NMR (CDCl$_3$, 300 MHz): 3.34 (s, 3H), 3.75 (t, J=5.2 Hz, 2H), 4.22 (t, J=5.2 Hz, 2H), 6.97-7.05 (m, 2H), 7.13-7.16 (m, 1H). MS (ES+) m/z 350.3, 352.3, 354.3 [M+H, Br & Cl isotopes].

Int-148

3-Bromo-5-(3-chloro-4-fluorophenoxy)-1-(2-methoxyethyl)-1H-1,2,4-triazole

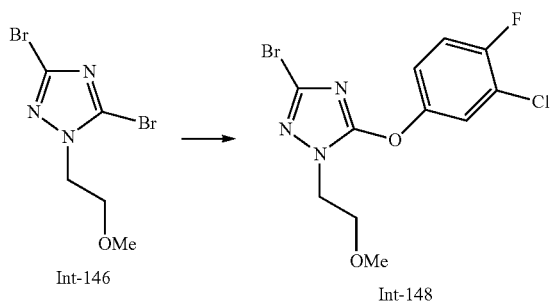 [SMILES: COCCn1nc(Br)nc1Br ; COCCn1nc(Br)nc1Oc1ccc(F)c(Cl)c1]

3,5-Dibromo-1-(2-methoxyethyl)-1,2,4-triazole (Int-146, 446 mg, 1.57 mmol) was dissolved in DMF (8 mL) and 3-chloro-4-fluorophenol (298 mg, 2.03 mmol) was added, followed by potassium carbonate (541 mg, 3.91 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with water (30 mL) and brine (30 mL), dried over sodium sulphate and concentrated in vacuo. The crude product was purified by column chromatography (silica gel, 25 g, eluting with ethyl acetate/n-heptane, gradient 0:100 to 20:80 v/v), to yield the title compound as a colorless oil, which solidified in the fridge (414 mg, 75%). HPLC (method LCMS_fastgradient) $t_R$=1.29 min. $^1$H NMR (CDCl$_3$, 300 MHz): 3.36 (s, 3H), 3.76 (t, J=5.2 Hz, 2H), 4.23 (t, J=5.2 Hz, 2H), 7.14-7.24 (m, 2H), 7.37-7.41 (m, 1H). MS (ES+) m/z 350.3, 352.3, 354.3 [M+H, Br & Cl isotopes].

Int-149

3-Bromo-5-(3-chlorophenoxy)-1-(2,2-difluoroethyl)-1H-1,2,4-triazole

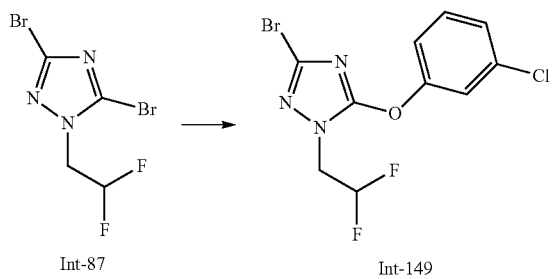 [SMILES: FC(F)Cn1nc(Br)nc1Br ; FC(F)Cn1nc(Br)nc1Oc1cccc(Cl)c1]

3,5-Dibromo-1-(2,2-difluoroethyl)-1H-1,2,4-triazole (Int-87, 439 mg, 1.51 mmol) was dissolved in DMF (5 mL) and 3-chlorophenol (152 mg, 1.96 mmol) was added, followed by potassium carbonate (521 mg, 3.77 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a colorless oil (340 mg, 66%). HPLC (method LCMS_fastgradient) $t_R$=1.30 min. $^1$H NMR (CDCl$_3$, 300 MHz): 4.43 (dt, J=4.2, 13.0 Hz, 2H), 6.16 (tt, J=4.2, 55.0 Hz, 1H), 7.21-7.30 (m, 2H), 7.33-7.40 (m, 2H). MS (ES+) m/z 338.3, 340.3, 342.3 [M+H, Br & Cl isotopes].

Int-150

3-Bromo-5-(2-chlorophenoxy)-1-(2,2,2-trifluoroethyl)-1H-1,2,4-triazole

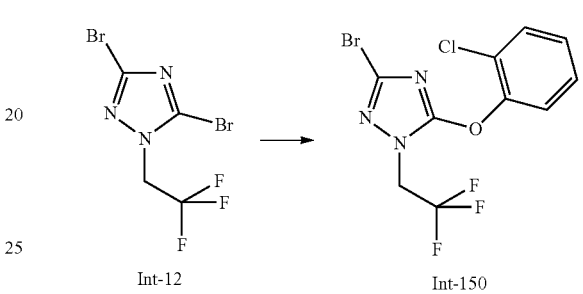

3,5-Dibromo-1-(2,2,2-trifluoroethyl)-1H-1,2,4-triazole (Int-12, 705 mg, 2.28 mmol) was dissolved in DMF (5 mL) and 2-chlorophenol (381 mg, 2.97 mmol) was added, followed by potassium carbonate (789 mg, 5.71 mmol). The reaction mixture was stirred for 16 h at 110° C. in a sealed tube. After cooling to room temperature, the reaction mixture was poured into water (50 mL) and extracted with MTBE (2×100 mL). The combined organic layers were washed with 0.5 N sodium hydroxide solution (50 mL), water (50 mL) and brine (50 mL), dried over sodium sulphate and concentrated in vacuo. The crude product was purified by column chromatography (silica gel, 25 g, eluting with ethyl acetate/n-heptane, gradient 0:100 to 20:80 v/v), to afford the title compound as a white solid (610 mg, 75%). HPLC (method LCMS_fastgradient) $t_R$=1.34 min. $^1$H NMR (CDCl$_3$, 300 MHz): 4.72 (q, J=8.1 Hz, 2H), 7.24-7.31 (m, 1H), 7.33-7.40 (m, 1H), 7.44-7.52 (m, 2H). MS (ES+) m/z 356.3, 358.3, 360.3 [M+H, Br & Cl isotopes].

Int-151

3-Bromo-5-(3,5-difluorophenoxy)-1-(2-fluoroethyl)-1H-1,2,4-triazole

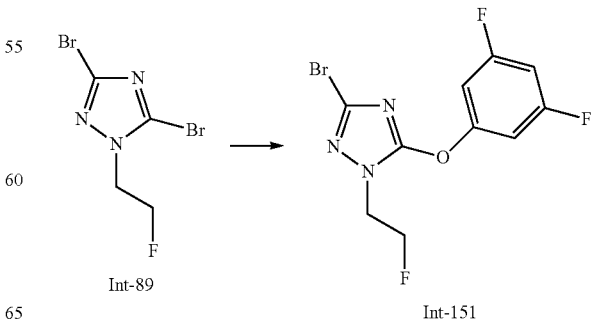

3,5-Dibromo-1-(2-fluorethyl)-1H-1,2,4-triazole (Int-89, 310 mg, 1.14 mmol) was dissolved in DMF (3.2 mL) and 3,5-difluorophenol (192 mg, 1.48 mmol) was added, followed by potassium carbonate (392 mg, 2.84 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a colorless oil, which solidified in the fridge (228 mg, 62%). $^1$H NMR (CDCl$_3$, 300 MHz): 4.37 (td, J=4.7, 25.0 Hz, 2H), 4.79 (td, J=4.7, 46.5 Hz, 2H), 6.74 (tt, J=2.3, 8.8 Hz, 1H), 6.89-6.98 (m, 2H). MS (ES+) m/z 322.3, 324.3 [M+H, Br isotopes].

Int-152

3-Bromo-5-(2-chlorophenoxy)-1-(2,2-difluoroethyl)-1H-1,2,4-triazole

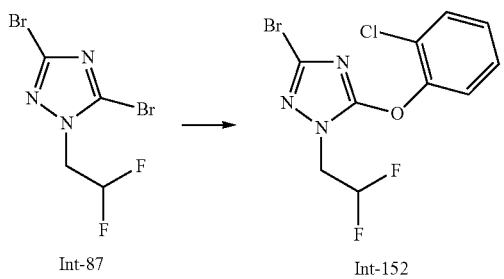 [SMILES: FC(F)Cn1nc(Br)nc1Br ; FC(F)Cn1nc(Br)nc1Oc1ccccc1Cl]

3,5-Dibromo-1-(2,2-difluoroethyl)-1H-1,2,4-triazole (Int-87, 559 mg, 1.92 mmol) was dissolved in DMF (7 mL) and 2-chlorophenol (321 mg, 2.5 mmol) was added, followed by potassium carbonate (664 mg, 4.8 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with water (50 mL) and brine (50 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a white solid (575 mg, 80%). HPLC (method LCMS_fastgradient) $t_R$=1.25 min. $^1$H NMR (CDCl$_3$, 300 MHz): 4.49 (dt, J=4.2, 12.9 Hz, 2H), 6.21 (tt, J=4.3, 55.0 Hz, 1H), 7.23-7.30 (m, 1H), 7.33-7.39 (m, 1H), 7.44-7.51 (m, 2H). MS (ES+) m/z 338.3, 340.3, 342.3 [M+H, Br & Cl isotopes].

Int-154

3-Bromo-5-(3-chloro-5-fluorophenoxy)-1-(methoxymethyl)-1H-1,2,4-triazole

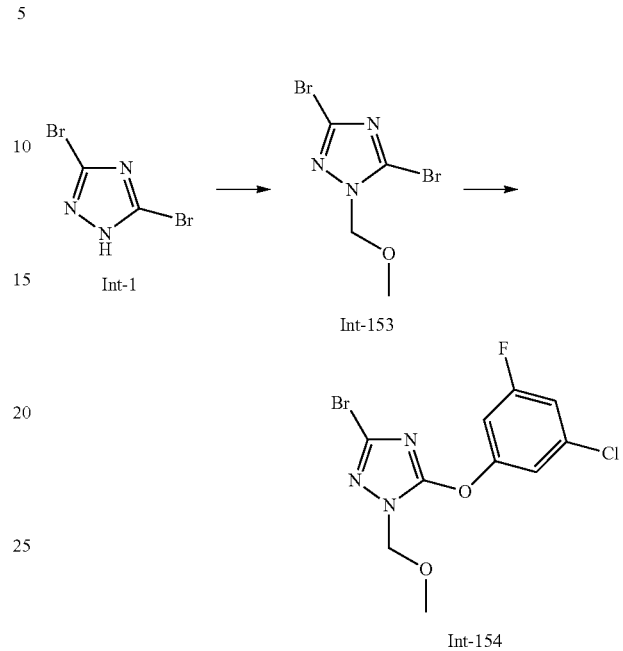

Step 1: 3,5-Bibromo-1-(methoxymethyl)-1H-1,2,4-triazole (Int-153)

3,5-Dibromo-1H-1,2,4-triazole (Int-1, 834 mg, 3.68 mmol) was dissolved in DMF (15 mL), sodium hydride (60% dispersion in mineral oil, 221 mg, 5.51 mmol) was added carefully in one portion (gas evolution), and the reaction mixture was stirred at room temperature for 30 min. Then, chloro(methoxy)methane (355 mg, 4.41 mmol) was added dropwise and the reaction mixture was stirred at room temperature for 6 h. After that, the reaction mixture was poured into water (40 mL) and extracted with MTBE (2×100 mL). The combined organic layers were washed with water (50 mL) and brine (50 mL), dried over sodium sulphate and concentrated in vacuo. The crude product was purified by column chromatography (silica gel, 24 g, eluting with ethyl acetate/n-heptane, gradient 0:100 to 30:70 v/v), followed by preparative HPLC (YMC-Actus Triart C18, 100×30 mm×5 µm, eluting with acetonitrile/(water+0.1% triethylamine), gradient 20:80 to 98:2 v/v) to yield the title compound as a white solid (798 mg, 80%). HPLC (method LCMS_fastgradient) $t_R$=0.85 min. $^1$H NMR (CDCl$_3$, 300 MHz): 3.46 (s, 3H), 5.43 (s, 2H). MS (ES+) m/z 270.2, 272.2, 274.2 [M+H, 2 Br isotopes].

Step 2: 3-Bromo-5-(3-chloro-5-fluorophenoxy)-1-(methoxymethyl)-1H-1,2,4-triazole (Int-154)

3,5-Dibromo-1-(methoxymethyl)-1H-1,2,4-triazole (Int-153, 399 mg, 1.47 mmol) was dissolved in DMF (8 mL) and 3-chloro-5-fluorophenol (281 mg, 1.91 mmol) was added, followed by potassium carbonate (509 g, 3.68 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with water (50 mL) and brine (50 mL), dried over sodium sulphate and concentrated in vacuo. The crude product was purified by column chromatography (silica gel, 24 g, eluting with ethyl acetate/n-heptane, gradient 0:100 to 20:80 v/v), followed by preparative HPLC (YMC-Actus Triart C18, 100×30 mm×5 μm, eluting with acetonitrile/(water+0.1% triethylamine), gradient 20:80 to 98:2 v/v) to yield the title compound as a colorless oil (283 mg, 57%). HPLC (method LCMS_fastgradient) $t_R$=1.32 min. $^1$H NMR (CDCl$_3$, 300 MHz): 3.50 (s, 3H), 5.36 (s, 2H), 7.01-7.12 (m, 2H), 7.18-7.22 (m, 1H). MS (ES+) m/z 336.3, 338.3, 340.3 [M+H, Br & Cl isotopes].

Int-155

3-Bromo-5-(3-chloro-2-fluorophenoxy)-1-(2,2-difluoroethyl)-1H-1,2,4-triazole

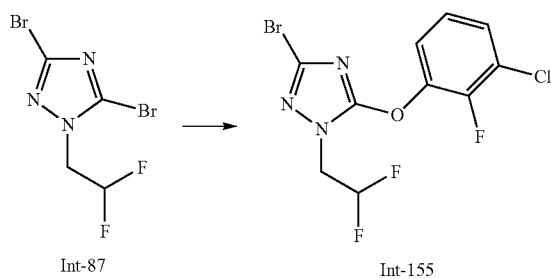 [SMILES: FC(F)Cn1nc(Br)nc1Br ; Fc1c(Cl)cccc1Oc1nc(Br)nn1CC(F)F]

3,5-Dibromo-1-(2,2-difluoroethyl)-1H-1,2,4-triazole (Int-87, 539 mg, 1.85 mmol) was dissolved in DMF (7 mL) and 3-chloro-2-fluorophenol (353 mg, 2.41 mmol) was added, followed by potassium carbonate (640 mg, 4.63 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with water (50 mL) and brine (50 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a white solid (588 mg, 89%). HPLC (method LCMS_fastgradient) $t_R$=1.30 min. $^1$H NMR (CDCl$_3$, 300 MHz): 4.46 (dt, J=4.2, 12.9 Hz, 2H), 6.18 (tt, J=4.3, 54.9 Hz, 1H), 7.12-7.19 (m, 1H), 7.33-7.40 (m, 2H). MS (ES+) m/z 356.3, 358.3, 360.3 [M+H, Br & Cl isotopes].

Int-156

3-Bromo-5-(2-chlorophenoxy)-1-(2-fluoroethyl)-1H-1,2,4-triazole

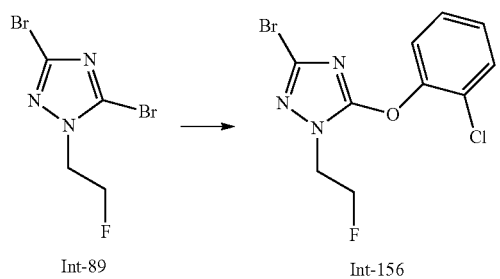 [SMILES: FCCn1nc(Br)nc1Br ; FCCn1nc(Br)nc1Oc1ccccc1Cl]

3,5-Dibromo-1-(2-fluoroethyl)-1H-1,2,4-triazole (Int-89, 525 mg, 1.92 mmol) was dissolved in DMF (7 mL) and 2-chlorophenol (322 mg, 2.5 mmol) was added, followed by potassium carbonate (665 mg, 4.81 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with water (50 mL) and brine (50 mL), dried over sodium sulphate and concentrated in vacuo. The crude product was purified by column chromatography (silica gel, 24 g, eluting with ethyl acetate/n-heptane, gradient 0:100 to 20:80 v/v), to afford the title compound as a white solid (293 mg, 47%). HPLC (method LCMS_fastgradient) $t_R$=1.20 min. $^1$H NMR (CDCl$_3$, 300 MHz): 4.43 (td, J=4.9, 24.4 Hz, 2H), 4.84 (td, J=4.8, 46.5 Hz, 2H), 7.21-7.28 (m, 1H), 7.31-7.38 (m, 1H), 7.44-7.50 (m, 2H). MS (ES+) m/z 320.3, 322.3, 324.3 [M+H, Br & Cl isotopes].

Int-157

3-Bromo-5-(3-chloro-2-fluorophenoxy)-1-(2-fluoroethyl)-1H-1,2,4-triazole

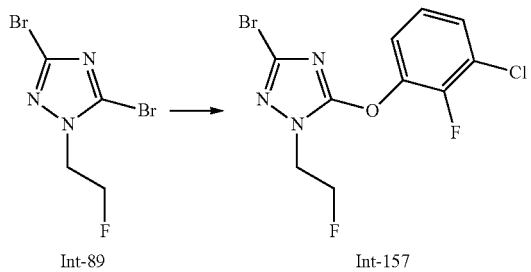 [SMILES: FCCn1nc(Br)nc1Br ; FCCn1nc(Br)nc1Oc1cccc(Cl)c1F]

3,5-Dibromo-1-(2-fluoroethyl)-1H-1,2,4-triazole (Int-89, 507 mg, 1.86 mmol) was dissolved in DMF (7 mL) and 3-chloro-2-fluorophenol (354 mg, 2.42 mmol) was added, followed by potassium carbonate (642 mg, 4.64 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with water (50 mL) and brine (50 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a white solid (505 mg, 80%). HPLC (method LCMS_fastgradient) $t_R$=1.26 min. $^1$H NMR (CDCl$_3$, 300 MHz): 4.41 (td, J=4.8, 24.6 Hz, 2H), 4.82 (td, J=4.8, 46.5 Hz, 2H), 7.10-7.19 (m, 1H), 7.30-7.41 (m, 2H). MS (ES+) m/z 338.3, 340.3, 342.3 [M+H, Br & Cl isotopes].

Int-158

3-Bromo-5-(3-chloro-2-fluoro-phenoxy)-1-isopropyl-1,2,4-triazole

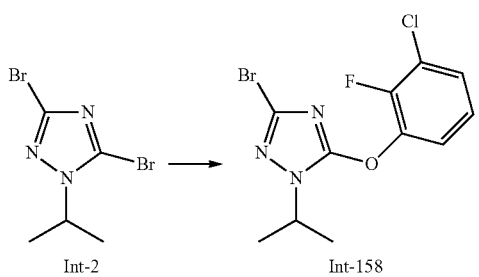

To a solution of 3,5-dibromo-1-isopropyl-1,2,4-triazole (Int-2, 600.0 mg, 2.2 mmol) in DMF (2 mL) was added 3-chloro-2-fluorophenol (436.0 mg, 3.0 mmol) followed by K$_2$CO$_3$ (308.0 mg, 2.2 mmol) under argon atmosphere. After complete addition reaction was allowed to irradiate at 145° C. for 1 h in microwave. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel (10 gm), eluting with ethyl acetate/n-hexane 35:65 v/v) to afford title compound as white solid (350.0 mg, 35%). HPLC (method LCMS_fastgradient) t$_R$=1.14 min. $^1$H NMR (CDCl$_3$, 400 MHz): 1.52 (d, J=6.7 Hz, 6H), 4.64 (dt, J=13.3, 6.6 Hz, 1H), 7.12 (t, J=7.4 Hz, 1H), 7.28-7.32 (m, 1H), 7.35 (t, J=7.6 Hz, 1H). MS (ES+) m/z 336.2 [M+H].

Int-159

3-Bromo-5-(2-chloro-3-fluoro-phenoxy)-1-isopropyl-1,2,4-triazole

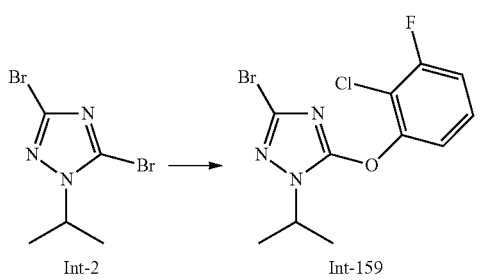

3,5-Dibromo-1-isopropyl-1,2,4-triazole (Int-2, 841 mg, 3.13 mmol) was dissolved in DMF (6 mL) and 2-chloro-3-fluorophenol (596 mg, 4.07 mmol) was added, followed by potassium carbonate (1.08 g, 7.82 mmol). The reaction mixture was stirred for 20 h in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 20:80 v/v), to yield the title compound as a white solid (653 mg, 62%). HPLC (method LCMS_fastgradient) t$_R$=1.41 min. $^1$H NMR (CDCl$_3$, 300 MHz): 1.56 (d, J=6.6 Hz, 6H), 4.69 (hept, J=6.6 Hz, 1H), 7.06-7.16 (m, 1H), 7.29-7.35 (m, 2H). MS (ES+) m/z 334.3, 336.3, 338.3 [M+H, Br & Cl isotopes].

Int-160

3-Bromo-5-(3-chloro-2-fluoro-phenoxy)-1-(2,2,2-trifluoroethyl)-1,2,4-triazole

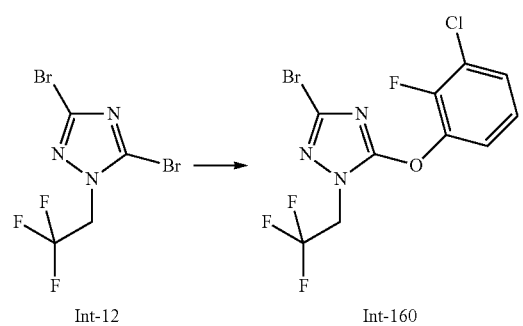 [SMILES: FC(F)(F)Cn1nc(Br)nc1Br ; Fc1c(Cl)cccc1Oc1nc(Br)nn1CC(F)(F)F]

To a solution of 3,5-dibromo-1-(2,2,2-trifluoroethyl)-1,2,4-triazole (Int-12, 150 mg, 0.5 mmol) and 3-chloro-2-fluorophenol (71 mg, 0.5 mmol) in DMF (5 mL) was added K$_2$CO$_3$ (67 mg, 0.5 mmol). The stirring was continued in conventional heating at 100° C. for 16 h. After complete consumption of starting material (as monitored by TLC) reaction mixture was poured into water and extracted with MTBE. The organic layer was separated and dried over sodium sulphate. Solvent was evaporated under reduced pressure and purified by combi-flash column chromatography (silica gel (8 gm), eluting with ethyl acetate/n-hexane 35:65 v/v) to afford title compound as white solid (70.0 mg, 37%). $^1$H NMR (CDCl$_3$, 400 MHz): 4.68 (q, J=7.9 Hz, 2H), 7.14 (t, J=8.2 Hz, 1H), 7.34 (t, J=7.2 Hz, 2H). MS (ES+) m/z 376.0 [M+H].

Int-161

3-Bromo-5-(3,5-difluorophenoxy)-1-methyl-1,2,4-triazole

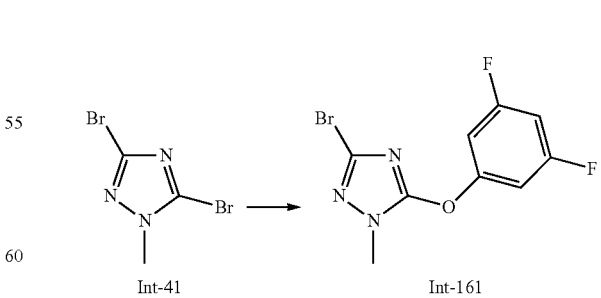

The title compound was prepared in analogy to Int-84 from 3,5-dibromo-1-methyl-1H-1,2,4-triazole (Int-41, 400 mg, 1.66 mmol) and 3,5-difluorophenol (324 mg, 2.49 mmol) with potassium carbonate in DMF heating in a sealed vial for 15 h at 100° C. The title compound was isolated as a white solid (408 mg, 84.7% yield). MS (ES+) m/z: 290.0 [(M+H)⁺].

Int-162

3-Bromo-5-(3-chloro-5-fluorophenoxy)-1-methyl-1,2,4-triazole

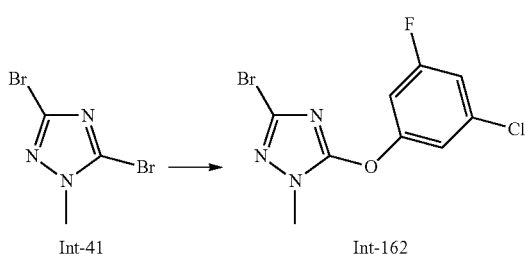

The title compound was prepared in analogy to Int-84 from 3,5-dibromo-1-methyl-1H-1,2,4-triazole (Int-41, 270 mg, 1.12 mmol) and 3-chloro-5-fluorophenol (246 mg, 1.68 mmol), with potassium carbonate in DMF heating in a sealed vial for 15 h at 100° C. The title compound was isolated as an off-white solid (318 mg, 93% yield). MS (ES+) m/z: 305.6 [(M+H)⁺].

Int-163

3-Bromo-5-(4-chlorophenoxy)-1-methyl-1H-1,2,4-triazole

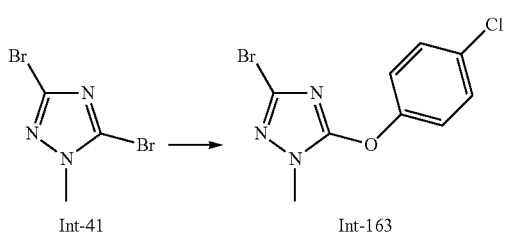

The title compound was prepared in analogy to Int-84 from 3,5-dibromo-1-methyl-1H-1,2,4-triazole (Int-41, 250 mg, 1.04 mmol) and 4-chlorophenol (200 mg, 1.56 mmol) with potassium carbonate in DMF heating in a sealed vial for 15 h at 100° C. The desired compound was isolated as a white solid (242 mg, 80.8% yield). MS (ES+) m/z: 289.9 [(M+H)⁺].

Int-164

3-Bromo-5-(3-chloro-4-fluorophenoxy)-1-methyl-1,2,4-triazole

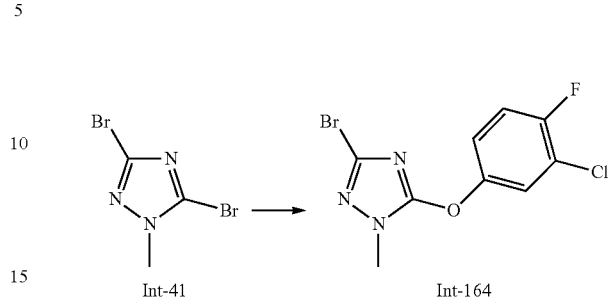

The title compound was prepared in analogy to Int-84 from 3,5-dibromo-1-methyl-1H-1,2,4-triazole (Int-41, 400 mg, 1.66 mmol) and 3-chloro-4-fluorophenol (365 mg, 2.49 mmol) with potassium carbonate in DMF heating in a sealed vial for 15 h at 100° C. The desired compound was isolated as a light red solid (499.7 mg, 98.2% yield). MS (ES+) m/z: 307.9 [(M+H)⁺].

Int-165

3-Bromo-5-(3-chloro-2-fluorophenoxy)-1-methyl-1,2,4-triazole

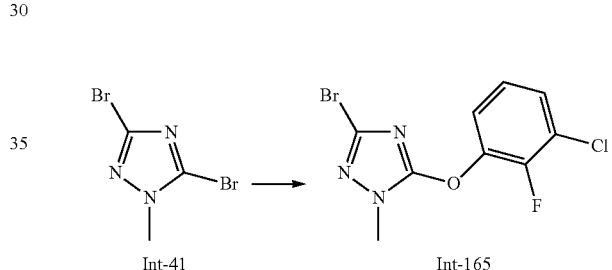

The title compound was prepared in analogy to Int-84 from 3,5-dibromo-1-methyl-1H-1,2,4-triazole (Int-41, 250 mg, 1.04 mmol) and 3-chloro-2-fluorophenol (228 mg, 1.56 mmol) with potassium carbonate in DMF heating in a sealed vial for 15 h at 100° C. The title compound was isolated as a white solid (288.6 mg, 90.7% yield). MS (ES+) m/z: 307.9 [(M+H)⁺].

Int-166

3-Bromo-5-(2-chloro-3-fluorophenoxy)-1-methyl-1,2,4-triazole

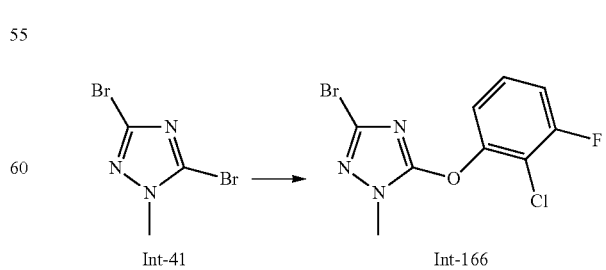

The title compound was prepared in analogy to Int-84 from 3,5-dibromo-1-methyl-1H-1,2,4-triazole (Int-41, 250 mg, 1.04 mmol) and 2-chloro-3-fluorophenol (228 mg, 1.56 mmol) with potassium carbonate in DMF heating in a sealed vial for 15 h at 100° C. The compound was isolated as a light yellow solid (291.4 mg, 91.6% yield). MS (ES+) m/z: 308.0 [(M+H)+].

Int-167

3-Bromo-5-(3-chloro-5-fluorophenoxy)-1-ethyl-1,2,4-triazole

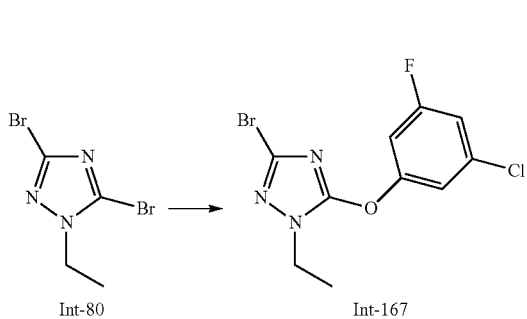

The title compound was prepared in analogy to Int-81 from 3,5-dibromo-1-ethyl-1H-1,2,4-triazole (Int-80, 250 mg, 0.981 mmol) and 3-chloro-5-fluorophenol (216 mg, 1.47 mmol) with potassium carbonate in DMF heating in a sealed vial for 15 h at 100° C. The title compound was isolated as a light red solid (283.7 mg, 90.2% yield). MS (ES+) m/z: 321.9 [(M+H)+].

Int-168

3-Bromo-5-(3,5-difluorophenoxy)-1-ethyl-1,2,4-triazole

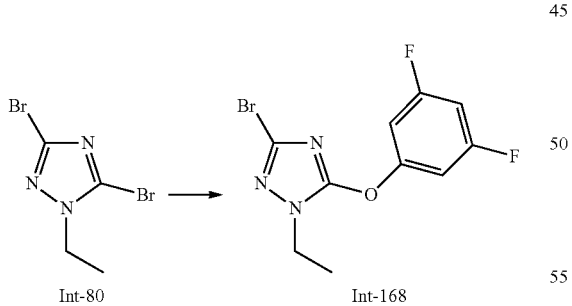

The title compound was prepared in analogy to Int-81 from 3,5-dibromo-1-ethyl-1H-1,2,4-triazole (Int-80, 250 mg, 0.981 mmol) and 3,5-difluorophenol (191 mg, 1.47 mmol) with potassium carbonate in DMF heating in a sealed vial for 15 h at 100° C. The title compound was isolated as a light red solid (222 mg, 74.4% yield). MS (ES+) m/z: 304.0 [(M+H)+].

Int-169

3-Bromo-5-(2-chlorophenoxy)-1-ethyl-1H-1,2,4-triazole

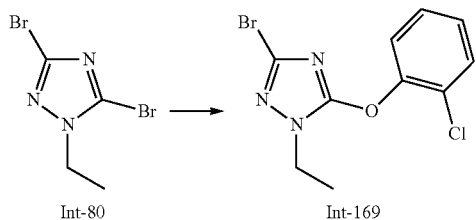

The title compound was prepared in analogy to Int-81 from 3,5-dibromo-1-ethyl-1H-1,2,4-triazole (Int-80, 100 mg, 0.392 mmol) and 2-chlorophenol (75.6 mg, 0.588 mmol) with potassium carbonate in DMF heating in a sealed vial for 15 h at 100° C. The title compound was isolated as a off-white solid (104 mg, 87.6% yield). MS (ES+) m/z: 303.9 [(M+H)+].

Int-170

3-Bromo-5-(3-chloro-4-fluorophenoxy)-1-ethyl-1,2,4-triazole

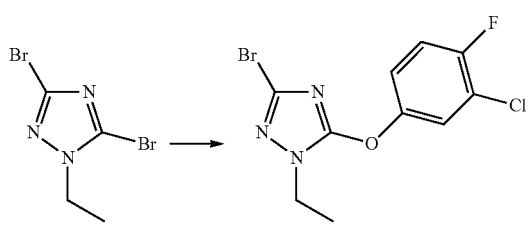

The title compound was prepared in analogy to Int-81 from 3,5-dibromo-1-ethyl-1H-1,2,4-triazole (Int-80, 250 mg, 0.981 mmol) and 3-chloro-4-fluorophenol (216 mg, 1.47 mmol) with potassium carbonate in DMF heating in a sealed vial for 15 h at 100° C. The compound was isolated as a light red solid (254.3 mg, 80.9% yield). MS (ES+) m/z: 321.9 [(M+H)+].

Int-171

3-Bromo-5-(3-chloro-5-fluorophenoxy)-1-propyl-1,2,4-triazole

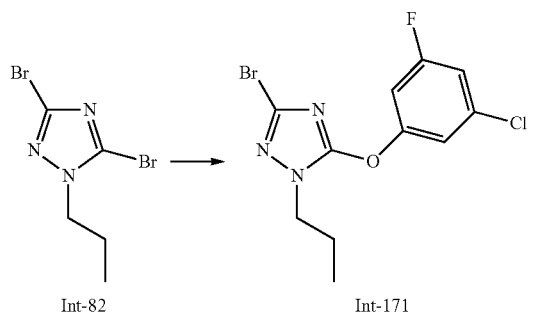

The title compound was prepared in analogy to Int-83 from 3,5-dibromo-1-propyl-1H-1,2,4-triazole (Int-82, 250 mg, 0.930 mmol) and 3-chloro-5-fluorophenol (204 mg, 1.39 mmol) with potassium carbonate in DMF heating in a sealed vial overnight at 110° C. The compound was isolated as a light yellow oil (279.5 mg, 89.9% yield). MS (ES+) m/z: 335.9 [(M+H)$^+$].

Int-172

3-Bromo-5-(3,5-difluorophenoxy)-1-propyl-1,2,4-triazole

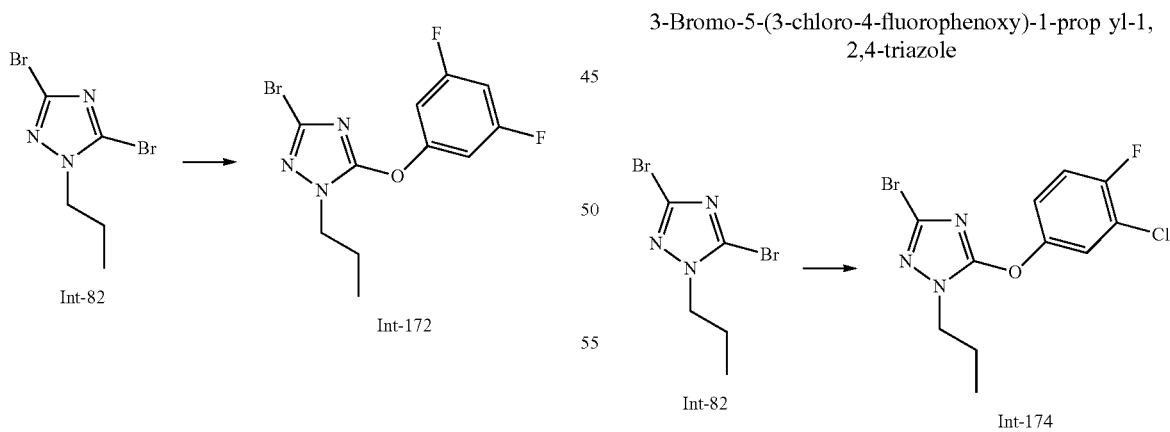

The title compound was prepared in analogy to Int-83 from 3,5-dibromo-1-propyl-1H-1,2,4-triazole (Int-82, 250 mg, 0.930 mmol) and 3,5-difluorophenol (181 mg, 1.39 mmol) with potassium carbonate in DMF heating in a sealed vial overnight at 110° C. The desired compound was isolated as a light brown liquid (235.2 mg, 79.5% yield). MS (ES+) m/z: 320.0 [(M+H)$^+$].

Int-173

3-Bromo-5-(2-chlorophenoxy)-1-propyl-1H-1,2,4-triazole

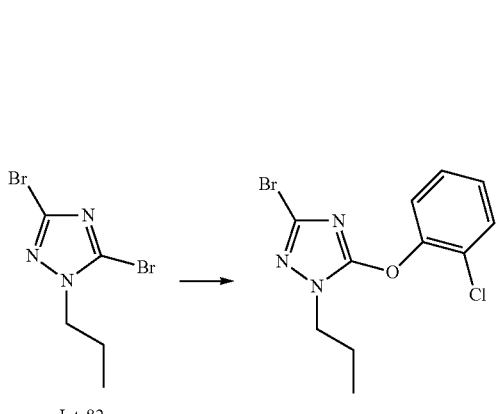

The title compound was prepared in analogy to Int-83 from 3,5-dibromo-1-propyl-1H-1,2,4-triazole (Int-82, 100 mg, 0.372 mmol) and 2-chlorophenol (71.7 mg, 0.558 mmol) with potassium carbonate in DMF heating in a sealed vial overnight at 110° C. The title compound was isolated as a light yellow liquid (112 mg, 95.1% yield). MS (ES+) m/z: 317.9 [(M+H)$^+$].

Int-174

3-Bromo-5-(3-chloro-4-fluorophenoxy)-1-propyl-1,2,4-triazole

The title compound was prepared in analogy to Int-83 from 3,5-dibromo-1-propyl-1H-1,2,4-triazole (Int-82, 250 mg, 0.930 mmol) and 3-chloro-4-fluorophenol (204 mg, 1.39 mmol) with potassium carbonate in DMF heating in a sealed vial overnight at 110° C. The title compound was isolated as a light brown liquid (268.5 mg, 86.3% yield). MS (ES+) m/z: 336.0 [(M+H)$^+$].

Int-176

3-Bromo-5-(3-chloro-5-fluorophenoxy)-1-(2-methyl-propyl)-1,2,4-triazole

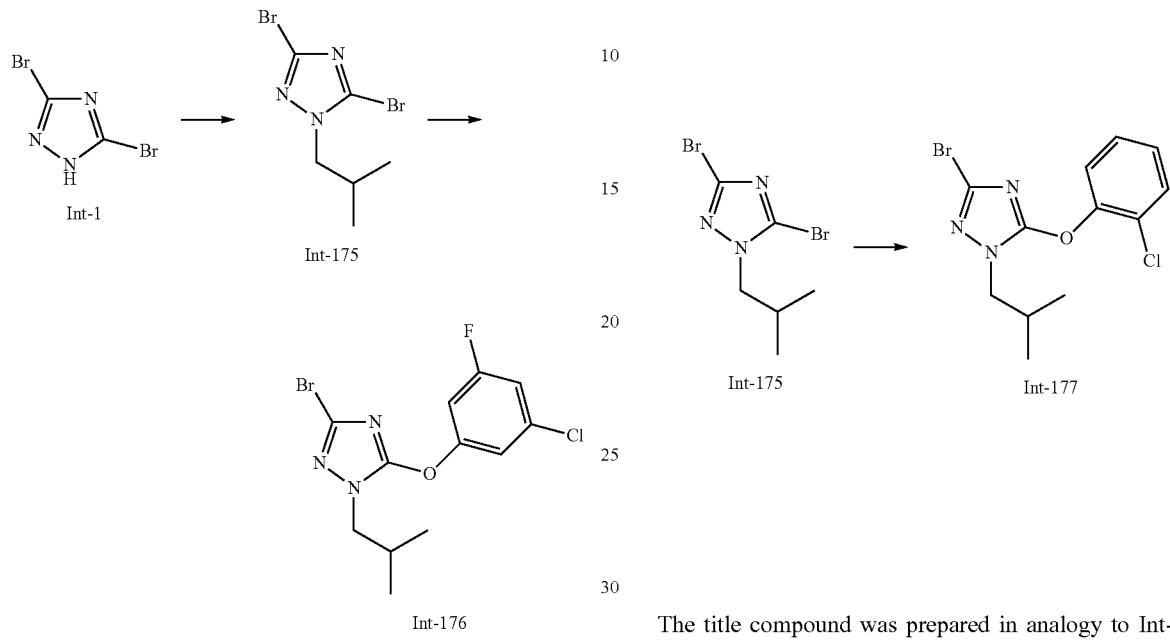

Int-1

Int-175

Int-176

Step 1: 3,5-Dibromo-1-isobutyl-1H-1,2,4-triazole (Int-175)

In a 250 mL round bottomed flask sodium hydride (60% dispersion in mineral oil) (264 mg, 6.61 mmol) was added to a colorless solution of 3,5-dibromo-1H-1,2,4-triazole (Int-1, 1 g, 4.41 mmol) in DMF (22 ml) The resulting suspension was stirred at room temp during 30 min and 1-iodo-2-methylpropane (973 mg, 5.29 mmol) was added and the reaction was stirred at 40° C. over night. The reaction mixture was poured into 50 mL H2O and extracted with EtOAc. The organic layers were washed with sat NaCl (3×50 mL), dried over MgSO4 and concentrated in vacuo. The title compound was isolated as a light red liquid (1.033 g, 82.8% yield). MS (ES+) m/z: 283.9 [(M+H)⁺].

Step 2: 3-Bromo-5-(3-chloro-5-fluorophenoxy)-1-isobutyl-1H-1,2,4-triazole (Int-176)

To a light yellow solution of 3,5-dibromo-1-isobutyl-1H-1,2,4-triazole (Int-175, 250 mg, 884 µmol) and 3-chloro-5-fluorophenol (194 mg, 1.33 mmol) in DMF (3 ml) was added potassium carbonate (305 mg, 2.21 mmol). The vial was closed under Argon and stirred over night at 110° C. The reaction mixture was diluted with 50 mL H₂O and extracted with tBuOMe (2×50 mL). The organic layers were back-extracted with 1 M NaOH (2×50 mL) and sat NaCl (3×50 mL), dried over MgSO₄ and concentrated in vacuo. The title compound was isolated as a light red liquid (288 mg, 93.5% yield). MS (ES+) m/z: 350.0 [(M+H)⁺].

Int-177

3-Bromo-5-(2-chlorophenoxy)-1-isobutyl-1H-1,2,4-triazole

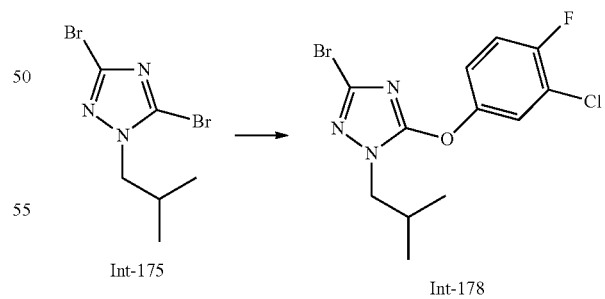

Int-175

Int-177

The title compound was prepared in analogy to Int-176 from 3,5-dibromo-1-isobutyl-1H-1,2,4-triazole (Int-175, 100 mg, 353 µmol) and 2-chlorophenol (68.1 mg, 530 µmol) with potassium carbonate in DMF heating in a sealed vial overnight at 110° C. The title compound was isolated as an orange oil (111 mg, 95% yield). MS (ES+) m/z: 332.0 [(M+H)⁺].

Int-178

3-Bromo-5-(3-chloro-4-fluorophenoxy)-1-isobutyl-1H-1,2,4-triazole

Int-175

Int-178

The title compound was prepared in analogy to Int-176 from 3,5-dibromo-1-isobutyl-1H-1,2,4-triazole (Int-175, 250 mg, 884 µmol) and 3-chloro-4-fluorophenol (194 mg, 1.33 mmol) with potassium carbonate in DMF heating in a sealed vial overnight at 110° C. The title compound was isolated as a light brown liquid (291 mg, 94.5% yield). MS (ES+) m/z: 350.3 [(M+H)⁺].

Int-180

3-Bromo-5-(3-chloro-5-fluorophenoxy)-1-[(3-methyloxetan-3-yl)methyl]-1,2,4-triazole

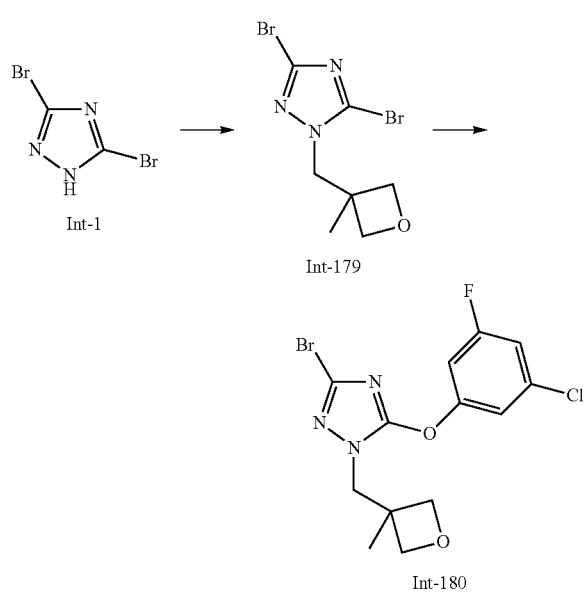

Int-181

3-Bromo-5-(3-chloro-4-fluorophenoxy)-1-[(3-methyloxetan-3-yl)methyl]-1,2,4-triazole

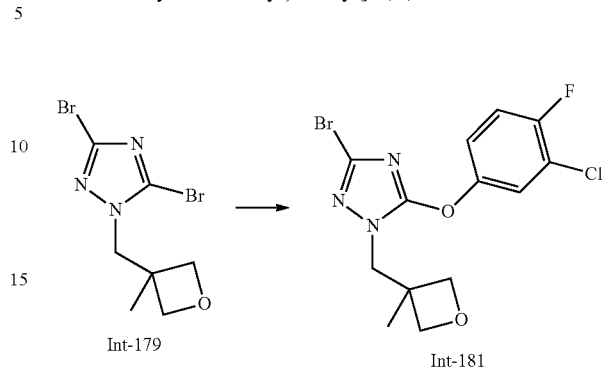

The title compound was prepared in analogy to Int-180 from 3,5-dibromo-1-((3-methyloxetan-3-yl)methyl)-1H-1,2,4-triazole (Int-179, 400 mg, 1.29 mmol) and 3-chloro-4-fluorophenol (283 mg, 1.93 mmol) with potassium carbonate in DMF heating in a sealed vial overnight at 110° C. The compound was isolated as a light red oil (441.8 mg, 91.2% yield). MS (ES+) m/z: 378.0 [(M+H)+].

Int-183

3-Bromo-5-(3-chloro-5-fluorophenoxy)-1-[(3-methyloxetan-3-yl)methyl]-1,2,4-triazole

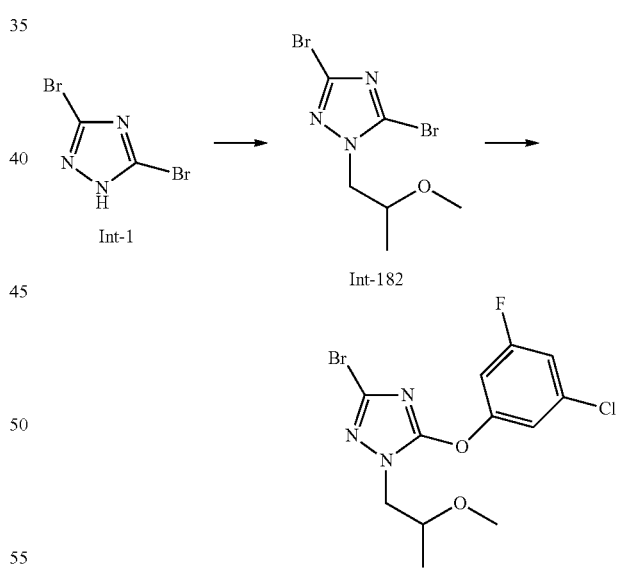

Step 1: 3,5-dibromo-1-[(3-methyloxetan-3-yl)methyl]-1,2,4-triazole (Int-179)

In a 250 mL round bottomed flask sodium hydride (60% dispersion in mineral oil) (264 mg, 6.61 mmol) was added to a colorless solution of 3,5-dibromo-1H-1,2,4-triazole (Int-1, 1 g, 4.41 mmol) in DMF (22 ml). The resulting suspension was stirred at room temp during 30 min and 3-(bromomethyl)-3-methyloxetane (873 mg, 5.29 mmol) was added and the reaction was stirred at 40° C. over night. The reaction mixture was poured into 50 mL H2O and extracted with EtOAc (3×50 mL). The organic layers were washed with sat NaCl (3×50 mL), dried over MgSO4 and concentrated in vacuo. The title compound was isolated as a colorless liquid (1.35 g, 98.5% yield). MS (ES+) m/z: 311.9 [(M+H)+].

Step 2: 3-Bromo-5-(3-chloro-5-fluorophenoxy)-1-[(3-methyloxetan-3-yl)methyl]-1,2,4-triazole (Int-180)

To a light brown solution of 3,5-dibromo-1-((3-methyloxetan-3-yl)methyl)-1H-1,2,4-triazole (Int-179, 300 mg, 965 µmol) and 3-chloro-5-fluorophenol (212 mg, 1.45 mmol) in DMF (3 ml) was added potassium carbonate (333 mg, 2.41 mmol). The vial was closed under Argon and stirred over night at 100° C. The reaction mixture was diluted with 50 mL H2O and extracted with tBuOMe (2×50 mL). The organic layers were back-extracted with 1 M NaOH (2×50 mL) and sat NaCl (3×50 mL), dried over MgSO4 and concentrated in vacuo. The title compound was isolated as a light brown liquid (316.7 mg, 87.2% yield). MS (ES+) m/z: 378.0 [(M+H)+].

Step 1: 3,5-Bibromo-1-(2-methoxypropyl)-1,2,4-triazole (Int-182)

In a 250 mL round bottomed flask sodium hydride (60% dispersion in mineral oil) (264 mg, 6.61 mmol) was added to a colorless solution of 3,5-dibromo-1H-1,2,4-triazole (Int-1, 1 g, 4.41 mmol) in DMF (22 ml). The resulting suspension was stirred at room temp during 30 min and 1-bromo-2-methoxypropane (809 mg, 5.29 mmol) was added and the reaction was stirred at 40° C. over night. The reaction mixture was poured into 50 mL H2O and extracted with EtOAc (3×50 mL). The organic layers were washed with sat NaCl (3×50 mL), dried over MgSO4 and concentrated in vacuo. The title compound was isolated as a red liquid (383 mg, 14.5% yield). MS (ES+) m/z: 299.9 [(M+H)$^+$].

Step 2: 3-Bromo-5-(3-chloro-5-fluorophenoxy)-1-(2-methoxypropyl)-1,2,4-triazole (Int-183)

To a light yellow solution of 3,5-dibromo-1-(2-methoxypropyl)-1H-1,2,4-triazole (Int-182, 120 mg, 401 µmol) and 3-chloro-5-fluorophenol (88.2 mg, 602 µmol) in DMF (1.5 ml) was added potassium carbonate (139 mg, 1 mmol). The vial was closed under Argon and stirred over night at 110° C. The reaction mixture was poured into water and extracted with MTBE. The organic layers were separated and dried over MgSO4. Solvent was evaporated under reduced pressure and purified by combi-flash column chromatography (silica gel, eluting with ethyl acetate/n-heptane, gradient 0:100 to 50:50). The title compound was isolated as a yellow liquid (30.2 mg, 20.6% yield). MS (ES+) m/z: 365.9 [(M+H)$^+$].

Int-185

3-Bromo-5-(3-chloro-5-fluorophenoxy)-1-(3,3,3-trifluoroprop yl)-1,2,4-triazole

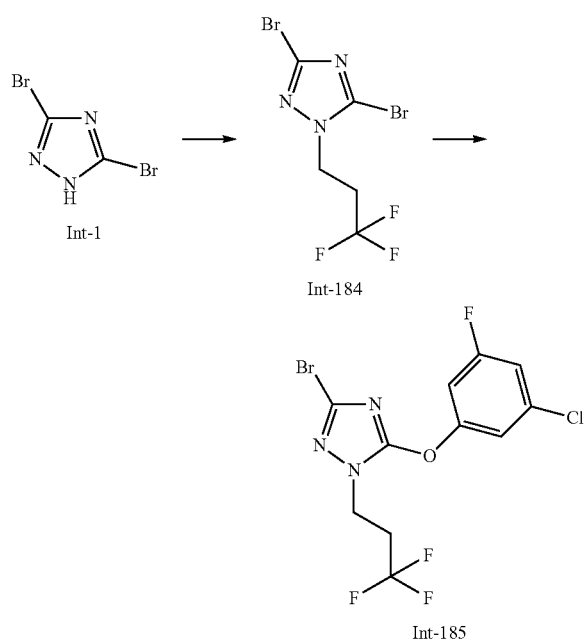

Step 1: 3,5-Dibromo-1-(3,3,3-trifluoropropyl)-1,2,4-triazole (Int-184)

In a 50 mL round bottomed flask sodium hydride (60% dispersion in mineral oil) (132 mg, 3.31 mmol) was added to a colorless solution of 3,5-dibromo-1H-1,2,4-triazole (Int-1, 500 mg, 2.2 mmol) in DMF (7 ml). The resulting suspension was stirred at room temp during 30 min and 3,3,3-trifluoropropyl 4-methylbenzenesulfonate (591 mg, 2.2 mmol) solved in DMF (3 ml) was added and the reaction was stirred at 40° C. over night. The reaction mixture was poured into 50 mL H2O and extracted with EtOAc (3×50 mL). The organic layers were washed with sat NaCl (3×50 mL), dried over MgSO4 and concentrated in vacuo. The title compound was isolated as a light yellow liquid (288 mg, 40.5% yield). MS (ES+) m/z: 323.8 [(M+H)$^+$].

Step 2: 3-Bromo-5-(3-chloro-5-fluorophenoxy)-1-(3,3,3-trifluoropropyl)-1,2,4-triazole (Int-185)

To a light yellow solution of 3,5-dibromo-1-(3,3,3-trifluoropropyl)-1,2,4-triazole (Int-184, 120 mg, 401 µmol) and 3-chloro-5-fluorophenol (68.1 mg, 465 µmol) in DMF (1.5 ml) was added potassium carbonate (107 mg, 774 µmol). The vial was closed under Argon and stirred over night at 110° C. The reaction mixture was diluted with 50 mL H2O and extracted with tBuOMe (2×50 mL). The organic layers were back-extracted with 1 M NaOH (2×50 mL) and sat NaCl (3×50 mL), dried over MgSO4 and concentrated in vacuo. The title compound was isolated as a light red liquid (93.2 mg, 77.5% yield). MS (ES+) m/z: 390.0 [(M+H)$^+$].

Int-187

3-Bromo-5-(3-chloro-5-fluorophenoxy)-1-((3,3-difluorocyclobutyl)methyl)-1H-1,2,4-triazole

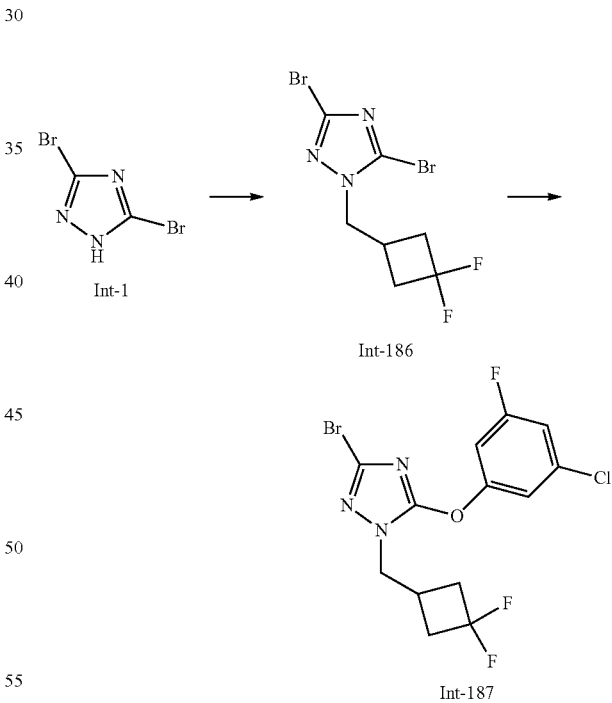

Preparation of Step 1 Precursor: (3,3-Difluorocyclobutyl)methyl Trifluoromethanesulfonate To a solution of (3,3-difluorocyclobutyl)methanol (500 mg, 4.09 mmol) and pyridine (324 mg, 4.09 mmol) in DCM (5.5 ml) was added at −15° C. trifluoromethanesulfonic anhydride (1.21 g, 4.3 mmol). The resulting suspension was stirred at room temp during 2 h. The reaction mixture was quenched with 50 ml ice-cold 0.1 M HCl and extracted with DCM (2×50 ml). The organic layers were back-extracted with 0.1 M HCl (1×50 ml). The organic layers were dried over MgSO4 and concentrated in vacuo. The title compound was isolated as a light yellow liquid (1.04 g, 99.9% yield). ¹H NMR (CDCl₃, 300 MHz): δ 2.33-2.54 (m, 2H), 2.57-2.92 (m, 3H), 4.49-4.63 (m, 2H).

Step 1: 3,5-Dibromo-1-((3,3-difluorocyclobutyl) methyl)-1H-1,2,4-triazole (Int-186)

In a 50 mL round bottomed flask sodium hydride (60% dispersion in mineral oil) (204 mg, 5.09 mmol) was added to a colorless solution of 3,5-dibromo-1H-1,2,4-triazole (Int-1, 770 mg, 3.39 mmol) in DMF (15 ml). The resulting suspension was stirred at room temp during 30 min and (3,3-difluorocyclobutyl)methyl trifluoromethanesulfonate (591 mg, 2.2 mmol) was added and the reaction was stirred at RT over night. The reaction mixture was poured into 50 mL H2O and extracted with EtOAc (3×50 mL). The organic layers were washed with sat NaCl (3×50 mL), dried over MgSO4 and concentrated in vacuo. The title compound was isolated as a orange liquid (1 g, 89% yield). MS (ES+) m/z: 333.9 [(M+H)⁺].

Step 2: 3-Bromo-5-(3-chloro-5-fluorophenoxy)-1-((3,3-difluorocyclobutyl)methyl)-1H-1,2,4-triazole (Int-187)

To a light yellow solution of 3,5-dibromo-1-((3,3-difluorocyclobutyl)methyl)-1H-1,2,4-triazole (Int-186, 200 mg, 604 µmol) and 3-chloro-5-fluorophenol (133 mg, 906 µmol) in DMF (2.4 ml) was added potassium carbonate (209 mg, 1.51 mmol). The vial was closed under Argon and stirred over night at 110° C. The reaction mixture was diluted with 50 mL H2O and extracted with tBuOMe (2×50 mL). The organic layers were back-extracted with 1 M NaOH (2×50 mL) and sat NaCl (3×50 mL), dried over MgSO4 and concentrated in vacuo. The title compound was isolated as a brown oil (220 mg, 91.8% yield). MS (ES+) m/z: 398.0 [(M+H)⁺].

Int-188

3-Bromo-5-(3-chloro-4-fluorophenoxy)-1-((3,3-difluorocyclobutyl)methyl)-1H-1,2,4-triazole

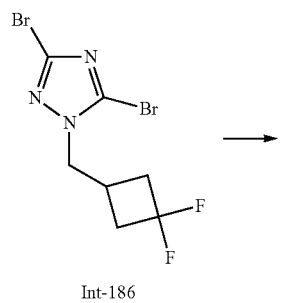

Int-186

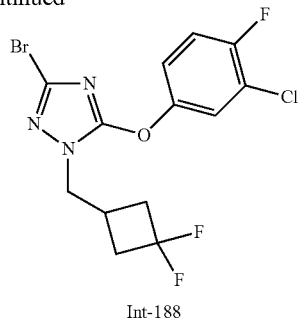

Int-188

The title compound was prepared in analogy to Int-187 from 3,5-dibromo-1-((3,3-difluorocyclobutyl)methyl)-1H-1,2,4-triazole (Int-186, 200 mg, 604 µmol) and 3-chloro-4-fluorophenol (133 mg, 906 µmol) with potassium carbonate in DMF heating in a sealed vial overnight at 110° C. The desired compound was isolated as a brown oil (223 mg, 93% yield). MS (ES+) m/z: 398.0 [(M+H)⁺].

Int-190

3-Bromo-5-(3-chloro-5-fluorophenoxy)-1-(oxetan-3-yl)-1,2,4-triazole

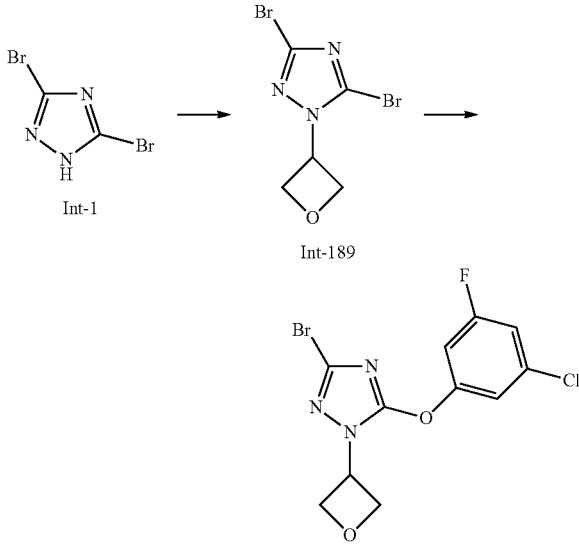

Int-190

Step 1: 3,5-Dibromo-1-(oxetan-3-yl)-1,2,4-triazole (Int-189)

To a colorless solution of 3,5-dibromo-1H-1,2,4-triazole (Int-1, 250 mg, 1.1 mmol, Eq: 1) and 3-iodooxetane (243 mg, 1.32 mmol) in DMF (3 ml) was added K2CO3 (305 mg, 2.2 mmol). The vial was closed under Argon and stirred over night at 120° C. The reaction mixture was diluted with 25 mL H2O and extracted with EtOAc (2×25 mL) and the organic layers were washed with sat NaCl (3×25 mL), dried over MgSO4 and concentrated in vacuo. The title compound was isolated as a white solid (198 mg, 63.5% yield). MS (ES+) m/z: 283.9 [(M+H)⁺].

Step 2: 3-Bromo-5-(3-chloro-5-fluorophenoxy)-1-(oxetan-3-yl)-1,2,4-triazole (Int-190)

To a light brown solution of 3,5-dibromo-1-(oxetan-3-yl)-1,2,4-triazole (Int-189, 90 mg, 318 μmol) and 3-chloro-5-fluorophenol (69.9 mg, 477 μmol) in DMF (1.5 ml) was added potassium carbonate (110 mg, 795 μmol). The vial was closed under Argon and stirred over night at 100° C. The reaction mixture was diluted with 25 mL H2O and extracted with tBuOMe (2×25 mL). The organic layers were washed with 1 M NaOH (2×25 mL) and sat NaCl (3×25 mL), dried over MgSO4 and concentrated in vacuo. The title compound was isolated as a white solid (68 mg, 61.3% yield). MS (ES+) m/z: 350.0 [(M+H)$^+$].

Int-191

3-Bromo-5-(3-chloro-4-fluorophenoxy)-1-(oxetan-3-yl)-1,2,4-triazole

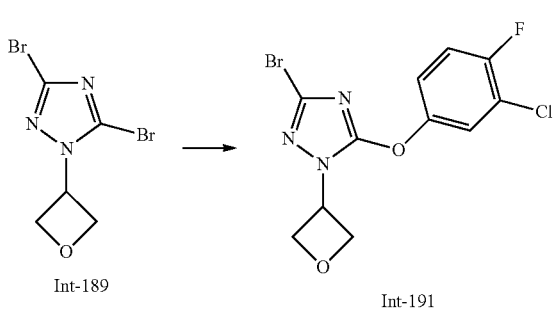 [SMILES: Brc1nc(Br)n(C2COC2)n1 ; Fc1ccc(Oc2nc(Br)nn2C2COC2)cc1Cl]

The title compound was prepared in analogy to Int-190 from 3,5-dibromo-1-(oxetan-3-yl)-1,2,4-triazole (Int-189, 90 mg, 318 μmol) and 3-chloro-4-fluorophenol (69.9 mg, 477 μmol) with potassium carbonate in DMF heating in a sealed vial overnight at 110° C. The desired compound was isolated as a white solid (83 mg, 74.9% yield). MS (ES+) m/z: 350.0 [(M+H)$^+$].

Int-193

3-Bromo-5-(3-chloro-5-fluorophenoxy)-1-(oxolan-3-yl)-1,2,4-triazole

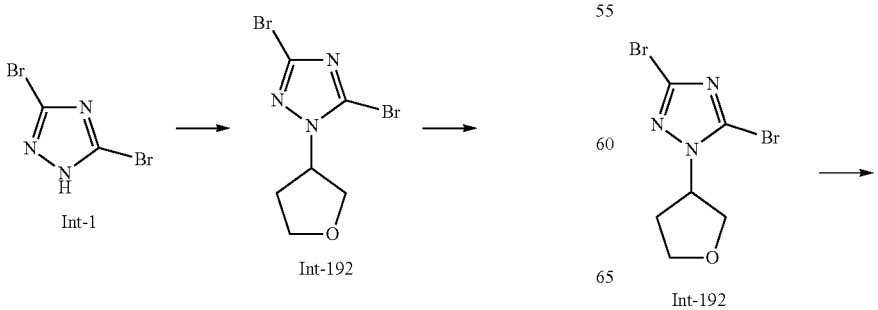

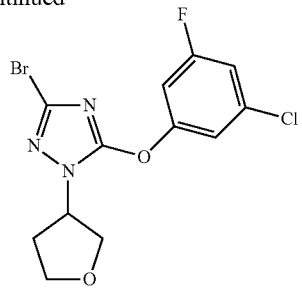

Step 1: 3,5-Dibromo-1-(oxolan-3-yl)-1,2,4-triazole (Int-192)

To a colorless solution of 3,5-dibromo-1H-1,2,4-triazole (Int-1, 500 mg, 2.2 mmol) and 3-iodotetrahydrofuran (524 mg, 2.64 mmol) in DMF (3 ml) was added K2CO3 (305 mg, 2.2 mmol). The vial was closed under Argon and stirred over night at 120° C. The reaction mixture was diluted with 50 mL H2O and extracted with EtOAc (2×50 mL). The organic layers were washed with sat NaCl (3×50 mL), dried over MgSO4 and concentrated in vacuo. The title compound was isolated as a white solid (619 mg, 2.08 mmol, 94.6% yield). MS (ES+) m/z: 297.9 [(M+H)$^+$].

Step 2: 3-Bromo-5-(3-chloro-5-fluorophenoxy)-1-(oxolan-3-yl)-1,2,4-triazole (Int-193)

To a light brown solution of 3,5-dibromo-1-(oxolan-3-yl)-1,2,4-triazole (Int-192, 150 mg, 505 μmol) and 3-chloro-5-fluorophenol (111 mg, 758 μmol) in DMF (2.5 ml) was added potassium carbonate (175 mg, 1.26 mmol). The vial was closed under Argon and stirred over night at 100° C. The reaction mixture was diluted with 50 mL H2O and extracted with tBuOMe (2×50 mL). The organic layers were washed with 1 M NaOH (2×50 mL) and sat NaCl (3×50 mL), dried over MgSO4 and concentrated in vacuo. The title compound was isolated as a white solid (182 mg, 99.4% yield). MS (ES+) m/z: 364.0 [(M+H)$^+$].

Int-194

3-Bromo-5-(3-chloro-4-fluorophenoxy)-1-(oxolan-3-yl)-1H-1,2,4-triazole

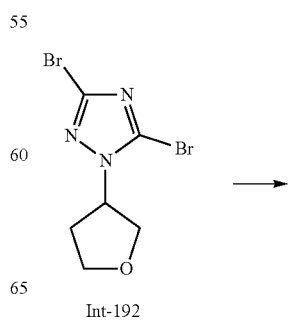

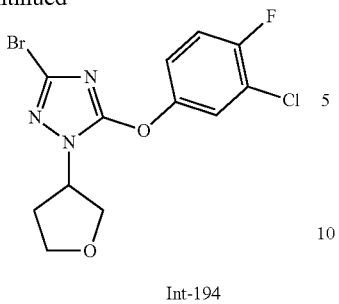

Int-194

The title compound was prepared in analogy to Int-193 from 3,5-dibromo-1-(oxolan-3-yl)-1,2,4-triazole (Int-192, 150 mg, 505 µmol) and 3-chloro-4-fluorophenol (111 mg, 758 µmol) with potassium carbonate in DMF heating in a sealed vial overnight at 110° C. The title compound was isolated as a white solid (177 mg, 96.6% yield). MS (ES+) m/z: 364.0 [(M+H)$^+$].

Int-196

3-Bromo-5-(3-chloro-5-fluorophenoxy)-1-cyclobutyl-1H-1,2,4-triazole mL). The organic layers were washed with sat NaCl (3×25 mL), dried over MgSO4 and concentrated in vacuo. The title compound was isolated as a yellow liquid (288 mg, 93% yield). MS (ES+) m/z: 281.9 [(M+H)$^+$].

Step 2: 3-Bromo-5-(3-chloro-5-fluorophenoxy)-1-cyclobutyl-1H-1,2,4-triazole (Int-196)

To a light brown solution of 3,5-dibromo-1-cyclobutyl-1H-1,2,4-triazole (Int-195, 130 mg, 463 µmol) and 3-chloro-5-fluorophenol (102 mg, 694 µmol) in DMF (1.5 ml) was added potassium carbonate (160 mg, 1.16 mmol). The vial was closed under Argon and stirred over night at 100° C. The reaction mixture was diluted with 50 mL H2O and extracted with tBuOMe (2×50 mL). The organic layers were back-extracted with 1 M NaOH (2×50 mL) and sat NaCl (3×50 mL), dried over MgSO4 and concentrated in vacuo. The title compound was isolated as a off white solid (156 mg, 97.3% yield). MS (ES+) m/z: 348.0 [(M+H)$^+$].

Int-197

3-Bromo-5-(3-chloro-4-fluorophenoxy)-1-cyclobutyl-1H-1,2,4-triazole

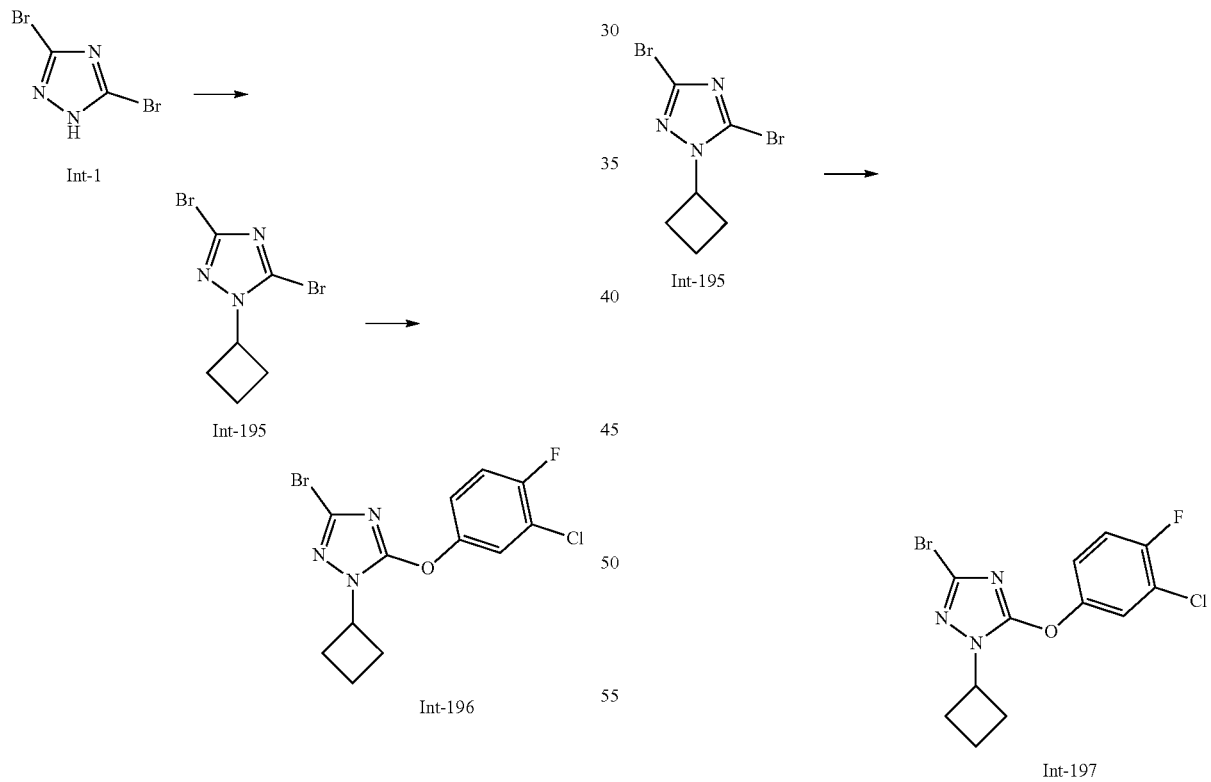

Step 1: 3,5-Dibromo-1-cyclobutyl-1H-1,2,4-triazole (Int-195)

To a colorless solution of 3,5-dibromo-1H-1,2,4-triazole (Int-1, 250 mg, 1.1 mmol, Eq: 1) and bromocyclobutane (179 mg, 1.32 mmol) in DMF (3 ml) was added K2CO3 (305 mg, 2.2 mmol). The vial was closed under argon and stirred over night at 120° C. The reaction mixture was diluted with 25 mL H2O and extracted with EtOAc (2×25

The title compound was prepared in analogy to Int-196 from 3,5-dibromo-1-cyclobutyl-1H-1,2,4-triazole (Int-195, 130 mg, 463 µmol) and 3-chloro-4-fluorophenol (102 mg, 694 µmol) with potassium carbonate in DMF heating in a sealed vial overnight at 110° C. The compound was isolated as a off white solid (149 mg, 92.9% yield). MS (ES+) m/z: 348.0 [(M+H)$^+$].

Int-199

3-Bromo-5-(3-chloro-5-fluorophenoxy)-1-(1,1,1,3,3,3-hexadeuteriopropan-2-yl)-1,2,4-triazole

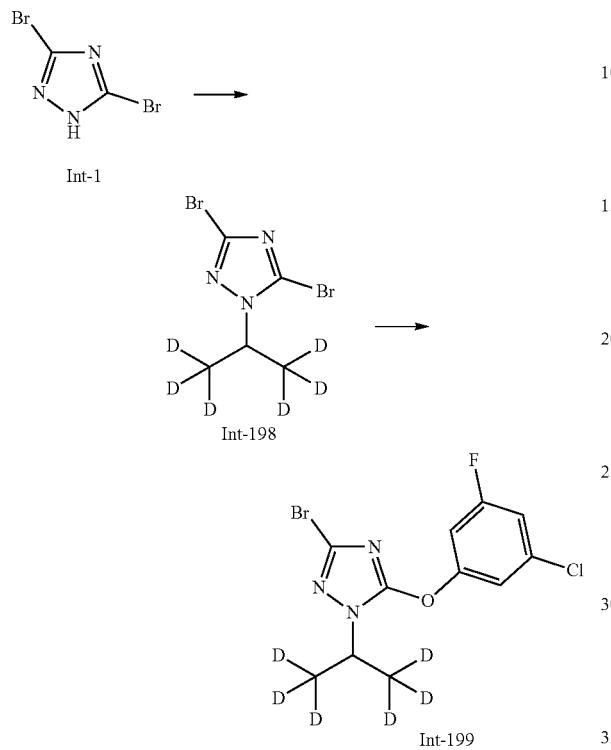

Step 1: 3,5-Dibromo-1-(1,1,1,3,3,3-hexadeuteriopropan-2-yl)-1,2,4-triazole (Int-198)

In a 250 mL round bottomed flask sodium hydride (60% dispersion in mineral oil) (264 mg, 6.61 mmol) was added to a colorless solution of 3,5-dibromo-1H-1,2,4-triazole (Int-1, 1 g, 4.41 mmol) in DMF (22 ml). The resulting suspension was stirred at room temp during 30 min and 1,1,1,3,3,3-hexadeuterio-2-bromopropane (683 mg, 5.29 mmol) was added and the reaction was stirred at 40° C. over night. The reaction mixture was poured into 50 mL H2O and extracted with EtOAc (3×50 mL). The organic layers were washed with sat NaCl (3×50 mL), dried over MgSO4 and concentrated in vacuo. The title compound was isolated as a colourless liquid (644 mg, 2.34 mmol, 53.1% yield). MS (ES+) m/z: 275.9 [(M+H)$^+$].

Step 2: 3-Bromo-5-(3-chloro-5-fluorophenoxy)-1-(1,1,1,3,3,3-hexadeuteriopropan-2-yl)-1,2,4-triazole (Int-199)

To a light brown solution of 3,5-dibromo-1-(1,1,1,3,3,3-hexadeuteriopropan-2-yl)-1,2,4-triazole (Int-198, 120 mg, 436 μmol) and 3-chloro-5-fluorophenol (95.9 mg, 655 μmol) in DMF (1.5 ml) was added potassium carbonate (151 mg, 1.09 mmol). The vial was closed under Argon and stirred over night at 100° C. The reaction mixture was diluted with 25 mL H2O and extracted with tBuOMe (2×25 mL). The organic layers were back-extracted with 1 M NaOH (2×25 mL) and sat NaCl (3×25 mL), dried over MgSO4 and concentrated in vacuo. The title compound was isolated as a light red liquid (124 mg, 83.4% yield). MS (ES+) m/z: 341.9 [(M+H)$^+$].

Int-201

3-Bromo-5-(3-chloro-5-fluorophenoxy)-1-(1,1,1,2,3,3,3-heptadeuteriopropan-2-yl)-1,2,4-triazole

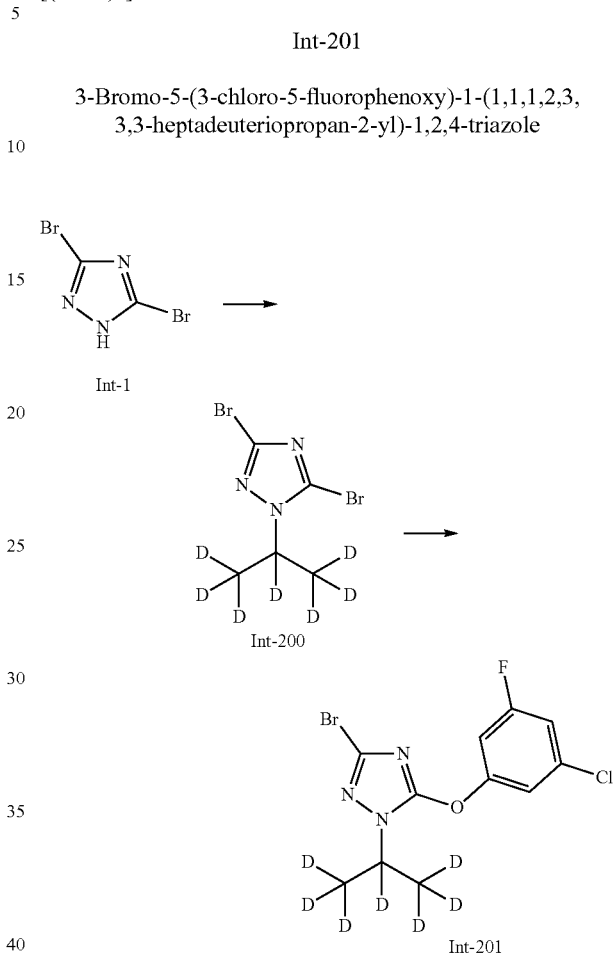

Step 1: 3,5-Dibromo-1-(1,1,1,2,3,3,3-heptadeuteriopropan-2-yl)-1,2,4-triazole (Int-200)

In a 250 mL round bottomed flask sodium hydride (60% dispersion in mineral oil) (264 mg, 6.61 mmol) was added to a colorless solution of 3,5-Dibromo-1H-1,2,4-triazole (Int-1, 1 g, 4.41 mmol) in DMF (22 ml). The resulting suspension was stirred at room temp during 30 min and 1,1,1,2,3,3,3-heptadeuterio-2-iodopropane (936 mg, 5.29 mmol) was added and the reaction was stirred at 40° C. over night. The reaction mixture was poured into 50 mL H2O and extracted with EtOAc (3×50 mL). The organic layers were washed with sat NaCl (3×50 mL), dried over MgSO4 and concentrated in vacuo. The title compound was isolated as a light yellow liquid (1.35 g, 111% yield). MS (ES+) m/z: 276.9 [(M+H)$^+$].

Step 2: 3-Bromo-5-(3-chloro-5-fluorophenoxy)-1-(1,1,1,2,3,3,3-heptadeuteriopropan-2-yl)-1,2,4-triazole (Int-201)

To a light brown solution 3,5-dibromo-1-(1,1,1,2,3,3,3-heptadeuteriopropan-2-yl)-1,2,4-triazole (Int-200, 250 mg, 906 μmol) and 3-chloro-5-fluorophenol (199 mg, 1.36 mmol) in DMF (3 ml) was added potassium carbonate (313 mg, 2.26 mmol). The vial was closed under Argon and stirred over night at 100° C. The reaction mixture was diluted with 50 mL H2O and extracted with tBuOMe (2×50 mL). The organic layers were washed with 1 M NaOH (2×50 mL) and sat NaCl (3×50 mL), dried over MgSO4 and concentrated in vacuo. The title compound was isolated as a light yellow liquid (284.6 mg, 92% yield). MS (ES+) m/z: 343.0 [(M+H)+].

Int-202

3-Bromo-5-(3-chloro-4-fluorophenoxy)-1-(1,1,1,2,3,3,3-heptadeuteriopropan-2-yl)-1,2,4-triazole

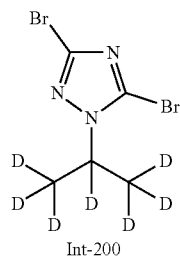
Int-200

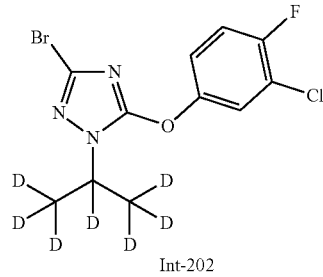
Int-202

The title compound was prepared in analogy to Int-201 from 3,5-dibromo-1-(1,1,1,2,3,3,3-heptadeuteriopropan-2-yl)-1,2,4-triazole (Int-200, 250 mg, 906 μmol) and 3-chloro-4-fluorophenol (199 mg, 1.36 mmol) with potassium carbonate in DMF heating in a sealed vial overnight at 110° C. The title compound was isolated as a off white solid (259.3 mg, 83.8% yield). MS (ES+) m/z: 343.1 [(M+H)+].

Int-204

3-Bromo-5-(3-chloro-5-fluorophenoxy)-1-(trideuteriomethyl)-1,2,4-triazole

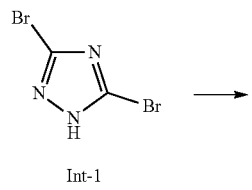
Int-1

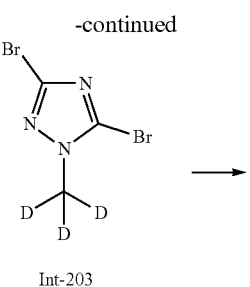
Int-203

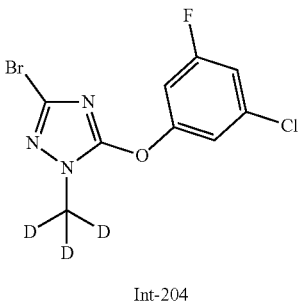
Int-204

Step 1: 3,5-Dibromo-1-(trideuteriomethyl)-1,2,4-triazole (Int-203)

In a 250 mL round bottomed flask sodium hydride (60% dispersion in mineral oil) (132 mg, 3.31 mmol) was added to a colorless solution of 3,5-dibromo-1H-1,2,4-triazole (Int-1, 500 mg, 2.2 mmol) in DMF (10 ml). The resulting suspension was stirred at room temp during 30 min and trideuterio(iodo)methane (319 mg, 2.2 mmol) was added and the reaction was stirred at 40° C. over night. The reaction mixture was poured into 50 mL H2O and extracted with EtOAc (3×50 mL). The organic layers were washed with sat NaCl (3×50 mL), dried over MgSO4 and concentrated in vacuo. The title compound was isolated as an off-white solid (456 mg, 84.8% yield). MS (ES+) m/z: 244.9 [(M+H)+].

Step 2: 3-Bromo-5-(3-chloro-5-fluorophenoxy)-1-(trideuteriomethyl)-1,2,4-triazole (Int-204)

To a light brown solution 3,5-dibromo-1-(trideuteriomethyl)-1,2,4-triazole (Int-203, 150 mg, 615 μmol) and 3-chloro-5-fluorophenol (135 mg, 922 μmol) in DMF (1.8 ml) was added potassium carbonate (212 mg, 1.54 mmol). The vial was closed under Argon and stirred over night at 100° C. The reaction mixture was diluted with 50 mL H2O and extracted with tBuOMe (2×50 mL). The organic layers were back-extracted with 1 M NaOH (2×50 mL) and sat NaCl (3×50 mL), dried over MgSO4 and concentrated in vacuo. The title compound was isolated as an off-white solid (178.7 mg, 93.9% yield). MS (ES+) m/z: 311.0 [(M+H)+].

Int-205

3-Bromo-5-(3-chloro-4-fluorophenoxy)-1-(trideuteriomethyl)-1,2,4-triazole

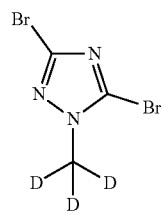

Int-203

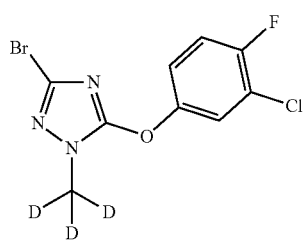

Int-205

The title compound was prepared in analogy to Int-204 from 3,5-dibromo-1-(trideuteriomethyl)-1,2,4-triazole (Int-203, 150 mg, 615 µmol) and 3-chloro-4-fluorophenol (135 mg, 922 µmol) with potassium carbonate in DMF heating in a sealed vial overnight at 110° C. The compound was isolated as an off white solid (176.2 mg, 92.6% yield). MS (ES+) m/z: 311.0 [(M+H)$^+$].

Int-207

3-Bromo-5-(3-chloro-5-fluorophenoxy)-1-(1,1,2,2,2-pentadeuterioethyl)-1,2,4-triazole

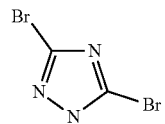

Int-1

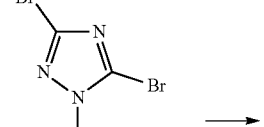

Int-206

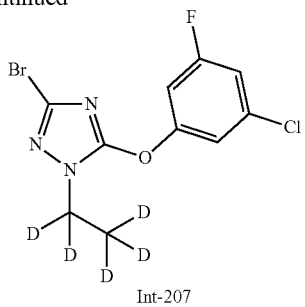

Int-207

Step 1: 3,5-Dibromo-1-(1,1,2,2,2-pentadeuterioethyl)-1,2,4-triazole (Int-206)

In a 250 mL round bottomed flask sodium hydride (60% dispersion in mineral oil) (132 mg, 3.31 mmol) was added to a colorless solution of 3,5-dibromo-1H-1,2,4-triazole (Int-1, 500 mg, 2.2 mmol) in DMF (10 ml). The resulting suspension was stirred at room temp during 30 min and 1,1,1,2,2-pentadeuterio-2-iodoethane (355 mg, 2.2 mmol) was added and the reaction was stirred at 40° C. over night. The reaction mixture was poured into 50 mL H2O and extracted with EtOAc (3×50 mL). The organic layers were washed with sat NaCl (3×50 mL), dried over MgSO4 and concentrated in vacuo. The title compound was isolated as a colorless liquid (465 mg, 81.2% yield). MS (ES+) m/z: 260.9 [(M+H)$^+$].

Step 2: 3-Bromo-5-(3-chloro-5-fluorophenoxy)-1-(1,1,2,2,2-pentadeuterioethyl)-1,2,4-triazole (Int-207)

To a light brown solution 3,5-dibromo-1-(1,1,2,2,2-pentadeuterioethyl)-1,2,4-triazole (Int-206, 150 mg, 577 µmol) and 3-chloro-5-fluorophenol (127 mg, 866 µmol) in DMF (1.8 ml) was added potassium carbonate (199 mg, 1.44 mmol). The vial was closed under Argon and stirred over night at 100° C. The reaction mixture was diluted with 50 mL H2O and extracted with tBuOMe (2×50 mL). The organic layers were back-extracted with 1 M NaOH (2×50 mL) and sat NaCl (3×50 mL), dried over MgSO4 and concentrated in vacuo. The title compound was isolated as an off-white solid (173.6 mg, 92.4% yield). MS (ES+) m/z: 327.0 [(M+H)$^+$].

Int-208

3-Bromo-5-(3-chloro-4-fluorophenoxy)-1-(1,1,2,2,2-pentadeuterioethyl)-1,2,4-triazole

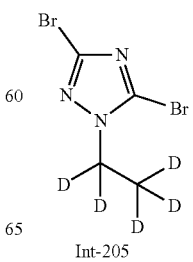

Int-205

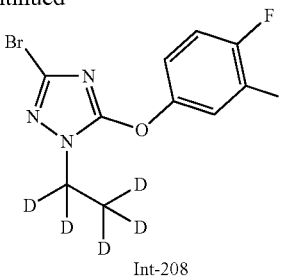

Int-208

The title compound was prepared in analogy to Int-207 from 3,5-dibromo-1-(1,1,2,2,2-pentadeuterioethyl)-1,2,4-triazole (Int-206, 150 mg, 577 μmol) and 3-chloro-4-fluorophenol (127 mg, 866 μmol) with potassium carbonate in DMF heating in a sealed vial overnight at 110° C. The compound was isolated as a off white solid (173.9 mg, 92.6% yield). MS (ES+) m/z: 327.0 [(M+H)$^+$].

Int-209

3-Bromo-5-(4-chlorophenoxy)-1-isopropyl-1H-1,2,4-triazole

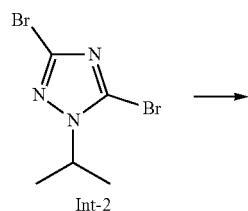

Int-2

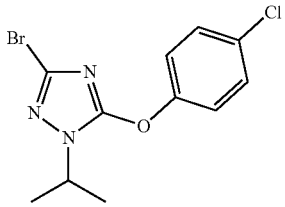

Int-209

3,5-Dibromo-1-isopropyl-1,2,4-triazole (Int-2, 400 mg, 1.5 mmol) was dissolved in DMF (8 mL) and 4-chlorophenol (249 mg, 1.93 mmol) was added, followed by potassium carbonate (514 mg, 3.72 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 24 g, eluting with ethyl acetate/n-heptane, gradient 0:100 to 50:50 v/v), to yield the title compound as a white solid (479 mg, 92%). HPLC (method LCMS_fastgradient) $t_R$=1.42 min. $^1$H NMR (CDCl$_3$, 300 MHz): 1.52 (d, J=6.8 Hz, 6H), 4.61 (hept, J=6.6 Hz, 1H), 7.24 (d, J=9.3 Hz, 2H), 7.38 (d, J=9.1 Hz, 2H). MS (ES+) m/z 316.3, 318.3, 320.3 [M+H, Br & Cl isotopes].

Int-210

3-Bromo-5-(3-chloro-5-fluorophenoxy)-1-(2,2,2-trifluoroethyl)-1H-1,2,4-triazole

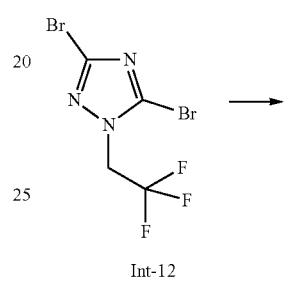

Int-12

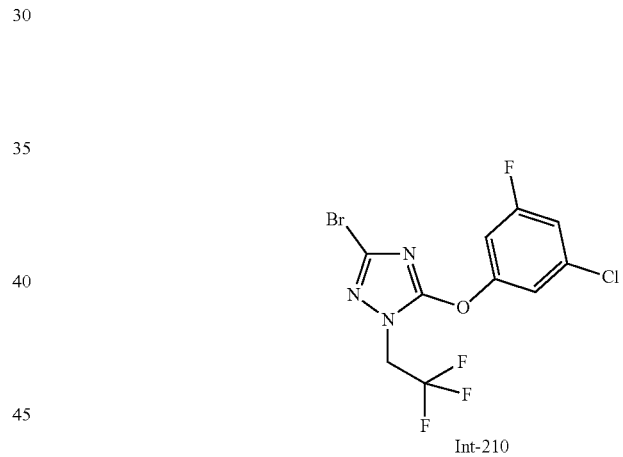

Int-210

3,5-Dibromo-1-(2,2,2-trifluoroethyl)-1H-1,2,4-triazole (Int-12, 1.26 g, 4.08 mmol) was dissolved in DMF (10 mL) and 3-chloro-5-fluorophenol (861 mg, 5.9 mmol) was added, followed by potassium carbonate (1.36 g, 9.84 mmol). The reaction mixture was stirred for 20 h at 110° C. in a sealed tube. After cooling to room temperature, the reaction mixture was poured into water (50 mL) and extracted with MTBE (2×100 mL). The combined organic layers were washed with 0.5 N sodium hydroxide solution (30 mL), water (30 mL) and brine (30 mL), dried over sodium sulphate and concentrated in vacuo. The crude product was purified by column chromatography (silica gel, 40 g, eluting with ethyl acetate/n-heptane, gradient 0:100 to 20:80 v/v), to afford the title compound as a colorless oil (890 mg, 58%). HPLC (method LCMS_fastgradient) $t_R$=1.43 min. $^1$H NMR (CDCl$_3$, 300 MHz): 4.67 (q, J=8.2 Hz, 2H), 7.01-7.10 (m, 2H), 7.17-7.20 (m, 1H). MS (ES+) m/z 374.3, 376.3, 378.3 [M+H, Br & Cl isotopes].

Example 1

(1R,5S,8s)-N-(5-(2-Chlorophenoxy)-1-(propan-2-yl)-1H-1,2,4-triazol-3-yl)-3-(3-methyl-1,2,4-thiadiazol-5-yl)-3-azabicyclo[3.2.1]octan-8-amine

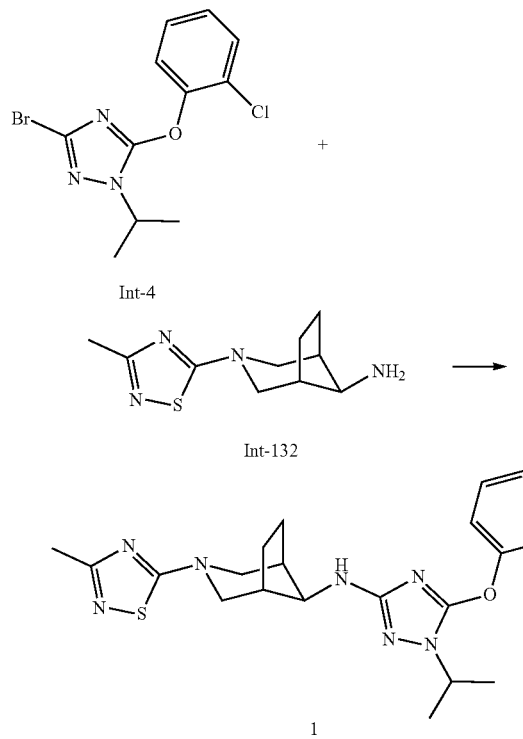

Example 2

(1R,5S,8s)-N-(5-(2-Chlorophenoxy)-1-(propan-2-yl)-1H-1,2,4-triazol-3-yl)-3-(3-methylisothiazol-5-yl)-3-azabicyclo[3.2.1]octan-8-amine

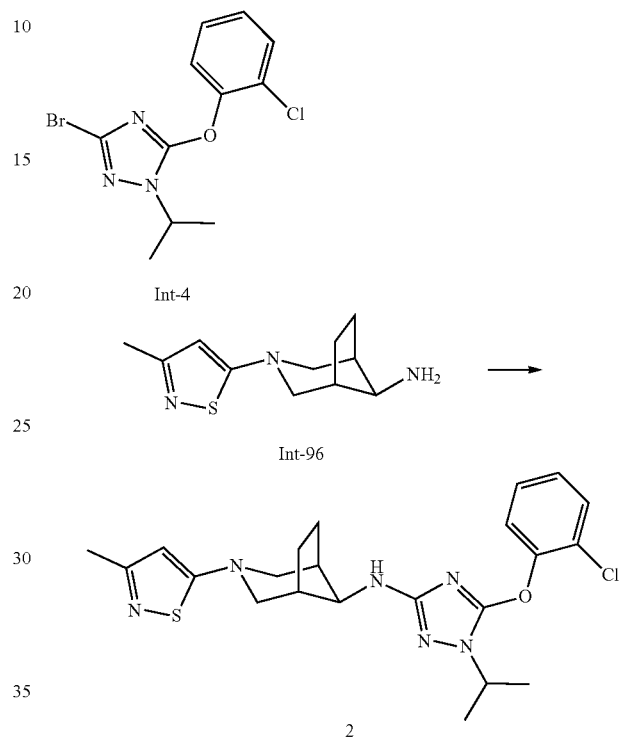

In a 8 mL microwave vial, 3-bromo-5-(2-chlorophenoxy)-1-(propan-2-yl)-1H-1,2,4-triazole (Int-4, 50 mg, 158 µmol) was suspended in 1,4-dioxane (1.75 mL) and (1R,5S,8s)-3-(3-methyl-1,2,4-thiadiazol-5-yl)-3-azabicyclo[3.2.1]octan-8-amine (Int-132, 35.4 mg, 158 µmol), sodium tert-butoxide (31.1 mg, 324 µmol), 4,5-bis(diphenylphosphino)-9,9-dimethylxanthene ("xantphos", CAS [161265-03-8], 14.6 mg, 25.3 µmol), and tris(dibenzylideneacetone)di-palladium(0) chloroform adduct (13.1 mg, 12.6 µmol) were added subsequently. The vial was degassed with Argon and sealed. The reaction mixture was heated under microwave irradiation at 145° C. for 30 minutes. After that, water (5 mL) was added and the mixture was extracted with ethyl acetate (3×20 mL). The combined organic layers were dried (magnesium sulfate), and concentrated in vacuo. The crude product was purified by column chromatography (silica gel, 20 g, eluting with ethyl acetate/n-heptane 20:80 v/v) to yield the title compound as a light yellow amorphous powder (20 mg, 27%). HPLC (method LCMS_fastgradient) $t_R$=1.37 min. $^1$H NMR (CDCl$_3$, 300 MHz): δ 1.48 (d, J=6.9 Hz, 6H), 1.54-1.65 (m, 2H), 1.83-1.91 (m, 2H), 2.41 (s, 3H), 2.40-2.48 (m, 2H), 3.33-3.42 (m, 2H), 3.58-3.70 (m, 1H), 3.75-3.90 (m, 2H), 4.55 (hept, J=6.6 Hz, 1H), 7.15-7.23 (m, 1H), 7.27-7.36 (m, 1H), 7.38-7.48 (m, 2H). MS (ES+) m/z 460.3, 462.3 [M+H, Cl isotopes].

In a 2 mL microwave vial, 3-bromo-5-(2-chlorophenoxy)-1-(propan-2-yl)-1H-1,2,4-triazole (Int-4, 50 mg, 158 µmol) was suspended in 1,4-dioxane (1.0 mL) and (1R,5S,8s)-3-(3-methylisothiazol-5-yl)-3-azabicyclo[3.2.1]octan-8-amine (Int-96, 20.0 mg, 89.6 µmol), sodium tert-butoxide (17.6 mg, 184 µmol), 4,5-bis(diphenylphosphino)-9,9-dimethylxanthene ("xantphos", CAS [161265-03-8], 8.3 mg, 14 µmol), and tris(dibenzylideneacetone)-dipalladium(0) chloroform adduct (7.4 mg, 7.2 µmol) were added subsequently. The vial was degassed with Argon and sealed. The reaction mixture was heated under microwave irradiation at 145° C. for 30 minutes. After that, water (3 mL) was added and the mixture was extracted with ethyl acetate (3×20 mL). The combined organic layers were dried (magnesium sulfate), and concentrated in vacuo. The crude product was purified by column chromatography (silica gel, 20 g, eluting with ethyl acetate/n-heptane 20:80 v/v) to yield the title compound as a light yellow oil (4.5 mg, 11%). $^1$H NMR (CDCl$_3$, 300 MHz): δ1.49 (d, J=6.7 Hz, 6H), 1.60-1.69 (m, 2H), 1.83-1.91 (m, 2H), 2.32 (s, 3H), 2.39-2.45 (m, 2H), 3.22-3.26 (m, 2H), 3.51-3.64 (m, 1H), 3.72 (d, J=6.1 Hz, 1H), 3.87 (d, J=6.1 Hz, 1H), 4.54 (hept, J=6.7 Hz, 1H), 5.90 (s, 1H), 7.19 (ddd, J=1.6, 7.7, 7.7 Hz, 1H), 7.31 (ddd, J=1.6, 8.1, 8.1 Hz, 1H), 7.41 (dd, J=1.6, 8.1 Hz, 1H), 7.46 (dd, J=1.6, 8.1 Hz, 1H).

Example 3

(1R,5S,8s)-N-(5-(3-Fluorophenoxy)-1-(propan-2-yl)-1H-1,2,4-triazol-3-yl)-3-(3-methylisothiazol-5-yl)-3-azabicyclo[3.2.1]octan-8-amine

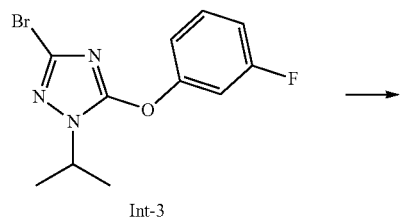

Int-3

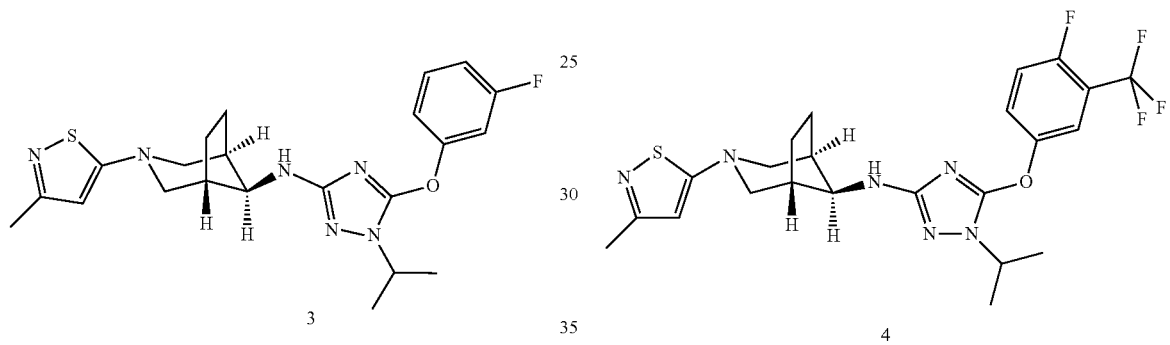

To a solution of (1R,5S,8s)-3-(3-methylisothiazol-5-yl)-3-azabicyclo[3.2.1]octan-8-amine (Int-96, 40 mg, 0.2 mmol) and 3-bromo-5-(3-fluorophenoxy)-1-(propan-2-yl)-1H-1,2,4-triazole (Int-3, 80.6 mg, 0.3 mmol) in dry 1,4-dioxane (1 mL) in sealed tube was added 2-dicyclohexylphosphino-2',6'-diisopropoxybiphenyl ("Ruphos", CAS [787618-22-8], 16.7 mg, 0.04 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 28.6 mg, 0.04 mmol). The reaction mixture was again degassed with argon for 10 min followed by addition of sodium tertbutoxide (68.8 mg, 0.7 mmol). The reaction mixture was stirred at 110° C. for 12 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, 5 g, eluting with EtOAc/n-hexane 40:60 v/v) to yield the title compound as white solid (35 mg, 44%). HPLC purity 97.97%. $^1$H NMR (DMSO-d6, 400 MHz): 1.35 (d, J=6.6 Hz, 6H), 1.43 (d, J=7.7 Hz, 2H), 1.87-1.90 (m, 2H), 2.19 (s, 3H), 2.37 (s, 2H), 3.10 (d, J=10.9 Hz, 2H), 3.21 (d, J=9.0 Hz, 2H), 3.51 (d, J=4.1 Hz, 1H), 4.41 (dt, J=13.0, 6.4 Hz, 1H), 6.00 (d, J=4.2 Hz, 1H), 6.07 (s, 1H), 7.11 (dd, J=21.9, 8.3 Hz, 2H), 7.07-7.15 (m, 1H), 7.47 (q, J=8.2 Hz, 1H). MS (ES+) m/z 442.7 [M+H].

Example 4

(1R,5S,8s)-N-(5-(4-Fluoro-3-(trifluoromethyl)phenoxy)-1-(propan-2-yl)-1H-1,2,4-triazol-3-yl)-3-(3-methylisothiazol-5-yl)-3-azabicyclo[3.2.1]octan-8-amine

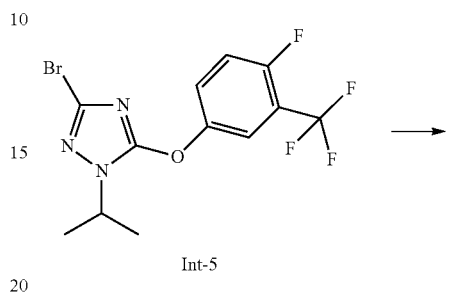

Int-5

To a solution of (1R,5S,8s)-3-(3-methylisothiazol-5-yl)-3-azabicyclo[3.2.1]octan-8-amine (Int-96, 40 mg, 0.2 mmol) and 3-bromo-5-[4-fluoro-3-(trifluoromethyl)phenoxy]-1-(propan-2-yl)-1H-1,2,4-triazole (Int-5, 98.9 mg, 0.3 mmol) in dry 1,4-dioxane (1 mL) in sealed tube was added 2-dicyclohexylphosphino-2',6'-diisopropoxybiphenyl ("Ruphos", CAS [787618-22-8], 16.7 mg, 0.04 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 28.6 mg, 0.04 mmol). The reaction mixture was again degassed with argon for 10 min followed by addition of sodium tertbutoxide (68.8 mg, 0.7 mmol). The reaction mixture was stirred at 110° C. for 12 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, 5 g, eluting with EtOAc/n-hexane 40:60 v/v) to yield the title compound as white solid (17 mg, 19%). HPLC purity 98.69%. $^1$H NMR (DMSO-d6, 400 MHz): 1.37 (d, J=6.6 Hz, 6H), 1.84-1.91 (m, 2H), 2.19 (s, 3H), 2.37 (s, 2H), 3.09 (d, J=10.9 Hz, 2H), 3.20 (d, J=8.7 Hz, 2H), 3.49 (d, J=4.1 Hz, 1H), 4.39-4.50 (m, 1H), 6.01 (d, J=4.3 Hz, 1H), 6.07 (s, 1H), 7.61 (t, J=9.7 Hz, 1H), 7.75 (dd, J=8.3, 4.4 Hz, 1H), 7.86-7.94 (m, 1H). MS (ES+) m/z 511.2 [M+H].

Example 5

(1R,5S,8s)-N-(1-(Propan-2-yl)-5-(2-(trifluoromethoxy)phenoxy)-1H-1,2,4-triazol-3-yl)-3-(3-methylisothiazol-5-yl)-3-azabicyclo[3.2.1]octan-8-amine

Example 6

(1R,5S,8s)-N-(5-(2-Fluorophenoxy)-1-(propan-2-yl)-1H-1,2,4-triazol-3-yl)-3-(3-methylisothiazol-5-yl)-3-azabicyclo[3.2.1]octan-8-amine

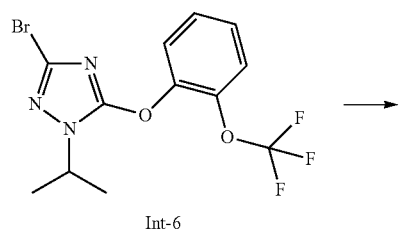

Int-6

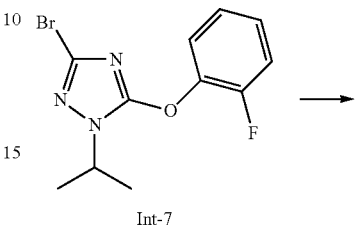

Int-7

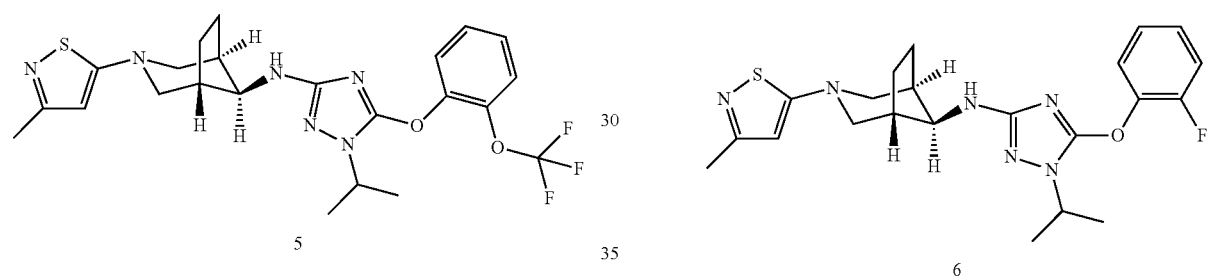

5

6

To a solution of (1R,5S,8s)-3-(3-methylisothiazol-5-yl)-3-azabicyclo[3.2.1]octan-8-amine (Int-96, 70 mg, 0.3 mmol) and 3-bromo-1-(propan-2-yl)-5-[2-(trifluoromethoxy)phenoxy]-1H-1,2,4-triazole (Int-6, 229.6 mg, 0.6 mmol) in dry 1,4-dioxane (2 mL) in sealed tube was added 2-dicyclohexylphosphino-2',6'-diisopropoxybiphenyl ("Ruphos", CAS [787618-22-8], 29.2 mg, 0.06 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 50 mg, 0.06 mmol). The reaction mixture was again degassed with argon for 10 min followed by addition of sodium tertbutoxide (120.4 mg, 1.2 mmol). The reaction mixture was stirred at 110° C. for 12 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as white solid (17 mg, 19%). HPLC purity 97.49%. $^1$H NMR (DMSO-d6, 400 MHz): 1.38 (d, J=6.6 Hz, 6H), 1.82-1.89 (m, 3H), 2.19 (s, 3H), 2.34 (s, 2H), 3.08 (d, J=10.8 Hz, 2H), 3.20 (d, J=11.2 Hz, 2H), 3.48 (d, J=4.2 Hz, 1H), 4.41 (p, J=6.6 Hz, 1H), 5.97 (d, J=4.5 Hz, 1H), 6.07 (s, 1H), 7.39 (t, J=7.1 Hz, 1H), 7.48 (t, J=7.8 Hz, 1H), 7.55 (d, J=7.9 Hz, 1H), 7.56-7.64 (m, 1H). MS (ES+) m/z 508.9 [M+H].

To a solution of (1R,5S,8s)-3-(3-methylisothiazol-5-yl)-3-azabicyclo[3.2.1]octan-8-amine (Int-96, 70 mg, 0.3 mmol) and 3-bromo-1-(propan-2-yl)-5-(2-fluorophenoxy)-1H-1,2,4-triazole (Int-7, 147.5 mg, 0.6 mmol) in dry 1,4-dioxane (2 mL) in sealed tube was added 2-dicyclohexylphosphino-2',6'-diisopropoxybiphenyl ("Ruphos", CAS [787618-22-8], 29.2 mg, 0.06 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 50 mg, 0.06 mmol). The reaction mixture was again degassed with argon for 10 min followed by addition of sodium tertbutoxide (120.4 mg, 1.2 mmol). The reaction mixture was stirred at 110° C. for 12 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as white solid (86.6 mg, 62%). HPLC purity 97.59%. $^1$H NMR (DMSO-d6, 400 MHz): 1.38 (d, J=6.6 Hz, 7H), 1.83-1.87 (m, 2H), 2.19 (s, 3H), 2.34 (s, 2H), 3.08 (d, J=10.8 Hz, 2H), 3.19 (d, J=8.8 Hz, 2H), 3.48 (d, J=4.2 Hz, 1H), 4.45 (p, J=6.5 Hz, 1H), 5.95 (d, J=4.4 Hz, 1H), 6.07 (s, 1H), 7.22-7.33 (m, 2H), 7.36-7.42 (m, 1H), 7.49 (t, J=7.3 Hz, 1H). MS (ES+) m/z 442.8 [M+H].

Example 7

(1R,5S,8s)-3-(3-Methyl-1,2-thiazol-5-yl)-N-[1-(propan-2-yl)-5-[4-(trifluoromethoxy)phenoxy]-1H-1,2,4-triazol-3-yl]-3-azabicyclo[3.2.1]octan-8-amine

Example 8

(1R,5S,8s)-N-[5-(4-Fluorophenoxy)-1-(propan-2-yl)-1H-1,2,4-triazol-3-yl]-3-(3-methyl-1,2-thiazol-5-yl)-3-azabicyclo[3.2.1]octan-8-amine

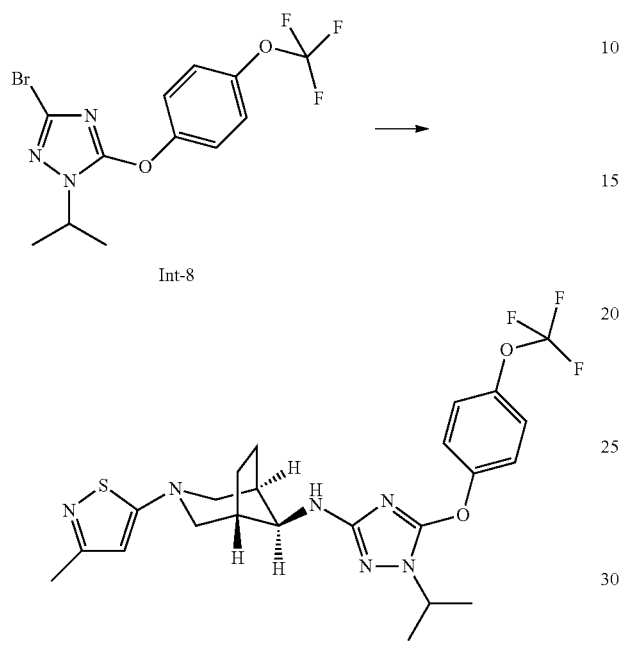

Int-8

Int-9

7

8

To a solution of (1R,5S,8s)-3-(3-methylisothiazol-5-yl)-3-azabicyclo[3.2.1]octan-8-amine (Int-96, 60 mg, 0.2 mmol) and 3-bromo-1-(propan-2-yl)-5-[3-(trifluoromethyl)phenoxy]-1H-1,2,4-triazole (Int-8, 196.8 mg, 0.5 mmol) in dry 1,4-dioxane (2 mL) in sealed tube was added 2-dicyclohexylphosphino-2',6'-diisopropoxybiphenyl ("Ruphos", CAS [787618-22-8], 25 mg, 0.05 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 42.9 mg, 0.05 mmol). The reaction mixture was again degassed with argon for 10 min followed by addition of sodium tertbutoxide (103.2 mg, 1.0 mmol). The reaction mixture was stirred at 110° C. for 14 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as colorless sticky solid (88.5 mg, 65%). HPLC purity 95.85%. $^1$H NMR (DMSO-d6, 400 MHz): 1.36 (d, J=6.6 Hz, 6H), 1.41-1.43 (d, J=7.6 Hz, 2H), 1.87 (d, J=9.2 Hz, 2H), 2.19 (s, 3H), 2.36 (s, 2H), 3.09 (d, J=10.9 Hz, 2H), 3.20 (d, J=9.4 Hz, 2H), 3.51 (d, J=3.7 Hz, 1H), 4.42 (dt, J=10.8, 5.4 Hz, 1H), 5.98 (d, J=3.9 Hz, 1H), 6.07 (s, 1H), 7.44 (s, 4H). MS (ES+) m/z 509.2 [M+H].

To a solution of (1R,5S,8s)-3-(3-methylisothiazol-5-yl)-3-azabicyclo[3.2.1]octan-8-amine (Int-96, 60 mg, 0.2 mmol) and 3-bromo-5-(4-fluorophenoxy)-1-(propan-2-yl)-1H-1,2,4-triazole (Int-8, 161.3 mg, 0.5 mmol) in dry 1,4-dioxane (2 mL) in sealed tube was added 2-dicyclohexylphosphino-2',6'-diisopropoxybiphenyl ("Ruphos", CAS [787618-22-8], 25 mg, 0.05 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 42.9 mg, 0.05 mmol). The reaction mixture was again degassed with argon for 10 min followed by addition of sodium tertbutoxide (103.2 mg, 1.0 mmol). The reaction mixture was stirred at 110° C. for 14 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as white solid (30 mg, 25%). HPLC purity 96.42%. $^1$H NMR (DMSO-d6, 400 MHz): 1.36 (d, J=6.6 Hz, 6H), 1.41-1.43 (d, J=7.8 Hz, 2H), 1.84-1.91 (m, 2H), 2.19 (s, 3H), 2.36 (s, 2H), 3.09 (d, J=11.3 Hz, 2H), 3.20 (d, J=9.6 Hz, 2H), 3.50 (d, J=3.5 Hz, 1H), 4.42 (dt, J=13.1, 5.9 Hz, 1H), 5.94 (d, J=4.3 Hz, 1H), 6.07 (s, 1H), 7.25 (t, J=8.7 Hz, 2H), 7.30-7.38 (m, 2H). MS (ES+) m/z 443.2 [M+H].

Example 9

(1R,5S,8s)-N-{5-[3-Fluoro-5-(trifluoromethyl)phenoxy]-1-(propan-2-yl)-1H-1,2,4-triazol-3-yl}-3-(3-methyl-1,2-thiazol-5-yl)-3-azabicyclo[3.2.1]octan-8-amine

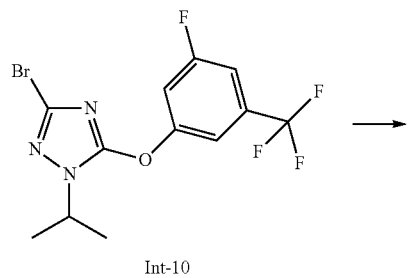

Int-10

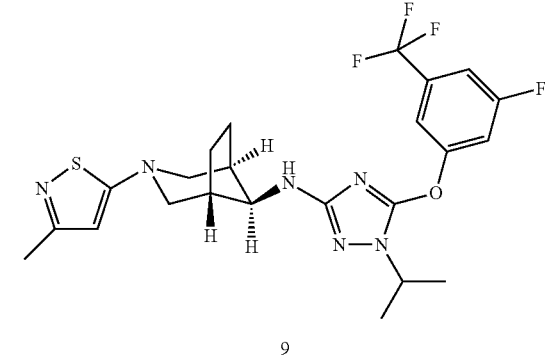

9

To a solution of (1R,5S,8s)-3-(3-methylisothiazol-5-yl)-3-azabicyclo[3.2.1]octan-8-amine (Int-96, 60 mg, 0.2 mmol) and 3-Bromo-5-[3-fluoro-5-(trifluoromethyl)phenoxy]-1-(propan-2-yl)-1H-1,2,4-triazole (Int-10, 197.9 mg, 0.5 mmol) in dry 1,4-dioxane (2 mL) in sealed tube was added 2-dicyclohexylphosphino-2',6'-diisopropoxybiphenyl ("Ruphos", CAS [787618-22-8], 25 mg, 0.05 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 42.9 mg, 0.05 mmol). The reaction mixture was again degassed with argon for 10 min followed by addition of sodium tertbutoxide (103.2 mg, 1.0 mmol). The reaction mixture was stirred at 110° C. for 12 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as white solid (80 mg, 58%). HPLC purity 93.48%. $^1$H NMR (DMSO-d6, 400 MHz): 1.37 (d, J=6.6 Hz, 6H), 1.43-1.45 (d, J=7.7 Hz, 2H), 1.87-1.91 (m, 2H), 2.19 (s, 3H), 2.38 (s, 2H), 3.10 (d, J=10.7 Hz, 2H), 3.21 (dd, J=11.3, 2.8 Hz, 2H), 3.52 (d, J=4.3 Hz, 1H), 4.45 (p, J=6.7 Hz, 1H), 6.04 (d, J=4.4 Hz, 1H), 6.07 (s, 1H), 7.62 (d, J=8.7 Hz, 1H), 7.74 (d, J=10.8 Hz, 2H). MS (ES+) m/z 510.8 [M+H].

Example 10

(1R,5S,8s)-3-(3-Methyl-1,2-thiazol-5-yl)-N-[1-(propan-2-yl)-5-[3-(trifluoromethyl)phenoxy]-1H-1,2,4-triazol-3-yl]-3-azabicyclo[3.2.1]octan-8-amine

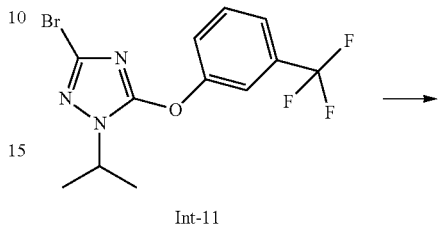

Int-11

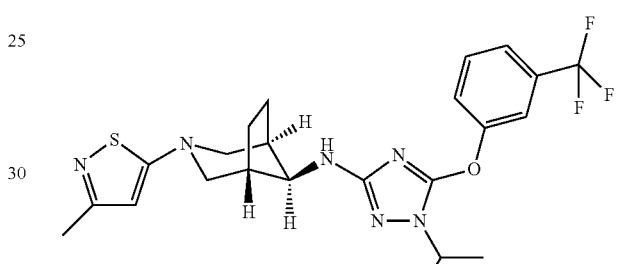

10

To a solution of (1R,5S,8s)-3-(3-methylisothiazol-5-yl)-3-azabicyclo[3.2.1]octan-8-amine (Int-96, 60 mg, 0.2 mmol) and 3-bromo-1-(propan-2-yl)-5-[3-(trifluoromethyl)phenoxy]-1H-1,2,4-triazole (Int-11, 188.2 mg, 0.5 mmol) in dry 1,4-dioxane (2 mL) in sealed tube was added 2-dicyclohexylphosphino-2',6'-diisopropoxybiphenyl ("Ruphos", CAS [787618-22-8], 25 mg, 0.05 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 42.9 mg, 0.05 mmol). The reaction mixture was again degassed with argon for 10 min followed by addition of sodium tertbutoxide (103.2 mg, 1.0 mmol). The reaction mixture was stirred at 110° C. for 12 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as colorless sticky solid (50 mg, 38%). HPLC purity 98.25%. $^1$H NMR (DMSO-d6, 400 MHz): 1.37 (d, J=6.6 Hz, 6H), 1.42-1.44 (d, J=7.7 Hz, 2H), 1.84-1.92 (m, 2H), 2.19 (s, 3H), 2.37 (s, 2H), 3.09 (d, J=11.0 Hz, 2H), 3.21 (d, J=8.8 Hz, 2H), 3.51 (d, J=4.1 Hz, 1H), 4.45 (dt, J=12.9, 6.3 Hz, 1H), 5.99 (d, J=4.3 Hz, 1H), 6.07 (s, 1H), 7.60-7.71 (m, 3H), 7.79 (s, 1H). MS (ES+) m/z 492.8 [M+H].

Example 11

(1R,5S,8s)-N-[5-(3,5-Difluorophenoxy)-1-(propan-2-yl)-1H-1,2,4-triazol-3-yl]-3-(3-methyl-1,2-thiazol-5-yl)-3-azabicyclo[3.2.1]octan-8-amine

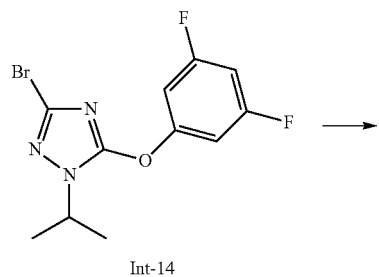

Int-14

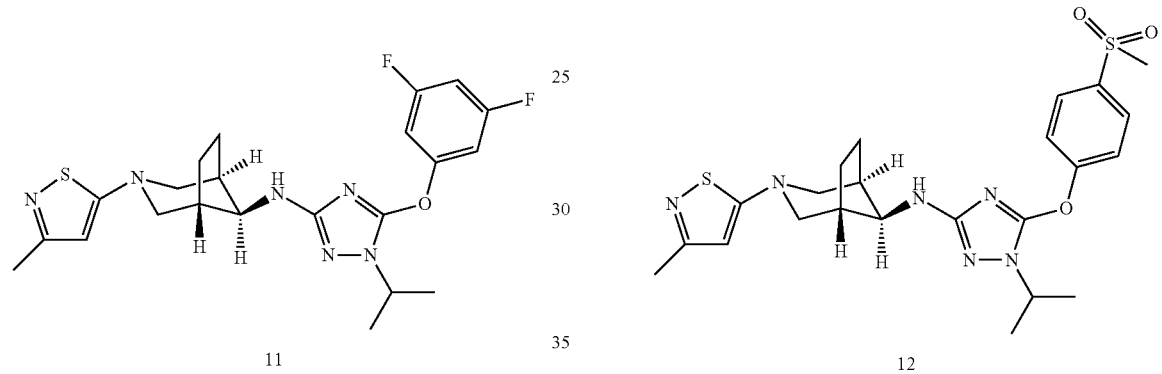

11

To a solution of (1R,5S,8s)-3-(3-methylisothiazol-5-yl)-3-azabicyclo[3.2.1]octan-8-amine (Int-96, 60 mg, 0.2 mmol) and 3-bromo-5-(3,5-difluorophenoxy)-1-(propan-2-yl)-1H-1,2,4-triazole (Int-14, 171 mg, 0.5 mmol) in dry 1,4-dioxane (2 mL) in sealed tube was added 2-dicyclohexylphosphino-2',6'-diisopropoxybiphenyl ("Ruphos", CAS [787618-22-8], 25 mg, 0.05 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 42.9 mg, 0.05 mmol). The reaction mixture was again degassed with argon for 10 min followed by addition of sodium tertbutoxide (103.2 mg, 1.0 mmol). The reaction mixture was stirred at 110° C. for 12 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as white solid (80 mg, 65%). HPLC purity 96.62%. $^1$H NMR (DMSO-d6, 400 MHz): 1.36 (d, J=6.6 Hz, 6H), 1.43-1.45 (d, J=7.6 Hz, 2H), 1.89 (d, J=9.1 Hz, 2H), 2.19 (s, 3H), 2.38 (s, 2H), 3.10 (d, J=11.0 Hz, 2H), 3.21 (d, J=9.4 Hz, 2H), 3.52 (d, J=4.3 Hz, 1H), 4.41 (dt, J=13.1, 6.3 Hz, 1H), 6.02 (d, J=4.3 Hz, 1H), 6.07 (s, 1H), 7.18 (dd, J=26.0, 8.1 Hz, 3H). MS (ES+) m/z 460.8 [M+H].

Example 12

(1R,5S,8s)-N-[5-(4-Methanesulfonylphenoxy)-1-(propan-2-yl)-1H-1,2,4-triazol-3-yl]-3-(3-methyl-1,2-thiazol-5-yl)-3-azabicyclo[3.2.1]octan-8-amine

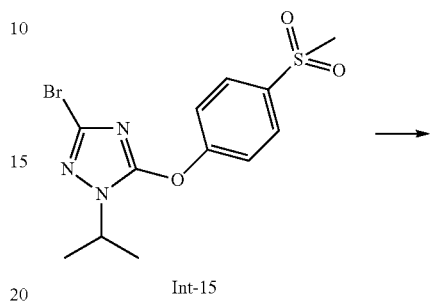

Int-15

12

To a solution of (1R,5S,8s)-3-(3-methylisothiazol-5-yl)-3-azabicyclo[3.2.1]octan-8-amine (Int-96, 50 mg, 0.2 mmol) and 3-bromo-5-(4-methanesulfonylphenoxy)-1-(propan-2-yl)-1H-1,2,4-triazole (Int-15, 161.3 mg, 0.4 mmol) in dry 1,4-dioxane (2 mL) in sealed tube was added 2-dicyclohexylphosphino-2',6'-diisopropoxybiphenyl ("Ruphos", CAS [787618-22-8], 20 mg, 0.04 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 35.7 mg, 0.04 mmol). The reaction mixture was again degassed with argon for 10 min followed by addition of sodium tertbutoxide (103.2 mg, 1.0 mmol). The reaction mixture was stirred at 110° C. for 12 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as white solid (40 mg, 36%). HPLC purity 99.30%. $^1$H NMR (DMSO-d6, 400 MHz): 1.38 (d, J=6.3 Hz, 6H), 1.43 (d, J=7.6 Hz, 2H), 1.89 (d, J=10.4 Hz, 2H), 2.19 (s, 3H), 2.37 (s, 2H), 3.10 (d, J=10.5 Hz, 2H), 3.19-3.23 (m, 5H), 4.43 (dt, J=13.0, 6.3 Hz, 1H), 6.03-6.08 (m, 2H), 7.55 (d, J=8.6 Hz, 2H), 7.99 (d, J=8.6 Hz, 2H). MS (ES+) m/z 502.9 [M+H].

Example 13

(1R,5S,8s)-N-[5-(3-Methanesulfonylphenoxy)-1-(propan-2-yl)-1H-1,2,4-triazol-3-yl]-3-(3-methyl-1,2-thiazol-5-yl)-3-azabicyclo[3.2.1]octan-8-amine

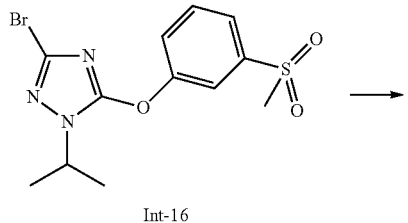

Int-16

Example 14

(1R,5S,8s)-N-{5-[4-Fluoro-3-(trifluoromethyl)phenoxy]-1-(propan-2-yl)-1H-1,2,4-triazol-3-yl}-3-[2-(trifluoromethyl)pyridin-4-yl]-3-azabicyclo[3.2.1]octan-8-amine

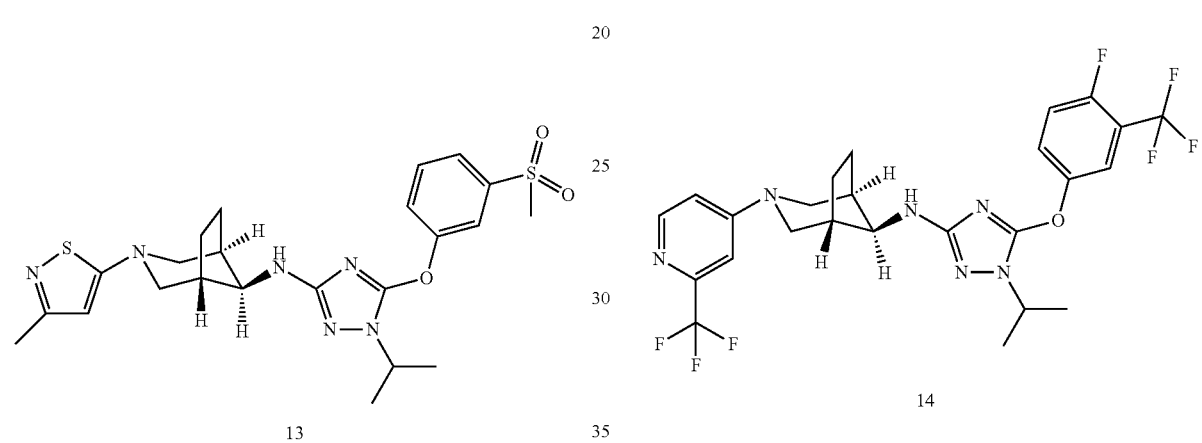

To a solution of (1R,5S,8s)-3-(3-methylisothiazol-5-yl)-3-azabicyclo[3.2.1]octan-8-amine (Int-96, 50 mg, 0.2 mmol) and 3-bromo-5-(3-methanesulfonylphenoxy)-1-(propan-2-yl)-1H-1,2,4-triazole (Int-16, 161.3 mg, 0.4 mmol) in dry 1,4-dioxane (2 mL) in sealed tube was added 2-dicyclohexylphosphino-2',6'-diisopropoxybiphenyl ("Ruphos", CAS [787618-22-8], 20 mg, 0.04 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 35 mg, 0.04 mmol). The reaction mixture was again degassed with argon for 10 min followed by addition of sodium tertbutoxide (103.2 mg, 1.0 mmol). The reaction mixture was stirred at 110° C. for 12 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as white solid (35 mg, 31%). HPLC purity 98.35%. $^1$H NMR (DMSO-d6, 400 MHz): 1.38 (d, J=6.3 Hz, 6H), 1.43 (d, J=7.5 Hz, 2H), 1.88 (d, J=10.7 Hz, 2H), 2.19 (s, 3H), 2.38 (s, 2H), 3.10 (d, J=10.8 Hz, 2H), 3.20 (d, J=11.4 Hz, 2H), 3.27 (s, 3H), 3.51 (d, J=3.9 Hz, 1H), 4.45 (dt, J=11.8, 6.1 Hz, 1H), 6.03 (d, J=2.6 Hz, 1H), 6.07 (s, 1H), 7.71 (d, J=8.5 Hz, 2H), 7.80 (d, J=6.5 Hz, 1H), 7.93 (s, 1H). MS (ES+) m/z 502.9 [M+H].

To a solution of (1R,5S,8s)-3-[2-(trifluoromethyl)pyridin-4-yl]-3-azabicyclo[3.2.1]octan-8-amine (Int-99, 60 mg, 0.3 mmol) and 3-bromo-5-[4-fluoro-3-(trifluoromethyl)phenoxy]-1-(propan-2-yl)-1H-1,2,4-triazole (Int-5, 122.1 mg, 0.3 mmol) in dry 1,4-dioxane (2 mL) in sealed tube was added 2-dicyclohexylphosphino-2',6'-diisopropoxybiphenyl ("Ruphos", CAS [787618-22-8], 20 mg, 0.04 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 35.3 mg, 0.04 mmol). The reaction mixture was again degassed with argon for 10 min followed by addition of sodium tertbutoxide (84.9 mg, 0.9 mmol). The reaction mixture was stirred at 120° C. for 8 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 50:50 v/v) to yield the title compound as white solid (68 mg, 55%). HPLC purity 98.69%. $^1$H NMR (DMSO-d6, 400 MHz): 1.38 (d, J=6.6 Hz, 6H), 1.41 (s, 2H), 1.81-1.91 (m, 2H), 2.44 (s, 2H), 3.00 (d, J=11.3 Hz, 2H), 3.52 (d, J=3.6 Hz, 1H), 3.74 (d, J=11.5 Hz, 2H), 4.45 (dt, J=12.5, 6.2 Hz, 1H), 6.01 (d, J=4.2 Hz, 1H), 6.91-6.97 (m, 1H), 7.09 (s, 1H), 7.61 (t, J=9.8 Hz, 1H), 7.76 (dd, J=7.6, 4.2 Hz, 1H), 7.90 (dd, J=5.3, 2.7 Hz, 1H), 8.24 (d, J=5.9 Hz, 1H). MS (ES+) m/z 559.2 [M+H].

Example 15

(1R,5S,8s)-N-[5-(3,5-Difluorophenoxy)-1-(propan-2-yl)-1H-1,2,4-triazol-3-yl]-3-[2-(trifluoromethyl)pyridin-4-yl]-3-azabicyclo[3.2.1]octan-8-amine

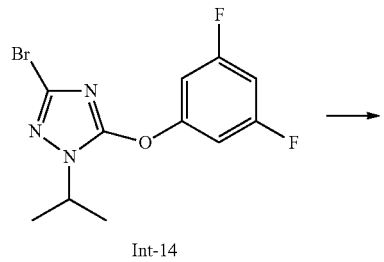

Int-14

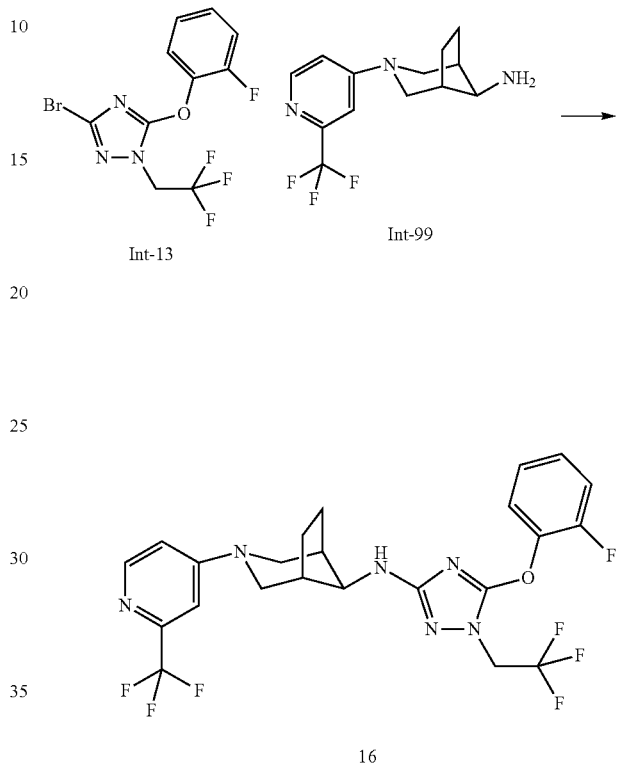

15

To a solution of (1R,5S,8s)-3-[2-(trifluoromethyl)pyridin-4-yl]-3-azabicyclo[3.2.1]octan-8-amine (Int-99, 60 mg, 0.3 mmol) and 3-bromo-5-(3,5-difluorophenoxy)-1-(propan-2-yl)-1H-1,2,4-triazole (Int-14, 105.5 mg, 0.3 mmol) in dry 1,4-dioxane (2 mL) in sealed tube was added 2-dicyclohexylphosphino-2',6'-diisopropoxybiphenyl ("Ruphos", CAS [787618-22-8], 20 mg, 0.04 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 35.3 mg, 0.04 mmol). The reaction mixture was again degassed with argon for 10 min followed by addition of sodium tertbutoxide (84.9 mg, 0.9 mmol). The reaction mixture was stirred at 120° C. for 8 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as white solid (66 mg, 59%). HPLC purity 96.42%. $^1$H NMR (DMSO-d6, 400 MHz): 1.26-1.39 (m, 6H), 1.41 (d, J=7.8 Hz, 2H), 1.85-1.95 (m, 2H), 2.45 (s, 2H), 3.01 (d, J=11.3 Hz, 2H), 3.54 (d, J=3.0 Hz, 1H), 3.74 (d, J=9.8 Hz, 2H), 4.39-4.45 (m, 1H), 6.04 (d, J=3.8 Hz, 1H), 6.94 (d, J=4.0 Hz, 1H), 7.08-7.13 (m, 1H), 7.12-7.25 (m, 3H), 8.23 (d, J=5.7 Hz, 1H). MS (ES+) m/z 509.1 [M+H].

Example 16

(1R,5S,8s)-N-(5-(2-Fluorophenoxy)-1-(2,2,2-trifluoroethyl)-1H-1,2,4-triazol-3-yl)-3-(2-[trifluoromethyl)pyridin-4-yl)-3-azabicyclo[3.2.1]octan-8-amine Int-13    Int-99

16

In an 8 mL microwave vial, 3-bromo-5-(2-fluorophenoxy)-1-(2,2,2-trifluoroethyl)-1H-1,2,4-triazole (Int-13, 113 mg, 332 µmol) was suspended in 1,4-dioxane (2.0 mL) and (1R,5S,8s)-3-(2-(trifluoromethyl)pyridin-4-yl)-3-azabicyclo [3.2.1]octan-8-amine (Int-99, 60 mg, 221 µmol), sodium tert-butoxide (85 mg, 885 µmol), [2',6'-bis(1-methylethoxy)[1,1'-biphenyl]-2-yl]dicyclohexylphosphine ("Ruphos", CAS [787618-22-8], 21.7 mg, 44.2 µmol), and (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium ("Brettphos-palladacycle", CAS [1148148-01-9], 35.3 mg, 44.2 µmol) were added subsequently. The vial was degassed thoroughly with Argon and sealed. The reaction mixture was heated in an oil bath at 120° C. for 16 h. After that, dichloromethane (10 mL) was added and the mixture was concentrated in vacuo. The resulting crude product was directly purified by column chromatography (silica gel, 70 g, eluting with ethyl acetate/n-heptane, gradient 0:100 to 90:10 v/v) to yield the title compound as an off-white foam (55 mg, 47%). HPLC (method LCMS_fastgradient) $t_R$=1.31 min. $^1$H NMR (CDCl$_3$, 300 MHz): δ1.57-1.64 (m, 2H), 1.84-1.93 (m, 2H), 2.49-2.57 (m, 2H), 3.11-3.19 (m, 2H), 3.66 (dd, J=3.2, 11.9 Hz, 2H), 3.73 (d, J=5.7 Hz, 1H), 4.01 (d, J=5.8 Hz, 1H), 4.55 (q, J=8.2 Hz, 2H), 6.70 (dd, J=2.5, 6.0 Hz, 1H), 6.97 (d, J=2.6 Hz, 1H), 7.16-7.30 (m, 3H), 7.35-7.42 (m, 1H), 8.33 (d, J=6.1 Hz, 1H). MS (ES+) m/z 531.3 [M+H].

Example 17

(1R,5S,8s)-N-[1-(Propan-2-yl)-5-[3-(trifluoromethyl)phenoxy]-1H-1,2,4-triazol-3-yl]-3-[2-(trifluoromethyl)pyridin-4-yl]-3-azabicyclo[3.2.1]octan-8-amine

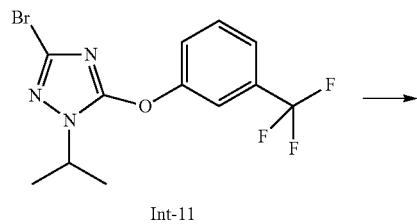

Int-11

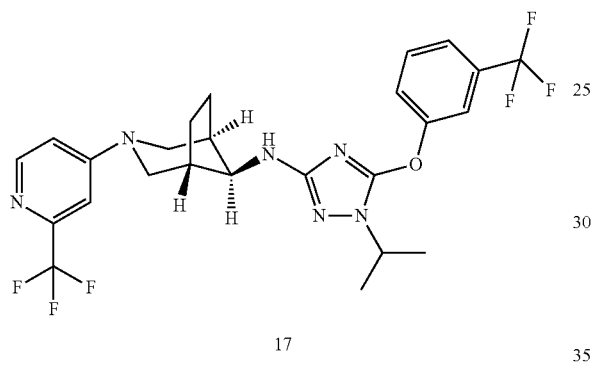

17

To a solution of (1R,5S,8s)-3-[2-(trifluoromethyl)pyridin-4-yl]-3-azabicyclo[3.2.1]octan-8-amine (Int-99, 60 mg, 0.3 mmol) and 3-bromo-1-(propan-2-yl)-5-[3-(trifluoromethyl)phenoxy]-1H-1,2,4-triazole (Int-11, 116.2 mg, 0.3 mmol) in dry 1,4-dioxane (2 mL) in sealed tube was added 2-dicyclohexylphosphino-2',6'-diisopropoxybiphenyl ("Ruphos", CAS [787618-22-8], 20.6 mg, 0.04 mmol). The reaction mixture was degassed with argon in a sealed tube over a period of 15 min. To it then added Chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 35.3 mg, 0.04 mmol). The reaction mixture was again degassed with argon for 10 min followed by addition of sodium tertbutoxide (84.9 mg, 0.9 mmol). The reaction mixture was stirred at 120° C. for 8 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as white solid (47.5 mg, 40%). HPLC purity 98.19%. $^1$H NMR (DMSO-d6, 400 MHz): 1.38 (d, J=6.6 Hz, 6H), 1.41 (s, 1H), 1.87 (dd, J=8.8, 4.2 Hz, 2H), 2.42-2.48 (m, 2H), 3.00 (d, J=11.5 Hz, 2H), 3.53 (d, J=3.6 Hz, 1H), 3.74 (d, J=12.7 Hz, 2H), 4.46 (dt, J=13.3, 6.5 Hz, 1H), 6.02 (d, J=3.8 Hz, 1H), 6.94 (d, J=6.4 Hz, 1H), 7.10 (s, 1H), 7.65 (q, J=9.8, 7.5 Hz, 3H), 7.79 (s, 1H), 8.24 (d, J=5.6 Hz, 1H). MS (ES+) m/z 541.2 [M+H].

Example 18

(1R,5S,8s)-N-[5-(3-Fluorophenoxy)-1-(propan-2-yl)-1H-1,2,4-triazol-3-yl]-3-[2-(trifluoromethyl)pyridin-4-yl]-3-azabicyclo[3.2.1]octan-8-amine

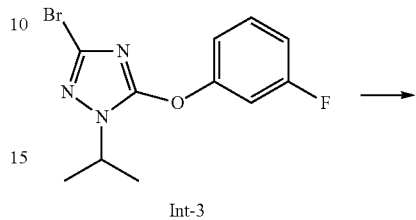

Int-3

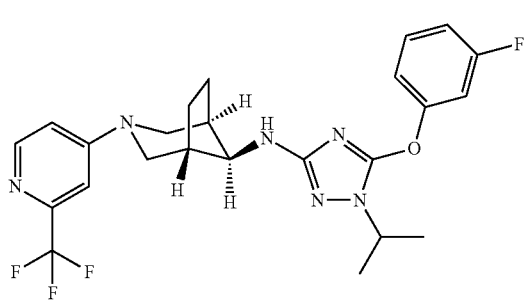

18

To a solution of (1R,5S,8s)-3-[2-(trifluoromethyl)pyridin-4-yl]-3-azabicyclo[3.2.1]octan-8-amine (Int-99, 60 mg, 0.3 mmol) and 3-bromo-5-(3-fluorophenoxy)-1-(propan-2-yl)-1H-1,2,4-triazole (Int-3, 99.5 mg, 0.3 mmol) in dry 1,4-dioxane (2 mL) in sealed tube was added 2-dicyclohexylphosphino-2',6'-diisopropoxybiphenyl ("Ruphos", CAS [787618-22-8], 35.3 mg, 0.04 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 20.6 mg, 0.04 mmol). The reaction mixture was again degassed with argon for 10 min followed by addition of sodium tertbutoxide (84.9 mg, 0.9 mmol). The reaction mixture was stirred at 120° C. for 8 h. Reaction mixture was then filtered through plug of celite and washed with EtOAc (10 mL) and dichloromethane (10 mL). Combined organic filtrates were concentrated under reduced pressure. The resulting crude product was purified two times by column chromatography (amino modified silica gel, eluting with EtOAc/n-hexane 40:60 v/v) to yield the title compound as white solid (24 mg, 22%). HPLC purity 95.31%. $^1$H NMR (DMSO-d6, 400 MHz): 1.36 (d, J=6.6 Hz, 6H), 1.40 (d, J=7.9 Hz, 2H), 1.87-1.89 (m, 2H), 2.45 (s, 2H), 3.00 (d, J=11.1 Hz, 2H), 3.54 (d, J=4.2 Hz, 1H), 3.74 (d, J=9.3 Hz, 2H), 4.42 (p, J=6.8 Hz, 1H), 5.99 (d, J=4.3 Hz, 1H), 6.94 (d, J=6.2 Hz, 1H), 7.05-7.18 (m, 3H), 7.28 (d, J=10.2 Hz, 1H), 7.47 (q, J=8.3 Hz, 1H), 8.23 (d, J=5.8 Hz, 1H). MS (ES+) m/z 491.1 [M+H].

Example 19

(1R,5S,8s)-N-{5-[4-Fluoro-3-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine

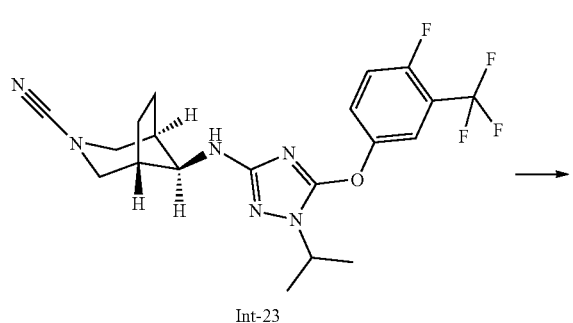

Int-23

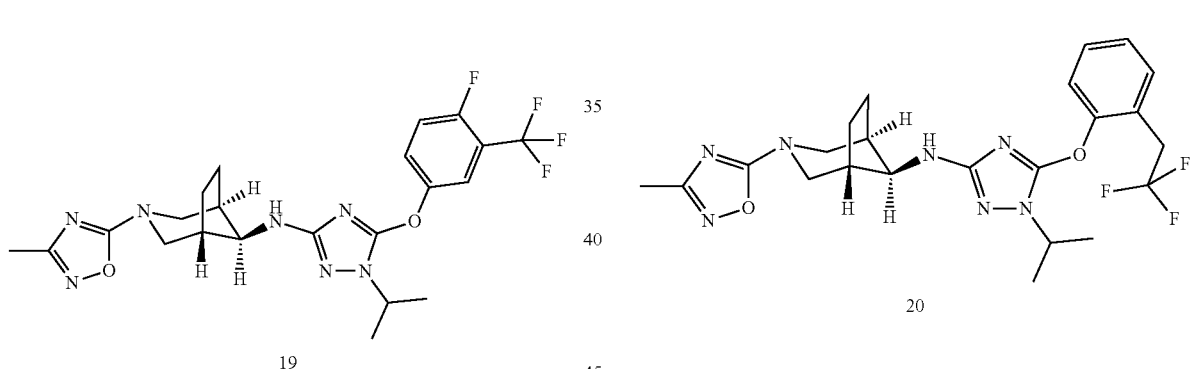

19

To a solution of (1R,5S,8s)-8-({5-[4-fluoro-3-(trifluoromethyl)phenoxy]-1-(propan-2-yl)-1H-1,2,4-triazol-3-yl}amino)-3-azabicyclo[3.2.1]octane-3-carbonitrile (Int-23, 250 mg, 0.6 mmol) and N-hydroxyethanimidamide (42.2 mg, 0.6 mmol) in DMF (2 mL) was added p-toluenesulfonic acid (32.5 mg, 0.2 mmol) and solid ZnCl$_2$ (23 mg, 0.2 mmol). The reaction mixture was stirred at 80° C. for a period of 5 h. Then, ice-water was added and the reaction mixture was extracted with EtOAc (3×20 mL). The organic layer was dried and concentrated under reduced pressure to afford the crude which was purified by column chromatography (amino modified silica gel, eluting with EtOAc/n-hexane 30:70 v/v) to yield the title compound as white solid (100 mg, 35%). HPLC purity 98.39%. $^1$H NMR (DMSO-d6, 400 MHz): 1.38 (d, J=5.7 Hz, 6H), 1.85 (dd, J=9.2, 3.1 Hz, 2H), 2.09 (s, 3H), 2.31-2.37 (m, 2H), 2.41-2.47 (m, 1H), 3.23-3.31 (m, 2H), 3.52 (d, J=3.7 Hz, 1H), 3.65-3.73 (m, 2H), 4.39-4.49 (m, 1H), 5.97-6.03 (m, 1H), 7.56-7.66 (m, 1H), 7.72-7.80 (m, 1H), 7.90 (dd, J=4.7, 1.7 Hz, 1H). MS (ES+) m/z 496.1 [M+H].

Example 20

(1R,5S,8s)-N-(1-(Propan-2-yl)-5-(2-(trifluoromethoxy)phenoxy)-1H-1,2,4-triazol-3-yl)-3-(3-methyl-1,2,4-oxadiazol-5-yl)-3-azabicyclo[3.2.1]octan-8-amine

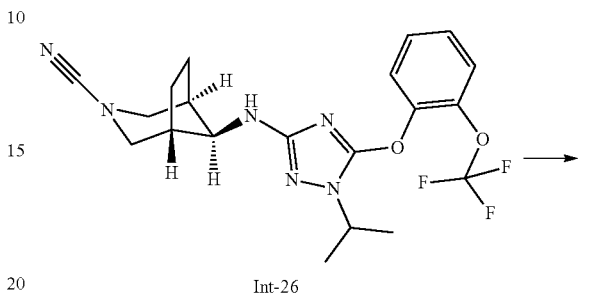

Int-26

20

To a solution of (1R,5S,8s)-8-{[1-(propan-2-yl)-5-[2-(trifluoromethoxy)phenoxy]-1H-1,2,4-triazol-3-yl]amino}-3-azabicyclo[3.2.1]octane-3-carbonitrile (Int-26, 150 mg, 0.3 mmol) and N-hydroxyethanimidamide (25.5 mg, 0.3 mmol) in DMF (2 mL) was added p-toluenesulfonic acid (19.6 mg, 0.1 mmol) and solid ZnCl$_2$ (14 mg, 0.1 mmol). The reaction mixture was stirred at 80° C. for a period of 5 h. Then, ice-water was added and the reaction mixture was extracted with EtOAc (3×20 mL). The organic layer was dried and concentrated under reduced pressure to afford the crude which was purified by column chromatography (amino modified silica gel, eluting with EtOAc/n-hexane 30:70 v/v) to yield the title compound as white solid (50 mg, 30%). HPLC purity 99.59%. $^1$H NMR (DMSO-d6, 400 MHz): 1.23-1.32 (m, 2H), 1.36 (dd, J=19.5, 6.8 Hz, 6H), 1.80-1.89 (m, 2H), 2.32 (s, 3H), 3.26 (d, J=12.4 Hz, 2H), 3.50 (d, J=3.9 Hz, 1H), 3.65-3.73 (m, 2H), 4.37-4.46 (m, 1H), 5.96 (d, J=4.2 Hz, 1H), 7.39 (t, J=6.9 Hz, 1H), 7.48 (t, J=8.0 Hz, 1H), 7.51-7.58 (m, 1H), 7.60 (d, J=8.3 Hz, 1H). MS (ES+) m/z 494.2 [M+H].

Example 21

(1R,5S,8s)-3-(3-Methyl-1,2,4-oxadiazol-5-yl)-N-[1-(propan-2-yl)-5-[3-(trifluoromethoxy)phenoxy]-1H-1,2,4-triazol-3-yl]-3-azabicyclo[3.2.1]octan-8-amine

Example 22

(1R,5S,8s)-3-(3-Methyl-1,2,4-oxadiazol-5-yl)-N-[1-(propan-2-yl)-5-[4-(trifluoromethoxy)phenoxy]-1H-1,2,4-triazol-3-yl]-3-azabicyclo[3.2.1]octan-8-amine

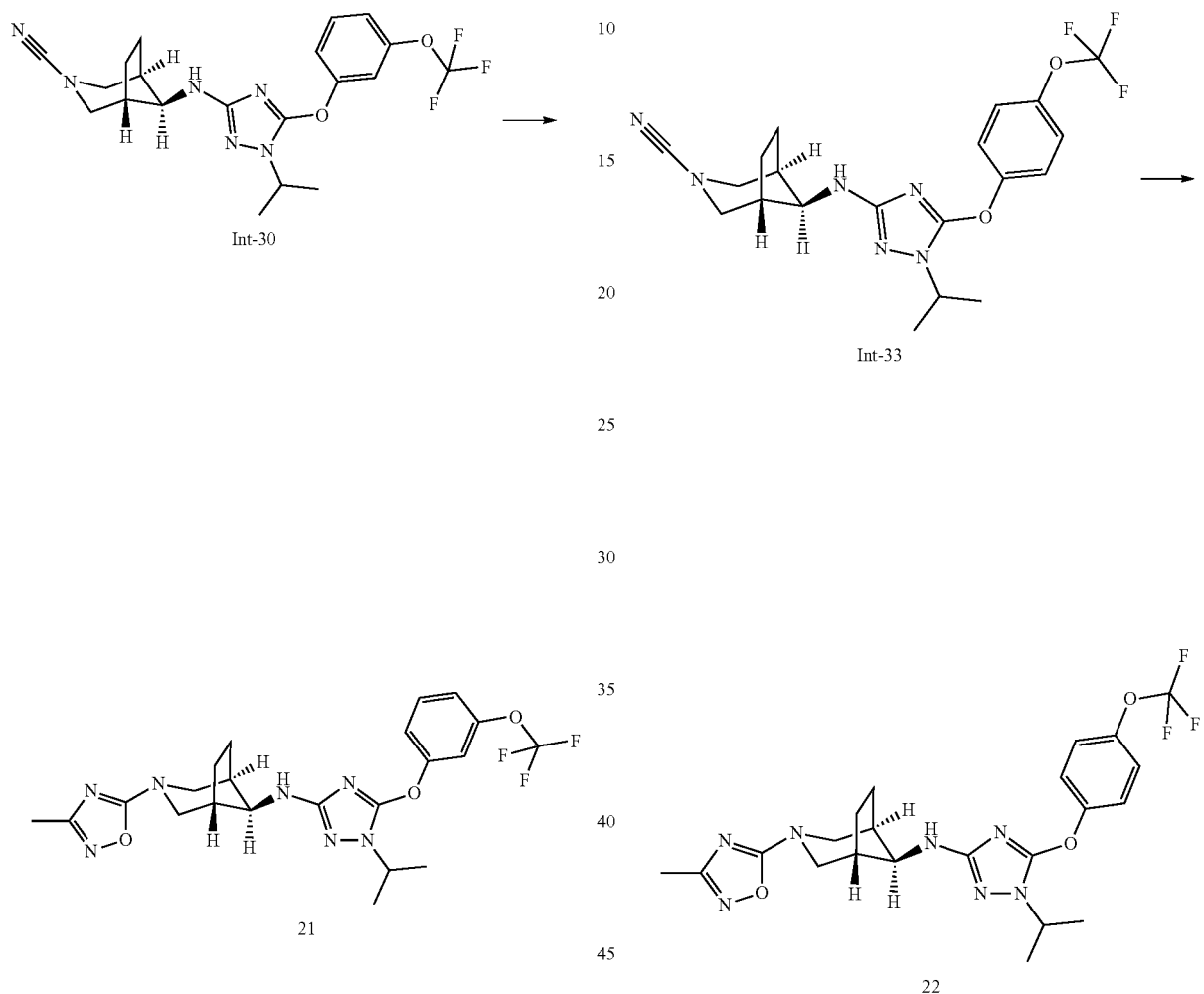

To a solution of (1R,5S,8s)-8-{[1-(propan-2-yl)-5-[3-(trifluoromethoxy)phenoxy]-1H-1,2,4-triazol-3-yl]amino}-3-azabicyclo[3.2.1]octane-3-carbonitrile (Int-30, 150 mg, 0.3 mmol) and N-hydroxyethanimidamide (25.5 mg, 0.3 mmol) in DMF (2 mL) was added p-toluenesulfonic acid (19.6 mg, 0.1 mmol) and solid $ZnCl_2$ (14 mg, 0.1 mmol). The reaction mixture was stirred at 80° C. for a period of 5 h. Then, ice-water was added and the reaction mixture was extracted with EtOAc (3×20 mL). The organic layer was dried and concentrated under reduced pressure to afford the crude which was purified by column chromatography (amino modified silica gel, eluting with EtOAc/n-hexane 30:70 v/v) to yield the title compound as off-white sticky solid (50 mg, 30%). HPLC purity 96.70%. $^1$H NMR (DMSO-d6, 400 MHz): 1.36 (d, J=6.0 Hz, 6H), 1.84-1.91 (m, 1H), 2.09 (s, 3H), 2.34 (s, 2H), 3.21-3.28 (m, 4H), 3.53 (s, 1H), 3.69 (d, J=10.8 Hz, 2H), 4.39-4.47 (m, 1H), 5.99 (d, J=4.5 Hz, 1H), 7.26 (d, J=7.6 Hz, 1H), 7.36 (d, J=7.9 Hz, 1H), 7.45 (s, 1H), 7.57 (t, J=7.7 Hz, 1H). MS (ES+) m/z 494.2 [M+H].

To a solution of (1R,5S,8s)-8-{[1-(propan-2-yl)-5-[4-(trifluoromethoxy)phenoxy]-1H-1,2,4-triazol-3-yl]amino}-3-azabicyclo[3.2.1]octane-3-carbonitrile (Int-33, 150 mg, 0.3 mmol) and N-hydroxyethanimidamide (25.5 mg, 0.3 mmol) in DMF (2 mL) was added p-toluenesulfonic acid (19.6 mg, 0.1 mmol) and solid $ZnCl_2$ (14 mg, 0.1 mmol). The reaction mixture was stirred at 80° C. for a period of 5 h. Then, ice-water was added and the reaction mixture was extracted with EtOAc (3×20 mL). The organic layer was dried and concentrated under reduced pressure to afford the crude which was purified by column chromatography (amino modified silica gel, eluting with EtOAc/n-hexane 30:70 v/v) to yield the title compound as white sticky solid (100 mg, 59%). HPLC purity 98.56%. $^1$H NMR (DMSO-d6, 400 MHz): 1.36 (d, J=6.5 Hz, 6H), 1.80-1.90 (m, 2H), 2.09 (s, 3H), 2.33 (s, 2H), 3.25-3.28 (m, 3H), 3.52 (s, 1H), 3.69 (d, J=11.5 Hz, 2H), 4.39-4.45 (m, 1H), 5.98 (d, J=4.4 Hz, 1H), 7.44 (s, 4H). MS (ES+) m/z 494.2 [M+H].

Example 23

(1R,5S,8s)-N-[5-(3-Fluorophenoxy)-1-(propan-2-yl)-1H-1,2,4-triazol-3-yl]-3-(3-methyl-1,2,4-oxadiazol-5-yl)-3-azabicyclo[3.2.1]octan-8-amine

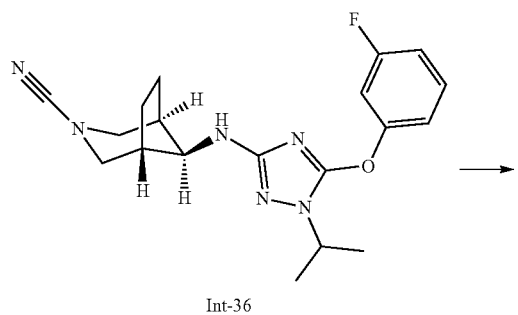

Int-36

Example 24

(1R,5S,8s)-3-(3-Methyl-1,2,4-oxadiazol-5-yl)-N-[1-(propan-2-yl)-5-[3-(trifluoromethyl)phenoxy]-1H-1,2,4-triazol-3-yl]-3-azabicyclo[3.2.1]octan-8-amine

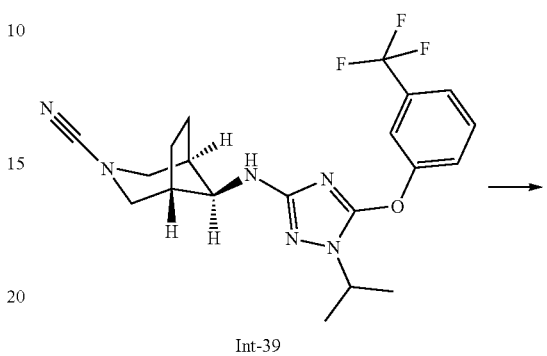

Int-39

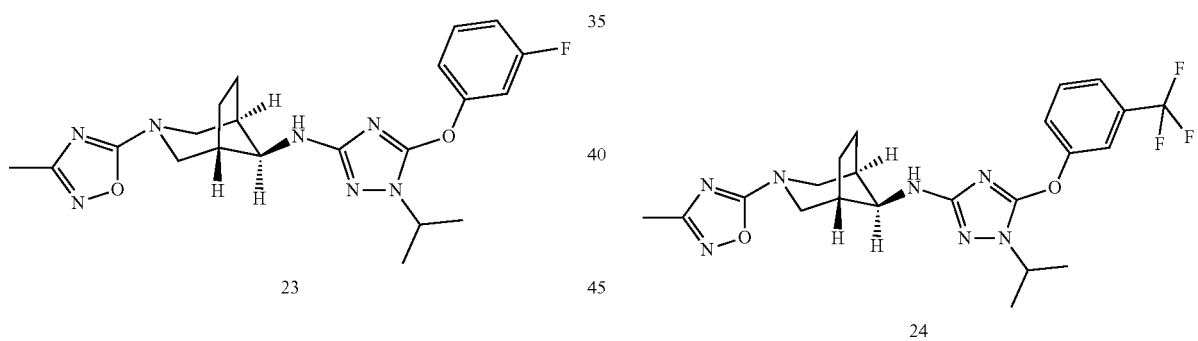

23

24

To a solution of (1R,5S,8s)-8-{[5-(3-fluorophenoxy)-1-(propan-2-yl)-1H-1,2,4-triazol-3-yl]amino}-3-azabicyclo[3.2.1]octane-3-carbonitrile (Int-36, 100 mg, 0.3 mmol) and N-hydroxyethanimidamide (20 mg, 0.3 mmol) in DMF (2 mL) was added p-toluenesulfonic acid (15.4 mg, 0.1 mmol) and solid $ZnCl_2$ (11 mg, 0.1 mmol). The reaction mixture was stirred at 80° C. for a period of 5 h. Then, ice-water was added and the reaction mixture was extracted with EtOAc (3×20 mL). The organic layer was dried and concentrated under reduced pressure to afford the crude which was purified by column chromatography (amino modified silica gel, eluting with EtOAc/n-hexane 30:70 v/v) to yield the title compound as white solid (50 mg, 43%). HPLC purity 99.85%. $^1$H NMR (DMSO-d6, 400 MHz): 1.36 (d, J=6.6 Hz, 6H), 1.83-1.91 (m, 2H), 2.09 (s, 3H), 2.35 (s, 2H), 3.26-3.29 (m, 3H), 3.54 (d, J=4.8 Hz, 1H), 3.70 (d, J=9.8 Hz, 2H), 4.41 (dt, J=13.0, 6.4 Hz, 1H), 5.98 (d, J=4.5 Hz, 1H), 7.08 (dd, J=8.7, 2.3 Hz, 1H), 7.14 (dd, J=8.5, 1.9 Hz, 1H), 7.28 (dt, J=10.1, 2.3 Hz, 1H), 7.47 (q, J=8.2 Hz, 1H). MS (ES+) m/z 428.3 [M+H].

To a solution of (1R,5S,8s)-8-{[1-(propan-2-yl)-5-[3-(trifluoromethyl)phenoxy]-1H-1,2,4-triazol-3-yl]amino}-3-azabicyclo[3.2.1]octane-3-carbonitrile (Int-39, 150 mg, 0.4 mmol) and N-hydroxyethanimidamide (26.4 mg, 0.4 mmol) in DMF (2 mL) was added p-toluenesulfonic acid (20.4 mg, 0.1 mmol) and solid $ZnCl_2$ (14 mg, 0.1 mmol). The reaction mixture was stirred at 80° C. for a period of 5 h. Then, ice-water was added and the reaction mixture was extracted with EtOAc (3×20 mL). The organic layer was dried and concentrated under reduced pressure to afford the crude which was purified by column chromatography (amino modified silica gel, eluting with EtOAc/n-hexane 30:70 v/v) to yield the title compound as white solid (70 mg, 41%). HPLC purity 95.14%. $^1$H NMR (DMSO-d6, 400 MHz): 1.38 (d, J=6.5 Hz, 6H), 1.86 (d, J=10.6 Hz, 2H), 2.09 (s, 3H), 2.35 (s, 2H), 3.20-3.29 (m, 2H), 3.53 (d, J=3.6 Hz, 1H), 3.65-3.74 (m, 2H), 4.42-4.48 (m, 1H), 6.00 (d, J=4.4 Hz, 1H), 7.58-7.71 (m, 3H), 7.79 (s, 1H). MS (ES+) m/z 478.2 [M+H].

Example 25

(1R,5S,8s)-N-(5-(3-Fluorophenoxy)-1-(2,2,2-trifluoroethyl)-1H-1,2,4-triazol-3-yl)-3-(2-(trifluoromethyl)pyridin-4-yl)-3-azabicyclo[3.2.1]octan-8-amine

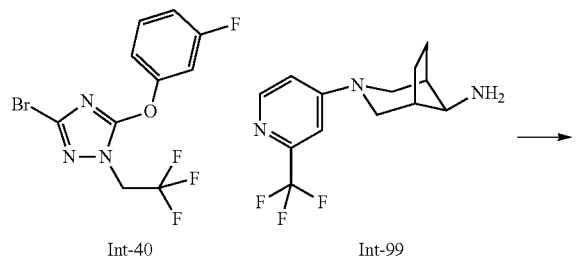

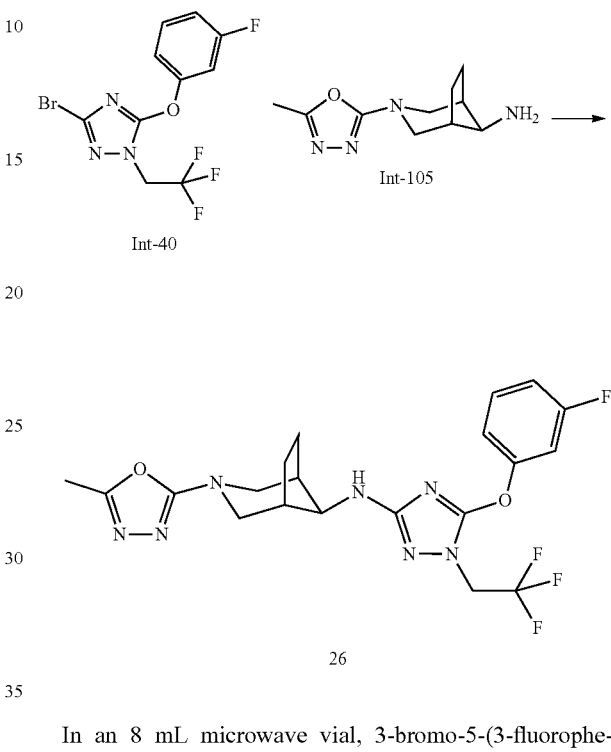

25

In an 8 mL microwave vial, 3-bromo-5-(3-fluorophenoxy)-1-(2,2,2-trifluoroethyl)-1H-1,2,4-triazole (Int-40, 113 mg, 332 µmol) was suspended in 1,4-dioxane (2.0 mL) and (1R,5S,8s)-3-(2-(trifluoromethyl)pyridin-4-yl)-3-azabicyclo[3.2.1]octan-8-amine (Int-99, 60 mg, 221 µmol), sodium tert-butoxide (85 mg, 885 µmol), [2',6'-bis(1-methylethoxy)[1,1'-biphenyl]-2-yl]dicyclohexylphosphine ("Ruphos", CAS [787618-22-8], 21.7 mg, 44.2 µmol), and (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium ("Brettphos-palladacycle", CAS [1148148-01-9], 35.3 mg, 44.2 µmol) were added subsequently. The vial was degassed thoroughly with Argon and sealed. The reaction mixture was heated in an oil bath at 120° C. for 22 h. After that, dichloromethane (10 mL) was added and the mixture was concentrated in vacuo. The resulting crude product was directly purified by column chromatography (silica gel, 70 g, eluting with ethyl acetate/n-heptane, gradient 0:100 to 2:1 v/v) to yield the title compound as a white solid (58 mg, 49%). HPLC (method LCMS_fastgradient) $t_R$=1.34 min. $^1$H NMR (CDCl$_3$, 300 MHz): δ 1.58-1.67 (m, 2H), 1.87-1.95 (m, 2H), 2.51-2.58 (m, 2H), 3.12-3.20 (m, 2H), 3.67 (dd, J=3.1, 11.8 Hz, 2H), 3.75 (d, J=6.1 Hz, 1H), 4.04 (d, J=5.8 Hz, 1H), 4.52 (q, J=8.2 Hz, 2H), 6.70 (dd, J=2.6, 6.0 Hz, 1H), 6.95-7.03 (m, 2H), 7.06-7.12 (m, 2H), 7.33-7.44 (m, 1H), 8.33 (d, J=6.1 Hz, 1H). MS (ES+) m/z 531.2 [M+H].

Example 26

(1R,5S,8s)-N-(5-(3-Fluorophenoxy)-1-(2,2,2-trifluoroethyl)-1H-1,2,4-triazol-3-yl)-3-(5-methyl-1,3,4-oxadiazol-2-yl)-3-azabicyclo[3.2.1]octan-8-amine

26

In an 8 mL microwave vial, 3-bromo-5-(3-fluorophenoxy)-1-(2,2,2-trifluoroethyl)-1H-1,2,4-triazole (Int-40, 98 mg, 288 µmol) was suspended in 1,4-dioxane (2.5 mL) and (1R,5S,8s)-3-(5-methyl-1,3,4-oxadiazol-2-yl)-3-azabicyclo[3.2.1]octan-8-amine (Int-105, 50 mg, 240 µmol), sodium tert-butoxide (92.3 mg, 960 µmol), [2',6'-bis(1-methylethoxy)[1,1'-biphenyl]-2-yl]dicyclohexylphosphine ("Ruphos", CAS [787618-22-8], 23.6 mg, 48 µmol), and (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium ("Brettphos-palladacycle", CAS [1148148-01-9], 38.4 mg, 48 µmol) were added subsequently. The vial was degassed thoroughly with Argon and sealed. The reaction mixture was heated in an oil bath at 130° C. for 24 h. After that, dichloromethane (10 mL) was added and the mixture was concentrated in vacuo. The resulting crude product was directly purified by column chromatography (amino modified silica gel, 50 g, eluting with ethyl acetate/n-heptane, gradient 0:100 to 1:1 v/v), followed by preparative HPLC (YMC-Actus Triart C18, 100×30 mm×5 µm, eluting with acetonitrile/(water+0.1% triethylamine), gradient 20:80 to 98:2 v/v) to afford the title compound as a white foam (20.8 mg, 18%). HPLC (method LCMS_fastgradient) $t_R$=1.12 min. $^1$H NMR (CDCl$_3$, 300 MHz): δ 1.61-1.70 (m, 2H), 1.82-1.90 (m, 2H), 2.39 (s, 3H), 2.40-2.45 (m, 2H), 3.24-3.31 (m, 2H), 3.69 (d, J=5.8 Hz, 1H), 3.70-3.77 (m, 2H), 4.00 (d, J=6.1 Hz, 1H), 4.52 (q, J=8.2 Hz, 2H), 6.99 (dddd, J=0.9, 2.3, 5.8, 8.3 Hz, 1H), 7.05-7.12 (m, 2H), 7.34-7.43 (m, 1H). MS (ES+) m/z 468.3 [M+H].

Example 27

(1R,5S,8s)-N-(5-(3-Fluorophenoxy)-1-methyl-1H-1,2,4-triazol-3-yl)-3-(2-(trifluoromethyl)pyridin-4-yl)-3-azabicyclo[3.2.1]octan-8-amine

Example 28

(1R,5S,8s)-3-(2-Chloropyridin-4-yl)-N-(5-(4-fluoro-3-(trifluoromethyl)phenoxy)-1-methyl-1H-1,2,4-triazol-3-yl)-3-azabicyclo[3.2.1]octan-8-amine

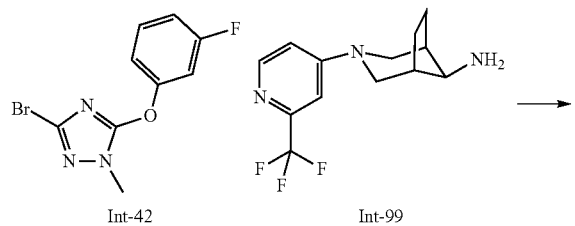

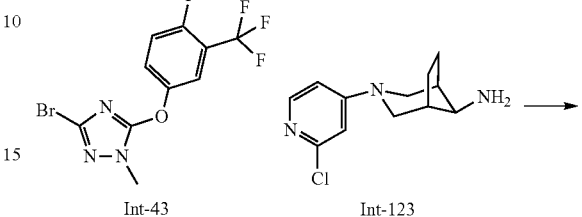

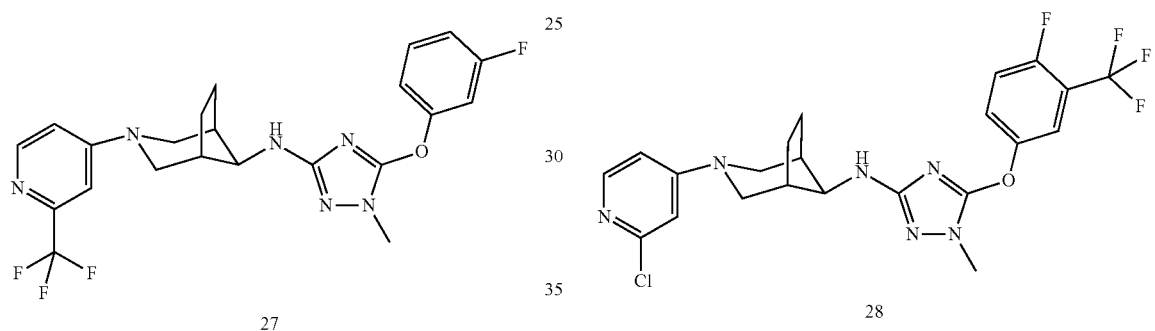

In an 8 mL microwave vial, 3-bromo-5-(3-fluorophenoxy)-1-methyl-1H-1,2,4-triazole (Int-42, 90.3 mg, 332 µmol) was suspended in 1,4-dioxane (2.0 mL) and (1R,5S,8s)-3-(2-(trifluoromethyl)pyridin-4-yl)-3-azabicyclo[3.2.1]octan-8-amine (Int-99, 60 mg, 221 µmol), sodium tert-butoxide (85 mg, 885 µmol), [2',6'-bis(1-methylethoxy)[1,1'-biphenyl]-2-yl]dicyclohexylphosphine ("Ruphos", CAS [787618-22-8], 21.7 mg, 44.2 µmol), and (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium ("Brettphos-palladacycle", CAS [1148148-01-9], 35.3 mg, 44.2 µmol) were added subsequently. The vial was degassed thoroughly with Argon and sealed. The reaction mixture was heated in an oil bath at 120° C. for 16 h. After that, the mixture was concentrated in vacuo. The resulting crude product was directly purified by column chromatography (silica gel, 20 g, eluting with ethyl acetate/n-heptane, gradient 0:100 to 2:1 v/v) to afford the title compound as a white solid (65.2 mg, 64%). HPLC (method LCMS_fastgradient) $t_R$=1.28 min. $^1$H NMR (CDCl$_3$, 300 MHz): δ 1.58-1.66 (m, 2H), 1.87-1.98 (m, 2H), 2.51-2.58 (m, 2H), 3.13-3.20 (m, 2H), 3.64 (s, 3H), 3.67 (dd, J=2.8, 11.7 Hz, 2H), 3.75 (d, J=6.3 Hz, 1H), 3.96 (d, J=6.1 Hz, 1H), 6.70 (dd, J=2.5, 6.0 Hz, 1H), 6.91-6.99 (m, 2H), 7.03-7.10 (m, 2H), 7.32-7.41 (m, 1H), 8.33 (d, J=6.1 Hz, 1H). MS (ES+) m/z 463.3 [M+H].

In an 8 mL microwave vial, 3-bromo-5-(4-fluoro-3-(trifluoromethyl)phenoxy)-1-methyl-1H-1,2,4-triazole (Int-43, 42.9 mg, 126 µmol) was suspended in 1,4-dioxane (2.0 mL) and (1R,5S,8s)-3-(2-chloropyridin-4-yl)-3-azabicyclo[3.2.1]octan-8-amine (Int-123, 20 mg, 84.1 µmol), sodium tert-butoxide (32.3 mg, 337 µmol), [2',6'-bis(1-methylethoxy)[1,1'-biphenyl]-2-yl]dicyclohexylphosphine ("Ruphos", CAS [787618-22-8], 8.3 mg, 17 µmol), and (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium ("Brettphos-palladacycle", CAS [1148148-01-9], 13.4 mg, 17 µmol) were added subsequently. The vial was degassed thoroughly with Argon and sealed. The reaction mixture was heated in an oil bath at 120° C. for 18 h. After that, the mixture was concentrated in vacuo. The resulting crude product was directly purified by column chromatography (silica gel, 20 g, eluting with ethyl acetate/n-heptane, gradient 0:100 to 80:20 v/v) to afford the title compound as a white solid (21 mg, 49%). HPLC (method LCMS_fastgradient) $t_R$=1.23 min. $^1$H NMR (CDCl$_3$, 300 MHz): δ 1.56-1.65 (m, 2H), 1.86-1.94 (m, 2H), 2.47-2.54 (m, 2H), 3.07-3.15 (m, 2H), 3.60 (dd, J=3.0, 11.9 Hz, 2H), 3.65 (s, 3H), 3.71 (d, J=6.1 Hz, 1H), 3.93 (d, J=6.1 Hz, 1H), 6.53 (dd, J=2.4, 6.1 Hz, 1H), 6.58-6.62 (m, 1H), 7.20-7.27 (m, 1H), 7.46-7.53 (m, 1H), 7.56-7.61 (m, 1H), 8.01 (d, J=6.1 Hz, 1H). MS (ES+) m/z 497.2 [M+H].

Example 29

(1R,5S,8s)-N-(5-(3-Fluorophenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine

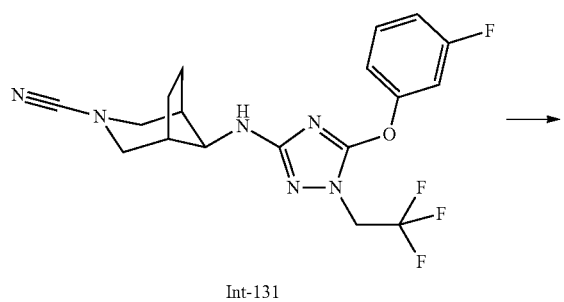

Int-131

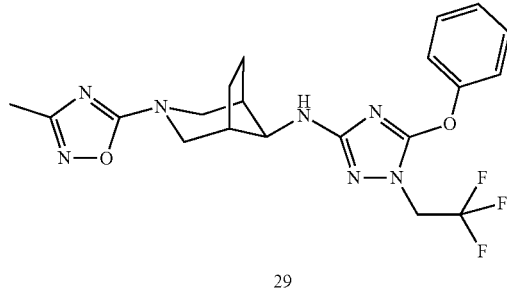

29

In a 2 mL flask, (1R,5S,8s)-8-((5-(3-fluorophenoxy)-1-(2,2,2-trifluoroethyl)-1H-1,2,4-triazol-3-yl)amino)-3-azabicyclo[3.2.1]octane-3-carbonitrile (Int-131, 21.2 mg, 51.7 µmol) was dissolved in ethanol (0.5 mL) and N-hydroxyacetamide (4.7 mg, 62 µmol) was added, followed by a solution of carefully dried zinc chloride (8.6 mg, 62 µmol) in ethanol (250 µL). The reaction mixture was stirred at room temperature for 16 h. Then, concentrated hydrochloric acid (12.9 µL) was added and the mixture was stirred for 5 h at 65° C. After cooling, it was concentrated in vacuo. The resulting crude product was directly purified by column chromatography (amino modified silica gel, 50 g, eluting with ethyl acetate/n-heptane, gradient 0:100 to 1:1 v/v) to yield the title compound as a white solid (18.1 mg, 75%). $^1$H NMR (CDCl$_3$, 300 MHz): δ 1.57-1.67 (m, 2H), 1.81-1.91 (m, 2H), 2.22 (s, 3H), 2.39-2.46 (m, 2H), 3.30-3.39 (m, 2H), 3.72 (d, J=6.1 Hz, 1H), 3.89 (dd, J=3.4, 12.9 Hz, 2H), 3.99 (d, J=5.8 Hz, 1H), 4.52 (q, J=8.2 Hz, 2H), 6.95-7.03 (m, 1H), 7.05-7.12 (m, 2H), 7.34-7.43 (m, 1H). MS (ES+) m/z 468.3 [M+H].

Example 30

(1R,5S,8s)-N-(5-(4-Fluoro-3-(trifluoromethyl)phenoxy)-1-(2,2,2-trifluoroethyl)-1H-1,2,4-triazol-3-yl)-3-(5-methyl-1,3,4-oxadiazol-2-yl)-3-azabicyclo[3.2.1]octan-8-amine

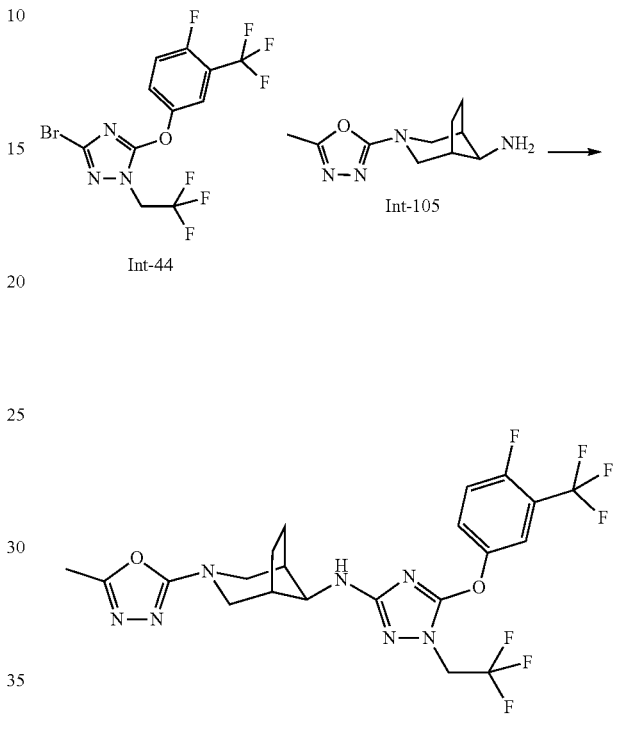

30

In an 8 mL microwave vial, 3-bromo-5-(4-fluoro-3-(trifluoromethyl)phenoxy)-1-(2,2,2-trifluoroethyl)-1H-1,2,4-triazole (Int-44, 130 mg, 319 µmol) was suspended in 1,4-dioxane (4.0 mL) and (1R,5S,8s)-3-(5-methyl-1,3,4-oxadiazol-2-yl)-3-azabicyclo[3.2.1]octan-8-amine (Int-105, 50 mg, 240 µmol), sodium tert-butoxide (92.3 mg, 960 µmol), [2',6'-bis(1-methylethoxy)[1,1'-biphenyl]-2-yl]dicyclohexylphosphine ("Ruphos", CAS [787618-22-8], 23.6 mg, 48 µmol), and (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium ("Brettphos-palladacycle", CAS [1148148-01-9], 38.4 mg, 48 µmol) were added subsequently. The vial was degassed thoroughly with Argon and sealed. The reaction mixture was heated in an oil bath at 130° C. for 20 h. After that, the mixture was concentrated in vacuo. The resulting crude product was directly purified by column chromatography (amino modified silica gel, 20 g, eluting with ethyl acetate/n-heptane, gradient 0:100 to 80:20 v/v) to afford the title compound as a colorless amorphous solid (4 mg, 3%). HPLC (method LCMS_fastgradient) t$_R$=1.24 min. $^1$H NMR (CDCl$_3$, 300 MHz): δ1.62-1.71 (m, 2H), 1.81-1.90 (m, 2H), 2.39 (s, 3H), 2.39-2.45 (m, 2H), 3.23-3.30 (m, 2H), 3.68 (d, J=5.8 Hz, 1H), 3.73 (dd, J=3.2, 12.5 Hz, 2H), 3.99 (d, J=6.1 Hz, 1H), 4.53 (q, J=8.2 Hz, 2H), 7.22-7.31 (m, 1H), 7.48-7.54 (m, 1H), 7.58-7.62 (m, 1H). MS (ES+) m/z 536.3 [M+H].

Example 31

(1R,5S,8s)-N-(5-(4-Fluoro-3-(trifluoromethyl)phenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine

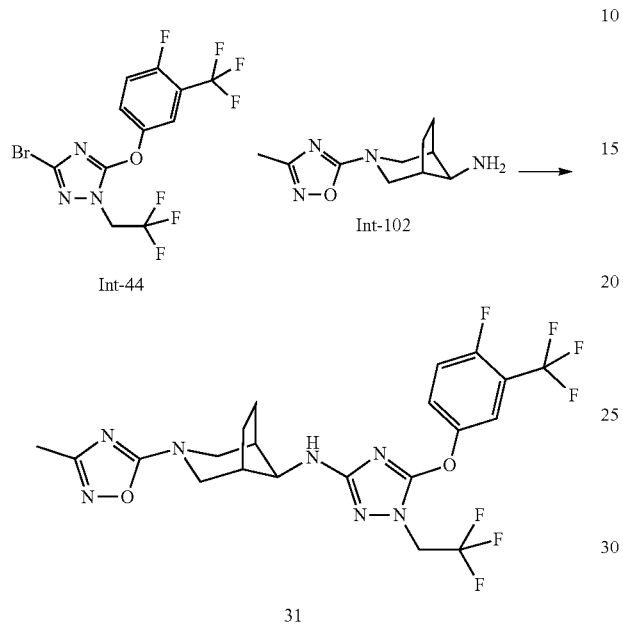

In an 8 mL microwave vial, 3-bromo-5-(4-fluoro-3-(trifluoromethyl)phenoxy)-1-(2,2,2-trifluoroethyl)-1H-1,2,4-triazole (Int-44, 50.9 mg, 125 µmol) was suspended in 1,4-dioxane (2 mL) and (1R,5S,8s)-3-(3-methyl-1,2,4-oxadiazol-5-yl)-3-azabicyclo[3.2.1]octan-8-amine (Int-102, 20 mg, 96 µmol), sodium tert-butoxide (19.4 mg, 192 µmol), 1,2,3,4,5-pentaphenyl-1'-(di-tert-butylphosphino)ferrocene ("Q-phos", CAS [312959-24-3], 11.5 mg, 15.4 µmol), and tris(dibenzylideneacetone)dipalladium (0) chloroform adduct (8.2 mg, 7.7 µmol) were added subsequently. The vial was degassed thoroughly with Argon and sealed. The reaction mixture was heated under microwave irradiation at 120° C. for 20 min. After that, the mixture was concentrated in vacuo. The resulting crude product was directly purified by column chromatography (amino modified silica gel, 50 g, eluting with ethyl acetate/n-heptane, gradient 0:100 to 50:50 v/v), followed by preparative HPLC (YMC-Actus Triart C18, 100×30 mm×5 µm, eluting with acetonitrile/(water+0.1% triethylamine), gradient 20:80 to 98:2 v/v) and lyophilization, followed by extraction of the lyophilized powder from a saturated aqueous solution of sodium hydrogencarbonate (1 mL) with dichloromethane (4×5 mL), drying (sodium sulfate) and concentration in vacuo to yield the title compound as a white foam (16 mg, 31%). HPLC (method LCMS_fastgradient) $t_R$=1.31 min. $^1$H NMR (CDCl$_3$, 300 MHz): δ1.58-1.67 (m, 2H), 1.82-1.91 (m, 2H), 2.22 (s, 3H), 2.39-2.46 (m, 2H), 3.30-3.38 (m, 2H), 3.71 (d, J=5.8 Hz, 1H), 3.89 (dd, J=3.4, 12.9 Hz, 2H), 3.97 (d, J=5.8 Hz, 1H), 4.53 (q, J=8.1 Hz, 2H), 7.22-7.31 (m, 1H), 7.47-7.54 (m, 1H), 7.60 (dd, J=3.0, 5.6 Hz, 1H). MS (ES+) m/z 536.3 [M+H].

Example 32

(1R,5S,8s)-N-(5-(4-Fluoro-3-(trifluoromethyl)phenoxy)-1-methyl-1H-1,2,4-triazol-3-yl)-3-(6-methylpyrimidin-4-yl)-3-azabicyclo[3.2.1]octan-8-amine

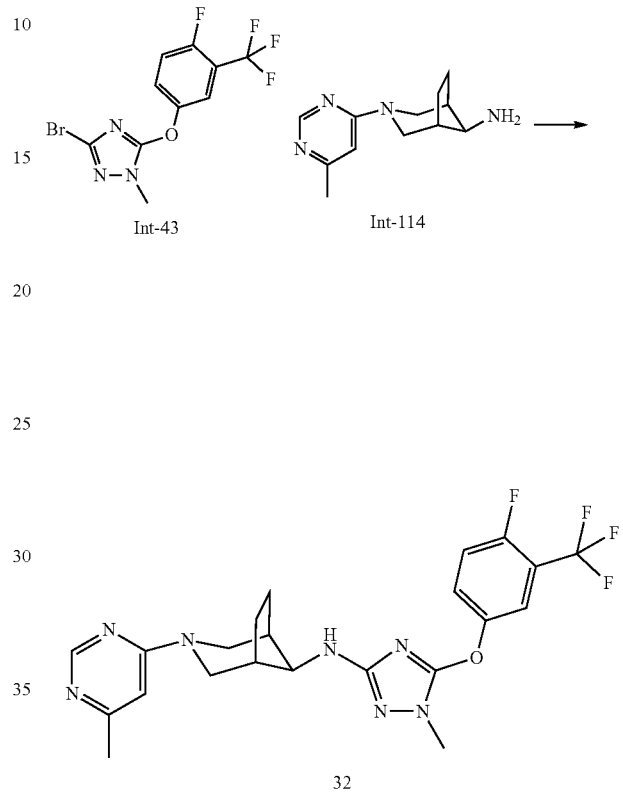

In an 8 mL microwave vial 3-bromo-5-(4-fluoro-3-(trifluoromethyl)phenoxy)-1-methyl-1H-1,2,4-triazole (Int-43, 105 mg, 309 µmol) was suspended in 1,4-dioxane (5.0 mL) and (1R,5S,8s)-3-(6-methylpyrimidin-4-yl)-3-azabicyclo[3.2.1]octan-8-amine (Int-114, 45 mg, 206 µmol), sodium tert-butoxide (105 mg, 825 µmol), [2',6'-bis(1-methylethoxy)[1,1'-biphenyl]-2-yl]dicyclohexylphosphine ("Ruphos", CAS [787618-22-8], 20.3 mg, 41.2 µmol), and (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium ("Brettphos-palladacycle", CAS [1148148-01-9], 32.9 mg, 41.2 µmol) were added subsequently. The vial was degassed thoroughly with Argon and sealed. The reaction mixture was heated in an oil bath at 145° C. for 18 h. After that, the mixture was concentrated in vacuo. The resulting crude product was directly purified by column chromatography (amino modified silica gel, 50 g, eluting with ethyl acetate/n-heptane, gradient 0:100 to 80:20 v/v) to yield the title compound as a white powder (25 mg, 25%). HPLC (method LCMS_fastgradient) $t_R$=0.96 min. $^1$H NMR (CDCl$_3$, 300 MHz): δ1.48-1.60 (m, 2H), 1.77-1.90 (m, 2H), 2.36 (s, 3H), 2.42-2.50 (m, 2H), 3.04-3.13 (m, 2H), 3.65 (s, 3H), 3.74 (d, J=6.1 Hz, 1H), 3.93 (d, J=6.3 Hz, 1H), 4.04-4.21 (m, 2H), 6.34 (s, 1H), 7.20-7.28 (m, 1H), 7.46-7.54 (m, 2H), 7.59 (dd, J=2.9, 5.5 Hz, 1H), 8.50 (s, 1H). MS (ES+) m/z 478.3 [M+H].

Example 33

(1R,5S,8s)-3-(2-Chloropyridin-4-yl)-N-(5-(3-fluoro-phenoxy)-1-(2,2,2-trifluoroethyl)-1H-1,2,4-triazol-3-yl)-3-azabicyclo[3.2.1]octan-8-amine

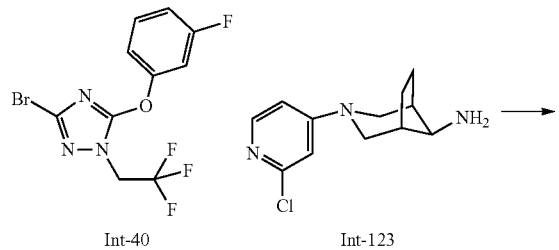

In an 8 mL microwave vial, 3-bromo-5-(3-fluorophenoxy)-1-(2,2,2-trifluoroethyl)-1H-1,2,4-triazole (Int-40, 46.5 mg, 137 µmol) was suspended in 1,4-dioxane (3 mL) and (1R,5S,8s)-3-(2-chloropyridin-4-yl)-3-azabicyclo[3.2.1]octan-8-amine (Int-123, 25 mg, 105 µmol), sodium tert-butoxide (21.3 mg, 210 µmol), 1,2,3,4,5-pentaphenyl-1'-(di-tert-butylphosphino)ferrocene ("Q-phos", CAS [312959-24-3], 12.6 mg, 16.8 µmol), and tris(dibenzylideneacetone)dipalladium (0) chloroform adduct (9 mg, 8.4 µmol) were added subsequently. The vial was degassed thoroughly with Argon and sealed. The reaction mixture was heated under microwave irradiation at 120° C. for 20 min. After that, the mixture was concentrated in vacuo. The resulting crude product was directly purified by column chromatography (silica gel, 50 g, eluting with dichloromethane/ethyl acetate, gradient 100:0 to 2:1 v/v) to yield the title compound as an off-white solid (20.2 mg, 39%). HPLC (method LCMS_fastgradient) $t_R$=1.26 min. $^1$H NMR (CDCl$_3$, 300 MHz): δ 1.56-1.65 (m, 2H), 1.84-1.93 (m, 2H), 2.47-2.54 (m, 2H), 3.07-3.15 (m, 2H), 3.60 (dd, J=3.0, 11.9 Hz, 2H), 3.73 (d, J=5.8 Hz, 1H), 4.03 (d, J=5.8 Hz, 1H), 4.52 (q, J=8.2 Hz, 2H), 6.53 (dd, J=2.4, 6.1 Hz, 1H), 6.61 (d, J=2.2 Hz, 1H), 6.95-7.03 (m, 1H), 7.06-7.13 (m, 2H), 7.34-7.44 (m, 1H), 8.01 (d, J=6.1 Hz, 1H). MS (ES+) m/z 497.3, 499.3 [M+H, Cl isotopes].

Example 34

(1R,5S,8s)-N-(5-(4-Fluoro-3-(trifluoromethyl)phenoxy)-1-(2,2,2-trifluoroethyl)-1H-1,2,4-triazol-3-yl)-3-(6-methylpyrimidin-4-yl)-3-azabicyclo[3.2.1]octan-8-amine

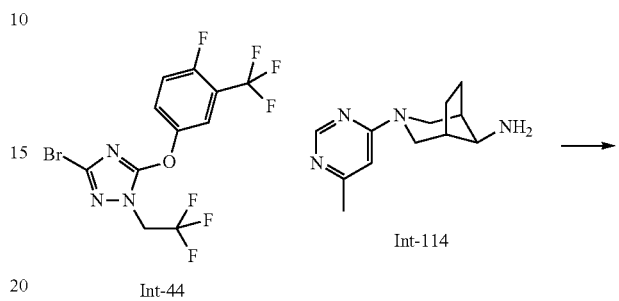

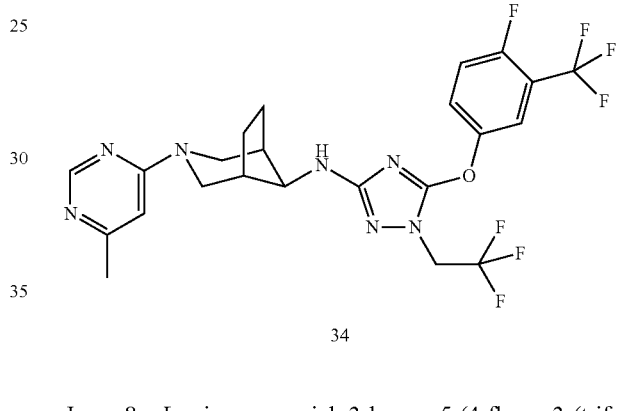

In an 8 mL microwave vial, 3-bromo-5-(4-fluoro-3-(trifluoromethyl)phenoxy)-1-(2,2,2-trifluoroethyl)-1H-1,2,4-triazole (Int-44, 72.9 mg, 179 µmol) was suspended in 1,4-dioxane (3.0 mL) and (1R,5S,8s)-3-(6-methylpyrimidin-4-yl)-3-azabicyclo[3.2.1]octan-8-amine (Int-114, 30 mg, 137 µmol), sodium tert-butoxide (27.8 mg, 275 µmol), 1,2,3,4,5-pentaphenyl-1'-(di-tert-butylphosphino)ferrocene ("Q-phos", CAS [312959-24-3], 16.4 mg, 22 µmol), and tris (dibenzylideneacetone)dipalladium (0) chloroform adduct (11.7 mg, 11 µmol) were added subsequently. The vial was degassed thoroughly with Argon and sealed. The reaction mixture was heated under microwave irradiation at 120° C. for 20 min. After that, the mixture was concentrated in vacuo. The resulting crude product was directly purified by column chromatography (amino modified silica gel, 50 g, eluting with ethyl acetate/n-heptane, gradient 0:100 to 1:2 v/v), followed by preparative HPLC (YMC-Actus Triart C18, 100×30 mm×5 µm, eluting with acetonitrile/(water+ 0.1% triethylamine), gradient 20:80 to 98:2 v/v) and lyophilization to yield the title compound as a white foam (13.8 mg, 18%). HPLC (method LCMS_fastgradient) $t_R$=1.07 min. $^1$H NMR (CDCl$_3$, 300 MHz): δ 1.51-1.64 (m, 2H), 1.79-1.88 (m, 2H), 2.37 (s, 3H), 2.43-2.50 (m, 2H), 3.05-3.12 (m, 2H), 3.74 (d, J=6.1 Hz, 1H), 4.00 (d, J=6.1 Hz, 1H), 4.06-4.20 (m, 2H), 4.53 (q, J=8.2 Hz, 2H), 6.34 (s, 1H), 7.23-7.31 (m, 1H), 7.48-7.55 (m, 1H), 7.58-7.63 (m, 1H), 8.51 (s, 1H). MS (ES+) m/z 546.7 [M+H].

Example 35

(1R,5S,8s)-N-(5-(4-Fluoro-3-(trifluoromethyl)phenoxy)-1-methyl-1H-1,2,4-triazol-3-yl)-3-(3-methyl-1,2,4-oxadiazol-5-yl)-3-azabicyclo[3.2.1]octan-8-amine

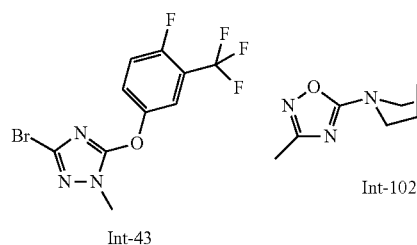

Int-43 Int-102

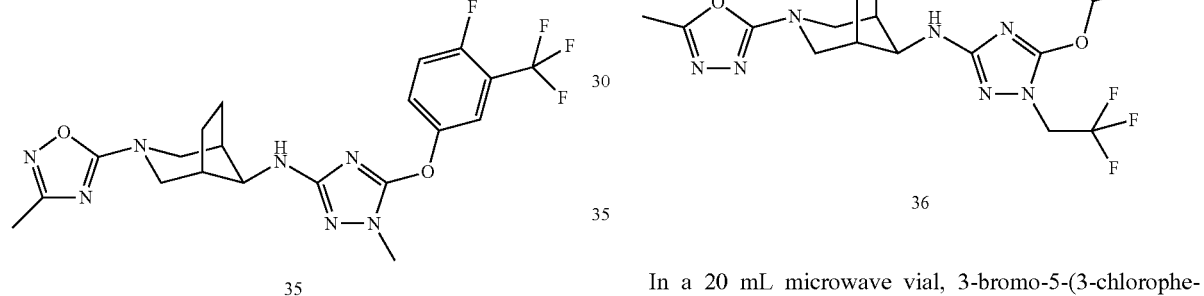

35

In an 8 mL microwave vial, 3-bromo-5-(4-fluoro-3-(trifluoromethyl)phenoxy)-1-methyl-1H-1,2,4-triazole (Int-43, 63.7 mg, 187 µmol) was suspended in 1,4-dioxane (3.0 mL) and (1R,5S,8s)-3-(3-methyl-1,2,4-oxadiazol-5-yl)-3-azabicyclo[3.2.1]octan-8-amine (Int-102, 30 mg, 144 µmol), sodium tert-butoxide (29.1 mg, 288 µmol), 1,2,3,4,5-pentaphenyl-1'-(di-tert-butylphosphino)ferrocene ("Q-phos", CAS [312959-24-3], 17.2 mg, 23 µmol), and tris(dibenzylideneacetone)dipalladium (0) chloroform adduct (12.3 mg, 11.5 µmol) were added subsequently. The vial was degassed thoroughly with Argon and sealed. The reaction mixture was heated under microwave irradiation at 120° C. for 20 min. After that, the mixture was concentrated in vacuo. The resulting crude product was filtered through a plug of silica gel (eluting with dichloromethane/methanol 1:1 v/v) and purified by preparative HPLC (YMC-Actus Triart C18, 100×30 mm×5 µm, eluting with acetonitrile/(water+0.1% triethylamine), gradient 20:80 to 98:2 v/v), followed by lyophilization to yield the title compound as a brown solid (12 mg, 18%). HPLC (method LCMS_fastgradient) $t_R$=1.18 min. $^1$H NMR (CDCl$_3$, 300 MHz): δ1.56-1.68 (m, 2H), 1.81-1.92 (m, 2H), 2.22 (s, 3H), 2.39-2.46 (m, 2H), 3.30-3.38 (m, 2H), 3.65 (s, 3H), 3.70 (d, J=6.1 Hz, 1H), 3.85-3.93 (m, 3H), 7.22 (d, J=9.3 Hz, 1H), 7.46-7.53 (m, 1H), 7.58 (dd, J=3.1, 5.5 Hz, 1H). MS (ES+) m/z 468.3 [M+H].

Example 36

(1R,5S,8s)-N-(5-(3-Chlorophenoxy)-1-(2,2,2-trifluoroethyl)-1H-1,2,4-triazol-3-yl)-3-(5-methyl-1,3,4-oxadiazol-2-yl)-3-azabicyclo[3.2.1]octan-8-amine

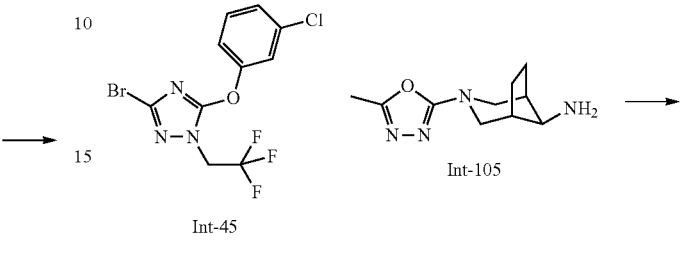

Int-45 Int-105

36

In a 20 mL microwave vial, 3-bromo-5-(3-chlorophenoxy)-1-(2,2,2-trifluoroethyl)-1H-1,2,4-triazole (Int-45, 282 mg, 792 µmol) was suspended in 1,4-dioxane (8 mL) and (1R,5S,8s)-3-(5-methyl-1,3,4-oxadiazol-2-yl)-3-azabicyclo[3.2.1]octan-8-amine (Int-105, 150 mg, 720 µmol), sodium tert-butoxide (146 mg, 1.44 mmol), 1,2,3,4,5-pentaphenyl-1'-(di-tert-butylphosphino)ferrocene ("Q-phos", CAS [312959-24-3], 86.2 mg, 115 µmol), and tris(dibenzylideneacetone)dipalladium (0) chloroform adduct (61.5 mg, 57.6 µmol) were added subsequently. The vial was degassed thoroughly with Argon and sealed. The reaction mixture was heated under microwave irradiation at 120° C. for 30 min. After that, the mixture was concentrated in vacuo. The resulting crude product was filtered through a plug of silica gel (eluting first with ethyl acetate/n-heptane, gradient 0:100 to 100:0 v/v to remove impurities, then with dichloromethane/methanol 9:1 v/v), then purified by column chromatography (amino modified silica gel, 50 g, eluting with ethyl acetate/n-heptane, gradient 0:100 to 40:60 v/v), followed by preparative HPLC (YMC-Actus Triart C18, 100×30 mm×5 µm, eluting with acetonitrile/(water+0.1% triethylamine), gradient 20:80 to 98:2 v/v) and lyophilization to yield the title compound as a white solid (78 mg, 22%). $^1$H NMR (CDCl$_3$, 300 MHz): δ 1.60-1.70 (m, 2H), 1.80-1.92 (m, 2H), 2.39 (s, 3H), 2.39-2.45 (m, 2H), 3.23-3.31 (m, 2H), 3.69 (d, J=6.2 Hz, 1H), 3.73 (dd, J=3.4, 12.5 Hz, 2H), 4.00 (d, J=6.0 Hz, 1H), 4.52 (q, J=8.2 Hz, 2H), 7.20 (ddd, J=1.2, 2.4, 8.2 Hz, 1H), 7.23-7.28 (m, 1H), 7.32-7.39 (m, 2H). MS (ES+) m/z 484.2, 486.1 [M+H, Cl isotopes].

Example 37

(1R,5S,8s)-3-(5-Methyl-1,3,4-oxadiazol-2-yl)-N-(1-(2,2,2-trifluoroethyl)-5-(4-(trifluoromethyl)phenoxy)-1H-1,2,4-triazol-3-yl)-3-azabicyclo[3.2.1]octan-8-amine

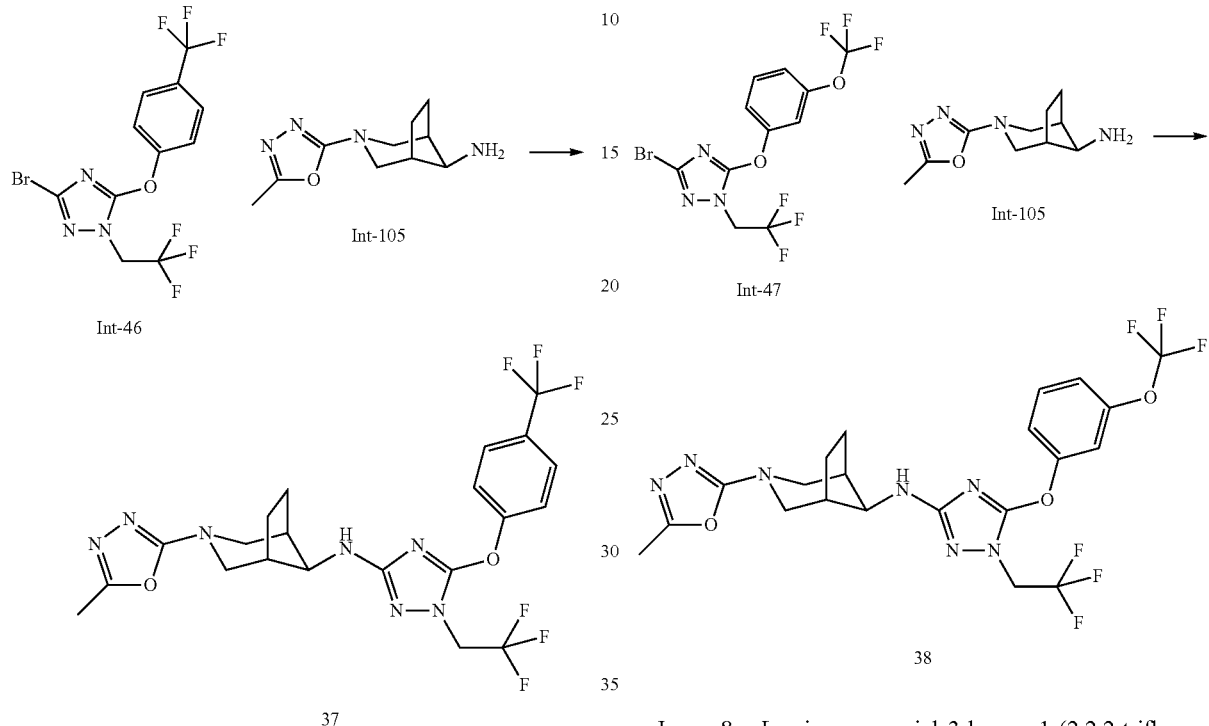

In an 8 mL microwave vial 3-bromo-1-(2,2,2-trifluoroethyl)-5-(4-(trifluoromethyl)-phenoxy)-1H-1,2,4-triazole (Int-46, 112 mg, 288 µmol) was suspended in 1,4-dioxane (2.5 mL) and (1R,5S,8s)-3-(5-methyl-1,3,4-oxadiazol-2-yl)-3-azabicyclo[3.2.1]octan-8-amine (Int-105, 50 mg, 240 µmol), sodium tert-butoxide (92.3 mg, 960 µmol), [2',6'-bis(1-methylethoxy)[1,1'-biphenyl]-2-yl]dicyclohexylphosphine ("Ruphos", CAS [787618-22-8], 23.6 mg, 48 µmol), and (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium ("Brettphos-palladacycle", CAS [1148148-01-9], 38.4 mg, 48 µmol) were added subsequently. The vial was degassed thoroughly with Argon and sealed. The reaction mixture was heated in an oil bath at 130° C. for 15 h. After that, the mixture was concentrated in vacuo. The resulting crude product was directly purified by column chromatography (amino modified silica gel, 50 g, eluting with ethyl acetate/n-heptane, gradient 0:100 to 2:1 v/v) followed by preparative HPLC (YMC-Actus Triart C18, 100×30 mm×5 µm, eluting with acetonitrile/(water+0.1% triethylamine), gradient 20:80 to 98:2 v/v) and lyophilization to yield the title compound as a white foam (9 mg, 7%). HPLC (method LCMS_fastgradient) $t_R$=1.27 min. $^1$H NMR (CDCl$_3$, 300 MHz): δ 1.60-1.70 (m, 2H), 1.80-1.90 (m, 2H), 2.39 (s, 3H), 2.39-2.46 (m, 2H), 3.23-3.31 (m, 2H), 3.69 (d, J=6.1 Hz, 1H), 3.73 (dd, J=3.2, 12.5 Hz, 2H), 4.01 (d, J=6.1 Hz, 1H), 4.54 (q, J=8.2 Hz, 2H), 7.43 (d, J=8.7 Hz, 2H), 7.70 (d, J=8.7 Hz, 2H). MS (ES+) m/z 518.3 [M+H].

Example 38

(1R,5S,8s)-3-(5-Methyl-1,3,4-oxadiazol-2-yl)-N-(1-(2,2,2-trifluoroethyl)-5-(3-(trifluoromethoxy)phenoxy)-1H-1,2,4-triazol-3-yl)-3-azabicyclo[3.2.1]octan-8-amine

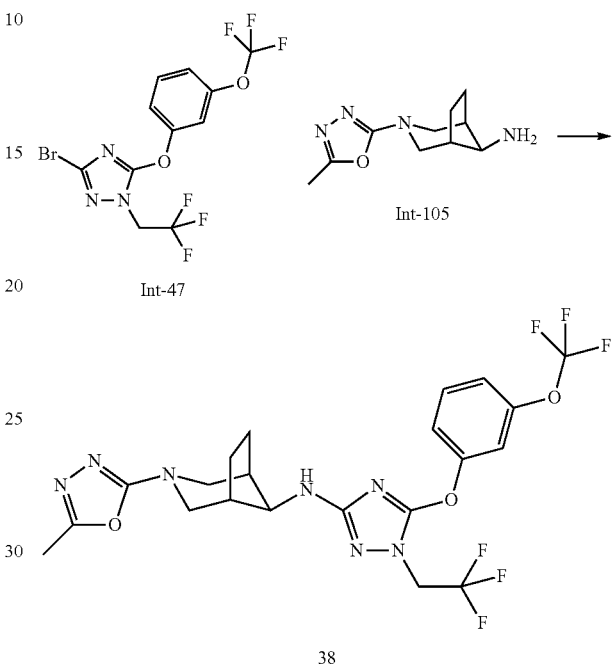

In an 8 mL microwave vial 3-bromo-1-(2,2,2-trifluoroethyl)-5-(3-(trifluoromethoxy)-phenoxy)-1H-1,2,4-triazole (Int-47, 117 mg, 288 µmol) was suspended in 1,4-dioxane (2.5 mL) and (1R,5S,8s)-3-(5-methyl-1,3,4-oxadiazol-2-yl)-3-azabicyclo[3.2.1]octan-8-amine (Int-105, 50 mg, 240 µmol), sodium tert-butoxide (92.3 mg, 960 µmol), [2',6'-bis(1-methylethoxy)[1,1'-biphenyl]-2-yl]dicyclohexylphosphine ("Ruphos", CAS [787618-22-8], 23.6 mg, 48 µmol), and (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium ("Brettphos-palladacycle", CAS [1148148-01-9], 38.4 mg, 48 µmol) were added subsequently. The vial was degassed thoroughly with Argon and sealed. The reaction mixture was heated in an oil bath at 130° C. for 15 h. After that, the mixture was diluted with ethyl acetate (10 mL) concentrated in vacuo. The resulting crude product was directly purified by column chromatography (amino modified silica gel, 50 g, eluting with ethyl acetate/n-heptane, gradient 0:100 to 2:1 v/v) followed by preparative HPLC (YMC-Actus Triart C18, 100×30 mm×5 µm, eluting with acetonitrile/(water+0.1% triethylamine), gradient 20:80 to 98:2 v/v) and lyophilization to afford the title compound as a white foam (10 mg, 8%). HPLC (method LCMS_fastgradient) $t_R$=1.25 min. $^1$H NMR (CDCl$_3$, 300 MHz): δ 1.60-1.70 (m, 2H), 1.81-1.92 (m, 2H), 2.39 (s, 3H), 2.39-2.46 (m, 2H), 3.22-3.31 (m, 2H), 3.69 (d, J=6.1 Hz, 1H), 3.73 (dd, J=3.2, 12.5 Hz, 2H), 4.02 (d, J=5.8 Hz, 1H), 4.53 (q, J=8.2 Hz, 2H), 7.11-7.17 (m, 1H), 7.21-7.29 (m, 2H), 7.45 (dd, J=8.2, 8.2 Hz, 1H). MS (ES+) m/z 534.3 [M+H].

Example 39

(1R,5S,8s)-3-(5-Methyl-1,3,4-oxadiazol-2-yl)-N-(1-(2,2,2-trifluoroethyl)-5-(3-(trifluoromethyl)phenoxy)-1H-1,2,4-triazol-3-yl)-3-azabicyclo[3.2.1]octan-8-amine

Example 40

(1R,5S,8s)-3-(3-Methyl-1,2,4-oxadiazol-5-yl)-N-[1-(propan-2-yl)-5-[2-fluoro-3-(trifluoromethyl)phenoxy]-1H-1,2,4-triazol-3-yl]-3-azabicyclo[3.2.1]octan-8-amine

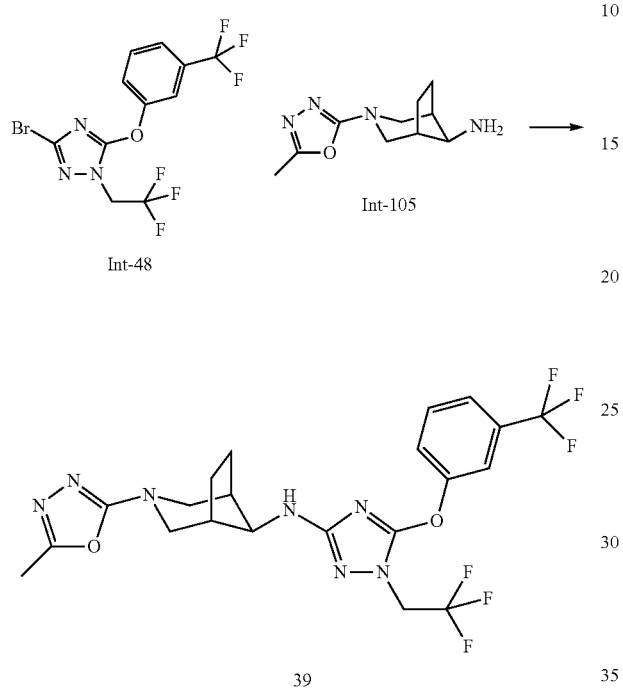

In an 8 mL microwave vial 3-bromo-1-(2,2,2-trifluoroethyl)-5-(3-(trifluoromethyl)-phenoxy)-1H-1,2,4-triazole (Int-48, 112 mg, 288 μmol) was suspended in 1,4-dioxane (2.5 mL) and (1R,5S,8s)-3-(5-methyl-1,3,4-oxadiazol-2-yl)-3-azabicyclo[3.2.1]octan-8-amine (Int-105, 50 mg, 240 μmol), sodium tert-butoxide (92.3 mg, 960 μmol), [2',6'-bis(1-methylethoxy)[1,1'-biphenyl]-2-yl]dicyclohexylphosphine ("Ruphos", CAS [787618-22-8], 23.6 mg, 48 μmol), and (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]palladium ("Brettphos-palladacycle", CAS [1148148-01-9], 38.4 mg, 48 μmol) were added subsequently. The vial was degassed thoroughly with Argon and sealed. The reaction mixture was heated in an oil bath at 130° C. for 15 h. After that, the mixture was diluted with ethyl acetate (10 mL) concentrated in vacuo. The resulting crude product was directly purified by column chromatography (amino modified silica gel, 50 g, eluting with ethyl acetate/n-heptane, gradient 0:100 to 2:1 v/v) followed by preparative HPLC (YMC-Actus Triart C18, 100×30 mm×5 μm, eluting with acetonitrile/(water+0.1% triethylamine), gradient 20:80 to 98:2 v/v) and lyophilization to afford the title compound as a white foam (13 mg, 11%). HPLC (method LCMS_fastgradient) $t_R$=1.22 min. $^1$H NMR (CDCl$_3$, 300 MHz): δ 1.60-1.70 (m, 2H), 1.81-1.90 (m, 2H), 2.39 (s, 3H), 2.39-2.45 (m, 2H), 3.23-3.31 (m, 2H), 3.69 (d, J=6.2 Hz, 1H), 3.73 (dd, J=3.2, 12.5 Hz, 2H), 4.02 (d, J=6.1 Hz, 1H), 4.54 (q, J=8.2 Hz, 2H), 7.48-7.57 (m, 3H), 7.59-7.62 (m, 1H). MS (ES+) m/z 518.3 [M+H].

To a solution of (1R,5S,8s)-8-({5-[2-fluoro-3-(trifluoromethyl)phenoxy]-1-(propan-2-yl)-1H-1,2,4-triazol-3-yl}amino)-3-azabicyclo[3.2.1]octane-3-carbonitrile (Int-52, 350 mg, 0.8 mmol) and N-hydroxyethanimidamide (59.1 mg, 0.8 mmol) in DMF (5 mL) was added p-toluenesulfonic acid (45.6 mg, 0.2 mmol) and solid ZnCl$_2$ (32.6 mg, 0.2 mmol). The reaction mixture was heated at 80° C. for a period of 5 h. Then, ice-water was added and the reaction mixture was Then, ice-water was added and the reaction mixture was extracted with EtOAc (3×20 mL). The organic layer was dried and concentrated under reduced pressure to afford the crude which was purified by column chromatography (amino modified silica gel, 12 g, eluting with EtOAc/n-hexane 30:70 v/v) to yield the title compound as white solid (220 mg, 56%). HPLC purity 97.40%. $^1$H NMR (DMSO-d6, 400 MHz): 1.23-1.34 (m, 2H), 1.40 (d, J=6.5 Hz, 6H), 1.84 (d, J=10.6 Hz, 2H), 2.08 (s, 3H), 2.32 (s, 2H), 3.26 (d, J=12.0 Hz, 2H), 3.50 (d, J=3.7 Hz, 1H), 3.68 (d, J=10.5 Hz, 2H), 4.47 (dt, J=12.0, 6.1 Hz, 1H), 6.01 (d, J=4.1 Hz, 1H), 7.49 (t, J=8.1 Hz, 1H), 7.70 (t, J=6.6 Hz, 1H), 7.91 (t, J=7.6 Hz, 1H). MS (ES+) m/z 495.8 [M+H].

Example 41

(1R,5S,8s)-N-{5-[2-Fluoro-5-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine

Example 42

(1R,5S,8s)-N-{5-[3-Fluoro-4-(trifluoromethoxy)phenoxy]-1-(propan-2-yl)-1H-1,2,4-triazol-3-yl}-3-(3-methyl-1,2,4-oxadiazol-5-yl)-3-azabicyclo[3.2.1]octan-8-amine

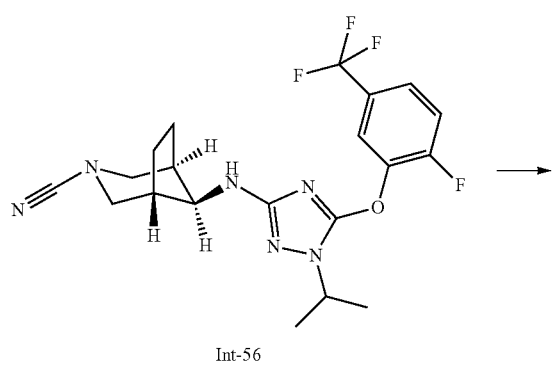

Int-56

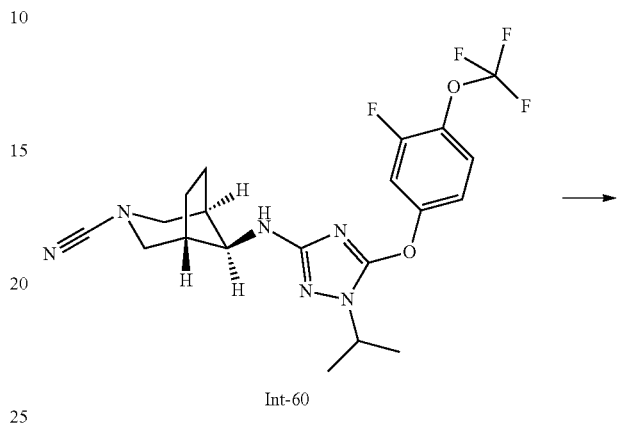

Int-60

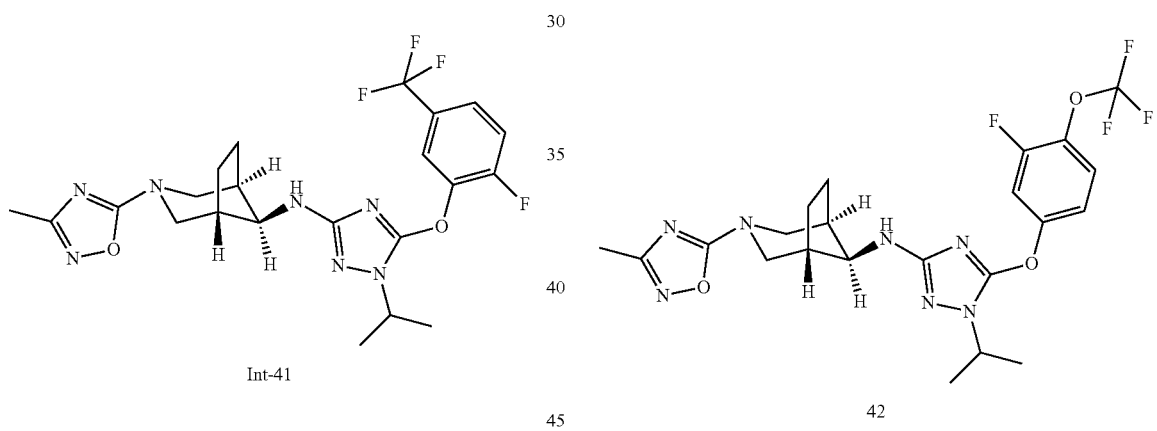

Int-41

42

To a solution of (1R,5S,8s)-8-({5-[2-fluoro-5-(trifluoromethyl)phenoxy]-1-(propan-2-yl)-1H-1,2,4-triazol-3-yl}amino)-3-azabicyclo[3.2.1]octane-3-carbonitrile (Int-56, 200 mg, 0.5 mmol) and N-hydroxyethanimidamide (33.8 mg, 0.5 mmol) in DMF (3 mL) was added p-toluenesulfonic acid (26 mg, 0.1 mmol) and solid ZnCl$_2$ (18.6 mg, 0.1 mmol). The reaction mixture was heated at 80° C. for a period of 5 h. Then, ice-water was added and the reaction mixture was Then, ice-water was added and the reaction mixture was extracted with EtOAc (3×20 mL). The organic layer was dried and concentrated under reduced pressure to afford the crude which was purified by column chromatography (amino modified silica gel, 12 g, eluting with EtOAc/n-hexane 30:70 v/v) to yield the title compound as white solid (80 mg, 35%). HPLC purity 99.26%. $^1$H NMR (DMSO-d6, 400 MHz): 1.23-1.34 (m, 2H), 1.40 (d, J=6.5 Hz, 6H), 1.80-1.87 (m, 1H), 2.08 (s, 3H), 2.32 (s, 2H), 3.22-3.30 (m, 2H), 3.50 (d, J=4.5 Hz, 1H), 3.63-3.72 (m, 2H), 4.40-4.52 (m, 1H), 6.01 (d, J=4.1 Hz, 1H), 7.63-7.72 (m, 1H), 7.74 (ddd, J=6.6, 5.2, 3.7 Hz, 1H), 8.08-8.15 (m, 1H). MS (ES+) m/z 496.0 [M+H].

To a solution of (1R,5S,8s)-N-{5-[3-fluoro-4-(trifluoromethoxy)phenoxy]-1-(propan-2-yl)-1H-1,2,4-triazol-3-yl}-3-azabicyclo[3.2.1]octan-8-amine (Int-60, 250 mg, 0.6 mmol) and N-hydroxyethanimidamide (42.2 mg, 0.6 mmol) in DMF (3 mL) was added p-toluenesulfonic acid (32.5 mg, 0.1 mmol) and solid ZnCl$_2$ (23.2 mg, 0.1 mmol). The reaction mixture was heated at 80° C. for a period of 5 h. Then, ice-water was added and the reaction mixture was Then, ice-water was added and the reaction mixture was extracted with EtOAc (3×20 mL). The organic layer was dried and concentrated under reduced pressure to afford the crude which was purified by column chromatography (amino modified silica gel, 12 g, eluting with EtOAc/n-hexane 30:70 v/v) to yield the title compound as white solid (100 mg, 34%). HPLC purity 95.06%. $^1$H NMR (DMSO-d6, 400 MHz): 1.37 (d, J=6.3 Hz, 6H), 1.86 (s, 2H), 2.09 (s, 3H), 2.35 (s, 2H), 3.14-3.29 (m, 2H), 3.53 (d, J=3.0 Hz, 1H), 3.70 (d, J=11.0 Hz, 2H), 4.41 (dd, J=13.5, 6.5 Hz, 1H), 6.02 (d, J=4.2 Hz, 1H), 7.30 (d, J=10.5 Hz, 1H), 7.61-7.72 (m, 2H). MS (ES+) m/z 511.8 [M+H].

Example 43

((1R,5S,8s)-N-(5-(3-Fluorophenoxy)-1-(2,2,2-trifluoroethyl)-1H-1,2,4-triazol-3-yl)-3-(6-methylpyrimidin-4-yl)-3-azabicyclo[3.2.1]octan-8-amine

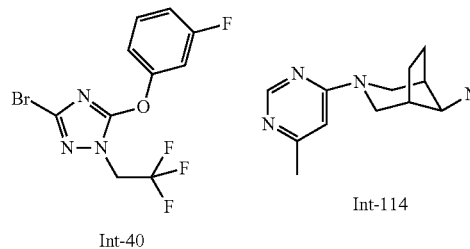

Int-40

Int-114

Example 44

(1R,5S,8s)-3-(3-Methyl-1,2,4-oxadiazol-5-yl)-N-(1-(2,2,2-trifluoroethyl)-5-(3-(trifluoromethyl)phenoxy)-1H-1,2,4-triazol-3-yl)-3-azabicyclo[3.2.1]octan-8-amine

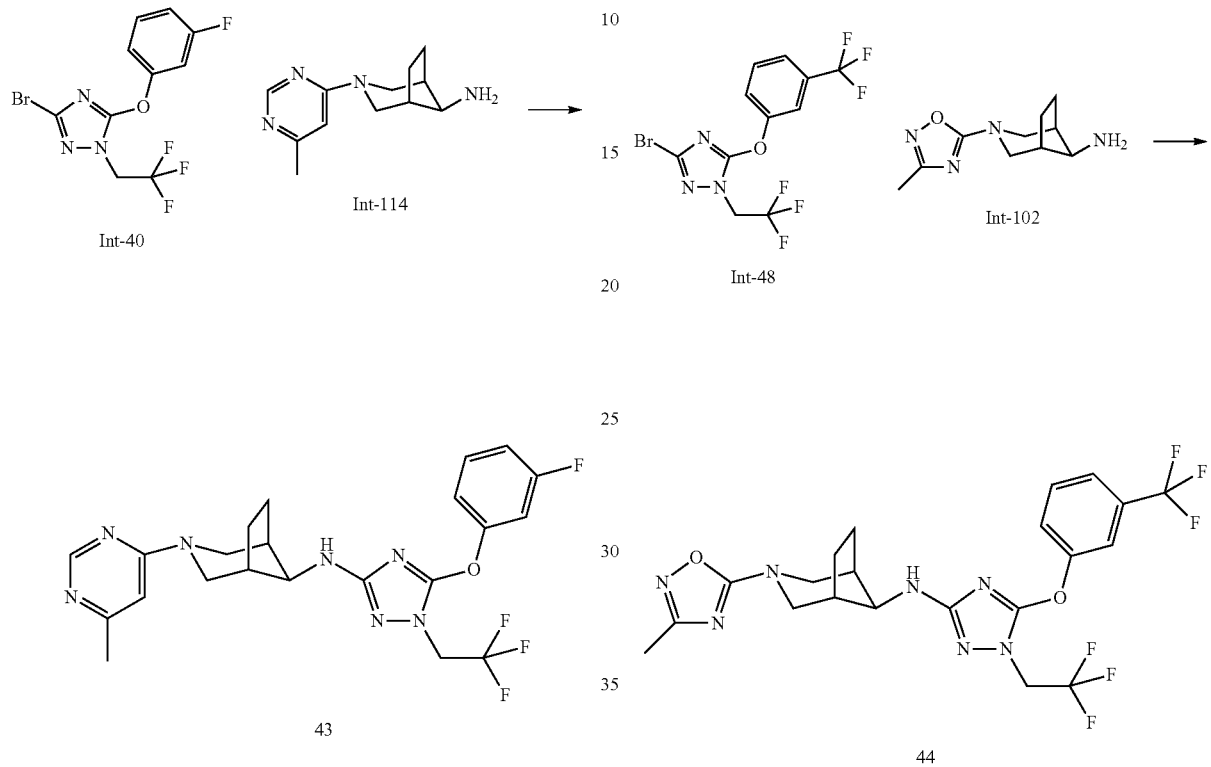

Int-48

Int-102

43

44

In a 20 mL microwave vial (1R,5S,8s)-3-(6-methylpyrimidin-4-yl)-3-azabicyclo[3.2.1]octan-8-amine (Int-114, 60 mg, 275 μmol) was suspended in 1,4-dioxane (6 mL) and 3-bromo-5-(3-fluorophenoxy)-1-(2,2,2-trifluoroethyl)-1H-1,2,4-triazole (Int-40, 122 mg, 357 μmol), sodium tert-butoxide (55.6 mg, 550 μmol), 1,2,3,4,5-pentaphenyl-1'-(di-tert-butylphosphino)ferrocene ("Q-phos", CAS [312959-24-3], 32.9 mg, 44 μmol), and tris(dibenzylideneacetone)dipalladium (0) chloroform adduct (23.5 mg, 22 μmol) were added subsequently. The vial was degassed thoroughly with Argon and sealed. The reaction mixture was heated under microwave irradiation at 120° C. for 20 min. After that, the mixture was concentrated in vacuo. The resulting crude product was purified by column chromatography (amino modified silica gel, 50 g, eluting with ethyl acetate/n-heptane, gradient 0:100 to 2:1 v/v), followed by preparative HPLC (YMC-Actus Triart C18, 100×30 mm×5 μm, eluting with acetonitrile/(water+0.1% triethylamine), gradient 20:80 to 98:2 v/v) and lyophilization to yield the title compound as a white foam (10 mg, 8%). HPLC (method LCMS_fastgradient) $t_R$=0.95 min. $^1$H NMR (CDCl$_3$, 300 MHz): δ1.60-1.70 (m, 2H), 1.74-1.88 (m, 2H), 2.37 (s, 3H), 2.43-2.50 (m, 2H), 3.05-3.14 (m, 2H), 3.75 (d, J=6.1 Hz, 1H), 4.03 (d, J=6.1 Hz, 1H), 4.06-4.20 (m, 2H), 4.52 (q, J=8.2 Hz, 2H), 6.34 (s, 1H), 6.95-7.02 (m, 1H), 7.05-7.12 (m, 2H), 7.34-7.43 (m, 1H), 8.50 (d, J=0.6 Hz, 1H). MS (ES+) m/z 478.3 [M+H].

In an 8 mL microwave vial (1R,5S,8s)-3-(3-methyl-1,2,4-oxadiazol-5-yl)-3-azabicyclo[3.2.1]octan-8-amine (Int-102, 50 mg, 240 μmol) was suspended in 1,4-dioxane (4 mL) and 3-bromo-1-(2,2,2-trifluoroethyl)-5-(3-(trifluoromethyl)phenoxy)-1H-1,2,4-triazole (Int-48, 122 mg, 312 μmol), sodium tert-butoxide (48.6 mg, 480 μmol), 1,2,3,4,5-pentaphenyl-1'-(di-tert-butylphosphino)ferrocene ("Q-phos", CAS [312959-24-3], 28.7 mg, 38.7 μmol), and tris(dibenzylideneacetone)dipalladium (0) chloroform adduct (20.5 mg, 19.2 μmol) were added subsequently. The vial was degassed thoroughly with Argon and sealed. The reaction mixture was heated under microwave irradiation at 120° C. for 20 min. After that, the mixture was concentrated in vacuo. The resulting crude product was purified by column chromatography (amino modified silica gel, 50 g, eluting with ethyl acetate/n-heptane, gradient 0:100 to 100:0 v/v), followed by preparative HPLC (YMC-Actus Triart C18, 100×30 mm×5 μm, eluting with acetonitrile/(water+0.1% triethylamine), gradient 20:80 to 98:2 v/v) and lyophilization to yield the title compound as a white foam (24 mg, 19%). HPLC (method LCMS_fastgradient) $t_R$=1.29 min. $^1$H NMR (CDCl$_3$, 300 MHz): δ1.57-1.68 (m, 2H), 1.82-1.92 (m, 2H), 2.22 (s, 3H), 2.39-2.46 (m, 2H), 3.29-3.38 (m, 2H), 3.68-3.74 (m, 1H), 3.89 (dd, J=2.6, 12.9 Hz, 2H), 4.00 (d, J=5.6 Hz, 1H), 4.54 (q, J=8.1 Hz, 2H), 7.48-7.58 (m, 3H), 7.59-7.63 (m, 1H). MS (ES+) m/z 518.3 [M+H].

Example 45

(1R,5S,8s)-3-(3-Methyl-1,2,4-oxadiazol-5-yl)-N-(1-(2,2,2-trifluoroethyl)-5-(4-(trifluoromethyl)phenoxy)-1H-1,2,4-triazol-3-yl)-3-azabicyclo[3.2.1]octan-8-amine

Example 46

(1R,5S,8s)-N-(5-(3-Chlorophenoxy)-1-methyl-1H-1,2,4-triazol-3-yl)-3-(6-methylpyrimidin-4-yl)-3-azabicyclo[3.2.1]octan-8-amine

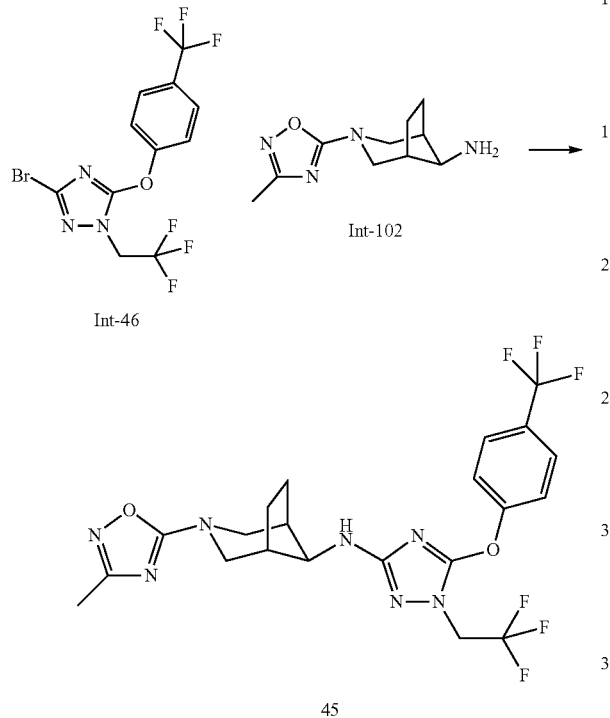

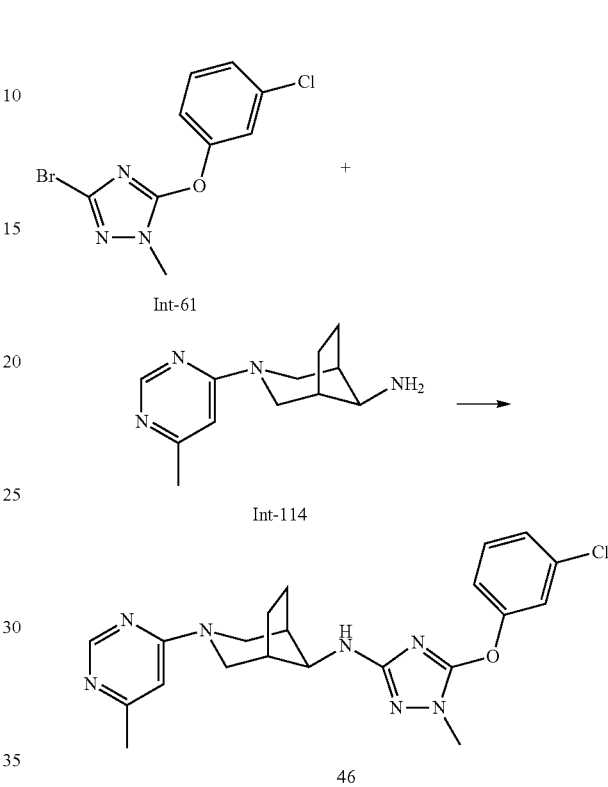

In an 8 mL microwave vial (1R,5S,8s)-3-(3-methyl-1,2,4-oxadiazol-5-yl)-3-azabicyclo[3.2.1]octan-8-amine (Int-102, 50 mg, 240 µmol) was suspended in 1,4-dioxane (4 mL) and 3-bromo-1-(2,2,2-trifluoroethyl)-5-(4-(trifluoromethyl)phenoxy)-1H-1,2,4-triazole (Int-46, 122 mg, 312 µmol), sodium tert-butoxide (48.6 mg, 480 µmol), 1,2,3,4,5-pentaphenyl-1'-(di-tert-butylphosphino)ferrocene ("Q-phos", CAS [312959-24-3], 28.7 mg, 38.7 µmol), and tris(dibenzylideneacetone)dipalladium (0) chloroform adduct (20.5 mg, 19.2 µmol) were added subsequently. The vial was degassed thoroughly with Argon and sealed. The reaction mixture was heated under microwave irradiation at 120° C. for 20 min. After that, the mixture was diluted with dichloromethane (10 mL) and concentrated in vacuo. The resulting crude product was purified by column chromatography (silica gel, 50 g, eluting with ethyl acetate/n-heptane, gradient 0:100 to 100:0 v/v), followed by preparative HPLC (YMC-Actus Triart C18, 100×30 mm×5 µm, eluting with acetonitrile/(water+0.1% triethylamine), gradient 20:80 to 98:2 v/v) and lyophilization to afford the title compound as a white foam (10 mg, 8%). HPLC (method LCMS_fastgradient) $t_R$=1.30 min. $^1$H NMR (CDCl$_3$, 300 MHz): δ 1.58-1.67 (m, 2H), 1.80-1.90 (m, 2H), 2.22 (s, 3H), 2.39-2.46 (m, 2H), 3.30-3.38 (m, 2H), 3.72 (d, J=6.1 Hz, 1H), 3.89 (dd, J=3.4, 12.9 Hz, 2H), 3.99 (d, J=5.8 Hz, 1H), 4.54 (q, J=8.2 Hz, 2H), 7.42 (d, J=8.5 Hz, 2H), 7.70 (d, J=8.7 Hz, 2H). MS (ES+) m/z 518.3 [M+H].

In an 8 mL microwave vial, (1R,5S,8s)-3-(6-methylpyrimidin-4-yl)-3-azabicyclo[3.2.1]octan-8-amine (Int-114, 60 mg, 275 µmol) was suspended in 1,4-dioxane (4 mL) and 3-bromo-5-(3-chlorophenoxy)-1-methyl-1H-1,2,4-triazole (Int-61, 103 mg, 357 µmol), sodium tert-butoxide (55.6 mg, 550 µmol), 1,2,3,4,5-pentaphenyl-1'-(di-tert-butylphosphino)ferrocene ("Q-phos", CAS [312959-24-3], 32.9 mg, 44 µmol), and tris(dibenzylideneacetone)dipalladium (0) chloroform adduct (23.5 mg, 22 µmol) were added subsequently. The vial was degassed thoroughly with Argon and sealed. The reaction mixture was heated under microwave irradiation at 120° C. for 20 min. After that, the mixture was concentrated in vacuo. The resulting crude product was purified by column chromatography (amino modified silica gel, 50 g, eluting with ethyl acetate/n-heptane, gradient 0:100 to 50:50 v/v), followed by preparative HPLC (YMC-Actus Triart C18, 100×30 mm×5 µm, eluting with acetonitrile/(water+0.1% triethylamine), gradient 20:80 to 98:2 v/v) and lyophilization to yield the title compound as a white foam (43 mg, 37%). HPLC (method LCMS_fastgradient) $t_R$=0.90 min. $^1$H NMR (CDCl$_3$, 300 MHz): δ1.50-1.60 (m, 2H), 1.79-1.88 (m, 2H), 2.36 (s, 3H), 2.43-2.50 (m, 2H), 3.06-3.13 (m, 2H), 3.64 (s, 3H), 3.75 (d, J=6.1 Hz, 1H), 3.94 (d, J=6.3 Hz, 1H), 4.05-4.21 (m, 2H), 6.34 (s, 1H), 7.16-7.24 (m, 2H), 7.30-7.36 (m, 2H), 8.51 (d, J=0.8 Hz, 1H). MS (ES+) m/z 426.2, 428.2 [M+H, Cl isotopes].

Example 47

(1R,5S,8s)-N-(1-Methyl-5-(3-(trifluoromethoxy)phenoxy)-1H-1,2,4-triazol-3-yl)-3-(6-methylpyrimidin-4-yl)-3-azabicyclo[3.2.1]octan-8-amine

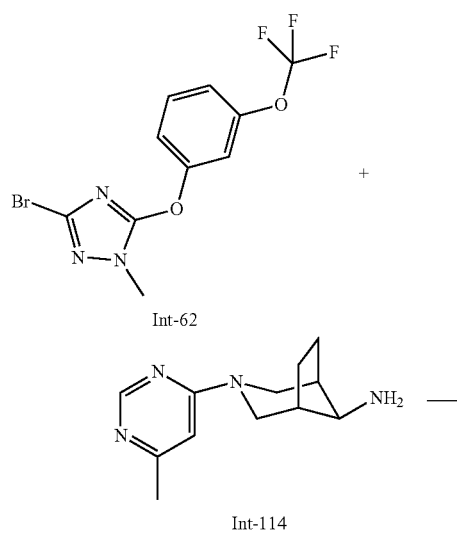

In an 8 mL microwave vial, (1R,5S,8s)-3-(6-methylpyrimidin-4-yl)-3-azabicyclo[3.2.1]octan-8-amine (Int-114, 60 mg, 275 µmol) was suspended in 1,4-dioxane (4 mL) and 3-bromo-1-methyl-5-(3-(trifluoromethoxy)phenoxy)-1H-1,2,4-triazole (Int-62, 102 mg, 302 µmol), sodium tert-butoxide (55.6 mg, 550 µmol), 1,2,3,4,5-pentaphenyl-1'-(di-tert-butylphosphino)ferrocene ("Q-phos", CAS [312959-24-3], 32.9 mg, 44 µmol), and tris(dibenzylideneacetone)dipalladium (0) chloroform adduct (23.5 mg, 22 µmol) were added subsequently. The vial was degassed thoroughly with Argon and sealed. The reaction mixture was heated under microwave irradiation at 120° C. for 20 min. After that, the mixture was concentrated in vacuo. The resulting crude product was purified by column chromatography (amino modified silica gel, 50 g, eluting with ethyl acetate/n-heptane, gradient 0:100 to 50:50 v/v), followed by preparative HPLC (YMC-Actus Triart C18, 100×30 mm×5 µm, eluting with acetonitrile/(water+0.1% triethylamine), gradient 20:80 to 98:2 v/v) and lyophilization to yield the title compound as a white foam (39 mg, 30%). HPLC (method LCMS_fastgradient) $t_R$=0.94 min. $^1$H NMR (CDCl$_3$, 300 MHz): δ1.51-1.59 (m, 2H), 1.80-1.88 (m, 2H), 2.36 (s, 3H), 2.43-2.51 (m, 2H), 3.05-3.13 (m, 2H), 3.65 (s, 3H), 3.75 (d, J=6.3 Hz, 1H), 3.94 (d, J=6.3 Hz, 1H), 4.05-4.21 (m, 2H), 6.34 (s, 1H), 7.07-7.13 (m, 1H), 7.20-7.24 (m, 1H), 7.25-7.28 (m, 1H), 7.43 (dd, J=8.2, 8.2 Hz, 1H), 8.51 (d, J=0.6 Hz, 1H). MS (ES+) m/z 476.3 [M+H].

Example 48

(1R,5S,8s)-3-(5-Methyl-1,3,4-oxadiazol-2-yl)-N-[1-(propan-2-yl)-5-[4-(trifluoromethoxy)phenoxy]-1H-1,2,4-triazol-3-yl]-3-azabicyclo[3.2.1]octan-8-amine

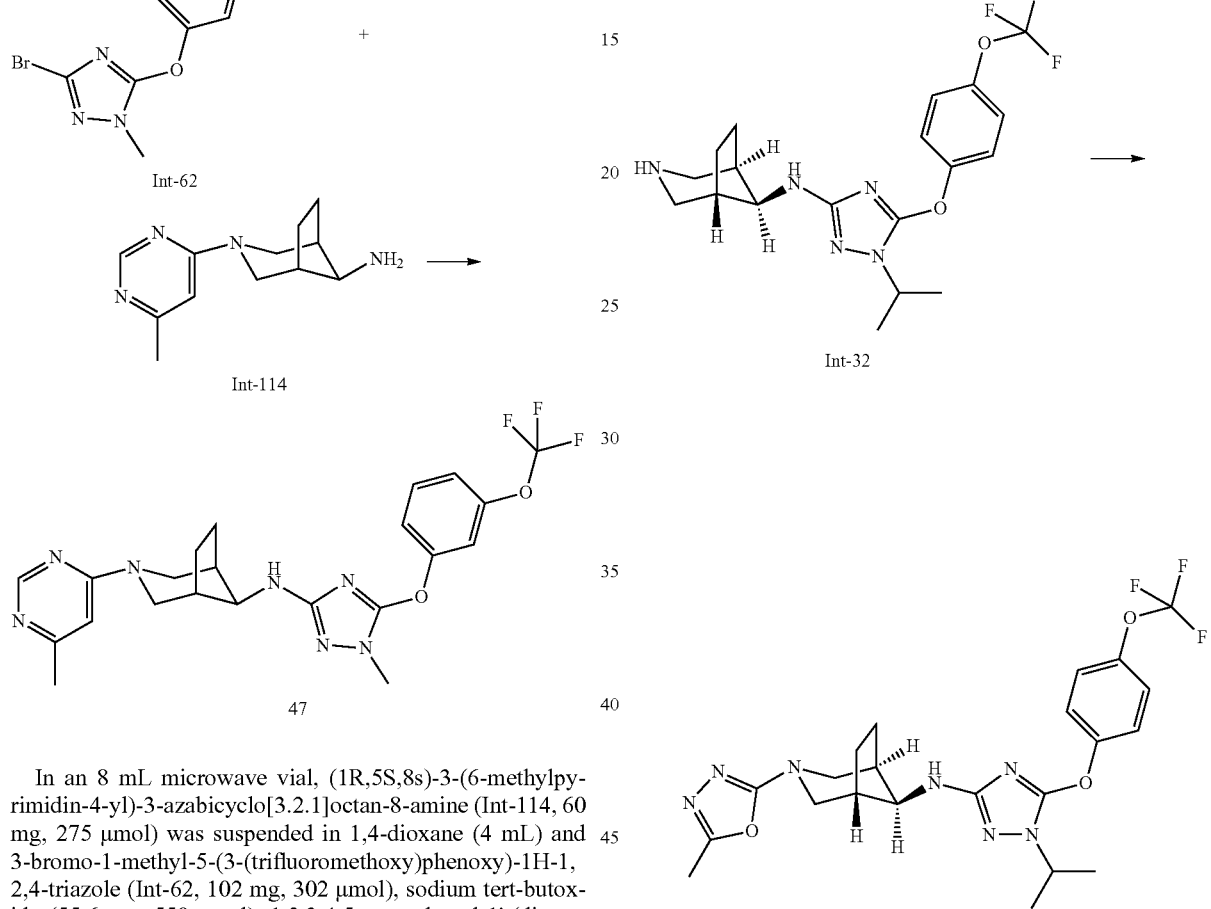

To a solution of (1R,5S,8s)-N-[1-(propan-2-yl)-5-[4-(trifluoromethoxy)phenoxy]-1H-1,2,4-triazol-3-yl]-3-azabicyclo[3.2.1]octan-8-amine (Int-32, 90 mg, 0.2 mmol) in MeOH (2.5 mL) was added triethylamine (0.1 mL, 0.9 mmol) and 2-bromo-5-methyl-1,3,4-oxadiazole (71 mg, 0.4 mmol) and this mixture was stirred at 130° C. for 6 h in a screw cap vial. After complete consumption of starting, as monitored by TLC, solvent was evaporated to get the crude which was purified by column chromatography (silica gel, eluting with EtOAc/n-hexane 70:30 v/v) to yield the title compound yield as colorless liquid (90 mg, 83%). HPLC purity 98.20%. $^1$H NMR (CDCl$_3$, 300 MHz): 1.35-1.41 (m, 8H), 1.84-1.87 (m, 2H), 2.30 (s, 3H), 2.33 (br s, 2H), 3.15 (d, J=11.6 Hz, 2H), 3.48-3.54 (m, 3H), 4.40-4.43 (m, 1H), 5.95 (d, J=4.6 Hz, 1H), 7.43 (s, 4H). MS (ES+) m/z 493.9 [M+H].

Example 49

(1R,5S,8s)-3-(5-Methyl-1,3,4-oxadiazol-2-yl)-N-[1-(propan-2-yl)-5-[3-(trifluoromethyl)phenoxy]-1H-1,2,4-triazol-3-yl]-3-azabicyclo[3.2.1]octan-8-amine

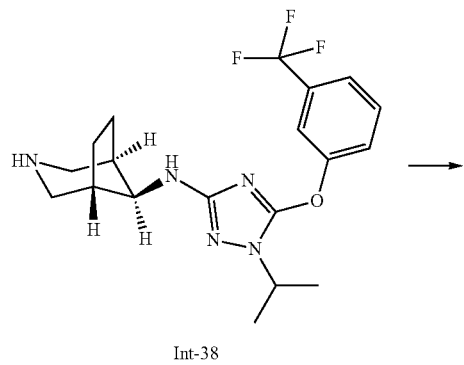

Int-38

Example 50

(1R,5S,8s)-3-(5-Methyl-1,3,4-oxadiazol-2-yl)-N-[1-(propan-2-yl)-5-[4-fluoro-3-(trifluoromethyl)phenoxy]-1H-1,2,4-triazol-3-yl]-3-azabicyclo[3.2.1]octan-8-amine

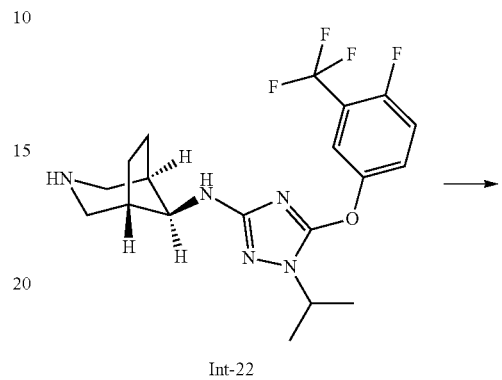

Int-22

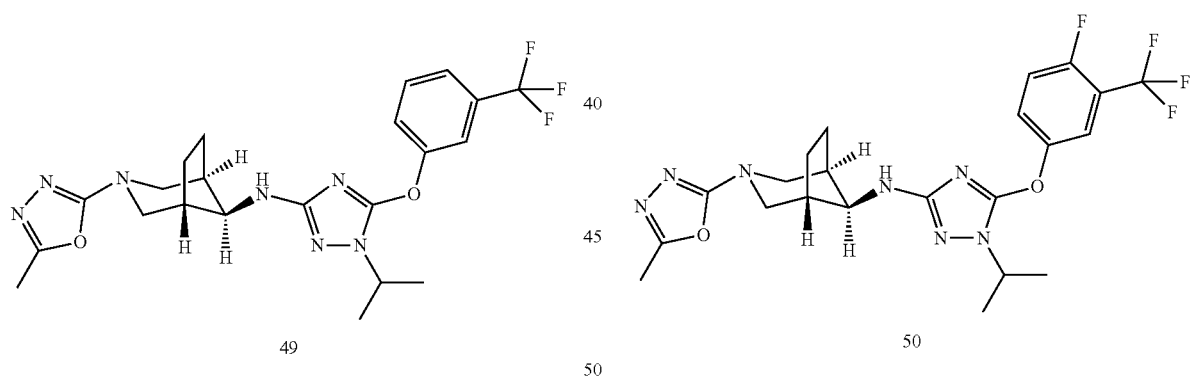

49

50

To a solution of (1R,5S,8s)-N-[1-(propan-2-yl)-5-[3-(trifluoromethyl)phenoxy]-1H-1,2,4-triazol-3-yl]-3-azabicyclo[3.2.1]octan-8-amine (Int-38, 170 mg, 0.4 mmol) in MeOH (3.0 mL) was added triethylamine (0.2 mL, 1.7 mmol) and 2-bromo-5-methyl-1,3,4-oxadiazole (140.1 mg, 0.9 mmol) and this mixture was stirred at 130° C. for 6 h in a screw cap vial. After complete consumption of starting, as monitored by TLC, solvent was evaporated to get the crude which was purified by column chromatography (silica gel, eluting with EtOAc/n-hexane 65:35 v/v) to yield the title compound yield as white solid (175 mg, 85%). HPLC purity 98.17%. $^1$H NMR (DMSO-d6, 400 MHz):1.36-1.40 (m, 7H), 1.85 (br s, 2H), 2.30 (s, 3H), 2.34 (br s, 2H), 3.15 (d, J=11.5 Hz, 2H), 3.50-3.53 (m, 3H), 4.43-4.46 (m, 3H), 5.99 (s, 1H), 7.62-7.68 (m, 3H), 7.79 (s, 1H). MS (ES+) m/z 477.8 [M+H].

To a solution of (1R,5S,8s)-N-{5-[4-fluoro-3-(trifluoromethyl)phenoxy]-1-(propan-2-yl)-1H-1,2,4-triazol-3-yl}-3-azabicyclo[3.2.1]octan-8-amine (Int-22, 90 mg, 0.2 mmol) in MeOH (0.5 mL) was added Et$_3$N (0.1 mL, 0.9 mmol) and 2-bromo-5-methyl-1,3,4-oxadiazole (71 mg, 0.4 mmol) and this mixture was stirred at 130° C. for 6 h in a screw cap vial. After complete consumption of starting, as monitored by TLC, solvent was evaporated to get the crude which was purified by column chromatography (silica gel, eluting with EtOAc/n-hexane 70:30 v/v) to yield the title compound yield as white solid (75 mg, 70%). HPLC purity 97.39%. $^1$H NMR (DMSO-d6, 400 MHz): 1.37 (d, J=6.6 Hz, 6H), 1.38-1.40 (m, 2H), 1.84-1.86 (m, 2H), 2.30-2.34 (m, 5H), 3.15 (d, J=11.5 Hz, 2H), 3.47-3.54 (m, 3H), 4.42-4.46 (m, 1H), 5.98 (d, J=4.3 Hz, 1H), 7.58-7.62 (m, 1H), 7.74-7.77 (m, 1H), 7.88-7.91 (m, 1H). MS (ES+) m/z 495.9 [M+H].

Example 51

(1R,5S,8s)-3-(3-Methyl-1,2,4-oxadiazol-5-yl)-N-{5-[3-methyl-5-(trifluoromethyl)phenoxy]-1-(propan-2-yl)-1H-1,2,4-triazol-3-yl}-3-azabicyclo[3.2.1]octan-8-amine

Example 52

(1R,5S,8s)-N-(5-(3-Chlorophenoxy)-1-(2,2,3,3,3-pentafluoropropyl)-1H-1,2,4-triazol-3-yl)-3-(5-methyl-1,3,4-oxadiazol-2-yl)-3-azabicyclo[3.2.1]octan-8-amine

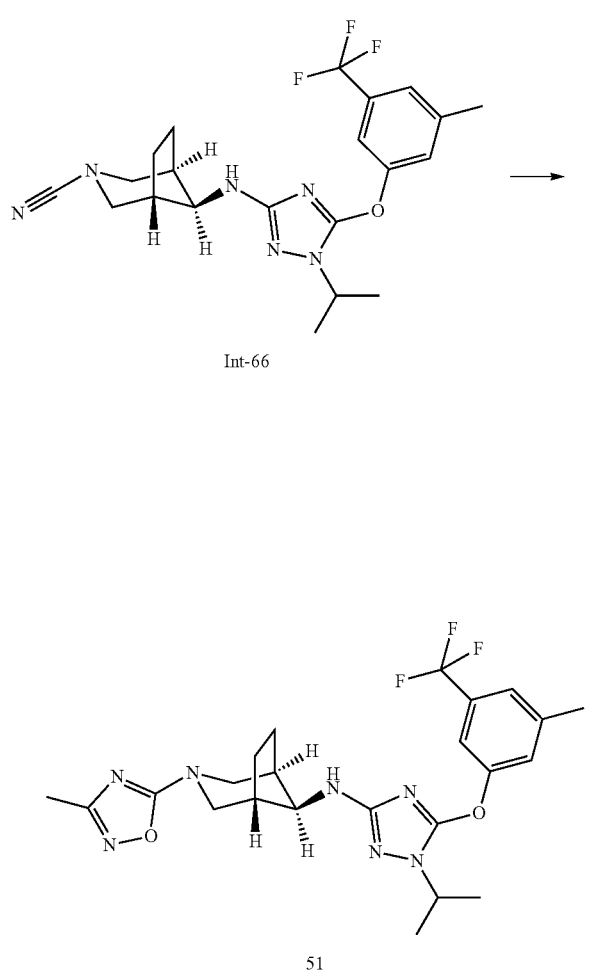

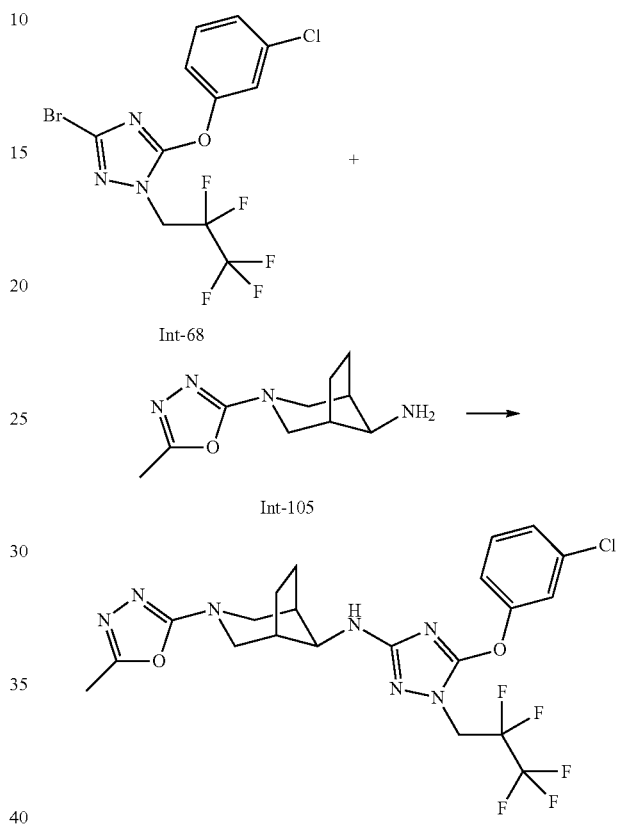

To a solution of (1R,5S,8s)-8-({5-[3-methyl-5-(trifluoromethyl)phenoxy]-1-(propan-2-yl)-1H-1,2,4-triazol-3-yl}amino)-3-azabicyclo[3.2.1]octane-3-carbonitrile (Int-66, 150 mg, 0.3 mmol) and N-hydroxyethanimidamide (25 mg, 0.3 mmol) in DMF (2 mL) was added p-toluenesulfonic acid (19.7 mg, 0.1 mmol) and solid $ZnCl_2$ (14.1 mg, 0.1 mmol). The reaction mixture was heated at 80° C. for a period of 5 h. Then, ice-water was added and the reaction mixture was extracted with EtOAc (3×20 mL). The organic layer was dried and concentrated under reduced pressure to afford the crude which was purified by column chromatography (amino modified silica gel, eluting with EtOAc/n-hexane 30:70 v/v) to yield the title compound as white solid (48 mg, 28%). HPLC purity 94.10%. $^1$H NMR (DMSO-d6, 400 MHz): 1.37 (d, J=6.5 Hz, 6H), 1.83-1.90 (m, 1H), 2.09 (s, 3H), 2.35 (s, 2H), 2.41 (s, 3H), 3.27 (m, 2H), 3.52 (d, J=3.1 Hz, 1H), 3.65-3.73 (m, 2H), 4.44 (dt, J=13.5, 7.2 Hz, 1H), 6.00 (d, J=4.3 Hz, 1H), 7.45 (s, 1H), 7.48 (s, 1H), 7.56 (s, 1H). MS (ES+) m/z 491.8 [M+H].

In an 8 mL microwave vial, (1R,5S,8s)-3-(5-methyl-1,3,4-oxadiazol-2-yl)-3-azabicyclo[3.2.1]octan-8-amine (Int-105, 72 mg, 346 μmol) was suspended in 1,4-dioxane (4 mL) and 3-bromo-5-(3-chlorophenoxy)-1-(2,2,3,3,3-pentafluoropropyl)-1H-1,2,4-triazole (Int-68, 155 mg, 380 μmol), sodium tert-butoxide (69.9 mg, 691 μmol), 1,2,3,4,5-pentaphenyl-1'-(di-tert-butylphosphino)ferrocene ("Q-phos", CAS [312959-24-3], 41.4 mg, 55.3 μmol), and tris(dibenzylideneacetone)dipalladium (0) chloroform adduct (29.5 mg, 27.7 μmol) were added subsequently. The vial was degassed thoroughly with Argon and sealed. The reaction mixture was heated under microwave irradiation at 120° C. for 30 min. After that, the mixture was concentrated in vacuo. The resulting crude product was purified by column chromatography (silica gel, 50 g, eluting with ethyl acetate to remove impurities, then dichloromethane/methanol 9:1 v/v), followed by another column chromatography (amino modified silica gel, 50 g, eluting with ethyl acetate/n-heptane, gradient 0:100 to 50:50 v/v), followed by preparative HPLC (YMC-Actus Triart C18, 100×30 mm×5 μm, eluting with acetonitrile/(water+0.1% triethylamine), gradient 20:80 to 98:2 v/v) and lyophilization to yield the title compound as a white solid (9 mg, 5%). HPLC (method LCMS_fastgradient) $t_R$=1.32 min. $^1$H NMR (CDCl$_3$, 300

MHz): δ1.61-1.70 (m, 2H), 1.81-1.91 (m, 2H), 2.39 (s, 3H), 2.39-2.46 (m, 2H), 3.23-3.32 (m, 2H), 3.68 (d, J=6.5 Hz, 1H), 3.73 (dd, J=3.3, 12.4 Hz, 2H), 4.00 (d, J=6.1 Hz, 1H), 4.56 (t, J=13.5 Hz, 2H), 7.17-7.28 (m, 2H), 7.32-7.39 (m, 2H). MS (ES+) m/z 534.2, 536.2 [M+H, Cl isotopes].

Example 53

(1R,5S,8s)-3-(3-Methyl-1,2,4-oxadiazol-5-yl)-N-[1-(propan-2-yl)-5-[2-fluoro-5-(trifluoromethyl)phenoxy]-1H-1,2,4-triazol-3-yl]-3-azabicyclo[3.2.1]octan-8-amine

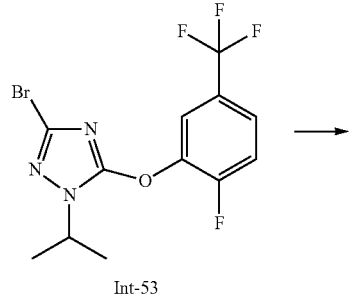

Int-53

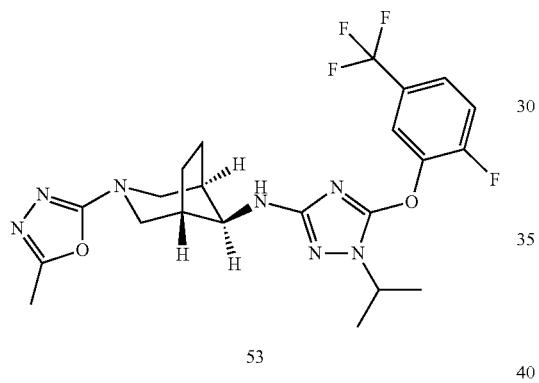

53

Example 54

(1R,5S,8s)-N-{5-[2-Fluoro-3-(trifluoromethyl)phenoxy]-1-(propan-2-yl)-1H-1,2,4-triazol-3-yl}-3-(5-methyl-1,3,4-oxadiazol-2-yl)-3-azabicyclo[3.2.1]octan-8-amine

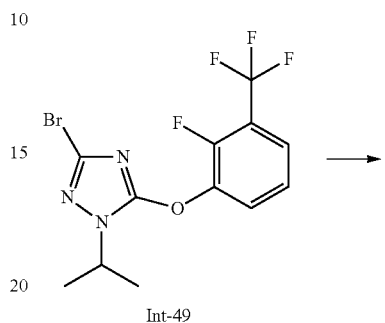

Int-49

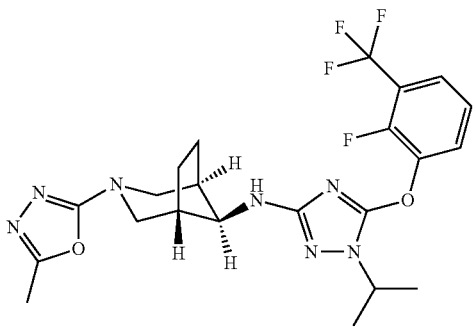

54

To a solution of (1R,5S,8s)-3-(5-methyl-1,3,4-oxadiazol-2-yl)-3-azabicyclo[3.2.1]octan-8-amine (Int-105, 60 mg, 0.3 mmol) and 3-bromo-5-[2-fluoro-5-(trifluoromethyl)phenoxy]-1-(propan-2-yl)-1H-1,2,4-triazole (Int-53, 137.9 mg, 0.4 mmol) in dry 1,4-dioxane (1.5 mL) in microwave tube was added 1,2,3,4,5-pentaphenyl-1'-(di-tert-butylphosphino)ferrocene ("Q-phos", CAS 312959-24-3, 33 mg, 0.04 mmol). The reaction mixture was degassed with argon. To it then added tris(dibenzylideneacetone)dipalladium-chloroform adduct ("Pd$_2$(dba)$_3$.CHCl$_3$", CAS 52522-40-4, 24 mg, 0.02 mmol) and sodium tertbutoxide (55 mg, 0.5 mmol). The reaction mixture was irradiated at 120° C. for 20 min in microwave. Reaction mixture was filtered and the filtrate was concentrated to get the crude which was purified by two times combi-flash column chromatography (amino modified silica gel, eluting with EtOAc/n-hexane 30:70 v/v) followed by reversed phase prep HPLC (YMC Triart C18 5μ 250×20 mm, flow 16 mL/min, eluting with acetonitrile/(water+20 mM ammonium bicarbonate), gradient 20:80 to 95:5) method to yield the title compound as off-white solid (20 mg, 14%). $^1$H NMR (MeOD, 400 MHz): 1.47 (d, J=6.7 Hz, 6H), 1.57 (d, J=8.2 Hz, 2H), 1.90-1.97 (m, 2H), 2.37 (s, 3H), 2.42 (s, 2H), 3.26 (s, 1H), 3.34 (s, 1H), 3.64 (s, 2H), 3.67 (d, J=2.9 Hz, 1H), 4.51-4.58 (m, 1H), 7.49 (t, J=9.4 Hz, 1H), 7.63 (s, 1H), 7.89 (dd, J=7.1, 1.6 Hz, 1H). MS (ES+) m/z 496.1 [M+H].

To a solution of (1R,5S,8s)-3-(5-methyl-1,3,4-oxadiazol-2-yl)-3-azabicyclo[3.2.1]octan-8-amine (Int-105, 70 mg, 0.3 mmol) and 3-bromo-5-[2-fluoro-3-(trifluoromethyl)phenoxy]-1-(propan-2-yl)-1H-1,2,4-triazole (Int-49, 160 mg, 0.4 mmol) in dry 1,4-dioxane (1.5 mL) in microwave tube was added 1,2,3,4,5-pentaphenyl-1'-(di-tert-butylphosphino)ferrocene ("Q-phos", CAS 312959-24-3, 38 mg, 0.05 mmol). The reaction mixture was degassed with argon. To it then added tris(dibenzylideneacetone)dipalladium-chloroform adduct ("Pd$_2$(dba)$_3$.CHCl$_3$", CAS 52522-40-4, 28 mg, 0.02 mmol) and sodium tertbutoxide (64.5 mg, 0.7 mmol). The reaction mixture was irradiated at 120° C. for 20 min in microwave. Reaction mixture was filtered and the filtrate was concentrated to get the crude which was purified by reversed phase prep HPLC (YMC Triart C18 5μ 250×20 mm, flow 16 mL/min, eluting with acetonitrile/(water+20 mM ammonium bicarbonate), gradient 30:70 to 100:0) method to yield the title compound as off-white solid (24.1 mg, 14%). HPLC purity 99.38%. $^1$H NMR (DMSO-d6, 400 MHz): 1.39 (d, J=6.6 Hz, 6H), 1.81-1.86 (m, 1H), 2.30-2.31 (m, 5H), 3.14 (d, J=11.7 Hz, 2H), 3.45-3.53 (m, 3H), 4.47 (dt, J=13.4, 6.7 Hz, 1H), 6.00 (d, J=4.6 Hz, 1H), 7.49 (t, J=8.1 Hz, 1H), 7.71 (t, J=6.9 Hz, 1H), 7.91 (t, J=7.9 Hz, 1H). MS (ES+) m/z 496.1 [M+H].

Example 55

(1R,5S,8s)-3-(5-Methyl-1,3,4-oxadiazol-2-yl)-N-{5-[4-methyl-3-(trifluoromethyl)phenoxy]-1-(propan-2-yl)-1H-1,2,4-triazol-3-yl}-3-azabicyclo[3.2.1]octan-8-amine

Example 56

(1R,5S,8s)-3-(5-Methyl-1,3,4-oxadiazol-2-yl)-N-{5-[3-methyl-5-(trifluoromethyl)phenoxy]-1-(propan-2-yl)-1H-1,2,4-triazol-3-yl}-3-azabicyclo[3.2.1]octan-8-amine

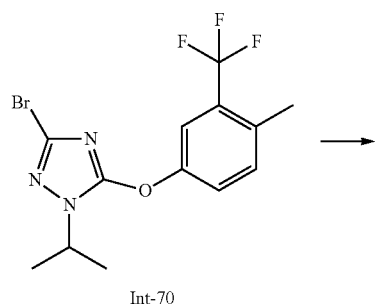

Int-70

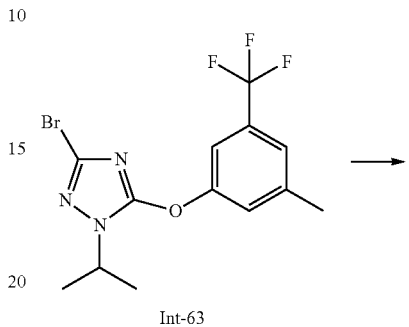

Int-63

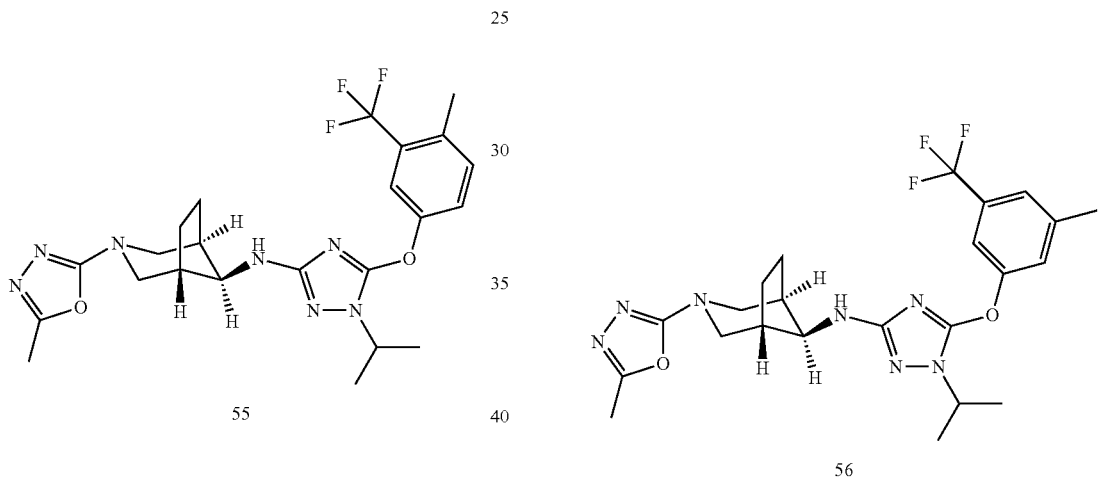

55

56

To a solution of (1R,5S,8s)-3-(5-methyl-1,3,4-oxadiazol-2-yl)-3-azabicyclo[3.2.1]octan-8-amine (Int-105, 60 mg, 0.3 mmol) and 3-bromo-5-[4-methyl-3-(trifluoromethyl)phenoxy]-1-(propan-2-yl)-1H-1,2,4-triazole (Int-70, 136.4 mg, 0.4 mmol) in dry 1,4-dioxane (1.5 mL) in microwave tube was added 1,2,3,4,5-pentaphenyl-1'-(di-tert-butylphosphino)ferrocene ("Q-phos", CAS 312959-24-3, 33 mg, 0.05 mmol). The reaction mixture was degassed with argon. To it then added tris(dibenzylideneacetone)dipalladium-chloroform adduct ("Pd$_2$(dba)$_3$.CHCl$_3$", CAS 52522-40-4, 24 mg, 0.02 mmol) and sodium tertbutoxide (55.5 mg, 0.6 mmol). The reaction mixture was irradiated at 120° C. for 20 min in microwave. Reaction mixture was filtered and the filtrate was concentrated to get the crude which was purified by reversed phase prep HPLC (YMC Triart C18 5µ 250×20 mm, flow 16 mL/min, eluting with acetonitrile/(water+20 mM ammonium bicarbonate), gradient 20:80 to 95:5) method to yield the title compound as off-white solid (40.1 mg, 28%). $^1$H NMR (DMSO-d6, 400 MHz): 1.37 (d, J=6.6 Hz, 6H), 1.38-1.40 (m, 2H), 1.86 (dd, J=7.6, 3.2 Hz, 2H), 2.31 (s, 3H), 2.34 (s, 2H), 2.43 (s, 3H), 3.15 (d, J=11.4 Hz, 2H), 3.50 (dd, J=16.3, 6.7 Hz, 3H), 4.40-4.47 (m, 1H), 5.96 (d, J=4.4 Hz, 1H), 7.51 (d, J=1.7 Hz, 2H), 7.68 (s, 1H). MS (ES+) m/z 492.1 [M+H].

To a solution of (1R,5S,8s)-3-(5-methyl-1,3,4-oxadiazol-2-yl)-3-azabicyclo[3.2.1]octan-8-amine (Int-105, 60 mg, 0.3 mmol) and 3-bromo-5-[3-methyl-5-(trifluoromethyl)phenoxy]-1-(propan-2-yl)-1H-1,2,4-triazole (Int-63, 136.4 mg, 0.4 mmol) in dry 1,4-dioxane (1.5 mL) in microwave tube was added 1,2,3,4,5-pentaphenyl-1'-(di-tert-butylphosphino)ferrocene ("Q-phos", CAS 312959-24-3, 33 mg, 0.05 mmol). The reaction mixture was degassed with argon. To it then added tris(dibenzylideneacetone)dipalladium-chloroform adduct ("Pd$_2$(dba)$_3$.CHCl$_3$", CAS 52522-40-4, 24 mg, 0.02 mmol) and sodium tertbutoxide (55.5 mg, 0.6 mmol). The reaction mixture was irradiated at 120° C. for 20 min in microwave. Reaction mixture was filtered and the filtrate was concentrated to get the crude which was purified by reversed phase prep HPLC (YMC Triart C18 5µ 250×20 mm, flow 16 mL/min, eluting with acetonitrile/(water+20 mM ammonium bicarbonate), gradient 20:80 to 95:5) method to yield the title compound as off-white solid (11.8 mg, 8%). $^1$H NMR (MeOD, 400 MHz): 1.44 (d, J=6.7 Hz, 6H), 1.58 (d, J=8.1 Hz, 2H), 1.93-1.98 (m, 2H), 2.37 (s, 3H), 2.44 (s, 5H), 3.30 (s, 2H), 3.64-3.67 (m, 3H), 4.51 (p, J=6.7 Hz, 1H), 7.35 (s, 1H), 7.37 (s, 1H), 7.39 (s, 1H).

Example 57

(1R,5S,8s)-N-{5-[4-Fluoro-3-methyl-5-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine

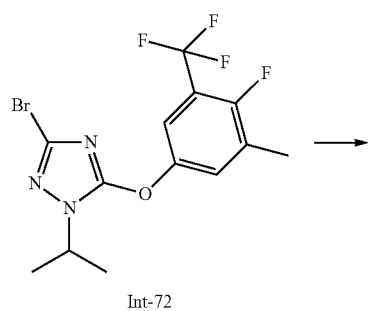

Int-72

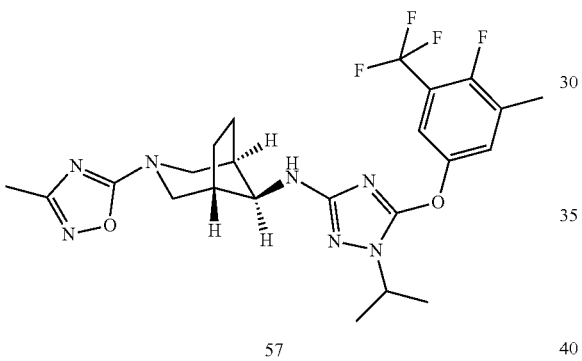

57

To a solution of (1R,5S,8s)-3-(3-methyl-1,2,4-oxadiazol-5-yl)-3-azabicyclo[3.2.1]octan-8-amine (Int-102, 40 mg, 0.2 mmol) and 3-bromo-5-[4-fluoro-3-methyl-5-(trifluoromethyl)phenoxy]-1-(propan-2-yl)-1H-1,2,4-triazole (Int-72, 95.4 mg, 0.3 mmol) in dry 1,4-dioxane (1.0 mL) in microwave tube was added 1,2,3,4,5-pentaphenyl-1'-(di-tert-butylphosphino)ferrocene ("Q-phos", CAS 312959-24-3, 21.8 mg, 0.03 mmol). The reaction mixture was degassed with argon in a microwave tube over a period of 15 min. To it then added tris(dibenzylideneacetone)dipalladium-chloroform adduct ("Pd$_2$(dba)$_3$.CHCl$_3$", CAS 52522-40-4, 16 mg, 0.01 mmol) and sodium tertbutoxide (36.8 mg, 0.4 mmol). The reaction mixture was irradiated at 120° C. for 20 min in microwave. Reaction mixture was filtered and the filtrate was concentrated to get the crude which was purified by reversed phase prep HPLC (YMC Triart C18 5μ 100×30 mm, flow 30 mL/min, eluting with acetonitrile/(water+20 mM ammonium bicarbonate), gradient 30:70 to 100:0) method to afford as brown solid (6.2 mg, 6%). $^1$H NMR (MeOD, 300 MHz): 1.45 (d, J=6.7 Hz, 6H), 1.53 (d, J=8.2 Hz, 2H), 1.92-1.97 (m, 2H), 2.16 (s, 3H), 2.34 (d, J=2.1 Hz, 3H), 2.43 (s, 2H), 3.34 (s, 1H), 3.37 (s, 1H), 3.67 (s, 1H), 3.82 (dd, J=12.8, 3.1 Hz, 2H), 4.52 (p, J=6.7 Hz, 1H), 7.49 (d, J=5.5 Hz, 2H). MS (ES+) m/z 510.1 [M+H].

Example 58

(1R,5S,8s)-N-{5-[3-Chloro-5-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine

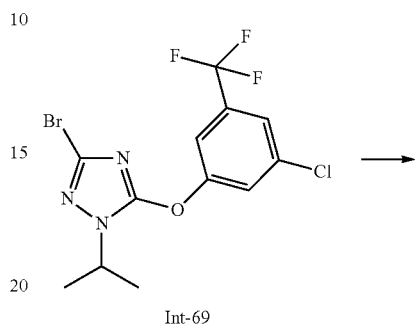

Int-69

58

To a solution of (1R,5S,8s)-3-(3-methyl-1,2,4-oxadiazol-5-yl)-3-azabicyclo[3.2.1]octan-8-amine (Int-102, 60 mg, 0.3 mmol) and 3-bromo-5-[3-chloro-5-(trifluoromethyl)phenoxy]-1-(propan-2-yl)-1H-1,2,4-triazole (Int-69, 144 mg, 0.4 mmol) in dry 1,4-dioxane (2.0 mL) in microwave tube was added 1,2,3,4,5-pentaphenyl-1'-(di-tert-butylphosphino)ferrocene ("Q-phos", CAS 312959-24-3, 32.7 mg, 0.04 mmol). The reaction mixture was degassed with argon in a microwave tube over a period of 15 min. To it then added tris(dibenzylideneacetone)dipalladium-chloroform adduct ("Pd$_2$(dba)$_3$.CHCl$_3$", CAS 52522-40-4, 23.8 mg, 0.02 mmol) and sodium tertbutoxide (55.3 mg, 0.6 mmol). The reaction mixture was irradiated at 120° C. for 20 min in microwave. Reaction mixture was filtered and the filtrate was concentrated to get the crude which was purified by reversed phase prep HPLC (YMC Triart C18 5μ 250×20 mm, flow 16 mL/min, eluting with acetonitrile/(water+20 mM ammonium bicarbonate), gradient 30:70 to 100:0) method to afford the title compound as brown solid (9 mg, 6%). $^1$H NMR (MeOD, 400 MHz): 1.45 (d, J=6.7 Hz, 6H), 1.53 (d, J=8.2 Hz, 2H), 1.94-1.98 (m, 2H), 2.16 (s, 3H), 2.45 (s, 2H), 3.36 (d, J=12.0 Hz, 2H), 3.69 (s, 1H), 3.82 (dd, J=12.8, 3.0 Hz, 2H), 4.53 (p, J=6.7 Hz, 1H), 7.60 (s, 1H), 7.65 (s, 1H), 7.72 (s, 1H). MS (ES+) m/z 512.3 [M+H].

Example 59

(1R,5S,8s)-N-(5-(3-Chlorophenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine

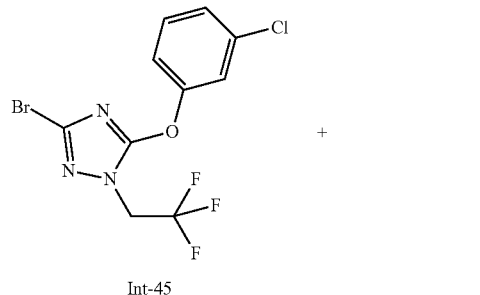

Int-45

+

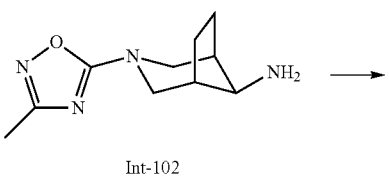

Int-102

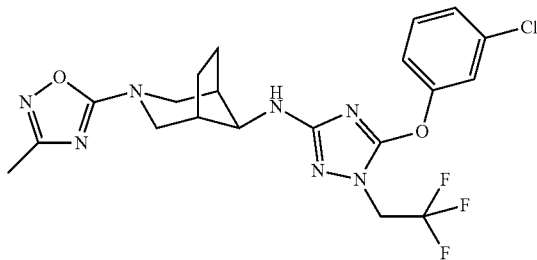

59

In an 8 mL microwave vial (1R,5S,8s)-3-(3-methyl-1,2,4-oxadiazol-5-yl)-3-azabicyclo[3.2.1]octan-8-amine (Int-102, 24 mg, 115 µmol) was suspended in 1,4-dioxane (2 mL) and 3-bromo-5-(3-chlorophenoxy)-1-(2,2,2-trifluoroethyl)-1H-1,2,4-triazole (Int-45, 41.1 mg, 115 µmol), sodium tert-butoxide (23.3 mg, 230 µmol), 1,2,3,4,5-pentaphenyl-1'-(di-tert-butylphosphino)ferrocene ("Q-phos", CAS [312959-24-3], 13.8 mg, 18.4 µmol), and tris(dibenzylideneacetone)dipalladium (0) chloroform adduct (9.8 mg, 9.2 µmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 1:2 v/v), followed by preparative HPLC (YMC-Actus Triart C18, 100×30 mm×5 µm, eluting with acetonitrile/(water+0.1% triethylamine), gradient 20:80 to 98:2 v/v) and lyophilization to yield the title compound as a white solid (14 mg, 25%). HPLC (method LCMS_fastgradient) $t_R$=1.31 min. $^1$H NMR (CDCl$_3$, 300 MHz): δ 1.58-1.67 (m, 2H), 1.82-1.91 (m, 2H), 2.22 (s, 3H), 2.39-2.46 (m, 2H), 3.31-3.39 (m, 2H), 3.72 (d, J=6.0 Hz, 1H), 3.89 (dd, J=3.4, 12.9 Hz, 2H), 3.99 (d, J=6.0 Hz, 1H), 4.52 (q, J=8.2 Hz, 2H), 7.17-7.22 (m, 1H), 7.23-7.29 (m, 1H), 7.32-7.39 (m, 2H). MS (ES+) m/z 484.2, 486.2 [M+H, Cl isotopes].

Example 60

(1R,5S,8s)-N-{5-[4-Methyl-3-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine

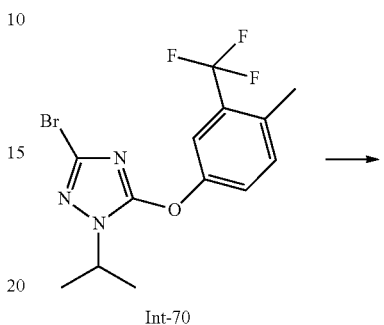

Int-70

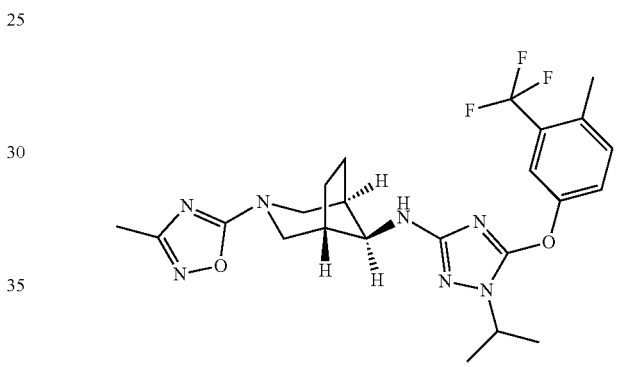

60

To a solution of (1R,5S,8s)-3-(3-methyl-1,2,4-oxadiazol-5-yl)-3-azabicyclo[3.2.1]octan-8-amine (Int-102, 80 mg, 0.4 mmol) and 3-bromo-5-[4-methyl-3-(trifluoromethyl)phenoxy]-1-(propan-2-yl)-1H-1,2,4-triazole (Int-70, 182 mg, 0.5 mmol) in dry 1,4-dioxane (2.0 mL) in microwave tube was added 1,2,3,4,5-pentaphenyl-1'-(di-tert-butylphosphino)ferrocene ("Q-phos", CAS 312959-24-3, 43.7 mg, 0.06 mmol). The reaction mixture was degassed with argon in a microwave tube over a period of 15 min. To it then added tris(dibenzylideneacetone)dipalladium-chloroform adduct ("Pd$_2$(dba)$_3$.CHCl$_3$", CAS 52522-40-4, 31.8 mg, 0.03 mmol) and sodium tertbutoxide (73.7 mg, 0.8 mmol). The reaction mixture was irradiated at 120° C. for 20 min in microwave. Reaction mixture was filtered and the filtrate was concentrated to get the crude which was purified by reversed phase prep HPLC (YMC Triart C18 5µ 250×20 mm, flow 16 mL/min, eluting with acetonitrile/(water+20 mM ammonium bicarbonate), gradient 30:70 to 100:0) method to afford as brown solid (4 mg, 4%). $^1$H NMR (MeOD, 400 MHz): 1.44 (d, J=6.7 Hz, 6H), 1.53 (d, J=8.2 Hz, 2H), 1.94 (dd, J=8.4, 2.7 Hz, 2H), 2.15 (s, 3H), 2.43 (s, 2H), 2.47 (s, 3H), 3.34 (s, 1H), 3.37 (s, 1H), 3.68 (s, 1H), 3.80 (d, J=2.9 Hz, 1H), 3.83 (d, J=2.9 Hz, 1H), 4.51 (p, J=6.7 Hz, 1H), 7.37-7.44 (m, 2H), 7.56 (d, J=2.1 Hz, 1H). MS (ES+) m/z 492.2 [M+H].

Example 61

(1R,5S,8s)-N-{5-[4-Chloro-3-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine

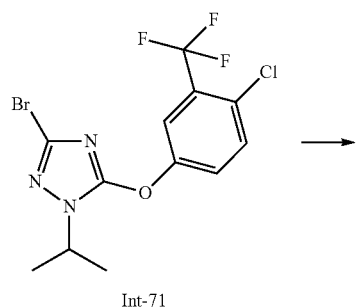

Int-71

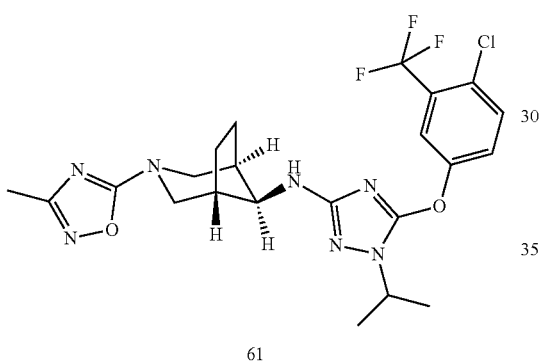

61

To a solution of (1R,5S,8s)-3-(3-methyl-1,2,4-oxadiazol-5-yl)-3-azabicyclo[3.2.1]octan-8-amine (Int-102, 80 mg, 0.4 mmol) and 3-bromo-5-[4-chloro-3-(trifluoromethyl)phenoxy]-1-(propan-2-yl)-1H-1,2,4-triazole (Int-71, 192 mg, 0.5 mmol) in dry 1,4-dioxane (2.0 mL) in microwave tube was added 1,2,3,4,5-pentaphenyl-1'-(di-tert-butylphosphino)ferrocene ("Q-phos", CAS 312959-24-3, 43.7 mg, 0.06 mmol). The reaction mixture was degassed with argon in a microwave tube over a period of 15 min. To it then added tris(dibenzylideneacetone)dipalladium-chloroform adduct ("Pd$_2$(dba)$_3$.CHCl$_3$", CAS 52522-40-4, 31.8 mg, 0.03 mmol) and sodium tertbutoxide (73.7 mg, 0.8 mmol). The reaction mixture was irradiated at 120° C. for 20 min in microwave. Reaction mixture was filtered and the filtrate was concentrated to get the crude which was purified by reversed phase prep HPLC (Xbridge C18 5μ 250×19 mm, flow 16 mL/min, eluting with acetonitrile/(water+20 mM ammonium bicarbonate), gradient 40:60 to 100:0) method to afford as brown solid (25 mg, 12%). $^1$H NMR (MeOD, 400 MHz): 1.44 (d, J=6.7 Hz, 6H), 1.53 (d, J=8.2 Hz, 2H), 1.93-1.97 (m, 2H), 2.15 (s, 3H), 2.44 (s, 2H), 3.35 (d, J=12.3 Hz, 2H), 3.68 (s, 1H), 3.81 (dd, J=12.7, 2.9 Hz, 2H), 4.52 (p, J=6.7 Hz, 1H), 7.55 (dd, J=8.8, 2.7 Hz, 1H), 7.66 (d, J=8.8 Hz, 1H), 7.79 (d, J=2.7 Hz, 1H). MS (ES+) m/z 512.1 [M+H].

Example 62

(1R,5S,8s)-3-(5-Methyl-1,3,4-oxadiazol-2-yl)-N-[1-(propan-2-yl)-5-[4-(trifluoromethoxy)-3-(trifluoromethyl)phenoxy]-1H-1,2,4-triazol-3-yl]-3-azabicyclo[3.2.1]octan-8-amine

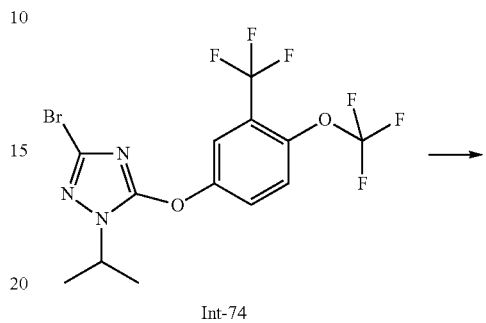

Int-74

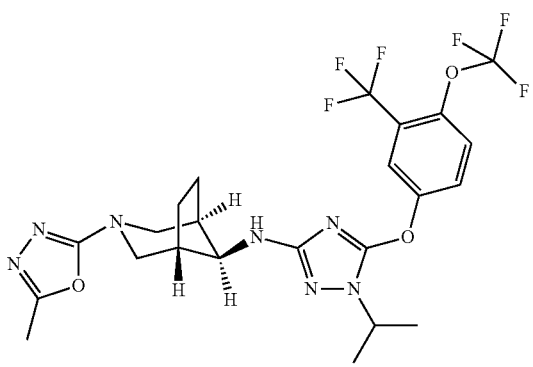

62

To a solution of (1R,5S,8s)-3-(5-methyl-1,3,4-oxadiazol-2-yl)-3-azabicyclo[3.2.1]octan-8-amine (Int-105, 100 mg, 0.5 mmol) and 3-bromo-1-(propan-2-yl)-5-[4-(trifluoromethoxy)-3-(trifluoromethyl)phenoxyl]-1H-1,2,4-triazole (Int-74, 270.8 mg, 0.6 mmol) in dry 1,4-dioxane (2.5 mL) in microwave tube was added 1,2,3,4,5-pentaphenyl-1'-(di-tert-butylphosphino)ferrocene ("Q-phos", CAS 312959-24-3, 54.6 mg, 0.07 mmol). The reaction mixture was degassed with argon. To it then added tris(dibenzylideneacetone)dipalladium-chloroform adduct ("Pd$_2$(dba)$_3$.CHCl$_3$", CAS 52522-40-4, 40 mg, 0.04 mmol) and sodium tertbutoxide (92 mg, 0.9 mmol). The reaction mixture was irradiated at 120° C. for 20 min in microwave. Reaction mixture was filtered and the filtrate was concentrated to get the crude which was purified by reversed phase prep HPLC (YMC Triart C18 5μ 250×20 mm, flow 16 mL/min, eluting with acetonitrile/(water+20 mM ammonium bicarbonate), gradient 20:80 to 95:5) method to yield the title compound as brown solid (37.6 mg, 14%). HPLC purity 98.96%. $^1$H NMR (MeOD, 400 MHz): 1.45 (d, J=6.7 Hz, 6H), 1.58 (d, J=8.1 Hz, 2H), 1.93-1.97 (m, 2H), 2.37 (s, 3H), 2.44 (s, 2H), 3.27 (s, 1H), 3.34 (s, 1H), 3.64-3.68 (m, 3H), 4.53 (p, J=6.8 Hz, 1H), 7.62 (d, J=9.2 Hz, 1H), 7.68 (dd, J=9.1, 2.8 Hz, 1H), 7.83 (d, J=2.7 Hz, 1H). MS (ES+) m/z 562.1 [M+H].

Example 63

(1R,5S,8s)-N-{5-[3,5-Bis(trifluoromethyl)phenoxy]-1-(propan-2-yl)-1H-1,2,4-triazol-3-yl}-3-(5-methyl-1,3,4-oxadiazol-2-yl)-3-azabicyclo[3.2.1]octan-8-amine

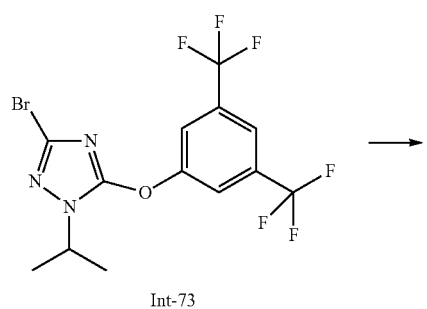

To a solution of (1R,5S,8s)-3-(5-methyl-1,3,4-oxadiazol-2-yl)-3-azabicyclo[3.2.1]octan-8-amine (Int-105, 80 mg, 0.4 mmol) and 5-[3,5-bis(trifluoromethyl)phenoxy]-3-bromo-1-(propan-2-yl)-1H-1,2,4-triazole (Int-73, 208.8 mg, 0.5 mmol) in dry 1,4-dioxane (2.5 mL) in microwave tube was added 1,2,3,4,5-pentaphenyl-1'-(di-tert-butylphosphino)ferrocene ("Q-phos", CAS 312959-24-3, 43.7 mg, 0.06 mmol). The reaction mixture was degassed with argon. To it then added tris(dibenzylideneacetone)dipalladium-chloroform adduct ("Pd$_2$(dba)$_3$.CHCl$_3$", CAS 52522-40-4, 31.8 mg, 0.03 mmol) and sodium tertbutoxide (73.8 mg, 0.7 mmol). The reaction mixture was irradiated at 120° C. for 20 min in microwave. Reaction mixture was filtered and the filtrate was concentrated to get the crude which was purified by reversed phase prep HPLC (Sunfire C18 10µ 150×19 mm, flow 16 mL/min, eluting with acetonitrile/(water+20 mM ammonium bicarbonate), gradient 20:80 to 95:5) method to yield the title compound as brown solid (25 mg, 12%). HPLC purity 94.62%. $^1$H NMR (MeOD, 400 MHz): 1.46 (d, J=6.7 Hz, 6H), 1.58 (d, J=8.1 Hz, 2H), 1.94-1.98 (m, 2H), 2.37 (s, 3H), 2.45 (s, 2H), 3.27 (s, 1H), 3.66 (dd, J=7.7, 4.1 Hz, 3H), 4.57 (p, J=6.7 Hz, 1H), 7.86 (s, 1H), 8.04 (s, 2H). MS (ES+) m/z 546.1 [M+H].

Example 64

(1R,5S,8s)-N-[1-(Propan-2-yl)-5-[4-(trifluoromethoxy)-3-(trifluoromethyl)phenoxy]-1,2,4-triazol-3-yl]-3-(3-methyl-1,2,4-oxadiazol-5-yl)-3-azabicyclo[3.2.1]octan-8-amine

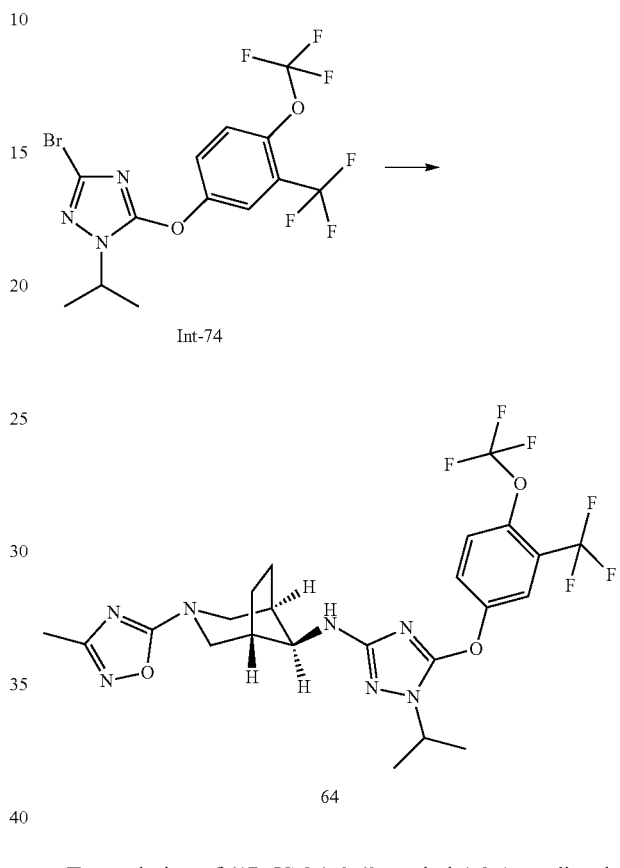

To a solution of (1R,5S,8s)-3-(3-methyl-1,2,4-oxadiazol-5-yl)-3-azabicyclo[3.2.1]octan-8-amine (Int-102, 80 mg, 0.4 mmol) and 3-bromo-1-(propan-2-yl)-5-[4-(trifluoromethoxy)-3-(trifluoromethyl)phenoxy]-1,2,4-triazole (Int-74, 216.7 mg, 0.5 mmol) in dry 1,4-dioxane (2.0 mL) in microwave tube was added 1,2,3,4,5-pentaphenyl-1'-(di-tert-butylphosphino)ferrocene ("Q-phos", CAS 312959-24-3, 43.6 mg, 0.06 mmol). The reaction mixture was degassed with argon in a microwave tube over a period of 15 min. To it then added tris(dibenzylideneacetone)dipalladium-chloroform adduct ("Pd$_2$(dba)$_3$.CHCl$_3$", CAS 52522-40-4, 31.8 mg, 0.03 mmol) and sodium tertbutoxide (73.7 mg, 0.7 mmol). The reaction mixture was irradiated at 120° C. for 20 min in microwave. Reaction mixture was filtered and the filtrate was concentrated to get the crude which was purified by reversed phase prep HPLC (Xterra RP18 10µ 250×19 mm, flow 16 mL/min, eluting with acetonitrile/(water+20 mM ammonium bicarbonate), gradient 40:60 to 95:5) method to afford the title compound as brown solid (25 mg, 12%). HPLC purity 93.01%. $^1$H NMR (MeOD, 400 MHz): 1.45 (d, J=6.6 Hz, 6H), 1.48-1.55 (m, 2H), 1.93-1.96 (m, 2H), 2.15 (s, 3H), 2.43 (br s, 2H), 3.35 (d, J=12.4 Hz, 2H), 3.68 (s, 1 H), 3.81 (dd, J=2.9, 12.6 Hz, 2H), 4.50-4.56 (m, 1H), 7.60-7.62 (m, 1H), 7.67 (dd, J=2.7, 9.1 Hz, 1H), 7.83 (d, J=2.7 Hz, 1H). MS (ES+) m/z 562.1 [M+H].

Example 65

(1R,5S,8s)(1R,5S,8s)-N-[5-[3,5-Bis(trifluoromethyl) phenoxy]-1-(propan-2-yl)-1H-1,2,4-triazol-3-yl]-3-(3-methyl-1,2,4-oxadiazol-5-yl)-3-azabicyclo[3.2.1] octan-8-amine

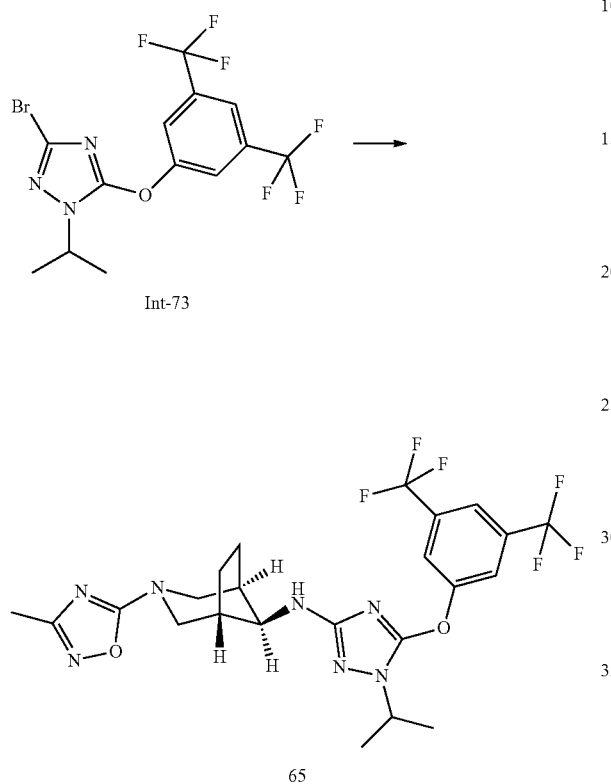

65

To a solution of (1R,5S,8s)(1R,5S,8s)-3-(3-methyl-1,2,4-oxadiazol-5-yl)-3-azabicyclo[3.2.1]octan-8-amine (Int-102, 80 mg, 0.4 mmol) and 5-[3,5-bis(trifluoromethyl)phenoxy]-3-bromo-1-(propan-2-yl)-1H-1,2,4-triazole (Int-73, 208.7 mg, 0.5 mmol) in dry 1,4-dioxane (2.0 mL) in microwave tube was added 1,2,3,4,5-pentaphenyl-1'-(di-tert-butylphosphino)ferrocene ("Q-phos", CAS 312959-24-3, 43.6 mg, 0.06 mmol). The reaction mixture was degassed with argon in a microwave tube over a period of 15 min. To it then added tris(dibenzylideneacetone)dipalladium-chloroform adduct ("Pd$_2$(dba)$_3$.CHCl$_3$", CAS 52522-40-4, 31.8 mg, 0.03 mmol) and sodium tertbutoxide (73.7 mg, 0.7 mmol). The reaction mixture was irradiated at 120° C. for 20 min in microwave. Reaction mixture was filtered and the filtrate was concentrated to get the crude which was purified by reversed phase prep HPLC (YMC Triart C18 5μ 250×20 mm, flow 16 mL/min, eluting with acetonitrile/(water+20 mM ammonium bicarbonate), gradient 40:60 to 95:5) method to afford the title compound as off white-solid (13.3 mg, 6%). HPLC purity 92.79%. $^1$H NMR (MeOD, 400 MHz): 1.46 (d, J=6.6 Hz, 6H), 1.54 (d, J=5.8 Hz, 2H), 1.95-1.97 (m, 2H), 2.15 (s, 3H), 2.45 (br s, 2H), 3.35 (d, J=12.3 Hz, 2H), 3.68 (s, 1H), 3.81 (dd, J=2.9, 12.6 Hz, 2H), 4.53-4.59 (m, 1H), 7.86 (s, 1H), 8.03 (s, 1H). MS (ES+) m/z 546.2 [M+H].

Example 66

(1R,5S,8s)-N-(5-(3-Chlorophenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine

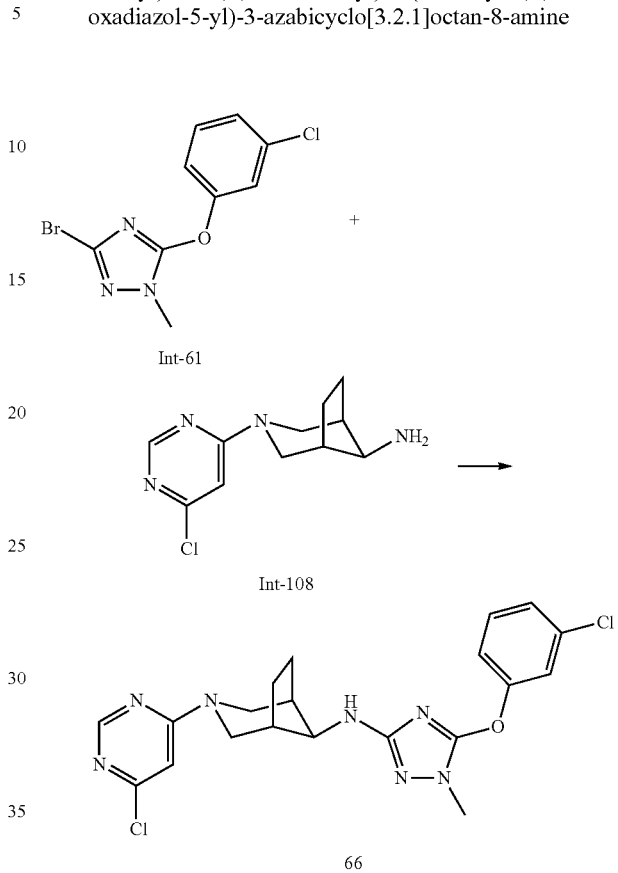

66

In an 8 mL microwave vial (1R,5S,8s)-3-(6-chloropyrimidin-4-yl)-3-azabicyclo-[3.2.1]octan-8-amine (Int-108, 50 mg, 209 μmol) was suspended in 1,4-dioxane (2 mL) and 3-bromo-5-(3-chlorophenoxy)-1-methyl-1H-1,2,4-triazole (Int-61, 60.4 mg, 209 μmol), sodium tert-butoxide (42.3 mg, 440 μmol), 1,2,3,4,5-pentaphenyl-1'-(di-tert-butylphosphino)ferrocene ("Q-phos", CAS [312959-24-3], 23.8 mg, 33.5 μmol), and tris(dibenzylideneacetone)dipalladium (0) chloroform adduct (17.3 mg, 16.8 μmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 60:40 v/v), followed by preparative HPLC (YMC-Actus Triart C18, 100×30 mm×5 μm, eluting with acetonitrile/(water+0.1% triethylamine), gradient 20:80 to 98:2 v/v) and lyophilization to yield the title compound as an off-white solid (12.5 mg, 13%). HPLC (method LCMS_fastgradient) t$_R$=1.29 min. $^1$H NMR (CDCl$_3$, 300 MHz): δ 1.48-1.57 (m, 2H), 1.80-1.90 (m, 2H), 2.44-2.52 (m, 2H), 3.08-3.19 (m, 2H), 3.64 (s, 3H), 3.76 (d, J=6.0 Hz, 1H), 3.86-4.36 (m, 2H), 3.94 (d, J=6.2 Hz, 1H), 6.48 (d, J=0.8 Hz, 1H), 7.15-7.23 (m, 2H), 7.30-7.36 (m, 2H), 8.37 (d, J=0.8 Hz, 1H). MS (ES+) m/z 446.2, 448.2 [M+H, Cl isotopes].

Example 67

(1R,5S,8s)-N-(5-(3-Chlorophenoxy)-1-methyl-1H-1,2,4-triazol-3-yl)-3-(5-fluoro-2-methylpyridin-4-yl)-3-azabicyclo[3.2.1]octan-8-amine

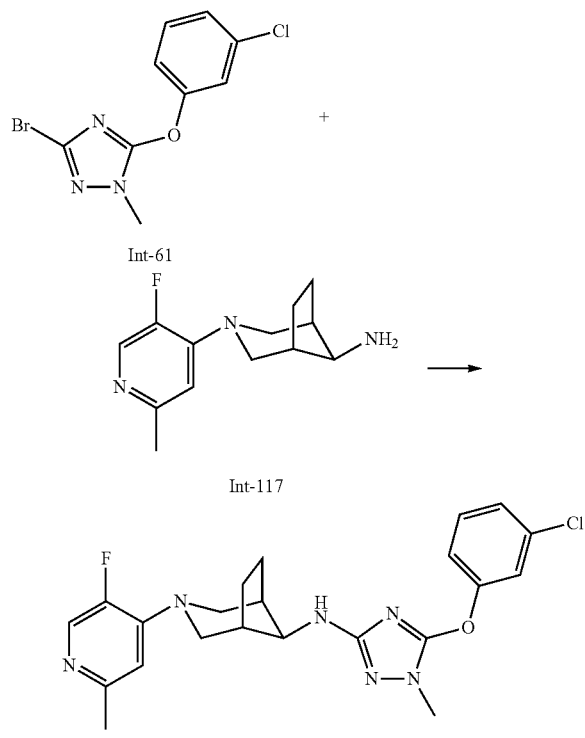

In an 8 mL microwave vial (1R,5S,8s)-3-(5-fluoro-2-methylpyridin-4-yl)-3-azabicyclo[3.2.1]octan-8-amine (Int-117, 73.7 mg, 313 µmol) was suspended in 1,4-dioxane (4 mL) and 3-bromo-5-(3-chlorophenoxy)-1-methyl-1H-1,2,4-triazole (Int-61, 90.4 mg, 313 µmol), sodium tert-butoxide (63.4 mg, 626 µmol), 1,2,3,4,5-pentaphenyl-1'-(di-tert-butylphosphino)ferrocene ("Q-phos", CAS [312959-24-3], 37.5 mg, 50 µmol), and tris(dibenzylideneacetone)dipalladium (0) chloroform adduct (26.7 mg, 25 µmol) were added subsequently. The vial was degassed thoroughly with Argon and sealed. The reaction mixture was heated under microwave irradiation at 120° C. for 20 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v, then eluting with dichloromethane/methanol, gradient 100:0 to 90:10 v/v), followed by column chromatography (amino modified silica gel, 50 g, eluting with ethyl acetate/n-heptane, gradient 0:100 to 50:50 v/v) to yield the title compound as an off-white foam (68 mg, 49%). HPLC (method LCMS_fastgradient) $t_R$=0.97 min. $^1$H NMR (CDCl$_3$, 300 MHz): δ1.70-1.90 (m, 4H), 2.40-2.45 (m, 2H), 2.45 (s, 3H), 3.03-3.09 (m, 2H), 3.57 (dd, J=3.8, 12.1 Hz, 2H), 3.64 (s, 3H), 3.66 (d, J=6.6 Hz, 1H), 3.95 (d, J=6.4 Hz, 1H), 6.51 (d, J=7.7 Hz, 1H), 7.16-7.24 (m, 2H), 7.30-7.37 (m, 2H), 8.06 (d, J=6.0 Hz, 1H). MS (ES+) m/z 443.2, 445.2 [M+H, Cl isotopes].

Example 68

(1R,5S,8s)-N-(5-(3-Chlorophenoxy)-1-methyl-1H-1,2,4-triazol-3-yl)-3-(2-methoxypyridin-4-yl)-3-azabicyclo[3.2.1]octan-8-amine

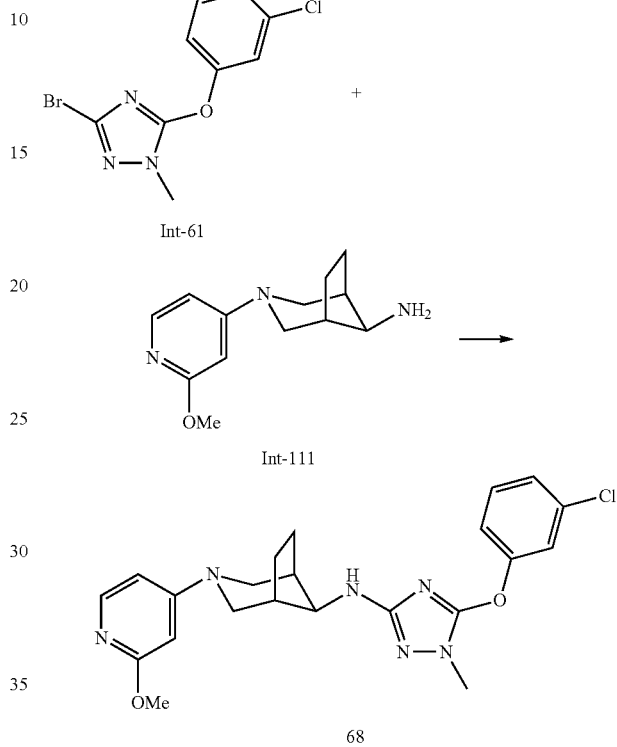

In an 8 mL microwave vial (1R,5S,8s)-3-(2-methoxypyridin-4-yl)-3-azabicyclo[3.2.1]octan-8-amine (Int-111, 74 mg, 317 µmol) was suspended in 1,4-dioxane (4 mL) and 3-bromo-5-(3-chlorophenoxy)-1-methyl-1H-1,2,4-triazole (Int-61, 91.5 mg, 317 µmol), sodium tert-butoxide (64.2 mg, 634 µmol), 1,2,3,4,5-pentaphenyl-1'-(di-tert-butylphosphino)ferrocene ("Q-phos", CAS [312959-24-3], 38 mg, 51 µmol), and tris(dibenzylideneacetone)dipalladium (0) chloroform adduct (27 mg, 25 µmol) were added subsequently. The vial was degassed thoroughly with Argon and sealed. The reaction mixture was heated under microwave irradiation at 120° C. for 20 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v), followed by column chromatography (silica gel, 70 g, eluting with dichloromethane/ethyl acetate, gradient 0:100 to 100:0 v/v) to yield the title compound as an off-white foam (61 mg, 44%). HPLC (method LCMS_fastgradient) $t_R$=0.93 min. $^1$H NMR (CDCl$_3$, 300 MHz): δ1.57-1.65 (m, 2H), 1.82-1.91 (m, 2H), 2.44-2.52 (m, 2H), 3.02-3.09 (m, 2H), 3.59 (dd, J=3.4, 11.9 Hz, 2H), 3.63 (s, 3H), 3.70 (d, J=6.2 Hz, 1H), 3.90 (s, 3H), 3.94 (d, J=6.2 Hz, 1H), 5.99 (d, J=2.2 Hz, 1H), 6.35 (dd, J=2.2, 6.0 Hz, 1H), 7.15-7.24 (m, 2H), 7.30-7.37 (m, 2H), 7.87 (d, J=6.0 Hz, 1H). MS (ES+) m/z 441.2, 443.2 [M+H, Cl isotopes].

Example 69

(1R,5S,8s)-N-[5-(3-Chlorophenoxy)-1-(propan-2-yl)-1H-1,2,4-triazol-3-yl]-3-(3-methyl-1,2,4-oxadiazol-5-yl)-3-azabicyclo[3.2.1]octan-8-amine

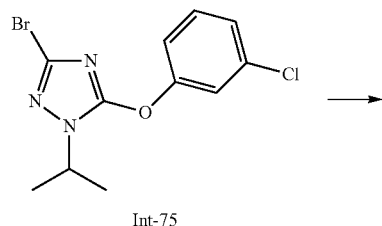

Int-75

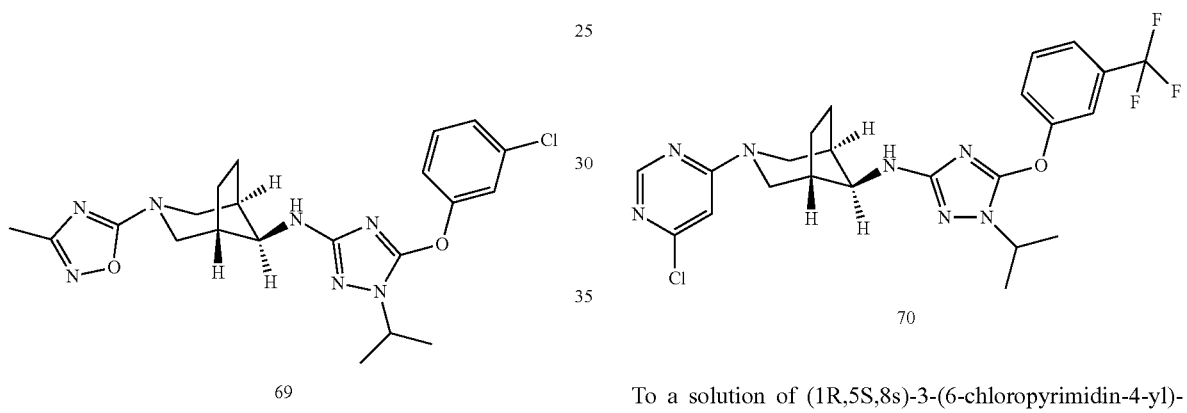

69

To a solution of (1R,5S,8s)-3-(3-methyl-1,2,4-oxadiazol-5-yl)-3-azabicyclo[3.2.1]octan-8-amine (Int-102, 70 mg, 0.3 mmol) and 3-bromo-5-(3-chlorophenoxy)-1-(propan-2-yl)-1H-1,2,4-triazole (Int-75, 138 mg, 0.4 mmol) in dry 1,4-dioxane (0.5 mL) in microwave tube was added 1,2,3,4,5-pentaphenyl-1'-(di-tert-butylphosphino)ferrocene ("Q-phos", CAS 312959-24-3, 38.2 mg, 0.05 mmol). The reaction mixture was degassed with argon in a microwave tube over a period of 15 min. To it then added tris(dibenzylideneacetone)dipalladium-chloroform adduct ("Pd$_2$(dba)$_3$.CHCl$_3$", CAS 52522-40-4, 27.8 mg, 0.02 mmol) and sodium tertbutoxide (64.5 mg, 0.7 mmol). The reaction mixture was irradiated at 120° C. for 20 min in microwave. Reaction mixture was filtered and the filtrate was concentrated to get the crude which was purified by reversed phase prep HPLC (Xterra RP18 10μ 250×19 mm, flow 16 mL/min, eluting with acetonitrile/(water+20 mM ammonium bicarbonate), gradient 30:70 to 95:5) method to afford the title compound as brown sticky solid (21.5 mg, 14%). HPLC purity 99.06%. $^1$H NMR (MeOD, 400 MHz): 1.44 (d, J=6.7 Hz, 6H), 1.53 (d, J=8.2 Hz, 2H), 1.95 (dd, J=8.0, 3.1 Hz, 2H), 2.16 (s, 3H), 2.44 (s, 2H), 3.35 (s, 1H), 3.38 (s, 1H), 3.69 (s, 1H), 3.82 (dd, J=12.9, 3.2 Hz, 2H), 4.49 (p, J=6.7 Hz, 1H), 7.18 (dd, J=8.3, 1.6 Hz, 1H), 7.25 (dd, J=7.6, 1.4 Hz, 1H), 7.34 (t, J=2.1 Hz, 1H), 7.40 (t, J=8.2 Hz, 1H). MS (ES+) m/z 444.1 [M+H].

Example 70

(1R,5S,8s)-3-(6-Chloropyrimidin-4-yl)-N-[1-(propan-2-yl)-5-[3-(trifluoromethyl)phenoxy]-1H-1,2,4-triazol-3-yl]-3-azabicyclo[3.2.1]octan-8-amine

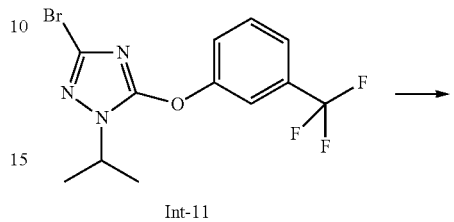

Int-11

70

To a solution of (1R,5S,8s)-3-(6-chloropyrimidin-4-yl)-3-azabicyclo[3.2.1]octan-8-amine (Int-108, 140 mg, 0.6 mmol) and 3-bromo-1-(propan-2-yl)-5-[3-(trifluoromethyl)phenoxy]-1H-1,2,4-triazole (Int-11, 308.8 mg, 0.9 mmol) in dry 1,4-dioxane (5 mL) in sealed tube was added 2-dicyclohexylphosphino-2',6'-diisopropoxybiphenyl ("Ruphos", CAS [787618-22-8], 94 mg, 0.1 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 54.8 mg, 0.1 mmol). The reaction mixture was again degassed with argon for 10 min followed by addition of sodium tertbutoxide (225.8 mg, 2.3 mmol). The reaction mixture was stirred at 120° C. for 5 h. Reaction mixture was then filtered through plug of celite and washed with EtOAc (10 mL) and dichloromethane (10 mL). Combined organic filtrates were concentrated under reduced pressure. The resulting crude product was purified two times by reversed phase prep HPLC (Xterra RP18 10μ 250×19 mm, flow 16 mL/min, eluting with acetonitrile/(water+20 mM ammonium bicarbonate), gradient 30:70 to 95:5) method to yield the title compound as white solid (18.9 mg, 6%). HPLC purity 93.60%. $^1$H NMR (MeOD, 400 MHz): 1.44-1.46 (m, 8H), 1.90-1.92 (m, 2H), 2.46 (s, 2H), 3.10 (d, J=11.7 Hz, 2H), 3.71 (s, 1H), 4.49-4.56 (m, 1H), 6.77 (s, 1H), 7.52-7.55 (m, 2H), 7.60-7.62 (m, 2H), 8.25 (s, 1H). MS (ES+) m/z 508.2 [M+H].

Example 71

(1R,5S,8s)-N-(5-(3-Chlorophenoxy)-1-methyl-1H-1,2,4-triazol-3-yl)-3-(2-chloropyridin-4-yl)-3-azabicyclo[3.2.1]octan-8-amine

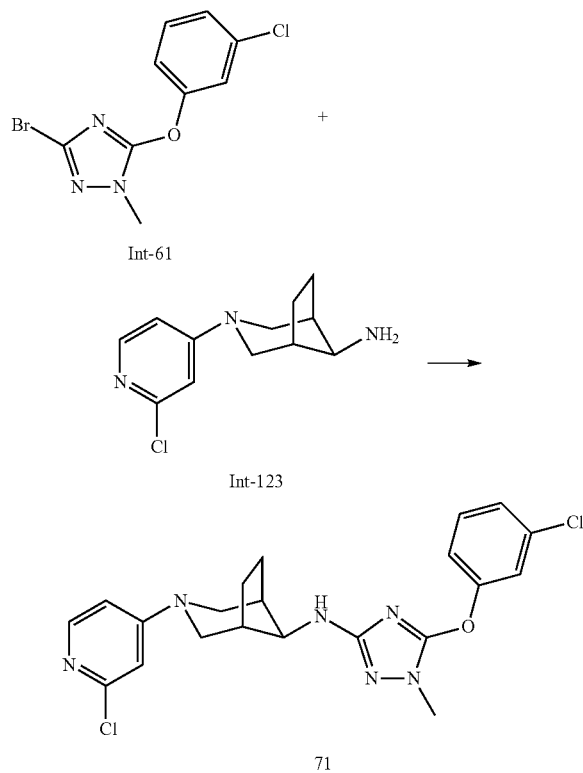

In an 8 mL microwave vial (1R,5S,8s)-3-(2-chloropyridin-4-yl)-3-azabicyclo[3.2.1]octan-8-amine (Int-123, 65 mg, 273 µmol) was suspended in 1,4-dioxane (4 mL) and 3-bromo-5-(3-chlorophenoxy)-1-methyl-1H-1,2,4-triazole (Int-61, 78.9 mg, 273 µmol), sodium tert-butoxide (55.3 mg, 547 µmol), 1,2,3,4,5-pentaphenyl-1'-(di-tert-butylphosphino)ferrocene ("Q-phos", CAS [312959-24-3], 32.7 mg, 43.7 µmol), and tris(dibenzylideneacetone)dipalladium (0) chloroform adduct (23.3 mg, 21.9 µmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v), followed by column chromatography (silica gel, 70 g, eluting with dichloromethane/ethyl acetate, gradient 0:100 to 100:0 v/v), followed by column chromatography (amino modified silica gel, 50 g, eluting with ethyl acetate/n-heptane, gradient 0:100 to 42:58 v/v) to afford the title compound as a white solid (38 mg, 31%). HPLC (method LCMS_fastgradient) $t_R$=1.23 min. $^1$H NMR (CDCl$_3$, 300 MHz): δ 1.55-1.64 (m, 2H), 1.86-1.94 (m, 2H), 2.47-2.54 (m, 2H), 3.08-3.15 (m, 2H), 3.60 (dd, J=3.2, 11.9 Hz, 2H), 3.63 (s, 3H), 3.72 (d, J=6.2 Hz, 1H), 3.95 (d, J=6.0 Hz, 1H), 6.53 (dd, J=2.4, 6.0 Hz, 1H), 6.61 (d, J=2.4 Hz, 1H), 7.15-7.24 (m, 2H), 7.30-7.37 (m, 2H), 8.00 (d, J=6.0 Hz, 1H). MS (ES+) m/z 445.2, 447.2 [M+H, Cl isotopes].

Example 72

(1R,5S,8s)-N-(5-(3-Chlorophenoxy)-1-methyl-1H-1,2,4-triazol-3-yl)-3-(6-methoxypyrimidin-4-yl)-3-azabicyclo[3.2.1]octan-8-amine

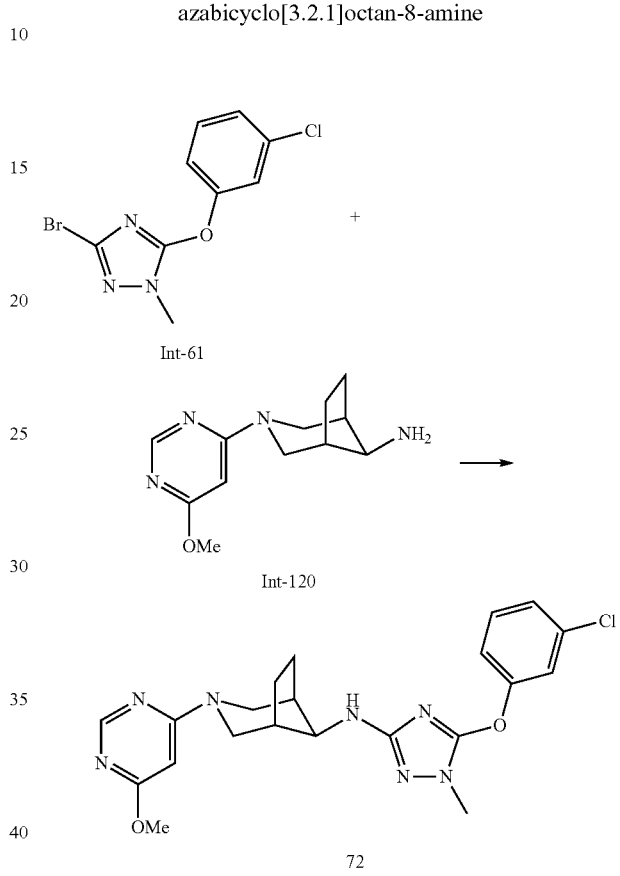

In an 8 mL microwave vial (1R,5S,8s)-3-(6-methoxypyrimidin-4-yl)-3-azabicyclo[3.2.1]octan-8-amine (Int-120, 72 mg, 307 µmol) was suspended in 1,4-dioxane (4 mL) and 3-bromo-5-(3-chlorophenoxy)-1-methyl-1H-1,2,4-triazole (Int-61, 88.7 mg, 307 µmol), sodium tert-butoxide (62.2 mg, 615 µmol), 1,2,3,4,5-pentaphenyl-1'-(di-tert-butylphosphino)ferrocene ("Q-phos", CAS [312959-24-3], 36.8 mg, 49.2 µmol), and tris(dibenzylideneacetone)dipalladium (0) chloroform adduct (26.2 mg, 24.6 µmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v), followed by column chromatography (amino modified silica gel, 50 g, eluting with ethyl acetate/n-heptane, gradient 0:100 to 28:72 v/v) to afford the title compound as a white foam (59 mg, 43%). HPLC (method LCMS_fastgradient) $t_R$=1.21 min. $^1$H NMR (CDCl$_3$, 300 MHz): δ 1.51-1.61 (m, 2H), 1.79-1.88 (m, 2H), 2.42-2.49 (m, 2H), 3.04-3.12 (m, 2H), 3.64 (s, 3H), 3.73 (d, J=6.2 Hz, 1H), 3.92 (s, 3H), 3.94 (d, J=6.4 Hz, 1H), 4.00-4.11 (m, 2H), 5.78 (d, J=0.8 Hz, 1H), 7.15-7.24 (m, 2H), 7.30-7.36 (m, 2H), 8.32 (d, J=0.8 Hz, 1H). MS (ES+) m/z 442.2, 444.2 [M+H, Cl isotopes].

Example 73

(1R,5S,8s)-N-[5-(3-Chloro-4-methylphenoxy)-1-(propan-2-yl)-1H-1,2,4-triazol-3-yl]-3-(3-methyl-1,2,4-oxadiazol-5-yl)-3-azabicyclo[3.2.1]octan-8-amine

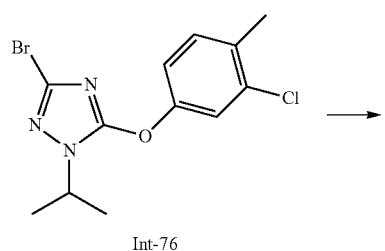

Int-76

Example 74

(1R,5S,8s)-N-[5-(3-Chloro-2-methylphenoxy)-1-(propan-2-yl)-1H-1,2,4-triazol-3-yl]-3-(3-methyl-1,2,4-oxadiazol-5-yl)-3-azabicyclo[3.2.1]octan-8-amine

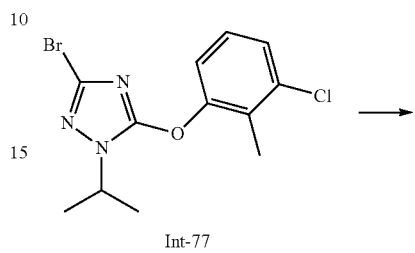

Int-77

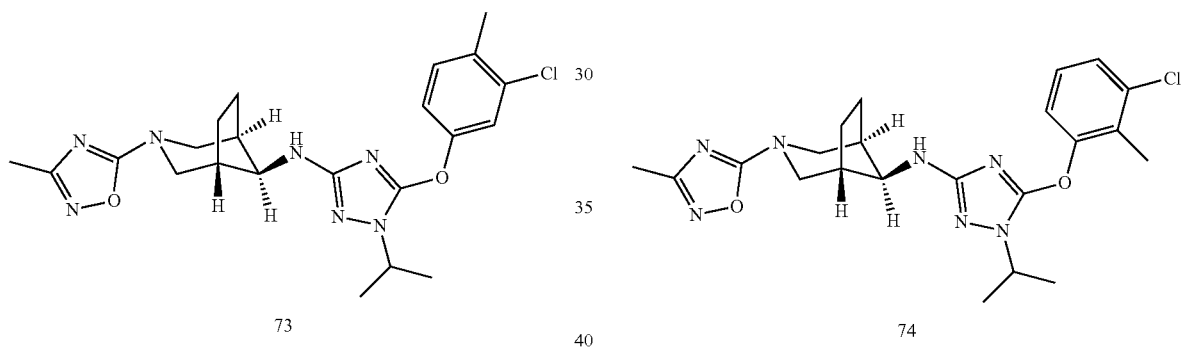

73

74

To a solution of (1R,5S,8s)-3-(3-methyl-1,2,4-oxadiazol-5-yl)-3-azabicyclo[3.2.1]octan-8-amine (Int-102, 70 mg, 0.3 mmol) and 3-bromo-5-(3-chloro-4-methylphenoxy)-1-(propan-2-yl)-1H-1,2,4-triazole (Int-76, 144 mg, 0.4 mmol) in dry 1,4-dioxane (1.5 mL) in microwave tube was added 1,2,3,4,5-pentaphenyl-1'-(di-tert-butylphosphino)ferrocene ("Q-phos", CAS 312959-24-3, 38.2 mg, 0.05 mmol). The reaction mixture was degassed with argon in a microwave tube over a period of 15 min. To it then added tris(dibenzylideneacetone)dipalladium-chloroform adduct ("Pd$_2$(dba)$_3$·CHCl$_3$", CAS 52522-40-4, 27.8 mg, 0.02 mmol) and sodium tertbutoxide (64.5 mg, 0.7 mmol). The reaction mixture was irradiated at 70° C. for 10 min in microwave. Reaction mixture was filtered and the filtrate was concentrated to get the crude which was purified by reversed phase prep HPLC (Xterra RP18 10μ 250×19 mm, flow 16 mL/min, eluting with acetonitrile/(water+20 mM ammonium bicarbonate), gradient 30:70 to 95:5) method to afford the title compound as brown sticky solid (25 mg, 16%). HPLC purity 99.35%. $^1$H NMR (MeOD, 400 MHz): 1.43 (d, J=6.7 Hz, 6H), 1.53 (d, J=8.2 Hz, 2H), 1.93-1.98 (m, 3H), 2.16 (s, 3H), 2.34 (s, 3H), 2.44 (s, 2H), 3.34 (s, 1H), 3.37 (d, J=12.4 Hz, 2H), 3.69 (s, 1H), 3.82 (dd, J=12.7, 3.0 Hz, 2H), 4.48 (p, J=6.7 Hz, 1H), 7.00 (s, 1H), 7.10 (d, J=7.6 Hz, 2H). MS (ES+) m/z 458.2 [M+H].

To a solution of (1R,5S,8s)-3-(3-methyl-1,2,4-oxadiazol-5-yl)-3-azabicyclo[3.2.1]octan-8-amine (Int-102, 70 mg, 0.3 mmol) and 3-bromo-5-(3-chloro-2-methylphenoxy)-1-(propan-2-yl)-1H-1,2,4-triazole (Int-77, 144 mg, 0.4 mmol) in dry 1,4-dioxane (1.5 mL) in microwave tube was added 1,2,3,4,5-pentaphenyl-1'-(di-tert-butylphosphino)ferrocene ("Q-phos", CAS 312959-24-3, 38.2 mg, 0.05 mmol). The reaction mixture was degassed with argon in a microwave tube over a period of 15 min. To it then added tris(dibenzylideneacetone)dipalladium-chloroform adduct ("Pd$_2$(dba)$_3$·CHCl$_3$", CAS 52522-40-4, 27.8 mg, 0.02 mmol) and sodium tertbutoxide (64.5 mg, 0.7 mmol). The reaction mixture was irradiated at 70° C. for 10 min in microwave. Reaction mixture was filtered and the filtrate was concentrated to get the crude which was purified by reversed phase prep HPLC (Xterra RP18 10μ 250×19 mm, flow 16 mL/min, eluting with acetonitrile/(water+20 mM ammonium bicarbonate), gradient 30:70 to 95:5) method to afford the title compound as off-white solid (25.5 mg, 17%). HPLC purity 98.69%. $^1$H NMR (MeOD, 400 MHz): 1.47 (d, J=6.7 Hz, 6H), 1.52 (d, J=8.2 Hz, 2H), 1.90-1.94 (m, 2H), 2.15 (s, 3H), 2.31 (s, 3H), 2.41 (s, 2H), 3.35 (d, J=12.4 Hz, 2H), 3.66 (s, 1H), 3.81 (dd, J=12.8, 3.2 Hz, 2H), 4.52 (p, J=6.7 Hz, 1H), 7.10 (d, J=8.0 Hz, 1H), 7.22 (t, J=8.1 Hz, 1H), 7.30 (d, J=7.4 Hz, 1H). MS (ES+) m/z 458.2 [M+H].

Example 75

(1R,5S,8s)-N-[5-(3-Chloro-5-methylphenoxy)-1-(propan-2-yl)-1H-1,2,4-triazol-3-yl]-3-(3-methyl-1,2,4-oxadiazol-5-yl)-3-azabicyclo[3.2.1]octan-8-amine

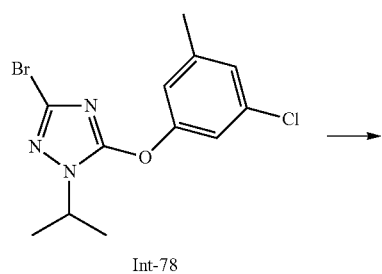

Int-78

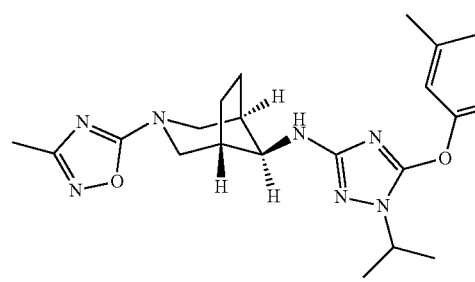

75

To a solution of (1R,5S,8s)-3-(3-methyl-1,2,4-oxadiazol-5-yl)-3-azabicyclo[3.2.1]octan-8-amine (Int-102, 70 mg, 0.3 mmol) and 3-bromo-5-(3-chloro-5-methylphenoxy)-1-(propan-2-yl)-1H-1,2,4-triazole (Int-78, 144 mg, 0.4 mmol) in dry 1,4-dioxane (1.5 mL) in microwave tube was added 1,2,3,4,5-pentaphenyl-1'-(di-tert-butylphosphino)ferrocene ("Q-phos", CAS 312959-24-3, 38.2 mg, 0.05 mmol). The reaction mixture was degassed with argon in a microwave tube over a period of 15 min. To it then added tris(dibenzylideneacetone)dipalladium-chloroform adduct ("Pd$_2$(dba)$_3$.CHCl$_3$", CAS 52522-40-4, 27.8 mg, 0.02 mmol) and sodium tertbutoxide (64.5 mg, 0.7 mmol). The reaction mixture was irradiated at 70° C. for 10 min in microwave. Reaction mixture was filtered and the filtrate was concentrated to get the crude which was purified by reversed phase prep HPLC (YMC Triart C18 5µ 250×20 mm, flow 16 mL/min, eluting with acetonitrile/(water+20 mM ammonium bicarbonate), gradient 30:70 to 95:5) method to afford the title compound as brown sticky solid (16.3 mg, 11%). HPLC purity 99.53%. $^1$H NMR (MeOD, 400 MHz): 1.43 (d, J=6.7 Hz, 6H), 1.50-1.56 (m, 2H), 1.92-1.97 (m, 2H), 2.15 (s, 3H), 2.35 (s, 3H), 2.43 (s, 2H), 3.36 (d, J=12.4 Hz, 2H), 3.68 (s, 1H), 3.81 (dd, J=12.7, 3.0 Hz, 2H), 4.48 (p, J=6.7 Hz, 1H), 7.08 (dd, J=8.5, 2.4 Hz, 1H), 7.31-7.33 (m, 2H). MS (ES+) m/z 458.2 [M+H].

Example 76

(1R,5S,8s)-N-(5-(3-Chlorophenoxy)-1-methyl-1H-1,2,4-triazol-3-yl)-3-(6-chloropyridazin-4-yl)-3-azabicyclo[3.2.1]octan-8-amine

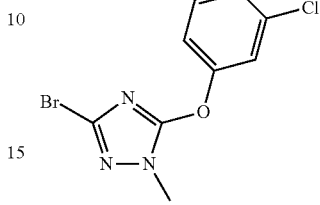

Int-61

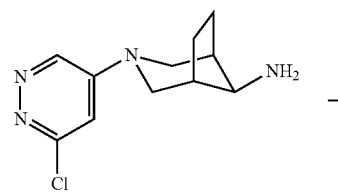

Int-126

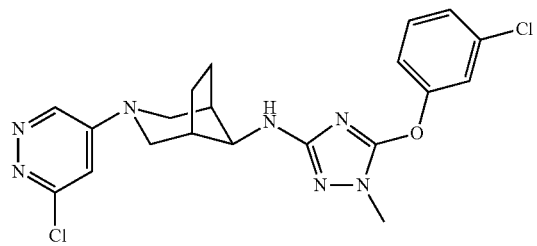

76

In an 8 mL microwave vial (1R,5S,8s)-3-(6-chloropyridazin-4-yl)-3-azabicyclo[3.2.1]octan-8-amine (Int-126, 57.9 mg, 243 µmol) was suspended in 1,4-dioxane (4 mL) and 3-bromo-5-(3-chlorophenoxy)-1-methyl-1H-1,2,4-triazole (Int-61, 70 mg, 243 µmol), sodium tert-butoxide (49.1 mg, 485 µmol), 1,2,3,4,5-pentaphenyl-1'-(di-tert-butylphosphino)ferrocene ("Q-phos", CAS [312959-24-3], 29 mg, 39 µmol), and tris(dibenzylideneacetone)dipalladium (0) chloroform adduct (20.7 mg, 19.4 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v, then eluting with dichloromethane/methanol, gradient 100:0 to 86:14), followed by column chromatography (amino modified silica gel, 50 g, eluting with ethyl acetate/n-heptane, gradient 0:100 to 63:37 v/v) to afford the title compound as an off-white solid (47 mg, 43%). HPLC (method LCMS_fast-gradient) t$_R$=1.14 min. $^1$H NMR (CDCl$_3$, 300 MHz): δ1.55-1.64 (m, 2H), 1.91-1.99 (m, 2H), 2.53-2.60 (m, 2H), 3.18-3.26 (m, 2H), 3.62-3.68 (m, 2H), 3.64 (s, 3H), 3.76 (d, J=5.8 Hz, 1H), 3.95 (d, J=5.8 Hz, 1H), 6.63 (d, J=2.6 Hz, 1H), 7.15-7.24 (m, 2H), 7.31-7.37 (m, 2H), 8.72 (d, J=2.8 Hz, 1H). MS (ES+) m/z 446.2, 448.2 [M+H, Cl isotopes].

Example 77

(1R,5S,8s)-N-(5-(3-Chloro-5-methylphenoxy)-1-methyl-1H-1,2,4-triazol-3-yl)-3-(6-chloropyridazin-4-yl)-3-azabicyclo[3.2.1]octan-8-amine

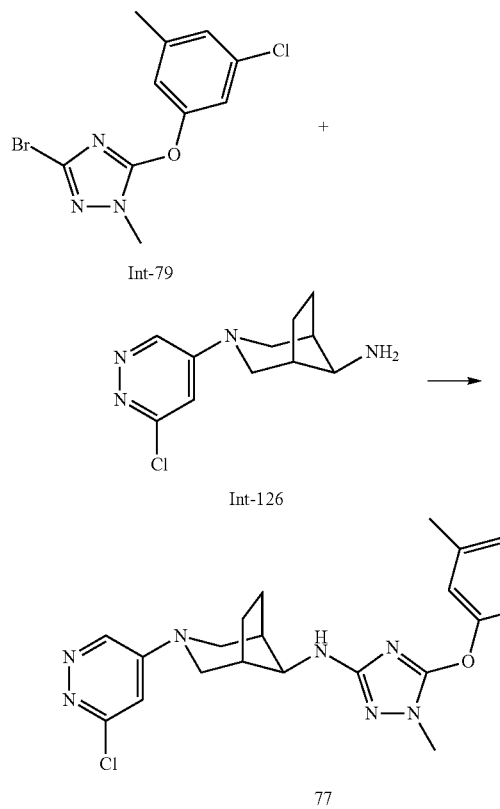

In an 8 mL microwave vial (1R,5S,8s)-3-(6-chloropyridazin-4-yl)-3-azabicyclo[3.2.1]octan-8-amine (Int-126, 45 mg, 189 µmol) was suspended in 1,4-dioxane (3 mL) and 3-bromo-5-(3-chloro-5-methylphenoxy)-1-methyl-1H-1,2,4-triazole (Int-79, 57 mg, 189 µmol), sodium tert-butoxide (38.1 mg, 377 µmol), 1,2,3,4,5-pentaphenyl-1'-(di-tert-butylphosphino)ferrocene ("Q-phos", CAS [312959-24-3], 22.6 mg, 30.2 µmol), and tris(dibenzylideneacetone)dipalladium (0) chloroform adduct (16.1 mg, 15.1 µmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v, then eluting with dichloromethane/methanol 90:10 v/v), followed by column chromatography (amino modified silica gel, 50 g, eluting with ethyl acetate/n-heptane, gradient 0:100 to 40:60 v/v) to afford the title compound as a white solid (40 mg, 46%). $^1$H NMR (CDCl$_3$, 300 MHz): δ1.55-1.64 (m, 2H), 1.90-1.99 (m, 2H), 2.36 (d, J=0.6 Hz, 3H), 2.53-2.60 (m, 2H), 3.18-3.26 (m, 2H), 3.61-3.69 (m, 2H), 3.62 (s, 3H), 3.76 (d, J=5.8 Hz, 1H), 3.95 (d, J=5.6 Hz, 1H), 6.63 (d, J=2.8 Hz, 1H), 6.95-6.98 (m, 1H), 7.03-7.06 (m, 1H), 7.09-7.12 (m, 1H), 8.72 (d, J=2.8 Hz, 1H). MS (ES+) m/z 460.2, 462.1 [M+H, Cl isotopes].

Example 78

(1R,5S,8s)-N-[5-(3-Chlorophenoxy)-1-(propan-2-yl)-1H-1,2,4-triazol-3-yl]-3-(6-chloropyrimidin-4-yl)-3-azabicyclo[3.2.1]octan-8-amine

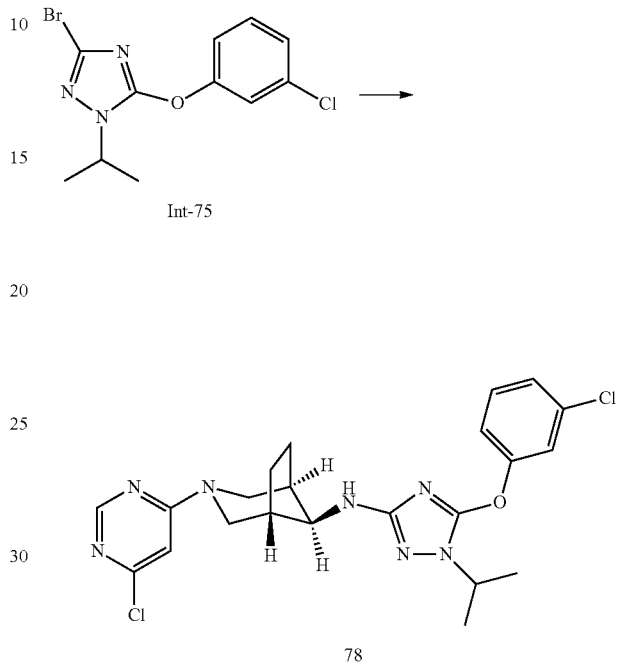

To a solution of (1R,5S,8s)-3-(6-chloropyrimidin-4-yl)-3-azabicyclo[3.2.1]octan-8-amine (Int-108, 70 mg, 0.3 mmol) and 3-bromo-5-(3-chlorophenoxy)-1-(propan-2-yl)-1H-1,2,4-triazole (Int-75, 139.4 mg, 0.4 mmol) in dry 1,4-dioxane (1.5 mL) in sealed tube was added 2-dicyclohexylphosphino-2',6'-diisopropoxybiphenyl ("Ruphos", CAS [787618-22-8], 27.4 mg, 0.06 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 47 mg, 0.06 mmol). The reaction mixture was again degassed with argon for 10 min followed by addition of sodium tertbutoxide (112.9 mg, 1.2 mmol). The reaction mixture was stirred at 120° C. for 5 h. Reaction mixture was then filtered through plug of celite and washed with EtOAc (10 mL) and dichloromethane (10 mL). Combined organic filtrates were concentrated under reduced pressure. The resulting crude product was purified by column chromatography (amino modified silica gel, 12 g, eluting with MeOH/dichloromethane 5:95 v/v) followed by reversed phase prep HPLC (Xterra RP18 10µ 250×19 mm, flow 16 mL/min, eluting with acetonitrile/(water+20 mM ammonium bicarbonate), gradient 30:70 to 95:5) method to yield the title compound as brown sticky solid (6.9 mg, 5%). HPLC purity 98.31%. $^1$H NMR (MeOD, 400 MHz): 1.43-1.49 (m, 8H), 1.90-1.92 (m, 2H), 2.46 (s, 2H), 3.11 (d, J=11.7 Hz, 2H), 3.71 (s, 1H), 3.77 (s, 1H), 4.46-4.52 (m, 1H), 6.78 (s, 1H), 7.16-7.41 (m, 4H), 8.25 (s, 1H). MS (ES+) m/z 474.2 [M+H].

Example 79

(1R,5S,8s)-3-(6-Chloropyrimidin-4-yl)-N-[5-(3-fluorophenoxy)-1-(propan-2-yl)-1H-1,2,4-triazol-3-yl]-3-azabicyclo[3.2.1]octan-8-amine

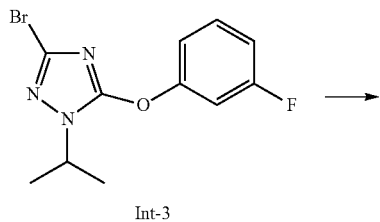

Int-3

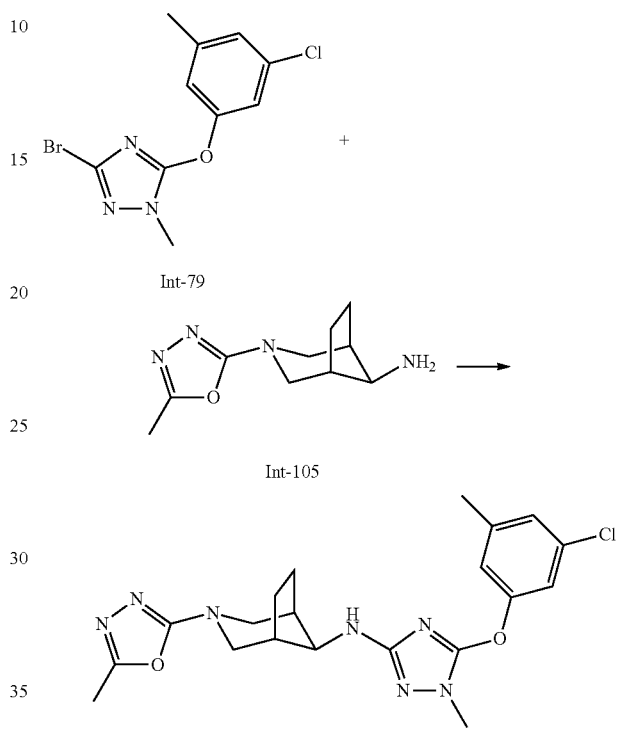

79

To a solution of (1R,5S,8s)-3-(6-chloropyrimidin-4-yl)-3-azabicyclo[3.2.1]octan-8-amine (Int-108, 70 mg, 0.3 mmol) and 3-bromo-5-(3-fluorophenoxy)-1-(propan-2-yl)-1H-1,2,4-triazole (Int-3, 132.3 mg, 0.4 mmol) in dry 1,4-dioxane (1.5 mL) in sealed tube was added 2-dicyclohexylphosphino-2',6'-diisopropoxybiphenyl ("Ruphos", CAS [787618-22-8], 27.4 mg, 0.06 mmol). The reaction mixture was degassed with argon in a sealed tube over a period of 15 min. To it then added chloro[2-(dicyclohexylphosphino)-3,6-dimethoxy-2',4',6'-triisopropyl-1,1'-biphenyl][2-(2-aminoethyl)phenyl]palladium(II) ("Brettphos palladacycle", CAS [1148148-01-9], 47 mg, 0.06 mmol). The reaction mixture was again degassed with argon for 10 min followed by addition of sodium tertbutoxide (112.9 mg, 1.2 mmol). The reaction mixture was stirred at 120° C. for 5 h. Reaction mixture was then filtered through plug of celite and washed with EtOAc (10 mL) and dichloromethane (10 mL). Combined organic filtrates were concentrated under reduced pressure. The resulting crude product was purified by column chromatography (amino modified silica gel, eluting with MeOH/dichloromethane 5:95 v/v) followed by reversed phase prep HPLC (Xterra RP18 10μ 250×19 mm, flow 16 mL/min, eluting with acetonitrile/(water+20 mM ammonium bicarbonate), gradient 30:70 to 95:5) method to yield the title compound as brown sticky solid (12.8 mg, 10%). HPLC purity 98.26%. $^1$H NMR (MeOD, 400 MHz): 1.42-1.49 (m, 8H), 1.89-1.92 (m, 2H), 2.46 (s, 2H), 3.11 (d, J=12.0 Hz, 2H), 3.72 (s, 1H), 3.77 (s, 1H), 4.45-4.52 (m, 1H), 6.77 (s, 1H), 6.96-7.44 (m, 4H), 8.25 (s, 1H). MS (ES+) m/z 458.2 [M+H].

Example 80

(1R,5S,8s)-N-(5-(3-Chloro-5-methylphenoxy)-1-methyl-1H-1,2,4-triazol-3-yl)-3-(5-methyl-1,3,4-oxadiazol-2-yl)-3-azabicyclo[3.2.1]octan-8-amine In an 8 mL microwave vial (1R,5S,8s)-3-(5-methyl-1,3,4-oxadiazol-2-yl)-3-azabicyclo[3.2.1]octan-8-amine (Int-105, 45 mg, 216 μmol) was suspended in 1,4-dioxane (3 mL) and 3-bromo-5-(3-chloro-5-methylphenoxy)-1-methyl-1H-1,2,4-triazole (Int-79, 65.4 mg, 216 μmol), sodium tert-butoxide (43.7 mg, 432 μmol), 1,2,3,4,5-pentaphenyl-1'-(di-tert-butylphosphino)ferrocene ("Q-phos", CAS [312959-24-3], 25.9 mg, 34.6 μmol), and tris(dibenzylideneacetone)dipalladium (0) chloroform adduct (18.4 mg, 17.3 μmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v, then eluting with dichloromethane/methanol 90:10 v/v), followed by column chromatography (amino modified silica gel, 50 g, eluting with ethyl acetate/n-heptane, gradient 0:100 to 40:60 v/v), followed by preparative HPLC (YMC-Actus Triart C18, 100×30 mm×5 μm, eluting with acetonitrile/triethylamine 97.2:2.5 v/v) and lyophilization to yield the title compound as a white solid (18 mg, 19%). $^1$H NMR (CDCl$_3$, 300 MHz): δ 1.59-1.69 (m, 2H), 1.81-1.93 (m, 2H), 2.35 (s, 3H), 2.39 (s, 3H), 2.40-2.46 (m, 2H), 3.24-3.32 (m, 2H), 3.62 (s, 3H), 3.69 (d, J=6.4 Hz, 1H), 3.73 (dd, J=3.2, 12.3 Hz, 2H), 3.93 (d, J=6.2 Hz, 1H), 6.95-6.98 (m, 1H), 7.02-7.05 (m, 1H), 7.08-7.11 (m, 1H). MS (ES+) m/z 430.3, 432.3 [M+H, Cl isotopes].

Example 81

(1R,5S,8s)-N-(5-(3-Chlorophenoxy)-1-ethyl-1H-1,2,4-triazol-3-yl)-3-(6-methoxypyridazin-4-yl)-3-azabicyclo[3.2.1]octan-8-amine

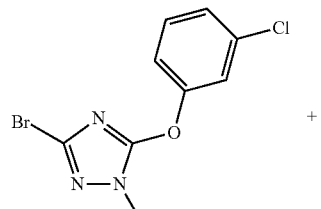

Int-81

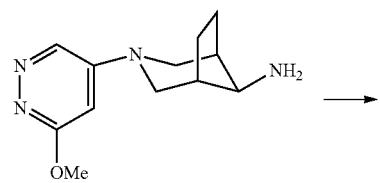

Int-128

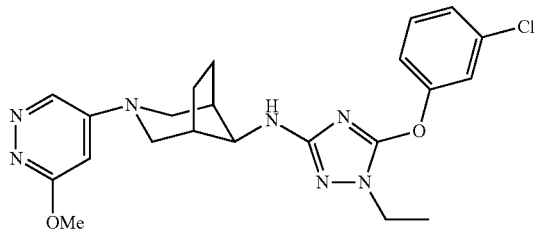

81

In an 8 mL microwave vial (1R,5S,8s)-3-(6-methoxypyridazin-4-yl)-3-azabicyclo[3.2.1]octan-8-amine (Int-128, 50 mg, 213 µmol) was suspended in 1,4-dioxane (4 mL) and 3-bromo-5-(3-chlorophenoxy)-1-ethyl-1H-1,2,4-triazole (Int-81, 80.7 mg, 213 µmol), sodium tert-butoxide (43.2 mg, 427 µmol), 1,2,3,4,5-pentaphenyl-1'-(di-tert-butylphosphino)ferrocene ("Q-phos", CAS [312959-24-3], 25.5 mg, 34.1 µmol), and tris(dibenzylideneacetone)dipalladium (0) chloroform adduct (18.2 mg, 17.1 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 39:61 v/v), followed by column chromatography (silica gel, 20 g, eluting with dichloromethane/methanol, gradient 100:0 to 96.5:3.5 v/v) to yield the title compound as an off-white solid (47 mg, 48%). $^1$H NMR (CDCl$_3$, 300 MHz): δ 1.43 (t, J=7.2 Hz, 3H), 1.57-1.65 (m, 2H), 1.87-1.96 (m, 2H), 2.48-2.56 (m, 2H), 3.10-3.18 (m, 2H), 3.62 (dd, J=3.2, 11.9 Hz, 2H), 3.74 (d, J=6.0 Hz, 1H), 3.94 (d, J=6.0 Hz, 1H), 3.97 (q, J=7.2 Hz, 2H), 4.08 (s, 3H), 6.02 (d, J=2.6 Hz, 1H), 7.14-7.23 (m, 2H), 7.29-7.36 (m, 2H), 8.57 (d, J=2.6 Hz, 1H). MS (ES+) m/z 456.3, 458.2 [M+H, Cl isotopes].

Example 82

(1R,5S,8s)-N-(5-(3-Chlorophenoxy)-1-propyl-1H-1,2,4-triazol-3-yl)-3-(6-methoxypyridazin-4-yl)-3-azabicyclo[3.2.1]octan-8-amine

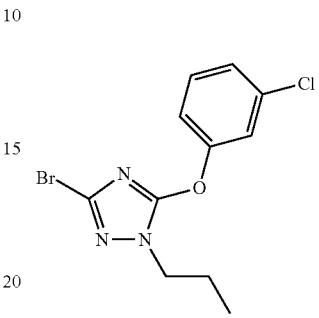

Int-83

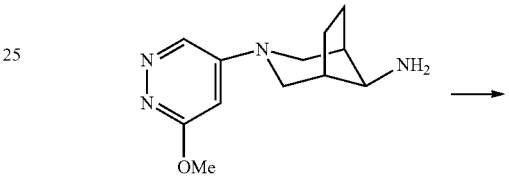

Int-128

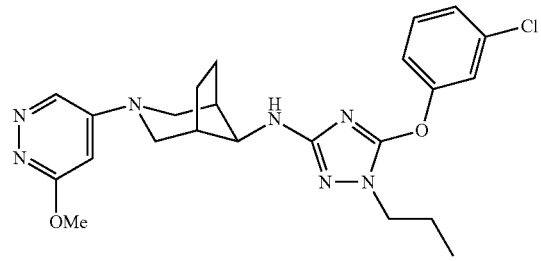

82

In an 8 mL microwave vial (1R,5S,8s)-3-(6-methoxypyridazin-4-yl)-3-azabicyclo[3.2.1]octan-8-amine (Int-128, 50 mg, 213 µmol) was suspended in 1,4-dioxane (4 mL) and 3-bromo-5-(3-chlorophenoxy)-1-propyl-1H-1,2,4-triazole (Int-83, 84.4 mg, 213 µmol), sodium tert-butoxide (43.2 mg, 427 µmol), 1,2,3,4,5-pentaphenyl-1'-(di-tert-butylphosphino)ferrocene ("Q-phos", CAS [312959-24-3], 25.5 mg, 34.1 µmol), and tris(dibenzylideneacetone)dipalladium (0) chloroform adduct (18.2 mg, 17.1 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 40:60 v/v), followed by column chromatography (silica gel, 20 g, eluting with dichloromethane/methanol, gradient 100:0 to 96.5:3.5 v/v) to yield the title compound as a white solid (39 mg, 39%). $^1$H NMR (CDCl$_3$, 300 MHz): δ 0.97 (t, J=7.3 Hz, 3H), 1.55-1.65 (m, 2H), 1.79-1.96 (m, 2H), 2.48-2.55 (m, 2H), 3.10-3.18 (m, 2H), 3.61 (dd, J=3.0, 11.9 Hz, 2H), 3.74 (d, J=6.2 Hz, 1H), 3.84-3.95 (m, 3H), 4.08 (s, 3H), 6.02 (d, J=2.6 Hz, 1H), 7.14-7.23 (m, 2H), 7.29-7.36 (m, 2H), 8.57 (d, J=2.6 Hz, 1H). MS (ES+) m/z 470.3, 472.3 [M+H, Cl isotopes].

Example 83

(1R,5S,8s)-N-(5-(3-Chlorophenoxy)-1-propyl-1H-1,2,4-triazol-3-yl)-3-(6-chloropyridazin-4-yl)-3-azabicyclo[3.2.1]octan-8-amine

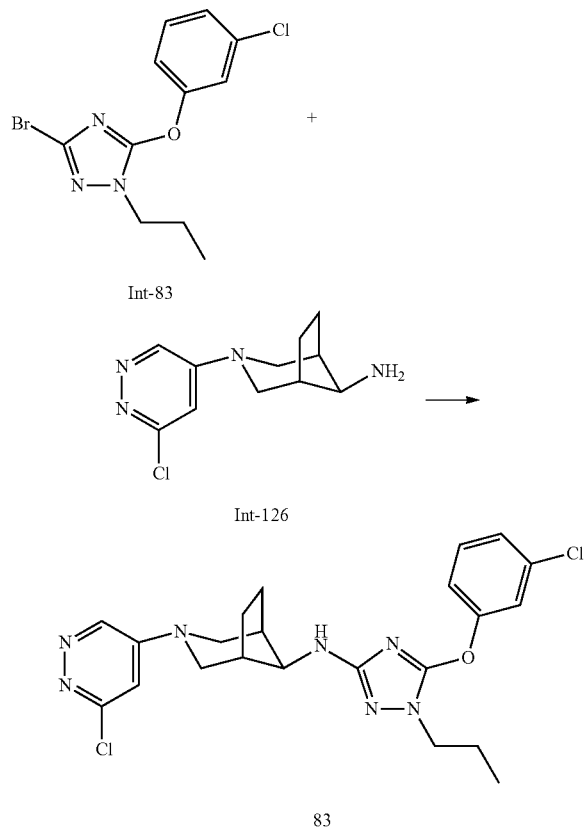

In an 8 mL microwave vial (1R,5S,8s)-3-(6-chloropyridazin-4-yl)-3-azabicyclo[3.2.1]octan-8-amine (Int-126, 50 mg, 209 µmol) was suspended in 1,4-dioxane (4 mL) and 3-bromo-5-(3-chlorophenoxy)-1-propyl-1H-1,2,4-triazole (Int-83, 82.9 mg, 209 µmol), sodium tert-butoxide (42.4 mg, 419 µmol), 1,2,3,4,5-pentaphenyl-1'-(di-tert-butylphosphino)ferrocene ("Q-phos", CAS [312959-24-3], 25.1 mg, 33.5 µmol), and tris(dibenzylideneacetone)dipalladium (0) chloroform adduct (17.9 mg, 16.8 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 40:60 v/v), followed by column chromatography (silica gel, 20 g, eluting with dichloromethane/methanol, gradient 100:0 to 96.5:3.5 v/v) to yield the title compound as a white solid (35 mg, 35%). HPLC (method LCMS_fastgradient) $t_R$=1.29 min. $^1$H NMR (CDCl$_3$, 300 MHz): δ 0.98 (t, J=7.4 Hz, 3H), 1.55-1.64 (m, 2H), 1.79-1.92 (m, 2H), 1.92-1.99 (m, 2H), 2.53-2.60 (m, 2H), 3.19-3.26 (m, 2H), 3.65 (dd, J=3.0, 12.1 Hz, 2H), 3.78 (d, J=6.0 Hz, 1H), 3.88 (t, J=7.0 Hz, 2H), 3.94 (d, J=5.8 Hz, 1H), 6.63 (d, J=2.8 Hz, 1H), 7.14-7.24 (m, 2H), 7.30-7.37 (m, 2H), 8.72 (d, J=2.8 Hz, 1H). MS (ES+) m/z 474.2, 476.2 [M+H, Cl isotopes].

Example 84

(1R,5S,8s)-N-(5-(3-Chloro-5-methylphenoxy)-1-methyl-1H-1,2,4-triazol-3-yl)-3-(6-methoxypyridazin-4-yl)-3-azabicyclo[3.2.1]octan-8-amine

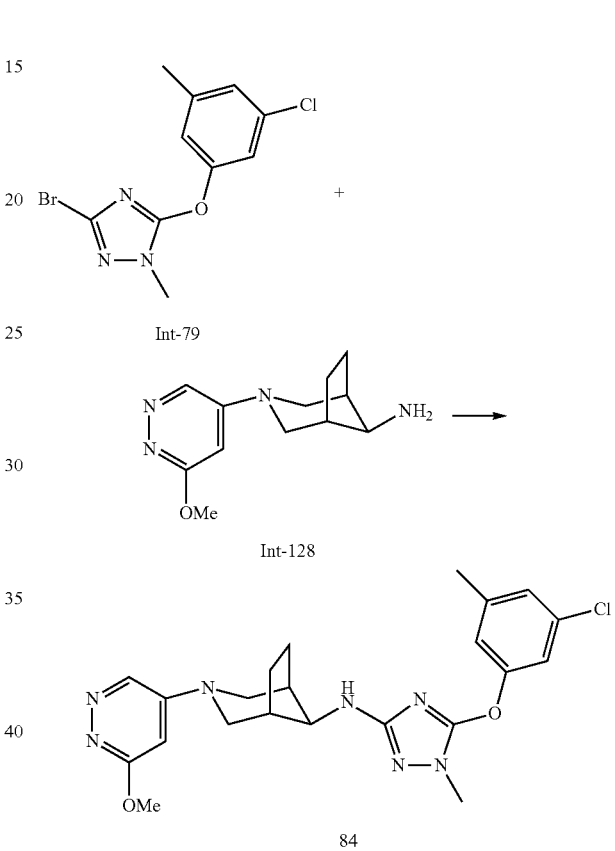

In an 8 mL microwave vial (1R,5S,8s)-3-(6-methoxypyridazin-4-yl)-3-azabicyclo[3.2.1]octan-8-amine (Int-128, 40 mg, 171 µmol) was suspended in 1,4-dioxane (3 mL) and 3-bromo-5-(3-chloro-5-methylphenoxy)-1-methyl-1H-1,2,4-triazole (Int-79, 51.7 mg, 171 µmol), sodium tert-butoxide (34.5 mg, 341 µmol), 1,2,3,4,5-pentaphenyl-1'-(di-tert-butylphosphino)ferrocene ("Q-phos", CAS [312959-24-3], 20.4 mg, 27.3 µmol), and tris(dibenzylideneacetone)dipalladium (0) chloroform adduct (14.6 mg, 13.7 µmol) were added subsequently. The vial was degassed thoroughly with Argon and sealed. The reaction mixture was heated under microwave irradiation at 110° C. for 25 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 40:60 v/v), followed by preparative HPLC (YMC-Actus Triart C18, 100×30 mm×5 µm, eluting with acetonitrile/(water+0.1% triethylamine), gradient 20:80 to 98:2 v/v) and lyophilization to yield the title compound as an off-white solid (9 mg, 12%). $^1$H NMR (CDCl$_3$, 300 MHz):

δ 1.56-1.64 (m, 2H), 1.86-1.95 (m, 2H), 2.35 (d, J=0.6 Hz, 3H), 2.49-2.55 (m, 2H), 3.10-3.17 (m, 2H), 3.61 (dd, J=3.0, 11.9 Hz, 2H), 3.62 (s, 3H), 3.72 (d, J=6.0 Hz, 1H), 3.95 (d, J=6.2 Hz, 1H), 4.08 (s, 3H), 6.02 (d, J=2.6 Hz, 1H), 6.95-6.98 (m, 1H), 7.03-7.05 (m, 1H), 7.09-7.12 (m, 1H), 8.57 (d, J=2.6 Hz, 1H). MS (ES+) m/z 456.2, 458.2 [M+H, Cl isotopes].

Example 85

(1R,5S,8s)-N-(5-(3-Chlorophenoxy)-1-methyl-1H-1,2,4-triazol-3-yl)-3-(6-methoxypyridazin-4-yl)-3-azabicyclo[3.2.1]octan-8-amine

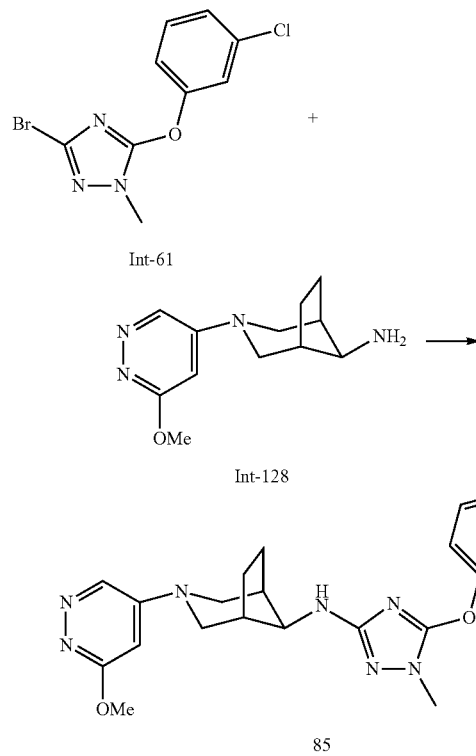

In an 8 mL microwave vial (1R,5S,8s)-3-(6-methoxypyridazin-4-yl)-3-azabicyclo[3.2.1]octan-8-amine (Int-128, 40 mg, 171 μmol) was suspended in 1,4-dioxane (3 mL) and 3-bromo-5-(3-chlorophenoxy)-1-methyl-1H-1,2,4-triazole (Int-61, 49.3 mg, 171 μmol), sodium tert-butoxide (34.5 mg, 341 μmol), 1,2,3,4,5-pentaphenyl-1'-(di-tert-butylphosphino)ferrocene ("Q-phos", CAS [312959-24-3], 20.4 mg, 27.3 μmol), and tris(dibenzylideneacetone)dipalladium (0) chloroform adduct (14.6 mg, 13.7 μmol) were added subsequently. The vial was degassed thoroughly with Argon and sealed. The reaction mixture was heated under microwave irradiation at 110° C. for 25 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 100:0 v/v), followed by preparative HPLC (YMC-Actus Triart C18, 100×30 mm×5 μm, eluting with acetonitrile/(water+0.1% triethylamine), gradient 20:80 to 98:2 v/v) and lyophilization to yield the title compound as a solid (7 mg, 9%). ¹H NMR (CDCl₃, 300 MHz): δ 1.55-1.64 (m, 2H), 1.85-1.95 (m, 2H), 2.48-2.55 (m, 2H), 3.08-3.17 (m, 2H), 3.56-3.65 (m, 2H), 3.63 (s, 3H), 3.72 (d, J=6.0 Hz, 1H), 3.94 (d, J=6.0 Hz, 1H), 4.07 (s, 3H), 6.01 (d, J=2.6 Hz, 1H), 7.14-7.23 (m, 2H), 7.29-7.36 (m, 2H), 8.56 (d, J=2.6 Hz, 1H). MS (ES+) m/z 442.2, 444.2 [M+H, Cl isotopes].

Example 86

(1R,5S,8s)-N-(5-(3-Chlorophenoxy)-1-ethyl-1H-1,2,4-triazol-3-yl)-3-(6-methylpyrimidin-4-yl)-3-azabicyclo[3.2.1]octan-8-amine

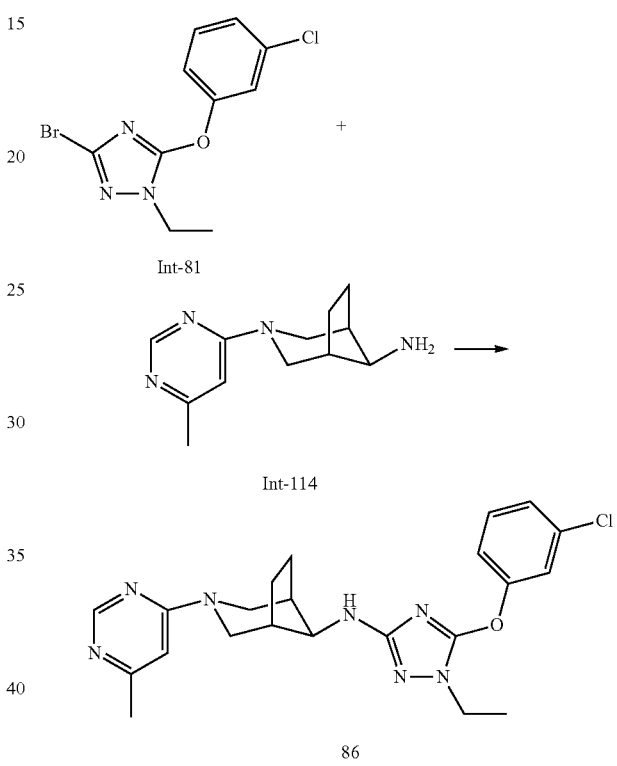

In an 8 mL microwave vial (1R,5S,8s)-3-(6-methylpyrimidin-4-yl)-3-azabicyclo[3.2.1]octan-8-amine (Int-114, 50 mg, 229 μmol) was suspended in 1,4-dioxane (4 mL) and 3-bromo-5-(3-chlorophenoxy)-1-ethyl-1H-1,2,4-triazole (Int-81, 86.6 mg, 229 μmol), sodium tert-butoxide (46.3 mg, 458 μmol), 1,2,3,4,5-pentaphenyl-1'-(di-tert-butylphosphino)ferrocene ("Q-phos", CAS [312959-24-3], 27.4 mg, 36.6 μmol), and tris(dibenzylideneacetone)dipalladium (0) chloroform adduct (19.6 mg, 18.3 μmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate, then dichloromethane/methanol, gradient 100:0 to 86:14 v/v), followed by column chromatography (amino modified silica gel, 50 g, eluting with ethyl acetate/n-heptane, gradient 0:100 to 34:66 v/v) to yield the title compound as an off-white foam (39 mg, 39%). ¹H NMR (CDCl₃, 300 MHz): δ 1.43 (t, J=7.2 Hz, 3H), 1.50-1.60 (m, 2H), 1.80-1.89 (m, 2H), 2.36 (s, 3H), 2.43-2.50 (m, 2H), 3.06-3.14 (m, 2H), 3.77 (d, J=6.2 Hz, 1H), 3.90-4.02 (m, 3H), 4.05-4.20

2H), 6.34 (s, 1H), 7.15-7.23 (m, 2H), 7.29-7.36 (m, 2H), 8.51 (d, J=0.8 Hz, 1H). MS (ES+) m/z 440.3, 442.3 [M+H, Cl isotopes].

Example 87

(1R,5S,8s)-N-(5-(3-Chlorophenoxy)-1-ethyl-1H-1,2,4-triazol-3-yl)-3-(6-chloropyridazin-4-yl)-3-azabicyclo[3.2.1]octan-8-amine

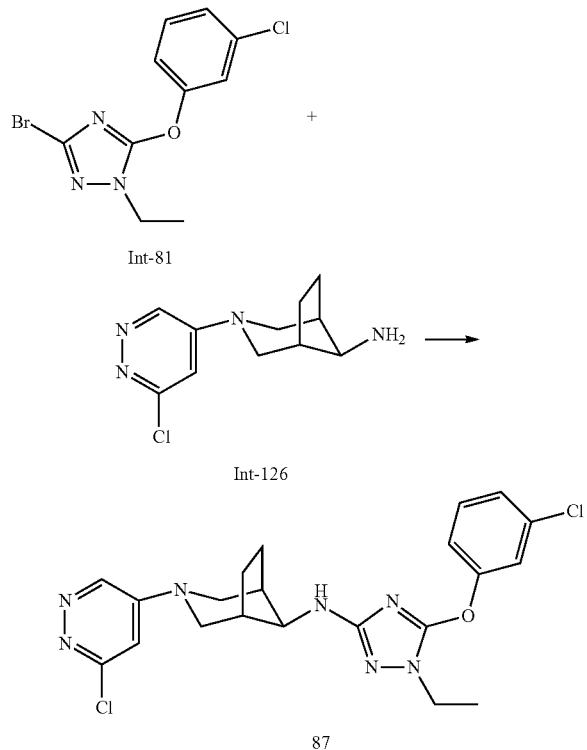

In an 8 mL microwave vial (1R,5S,8s)-3-(6-chloropyridazin-4-yl)-3-azabicyclo[3.2.1]octan-8-amine (Int-126, 60 mg, 251 µmol) was suspended in 1,4-dioxane (4 mL) and 3-bromo-5-(3-chlorophenoxy)-1-ethyl-1H-1,2,4-triazole (Int-81, 95.1 mg, 251 µmol), sodium tert-butoxide (50.9 mg, 503 µmol), 1,2,3,4,5-pentaphenyl-1'-(di-tert-butylphosphino)ferrocene ("Q-phos", CAS [312959-24-3], 30.1 mg, 40.2 µmol), and tris(dibenzylideneacetone)dipalladium (0) chloroform adduct (21.5 mg, 20.1 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 44:56 v/v), followed by column chromatography (silica gel, 20 g, eluting with dichloromethane/methanol, gradient 100:0 to 96.5:3.5 v/v) to afford the title compound as a white foam (42 mg, 36%). HPLC (method LCMS_fastgradient) $t_R$=1.22 min. $^1$H NMR (CDCl$_3$, 300 MHz): δ 1.43 (t, J=7.1 Hz, 3H), 1.55-1.64 (m, 2H), 1.92-2.00 (m, 2H), 2.53-2.60 (m, 2H), 3.19-3.27 (m, 2H), 3.65 (dd, J=3.1, 12.0 Hz, 2H), 3.78 (d, J=5.8 Hz, 1 H), 3.95 (d, J=5.6 Hz, 1H), 3.97 (q, J=7.2 Hz, 2H), 6.63 (d, J=2.6 Hz, 1H), 7.14-7.24 (m, 2H), 7.30-7.37 (m, 2H), 8.72 (d, J=2.6 Hz, 1H). MS (ES+) m/z 460.2, 462.1 [M+H, Cl isotopes].

Example 88

(1R,5S,8s)-N-(5-(3-Chlorophenoxy)-1-ethyl-1H-1,2,4-triazol-3-yl)-3-(6-chloropyrimidin-4-yl)-3-azabicyclo[3.2.1]octan-8-amine

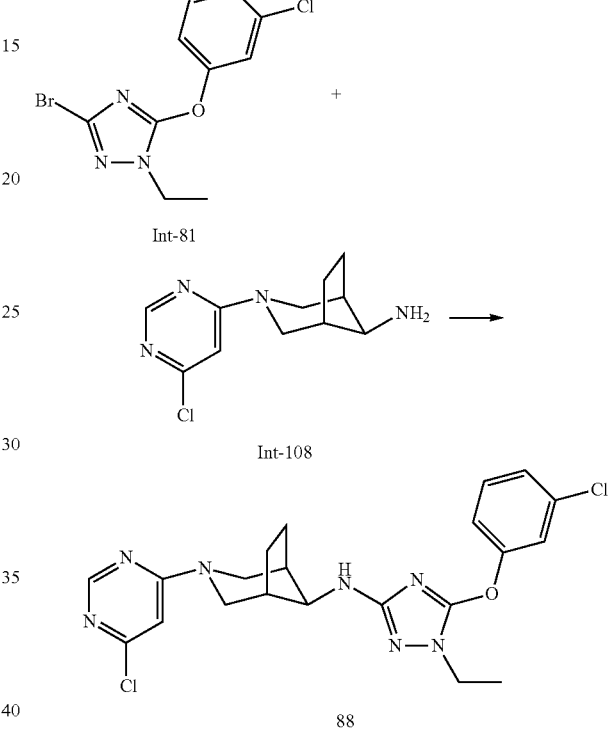

In an 8 mL microwave vial (1R,5S,8s)-3-(6-chloropyrimidin-4-yl)-3-azabicyclo[3.2.1]octan-8-amine (Int-108, 60 mg, 251 µmol) was suspended in 1,4-dioxane (4 mL) and 3-bromo-5-(3-chlorophenoxy)-1-ethyl-1H-1,2,4-triazole (Int-81, 95.1 mg, 251 µmol), sodium tert-butoxide (50.9 mg, 503 µmol), 1,2,3,4,5-pentaphenyl-1'-(di-tert-butylphosphino)ferrocene ("Q-phos", CAS [312959-24-3], 30.1 mg, 40.2 µmol), and tris(dibenzylideneacetone)dipalladium (0) chloroform adduct (21.5 mg, 20.1 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate/n-heptane, 90:10 v/v), followed by column chromatography (amino modified silica gel, 50 g, eluting with ethyl acetate/n-heptane, gradient 0:100 to 28:72 v/v) to afford the title compound as an off-white foam (34 mg, 30%). $^1$H NMR (CDCl$_3$, 300 MHz): δ1.43 (t, J=7.2 Hz, 3H), 1.48-1.57 (m, 2H), 1.83-1.91 (m, 2H), 2.45-2.52 (m, 2H), 3.10-3.19 (m, 2H), 3.78 (d, J=6.0 Hz, 1H), 3.90-4.42 (m, 5H), 6.49 (d, J=0.6 Hz, 1H), 7.14-7.23 (m, 2H), 7.29-7.36 (m, 2H), 8.38 (d, J=0.6 Hz, 1H). MS (ES+) m/z 460.2, 462.2 [M+H, Cl isotopes].

Example 89

(1R,5S,8s)-N-(5-(3-Chlorophenoxy)-1-ethyl-1H-1,2,4-triazol-3-yl)-3-(5-methyl-1,3,4-oxadiazol-2-yl)-3-azabicyclo[3.2.1]octan-8-amine

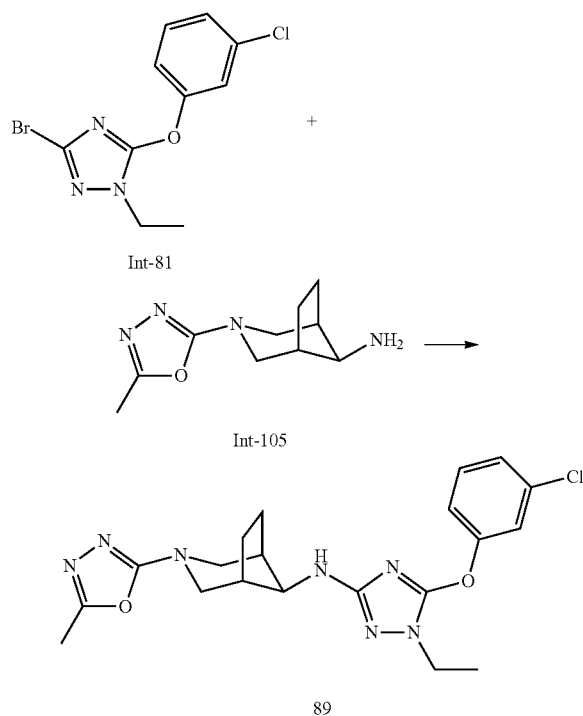

In an 8 mL microwave vial (1R,5S,8s)-3-(5-methyl-1,3,4-oxadiazol-2-yl)-3-azabicyclo[3.2.1]octan-8-amine (Int-105, 60 mg, 288 µmol) was suspended in 1,4-dioxane (4 mL) and 3-bromo-5-(3-chlorophenoxy)-1-ethyl-1H-1,2,4-triazole (Int-81, 109 mg, 288 µmol), sodium tert-butoxide (58.3 mg, 576 µmol), 1,2,3,4,5-pentaphenyl-1'-(di-tert-butylphosphino)ferrocene ("Q-phos", CAS [312959-24-3], 34.5 mg, 46.1 µmol), and tris(dibenzylideneacetone)dipalladium (0) chloroform adduct (24.6 mg, 23 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v, then dichloromethane/methanol, gradient 100:0 to 97.7:2.3 v/v), followed by column chromatography (amino modified silica gel, 50 g, eluting with ethyl acetate/n-heptane, gradient 0:100 to 66:34 v/v) to yield the title compound as a white foam (20 mg, 16%). $^1$H NMR (CDCl$_3$, 300 MHz): δ 1.43 (t, J=7.2 Hz, 3H), 1.60-1.69 (m, 2H), 1.84-1.91 (m, 2H), 2.39 (s, 3H), 2.40-2.45 (m, 2H), 3.25-3.32 (m, 2H), 3.68-3.77 (m, 3H), 3.91 (d, J=6.4 Hz, 1H), 3.97 (d, J=7.2 Hz, 2H), 7.14-7.23 (m, 2H), 7.29-7.36 (m, 2H). MS (ES+) m/z 430.4, 432.3 [M+H, Cl isotopes].

Example 90

(1R,5S,8s)-N-(5-(3-Chlorophenoxy)-1-ethyl-1H-1,2,4-triazol-3-yl)-3-(2-methoxypyridin-4-yl)-3-azabicyclo[3.2.1]octan-8-amine

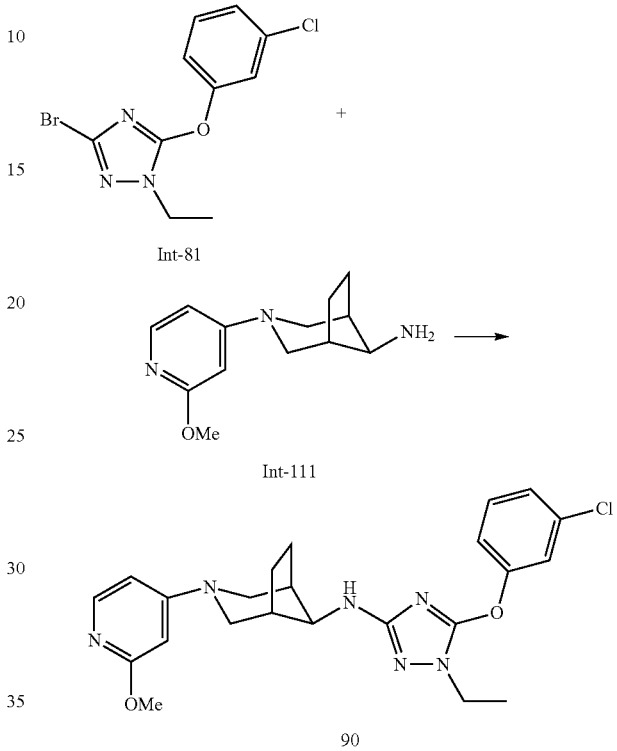

In an 8 mL microwave vial (1R,5S,8s)-3-(2-methoxypyridin-4-yl)-3-azabicyclo[3.2.1]octan-8-amine (Int-111, 50 mg, 214 µmol) was suspended in 1,4-dioxane (4 mL) and 3-bromo-5-(3-chlorophenoxy)-1-ethyl-1H-1,2,4-triazole (Int-81, 81 mg, 214 µmol), sodium tert-butoxide (43.4 mg, 429 µmol), 1,2,3,4,5-pentaphenyl-1'-(di-tert-butylphosphino)ferrocene ("Q-phos", CAS [312959-24-3], 25.7 mg, 34.3 µmol), and tris(dibenzylideneacetone)dipalladium (0) chloroform adduct (18.3 mg, 17.1 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 30:70 v/v), followed by column chromatography (silica gel, 20 g, eluting with dichloromethane/ethyl acetate, gradient 100:0 to 40:60 v/v) to afford the title compound as a light red foam (38 mg, 39%). HPLC (method LCMS_fastgradient) t$_R$=0.95 min. $^1$H NMR (CDCl$_3$, 300 MHz): δ1.43 (t, J=7.2 Hz, 3H), 1.57-1.65 (m, 2H), 1.84-1.91 (m, 2H), 2.44-2.50 (m, 2H), 3.03-3.10 (m, 2H), 3.59 (dd, J=3.2, 11.9 Hz, 2H), 3.72 (d, J=6.2 Hz, 1H), 3.90 (s, 3H), 3.93 (d, J=6.0 Hz, 1H), 3.97 (q, J=7.2 Hz, 2H), 5.99 (d, J=2.2 Hz, 1H), 6.35 (dd, J=2.2, 6.2 Hz, 1H), 7.14-7.23 (m, 2H), 7.29-7.36 (m, 2H), 7.87 (d, J=6.0 Hz, 1H). MS (ES+) m/z 455.3, 457.2 [M+H, Cl isotopes].

Example 91

(1R,5S,8s)-N-(5-(3-Chlorophenoxy)-1-propyl-1H-1,2,4-triazol-3-yl)-3-(6-methylpyrimidin-4-yl)-3-azabicyclo[3.2.1]octan-8-amine

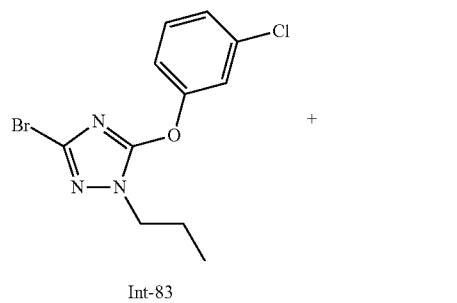

Int-83

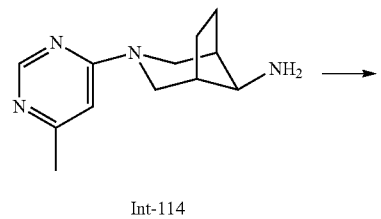

Int-114

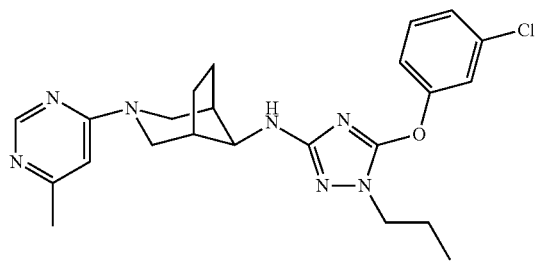

91

In an 8 mL microwave vial (1R,5S,8s)-3-(6-methylpyrimidin-4-yl)-3-azabicyclo[3.2.1]octan-8-amine (Int-114, 50 mg, 229 µmol) was suspended in 1,4-dioxane (4 mL) and 3-bromo-5-(3-chlorophenoxy)-1-propyl-1H-1,2,4-triazole (Int-83, 90.6 mg, 229 µmol), sodium tert-butoxide (46.3 mg, 458 µmol), 1,2,3,4,5-pentaphenyl-1'-(di-tert-butylphosphino)ferrocene ("Q-phos", CAS [312959-24-3], 27.4 mg, 36.6 µmol), and tris(dibenzylideneacetone)dipalladium (0) chloroform adduct (19.6 mg, 18.3 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate, then dichloromethane/methanol, gradient 100:0 to 90:10 v/v), followed by column chromatography (amino modified silica gel, 50 g, eluting with ethyl acetate/n-heptane, gradient 0:100 to 33:67 v/v) to yield the title compound as an off-white foam (43 mg, 41%). $^1$H NMR (CDCl$_3$, 300 MHz): δ 0.98 (t, J=7.4 Hz, 3H), 1.50-1.59 (m, 2H), 1.79-1.93 (m, 4H), 2.36 (s, 3H), 2.43-2.49 (m, 2H), 3.06-3.14 (m, 2H), 3.77 (d, J=6.2 Hz, 1H), 3.88 (t, J=7.0 Hz, 2H), 3.92 (t, J=6.6 Hz, 1H), 4.04-4.20 (m, 2H), 6.34 (s, 1H), 7.14-7.23 (m, 2H), 7.29-7.36 (m, 2H), 8.51 (d, J=0.8 Hz, 1H). MS (ES+) m/z 454.4, 456.3 [M+H, Cl isotopes].

Example 92

(1R,5S,8s)-N-(5-(3-Chlorophenoxy)-1-(2,2,2-trifluoroethyl)-1H-1,2,4-triazol-3-yl)-3-(6-chloropyridazin-4-yl)-3-azabicyclo[3.2.1]octan-8-amine

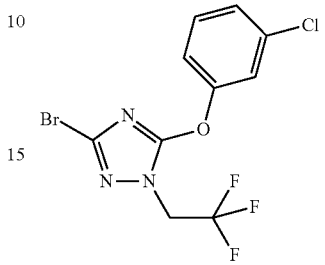

Int-45

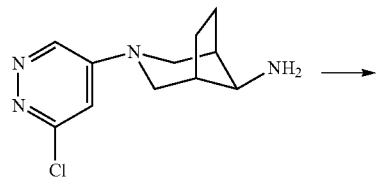

Int-126

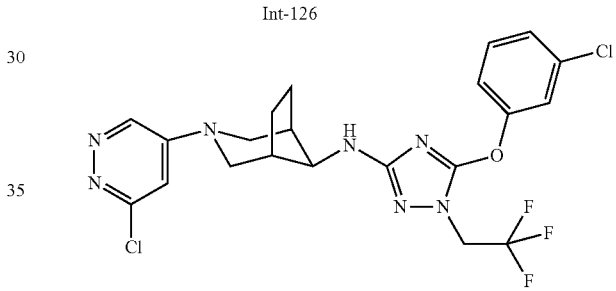

92

In an 8 mL microwave vial (1R,5S,8s)-3-(6-chloropyridazin-4-yl)-3-azabicyclo[3.2.1]octan-8-amine (Int-126, 60 mg, 251 µmol) was suspended in 1,4-dioxane (4 mL) and 3-bromo-5-(3-chlorophenoxy)-1-(2,2,2-trifluoroethyl)-1H-1,2,4-triazole (Int-45, 89.6 mg, 251 µmol), sodium tert-butoxide (50.9 mg, 503 µmol), 1,2,3,4,5-pentaphenyl-1'-(di-tert-butylphosphino)ferrocene ("Q-phos", CAS [312959-24-3], 30.1 mg, 40.2 µmol), and tris(dibenzylideneacetone)dipalladium (0) chloroform adduct (21.5 mg, 20.1 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v), followed by column chromatography (amino modified silica gel, 50 g, eluting with ethyl acetate/n-heptane, gradient 0:100 to 57:43 v/v) to afford the title compound as a white solid (52 mg, 40%). HPLC (method LCMS_fastgradient) $t_R$=1.28 min. $^1$H NMR (CDCl$_3$, 300 MHz): δ1.56-1.65 (m, 2H), 1.89-1.99 (m, 2H), 2.53-2.60 (m, 2H), 3.17-3.26 (m, 2H), 3.65 (dd, J=3.0, 12.1 Hz, 2H), 3.76 (d, J=5.6 Hz, 1H), 4.04 (d, J=5.6 Hz, 1H), 4.52 (q, J=8.1 Hz, 2H), 6.64 (d, J=2.8

Hz, 1H), 7.17-7.29 (m, 2H), 7.33-7.40 (m, 2H), 8.72 (d, J=2.8 Hz, 1H). MS (ES+) m/z 514.2, 516.1 [M+H, Cl isotopes].

Example 93

(1R,5S,8s)-N-(5-(3-Chlorophenoxy)-1-(2,2,2-trifluoroethyl)-1H-1,2,4-triazol-3-yl)-3-(6-methylpyrimidin-4-yl)-3-azabicyclo[3.2.1]octan-8-amine

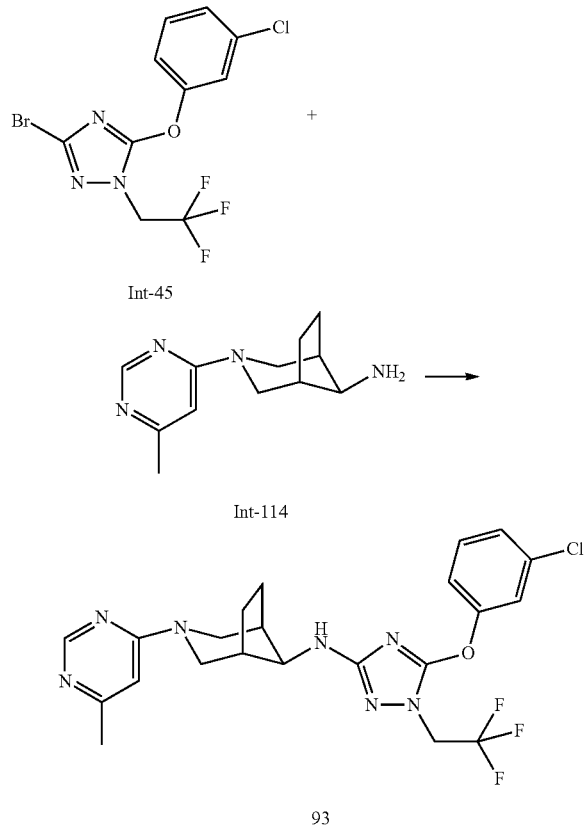

In an 8 mL microwave vial, (1R,5S,8s)-3-(6-methylpyrimidin-4-yl)-3-azabicyclo[3.2.1]octan-8-amine (Int-114, 60 mg, 275 µmol) was suspended in 1,4-dioxane (4 mL) and 3-bromo-5-(3-chlorophenoxy)-1-(2,2,2-trifluoroethyl)-1H-1,2,4-triazole (Int-45, 98 mg, 275 µmol), sodium tert-butoxide (55.6 mg, 550 µmol), 1,2,3,4,5-pentaphenyl-1'-(di-tert-butylphosphino)ferrocene ("Q-phos", CAS [312959-24-3], 32.9 mg, 44 µmol), and tris(dibenzylideneacetone)dipalladium (0) chloroform adduct (23.5 mg, 22 µmol) were added subsequently. The vial was degassed thoroughly with Argon and sealed. The reaction mixture was heated under microwave irradiation at 110° C. for 30 min. After that, the mixture was concentrated in vacuo. The resulting crude product was purified by column chromatography (silica gel, 70 g, eluting with ethyl acetate/n-heptane, gradient 0:100 to 100:0 v/v, then dichloromethane/methanol, gradient 100:0 to 85:15 v/v), followed by column chromatography (amino modified silica gel, 50 g, eluting with ethyl acetate/n-heptane, gradient 0:100 to 38:62 v/v), followed by preparative HPLC (YMC-Actus Triart C18, 100×30 mm×5 µm, eluting with acetonitrile/(water+0.1% triethylamine), gradient 20:80 to 98:2 v/v) and lyophilization to yield the title compound as a light yellow foam (44 mg, 32%). HPLC (method LCMS_fastgradient) $t_R$=0.99 min. $^1$H NMR (CDCl$_3$, 300 MHz): δ1.50-1.61 (m, 2H), 1.78-1.87 (m, 2H), 2.36 (s, 3H), 2.43-2.50 (m, 2H), 3.05-3.14 (m, 2H), 3.75 (d, J=6.0 Hz, 1H), 4.02 (d, J=6.0 Hz, 1H), 4.06-4.20 (m, 2H), 4.52 (q, J=8.2 Hz, 2H), 6.34 (s, 1H), 7.17-7.25 (m, 2H), 7.32-7.39 (m, 2H), 8.51 (d, J=0.8 Hz, 1H). MS (ES+) m/z 494.2, 496.2 [M+H, Cl isotopes].

Example 94

(1R,5S,8s)-N-(5-(3-Chlorophenoxy)-1-propyl-1H-1,2,4-triazol-3-yl)-3-(6-chloropyrimidin-4-yl)-3-azabicyclo[3.2.1]octan-8-amine

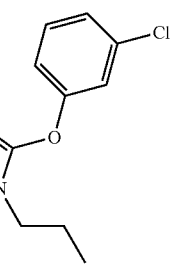

In an 8 mL microwave vial (1R,5S,8s)-3-(6-chloropyrimidin-4-yl)-3-azabicyclo[3.2.1]octan-8-amine (Int-108, 60 mg, 251 µmol) was suspended in 1,4-dioxane (4 mL) and 3-bromo-5-(3-chlorophenoxy)-1-propyl-1H-1,2,4-triazole (Int-83, 99.5 mg, 251 µmol), sodium tert-butoxide (50.9 mg, 503 µmol), 1,2,3,4,5-pentaphenyl-1'-(di-tert-butylphosphino)ferrocene ("Q-phos", CAS [312959-24-3], 30.1 mg, 40.2 µmol), and tris(dibenzylideneacetone)dipalladium (0) chloroform adduct (21.5 mg, 20.1 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate), followed by column chromatography (amino modified silica gel, 50 g, eluting with ethyl acetate/n-heptane, gradient 0:100 to 28:72 v/v) to afford the title compound as a white foam (32 mg, 27%). HPLC (method LCMS_fastgradient) $t_R$=1.46 min. $^1$H NMR (CDCl$_3$, 300 MHz): δ 0.98 (t, J=7.4 Hz, 3H), 1.48-1.57 (m, 2H), 1.80-1.93 (m, 4H), 2.45-2.51 (m, 2H), 3.09-3.19 (m, 2H), 3.78 (d, J=6.2 Hz, 1H), 3.84-3.94 (m, 3H), 3.85-4.39 (m, 2H), 6.48 (d, J=0.6 Hz, 1H), 7.14-7.23 (m, 2H), 7.29-7.36 (m, 2H), 8.38 (d, J=0.8 Hz, 1H). MS (ES+) m/z 474.2, 476.2 [M+H, Cl isotopes].

Example 95

(1R,5S,8s)-N-(5-(3-Fluoro-5-methylphenoxy)-1-methyl-1H-1,2,4-triazol-3-yl)-3-(6-chloropyridazin-4-yl)-3-azabicyclo[3.2.1]octan-8-amine

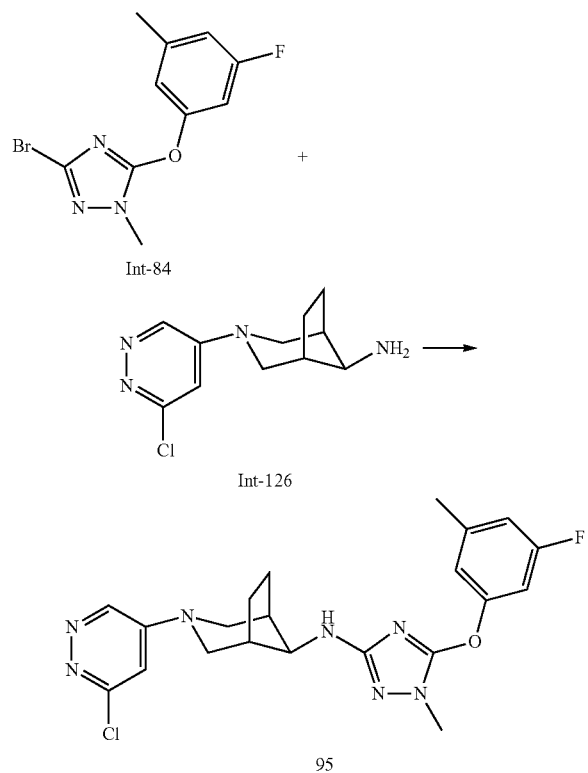

In an 8 mL microwave vial (1R,5S,8s)-3-(6-chloropyridazin-4-yl)-3-azabicyclo[3.2.1]octan-8-amine (Int-126, 45 mg, 189 μmol) was suspended in 1,4-dioxane (3 mL) and 3-bromo-5-(3-fluoro-5-methylphenoxy)-1-methyl-1H-1,2,4-triazole (Int-84, 53.9 mg, 189 μmol), sodium tert-butoxide (38.1 mg, 377 μmol), 1,2,3,4,5-pentaphenyl-1'-(di-tert-butylphosphino)ferrocene ("Q-phos", CAS [312959-24-3], 22.6 mg, 30.2 μmol), and tris(dibenzylideneacetone)dipalladium (0) chloroform adduct (16.1 mg, 15.1 μmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v, then eluting with dichloromethane/methanol 90:10 v/v), followed by column chromatography (amino modified silica gel, 50 g, eluting with ethyl acetate/n-heptane, gradient 0:100 to 50:50 v/v) to afford the title compound as a white solid (34 mg, 41%). HPLC (method LCMS_fastgradient) $t_R$=1.14 min. $^1$H NMR (CDCl$_3$, 300 MHz): δ 1.55-1.64 (m, 2H), 1.89-1.99 (m, 2H), 2.37 (s, 3H), 2.53-2.60 (m, 2H), 3.18-3.26 (m, 2H), 3.63 (s, 3H), 3.64-3.70 (m, 2H), 3.76 (d, J=5.8 Hz, 1H), 3.96 (d, J=5.8 Hz, 1H), 6.63 (d, J=2.8 Hz, 1H), 6.67-6.79 (m, 1H), 6.81-6.87 (m, 2H), 8.71 (d, J=2.8 Hz, 1H). MS (ES+) m/z 444.1, 446.1 [M+H, Cl isotopes].

Example 96

(1R,5S,8s)-N-(5-(3-Chlorophenoxy)-1-(2,2,2-trifluoroethyl)-1H-1,2,4-triazol-3-yl)-3-(2-methoxypyridin-4-yl)-3-azabicyclo[3.2.1]octan-8-amine

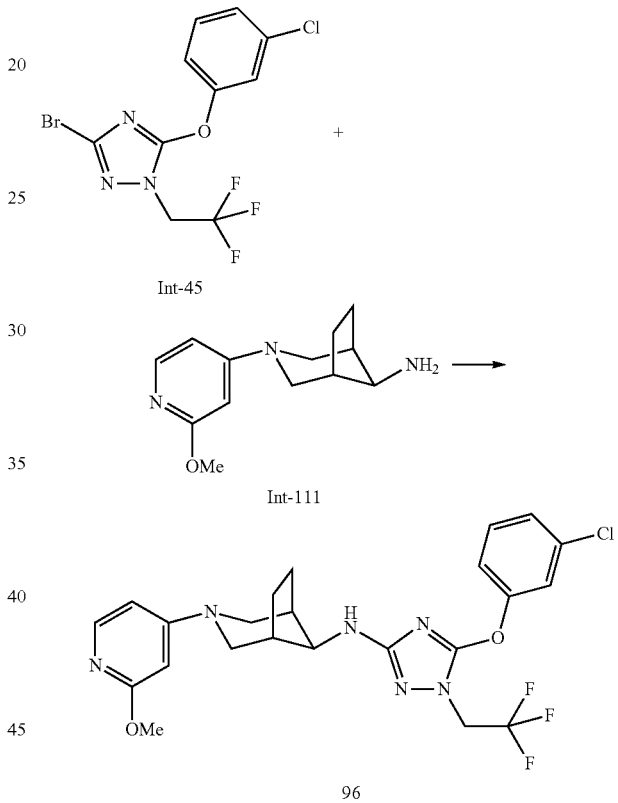

In an 8 mL microwave vial (1R,5S,8s)-3-(2-methoxypyridin-4-yl)-3-azabicyclo[3.2.1]octan-8-amine (Int-111, 50 mg, 214 μmol) was suspended in 1,4-dioxane (4 mL) and 3-bromo-5-(3-chlorophenoxy)-1-(2,2,2-trifluoroethyl)-1H-1,2,4-triazole (Int-45, 76.4 mg, 214 μmol), sodium tert-butoxide (43.4 mg, 429 μmol), 1,2,3,4,5-pentaphenyl-1'-(di-tert-butylphosphino)ferrocene ("Q-phos", CAS [312959-24-3], 25.7 mg, 34.3 μmol), and tris(dibenzylideneacetone)dipalladium (0) chloroform adduct (18.3 mg, 17.1 μmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 73:27 v/v), followed by column chromatography (amino modified silica gel, 50 g, eluting with ethyl acetate/n-heptane, gradient 0:100 to 43:57 v/v) to afford the title compound as a white foam (45 mg, 41%). HPLC (method LCMS_fastgradient) $t_R$=1.01 min. $^1$H NMR (CDCl$_3$, 300 MHz): δ1.57-1.66 (m, 2H), 1.81-1.90 (m, 2H), 2.43-2.50 (m, 2H), 3.01-3.09 (m, 2H), 3.59 (dd, J=3.2, 11.9 Hz, 2H), 3.70 (d, J=6.0 Hz, 1H), 3.90 (s, 3H), 4.02 (d, J=5.8 Hz, 1H), 4.52 (q, J=8.2 Hz, 2H), 5.99 (d, J=2.2 Hz, 1H), 6.35 (dd, J=2.4, 6.2 Hz, 1H), 7.18-7.26 (m, 2H), 7.32-7.39 (m, 2H), 7.87 (d, J=6.0 Hz, 1H). MS (ES+) m/z 509.2, 511.2 [M+H, Cl isotopes].

Example 97

(1R,5S,8s)-N-(5-(3-Chlorophenoxy)-1-(2,2,2-trifluoroethyl)-1H-1,2,4-triazol-3-yl)-3-(6-chloropyrimidin-4-yl)-3-azabicyclo[3.2.1]octan-8-amine

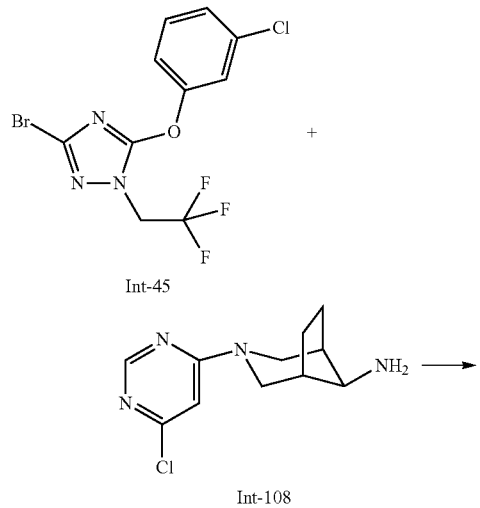

gel, 50 g, eluting with ethyl acetate/n-heptane, gradient 0:100 to 30:70 v/v) to afford the title compound as a white foam (38 mg, 29%). HPLC (method LCMS_fastgradient) $t_R$=1.43 min. $^1$H NMR (CDCl$_3$, 300 MHz): δ1.50-1.63 (m, 2H), 1.81-1.92 (m, 2H), 2.45-2.53 (m, 2H), 3.10-3.20 (m, 2H), 3.76 (d, J=5.8 Hz, 1H), 3.82-4.44 (m, 2H), 4.02 (d, J=6.0 Hz, 1H), 4.52 (q, J=8.2 Hz, 2H), 6.49 (d, J=0.8 Hz, 1H), 7.18-7.26 (m, 2H), 7.33-7.39 (m, 2H), 8.38 (d, J=0.6 Hz, 1H). MS (ES+) m/z 514.2, 516.2 [M+H, Cl isotopes].

Example 98

(1R,5S,8s)-N-(5-(3-Fluoro-5-methylphenoxy)-1-methyl-1H-1,2,4-triazol-3-yl)-3-(6-chloropyrimidin-4-yl)-3-azabicyclo[3.2.1]octan-8-amine

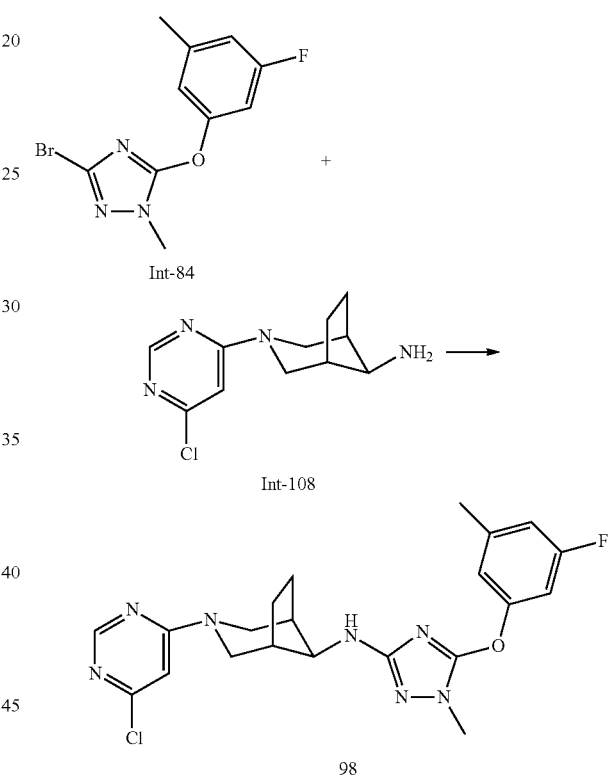

In an 8 mL microwave vial (1R,5S,8s)-3-(6-chloropyrimidin-4-yl)-3-azabicyclo[3.2.1]octan-8-amine (Int-108, 60 mg, 251 μmol) was suspended in 1,4-dioxane (4 mL) and 3-bromo-5-(3-chlorophenoxy)-1-(2,2,2-trifluoroethyl)-1H-1,2,4-triazole (Int-45, 89.6 mg, 251 μmol), sodium tert-butoxide (50.9 mg, 503 μmol), 1,2,3,4,5-pentaphenyl-1'-(di-tert-butylphosphino)ferrocene ("Q-phos", CAS [312959-24-3], 30.1 mg, 40.2 μmol), and tris(dibenzylideneacetone)dipalladium (0) chloroform adduct (21.5 mg, 20.1 μmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 68:32 v/v), followed by column chromatography (amino modified silica In an 8 mL microwave vial (1R,5S,8s)-3-(6-chloropyrimidin-4-yl)-3-azabicyclo[3.2.1]octan-8-amine (Int-108, 45 mg, 189 μmol) was suspended in 1,4-dioxane (3 mL) and 3-bromo-5-(3-fluoro-5-methylphenoxy)-1-methyl-1H-1,2, 4-triazole (Int-84, 53.9 mg, 189 μmol), sodium tert-butoxide (38.1 mg, 377 μmol), 1,2,3,4,5-pentaphenyl-1'-(di-tert-butylphosphino)ferrocene ("Q-phos", CAS [312959-24-3], 22.6 mg, 30.2 μmol), and tris(dibenzylideneacetone)dipalladium (0) chloroform adduct (16.1 mg, 15.1 μmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 40:60 v/v), followed by column chromatography (amino modified silica gel, 50 g, eluting with ethyl acetate/ n-heptane, gradient 0:100 to 25:75 v/v), followed by preparative HPLC (YMC-Actus Triart C18, 100×30 mm×5 µm, eluting with acetonitrile/(water+0.1% triethylamine), gradient 20:80 to 98:2 v/v) and lyophilization to afford the title compound as a white solid (13 mg, 15%). HPLC (method LCMS_fastgradient) $t_R$=1.30 min. $^1$H NMR (CDCl$_3$, 300 MHz): δ1.48-1.60 (m, 2H), 1.81-1.90 (m, 2H), 2.37 (s, 3H), 2.44-2.52 (m, 2H), 3.09-3.19 (m, 2H), 3.63 (s, 3H), 3.76 (d, J=6.0 Hz, 1H), 3.80-4.34 (m, 2H), 3.94 (d, J=6.0 Hz, 1H), 6.48 (d, J=0.6 Hz, 1H), 6.72-6.79 (m, 1H), 6.80-6.88 (m, 2H), 8.38 (d, J=0.6 Hz, 1H). MS (ES+) m/z 444.2, 446.2 [M+H, Cl isotopes].

Example 99

(1R,5S,8s)-N-(5-(3-Chloro-5-methylphenoxy)-1-methyl-1H-1,2,4-triazol-3-yl)-3-(6-methylpyrimidin-4-yl)-3-azabicyclo[3.2.1]octan-8-amine

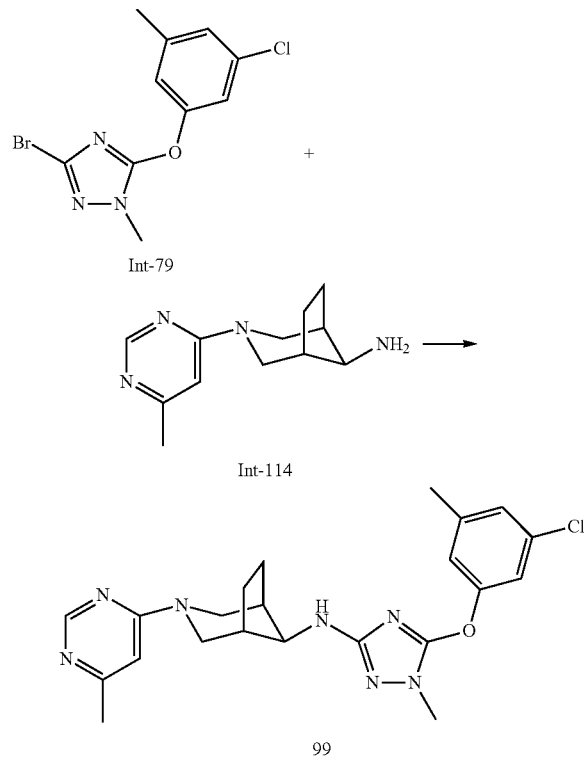

In an 8 mL microwave vial, (1R,5S,8s)-3-(6-methylpyrimidin-4-yl)-3-azabicyclo[3.2.1]octan-8-amine (Int-114, 45 mg, 206 µmol) was suspended in 1,4-dioxane (3 mL) and 3-bromo-5-(3-chloro-5-methylphenoxy)-1-methyl-1H-1,2,4-triazole (Int-79, 62.4 mg, 206 µmol), sodium tert-butoxide (41.7 mg, 412 µmol), 1,2,3,4,5-pentaphenyl-1'-(di-tert-butylphosphino)ferrocene ("Q-phos", CAS [312959-24-3], 24.7 mg, 33 µmol), and tris(dibenzylideneacetone)dipalladium (0) chloroform adduct (17.6 mg, 16.5 µmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (silica gel, 50 g, eluting with ethyl acetate/n-heptane, gradient 0:100 to 100:0 v/v, then dichloromethane/methanol, 90:10 v/v), followed by column chromatography (amino modified silica gel, 50 g, eluting with ethyl acetate/n-heptane, gradient 0:100 to 50:50 v/v) to yield the title compound as an off-white solid (39 mg, 43%). $^1$H NMR (CDCl$_3$, 300 MHz): δ1.50-1.59 (m, 2H), 1.79-1.88 (m, 2H), 2.35 (d, J=0.6 Hz, 3H), 2.36 (s, 3H), 2.43-2.50 (m, 2H), 3.05-3.14 (m, 2H), 3.63 (s, 3H), 3.75 (d, J=6.2 Hz, 1H), 3.94 (d, J=6.2 Hz, 1H), 4.05-4.21 (m, 2H), 6.34 (s, 1H), 6.95-6.98 (m, 1H), 7.02-7.05 (m, 1H), 7.09-7.12 (m, 1H), 8.51 (d, J=0.8 Hz, 1H). MS (ES+) m/z 440.3, 442.3 [M+H, Cl isotopes].

Example 100

(1R,5S,8s)-N-(5-(3-Fluoro-5-methylphenoxy)-1-methyl-1H-1,2,4-triazol-3-yl)-3-(6-methylpyrimidin-4-yl)-3-azabicyclo[3.2.1]octan-8-amine

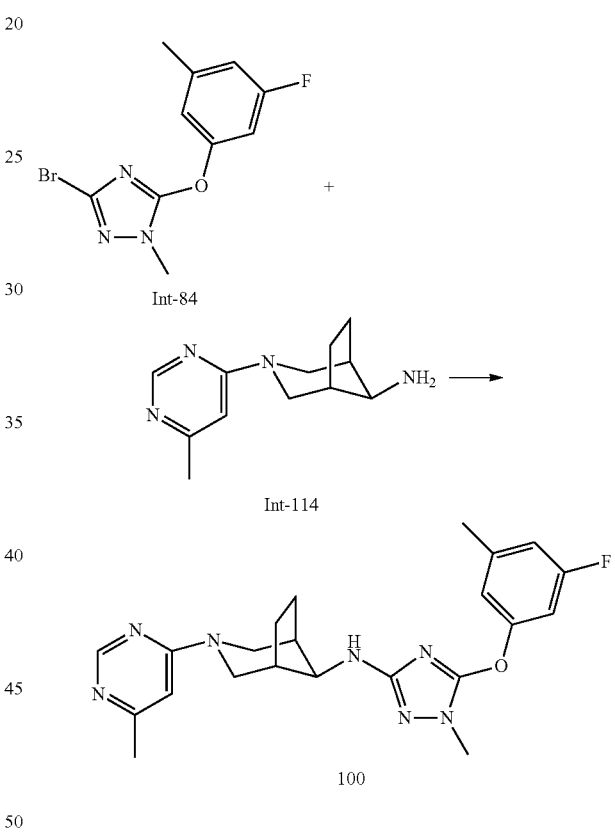

In an 8 mL microwave vial, (1R,5S,8s)-3-(6-methylpyrimidin-4-yl)-3-azabicyclo[3.2.1]octan-8-amine (Int-114, 45 mg, 206 µmol) was suspended in 1,4-dioxane (3 mL) and 3-bromo-5-(3-fluoro-5-methylphenoxy)-1-methyl-1H-1,2,4-triazole (Int-84, 59 mg, 206 µmol), sodium tert-butoxide (41.7 mg, 412 µmol), 1,2,3,4,5-pentaphenyl-1'-(di-tert-butylphosphino)ferrocene ("Q-phos", CAS [312959-24-3], 24.7 mg, 33 µmol), and tris(dibenzylideneacetone)dipalladium (0) chloroform adduct (17.6 mg, 16.5 µmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (silica gel, 50 g, eluting with ethyl acetate/n-heptane, gradient 0:100 to 100:0 v/v, then dichloromethane/methanol, 90:10 v/v), followed by column chromatography (amino modified silica gel, 50 g, eluting with ethyl acetate/n-heptane, gradient 0:100 to 50:50 v/v) to yield the title compound as a white solid (51 mg, 58%). $^1$H NMR (CDCl$_3$, 300 MHz): δ 1.50-1.58 (m, 2H), 1.79-1.88 (m, 2H), 2.36 (2s, 6H), 2.44-2.50 (m, 2H), 3.06-3.14 (m, 2H), 3.63 (s, 3H), 3.75 (d, J=6.2 Hz, 2H), 3.94 (d, J=6.2 Hz, 1H), 4.06-4.21 (m, 2H), 6.34 (s, 1H), 6.73-6.79 (m, 1H), 6.81-6.88 (m, 2H), 8.51 (d, J=0.8 Hz, 1H). MS (ES+) m/z 434.3 [M+H].

Example 101

(1R,5S,8s)-N-(5-(3-Chlorophenoxy)-1-ethyl-1H-1,2,4-triazol-3-yl)-3-(2-chloropyridin-4-yl)-3-azabicyclo[3.2.1]octan-8-amine

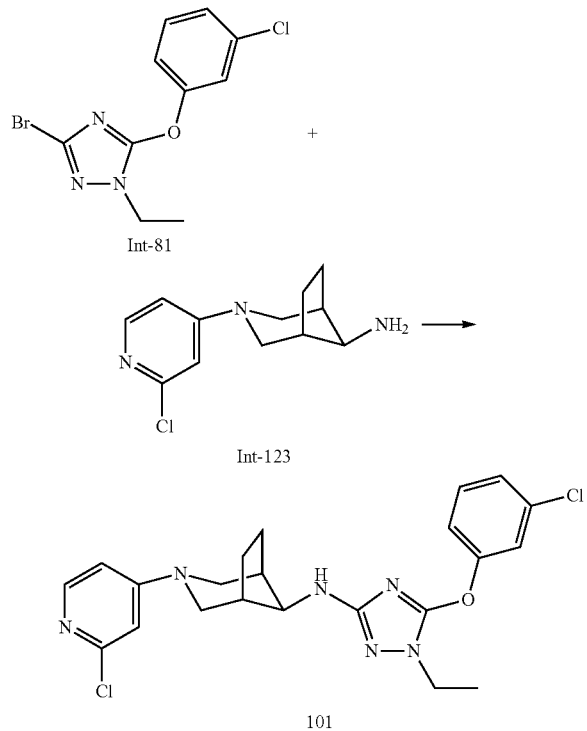

In an 8 mL microwave vial (1R,5S,8s)-3-(2-chloropyridin-4-yl)-3-azabicyclo[3.2.1]octan-8-amine (Int-123, 50 mg, 210 µmol) was suspended in 1,4-dioxane (4 mL) and 3-bromo-5-(3-chlorophenoxy)-1-ethyl-1H-1,2,4-triazole (Int-81, 79.5 mg, 210 µmol), sodium tert-butoxide (42.6 mg, 421 µmol), 1,2,3,4,5-pentaphenyl-1'-(di-tert-butylphosphino)ferrocene ("Q-phos", CAS [312959-24-3], 25.2 mg, 33.7 µmol), and tris(dibenzylideneacetone)dipalladium (0) chloroform adduct (18 mg, 16.8 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate/dichloromethane, 45:55 v/v), followed by preparative HPLC (YMC-Actus Triart C18, 100×30 mm×5 µm, eluting with acetonitrile/(water+0.1% triethylamine), gradient 20:80 to 98:2 v/v) and lyophilization to afford the title compound as an off-white foam (44 mg, 45%). HPLC (method LCMS-_fastgradient) t$_R$=1.21 min. $^1$H NMR (CDCl$_3$, 300 MHz): δ 1.43 (t, J=7.2 Hz, 3H), 1.56-1.64 (m, 2H), 1.87-1.94 (m, 2H), 2.48-2.54 (m, 2H), 3.09-3.16 (m, 2H), 3.60 (dd, J=3.2, 11.9 Hz, 2H), 3.75 (d, J=6.0 Hz, 1H), 3.94 (d, J=6.0 Hz, 1H), 3.97 (q, J=7.2 Hz, 2H), 6.53 (dd, J=2.4, 6.2 Hz, 1H), 6.61 (d, J=2.4 Hz, 1H), 7.14-7.23 (m, 2H), 7.30-7.36 (m, 2H), 8.00 (d, J=6.0 Hz, 1H). MS (ES+) m/z 459.2, 461.2 [M+H, Cl isotopes].

Example 102

(1R,5S,8s)-N-(5-(3-Chlorophenoxy)-1-propyl-1H-1,2,4-triazol-3-yl)-3-(2-methoxypyridin-4-yl)-3-azabicyclo[3.2.1]octan-8-amine

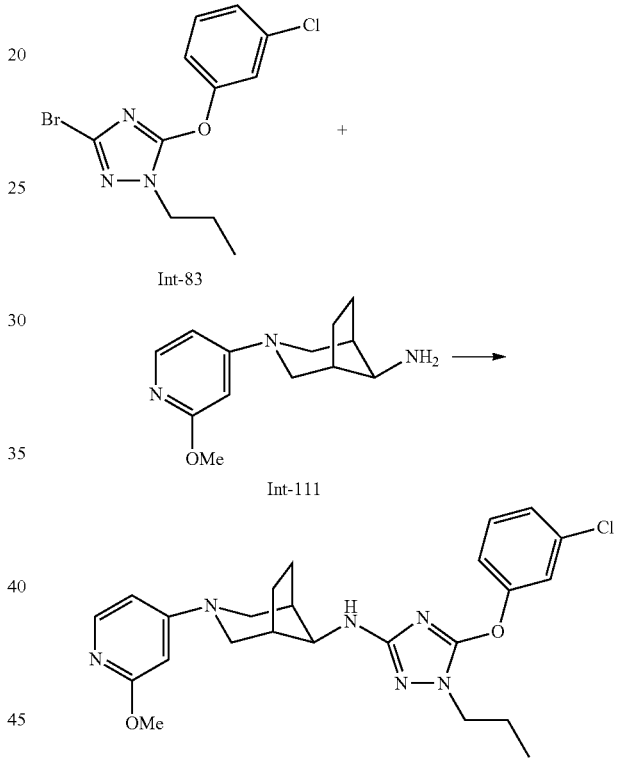

In an 8 mL microwave vial (1R,5S,8s)-3-(2-methoxypyridin-4-yl)-3-azabicyclo[3.2.1]octan-8-amine (Int-111, 50 mg, 214 µmol) was suspended in 1,4-dioxane (4 mL) and 3-bromo-5-(3-chlorophenoxy)-1-propyl-1H-1,2,4-triazole (Int-83, 84.8 mg, 214 µmol), sodium tert-butoxide (43.4 mg, 429 µmol), 1,2,3,4,5-pentaphenyl-1'-(di-tert-butylphosphino)ferrocene ("Q-phos", CAS [312959-24-3], 25.7 mg, 34.3 µmol), and tris(dibenzylideneacetone)dipalladium (0) chloroform adduct (18.3 mg, 17.1 µmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 28:72 v/v), followed by column chromatography (silica gel, 70 g, eluting with n-heptane/ethyl acetate, 18:82 v/v) to afford the title compound as a white foam (35 mg, 35%). HPLC (method LCMS_fastgradient) $t_R$=1.01 min. $^1$H NMR (CDCl$_3$, 300 MHz): δ 0.97 (t, J=7.4 Hz, 3H), 1.57-1.65 (m, 2H), 1.79-1.93 (m, 4H), 2.43-2.50 (m, 2H), 3.02-3.10 (m, 2H), 3.58 (dd, J=3.3, 11.8 Hz, 2H), 3.71 (d, J=6.2 Hz, 1H), 3.84-3.95 (m, 3H), 3.90 (s, 3H), 5.99 (d, J=2.2 Hz, 1H), 6.35 (dd, J=2.4, 6.2 Hz, 1H), 7.14-7.23 (m, 2H), 7.29-7.36 (m, 2H), 7.87 (d, J=6.2 Hz, 1H). MS (ES+) m/z 469.3, 471.2 [M+H, Cl isotopes].

Example 103

(1R,5S,8s)-N-(5-(3-Chlorophenoxy)-1-propyl-1H-1,2,4-triazol-3-yl)-3-(2-chloropyridin-4-yl)-3-azabicyclo[3.2.1]octan-8-amine

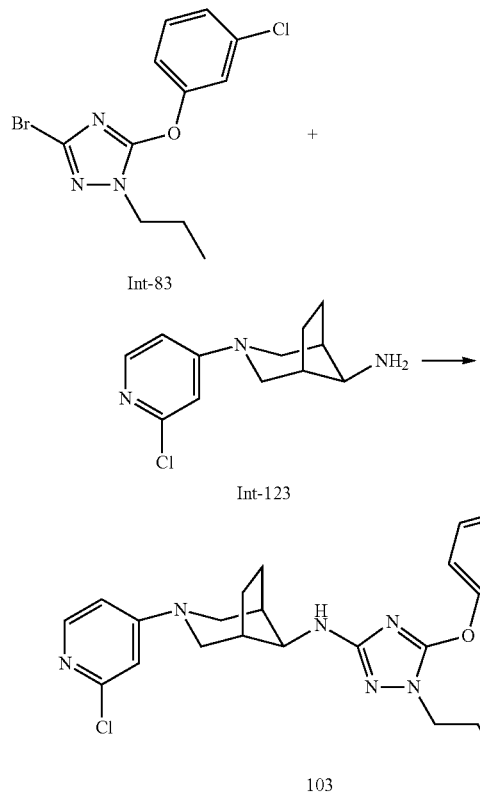

In an 8 mL microwave vial (1R,5S,8s)-3-(2-chloropyridin-4-yl)-3-azabicyclo[3.2.1]octan-8-amine (Int-123, 40 mg, 168 μmol) was suspended in 1,4-dioxane (4 mL) and 3-bromo-5-(3-chlorophenoxy)-1-propyl-1H-1,2,4-triazole (Int-83, 66.6 mg, 168 μmol), sodium tert-butoxide (34 mg, 337 μmol), 1,2,3,4,5-pentaphenyl-1'-(di-tert-butylphosphino)ferrocene ("Q-phos", CAS [312959-24-3], 20.1 mg, 26.9 μmol), and tris(dibenzylideneacetone)dipalladium (0) chloroform adduct (14.4 mg, 13.5 μmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate/n-heptane, 90:10 v/v), followed by column chromatography (amino modified silica gel, 50 g, eluting with ethyl acetate/n-heptane, gradient 0:100 to 41:59 v/v) to afford the title compound as an off-white solid (35 mg, 44%). $^1$H NMR (CDCl$_3$, 300 MHz): δ 0.97 (t, J=7.4 Hz, 3H), 1.55-1.64 (m, 2H), 1.79-1.95 (m, 4H), 2.47-2.54 (m, 2H), 3.08-3.16 (m, 2H), 3.59 (dd, J=3.0, 11.9 Hz, 2H), 3.74 (d, J=6.2 Hz, 1H), 3.88 (t, J=7.0 Hz, 2H), 3.93 (d, J=6.2 Hz, 1H), 6.53 (dd, J=2.4, 6.0 Hz, 1H), 6.61 (d, J=2.2 Hz, 1H), 7.14-7.23 (m, 2H), 7.29-7.36 (m, 2H), 8.00 (d, J=6.0 Hz, 1H). MS (ES+) m/z 473.4, 475.3 [M+H, Cl isotopes].

Example 104

(1R,5S,8s)-N-(5-(3-Chlorophenoxy)-1-propyl-1H-1,2,4-triazol-3-yl)-3-(5-methyl-1,3,4-oxadiazol-2-yl)-3-azabicyclo[3.2.1]octan-8-amine

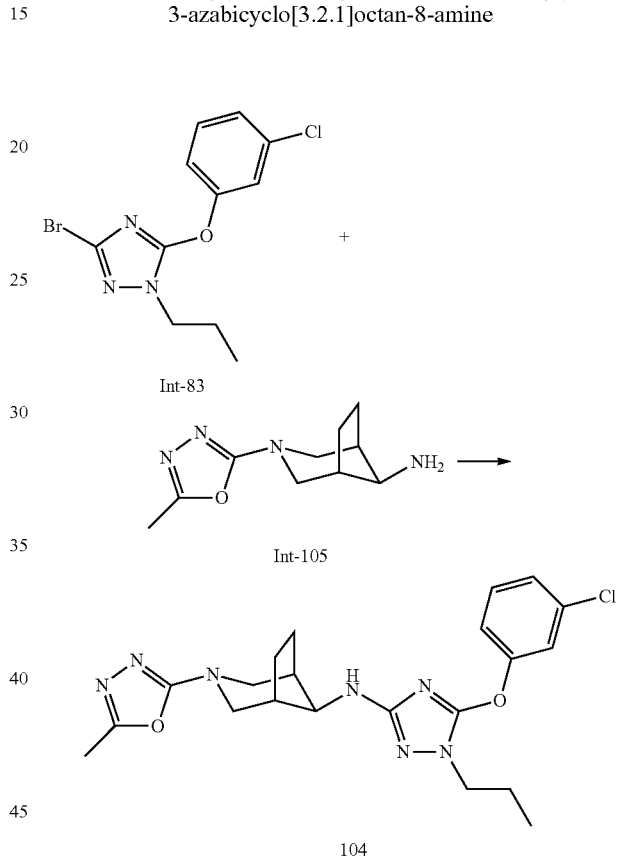

In an 8 mL microwave vial (1R,5S,8s)-3-(5-methyl-1,3,4-oxadiazol-2-yl)-3-azabicyclo[3.2.1]octan-8-amine (Int-105, 48 mg, 230 μmol) was suspended in 1,4-dioxane (4 mL) and 3-bromo-5-(3-chlorophenoxy)-1-propyl-1H-1,2,4-triazole (Int-83, 91.2 mg, 230 μmol), sodium tert-butoxide (46.6 mg, 461 μmol), 1,2,3,4,5-pentaphenyl-1'-(di-tert-butylphosphino)ferrocene ("Q-phos", CAS [312959-24-3], 27.6 mg, 36.9 μmol), and tris(dibenzylideneacetone)dipalladium (0) chloroform adduct (19.7 mg, 18.4 μmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate/n-heptane, gradient 0:100 to 100:0 v/v, then dichloromethane/methanol, gradient 100:0 to 84:16 v/v), followed by column chromatography (amino modified silica gel, 50 g, eluting with ethyl acetate/n-heptane, gradient 0:100 to 35:65 v/v) to yield the title compound as a white foam (17 mg, 17%). ¹H NMR (CDCl₃, 300 MHz): δ 0.97 (t, J=7.4 Hz, 3H), 1.60-1.68 (m, 2H), 1.79-1.93 (m, 4H), 2.39 (s, 3H), 2.39-2.45 (m, 2H), 3.25-3.32 (m, 2H), 3.68-3.76 (m, 3H), 3.88 (t, J=6.9 Hz, 2H), 3.90 (d, J=6.2 Hz, 1H), 7.14-7.23 (m, 2H), 7.29-7.36 (m, 2H). MS (ES+) m/z 444.4, 446.3 [M+H, Cl isotopes].

Example 105

(1R,5S,8s)-N-(5-(3-Chloro-5-methylphenoxy)-1-methyl-1H-1,2,4-triazol-3-yl)-3-(2-chloropyridin-4-yl)-3-azabicyclo[3.2.1]octan-8-amine

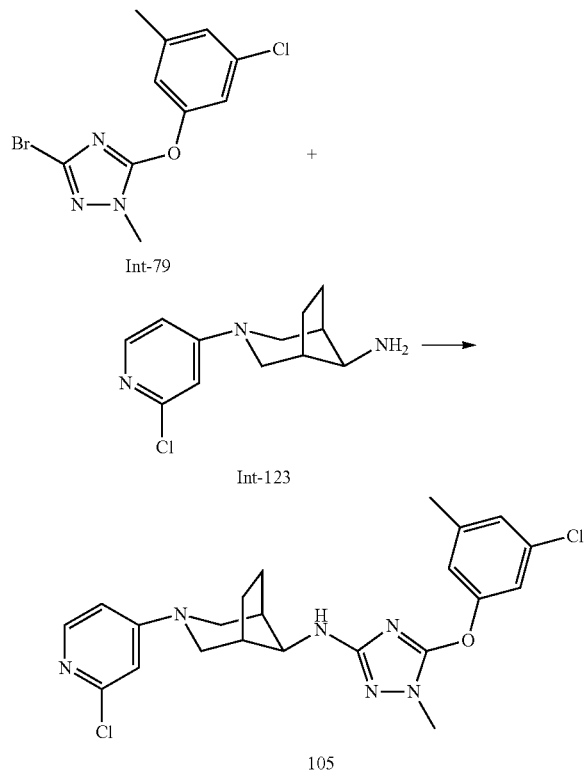

105

In an 8 mL microwave vial (1R,5S,8s)-3-(2-chloropyridin-4-yl)-3-azabicyclo[3.2.1]octan-8-amine (Int-123, 45 mg, 189 μmol) was suspended in 1,4-dioxane (3 mL) and 3-bromo-5-(3-chloro-5-methylphenoxy)-1-methyl-1H-1,2,4-triazole (Int-79, 57.3 mg, 189 μmol), sodium tert-butoxide (38.3 mg, 379 μmol), 1,2,3,4,5-pentaphenyl-1'-(di-tert-butylphosphino)ferrocene ("Q-phos", CAS [312959-24-3], 22.7 mg, 30.3 μmol), and tris(dibenzylideneacetone)dipalladium (0) chloroform adduct (16.2 mg, 15.1 μmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (silica gel, 50 g, eluting with ethyl acetate/n-heptane, gradient 0:100 to 100:0 v/v), followed by preparative HPLC (YMC-Actus Triart C18, 100×30 mm×5 μm, eluting with acetonitrile/(water+0.1% triethylamine), gradient 20:80 to 98:2 v/v) and lyophilization to afford the title compound as a white solid (36 mg, 41%). ¹H NMR (CDCl₃, 300 MHz): δ 1.55-1.64 (m, 2H), 1.85-1.95 (m, 2H), 2.36 (d, J=0.6 Hz, 3H), 2.48-2.54 (m, 2H), 3.08-3.15 (m, 2H), 3.59 (dd, J=3.0, 11.9 Hz, 2H), 3.62 (s, 3H), 3.72 (d, J=6.0 Hz, 1H), 3.95 (d, J=6.0 Hz, 1H), 6.53 (dd, J=2.4, 6.0 Hz, 1H), 6.61 (d, J=2.4 Hz, 1H), 6.95-6.98 (m, 1H), 7.03-7.05 (m, 1H), 7.09-7.12 (m, 1H), 8.00 (d, J=6.0 Hz, 1H). MS (ES+) m/z 459.3, 461.3 [M+H, Cl isotopes].

Example 106

(1R,5S,8s)-N-(5-(3-Fluoro-5-methylphenoxy)-1-methyl-1H-1,2,4-triazol-3-yl)-3-(2-chloropyridin-4-yl)-3-azabicyclo[3.2.1]octan-8-amine

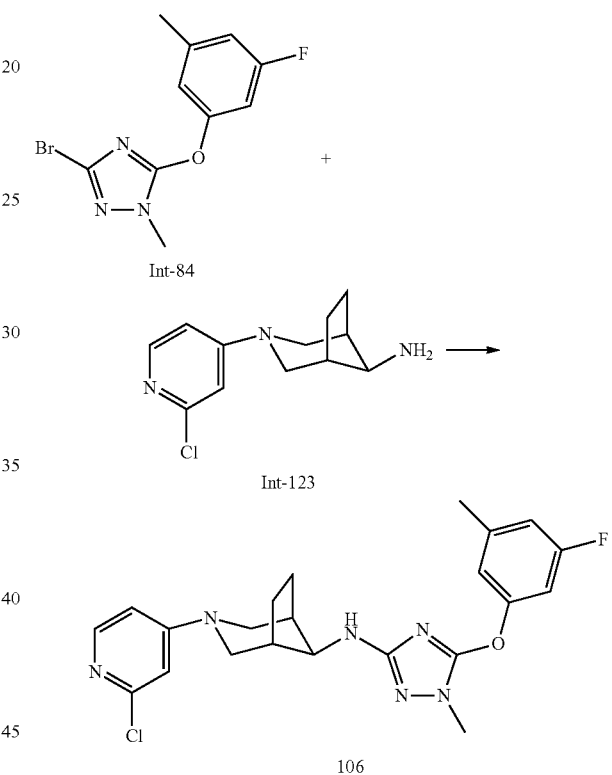

106

In an 8 mL microwave vial (1R,5S,8s)-3-(2-chloropyridin-4-yl)-3-azabicyclo[3.2.1]octan-8-amine (Int-123, 45 mg, 189 μmol) was suspended in 1,4-dioxane (3 mL) and 3-bromo-5-(3-fluoro-5-methylphenoxy)-1-methyl-1H-1,2,4-triazole (Int-84, 54.2 mg, 189 μmol), sodium tert-butoxide (38.3 mg, 379 μmol), 1,2,3,4,5-pentaphenyl-1'-(di-tert-butylphosphino)ferrocene ("Q-phos", CAS [312959-24-3], 22.7 mg, 30.3 μmol), and tris(dibenzylideneacetone)dipalladium (0) chloroform adduct (16.2 mg, 15.1 μmol) were added subsequently. The vial was degassed thoroughly with Argon and sealed. The reaction mixture was heated under microwave irradiation at 120° C. for 30 min. After that, the mixture was diluted with dichloromethane (10 mL) and concentrated in vacuo. The resulting crude product was purified by column chromatography (silica gel, 50 g, eluting with ethyl acetate/n-heptane, gradient 0:100 to 100:0 v/v), followed by preparative HPLC (YMC-Actus Triart C18, 100×30 mm×5 μm, eluting with acetonitrile/(water+0.1% triethylamine), gradient 20:80 to 98:2 v/v) and lyophiliza-

Example 107

(1R,5S,8s)-N-(5-(3-Chlorophenoxy)-1-(2,2-difluoro-ethyl)-1H-1,2,4-triazol-3-yl)-3-(6-chloropyridazin-4-yl)-3-azabicyclo[3.2.1]octan-8-amine

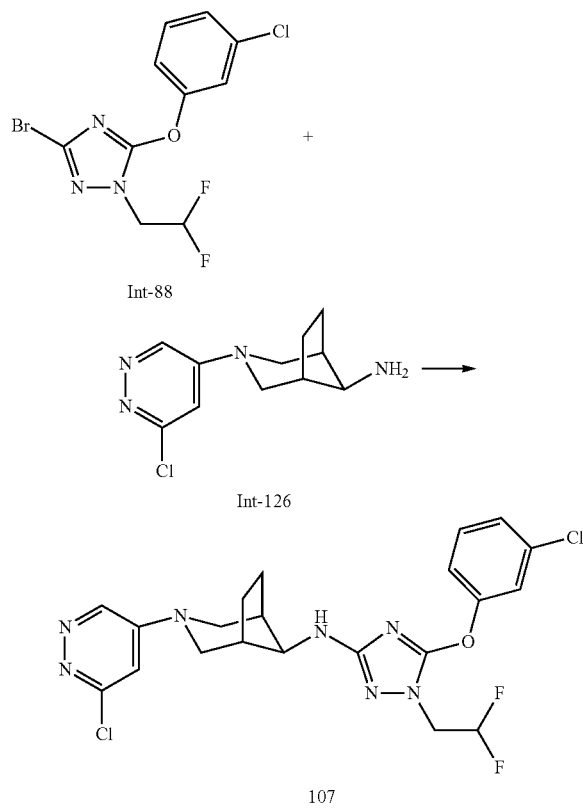

Example 108

(1R,5S,8s)-N-(5-(3-Chlorophenoxy)-1-(2-fluoro-ethyl)-1H-1,2,4-triazol-3-yl)-3-(6-chloropyridazin-4-yl)-3-azabicyclo[3.2.1]octan-8-amine

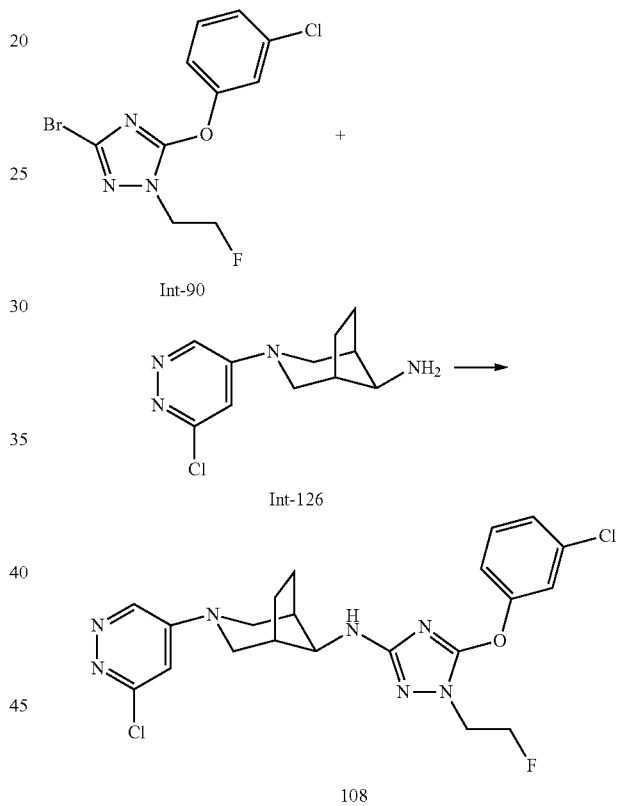

tion to afford the title compound as a white solid (25 mg, 30%). ¹H NMR (CDCl₃, 300 MHz): δ 1.56-1.64 (m, 2H), 1.85-1.94 (m, 2H), 2.37 (s, 3H), 2.47-2.55 (m, 2H), 3.07-3.16 (m, 2H), 3.59 (dd, J=3.0, 11.7 Hz, 2H), 3.73 (d, J=6.2 Hz, 1H), 3.95 (d, J=6.0 Hz, 1H), 6.53 (dd, J=2.4, 6.0 Hz, 1H), 6.60 (d, J=2.2 Hz, 1H), 6.73-6.79 (m, 1H), 6.81-6.88 (m, 2H), 8.00 (d, J=6.0 Hz, 1H). MS (ES+) m/z 443.3, 445.3 [M+H, Cl isotopes].

gradient 100:0 to 96.5:3.5 v/v) to afford the title compound as a white solid (46 mg, 37%). HPLC (method LCMS_fast-gradient) $t_R$=1.22 min. 1H NMR (CDCl₃, 300 MHz): δ1.56-1.65 (m, 2H), 1.90-1.99 (m, 2H), 2.53-2.60 (m, 2H), 3.17-3.26 (m, 2H), 3.65 (dd, J=3.0, 12.1 Hz, 2H), 3.75 (d, J=5.8 Hz, 1H), 4.03 (d, J=5.6 Hz, 1H), 4.28 (dt, J=4.4, 13.1 Hz, 2H), 6.15 (tt, J=4.4, 55.5 Hz, 1H), 6.64 (d, J=2.6 Hz, 1H), 7.16-7.25 (m, 2H), 7.32-7.39 (m, 2H), 8.72 (d, J=2.8 Hz, 1H). MS (ES+) m/z 496.1, 498.1 [M+H, Cl isotopes].

In an 8 mL microwave vial (1R,5S,8s)-3-(6-chloro-pyridazin-4-yl)-3-azabicyclo[3.2.1]octan-8-amine (Int-126, 60 mg, 251 μmol) was suspended in 1,4-dioxane (4 mL) and 3-bromo-5-(3-chlorophenoxy)-1-(2,2-difluoroethyl)-1H-1,2,4-triazole (Int-88, 88.8 mg, 251 μmol), sodium tert-butoxide (50.9 mg, 503 μmol), 1,2,3,4,5-pentaphenyl-1'-(di-tert-butylphosphino)ferrocene ("Q-phos", CAS [312959-24-3], 30.1 mg, 40.2 μmol), and tris(dibenzylideneacetone)dipalladium (0) chloroform adduct (21.5 mg, 20.1 μmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (amino modified silica gel, 50 g, eluting with ethyl acetate/n-heptane, gradient 0:100 to 45:55 v/v), followed by column chromatography (silica gel, 50 g, eluting with dichloromethane/methanol, In an 8 mL microwave vial (1R,5S,8s)-3-(6-chloro-pyridazin-4-yl)-3-azabicyclo[3.2.1]octan-8-amine (Int-126, 45 mg, 189 μmol) was suspended in 1,4-dioxane (3 mL) and 3-bromo-5-(3-chlorophenoxy)-1-(2-fluoroethyl)-1H-1,2,4-triazole (Int-90, 60.4 mg, 189 μmol), sodium tert-butoxide (38.1 mg, 377 μmol), 1,2,3,4,5-pentaphenyl-1'-(di-tert-butylphosphino)ferrocene ("Q-phos", CAS [312959-24-3], 22.6 mg, 30.2 μmol), and tris(dibenzylideneacetone)dipalladium (0) chloroform adduct (16.1 mg, 15.1 μmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 50 g, eluting with ethyl acetate/n-heptane, gradient 0:100 to 100:0 v/v, then dichloromethane/methanol 9:1 v/v), followed by col-

Example 109

(1R,5S,8s)-N-[5-(3-Chlorophenoxy)-1-(propan-2-yl)-1H-1,2,4-triazol-3-yl]-3-(5-methyl-1,3,4-oxadiazol-2-yl)-3-azabicyclo[3.2.1]octan-8-amine

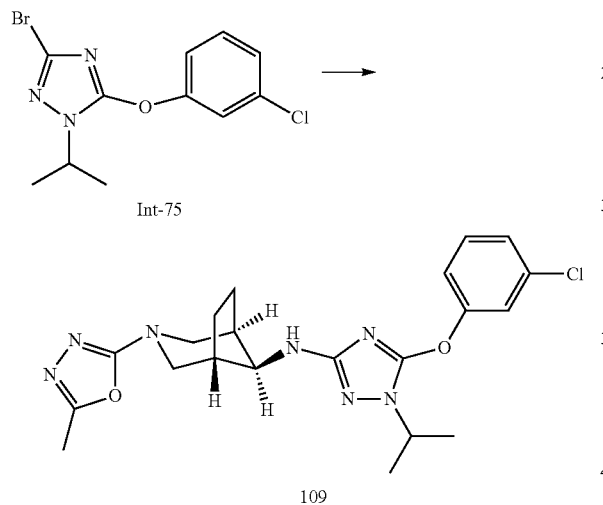

109

To a solution of (1R,5S,8s)-3-(5-methyl-1,3,4-oxadiazol-2-yl)-3-azabicyclo[3.2.1]octan-8-amine (Int-105, 200 mg, 1.0 mmol) and 3-bromo-5-(3-chlorophenoxy)-1-(propan-2-yl)-1H-1,2,4-triazole (Int-75, 304 mg, 1.0 mmol) in dry 1,4-dioxane (6.0 mL) in microwave tube was added 1,2,3,4,5-pentaphenyl-1'-(di-tert-butylphosphino)ferrocene ("Q-phos", CAS 312959-24-3, 109 mg, 0.2 mmol). The reaction mixture was degassed with argon. To it then added tris(dibenzylideneacetone)dipalladium-chloroform adduct ("Pd$_2$(dba)$_3$.CHCl$_3$", CAS 52522-40-4, 80 mg, 0.1 mmol) and sodium tertbutoxide (184 mg, 1.9 mmol). The reaction mixture was irradiated at 120° C. for 20 min in microwave. Reaction mixture was filtered and the filtrate was concentrated to get the crude which was purified by reversed phase prep HPLC (Sunfire C18 10μ 150×19 mm, flow 16 mL/min, eluting with acetonitrile/(water+20 mM ammonium bicarbonate), gradient 30:70 to 95:5) method to yield the title compound as brown semi-solid (17.4 mg, 4%). $^1$H NMR (MeOD, 400 MHz): 1.42-1.45 (m, 6H), 1.57 (d, J=8.1 Hz, 2H), 1.93-1.96 (m, 2H), 2.36 (s, 3H), 2.43 (br s, 2H), 3.27-3.30 (m, 2H), 3.64-3.67 (m, 3H), 4.45-4.51 (m, 1H), 7.17 (dd, J=1.9, 8.2 Hz, 1H), 7.24 (d, J=8.0 Hz, 1H), 7.34 (br s, 1H), 7.39 (t, J=8.2 Hz, 1H). MS (ES+) m/z 444.2 [M+H].

Example 110

(1R,5S,8s)-N-(5-(3-Chlorophenoxy)-1-(2,2-difluoroethyl)-1H-1,2,4-triazol-3-yl)-3-(6-methoxypyridazin-4-yl)-3-azabicyclo[3.2.1]octan-8-amine

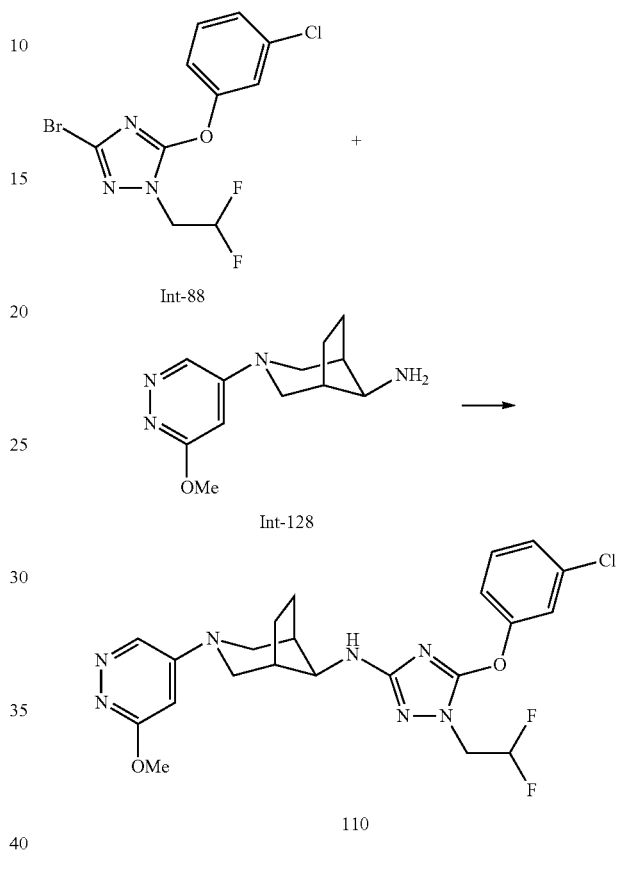

In an 8 mL microwave vial (1R,5S,8s)-3-(6-methoxypyridazin-4-yl)-3-azabicyclo[3.2.1]octan-8-amine (Int-128, 60 mg, 256 μmol) was suspended in 1,4-dioxane (4 mL) and 3-bromo-5-(3-chlorophenoxy)-1-(2,2-difluoroethyl)-1H-1,2,4-triazole (Int-88, 90.5 mg, 256 μmol), sodium tert-butoxide (51.8 mg, 512 μmol), 1,2,3,4,5-pentaphenyl-1'-(di-tert-butylphosphino)ferrocene ("Q-phos", CAS [312959-24-3], 30.7 mg, 41 μmol), and tris(dibenzylideneacetone)dipalladium (0) chloroform adduct (21.9 mg, 20.5 μmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate, then dichloromethane/methanol, gradient 100:0 to 87:13 v/v), followed by column chromatography (amino modified silica gel, 50 g, eluting with ethyl acetate/n-heptane, gradient 0:100 to 64:36 v/v) to yield the title compound as a white foam (56 mg, 44%). HPLC (method LCMS_fastgradient) $t_R$=1.02 min. $^1$H NMR (CDCl$_3$, 300 MHz): δ 1.56-1.65 (m, 2H), 1.85-1.95 (m, 2H), 2.47-2.56 (m, 2H), 3.08-3.16 (m, 2H), 3.62 (dd, J=3.2, 11.9 Hz, 2H), 3.71 (d, J=5.8 Hz, 1H), 4.02 (d, J=6.0 Hz, 1H), 4.08 (s, 3H), 4.28 (dt, J=4.3, 13.0 Hz, 2H), 6.02 (d, J=2.6 Hz, 1H), 6.15

--- umn chromatography (amino modified silica gel, 50 g, eluting with ethyl acetate/n-heptane, gradient 0:100 to 50:50 v/v) to yield the title compound as a white solid (21 mg, 23%). HPLC (method LCMS_fastgradient) $t_R$=1.17 min. $^1$H NMR (CDCl$_3$, 300 MHz): δ 1.55-1.65 (m, 2H), 1.89-2.00 (m, 2H), 2.52-2.61 (m, 2H), 3.17-3.26 (m, 2H), 3.65 (dd, J=3.0, 12.1 Hz, 2H), 3.77 (d, J=5.6 Hz, 1H), 4.00 (d, J=5.8 Hz, 1H), 4.23 (dt, J=4.8, 25.0 Hz, 2H), 4.77 (dt, J=4.8, 46.7 Hz, 2H), 6.63 (d, J=2.6 Hz, 1H), 7.15-7.25 (m, 2H), 7.30-7.37 (m, 2H), 8.72 (d, J=2.8 Hz, 1H). MS (ES+) m/z 478.2, 480.1 [M+H, Cl isotopes].

(tt, J=4.3, 55.5 Hz, 1H), 7.16-7.24 (m, 2H), 7.31-7.38 (m, 2H), 8.57 (d, J=2.6 Hz, 1H). MS (ES+) m/z 492.3, 494.3 [M+H, Cl isotopes].

Example 111

(1R,5S,8s)-N-(5-(3-Chlorophenoxy)-1-(2-fluoro-ethyl)-1H-1,2,4-triazol-3-yl)-3-(6-methoxypyridazin-4-yl)-3-azabicyclo[3.2.1]octan-8-amine

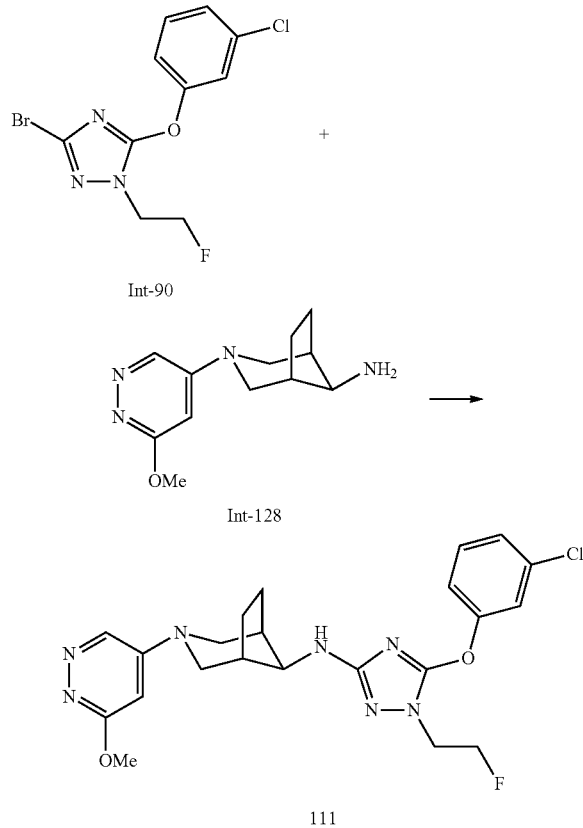

In an 8 mL microwave vial (1R,5S,8s)-3-(6-methoxy-pyridazin-4-yl)-3-azabicyclo[3.2.1]octan-8-amine (Int-128, 60 mg, 256 μmol) was suspended in 1,4-dioxane (4 mL) and 3-bromo-5-(3-chlorophenoxy)-1-(2-fluoroethyl)-1H-1,2,4-triazole (Int-90, 82.1 mg, 256 μmol), sodium tert-butoxide (51.8 mg, 512 μmol), 1,2,3,4,5-pentaphenyl-1'-(di-tert-butylphosphino)ferrocene ("Q-phos", CAS [312959-24-3], 30.7 mg, 41 μmol), and tris(dibenzylideneacetone)dipalladium (0) chloroform adduct (21.9 mg, 20.5 μmol) were added subsequently. The vial was degassed thoroughly with Argon and sealed. The reaction mixture was heated under microwave irradiation at 110° C. for 30 min. After that, the mixture was diluted with dichloromethane (10 mL) and concentrated in vacuo. The resulting crude product was purified by column chromatography (silica gel, 70 g, eluting with ethyl acetate, then dichloromethane/methanol, gradient 100:0 to 85.5:14.5 v/v), followed by column chromatography (amino modified silica gel, 50 g, eluting with ethyl acetate/n-heptane, gradient 0:100 to 65:35 v/v), followed by preparative HPLC (YMC-Actus Triart C18, 100×30 mm×5 μm, eluting with acetonitrile/(water+0.1% triethylamine), gradient 20:80 to 98:2 v/v) and lyophilization to yield the title compound as a white solid (11 mg, 9%). ¹H NMR (CDCl₃, 300 MHz): δ1.56-1.65 (m, 2H), 1.86-1.96 (m, 2H), 2.48-2.56 (m, 2H), 3.08-3.17 (m, 2H), 3.62 (dd, J=3.1, 11.8 Hz, 2H), 3.73 (d, J=6.0 Hz, 1H), 3.99 (d, J=5.8 Hz, 1H), 4.08 (s, 3H), 4.23 (dt, J=4.8, 25.0 Hz, 2H), 4.76 (dt, J=4.8, 46.7 Hz, 2H), 6.02 (d, J=2.6 Hz, 1H), 7.15-7.24 (m, 2H), 7.30-7.37 (m, 2H), 8.57 (d, J=2.6 Hz, 1H). MS (ES+) m/z 474.3, 476.3 [M+H, Cl isotopes].

Example 112

(1R,5S,8s)-N-[5-(3-Chlorophenoxy)-1-(propan-2-yl)-1H-1,2,4-triazol-3-yl]-3-(6-methylpyrimidin-4-yl)-3-azabicyclo[3.2.1]octan-8-amine

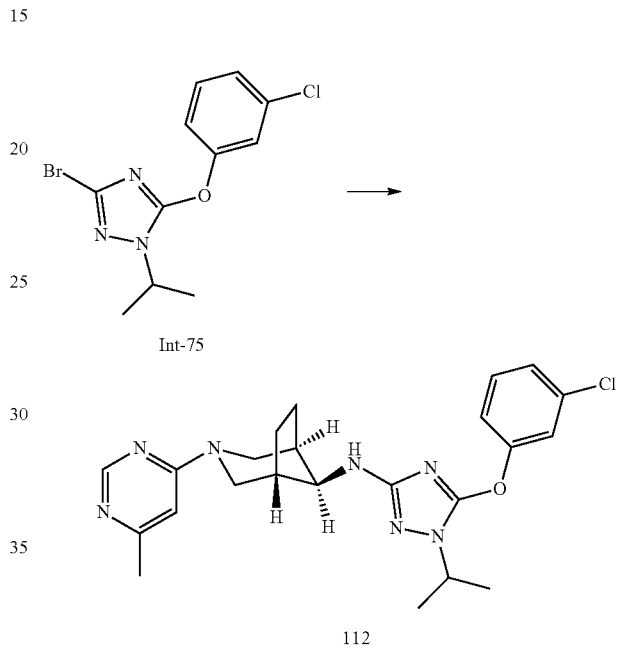

In a 50 mL flask, (1R,5S,8s)-3-(6-methylpyrimidin-4-yl)-3-azabicyclo[3.2.1]octan-8-amine (Int-114, 215 mg, 986 μmol) was suspended in 2-methyltetrahydrofuran (9 mL) and 3-bromo-5-(3-chlorophenoxy)-1-(propan-2-yl)-1H-1,2,4-triazole (Int-75, 300 mg, 948 μmol), sodium tert-butoxide (270 mg, 2.81 mmol), di-tert-butyl(2',4',6'-triisopropylbiphenyl-2-yl)phosphine ("tBuXPhos", CAS [564483-19-8], 24 mg, 56.5 μmol), and tris(dibenzylideneacetone)dipalladium (0) chloroform adduct (30 mg, 29 μmol) were added subsequently. The flask was degassed thoroughly with Argon and sealed. The reaction mixture was stirred at 80° C. for 1 h. After that, water (10 mL) was added and the mixture was extracted with ethyl acetate (2×90 mL). The organic extracts were separately washed with water (10 mL) and brine (10 mL), combined, dried (sodium sulfate) and concentrated in vacuo. The resulting crude product was purified by column chromatography (silica gel, 24 g, eluting with dichloromethane/methanol, gradient 100:0 to 95:5 v/v) to yield the title compound as a light yellow foam (343 mg, 80%). HPLC (method LCMS_fastgradient) t_R=0.99 min. ¹H NMR (CDCl₃, 300 MHz): δ 1.46 (d, J=6.6 Hz, 6H), 1.50-1.59 (m, 2H), 1.79-1.92 (m, 2H), 2.36 (s, 3H), 2.42-2.50 (m, 2H), 3.06-3.15 (m, 2H), 3.78 (d, J=6.0 Hz, 1H), 3.91 (d, J=6.2 Hz, 1H), 4.02-4.20 (m, 2H), 4.46 (hept, J=6.6 Hz, 1H), 6.34 (s, 1H), 7.13-7.22 (m, 2H), 7.29-7.35 (m, 2H), 8.51 (d, J=1.0 Hz, 1H). MS (ES+) m/z 454.4, 456.4 [M+H, Cl isotopes].

Example 113

(1R,5S,8s)-N-(1-Cyclopropyl-5-(3,4-difluorophenoxy)-1H-1,2,4-triazol-3-yl)-3-(6-methylpyrimidin-4-yl)-3-azabicyclo[3.2.1]octan-8-amine

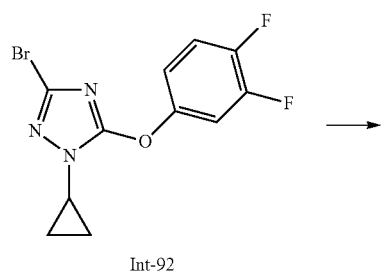

Int-92

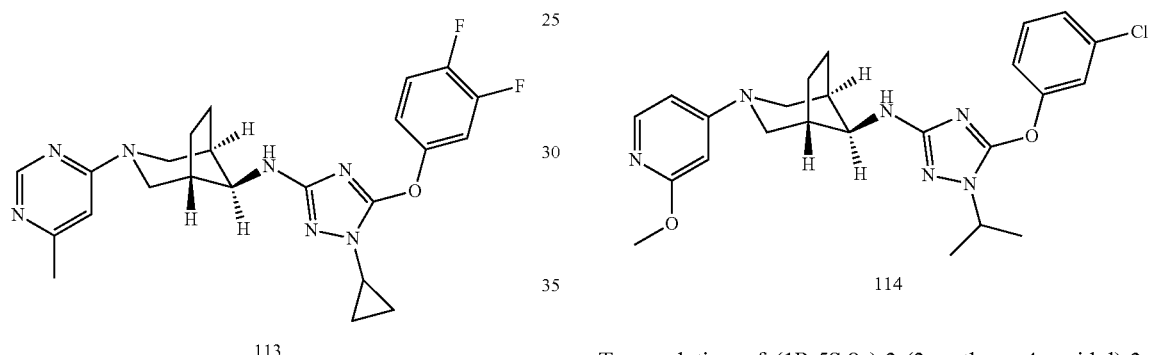

113

In a 10 mL flask, (1R,5S,8s)-3-(6-methylpyrimidin-4-yl)-3-azabicyclo[3.2.1]octan-8-amine (Int-114, 135 mg, 619 µmol) was suspended in 2-methyltetrahydrofuran (6 mL) and 3-bromo-1-cyclopropyl-5-(3,4-difluorophenoxy)-1H-1,2,4-triazole (Int-92, 188 mg, 595 µmol), sodium tert-butoxide (169 mg, 1.76 mmol), di-tert-butyl(2',4',6'-triisopropylbiphenyl-2-yl)phosphine ("tBuXPhos", CAS [564483-19-8], 15.1 mg, 35.4 µmol), and tris(dibenzylideneacetone)dipalladium (0) chloroform adduct (18.8 mg, 18.2 µmol) were added subsequently. The flask was degassed thoroughly with Argon and sealed. The reaction mixture was stirred at 80° C. for 2.5 h, followed by 18 h at room temperature. After that, water (3 mL) was added and the mixture was extracted with ethyl acetate (2×30 mL). The organic extracts were separately washed with water (3 mL) and brine (3 mL), combined, dried (sodium sulfate) and concentrated in vacuo. The resulting crude product was purified by column chromatography (silica gel, 12 g, eluting with dichloromethane/methanol, gradient 100:0 to 90:10 v/v) to yield the title compound as a light yellow foam (149 mg, 55%). $^1$H NMR (CDCl$_3$, 300 MHz): δ 1.00-1.05 (m, 2H), 1.13-1.17 (m, 2H), 1.50-1.56 (m, 2H), 1.79-1.85 (m, 2H), 2.38 (s, 3H), 2.42-2.46 (m, 2H), 3.07-3.13 (m, 2H), 3.24-3.28 (m, 1H), 3.75 (d, J=6.2 Hz, 1H), 3.90 (d, J=6.2 Hz, 1H), 4.04-4.20 (m, 2H), 6.34 (s, 1H), 7.01-7.05 (m, 1H), 7.16-7.22 (m, 2H), 8.50 (s, 1H). MS (ES+) m/z 454.2 [M+H].

Example 114

(1R,5S,8s)-N-[5-(3-Chlorophenoxy)-1-(propan-2-yl)-1H-1,2,4-triazol-3-yl]-3-(2-methoxy-4-pyridyl)-3-azabicyclo[3.2.1]octan-8-amine

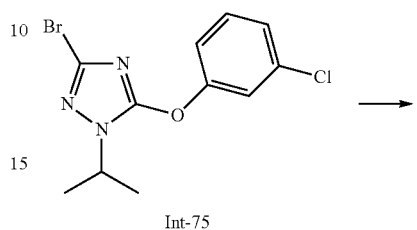

Int-75

114

To a solution of (1R,5S,8s)-3-(2-methoxy-4-pyridyl)-3-azabicyclo[3.2.1]octan-8-amine (Int-111, 110 mg, 0.5 mmol) in 2-methyltetrahydrofuran (15.0 mL) was added 3-bromo-5-(3-chlorophenoxy)-1-(propan-2-yl)-1H-1,2,4-triazole (Int-75, 150 mg, 0.5 mmol) and was degassed with argon over a period of 5 min. To it then added sodium tertbutoxide (68.3 mg, 0.7 mmol), di-tert-butyl(2',4',6'-triisopropylbiphenyl-2-yl)phosphine ("tBuXPhos", CAS [564483-19-8], 12 mg, 28.1 µmol). The reaction mixture was again degassed with argon for 5 min followed by addition of tris(dibenzylideneacetone)dipalladium(0) ("Pd$_2$(dba)$_3$", CAS [51364-51-3], 13 mg, 14.2 µmol). The reaction mixture was heated at 50° C. with stirring for a period of 15 min. Reaction mixture was then concentrated followed by dilution with ethyl acetate (50 mL) and this organic part was washed with water (2×25 mL) and brine (1×25 mL). After drying this was evaporated to dryness under reduced pressure to afford the crude which was purified by reversed phase prep HPLC (Xbridge C18 5µ 250×19 mm, flow 16 mL/min, eluting with acetonitrile/(water+20 mM ammonium bicarbonate), gradient 40:60 to 95:5) method to afford the title compound as off white-solid (13.3 mg, 6%). HPLC purity 98.67%. $^1$H NMR (MeOD, 400 MHz): 1.43 (d, J=6.6 Hz, 6H), 1.56 (d, J=7.8 Hz, 2H), 1.92-1.94 (m, 2H), 2.47 (s, 2H), 3.01 (d, J=11.5 Hz, 2H), 3.65-3.67 (m, 3H), 3.81 (s, 3H), 4.45-4.52 (m, 1H), 6.05 (s, 1H), 6.47 (d, J=4.1 Hz, 1H), 7.17 (d, J=8.1 Hz, 1H), 7.25 (d, J=7.1 Hz, 1H), 7.34 (s, 1H), 7.39 (t, J=8.0 Hz, 1H), 7.71 (d, J=6.0 Hz, 1H). MS (ES+) m/z 468.9 [M+H].

Example 115

(1R,5S,8s)-N-[5-(3,4-Difluorophenoxy)-1-(propan-2-yl)-1H-1,2,4-triazol-3-yl]-3-(6-methylpyrimidin-4-yl)-3-azabicyclo[3.2.1]octan-8-amine

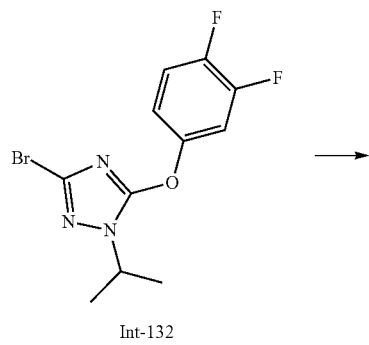

Int-132

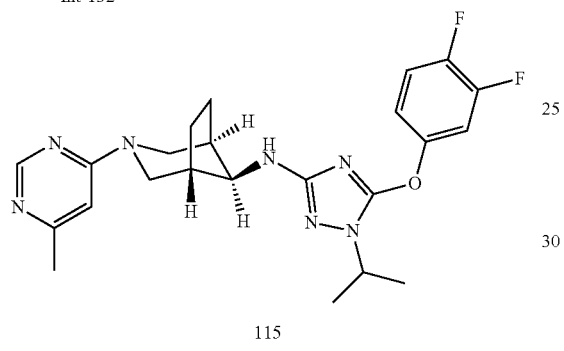

115

In a 10 mL flask, (1R,5S,8s)-3-(6-methylpyrimidin-4-yl)-3-azabicyclo[3.2.1]octan-8-amine (Int-114, 83.2 mg, 377 μmol) and 3-bromo-5-(3,4-difluorophenoxy)-1-(propan-2-yl)-1H-1,2,4-triazole (Int-132, 100 mg, 314 μmol), and sodium tert-butoxide (90.6 mg, 0.94 mmol) were charged. The flask was evacuated and backfilled with argon, Then, 2-methyltetrahydrofuran (4.5 mL), di-tert-butyl(2',4',6'-triisopropylbiphenyl-2-yl)phosphine ("tBuXPhos", CAS [564483-19-8], 8 mg, 19 μmol), and tris(dibenzylideneacetone)dipalladium (0) chloroform adduct (9.8 mg, 9.4 μmol) were added subsequently. The flask was degassed thoroughly with Argon and sealed. The reaction mixture was stirred at 80° C. for 1 h. After that, water (5 mL) was added and the mixture was extracted with ethyl acetate (2×30 mL). The combined organic extracts were washed with water (2×10 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as a light brown oil (116 mg, 81%). HPLC (method LCMS_fastgradient) $t_R$=0.93 min. $^1$H NMR (d6-DMSO, 300 MHz): δ 1.24-1.33 (m, 2H), 1.36 (d, J=6.6 Hz, 6H), 1.76-1.89 (m, 2H), 2.24 (s, 3H), 2.34-2.40 (m, 2H), 2.94 (d, J=12.3 Hz, 2H), 3.53 (d, J=4.4 Hz, 1H), 3.98-4.18 (m, 2H), 4.42 (hept, J=6.6 Hz, 1H), 5.95 (d, J=4.6 Hz, 1H), 6.61 (s, 1H), 7.17-7.24 (m, 1H), 7.51 (ddd, J=9.3, 9.3, 10.5 Hz, 1H), 7.61 (ddd, J=3.0, 4.6, 6.8 Hz, 1H), 8.34 (d, J=0.8 Hz, 1H). MS (ES+) m/z 456.7 [M+H].

Example 116

(1R,5S,8s)-N-[5-(3,4-Difluorophenoxy)-1-(propan-2-yl)-1H-1,2,4-triazol-3-yl]-3-(2-methoxypyridin-4-yl)-3-azabicyclo[3.2.1]octan-8-amine

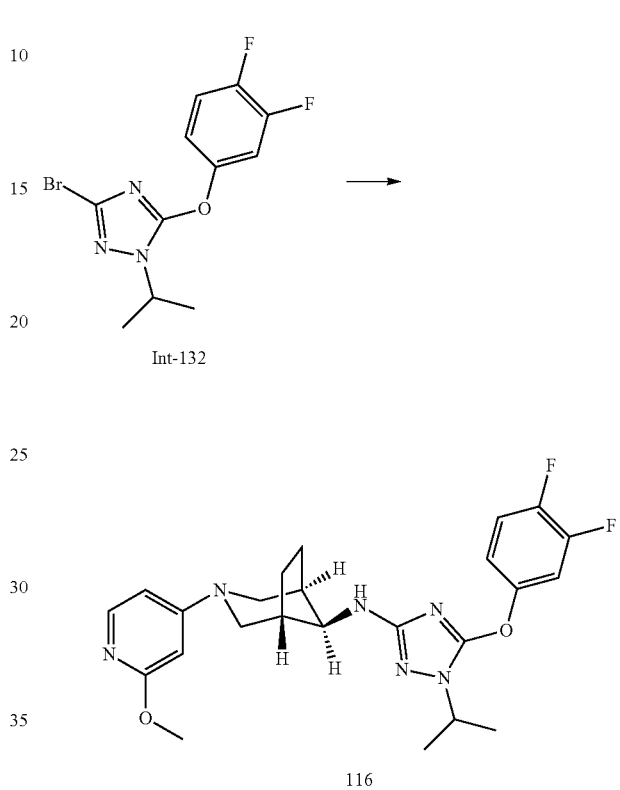

Int-132

116

In a 10 mL flask, (1R,5S,8s)-3-(2-methoxypyridin-4-yl)-3-azabicyclo[3.2.1]octan-8-amine (Int-111, 88 mg, 377 μmol) and 3-bromo-5-(3,4-difluorophenoxy)-1-(propan-2-yl)-1H-1,2,4-triazole (Int-132, 100 mg, 314 μmol), and sodium tert-butoxide (90.6 mg, 0.94 mmol) were charged. The flask was evacuated and backfilled with argon, Then, 2-methyltetrahydrofuran (4.5 mL), di-tert-butyl(2',4',6'-triisopropylbiphenyl-2-yl)phosphine ("tBuXPhos", CAS [564483-19-8], 8 mg, 19 μmol), and tris(dibenzylideneacetone)dipalladium (0) chloroform adduct (9.8 mg, 9.4 μmol) were added subsequently. The flask was degassed thoroughly with Argon and sealed. The reaction mixture was stirred at 80° C. for 1 h. After that, water (5 mL) was added and the mixture was extracted with ethyl acetate (2×30 mL). The combined organic extracts were washed with water (2×10 mL), dried (sodium sulfate) and concentrated in vacuo. The resulting crude product was purified by column chromatography (silica gel, 4 g, eluting with dichloromethane/methanol, gradient 100:0 to 95:5 v/v) to yield the title compound as a white foam (22 mg, 15%). HPLC (method LCMS_fastgradient) $t_R$=0.98 min. $^1$H NMR (CDCl$_3$, 300 MHz): δ 1.46 (d, J=6.8 Hz, 6H), 1.57-1.65 (m, 2H), 1.83-1.89 (m, 2H), 2.43-2.50 (m, 2H), 3.02-3.09 (m, 2H), 3.58 (dd, J=3.0, 11.7 Hz, 2H), 3.72 (d, J=6.2 Hz, 1H), 3.90 (s, 3H), 4.45 (hept, J=6.6 Hz, 1H), 5.99 (d, J=2.2 Hz, 1H), 6.35 (dd, J=2.2, 6.3 Hz, 1H), 6.98-7.05 (m, 1H), 7.13-7.23 (m, 2H), 7.87 (d, J=6.3 Hz, 1H). MS (ES+) m/z 471.7 [M+H].

Example 117

(1R,5S,8s)-N-[5-(3,4-Difluorophenoxy)-1-(propan-2-yl)-1H-1,2,4-triazol-3-yl]-3-(6-methoxypyridazin-4-yl)-3-azabicyclo[3.2.1]octan-8-amine

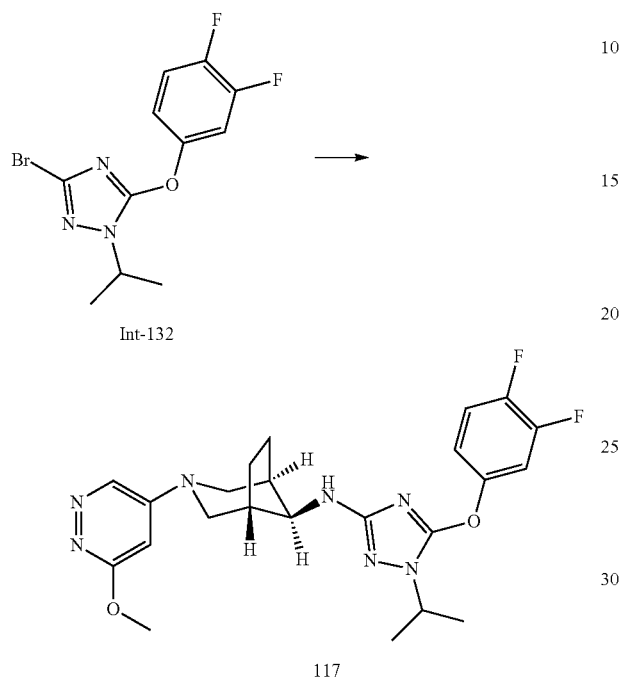

In a 10 mL flask, (1R,5S,8s)-3-(6-methoxypyridazin-4-yl)-3-azabicyclo[3.2.1]octan-8-amine (Int-128, 81 mg, 346 µmol) and 3-bromo-5-(3,4-difluorophenoxy)-1-(propan-2-yl)-1H-1,2,4-triazole (Int-132, 100 mg, 314 µmol), and sodium tert-butoxide (90.6 mg, 0.94 mmol) were charged. The flask was evacuated and backfilled with argon, Then, 2-methyltetrahydrofuran (4.5 mL), di-tert-butyl(2',4',6'-triisopropylbiphenyl-2-yl)phosphine ("tBuXPhos", CAS [564483-19-8], 8 mg, 19 µmol), and tris(dibenzylideneacetone)dipalladium (0) chloroform adduct (9.8 mg, 9.4 µmol) were added subsequently. The flask was degassed thoroughly with Argon and sealed. The reaction mixture was stirred at 80° C. for 1 h. After that, water (10 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as a light brown solid (99 mg, 67%). HPLC (method LCMS_fastgradient) $t_R$=0.99 min. $^1$H NMR (d6-DMSO, 300 MHz): δ 1.35-1.43 (m, 2H), 1.36 (d, J=6.6 Hz, 6H), 1.80-1.91 (m, 2H), 2.37-2.45 (m, 2H), 2.91-3.00 (m, 2H), 3.50 (d, J=4.0 Hz, 1H), 3.69 (dd, J=3.0, 11.9 Hz, 2H), 3.91 (s, 3H), 4.41 (hept, J=6.6 Hz, 1H), 5.98 (d, J=4.2 Hz, 1H), 6.18 (d, J=2.4 Hz, 1H), 7.17-7.24 (m, 1H), 7.51 (ddd, J=9.2, 9.2, 10.5 Hz, 1H), 7.61 (ddd, J=3.0, 4.6, 6.8 Hz, 1H), 8.65 (d, J=2.4 Hz, 1H). MS (ES+) m/z 472.7 [M+H].

Example 118

(1R,5S,8s)-N-(5-(3,4-Difluorophenoxy)-1-(2,2,2-trifluoroethyl)-1H-1,2,4-triazol-3-yl)-3-(6-methylpyrimidin-4-yl)-3-azabicyclo[3.2.1]octan-8-amine

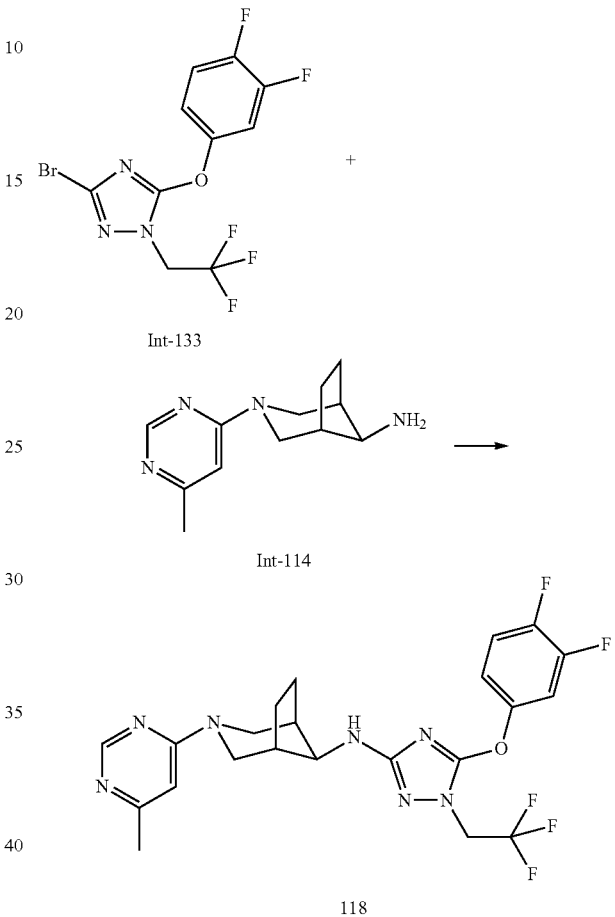

In an 8 mL microwave vial, (1R,5S,8s)-3-(6-methylpyrimidin-4-yl)-3-azabicyclo[3.2.1]octan-8-amine (Int-114, 114 mg, 523 µmol), 3-bromo-5-(3,4-difluorophenoxy)-1-(2,2,2-trifluoroethyl)-1H-1,2,4-triazole (Int-133, 156 mg, 436 µmol), and sodium tert-butoxide (83.7 mg, 871 µmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 49.5 mg, 69.7 µmol), and tris(dibenzylideneacetone)dipalladium (0) chloroform adduct (36.1 mg, 34.9 µmol) were added subsequently. The vial was again degassed thoroughly with Argon and sealed. The reaction mixture was heated under microwave irradiation at 110° C. for 30 min. After that, water (10 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100×30 mm×5 µm, eluting with acetonitrile/(water+0.1% triethylamine), gradient 20:80 to 98:2 v/v) to yield the title compound as white foam (61 mg, 28%).

HPLC (method LCMS_fastgradient) $t_R$=0.96 min. $^1$H NMR (d6-DMSO, 300 MHz): δ 1.23-1.34 (m, 2H), 1.75-1.87 (m, 2H), 2.24 (s, 3H), 2.34-2.41 (m, 2H), 2.89-2.98 (m, 2H), 3.52 (d, J=4.6 Hz, 1H), 4.01-4.20 (m, 2H), 4.91 (q, J=9.1 Hz, 2H), 6.26 (d, J=4.6 Hz, 1H), 6.62 (s, 1H), 7.21-7.29 (m, 1H), 7.55 (ddd, J=9.2, 9.2, 10.5 Hz, 1H), 4.65 (ddd, J=3.2, 4.4, 7.0 Hz, 1H), 8.34 (d, J=0.6 Hz, 1H). MS (ES+) m/z 496.6 [M+H].

Example 119

(1R,5S,8s)-N-(5-(3,4-Difluorophenoxy)-1-(2,2,2-trifluoroethyl)-1H-1,2,4-triazol-3-yl)-3-(2-methoxy-pyridin-4-yl)-3-azabicyclo[3.2.1]octan-8-amine

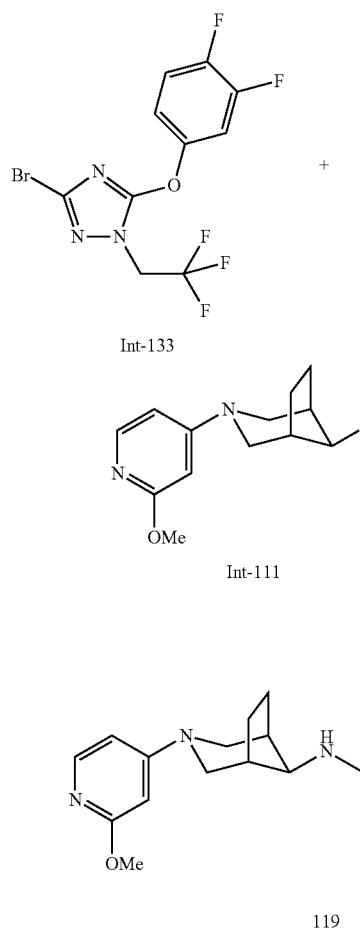

In an 8 mL microwave vial, (1R,5S,8s)-3-(2-methoxy-pyridin-4-yl)-3-azabicyclo[3.2.1]octan-8-amine (Int-111, 122 mg, 523 μmol), 3-bromo-5-(3,4-difluorophenoxy)-1-(2,2,2-trifluoroethyl)-1H-1,2,4-triazole (Int-133, 156 mg, 436 μmol), and sodium tert-butoxide (83.7 mg, 871 μmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 49.5 mg, 69.7 μmol), and tris(dibenzylideneacetone)dipalladium (0) chloroform adduct (36.1 mg, 34.9 μmol) were added subsequently. The vial was again degassed thoroughly with Argon and sealed. The reaction mixture was heated under microwave irradiation at 110° C. for 30 min. After that, water (10 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100×30 mm×5 μm, eluting with acetonitrile/(water+0.1% triethylamine), gradient 20:80 to 98:2 v/v) to yield the title compound as white solid (19 mg, 8%). HPLC (method LCMS_fastgradient) $t_R$=0.96 min. $^1$H NMR (d6-DMSO, 300 MHz): δ 1.33-1.44 (m, 2H), 1.78-1.90 (m, 2H), 2.35-2.45 (m, 2H), 2.81-2.90 (m, 2H), 3.45 (d, J=4.0 Hz, 1H), 3.54-3.64 (m, 2H), 3.75 (s, 3H), 4.90 (q, J=9.0 Hz, 2H), 6.00 (d, J=2.0 Hz, 1H), 6.26 (d, J=4.4 Hz, 1H), 6.47 (dd, J=2.2, 6.2 Hz, 1H), 7.21-7.29 (m, 1H), 7.54 (ddd, J=9.2, 9.2, 10.5 Hz, 1H), 7.65 (ddd, J=3.0, 4.4, 6.8 Hz, 1H), 7.75 (d, J=6.2 Hz, 1H). MS (ES+) m/z 511.6 [M+H].

Example 120

(1R,5S,8s)-N-[5-(3,5-Difluorophenoxy)-1-(propan-2-yl)-1H-1,2,4-triazol-3-yl]-3-(6-methylpyrimidin-4-yl)-3-azabicyclo[3.2.1]octan-8-amine

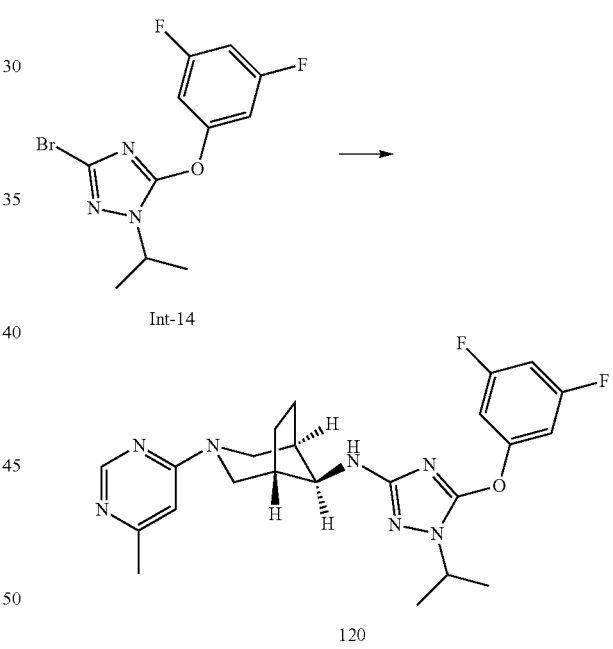

In a 10 mL flask, (1R,5S,8s)-3-(6-methylpyrimidin-4-yl)-3-azabicyclo[3.2.1]octan-8-amine (Int-114, 83.2 mg, 381 μmol) and 3-bromo-5-(3,5-difluorophenoxy)-1-(propan-2-yl)-1H-1,2,4-triazole (Int-14, 101 mg, 317 μmol), and sodium tert-butoxide (91.5 mg, 0.95 mmol) were charged. The flask was evacuated and backfilled with argon, Then, 2-methyltetrahydrofuran (4.5 mL), di-tert-butyl(2',4',6'-tri-isopropylbiphenyl-2-yl)phosphine ("tBuXPhos", CAS [564483-19-8], 8 mg, 19 μmol), and tris(dibenzylideneacetone)dipalladium (0) chloroform adduct (9.9 mg, 9.5 μmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL).

The combined organic extracts were washed with water (2×30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as off-white solid (78 mg, 54%). HPLC (method LCMS_fastgradient) $t_R$=0.97 min. $^1$H NMR (d6-DMSO, 300 MHz): δ 1.24-1.35 (m, 2H), 1.36 (d, J=6.6 Hz, 6H), 1.78-1.89 (m, 2H), 2.24 (s, 3H), 2.34-2.42 (m, 2H), 2.90-3.00 (m, 2H), 3.55 (d, J=4.6 Hz, 1H), 4.00-4.18 (m, 2H), 4.41 (hept, J=6.6 Hz, 1H), 6.00 (d, J=4.6 Hz, 1H), 6.62 (s, 1H), 7.11-7.27 (m, 3H), 8.34 (d, J=0.6 Hz, 1H). MS (ES+) m/z 456.7 [M+H].

Example 121

(1R,5S,8s)-N-[5-(2,3-Difluorophenoxy)-1-(propan-2-yl)-1H-1,2,4-triazol-3-yl]-3-(6-methylpyrimidin-4-yl)-3-azabicyclo[3.2.1]octan-8-amine

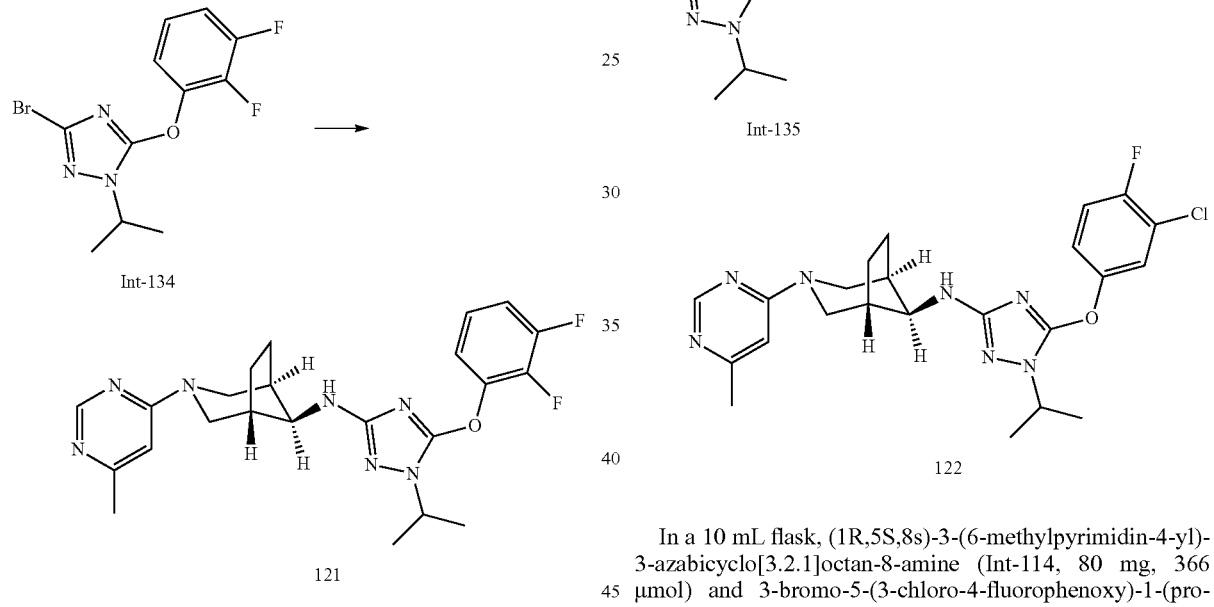

In a 10 mL flask, (1R,5S,8s)-3-(6-methylpyrimidin-4-yl)-3-azabicyclo[3.2.1]octan-8-amine (Int-114, 95.5 mg, 438 µmol) and 3-bromo-5-(2,3-difluorophenoxy)-1-(propan-2-yl)-1H-1,2,4-triazole (Int-134, 116 mg, 365 µmol), and sodium tert-butoxide (105 mg, 1.09 mmol) were charged. The flask was evacuated and backfilled with argon, Then, 2-methyltetrahydrofuran (4.5 mL), di-tert-butyl(2',4',6'-triisopropylbiphenyl-2-yl)phosphine ("tBuXPhos", CAS [564483-19-8], 9.3 mg, 21.9 µmol), and tris(dibenzylideneacetone)dipalladium (0) chloroform adduct (11.3 mg, 10.9 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (2×30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as a white foam (117 mg, 70%). HPLC (method LCMS_fastgradient) $t_R$=0.96 min. $^1$H NMR (CDCl$_3$, 300 MHz): δ 1.49 (d, J=6.6 Hz, 6H), 1.49-1.57 (m, 2H), 1.78-1.88 (m, 2H), 2.36 (s, 3H), 2.41-2.48 (m, 2H), 3.09 (d, J=12.9 Hz, 2H), 3.76 (d, J=6.0 Hz, 1H), 3.87 (d, J=6.0 Hz, 1H), 4.04-4.16 (m, 2H), 4.51 (hept, J=6.7 Hz, 1H), 6.34 (s, 1H), 7.01-7.15 (m, 2H), 7.17-7.24 (m, 1H), 8.51 (d, J=0.8 Hz, 1H). MS (ES+) m/z 456.7 [M+H].

Example 122

(1R,5S,8s)-N-(5-(3-Chloro-4-fluorophenoxy)-1-isopropyl-1H-1,2,4-triazol-3-yl)-3-(6-methylpyrimidin-4-yl)-3-azabicyclo[3.2.1]octan-8-amine In a 10 mL flask, (1R,5S,8s)-3-(6-methylpyrimidin-4-yl)-3-azabicyclo[3.2.1]octan-8-amine (Int-114, 80 mg, 366 µmol) and 3-bromo-5-(3-chloro-4-fluorophenoxy)-1-(propan-2-yl)-1H-1,2,4-triazole (Int-135, 102 mg, 305 µmol), and sodium tert-butoxide (87.9 mg, 0.91 mmol) were charged. The flask was evacuated and backfilled with argon, Then, 2-methyltetrahydrofuran (4.5 mL), di-tert-butyl(2',4', 6'-triisopropylbiphenyl-2-yl)phosphine ("tBuXPhos", CAS [564483-19-8], 7.8 mg, 18 µmol), and tris(dibenzylideneacetone)dipalladium (0) chloroform adduct (9.5 mg, 9.1 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100× 30 mm×5 µm, eluting with acetonitrile/(water+0.1% triethylamine), gradient 20:80 to 98:2 v/v) to yield the title compound as a white foam (66 mg, 46%). HPLC (method LCMS_fastgradient) $t_R$=1.03 min. $^1$H NMR (CDCl$_3$, 300 MHz): δ 1.46 (d, J=6.8 Hz, 6H), 1.49-1.59 (m, 2H), 1.80-

1.90 (m, 2H), 2.37 (s, 3H), 2.43-2.49 (m, 2H), 3.10 (d, J=12.7 Hz, 2H), 3.77 (d, J=6.0 Hz, 1H), 3.90 (d, J=6.4 Hz, 1H), 4.02-4.21 (m, 2H), 4.45 (hept, J=6.7 Hz, 1H), 6.34 (s, 1H), 7.13-7.19 (m, 2H), 7.36-7.41 (m, 1H), 8.51 (d, J=0.8 Hz, 1H). MS (ES+) m/z 472.6, 474.6 [M+H, Cl isotopes].

Example 123

(1R,5S,8s)-N-[5-(4-Fluorophenoxy)-1-(propan-2-yl)-1H-1,2,4-triazol-3-yl]-3-(6-methylpyrimidin-4-yl)-3-azabicyclo[3.2.1]octan-8-amine

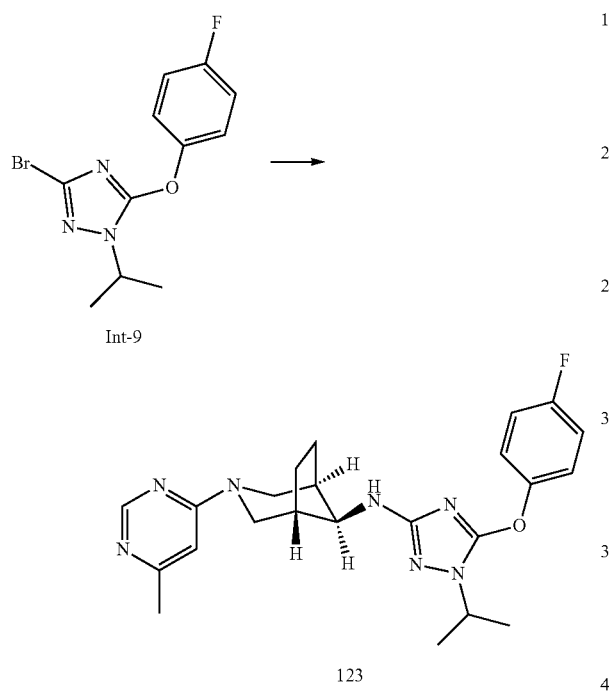

In a 10 mL flask, (1R,5S,8s)-3-(6-methylpyrimidin-4-yl)-3-azabicyclo[3.2.1]octan-8-amine (Int-114, 92.5 mg, 424 µmol) and 3-bromo-5-(4-fluorophenoxy)-1-(propan-2-yl)-1H-1,2,4-triazole (Int-9, 106 mg, 353 µmol), and sodium tert-butoxide (102 mg, 1.06 mmol) were charged. The flask was evacuated and backfilled with argon, Then, 2-methyl-tetrahydrofuran (4.5 mL), di-tert-butyl(2',4',6'-triisopropyl-biphenyl-2-yl)phosphine ("tBuXPhos", CAS [564483-19-8], 9 mg, 21 µmol), and tris(dibenzylideneacetone)dipalladium (0) chloroform adduct (11 mg, 10.6 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as an off-white foam (78 mg, 50%). HPLC (method LCMS_fastgradient) t$_R$=0.95 min. $^1$H NMR (CDCl$_3$, 300 MHz): δ 1.47 (d, J=6.6 Hz, 6H), 1.49-1.58 (m, 2H), 1.79-1.88 (m, 2H), 2.36 (s, 3H), 2.42-2.48 (m, 2H), 3.10 (d, J=13.1 Hz, 2H), 3.77 (d, J=6.2 Hz, 1H), 3.88 (d, J=6.2 Hz, 1H), 4.04-4.17 (m, 2H), 4.47 (hept, J=6.7 Hz, 1H), 6.34 (s, 1H), 7.03-7.12 (m, 2H), 7.18-7.25 (m, 2H), 8.51 (d, J=1.0 Hz, 1H). MS (ES+) m/z 438.7 [M+H].

Example 124

(1R,5S,8s)-N-[5-(3-Fluorophenoxy)-1-(propan-2-yl)-1H-1,2,4-triazol-3-yl]-3-(6-methylpyrimidin-4-yl)-3-azabicyclo[3.2.1]octan-8-amine

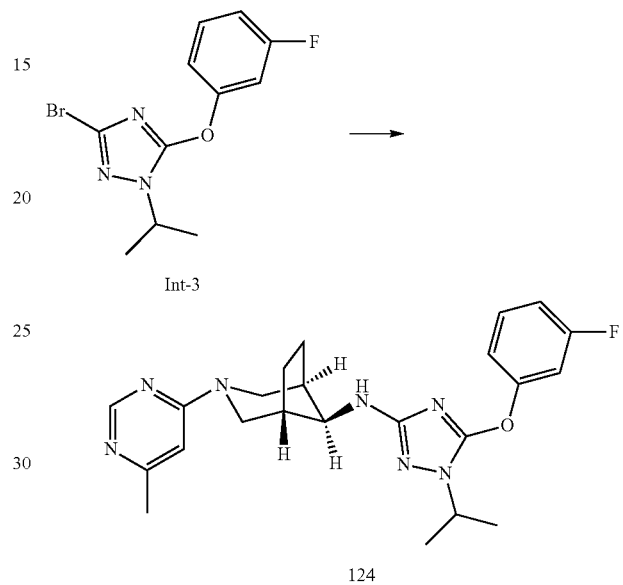

In a 10 mL flask, (1R,5S,8s)-3-(6-methylpyrimidin-4-yl)-3-azabicyclo[3.2.1]octan-8-amine (Int-114, 89 mg, 408 µmol), 3-bromo-5-(3-fluorophenoxy)-1-(propan-2-yl)-1H-1,2,4-triazole (Int-3, 102 mg, 340 µmol), and sodium tert-butoxide (98 mg, 1.02 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 8.7 mg, 20.4 µmol), and tris(dibenzylideneacetone)dipalladium (0) chloroform adduct (10.6 mg, 10.2 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as a white foam (81 mg, 54%). HPLC (method LCMS_fastgradient) t$_R$=0.90 min. $^1$H NMR (CDCl$_3$, 300 MHz): δ 1.46 (d, J=6.6 Hz, 6H), 1.50-1.59 (m, 2H), 1.81-1.91 (m, 2H), 2.36 (s, 3H), 2.43-2.50 (m, 2H), 3.06-3.14 (m, 2H), 3.79 (d, J=6.2 Hz, 1H), 3.91 (d, J=6.2 Hz, 1H), 4.05-4.19 (m, 2H), 4.46 (hept, J=6.6 Hz, 1H), 6.34 (s, 1H), 6.88-6.96 (m, 1H), 7.01-7.07 (m, 2H), 7.30-7.39 (m, 1H), 8.51 (d, J=0.8 Hz, 1H). MS (ES+) m/z 438.4 [M+H].

Example 125

(1R,5S,8s)-N-(5-(3-Fluorophenoxy)-1-(propan-2-yl)-1H-1,2,4-triazol-3-yl)-3-(2-methoxypyridin-4-yl)-3-azabicyclo[3.2.1]octan-8-amine

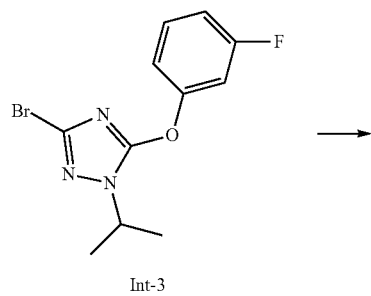

Int-3

Example 126

(1R,5S,8s)-N-[5-(3-Fluorophenoxy)-1-(propan-2-yl)-1H-1,2,4-triazol-3-yl]-3-(6-methoxypyridazin-4-yl)-3-azabicyclo[3.2.1]octan-8-amine

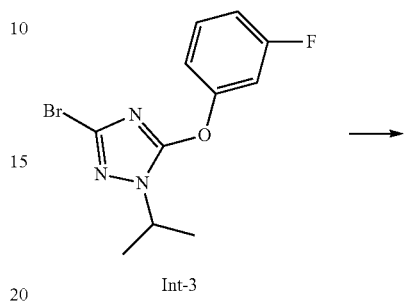

Int-3

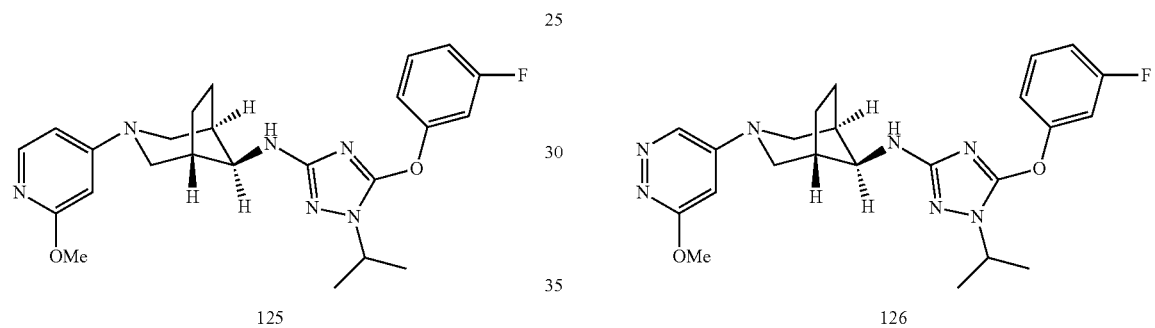

125

126

In a 10 mL flask, (1R,5S,8s)-3-(2-methoxypyridin-4-yl)-3-azabicyclo[3.2.1]octan-8-amine (Int-111, 100 mg, 428 µmol), 3-bromo-5-(3-fluorophenoxy)-1-(propan-2-yl)-1H-1,2,4-triazole (Int-3, 107 mg, 357 µmol), and sodium tert-butoxide (103 mg, 1.07 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 9.1 mg, 21 µmol), and tris(dibenzylideneacetone)dipalladium (0) chloroform adduct (11.1 mg, 10.7 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as a white foam (102 mg, 63%). HPLC (method LCMS_fastgradient) $t_R$=0.96 min. $^1$H NMR (CDCl$_3$, 300 MHz): δ 1.46 (d, J=6.6 Hz, 6H), 1.55-1.64 (m, 2H), 1.89-1.98 (m, 2H), 2.49-2.56 (m, 2H), 3.14-3.24 (m, 2H), 3.64 (dd, J=2.7, 11.8 Hz, 1H), 3.78 (d, J=5.4 Hz, 1H), 3.95 (d, J=5.8 Hz, 1H), 4.02 (s, 3H), 4.46 (hept, J=6.6 Hz, 1H), 6.00 (d, J=2.2 Hz, 1H), 6.43 (dd, J=2.0, 6.6 Hz, 1H), 6.88-6.97 (m, 1H), 7.00-7.07 (m, 2H), 7.30-7.40 (m, 1H), 7.90 (d, J=6.8 Hz, 1H). MS (ES+) m/z 453.6 [M+H].

In a 10 mL flask, (1R,5S,8s)-3-(6-methoxypyridazin-4-yl)-3-azabicyclo[3.2.1]octan-8-amine (Int-128, 99.3 mg, 424 µmol), 3-bromo-5-(3-fluorophenoxy)-1-(propan-2-yl)-1H-1,2,4-triazole (Int-3, 106 mg, 353 µmol), and sodium tert-butoxide (102 mg, 1.06 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 9 mg, 21 µmol), and tris(dibenzylideneacetone)dipalladium (0) chloroform adduct (11 mg, 10.6 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as an off-white solid (128 mg, 80%). HPLC (method LCMS_fastgradient) $t_R$=0.98 min. $^1$H NMR (d6-DMSO, 300 MHz): δ 1.35-1.43 (m, 2H), 1.36 (d, J=6.6 Hz, 6H), 1.81-1.93 (m, 2H), 2.38-2.46 (m, 2H), 2.91-3.01 (m, 2H), 3.51 (d, J=4.0 Hz, 1H), 3.70 (dd, J=3.0, 12.1 Hz, 1H), 3.91 (s, 3H), 4.41 (hept, J=6.6 Hz, 1H), 5.98 (d, J=4.4 Hz, 1H), 6.18 (d, J=2.6 Hz, 1H), 7.05-7.18 (m, 2H), 7.28 (dt, J=10.1, 2.3 Hz, 1H), 7.47 (dt, J=6.8, 8.3 Hz, 1H), 8.66 (d, J=2.4 Hz, 1H). MS (ES+) m/z 454.6 [M+H].

Example 127

(1R,5S,8s)-N-[5-(3-Chloro-5-fluorophenoxy)-1-(propan-2-yl)-1H-1,2,4-triazol-3-yl]-3-(6-methylpyrimidin-4-yl)-3-azabicyclo[3.2.1]octan-8-amine

Example 128

(1R,5S,8s)-N-(5-(2,3-Difluorophenoxy)-1-(propan-2-yl)-1H-1,2,4-triazol-3-yl)-3-(2-methoxypyridin-4-yl)-3-azabicyclo[3.2.1]octan-8-amine

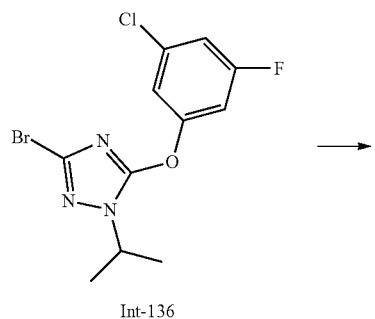

Int-136

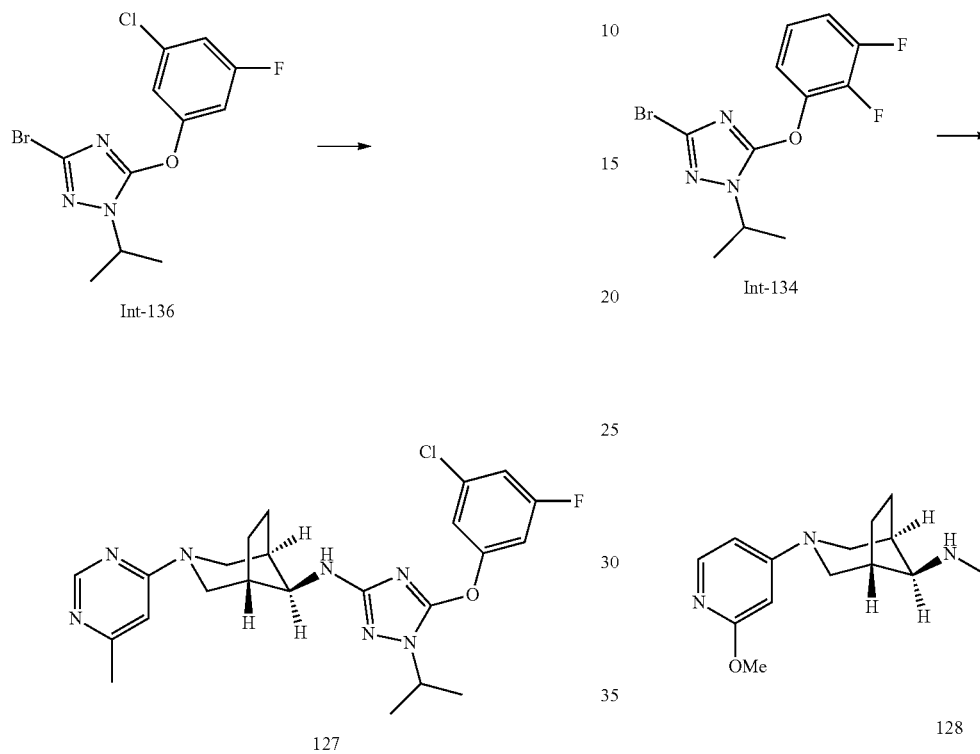

Int-134

127

128

In a 10 mL flask, (1R,5S,8s)-3-(6-methylpyrimidin-4-yl)-3-azabicyclo[3.2.1]octan-8-amine (Int-114, 94.7 mg, 434 μmol), 3-bromo-5-(3-chloro-5-fluorophenoxy)-1-(propan-2-yl)-1H-1,2,4-triazole (Int-136, 121 mg, 362 μmol), and sodium tert-butoxide (104 mg, 1.08 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 9.2 mg, 22 μmol), and tris(dibenzylideneacetone)dipalladium (0) chloroform adduct (11.2 mg, 10.8 μmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to afford the title compound as a white foam (57 mg, 33%). HPLC (method LCMS_fastgradient) $t_R$=1.00 min. $^1$H NMR (d6-DMSO, 300 MHz): δ 1.24-1.34 (m, 2H), 1.36 (d, J=6.6 Hz, 6H), 1.78-1.88 (m, 2H), 2.24 (s, 3H), 2.34-2.42 (m, 2H), 2.91-2.99 (m, 2H), 3.55 (d, J=4.6 Hz, 1H), 4.00-4.18 (m, 2H), 4.42 (hept, J=6.6 Hz, 1H), 6.01 (d, J=4.6 Hz, 1H), 6.62 (s, 1H), 7.32-7.44 (m, 3H), 8.34 (d, J=0.8 Hz, 1H). MS (ES+) m/z 472.2, 474.0 [M+H, Cl isotopes].

In a 10 mL flask, (1R,5S,8s)-3-(2-methoxypyridin-4-yl)-3-azabicyclo[3.2.1]octan-8-amine (Int-111, 102 mg, 438 μmol), 3-bromo-5-(2,3-difluorophenoxy)-1-(propan-2-yl)-1H-1,2,4-triazole (Int-134, 116 mg, 365 μmol), and sodium tert-butoxide (105 mg, 1.09 mmol) were charged. The flask was evacuated and backfilled with argon, Then, 2-methyltetrahydrofuran (4.5 mL), di-tert-butyl(2',4',6'-triisopropylbiphenyl-2-yl)phosphine ("tBuXPhos", CAS [564483-19-8], 9.3 mg, 22 μmol), and tris(dibenzylideneacetone) dipalladium (0) chloroform adduct (11.3 mg, 10.9 μmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as a light yellow foam (107 mg, 62%). HPLC (method LCMS_fastgradient) $t_R$=0.98 min. $^1$H NMR (d6-DMSO, 300 MHz): δ 1.34-1.40 (m, 2H), 1.39 (d, J=6.6 Hz, 6H), 1.78-1.88 (m, 2H), 2.34-2.41 (m, 2H), 2.82-2.90 (m, 2H), 3.45 (d, J=4.2 Hz, 1H), 3.58 (dd, J=3.0, 12.1 Hz, 2H), 3.75 (s, 3H), 4.45 (hept, J=6.6 Hz, 1H), 5.94-6.01 (m, 2H), 6.46 (dd, J=2.2, 6.2 Hz, 1H), 7.23-7.44 (m, 3H), 7.74 (d, J=6.2 Hz, 1H). MS (ES+) m/z 471.4 [M+H].

Example 129

(1R,5S,8s)-N-(5-(2,3-Difluorophenoxy)-1-(propan-2-yl)-1H-1,2,4-triazol-3-yl)-3-(6-methoxypyridazin-4-yl)-3-azabicyclo[3.2.1]octan-8-amine

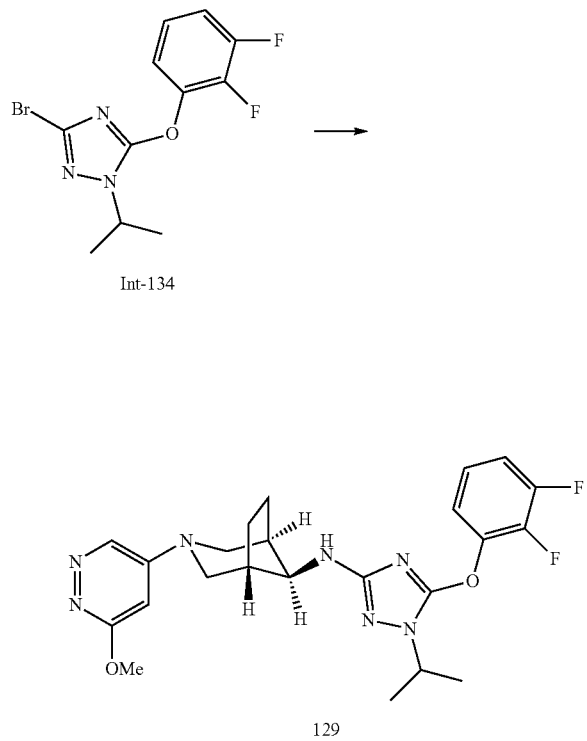

In a 10 mL flask, (1R,5S,8s)-3-(6-methoxypyridazin-4-yl)-3-azabicyclo[3.2.1]octan-8-amine (Int-128, 87.5 mg, 373 μmol), 3-bromo-5-(2,3-difluorophenoxy)-1-(propan-2-yl)-1H-1,2,4-triazole (Int-134, 99 mg, 311 μmol), and sodium tert-butoxide (89.7 mg, 0.93 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 7.9 mg, 19 μmol), and tris(dibenzylideneacetone)dipalladium (0) chloroform adduct (9.7 mg, 9.3 μmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as an off-white foam (98 mg, 67%). HPLC (method LCMS_fastgradient) $t_R$=0.99 min. $^1$H NMR (d6-DMSO, 300 MHz): δ 1.33-1.41 (m, 2H), 1.39 (d, J=6.6 Hz, 6H), 1.79-1.90 (m, 2H), 2.35-2.43 (m, 2H), 2.90-2.99 (m, 2H), 3.48 (d, J=4.0 Hz, 1H), 3.67 (d, J=2.8 Hz, 1H), 3.71 (d, J=2.8 Hz, 1H), 3.91 (s, 3H), 4.45 (hept, J=6.6 Hz, 1H), 5.99 (d, J=4.4 Hz, 1H), 6.17 (d, J=2.4 Hz, 1H), 7.23-7.44 (m, 3H), 8.65 (d, J=2.6 Hz, 1H). MS (ES+) m/z 472.4 [M+H].

Example 130

(1R,5S,8s)-N-(5-(3,5-Difluorophenoxy)-1-(2,2,2-trifluoroethyl)-1H-1,2,4-triazol-3-yl)-3-(6-methylpyrimidin-4-yl)-3-azabicyclo[3.2.1]octan-8-amine

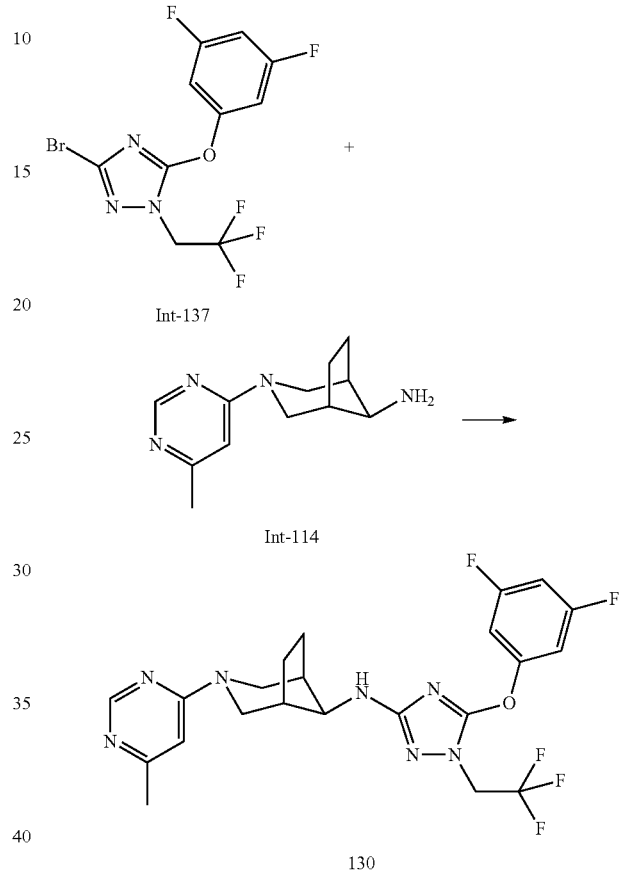

In an 8 mL microwave vial, (1R,5S,8s)-3-(6-methylpyrimidin-4-yl)-3-azabicyclo[3.2.1]octan-8-amine (Int-114, 115 mg, 526 μmol), 3-bromo-5-(3,5-difluorophenoxy)-1-(2,2,2-trifluoroethyl)-1H-1,2,4-triazole (Int-137, 157 mg, 438 μmol), and sodium tert-butoxide (105 mg, 1.1 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 49.9 mg, 70.2 μmol), and tris(dibenzylideneacetone)dipalladium (0) chloroform adduct (36.3 mg, 35.1 μmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100×30 mm×5 μm, eluting with acetonitrile/(water+0.1% triethylamine), gradient 20:80 to 98:2 v/v) to yield the title compound as white foam (26 mg, 12%). HPLC (method LCMS_fastgradient) $t_R$=0.96 min. $^1$H NMR (CDCl₃, 300 MHz): δ1.51-1.63 (m, 2H), 1.80-1.90 (m, 2H), 2.37 (s, 3H), 2.44-2.51 (m, 2H), 3.05-3.15 (m, 2H), 3.76 (d, J=6.2 Hz, 1H), 4.04 (d, J=5.8 Hz, 1H), 4.07-4.21 (m, 1H), 4.52 (q, J=8.2 Hz, 2H), 6.35 (s, 1H), 6.74 (tt, J=2.3, 8.8 Hz, 1H), 6.89-6.99 (m, 2H), 8.51 (s, 1H). MS (ES+) m/z 496.3 [M+H].

Example 131

(1R,5S)—N-[5-(5-Chloro-2-fluoro-phenoxy)-1-isopropyl-1,2,4-triazol-3-yl]-3-(6-methylpyrimidin-4-yl)-3-azabicyclo[3.2.1]octan-8-amine

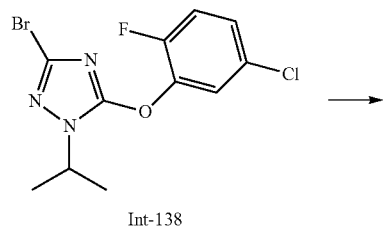

Int-138

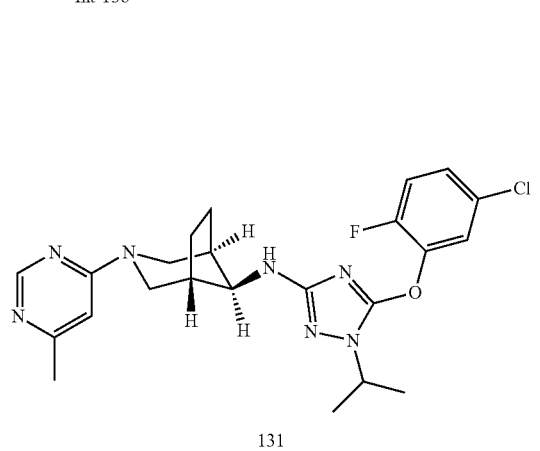

131

To a solution of (1R,5S)-3-(6-methylpyrimidin-4-yl)-3-azabicyclo[3.2.1]octan-8-amine (Int-114, 65.7 mg, 0.3 mmol) in 2-methyltetrahydrofuran (5.0 mL) was added 3-bromo-5-(5-chloro-2-fluoro-phenoxy)-1-isopropyl-1,2,4-triazole (Int-138, 100.0 mg, 0.3 mmol) and 2-di-tert-butylphosphino-2',4',6'-triisopropylbiphenyl ("tBuXPhos,", CAS [564483-19-8], 7.6 mg, 0.06 mmol) and was degassed with argon over a period of 5 min. To it then added tris(dibenzylideneacetone)dipalladium(0) ("Pd₂(dba)₃", CAS [51364-51-3], 8.2 mg, 0.03 mmol) and sodium tertbutoxide (86.0 mg, 0.9 mmol). The reaction mixture was heated at 80° C. with stirring for a period of 3h. Reaction mixture was then concentrated followed by purification of crude by combi-flash column chromatography (silica gel 15 gm), eluting with ethyl acetate/n-hexane 80:20 v/v) to afford title compound as light yellow solid (89.0 mg, 63%). HPLC purity 99.40%. ¹H NMR (DMSO-d6, 400 MHz): 1.27 (d, J=7.7 Hz, 3H), 1.39 (d, J=6.0 Hz, 6H), 1.80 (d, J=11.6 Hz, 2H), 2.23 (s, 3H), 2.35 (s, 2H), 2.93 (d, J=12.0 Hz, 2H), 3.51 (s, 1H), 3.96-4.17 (m, 2H), 4.38-4.50 (m, 1H), 5.97 (s, 1H), 6.61 (s, 1H), 7.41 (s, 1H), 7.48 (t, J=9.5 Hz, 1H), 7.78 (d, J=6.7 Hz, 1H), 8.33 (s, 1H). MS (ES+) m/z 471.9 [M+H].

Example 132

(1R,5S,8s)-N-(5-(3,5-Difluorophenoxy)-1-(propan-2-yl)-1H-1,2,4-triazol-3-yl)-3-(2-methoxypyridin-4-yl)-3-azabicyclo[3.2.1]octan-8-amine

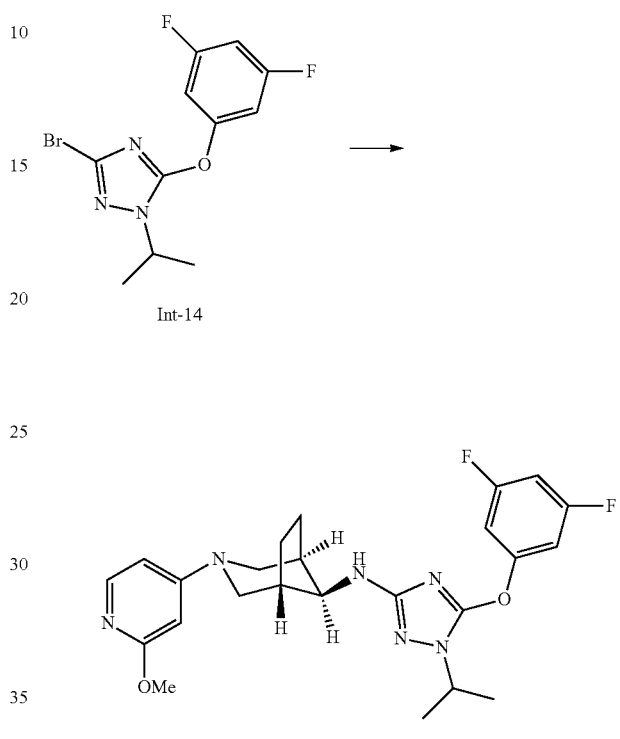

Int-14

132

In a 10 mL flask, (1R,5S,8s)-3-(2-methoxypyridin-4-yl)-3-azabicyclo[3.2.1]octan-8-amine (Int-111, 99.4 mg, 426 μmol) and 3-bromo-5-(3,5-difluorophenoxy)-1-(propan-2-yl)-1H-1,2,4-triazole (Int-14, 113 mg, 355 μmol), and sodium tert-butoxide (102 mg, 1.07 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 9 mg, 21 μmol), and tris(dibenzylideneacetone)dipalladium (0) chloroform adduct (11 mg, 10.7 μmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as white foam (117 mg, 70%). HPLC (method LCMS_fastgradient) t_R=1.00 min. ¹H NMR (d6-DMSO, 300 MHz): δ 1.36 (d, J=6.6 Hz, 6H), 1.36-1.43 (m, 2H), 1.81-1.92 (m, 2H), 2.36-2.45 (m, 2H), 2.84-2.92 (m, 2H), 3.48 (d, J=4.2 Hz, 1H), 3.58 (d, J=3.0 Hz, 1H), 3.62 (d, J=3.2 Hz, 1H), 3.75 (s, 3H), 4.41 (hept, J=6.6 Hz, 1H), 6.00 (s, 1H), 6.47 (dd, J=2.1, 6.1 Hz, 1H), 7.11-7.26 (m, 3H), 7.75 (d, J=6.0 Hz, 1H). MS (ES+) m/z 471.6 [M+H].

Example 133

(1R,5S,8s)-N-(5-(3,5-Difluorophenoxy)-1-(propan-2-yl)-1H-1,2,4-triazol-3-yl)-3-(6-methoxypyridazin-4-yl)-3-azabicyclo[3.2.1]octan-8-amine

Example 134

(1R,5S,8s)-N-(5-(3-Chloro-4-fluorophenoxy)-1-(propan-2-yl)-1H-1,2,4-triazol-3-yl)-3-(6-methoxypyridazin-4-yl)-3-azabicyclo[3.2.1]octan-8-amine

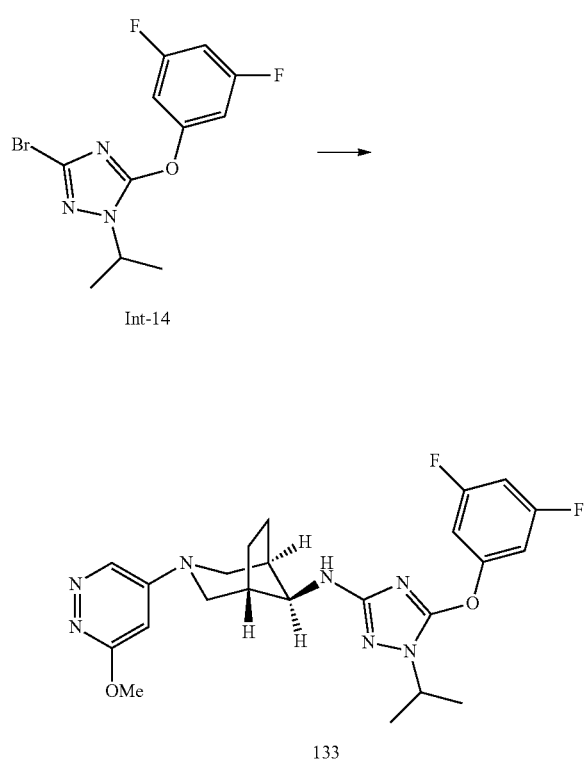

133

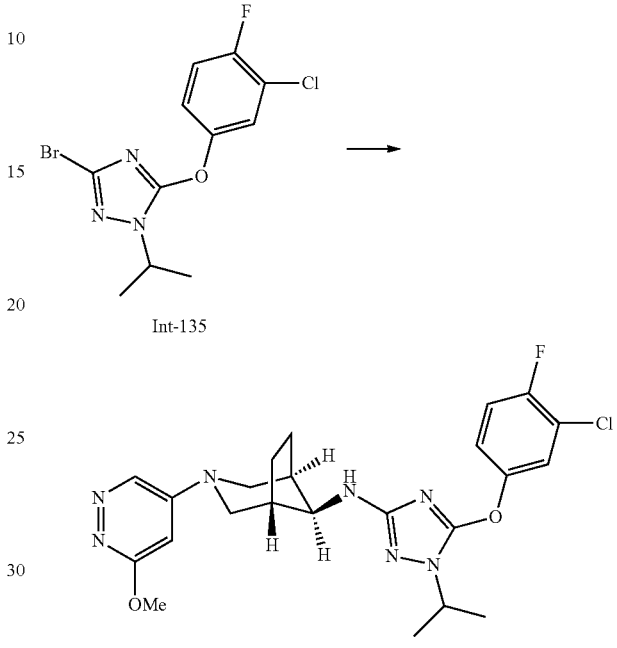

134

In a 10 mL flask, (1R,5S,8s)-3-(6-methoxypyridazin-4-yl)-3-azabicyclo[3.2.1]octan-8-amine (Int-128, 76 mg, 324 µmol) and 3-bromo-5-(3,5-difluorophenoxy)-1-(propan-2-yl)-1H-1,2,4-triazole (Int-14, 86 mg, 270 µmol), and sodium tert-butoxide (78 mg, 0.81 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 6.9 mg, 16 µmol), and tris(dibenzylideneacetone)dipalladium (0) chloroform adduct (8.4 mg, 8.1 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as an off-white solid (84 mg, 64%). HPLC (method LCMS_fastgradient) $t_R$=1.01 min. $^1$H NMR (d6-DMSO, 300 MHz): δ 1.36 (d, J=6.6 Hz, 6H), 1.36-1.44 (m, 2H), 1.81-1.93 (m, 2H), 2.38-2.46 (m, 2H), 2.91-3.01 (m, 2H), 3.51 (d, J=4.0 Hz, 1H), 3.68 (d, J=2.8 Hz, 1H), 3.72 (d, J=2.8 Hz, 1H), 3.91 (s, 3H), 4.41 (hept, J=6.6 Hz, 1H), 6.03 (d, J=4.4 Hz, 1H), 6.18 (d, J=2.4 Hz, 1H), 7.11-7.26 (m, 3H), 8.66 (d, J=2.4 Hz, 1H). MS (ES+) m/z 472.6 [M+H].

In a 10 mL flask, (1R,5S,8s)-3-(6-methoxypyridazin-4-yl)-3-azabicyclo[3.2.1]octan-8-amine (Int-128, 90 mg, 384 µmol), 3-bromo-5-(3-chloro-4-fluorophenoxy)-1-(propan-2-yl)-1H-1,2,4-triazole (Int-135, 107 mg, 320 µmol), and sodium tert-butoxide (92.2 mg, 0.96 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 8.2 mg, 19 µmol), and tris(dibenzylideneacetone)dipalladium (0) chloroform adduct (9.9 mg, 9.6 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100× 30 mm×5 µm, eluting with acetonitrile/(water+0.1% triethylamine), gradient 20:80 to 98:2 v/v) to afford the title compound as an off-white foam (64 mg, 40%). HPLC (method LCMS_fastgradient) $t_R$=1.06 min. $^1$H NMR (CDCl$_3$, 300 MHz): δ 1.46 (d, J=6.6 Hz, 6H), 1.56-1.64 (m, 2H), 1.86-1.97 (m, 2H), 2.47-2.55 (m, 2H), 3.09-3.17 (m, 2H), 3.61 (dd, J=3.2, 11.8 Hz, 1H), 3.75 (d, J=5.8 Hz, 1H), 3.90 (d, J=5.8 Hz, 1H), 4.08 (s, 3H), 4.45 (hept, J=6.6 Hz, 1H), 6.02 (d, J=2.4 Hz, 1H), 7.14-7.18 (m, 2H), 7.36-7.41 (m, 1H), 8.57 (d, J=2.6 Hz, 1H). MS (ES+) m/z 488.2, 490.1 [M+H, Cl isotopes].

Example 135

(1R,5S,8s)-N-(5-(3-Chloro-4-fluorophenoxy)-1-(propan-2-yl)-1H-1,2,4-triazol-3-yl)-3-(2-methoxypyridin-4-yl)-3-azabicyclo[3.2.1]octan-8-amine

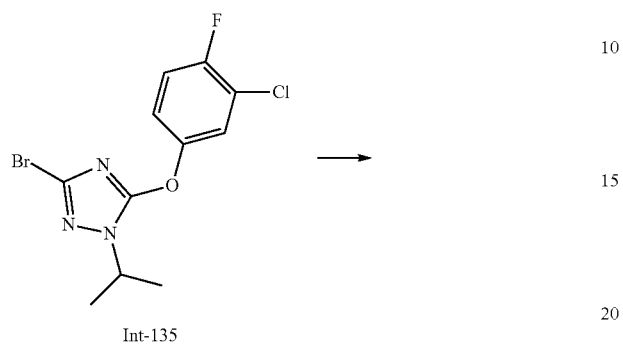

Int-135

135

In a 10 mL flask, (1R,5S,8s)-3-(2-methoxypyridin-4-yl)-3-azabicyclo[3.2.1]octan-8-amine (Int-111, 80.3 mg, 344 µmol), 3-bromo-5-(3-chloro-4-fluorophenoxy)-1-(propan-2-yl)-1H-1,2,4-triazole (Int-135, 96 mg, 287 µmol), and sodium tert-butoxide (82.7 mg, 0.86 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 7.3 mg, 17 µmol), and tris(dibenzylideneacetone)dipalladium (0) chloroform adduct (8.9 mg, 8.6 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100× 30 mm×5 µm, eluting with acetonitrile/(water+0.1% triethylamine), gradient 20:80 to 98:2 v/v) to afford the title compound as a white foam (65 mg, 46%). HPLC (method LCMS_fastgradient) $t_R$=1.02 min. $^1$H NMR (CDCl$_3$, 300 MHz): δ 1.46 (d, J=6.6 Hz, 6H), 1.57-1.65 (m, 2H), 1.81-1.93 (m, 2H), 2.42-2.50 (m, 2H), 3.01-3.10 (m, 2H), 3.58 (dd, J=3.2, 11.9 Hz, 2H), 3.72 (d, J=6.2 Hz, 1H), 3.86-3.92 (m, 1H), 3.90 (s, 3H), 4.45 (hept, J=6.6 Hz, 1H), 5.99 (d, J=2.2 Hz, 1H), 6.35 (dd, J=2.4, 6.2 Hz, 1H), 7.14-7.18 (m, 2H), 7.36-7.40 (m, 1H), 7.87 (d, J=6.0 Hz, 1H). MS (ES+) m/z 487.6, 489.6 [M+H, Cl isotopes].

Example 136

(1R,5S,8s)-N-[5-(3-Chloro-2-fluoro-phenoxy)-1-isopropyl-1,2,4-triazol-3-yl]-3-(6-methylpyrimidin-4-yl)-3-azabicyclo[3.2.1]octan-8-amine

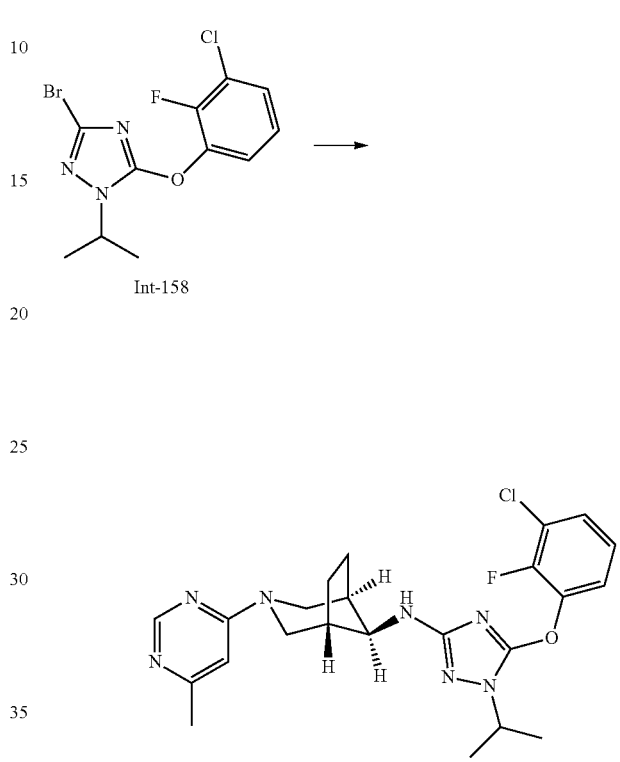

136

To a solution of (1R,5S)-3-azabicyclo[3.2.1]octan-8-amine; ethane; 4-methylpyrimidine (Int-114, 200.0 mg, 0.8 mmol) in 2-methyltetrahydrofuran (5.0 mL) was added 3-bromo-5-(3-chloro-2-fluoro-phenoxy)-1-isopropyl-1,2,4-triazole (Int-158, 200.0 mg, 0.8 mmol) and 2-di-tert-butylphosphino-2',4',6'-triisopropylbiphenyl ("tBuXPhos,", CAS [564483-19-8], 15.0 mg, 0.06 mmol) and was degassed with argon over a period of 5 min. To it then added tris(dibenzylideneacetone)dipalladium(0) ("Pd$_2$(dba)$_3$,", CAS [51364-51-3], 16.4 mg, 0.03 mmol) and sodium tert-butoxide (172.0 mg, 1.8 mmol). The reaction mixture was heated at 80° C. with stirring for a period of 3h. Reaction mixture was then concentrated followed by purification of crude by combi-flash column chromatography (silica gel 15 gm), eluting with ethyl acetate/n-hexane 80:20 v/v) and this followed by reversed phase prep HPLC (YMC-ACTUS Triart C18 5µ 250×20 mm, flow 16 mL/min, eluting with acetonitrile/(water+20 mM ammonium bicarbonate), gradient 20:80 to 95:5) method to yield title compound as off-white solid (67.7 mg, 18%). HPLC purity 99.22%. $^1$H NMR (DMSO-d6, 400 MHz): 1.27 (d, J=7.5 Hz, 3H), 1.39 (d, J=6.5 Hz, 6H), 2.23 (s, 3H), 2.35 (s, 2H), 2.93 (d, J=12.0 Hz, 2H), 3.51 (s, 1H), 3.96-4.22 (m, 2H), 4.43-4.47 (m, 1H), 5.97 (d, J=4.2 Hz, 1H), 6.61 (s, 1H), 7.30 (t, J=8.1 Hz, 1H), 7.52 (d, J=7.2 Hz, 2H), 8.33 (s, 1H). MS (ES+) m/z 471.9 [M+H].

Example 137

(1R,5S,8s)-N-[5-(3-Chloro-5-fluorophenoxy)-1-(propan-2-yl)-1H-1,2,4-triazol-3-yl]-3-(6-methoxypyridazin-4-yl)-3-azabicyclo[3.2.1]octan-8-amine

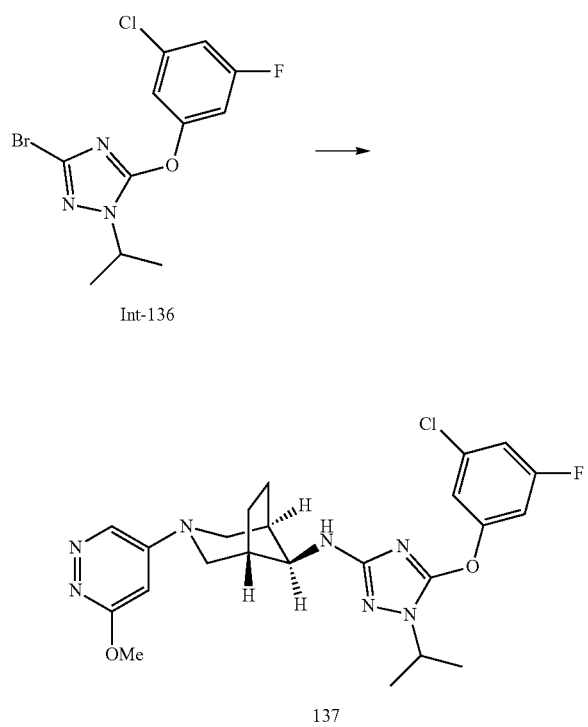 [SMILES: CC(C)n1nc(Br)nc1Oc1cc(F)cc(Cl)c1 ; COc1cc(N2C[C@H]3CC[C@@H](C2)[C@@H]3Nc2nc(Oc3cc(F)cc(Cl)c3)n(C(C)C)n2)cnn1]

In a 10 mL flask, (1R,5S,8s)-3-(6-methoxypyridazin-4-yl)-3-azabicyclo[3.2.1]octan-8-amine (Int-128, 90 mg, 384 µmol), 3-bromo-5-(3-chloro-5-fluorophenoxy)-1-(propan-2-yl)-1H-1,2,4-triazole (Int-136, 100 mg, 299 µmol), and sodium tert-butoxide (87 mg, 0.90 mmol) were charged. The flask was evacuated and backfilled with argon, Then, 2-methyltetrahydrofuran (4.3 mL), di-tert-butyl(2',4',6'-triisopropylbiphenyl-2-yl)phosphine ("tBuXPhos", CAS [564483-19-8], 8.4 mg, 20 µmol), and tris(dibenzylideneacetone)dipalladium (0) chloroform adduct (10.1 mg, 9.8 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (2×30 mL), dried (sodium sulfate) and concentrated in vacuo. The resulting crude product was purified by column chromatography (silica gel, 12 g, eluting with dichloromethane/methanol, gradient 100:0 to 95:5 v/v) to afford the title compound as a light brown solid (50 mg, 33%). HPLC (method LCMS_fastgradient) $t_R$=1.09 min. $^1$H NMR (d6-DMSO, 300 MHz): δ 1.35-1.44 (m, 2H), 1.36 (d, J=6.6 Hz, 6H), 1.80-1.94 (m, 2H), 2.37-2.46 (m, 2H), 2.91-3.01 (m, 2H), 3.51 (d, J=4.0 Hz, 1H), 3.68 (d, J=2.6 Hz, 1H), 3.72 (d, J=3.0 Hz, 1H), 3.91 (s, 3H), 4.42 (hept, J=6.6 Hz, 1H), 6.04 (d, J=4.2 Hz, 1H), 6.18 (d, J=2.4 Hz, 1H), 7.32-7.44 (m, 3H), 8.66 (d, J=2.4 Hz, 1H). MS (ES+) m/z 488.6, 490.6 [M+H, Cl isotopes].

Example 138

(1R,5S,8s)-N-(5-(3,5-Difluorophenoxy)-1-(2,2,2-trifluoroethyl)-1H-1,2,4-triazol-3-yl)-3-(2-methoxypyridin-4-yl)-3-azabicyclo[3.2.1]octan-8-amine

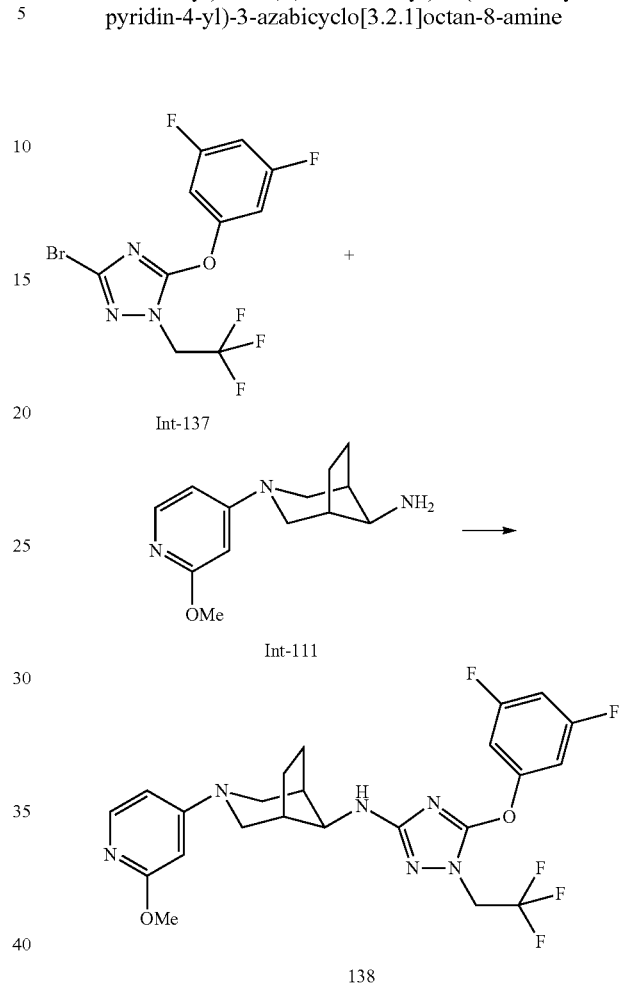

In an 8 mL microwave vial, (1R,5S,8s)-3-(2-methoxypyridin-4-yl)-3-azabicyclo[3.2.1]octan-8-amine (Int-111, 140 mg, 600 µmol), 3-bromo-5-(3,5-difluorophenoxy)-1-(2,2,2-trifluoroethyl)-1H-1,2,4-triazole (Int-137, 179 mg, 500 µmol), and sodium tert-butoxide (120 mg, 1.25 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 56.8 mg, 80 µmol), and tris(dibenzylideneacetone)dipalladium (0) chloroform adduct (41.4 mg, 40 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×30 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100×30 mm×5 µm, eluting with acetonitrile/(water+0.1% triethylamine), gradient 20:80 to 98:2 v/v) to yield the title compound as off-white solid (27 mg, 10%). HPLC (method LCMS_fastgradient) $t_R$=0.99 min. $^1$H NMR (d6-DMSO, 300 MHz): δ 1.34-1.45 (m, 2H), 1.80-1.92 (m, 2H), 2.37-2.46 (m, 2H), 2.81-2.91 (m, 2H), 3.47 (d, J=4.0 Hz, 1H), 3.58 (d, J=2.8 Hz, 1H), 3.62 (d, J=2.8 Hz, 1H), 3.75 (s, 3H), 4.91 (q, J=9.0 Hz, 2H), 5.75 (s, 1H), 6.01 (d, J=2.0 Hz, 1H), 6.31 (d, J=4.4 Hz, 1H), 6.47 (dd, J=2.2, 6.2 Hz, 1H), 7.17-7.32 (m, 3H), 7.75 (d, J=6.2 Hz, 1H). MS (ES+) m/z 511.6 [M+H].

Example 139

(1R,5S,8s)-N-(5-(2,3-Difluorophenoxy)-1-(2,2,2-trifluoroethyl)-1H-1,2,4-triazol-3-yl)-3-(2-methoxy-pyridin-4-yl)-3-azabicyclo[3.2.1]octan-8-amine

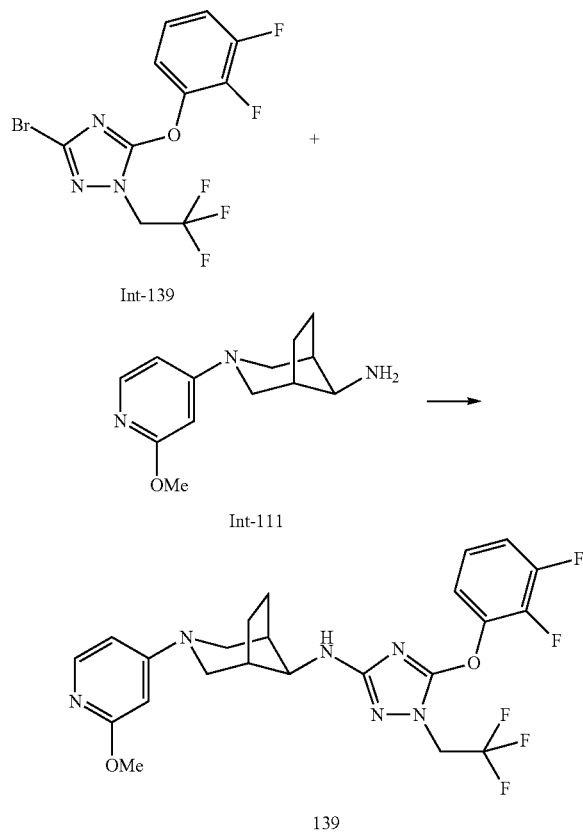

In an 8 mL microwave vial, (1R,5S,8s)-3-(2-methoxy-pyridin-4-yl)-3-azabicyclo[3.2.1]octan-8-amine (Int-111, 152 mg, 650 µmol), 3-bromo-5-(2,3-difluorophenoxy)-1-(2,2,2-trifluoroethyl)-1H-1,2,4-triazole (Int-139, 194 mg, 542 µmol), and sodium tert-butoxide (130 mg, 1.35 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 61.6 mg, 86.7 µmol), and tris(dibenzylideneacetone)dipalladium (0) chloroform adduct (45 mg, 43 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×30 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100×30 mm×5 µm, eluting with acetonitrile/(water+0.1% triethylamine), gradient 20:80 to 98:2 v/v) to yield the title compound as an off-white foam (14 mg, 5%). HPLC (method LCMS_fastgradient) t$_R$=0.99 min. $^1$H NMR (CDCl$_3$, 300 MHz): δ1.55-1.65 (m, 2H), 1.79-1.88 (m, 2H), 2.42-2.49 (m, 2H), 3.00-3.08 (m, 2H), 3.58 (dd, J=3.2, 11.7 Hz, 2H), 3.68 (d, J=5.8 Hz, 1H), 3.90 (s, 3H), 4.00 (d, J=6.0 Hz, 1H), 4.55 (q, J=8.2 Hz, 2H), 5.99 (d, J=2.2 Hz, 1H), 6.34 (dd, J=2.4, 6.0 Hz, 1H), 7.09-7.25 (m, 3H), 7.87 (d, J=6.2 Hz, 1H). MS (ES+) m/z 511.6 [M+H].

Example 140

(1R,5S,8s)-N-(5-(2,3-Difluorophenoxy)-1-(2,2,2-trifluoroethyl)-1H-1,2,4-triazol-3-yl)-3-(6-methylpyrimidin-4-yl)-3-azabicyclo[3.2.1]octan-8-amine

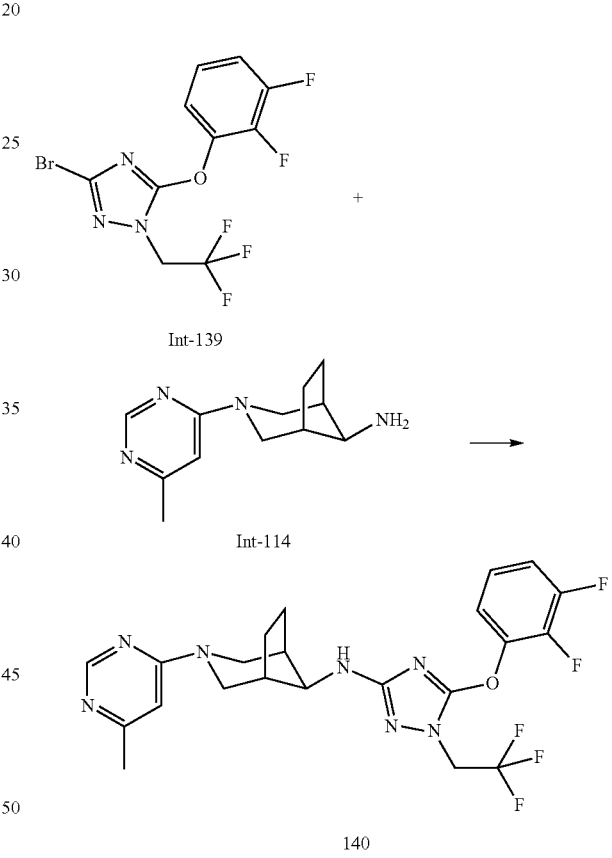

In an 8 mL microwave vial, (1R,5S,8s)-3-(6-methylpyrimidin-4-yl)-3-azabicyclo[3.2.1]octan-8-amine (Int-114, 136 mg, 623 µmol), 3-bromo-5-(2,3-difluorophenoxy)-1-(2,2,2-trifluoroethyl)-1H-1,2,4-triazole (Int-139, 186 mg, 519 µmol), and sodium tert-butoxide (125 mg, 1.3 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 59.1 mg, 83.1 µmol), and tris(dibenzylideneacetone)dipalladium (0) chloroform adduct (43 mg, 41.6 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100×30 mm×5 µm, eluting with acetonitrile/(water+0.1% triethylamine), gradient 20:80 to 98:2 v/v) to yield the title compound as light yellow foam (28 mg, 11%). HPLC (method LCMS_fastgradient) $t_R$=0.95 min. $^1$H NMR (CDCl$_3$, 300 MHz): δ1.49-1.60 (m, 2H), 1.76-1.86 (m, 2H), 2.37 (s, 3H), 2.42-2.49 (m, 2H), 3.05-3.13 (m, 2H), 3.74 (d, J=6.0 Hz, 1H), 3.99 (d, J=6.0 Hz, 1H), 4.05-4.19 (m, 2H), 4.56 (q, J=8.2 Hz, 2H), 6.34 (s, 1H), 7.09-7.24 (m, 3H), 8.51 (d, J=0.8 Hz, 1H). MS (ES+) m/z 496.3 [M+H].

Example 141

(1R,5S,8s)-N-(5-(3-Chloro-4-fluorophenoxy)-1-(2,2,2-trifluoroethyl)-1H-1,2,4-triazol-3-yl)-3-(6-methylpyrimidin-4-yl)-3-azabicyclo[3.2.1]octan-8-amine

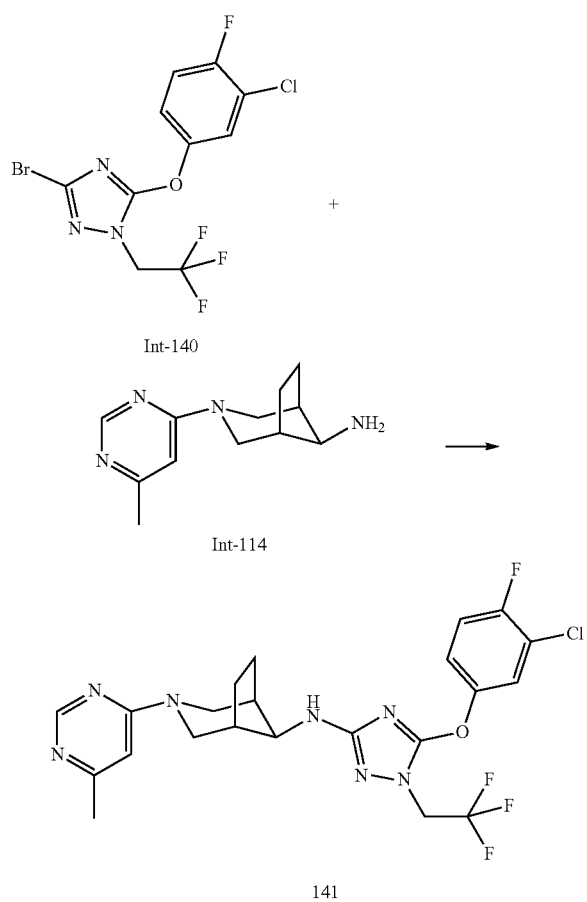

In an 8 mL microwave vial, (1R,5S,8s)-3-(6-methylpyrimidin-4-yl)-3-azabicyclo[3.2.1]octan-8-amine (Int-114, 124 mg, 567 µmol), 3-bromo-5-(3-chloro-4-fluorophenoxy)-1-(2,2,2-trifluoroethyl)-1H-1,2,4-triazole (Int-140, 177 mg, 473 µmol), and sodium tert-butoxide (114 mg, 1.2 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 53.7 mg, 75.6 µmol), and tris(dibenzylideneacetone)dipalladium (0) chloroform adduct (39.1 mg, 37.8 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100×30 mm×5 µm, eluting with acetonitrile/(water+0.1% triethylamine), gradient 20:80 to 98:2 v/v) to yield the title compound as white foam (64 mg, 26%). HPLC (method LCMS_fastgradient) $t_R$=1.01 min. $^1$H NMR (CDCl$_3$, 300 MHz): δ1.50-1.60 (m, 2H), 1.77-1.88 (m, 2H), 2.37 (s, 3H), 2.42-2.50 (m, 2H), 3.08-3.14 (m, 2H), 3.74 (d, J=6.0 Hz, 1H), 4.01 (d, J=6.0 Hz, 1H), 4.05-4.21 (m, 2H), 4.52 (q, J=8.2 Hz, 2H), 6.34 (s, 1H), 7.17-7.21 (m, 2H), 7.40-7.44 (m, 1H), 8.51 (d, J=0.6 Hz, 1H). MS (ES+) m/z 512.1, 514.0 [M+H, Cl isotopes].

Example 142

(1R,5S,8s)-N-(5-(3-Chloro-4-fluorophenoxy)-1-(2,2,2-trifluoroethyl)-1H-1,2,4-triazol-3-yl)-3-(2-methoxypyridin-4-yl)-3-azabicyclo[3.2.1]octan-8-amine

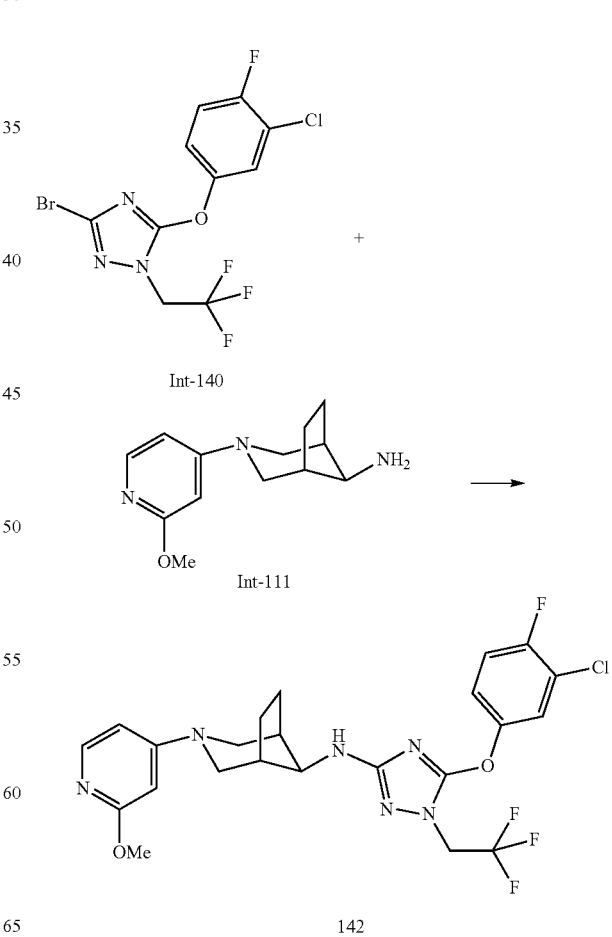

In an 8 mL microwave vial, (1R,5S,8s)-3-(2-methoxypyridin-4-yl)-3-azabicyclo[3.2.1]octan-8-amine (Int-111, 149 mg, 638 µmol), 3-bromo-5-(3-chloro-4-fluorophenoxy)-1-(2,2,2-trifluoroethyl)-1H-1,2,4-triazole (Int-140, 199 mg, 531 µmol), and sodium tert-butoxide (128 mg, 1.33 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 60.4 mg, 85 µmol), and tris(dibenzylideneacetone)dipalladium (0) chloroform adduct (44 mg, 42.5 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100×30 mm×5 µm, eluting with acetonitrile/(water+0.1% triethylamine), gradient 20:80 to 98:2 v/v) to yield the title compound as an off-white foam (35 mg, 12%). HPLC (method LCMS_fastgradient) $t_R$=1.03 min. $^1$H NMR (CDCl$_3$, 300 MHz): δ 1.55-1.66 (m, 2H), 1.81-1.90 (m, 2H), 2.43-2.50 (m, 2H), 3.01-3.09 (m, 2H), 3.59 (dd, J=3.2, 11.9 Hz, 2H), 3.69 (d, J=6.0 Hz, 1H), 3.90 (s, 3H), 4.01 (d, J=6.2 Hz, 1H), 4.51 (q, J=8.2 Hz, 2H), 5.99 (d, J=2.2 Hz, 1H), 6.35 (dd, J=2.4, 6.2 Hz, 1H), 7.17-7.21 (m, 2H), 7.40-7.44 (m, 1H), 7.87 (d, J=6.2 Hz, 1H). MS (ES+) m/z 527.1, 529.0 [M+H, Cl isotopes].

Example 143

(1R,5S,8s)-N-[5-(2-Chlorophenoxy)-1-(propan-2-yl)-1H-1,2,4-triazol-3-yl]-3-(6-methylpyrimidin-4-yl)-3-azabicyclo[3.2.1]octan-8-amine

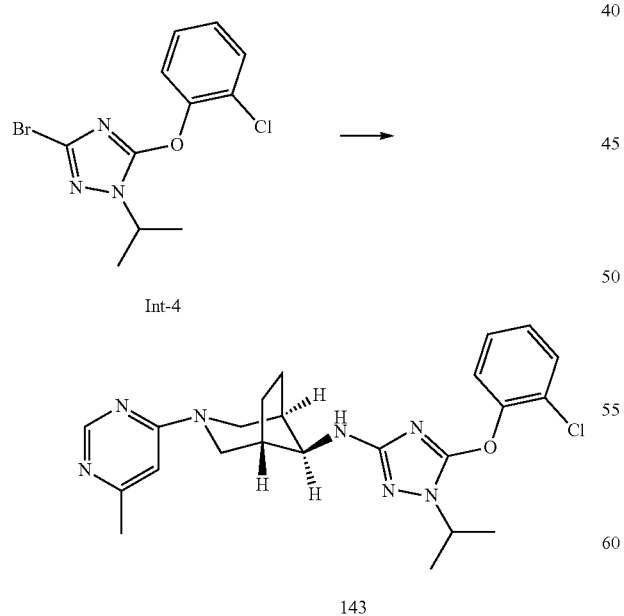

In a 10 mL flask, (1R,5S,8s)-3-(6-methylpyrimidin-4-yl)-3-azabicyclo[3.2.1]octan-8-amine (Int-114, 92.7 mg, 425 µmol), 3-bromo-5-(2-chlorophenoxy)-1-(propan-2-yl)-1H-1,2,4-triazole (Int-4, 112 mg, 354 µmol), and sodium tert-butoxide (102 mg, 1.06 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 9.0 mg, 21 µmol), and tris(dibenzylideneacetone)dipalladium (0) chloroform adduct (11.0 mg, 10.6 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to afford the title compound as an off-white foam (68 mg, 39%). $^1$H NMR (d6-DMSO, 300 MHz): δ 1.21-1.32 (m, 2H), 1.40 (d, J=6.6 Hz, 6H), 1.74-1.86 (m, 2H), 2.23 (s, 3H), 2.31-2.40 (m, 2H), 2.88-2.99 (m, 2H), 3.51 (d, J=4.4 Hz, 1H), 3.98-4.18 (m, 2H), 4.46 (hept, J=6.6 Hz, 1H), 5.91 (d, J=4.8 Hz, 1H), 6.61 (s, 1H), 7.30 (ddd, J=1.6, 7.4, 7.9 Hz, 1H), 7.42 (ddd, J=1.6, 7.4, 8.1 Hz, 1H), 7.50 (dd, J=1.6, 8.2 Hz, 1H), 7.59 (d, J=1.6, 7.9 Hz, 1H), 8.33 (s, 1H). MS (ES+) m/z 454.1, 456.1 [M+H, Cl isotopes].

Example 144

(1R,5S,8s)-N-[5-(3-Chloro-5-fluorophenoxy)-1-(propan-2-yl)-1H-1,2,4-triazol-3-yl]-3-(2-methoxypyridin-4-yl)-3-azabicyclo[3.2.1]octan-8-amine

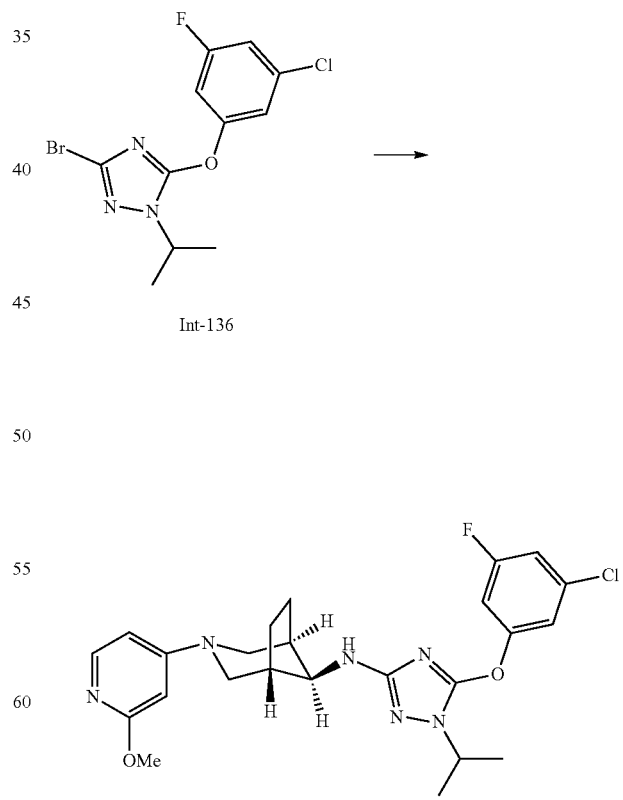

In a 10 mL flask, (1R,5S,8s)-3-(2-methoxypyridin-4-yl)-3-azabicyclo[3.2.1]octan-8-amine (Int-111, 99 mg, 424 µmol), 3-bromo-5-(3-chloro-5-fluorophenoxy)-1-(propan-2-yl)-1H-1,2,4-triazole (Int-136, 110 mg, 329 µmol), and sodium tert-butoxide (95.6 mg, 995 µmol) were charged. The flask was evacuated and backfilled with argon, Then, 2-methyltetrahydrofuran (4.8 mL), di-tert-butyl(2',4',6'-triisopropylbiphenyl-2-yl)phosphine ("tBuXPhos", CAS [564483-19-8], 9.2 mg, 22 µmol), and tris(dibenzylideneacetone)dipalladium (0) chloroform adduct (11.1 mg, 10.8 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (2×30 mL), dried (sodium sulfate) and concentrated in vacuo. The resulting crude product was purified by column chromatography (silica gel, 12 g, eluting with ethyl acetate/n-heptane, gradient 0:100 to 50:50 v/v) to afford the title compound as a white foam (63 mg, 39%). HPLC (method LCMS_fastgradient) $t_R$=1.03 min. $^1$H NMR (CDCl$_3$, 300 MHz): δ 1.45 (d, J=6.6 Hz, 6H), 1.58-1.66 (m, 2H), 1.84-1.95 (m, 2H), 2.43-2.52 (m, 2H), 3.02-3.11 (m, 2H), 3.59 (dd, J=2.8, 11.7 Hz, 2H), 3.73 (d, J=6.0 Hz, 1H), 3.87-3.96 (m, 4H), 4.43 (hept, J=6.7 Hz, 1H), 6.00 (d, J=2.4 Hz, 1H), 6.35 (dd, J=2.4, 6.2 Hz, 1H), 6.91-7.03 (m, 2H), 7.10-7.15 (m, 1H), 7.87 (d, J=6.0 Hz, 1H). MS (ES+) m/z 487.6, 489.6 [M+H, Cl isotopes].

Example 145 and example 146

(1R,5S,8s)-N-(5-(3-Chloro-4-fluorophenoxy)-1-(2,2-difluoroethyl)-1H-1,2,4-triazol-3-yl)-3-(6-methylpyrimidin-4-yl)-3-azabicyclo[3.2.1]octan-8-amine (145) and (1R,5S,8s)-N-(5-(3-chloro-4-fluorophenoxy)-1-(2-fluorovinyl)-1H-1,2,4-triazol-3-yl)-3-(6-methylpyrimidin-4-yl)-3-azabicyclo[3.2.1]octan-8-amine (146, E/Z mixture)

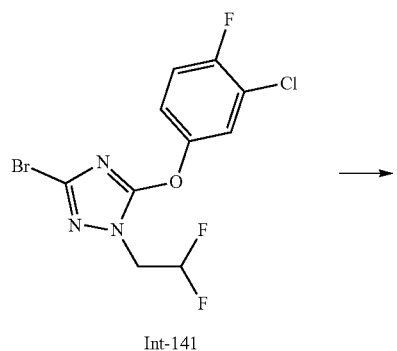

Int-141

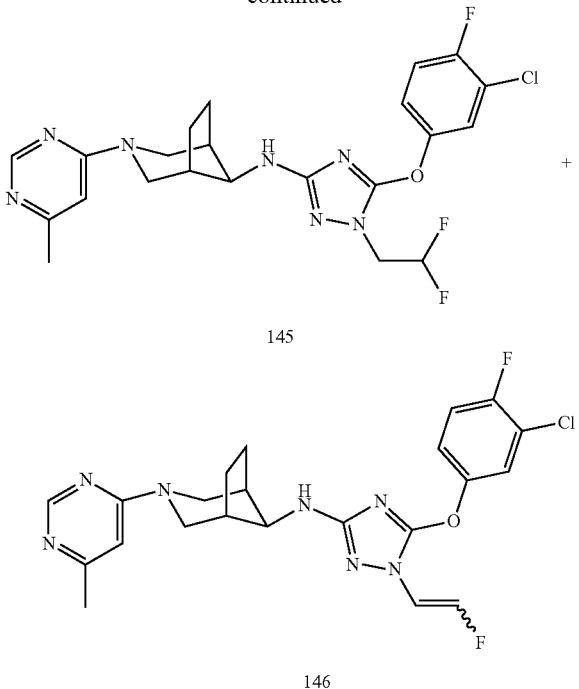

145

146

In an 8 mL microwave vial, (1R,5S,8s)-3-(6-methylpyrimidin-4-yl)-3-azabicyclo[3.2.1]octan-8-amine (Int-114, 138 mg, 633 µmol), 3-bromo-5-(3-chloro-4-fluorophenoxy)-1-(2,2-difluoroethyl)-1H-1,2,4-triazole (Int-141, 188 mg, 527 µmol), and sodium tert-butoxide (127 mg, 1.32 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 60.0 mg, 84.4 µmol), and tris(dibenzylideneacetone)dipalladium (0) chloroform adduct (43.7 mg, 42.2 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 95:5 v/v), followed by preparative chiral HPLC (Reprosil chiral-NR, eluting n-heptane/ethanol, 70:30 v/v isocratic) to afford example 145 (24 mg, 9%) as white foam and example 146 (66 mg, 25%) as white foam. Example 145: HPLC (method LCMS_fastgradient) $t_R$=0.96 min. $^1$H NMR (CDCl$_3$, 300 MHz): δ1.51-1.62 (m, 2H), 1.78-1.88 (m, 2H), 2.37 (s, 3H), 2.42-2.49 (m, 2H), 3.04-3.13 (m, 2H), 3.72 (d, J=6.0 Hz, 1H), 4.00 (d, J=6.0 Hz, 1H), 4.06-4.19 (m, 2H), 4.28 (dt, J=4.3, 13.0 Hz, 2H), 6.16 (tt, J=4.4, 55.6 Hz, 1H), 6.34 (s, 1H), 7.16-7.20 (m, 2H), 7.39-7.43 (m, 1H), 8.51 (d, J=0.8 Hz, 1H). MS (ES+) m/z 494.1, 496.0 [M+H, Cl isotopes].
Example 146: HPLC (method LCMS_fastgradient) $t_R$=0.96 min. $^1$H NMR (CDCl$_3$, 300 MHz): δ 1.51-1.61 (m, 2H), 1.77-1.88 (m, 2H), 2.36 (s, 3H), 2.44-2.52 (m, 2H), 3.05-3.13 (m, 2H), 3.80 (d, J=6.2 Hz, 1H), 4.08 (d, J=6.0 Hz, 1H), 4.08-4.20 (m, 2H), 6.13 & 6.23 (2d, J=4.2 Hz, 1H), 6.34 (s, 1H), 6.38 & 6.63 (2d, J=4.2 Hz, 1H), 7.17-7.23 (m, 2H), 7.41-7.46 (m, 1H), 8.51 (d, J=0.8 Hz, 1H). MS (ES+) m/z 474.6, 476.6 [M+H, Cl isotopes].

Example 147 and example 148

(1R,5S,8s)-N-(5-(3-Chloro-5-fluorophenoxy)-1-(2,2-difluoroethyl)-1H-1,2,4-triazol-3-yl)-3-(6-methylpyrimidin-4-yl)-3-azabicyclo[3.2.1]octan-8-amine (147) and (1R,5S,8s)-N-(5-(3-chloro-5-fluorophenoxy)-1-(2-fluorovinyl)-1H-1,2,4-triazol-3-yl)-3-(6-methylpyrimidin-4-yl)-3-azabicyclo[3.2.1]octan-8-amine (148, E/Z mixture)

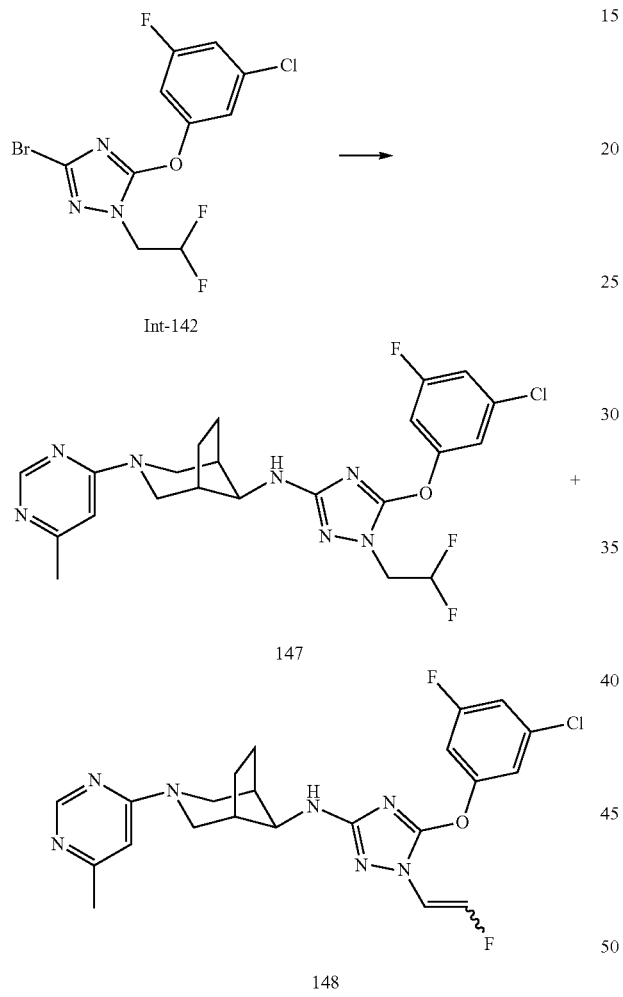

mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 95:5 v/v), followed by preparative chiral HPLC (Reprosil chiral-NR, eluting n-heptane/ethanol, 70:30 v/v isocratic) to afford example 147 (64 mg, 23%) as white foam and example 148 (33 mg, 12%) as white foam. Example 147: HPLC (method LCMS_fastgradient) $t_R$=0.98 min. $^1$H NMR (CDCl$_3$, 300 MHz): δ1.52-1.61 (m, 2H), 1.80-1.88 (m, 2H), 2.37 (s, 3H), 2.45-2.51 (m, 2H), 3.04-3.13 (m, 2H), 3.74 (d, J=6.0 Hz, 1H), 4.03 (d, J=5.8 Hz, 1H), 4.08-4.20 (m, 2H), 4.27 (dt, J=4.4, 13.0 Hz, 2H), 6.15 (tt, J=4.3, 55.5 Hz, 1H), 6.35 (s, 1H), 6.97-7.06 (m, 2H), 7.15-7.18 (m, 1H), 8.51 (d, J=0.8 Hz, 1H). MS (ES+) m/z 494.1, 496.1 [M+H, Cl isotopes]. Example 148: HPLC (method LCMS_fastgradient) $t_R$=0.98 min. $^1$H NMR (CDCl$_3$, 300 MHz): δ 1.52-1.62 (m, 2H), 1.80-1.90 (m, 2H), 2.36 (s, 3H), 2.45-2.53 (m, 2H), 3.05-3.14 (m, 2H), 3.81 (d, J=6.2 Hz, 1H), 4.09-4.20 (m, 2H), 4.11 (d, J=6.0 Hz, 1H), 6.12 & 6.22 (2d, J=4.2 Hz, 1H), 6.39 (s, 1H), 6.39 & 6.64 (2d, J=4.2 Hz, 1H), 6.98-7.09 (m, 2H), 7.18-7.21 (m, 1H), 8.51 (s, 1H). MS (ES+) m/z 474.1, 476.0 [M+H, Cl isotopes].

Example 149

(1R,5S,8s)-N-(5-(3-Fluorophenoxy)-1-(2,2,2-trifluoroethyl)-1H-1,2,4-triazol-3-yl)-3-(2-methoxypyridin-4-yl)-3-azabicyclo[3.2.1]octan-8-amine

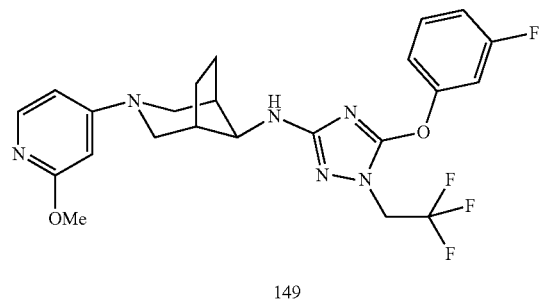

In an 8 mL microwave vial, (1R,5S,8s)-3-(6-methylpyrimidin-4-yl)-3-azabicyclo[3.2.1]octan-8-amine (Int-114, 144 mg, 660 μmol), 3-bromo-5-(3-chloro-5-fluorophenoxy)-1-(2,2-difluoroethyl)-1H-1,2,4-triazole (Int-142, 196 mg, 550 μmol), and sodium tert-butoxide (95.1 mg, 0.99 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 62.5 mg, 88 μmol), and tris(dibenzylideneacetone)dipalladium (0) chloroform adduct (45.5 mg, 44 μmol) were added subsequently. The vial was again degassed thoroughly with Argon and sealed. The reaction mixture was heated under microwave irradiation at 110° C. for 30 min. After that, water (30 mL) was added and the In an 8 mL microwave vial, (1R,5S,8s)-3-(6-methoxypyridin-4-yl)-3-azabicyclo[3.2.1]octan-8-amine (Int-111, 148 mg, 635 µmol), 3-bromo-5-(3-fluorophenoxy)-1-(2,2,2-trifluoroethyl)-1H-1,2,4-triazole (Int-40, 180 mg, 529 µmol), and sodium tert-butoxide (127 mg, 1.32 mmol) were suspended in 1,4-dioxane (15 mL). The flask was degassed thoroughly with Argon. 1,2,3,4,5-Pentaphenyl-1'-(di-tert-butylphosphino)ferrocene ("Q-phos", CAS [312959-24-3], 60.2 mg, 84.7 µmol), and tris(dibenzylideneacetone)dipalladium (0) chloroform adduct (43.8 mg, 42.3 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with ethyl acetate/n-heptane, gradient 0:100 to 20:80 v/v) to yield the title compound as light red foam (125 mg, 47%). HPLC (method LCMS_fastgradient) $t_R$=0.95 min. $^1$H NMR (CDCl$_3$, 300 MHz): δ 1.56-1.67 (m, 2H), 1.81-1.91 (m, 2H), 2.43-2.51 (m, 2H), 3.01-3.09 (m, 2H), 3.58 (dd, J=3.2, 11.9 Hz, 2H), 3.70 (d, J=6.0 Hz, 1H), 3.90 (s, 3H), 4.03 (d, J=6.0 Hz, 1H), 4.52 (q, J=8.2 Hz, 2H), 5.99 (d, J=2.2 Hz, 1H), 6.35 (dd, J=2.2, 6.2 Hz, 1H), 6.95-7.03 (m, 1H), 7.05-7.13 (m, 2H), 7.34-7.43 (m, 1H), 7.87 (d, J=6.0 Hz, 1H). MS (ES+) m/z 493.4 [M+H].

Example 150

(1R,5S)—N-[5-(3-chloro-2-fluoro-phenoxy)-1-isopropyl-1,2,4-triazol-3-yl]-3-(2-methoxy-4-pyridyl)-3-azabicyclo[3.2.1]octan-8-amine

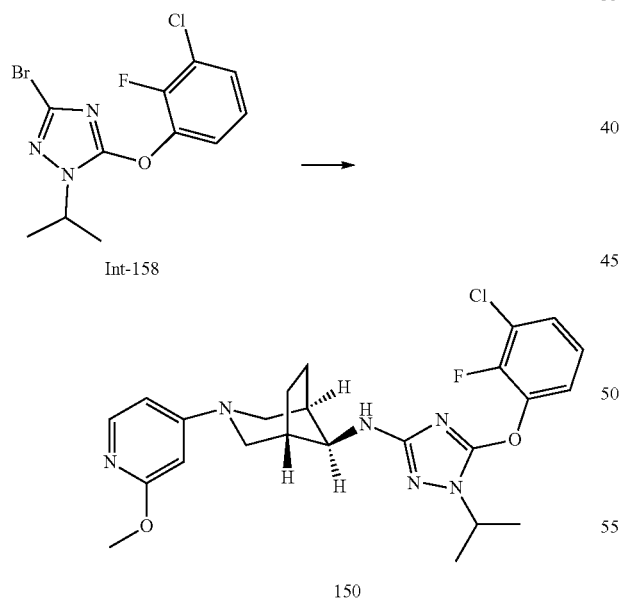

To a solution of (1R,5S,8s)-3-(2-methoxy-4-pyridyl)-3-azabicyclo[3.2.1]octan-8-amine (Int-111, 214.0 mg, 0.9 mmol) in 2-methyltetrahydrofuran (3.0 mL) was added 3-bromo-5-(3-chloro-2-fluoro-phenoxy)-1-(2,2,2-trifluoroethyl)-1,2,4-triazole (Int-158, 420.0 mg, 1.1 mmol) and 2-di-tert-butylphosphino-2',4',6'-triisopropylbiphenyl ("tBuXPhos,", CAS [564483-19-8], 30.5 mg, 0.1 mmol) and was degassed with argon over a period of 5 min. To it then added tris(dibenzylideneacetone)dipalladium(0) ("Pd$_2$(dba)$_3$", CAS [51364-51-3], 33.0 mg, 0.03 mmol) and sodium tertbutoxide (217.0 mg, 2.25 mmol). The reaction mixture was heated at 110° C. with stirring for a period of 1 h. Reaction mixture was then concentrated followed by purification of crude by combi-flash column chromatography (silica gel 15 gm), eluting with ethyl acetate/n-hexane 45:55 v/v) to yield title compound as yellow solid (82.0 mg, 17%). $^1$H NMR (DMSO-d6, 400 MHz): 1.23 (s, 1H), 1.39 (d, J=6.6 Hz, 7H), 1.81-1.85 (m, 2H), 2.37 (s, 2H), 2.86 (d, J=11.2 Hz, 2H), 3.45 (d, J=4.3 Hz, 1H), 3.58 (d, J=9.0 Hz, 2H), 3.75 (s, 3H), 4.45 (p, J=6.6 Hz, 1H), 5.97 (d, J=4.5 Hz, 1H), 5.99 (d, J=1.8 Hz, 1H), 6.46 (dd, J=6.1, 2.0 Hz, 1H), 7.25-7.34 (m, 1H), 7.47-7.57 (m, 2H), 7.74 (d, J=6.1 Hz, 1H). MS (ES+) m/z 486.8 [M+H].

Example 151 and example 152

(1R,5S,8s)-N-(5-(3,5-Difluorophenoxy)-1-(2,2-difluoroethyl)-1H-1,2,4-triazol-3-yl)-3-(6-methylpyrimidin-4-yl)-3-azabicyclo[3.2.1]octan-8-amine (151) and (1R,5S,8s)-N-(5-(3,5-difluorophenoxy)-1-(2-fluorovinyl)-1H-1,2,4-triazol-3-yl)-3-(6-methylpyrimidin-4-yl)-3-azabicyclo[3.2.1]octan-8-amine (152, E/Z mixture)

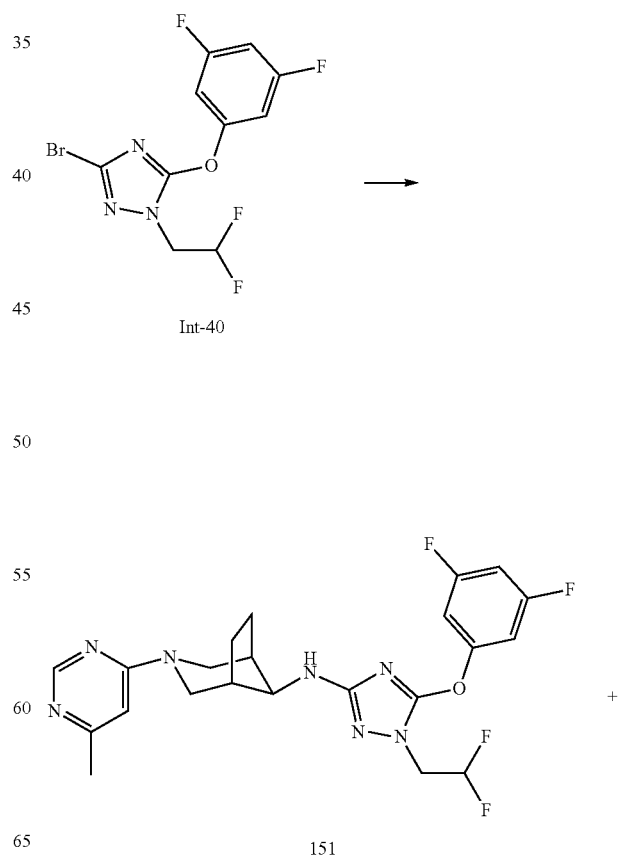

293

-continued

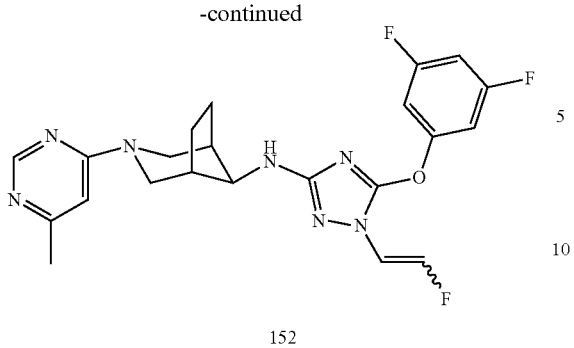

152

In an 8 mL microwave vial, (1R,5S,8s)-3-(6-methylpyrimidin-4-yl)-3-azabicyclo[3.2.1]octan-8-amine (Int-114, 128 mg, 586 μmol), 3-bromo-5-(3,5-difluorophenoxy)-1-(2,2-difluoroethyl)-1H-1,2,4-triazole (Int-143, 166 mg, 488 μmol), and sodium tert-butoxide (93.8 mg, 0.98 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 55.5 mg, 78.1 μmol), and tris(dibenzylideneacetone)dipalladium (0) chloroform adduct (40.4 mg, 39.1 μmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 95:5 v/v), followed by preparative chiral HPLC (Reprosil chiral-NR, eluting n-heptane/ethanol, 70:30 v/v isocratic) to afford example 151 (92 mg, 39%) as white foam and example 152 (48 mg, 21%) as white foam. Example 151: HPLC (method LCMS_fastgradient) $t_R$=0.92 min. $^1$H NMR (d6-DMSO, 300 MHz): δ 1.25-1.35 (m, 2H), 1.76-1.89 (m, 2H), 2.24 (s, 3H), 2.34-2.44 (m, 2H), 2.88-2.99 (m, 2H), 3.54 (d, J=4.4 Hz, 1H), 4.00-4.21 (m, 2H), 4.40 (td, J=3.4, 14.8 Hz, 2H), 6.20 (d, J=4.8 Hz, 1H), 6.36 (tt, J=3.6, 54.7 Hz, 1H), 6.62 (s, 1H), 7.15-7.29 (m, 3H), 8.34 (d, J=0.6 Hz, 1H). MS (ES+) m/z 478.6 [M+H]. Example 152: HPLC (method LCMS_fastgradient) $t_R$=0.91 min. $^1$H NMR (CDCl$_3$, 300 MHz): δ1.52-1.61 (m, 2H), 1.81-1.89 (m, 2H), 2.37 (s, 3H), 2.45-2.53 (m, 2H), 3.05-3.14 (m, 2H), 3.81 (d, J=6.0 Hz, 1H), 4.08-4.21 (m, 2H), 4.11 (d, J=6.0 Hz, 1H), 6.13 & 6.23 (2d, J=4.2 Hz, 1H), 6.35 (s, 3H), 6.39 & 6.64 (2d, J=4.2 Hz, 1H), 6.73 (tt, J=2.3, 8.8 Hz, 1H), 6.89-7.00 (m, 2H), 8.51 (d, J=0.6 Hz, 1H). MS (ES+) m/z 458.6 [M+H].

294

Example 153 and example 154

(1R,5S,8s)-N-(5-(3-Chloro-4-fluorophenoxy)-1-(2-fluoroethyl)-1H-1,2,4-triazol-3-yl)-3-(6-methylpyrimidin-4-yl)-3-azabicyclo[3.2.1]octan-8-amine (153) and (1R,5S,8s)-N-(5-(3-chloro-4-fluorophenoxy)-1-vinyl-1H-1,2,4-triazol-3-yl)-3-(6-methylpyrimidin-4-yl)-3-azabicyclo[3.2.1]octan-8-amine (154)

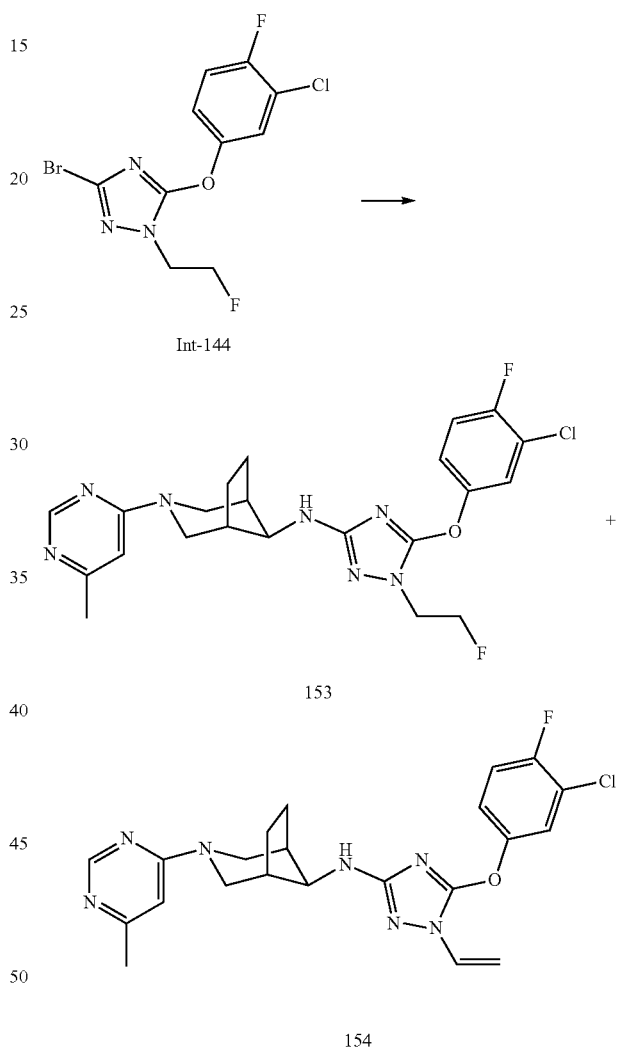

In an 8 mL microwave vial, (1R,5S,8s)-3-(6-methylpyrimidin-4-yl)-3-azabicyclo[3.2.1]octan-8-amine (Int-114, 142 mg, 652 μmol), 3-bromo-5-(3-chloro-4-fluorophenoxy)-1-(2-fluoroethyl)-1H-1,2,4-triazole (Int-144, 184 mg, 544 μmol), and sodium tert-butoxide (104 mg, 1.1 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 61.8 mg, 87 μmol), and tris(dibenzylideneacetone)dipalladium (0) chloroform adduct (45.0 mg, 43.5 μmol) were added subsequently. The vial was again degassed thoroughly with Argon and sealed. The reaction mixture was heated under microwave irradiation at 110° C.

for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 95:5 v/v), followed by preparative chiral HPLC (Reprosil chiral-NR, eluting n-heptane/ethanol, 70:30 v/v isocratic) to afford example 153 (63 mg, 23%) as white foam and example 154 (12 mg, 4%) as white foam. Example 153: HPLC (method LCMS_fastgradient) $t_R$=0.94 min. $^1$H NMR (CDCl$_3$, 300 MHz): δ1.50-1.60 (m, 2H), 1.78-1.89 (m, 2H), 2.37 (s, 3H), 2.42-2.49 (m, 2H), 3.05-3.13 (m, 2H), 3.75 (d, J=6.0 Hz, 1H), 3.97 (d, J=6.0 Hz, 1H), 4.23 (td, J=4.8, 25.2 Hz, 2H), 4.77 (tt, J=4.7, 46.7 Hz, 2H), 7.15-7.20 (m, 2H), 7.37-7.42 (m, 1H), 8.51 (d, J=0.8 Hz, 1H). MS (ES+) m/z 476.2, 478.2 [M+H, Cl isotopes]. Example 154: HPLC (method LCMS_fastgradient) $t_R$=1.03 min. $^1$H NMR (CDCl$_3$, 300 MHz): δ 1.52-1.61 (m, 2H), 1.79-1.88 (m, 2H), 2.37 (s, 3H), 2.47-2.54 (m, 2H), 3.06-3.15 (m, 2H), 3.82 (d, J=6.0 Hz, 1H), 4.08 (d, J=6.0 Hz, 1H), 4.08-4.21 (m, 2H), 4.83 (d, J=8.5 Hz, 1H), 5.50 (d, J=15.5 Hz, 1H), 6.35 (s, 1H), 6.93 (dd, J=9.0, 15.4 Hz, 1H), 7.17-7.23 (m, 2H), 7.40-7.45 (m, 1H), 8.51 (d, J=0.8 Hz, 1H). MS (ES+) m/z 456.2, 458.1 [M+H, Cl isotopes].

Example 155

(1R,5S)—N-[5-(3-Chloro-2-fluoro-phenoxy)-1-isopropyl-1,2,4-triazol-3-yl]-3-(6-methoxypyridazin-4-yl)-3-azabicyclo[3.2.1]octan-8-amine

155

To a solution of (1R,5S)-3-(6-methoxypyridazin-4-yl)-3-azabicyclo[3.2.1]octan-8-amine (Int-128, 200.0 mg, 0.9 mmol) in 2-methyltetrahydrofuran (5.0 mL) was added 3-bromo-5-(3-chloro-2-fluoro-phenoxy)-1-isopropyl-1,2,4-triazole (Int-158, 372.6 mg, 1.1 mmol) and 2-di-tert-butylphosphino-2',4',6'-triisopropylbiphenyl ("tBuXPhos,", CAS [564483-19-8], 28.4 mg, 0.1 mmol) and was degassed with argon over a period of 5 min. To it then added tris(dibenzylideneacetone)dipalladium(0) ("Pd$_2$(dba)$_3$", CAS [51364-51-3], 30.6 mg, 0.03 mmol) and sodium tert-butoxide (267.6 mg, 2.8 mmol). The reaction mixture was heated at 80° C. with stirring for a period of 3 h. Reaction mixture was then concentrated followed by purification of crude by combi-flash column chromatography (silica gel 15 gm), eluting with ethyl acetate/n-hexane 80:20 v/v) to yield title compound as light yellow solid (41.3 mg, 10%). $^1$H NMR (DMSO-d6, 400 MHz): 1.39 (d, J=6.6 Hz, 6H), 1.83 (d, J=9.1 Hz, 2H), 2.39 (s, 1H), 2.95 (d, J=11.6 Hz, 3H), 3.47 (s, 1H), 3.69 (d, J=9.6 Hz, 2H), 3.91 (s, 2H), 4.44-4.47 (m, 1H), 6.00 (d, J=3.8 Hz, 1H), 6.17 (s, 1H), 7.30 (t, J=7.6 Hz, 1H), 7.52 (t, J=7.7 Hz, 2H), 8.65 (s, 1H). MS (ES+) m/z 488.1 [M+H].

Example 156 and example 157

(1R,5S,8s)-N-(5-(3-Chloro-5-fluorophenoxy)-1-(2-fluoroethyl)-1H-1,2,4-triazol-3-yl)-3-(6-methylpyrimidin-4-yl)-3-azabicyclo[3.2.1]octan-8-amine (156) and (1R,5S,8s)-N-(5-(3-chloro-5-fluorophenoxy)-1-vinyl-1H-1,2,4-triazol-3-yl)-3-(6-methylpyrimidin-4-yl)-3-azabicyclo[3.2.1]octan-8-amine (157)

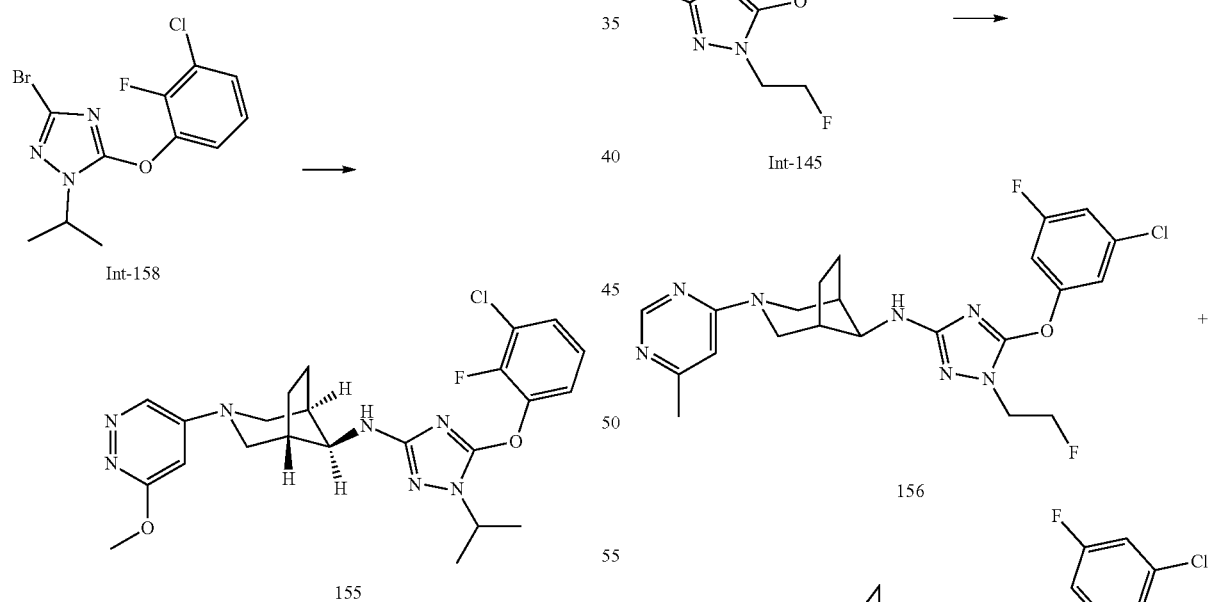

156

157

In an 8 mL microwave vial, (1R,5S,8s)-3-(6-methylpyrimidin-4-yl)-3-azabicyclo[3.2.1]octan-8-amine (Int-114, 148 mg, 677 μmol), 3-bromo-5-(3-chloro-5-fluorophenoxy)-1-(2-fluoroethyl)-1H-1,2,4-triazole (Int-145, 191 mg, 564 μmol), and sodium tert-butoxide (108 mg, 1.1 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 64.2 mg, 90.3 μmol), and tris(dibenzylideneacetone)dipalladium (0) chloroform adduct (46.7 mg, 45.1 μmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 95:5 v/v), followed by preparative chiral HPLC (Reprosil chiral-NR, eluting n-heptane/ethanol, 70:30 v/v isocratic) to afford example 156 (73 mg, 27%) as white foam and example 157 (12 mg, 5%) as white foam. Example 156: HPLC (method LCMS_fastgradient) $t_R$=0.95 min. $^1$H NMR (CDCl$_3$, 300 MHz): δ1.51-1.61 (m, 2H), 1.80-1.90 (m, 2H), 2.37 (s, 3H), 2.44-2.51 (m, 2H), 3.05-3.14 (m, 2H), 3.76 (d, J=6.2 Hz, 1H), 4.00 (d, J=6.0 Hz, 1H), 4.13-4.44 (m, 2H), 4.22 (td, J=4.8, 25.2 Hz, 2H), 4.76 (td, J=4.8, 46.7 Hz, 2H), 6.35 (s, 1H), 6.95-7.04 (m, 2H), 7.13-7.17 (m, 1H), 8.51 (d, J=0.8 Hz, 1H). MS (ES+) m/z 476.2, 478.1 [M+H, Cl isotopes]. Example 157: HPLC (method LCMS_fastgradient) $t_R$=1.11 min. $^1$H NMR (CDCl$_3$, 300 MHz): δ1.53-1.62 (m, 2H), 1.81-1.90 (m, 2H), 2.38 (s, 3H), 2.49-2.56 (m, 2H), 3.08-3.17 (m, 2H), 3.84 (d, J=5.8 Hz, 1H), 4.10-4.22 (m, 2H), 4.11 (d, J=5.8 Hz, 1H), 4.84 (d, J=8.5 Hz, 1H), 5.51 (dd, J=0.4, 15.4 Hz, 1H), 6.36 (s, 1H), 6.91 (dd, J=9.0, 15.4 Hz, 1H), 6.98-7.08 (m, 2H), 7.17-7.21 (m, 1H), 8.53 (s, 1H). MS (ES+) m/z 456.2, 458.2 [M+H, Cl isotopes].

Example 158

(1R,5S,8s)-N-(5-(3-Chloro-5-fluorophenoxy)-1-(2-methoxyethyl)-1H-1,2,4-triazol-3-yl)-3-(6-methylpyrimidin-4-yl)-3-azabicyclo[3.2.1]octan-8-amine

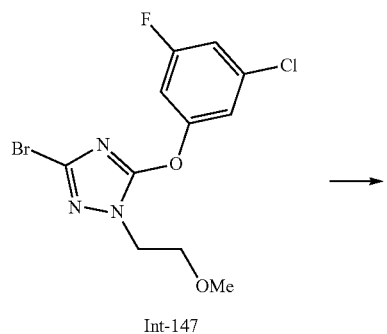

Int-147

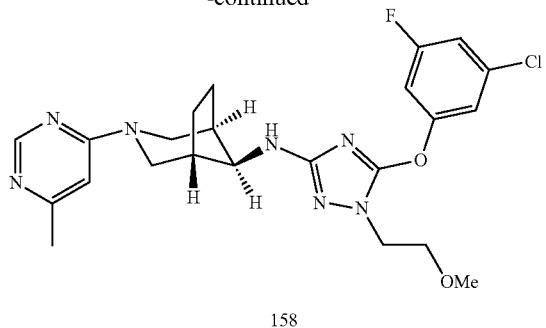

158

In a 10 mL flask, (1R,5S,8s)-3-(6-methylpyrimidin-4-yl)-3-azabicyclo[3.2.1]octan-8-amine (Int-114, 60.5 mg, 277 μmol), 3-bromo-5-(3-chloro-5-fluorophenoxy)-1-(2-methoxyethyl)-1H-1,2,4-triazole (Int-147, 81 mg, 231 μmol), and sodium tert-butoxide (66.6 mg, 693 μmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 5.9 mg, 14 μmol), and tris(dibenzylideneacetone)dipalladium (0) chloroform adduct (7.2 mg, 6.9 μmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as a white foam (56 mg, 49%). HPLC (method LCMS_fastgradient) $t_R$=0.91 min. $^1$H NMR (CDCl$_3$, 300 MHz): δ 1.51-1.60 (m, 2H), 1.80-1.90 (m, 2H), 2.36 (s, 3H), 2.43-2.51 (m, 2H), 3.06-3.14 (m, 2H), 3.35 (s, 3H), 3.73 (t, J=5.3 Hz, 2H), 3.77 (d, J=6.4 Hz, 1H), 3.96 (d, J=6.2 Hz, 1H), 4.08-4.20 (m, 2H), 4.08 (t, J=5.3 Hz, 2H), 6.34 (s, 1H), 6.93-7.02 (m, 2H), 7.12-7.15 (m, 1H), 8.51 (d, J=1.0 Hz, 1H). MS (ES+) m/z 488.2, 490.2 [M+H, Cl isotopes].

Example 159

(1R,5S,8s)-N-(5-(3-Chloro-4-fluorophenoxy)-1-(2-methoxyethyl)-1H-1,2,4-triazol-3-yl)-3-(6-methylpyrimidin-4-yl)-3-azabicyclo[3.2.1]octan-8-amine

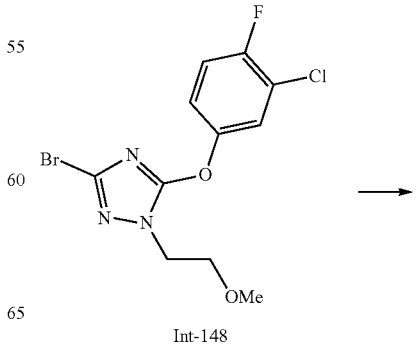

Int-148

299

-continued

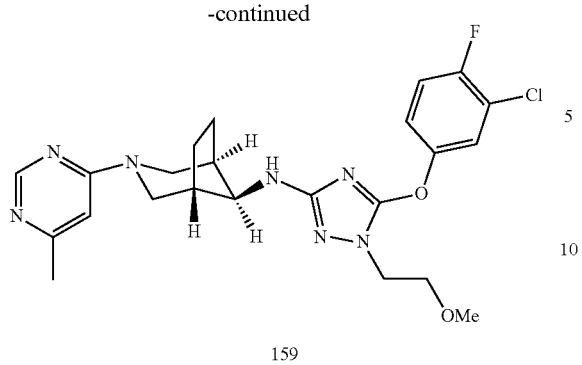

159

In a 10 mL flask, (1R,5S,8s)-3-(6-methylpyrimidin-4-yl)-3-azabicyclo[3.2.1]octan-8-amine (Int-114, 74.7 mg, 342 µmol), 3-bromo-5-(3-chloro-4-fluorophenoxy)-1-(2-methoxyethyl)-1H-1,2,4-triazole (Int-148, 100 mg, 285 µmol), and sodium tert-butoxide (82.2 mg, 856 µmol) were charged. The flask was evacuated and backfilled with argon, Then, 2-methyltetrahydrofuran (4.8 mL), di-tert-butyl(2',4',6'-triisopropylbiphenyl-2-yl)phosphine ("tBuXPhos", CAS [564483-19-8], 7.3 mg, 17 µmol), and tris(dibenzylideneacetone)dipalladium (0) chloroform adduct (8.9 mg, 8.6 µmol) were added subsequently. The flask was degassed thoroughly with Argon and sealed. The reaction mixture was stirred at 80° C. for 30 min. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to yield the title compound as a white foam (72 mg, 51%). HPLC (method LCMS_fastgradient) $t_R$=0.90 min. $^1$H NMR (CDCl$_3$, 300 MHz): δ 1.49-1.59 (m, 2H), 1.79-1.89 (m, 2H), 2.36 (s, 3H), 2.42-2.50 (m, 2H), 3.05-3.14 (m, 2H), 3.37 (s, 3H), 3.71-3.78 (m, 3H), 3.96 (d, J=6.2 Hz, 1H), 4.09-4.19 (m, 2H), 4.09 (t, J=5.3 Hz, 2H), 6.34 (s, 1H), 7.14-7.18 (m, 2H), 7.36-7.41 (m, 1H), 8.51 (d, J=0.6 Hz, 1H). MS (ES+) m/z 488.6, 490.6 [M+H, Cl isotopes].

Example 160

(1R,5S,8s)-N-[5-(2-Chlorophenoxy)-1-(propan-2-yl)-1H-1,2,4-triazol-3-yl]-3-(2-methoxypyridin-4-yl)-3-azabicyclo[3.2.1]octan-8-amine

300

-continued

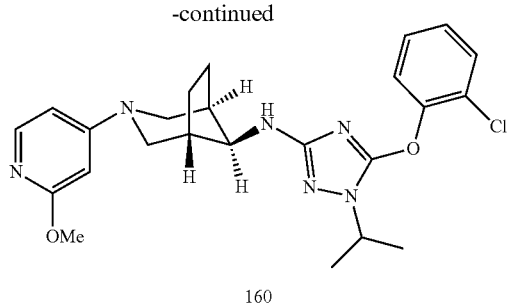

160

In a 10 mL flask, (1R,5S,8s)-3-(2-methoxypyridin-4-yl)-3-azabicyclo[3.2.1]octan-8-amine (Int-111, 88.4 mg, 379 µmol), 3-bromo-5-(2-chlorophenoxy)-1-(propan-2-yl)-1H-1,2,4-triazole (Int-4, 100 mg, 316 µmol), and sodium tert-butoxide (91.1 mg, 948 µmol) were charged. The flask was evacuated and backfilled with argon, Then, 2-methyltetrahydrofuran (4.5 mL), di-tert-butyl(2',4',6'-triisopropylbiphenyl-2-yl)phosphine ("tBuXPhos", CAS [564483-19-8], 8.0 mg, 19 µmol), and tris(dibenzylideneacetone)dipalladium (0) chloroform adduct (9.8 mg, 9.5 µmol) were added subsequently. The flask was degassed thoroughly with Argon and sealed. The reaction mixture was stirred at 80° C. for 40 min. After that, water (30 mL) was added and the mixture was extracted with ethyl acetate (2×50 mL). The combined organic extracts were washed with water (2×30 mL), dried (sodium sulfate) and concentrated in vacuo. The resulting crude product was purified by column chromatography (silica gel, 12 g, eluting with ethyl acetate/n-heptane, gradient 0:100 to 80:20 v/v) to afford the title compound as a white foam (80 mg, 54%). HPLC (method LCMS_fastgradient) $t_R$=0.99 min. $^1$H NMR (CDCl$_3$, 300 MHz): δ 1.50 (d, J=6.6 Hz, 6H), 1.54-1.62 (m, 2H), 1.81-1.90 (m, 2H), 2.42-2.49 (m, 2H), 3.01-3.09 (m, 2H), 3.57 (dd, J=3.2, 11.9 Hz, 2H), 3.71 (d, J=6.2 Hz, 1H), 3.88 (d, J=6.6 Hz, 1H), 3.90 (s, 3H), 4.54 (hept, J=6.7 Hz, 1H), 5.99 (d, J=2.2 Hz, 1H), 6.34 (dd, J=2.3, 6.1 Hz, 1H), 7.19 (ddd, J=1.6, 7.4, 7.9 Hz, 1H), 7.41 (dd, J=1.6, 8.3 Hz, 1H), 7.46 (dd, J=1.6, 7.9 Hz, 1H), 7.86 (d, J=6.0 Hz, 1H). MS (ES+) m/z 469.2, 471.2 [M+H, Cl isotopes].

Example 161 and example 162

(1R,5S,8s)-N-(5-(3-Chlorophenoxy)-1-(2,2-difluoroethyl)-1H-1,2,4-triazol-3-yl)-3-(6-methylpyrimidin-4-yl)-3-azabicyclo[3.2.1]octan-8-amine (161) and (1R,5S,8s)-N-(5-(3-chlorophenoxy)-1-(2-fluorovinyl)-1H-1,2,4-triazol-3-yl)-3-(6-methylpyrimidin-4-yl)-3-azabicyclo[3.2.1]octan-8-amine (162, E/Z mixture)

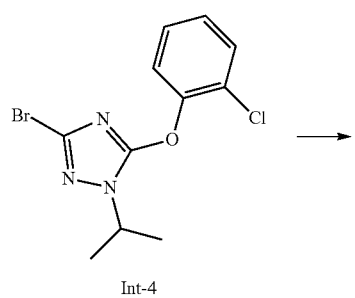

Int-4

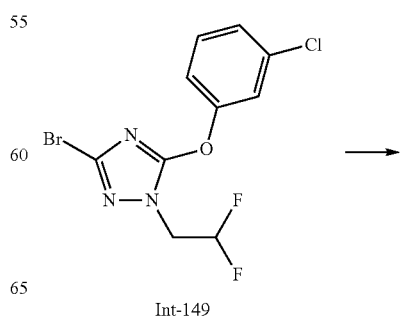

Int-149

-continued

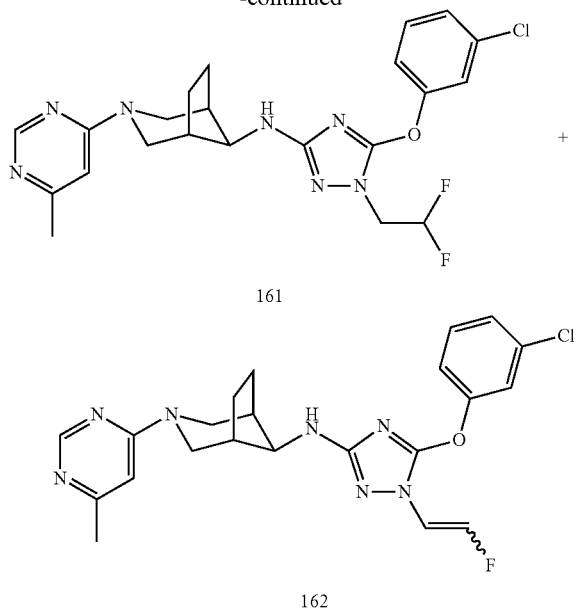

161

162

In an 8 mL microwave vial, (1R,5S,8s)-3-(6-methylpy-rimidin-4-yl)-3-azabicyclo[3.2.1]octan-8-amine (Int-114, 139 mg, 634 µmol), 3-bromo-5-(3-chlorophenoxy)-1-(2,2-difluoroethyl)-1H-1,2,4-triazole (Int-149, 179 mg, 529 µmol), and sodium tert-butoxide (102 mg, 1.06 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 60.1 mg, 84.6 µmol), and tris(dibenzylideneacetone)dipalladium (0) chloroform adduct (43.8 mg, 42.3 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 95:5 v/v), followed by preparative chiral HPLC (Reprosil chiral-NR, eluting n-heptane/ethanol, 70:30 v/v isocratic) to afford example 161 (55 mg, 21%) as white foam and example 162 (66 mg, 27%) as white foam. Example 161: HPLC (method LCMS_fastgradient) $t_R$=0.93 min. $^1$H NMR (CDCl$_3$, 300 MHz): δ 1.51-1.60 (m, 2H), 1.78-1.88 (m, 2H), 2.37 (s, 3H), 2.42-2.49 (m, 2H), 3.04-3.14 (m, 2H), 3.73 (d, J=6.0 Hz, 1H), 4.01 (d, J=6.2 Hz, 1H), 4.07-4.20 (m, 2H), 4.28 (td, J=4.4, 13.0 Hz, 2H), 6.16 (tt, J=4.4, 55.6 Hz, 1H), 6.34 (s, 1H), 7.16-7.26 (m, 2H), 7.31-7.38 (m, 2H), 8.51 (d, J=0.8 Hz, 1H). MS (ES+) m/z 476.1, 478.1 [M+H, Cl isotopes]. Example 162: HPLC (method LCMS_fastgradient) $t_R$=0.92 min. $^1$H NMR (CDCl$_3$, 300 MHz): δ 1.51-1.60 (m, 2H), 1.79-1.88 (m, 2H), 2.36 (s, 3H), 2.45-2.52 (m, 2H), 3.05-3.14 (m, 2H), 3.81 (d, J=6.0 Hz, 1H), 4.08-4.20 (m, 2H), 4.09 (d, J=6.0 Hz, 1H), 6.14 & 6.24 (2d, J=4.2 Hz, 1H), 6.34 (s, 1H), 6.37 & 6.62 (2d, J=4.2 Hz, 1H), 7.19-7.27 (m, 2H), 7.32-7.39 (m, 2H), 8.51 (d, J=0.8 Hz, 1H). MS (ES+) m/z 456.2, 458.2 [M+H, Cl isotopes].

Example 163

(1R,5S,8s)-N-(5-(2-Chlorophenoxy)-1-(2,2,2-trifluoroethyl)-1H-1,2,4-triazol-3-yl)-3-(2-methoxypyridin-4-yl)-3-azabicyclo[3.2.1]octan-8-amine

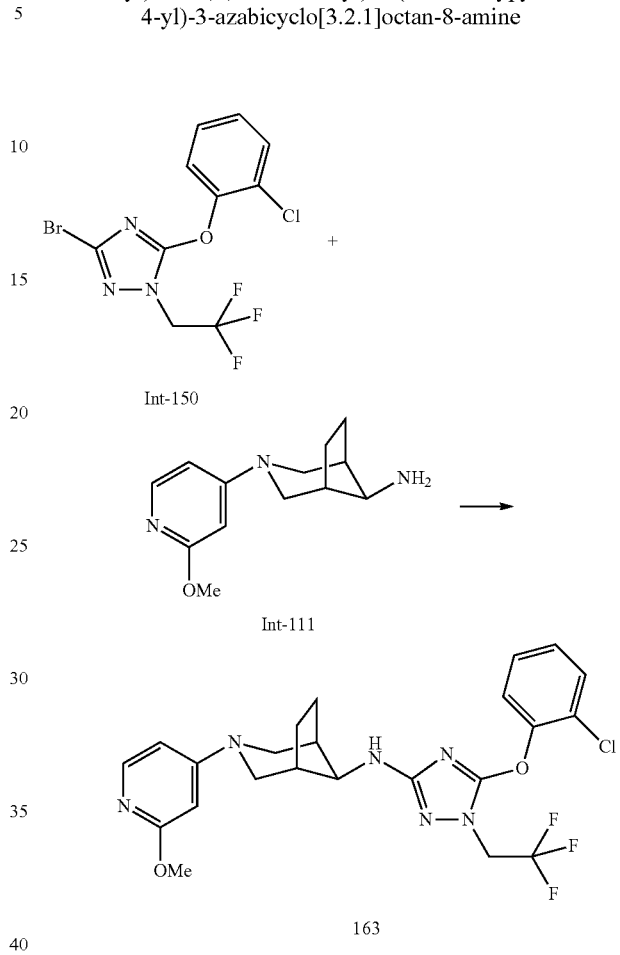

163

In an 8 mL microwave vial, (1R,5S,8s)-3-(2-methoxypyridin-4-yl)-3-azabicyclo[3.2.1]octan-8-amine (Int-111, 141 mg, 606 µmol), 3-bromo-5-(2-chlorophenoxy)-1-(2,2,2-trifluoroethyl)-1H-1,2,4-triazole (Int-150, 180 mg, 505 µmol), and sodium tert-butoxide (97 mg, 1.01 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 57.4 mg, 81 µmol), and tris(dibenzylideneacetone)dipalladium (0) chloroform adduct (41.8 mg, 40 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×30 mL), dried (sodium sulfate) and concentrated in vacuo. The resulting crude product was purified by column chromatography (silica gel, 12 g, eluting with ethyl acetate/n-heptane, gradient 0:100 to 80:20 v/v), followed by preparative HPLC (YMC-Actus Triart C18, 100×30 mm×5 µm, eluting with acetonitrile/(water+0.1% triethylamine), gradient 20:80 to 98:2 v/v) to yield the title compound as a white foam (39 mg, 15%). HPLC (method LCMS_fastgradient) $t_R$=0.99 min. $^1$H NMR (d6-DMSO, 300 MHz): δ 1.32-1.42 (m, 2H), 1.76-1.87 (m, 2H), 2.35-2.42 (m, 2H), 2.80-2.89 (m, 2H), 3.28-3.35 (m, 1H), 3.43 (d, J=4.2 Hz, 1H), 3.59 (dd, J=3.0, 11.9 Hz, 2H), 3.75 (s, 3H), 4.93 (q, J=8.9 Hz, 2H), 6.00 (d, J=2.2 Hz, 1H), 6.24 (d, J=4.4 Hz, 1H), 6.47 (dd, J=2.2, 6.2 Hz, 1H), 7.34 (ddd, J=1.8, 7.5, 7.9 Hz, 1H), 7.44 (ddd, J=1.8, 7.5, 8.1 Hz, 1H), 7.52 (dd, J=1.8, 8.1 Hz, 1H), 7.62 (dd, J=1.6, 8.1 Hz, 1H), 7.74 (d, J=6.0 Hz, 1H). MS (ES+) m/z 509.2, 511.1 [M+H, Cl isotopes].

Example 164 and example 165

(1R,5S,8s)-N-(5-(3,5-Difluorophenoxy)-1-(2-fluoroethyl)-1H-1,2,4-triazol-3-yl)-3-(6-methylpyrimidin-4-yl)-3-azabicyclo[3.2.1]octan-8-amine (164) and (1R,5S,8s)-N-(5-(3,5-difluorophenoxy)-1-vinyl-1H-1,2,4-triazol-3-yl)-3-(6-methylpyrimidin-4-yl)-3-azabicyclo[3.2.1]octan-8-amine (165)

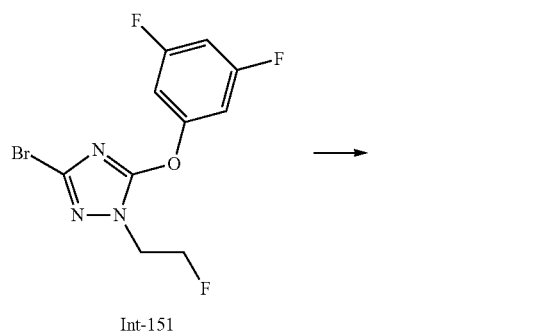

Int-151

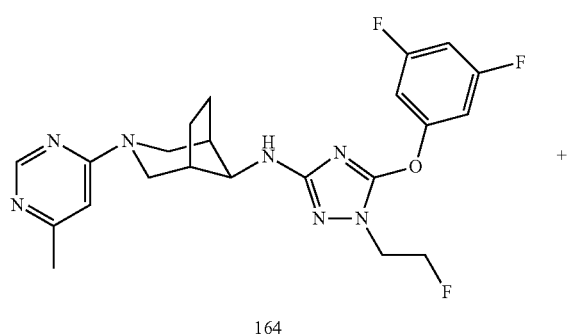

164

In an 8 mL microwave vial, (1R,5S,8s)-3-(6-methylpyrimidin-4-yl)-3-azabicyclo[3.2.1]octan-8-amine (Int-114, 129 mg, 589 µmol), 3-bromo-5-(3,5-difluorophenoxy)-1-(2-fluoroethyl)-1H-1,2,4-triazole (Int-151, 158 mg, 491 µmol), and sodium tert-butoxide (94 mg, 0.98 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 55.8 mg, 78.5 µmol), and tris(dibenzylideneacetone)dipalladium (0) chloroform adduct (40.6 mg, 39.2 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 95:5 v/v), followed by preparative chiral HPLC (Reprosil chiral-NR, eluting n-heptane/ethanol, 70:30 v/v isocratic) to afford example 164 (89 mg, 39%) as white foam and example 165 (46 mg, 21%) as white foam. Example 164: HPLC (method LCMS_fastgradient) $t_R$=0.88 min. $^1$H NMR (CDCl$_3$, 300 MHz): δ 1.50-1.60 (m, 2H), 1.79-1.90 (m, 2H), 2.36 (s, 3H), 2.42-2.51 (m, 2H), 3.04-3.14 (m, 2H), 3.75 (d, J=6.0 Hz, 1H), 3.99 (d, J=6.0 Hz, 1H), 4.21 (td, J=4.8, 25.0 Hz, 2H), 4.75 (td, J=4.7, 46.7 Hz, 2H), 6.34 (s, 1H), 6.65-6.73 (m, 1H), 6.84-6.94 (m, 2H), 8.50 (d, J=1.0 Hz, 1H). MS (ES+) m/z 460.3 [M+H]. Example 165: HPLC (method LCMS_fastgradient) $t_R$=0.94 min. $^1$H NMR (CDCl$_3$, 300 MHz): δ1.53-1.62 (m, 2H), 1.80-1.90 (m, 2H), 2.37 (s, 3H), 2.48-2.55 (m, 2H), 3.06-3.16 (m, 2H), 3.84 (d, J=5.8 Hz, 1H), 4.09-4.22 (m, 2H), 4.11 (d, J=6.0 Hz, 1H), 4.84 (d, J=8.5 Hz, 1H), 5.51 (d, J=15.3 Hz, 1H), 6.36 (s, 1H), 6.68-6.78 (m, 1H), 6.86-6.99 (m, 3H), 8.52 (d, J=0.8 Hz, 1H). MS (ES+) m/z 440.3 [M+H].

Example 166

(1R,5S,8s)-N-(5-(2-Chlorophenoxy)-1-(2,2,2-trifluoroethyl)-1H-1,2,4-triazol-3-yl)-3-(6-methylpyrimidin-4-yl)-3-azabicyclo[3.2.1]octan-8-amine

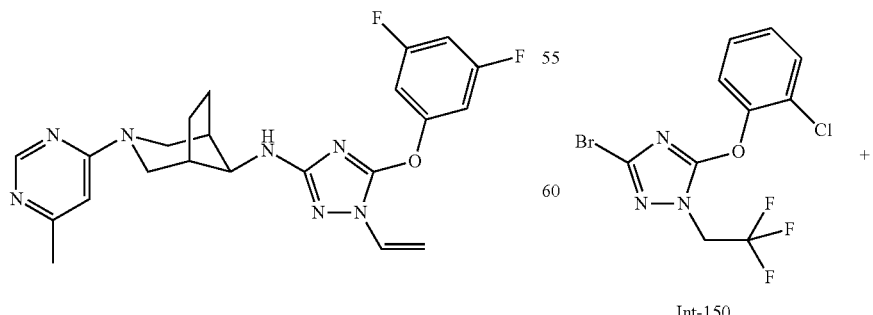

165

Int-150

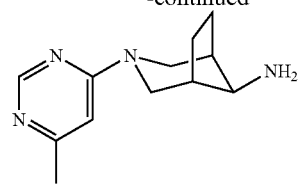

Int-114

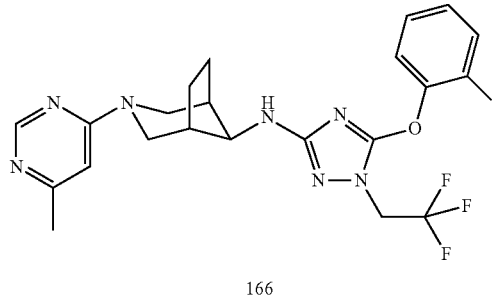

166

In an 8 mL microwave vial, (1R,5S,8s)-3-(6-methylpyrimidin-4-yl)-3-azabicyclo[3.2.1]octan-8-amine (Int-114, 132 mg, 606 μmol), 3-bromo-5-(2-Chlorophenoxy)-1-(2,2,2-trifluoroethyl)-1H-1,2,4-triazole (Int-150, 180 mg, 505 μmol), and sodium tert-butoxide (97 mg, 1.01 mmol) were suspended in 1,4-dioxane (5.4 mL). The flask was degassed thoroughly with Argon. 1,2,3,4,5-Pentaphenyl-1'-(di-tert-butylphosphino)ferrocene ("Q-phos", CAS [312959-24-3], 57 mg, 81 μmol), and tris(dibenzylideneacetone)dipalladium (0) chloroform adduct (42 mg, 40 μmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with dichloromethane/methanol, gradient 100:0 to 90:10 v/v), followed by preparative chiral HPLC (YMC-Actus Triart C18, 100×30 mm×5 μm, eluting with acetonitrile/(water+0.1% triethylamine), gradient 20:80 to 98:2 v/v) to afford the title compound as a white foam (60 mg, 24%). HPLC (method LCMS_fastgradient) $t_R$=0.95 min. $^1$H NMR (CDCl$_3$, 300 MHz): δ1.49-1.58 (m, 2H), 1.76-1.85 (m, 2H), 2.36 (s, 3H), 2.42-2.49 (m, 2H), 3.04-3.13 (m, 2H), 3.74 (d, J=6.0 Hz, 1H), 4.00 (d, J=6.0 Hz, 1H), 4.05-4.18 (m, 2H), 4.58 (q, J=8.2 Hz, 2H), 6.34 (s, 1H), 7.21-7.28 (m, 1H), 7.35 (ddd, J=1.6, 7.5, 8.1 Hz, 1H), 7.42 (dd, J=1.6, 8.3 Hz, 1H), 7.49 (dd, J=1.7, 8.0 Hz, 1H), 8.50 (d, J=0.8 Hz, 1H). MS (ES+) m/z 494.6, 496.6 [M+H, Cl isotopes].

Example 167

(1R,5S)—N-[5-(3-Chloro-2-fluoro-phenoxy)-1-(2,2,2-trifluoroethyl)-1,2,4-triazol-3-yl]-3-(6-methylpyrimidin-4-yl)-3-azabicyclo[3.2.1]octan-8-amine

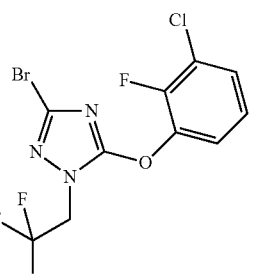

Int-160

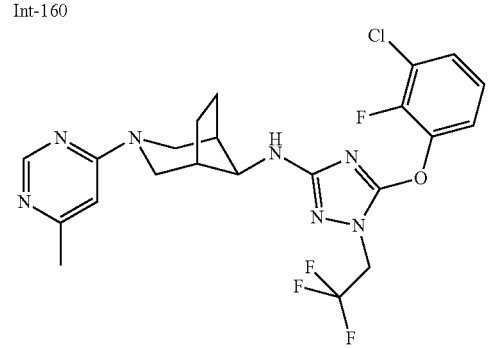

167

To a solution of (1R,5S)-3-(6-methylpyrimidin-4-yl)-3-azabicyclo[3.2.1]octan-8-amine (Int-114, 30.0 mg, 0.1 mmol) in 1,4-dioxane (2.0 mL) was added 3-bromo-5-(3-chloro-2-fluoro-phenoxy)-1-(2,2,2-trifluoroethyl)-1,2,4-triazole (Int-160, 154.0 mg, 0.4 mmol) and 2-Dicyclohexylphosphino-2',6'-diisopropoxybiphenyl ("Ruphos,", CAS [787618-22-8], 15.0 mg, 0.06 mmol) and was degassed with argon over a period of 5 min. To it then added chloro[2-(dicyclohexylphosphino)-3,6-dimethoxy-2',4',6'-triisopropyl-1,1'-biphenyl][2-(2-aminoethyl)phenyl]palladium(II) ("BrettPhos Pd G1", CAS [1148148-01-9], 50.0 mg, 0.03 mmol) and sodium tertbutoxide (33.0 mg, 0.3 mmol). The reaction mixture was irradiated at 110° C. in microwave for a period of 1h. Reaction mixture was then concentrated followed by purification of crude by combi-flash column chromatography (silica gel 15 gm), eluting with ethyl acetate/n-hexane 80:20 v/v) and this followed by reversed phase prep HPLC Sunfire C18 (19×150 mm, 10μ), flow 16 mL/min, eluting with acetonitrile/(water+20 mM ammonium bicarbonate), gradient 20:80 to 95:5) method to yield title compound as off-white solid (24.0 mg, 17%). $^1$H NMR (DMSO-d6, 400 MHz): 1.28 (d, J=7.5 Hz, 3H), 1.78 (d, J=4.6 Hz, 2H), 2.23 (s, 3H), 2.36 (s, 2H), 2.92 (d, J=12.2 Hz, 2H), 3.46-3.56 (m, 2H), 3.98-4.20 (m, 2H), 4.97 (d, J=9.0 Hz, 2H), 6.28 (d, J=3.9 Hz, 1H), 6.62 (s, 1H), 7.32 (t, J=8.0 Hz, 1H), 7.54 (dd, J=14.7, 6.9 Hz, 2H), 8.33 (s, 1H). MS (ES+) m/z 512.3 [M+H].

Example 168 and example 169

(1R,5S,8s)-N-(5-(2-Chlorophenoxy)-1-(2,2-difluoro-ethyl)-1H-1,2,4-triazol-3-yl)-3-(6-methylpyrimidin-4-yl)-3-azabicyclo[3.2.1]octan-8-amine (168) and (1R,5S,8s)-N-(5-(2-chlorophenoxy)-1-(2-fluorovi-nyl)-1H-1,2,4-triazol-3-yl)-3-(6-methylpyrimidin-4-yl)-3-azabicyclo[3.2.1]octan-8-amine (169, E/Z mixture)

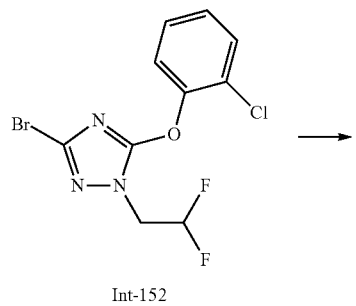

Int-152

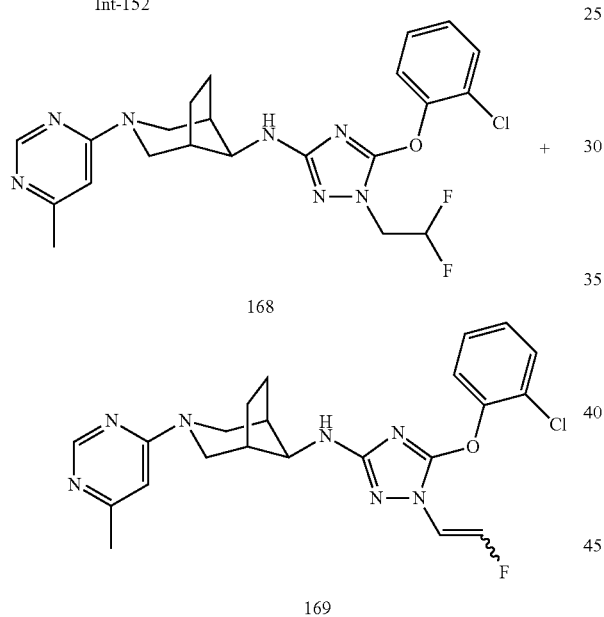

168

169

In an 8 mL microwave vial, (1R,5S,8s)-3-(6-methylpy-rimidin-4-yl)-3-azabicyclo[3.2.1]octan-8-amine (Int-114, 121 mg, 556 µmol), 3-bromo-5-(2-chlorophenoxy)-1-(2,2-difluoroethyl)-1H-1,2,4-triazole (Int-152, 171 mg, 505 µmol), and sodium tert-butoxide (97 mg, 1.01 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 57.4 mg, 81 µmol), and tris(dibenzylideneacetone)dipalladium (0) chloroform adduct (41.8 mg, 40.4 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichlorometh-ane/methanol, gradient 100:0 to 95:5 v/v), followed by preparative chiral HPLC (Reprosil chiral-NR, eluting n-heptane/ethanol, 70:30 v/v isocratic) to afford example 168 (29 mg, 11%) as white foam and example 169 (53 mg, 23%) as white foam. Example 168: HPLC (method LCMS_fastgra-dient) $t_R$=0.93 min. $^1$H NMR (CDCl$_3$, 300 MHz): δ 1.48-1.58 (m, 2H), 1.75-1.85 (m, 2H), 2.36 (s, 3H), 2.40-2.48 (m, 2H), 3.03-3.13 (m, 2H), 3.72 (d, J=6.0 Hz, 1H), 3.99 (d, J=6.0 Hz, 1H), 4.03-4.21 (m, 2H), 4.34 (dt, J=4.3, 13.0 Hz, 2H), 6.20 (tt, J=4.4, 55.6 Hz, 1H), 6.34 (s, 1H), 7.20-7.26 (m, 1H), 7.33 (ddd, J=1.6, 7.5, 8.1 Hz, 1H), 7.42 (dd, J=1.7, 8.2 Hz, 1H), 7.48 (dd, J=1.6, 7.9 Hz, 1H), 8.51 (d, J=0.8 Hz, 1H). MS (ES+) m/z 476.1, 478.0 [M+H, Cl isotopes]. Example 169: HPLC (method LCMS_fastgradient) $t_R$=0.92 min. $^1$H NMR (CDCl$_3$, 300 MHz): δ1.49-1.58 (m, 2H), 1.76-1.86 (m, 2H), 2.36 (s, 3H), 2.44-2.51 (m, 2H), 3.04-3.13 (m, 2H), 3.80 (d, J=6.2 Hz, 1H), 4.05-4.17 (m, 2H), 4.07 (d, J=6.0 Hz, 1H), 6.23 & 6.33 (2d, J=4.2 Hz, 1H), 6.34 (s, 1H), 6.37 & 6.63 (2d, J=4.2 Hz, 1H), 7.20-7.27 (m, 1H), 7.34 (ddd, J=1.8, 7.5, 8.3 Hz, 1H), 7.44 (dd, J=1.6, 8.1 Hz, 1H), 7.48 (dd, J=1.6, 7.9 Hz, 1H), 8.50 (d, J=1.0 Hz, 1H). MS (ES+) m/z 456.0, 458.0 [M+H, Cl isotopes].

Example 170

(1R,5S,8s)-N-(5-(3-Chloro-5-fluorophenoxy)-1-(methoxymethyl)-1H-1,2,4-triazol-3-yl)-3-(6-methylpyrimidin-4-yl)-3-azabicyclo[3.2.1]octan-8-amine

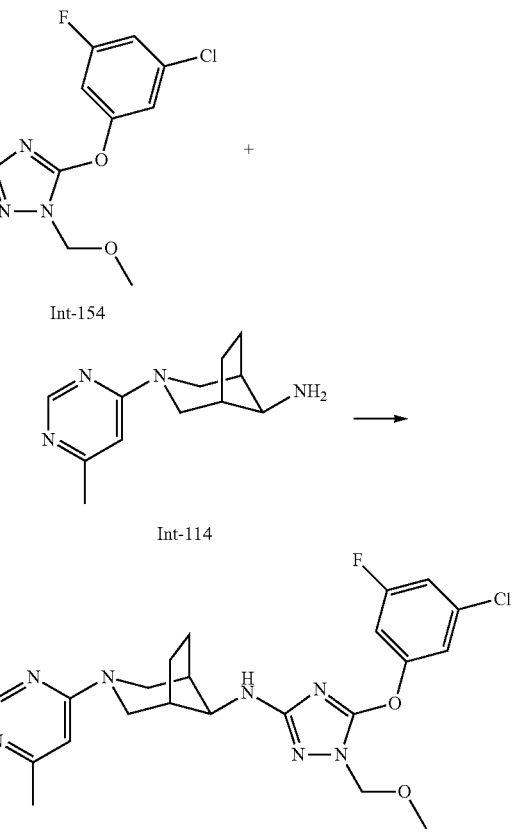

Int-154

Int-114

170

In an 8 mL microwave vial, (1R,5S,8s)-3-(6-methylpy-rimidin-4-yl)-3-azabicyclo[3.2.1]octan-8-amine (Int-114, 74.2 mg, 340 µmol), 3-bromo-5-(3-chloro-5-fluorophenoxy)-1-(methoxymethyl)-1H-1,2,4-triazole (Int-154, 104 mg, 309 µmol), and sodium tert-butoxide (89 mg, 927 µmol) were charged. The flask was evacuated and backfilled with argon, Then, 2-methyltetrahydrofuran (4 mL), di-tert-butyl (2',4',6'-triisopropylbiphenyl-2-yl)phosphine ("tBuXPhos", CAS [564483-19-8], 7.9 mg, 18 µmol), and tris(dibenzylideneacetone)dipalladium (0) chloroform adduct (9.6 mg, 9.3 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to afford the title compound as a white foam (77 mg, 49%). HPLC (method LCMS_fastgradient) $t_R$=0.95 min. $^1$H NMR (CDCl$_3$, 300 MHz): δ1.51-1.61 (m, 2H), 1.80-1.90 (m, 2H), 2.37 (s, 3H), 2.44-2.52 (m, 2H), 3.06-3.14 (m, 2H), 3.48 (s, 3H), 3.80 (d, J=6.2 Hz, 1H), 4.01 (d, J=6.0 Hz, 1H), 4.07-4.20 (m, 2H), 5.23 (s, 2H), 6.34 (s, 1H), 6.98-7.08 (m, 2H), 7.17-7.20 (m, 1H), 8.51 (d, J=1.0 Hz, 1H). MS (ES+) m/z 474.2, 476.2 [M+H, Cl isotopes].

Example 171

(1R,5S,8s)-N-[5-(4-Chlorophenoxy)-1-(propan-2-yl)-1H-1,2,4-triazol-3-yl]-3-(6-methylpyrimidin-4-yl)-3-azabicyclo[3.2.1]octan-8-amine

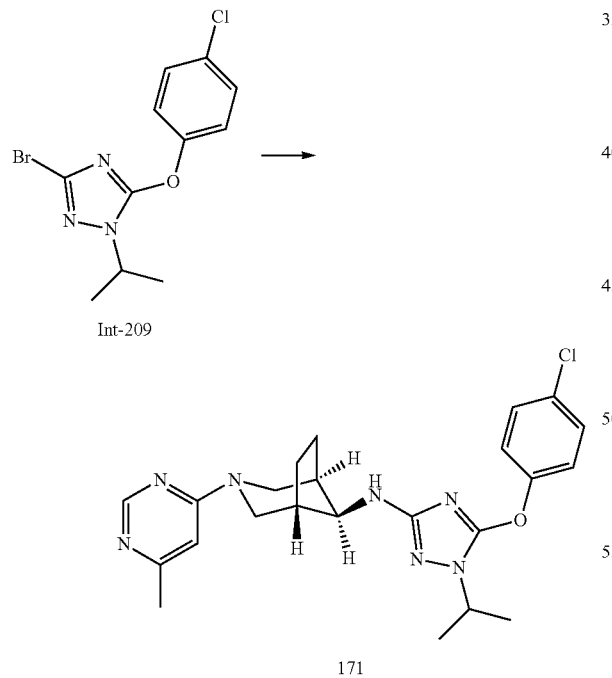

In a 10 mL flask, (1R,5S,8s)-3-(6-methylpyrimidin-4-yl)-3-azabicyclo[3.2.1]octan-8-amine (Int-114, 82.7 mg, 379 µmol), 3-bromo-5-(4-chlorophenoxy)-1-(propan-2-yl)-1H-1,2,4-triazole (Int-209, 100 mg, 316 µmol), and sodium tert-butoxide (91 mg, 0.95 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 8.0 mg, 19 µmol), and tris(dibenzylideneacetone)dipalladium (0) chloroform adduct (9.8 mg, 9.5 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 90:10 v/v) to afford the title compound as an off-white foam (100 mg, 70%). HPLC (method LCMS_fastgradient) $t_R$=0.94 min. $^1$H NMR (CDCl$_3$, 300 MHz): δ 1.46 (d, J=6.6 Hz, 6H), 1.49-1.59 (m, 2H), 1.79-1.90 (m, 2H), 2.36 (s, 3H), 2.42-2.49 (m, 2H), 3.05-3.14 (m, 2H), 3.77 (d, J=6.2 Hz, 1H), 3.89 (d, J=6.2 Hz, 1H), 4.02-4.19 (m, 2H), 4.46 (hept, J=6.6 Hz, 1H), 6.34 (s, 1H), 7.20 (d, J=9.1 Hz, 2H), 7.35 (d, J=9.1 Hz, 2H), 8.51 (d, J=0.8 Hz, 1H). MS (ES+) m/z 454.7, 456.1 [M+H, Cl isotopes].

Example 172

(1R,5S,8s)-N-(5-(3-Chloro-5-fluorophenoxy)-1-(propan-2-yl)-1H-1,2,4-triazol-3-yl)-3-(5-methyl-1,3,4-oxadiazol-2-yl)-3-azabicyclo[3.2.1]octan-8-amine

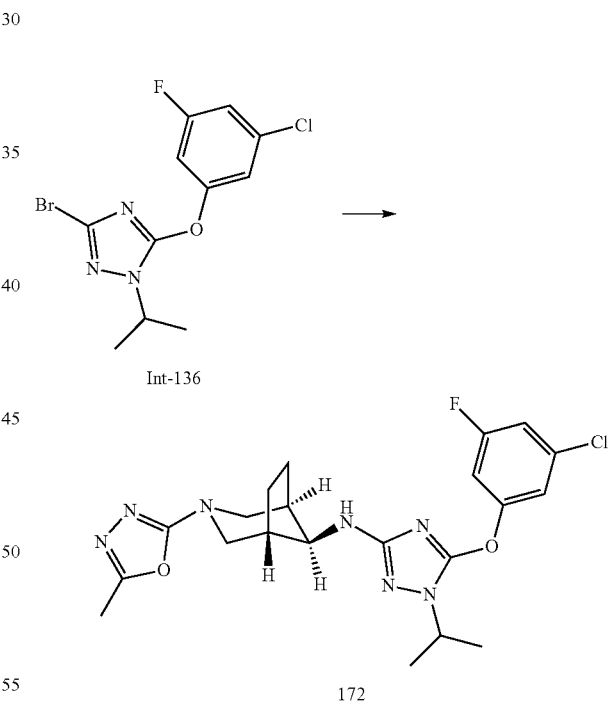

In a 10 mL flask, (1R,5S,8s)-3-(5-methyl-1,3,4-oxadiazol-2-yl)-3-azabicyclo[3.2.1]octan-8-amine (Int-105, 85.2 mg, 409 µmol), 3-bromo-5-(3-chloro-5-fluorophenoxy)-1-(propan-2-yl)-1H-1,2,4-triazole (Int-136, 114 mg, 341 µmol), and sodium tert-butoxide (98.2 mg, 1.02 mmol) were charged. The flask was evacuated and backfilled with argon, Then, 2-methyltetrahydrofuran (4 mL), di-tert-butyl(2',4',6'-triisopropylbiphenyl-2-yl)phosphine ("tBuXPhos", CAS [564483-19-8], 8.7 mg, 20 µmol), and tris(dibenzylideneacetone)dipalladium (0) chloroform adduct (10.6 mg, 10.2

μmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 95:5 v/v) to afford the title compound as a light yellow foam (73 mg, 45%). HPLC (method LCMS_fastgradient) t$_R$=1.31 min. $^1$H NMR (CDCl$_3$, 300 MHz): δ 1.44 (d, J=6.7 Hz, 6H), 1.61-1.70 (m, 2H), 1.86-1.93 (m, 2H), 2.39 (s, 3H), 2.40-2.46 (m, 2H), 3.25-3.32 (m, 2H), 3.69-3.77 (m, 3H), 3.91 (d, J=6.0 Hz, 1H), 4.43 (hept, J=6.7 Hz, 1H), 6.93-7.02 (m, 2H), 7.11-7.14 (m, 1H). MS (ES+) m/z 462.1, 464.0 [M+H, Cl isotopes].

Example 173

(1R,5S,8s)-N-[5-(3-Chloro-2-fluoro-phenoxy)-1-(2,2,2-trifluoroethyl)-1,2,4-triazol-3-yl]-3-(2-methoxy-4-pyridyl)-3-azabicyclo[3.2.1]octan-8-amine

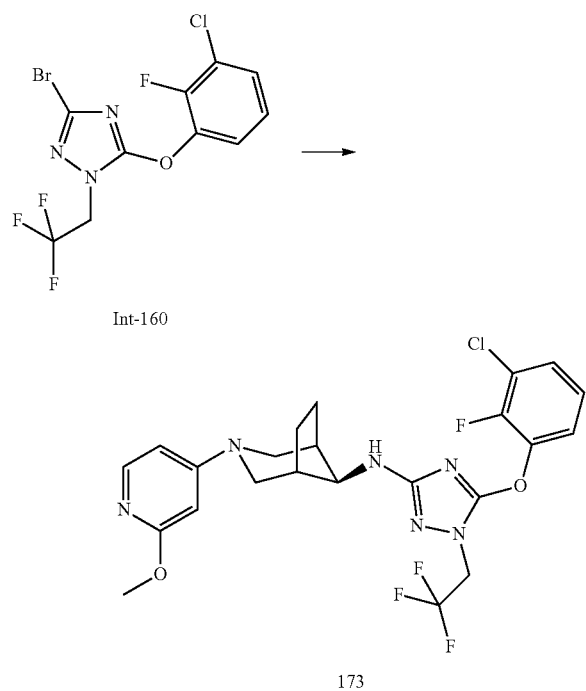

To a solution of (1R,5S)-3-(2-methoxy-4-pyridyl)-3-azabicyclo[3.2.1]octan-8-amine (Int-111, 60.0 mg, 0.3 mmol) in 1,4-dioxane (2.0 mL) was added 3-bromo-5-(3-chloro-2-fluoro-phenoxy)-1-(2,2,2-trifluoroethyl)-1,2,4-triazole (Int-160, 211.9 mg, 0.6 mmol) and 2-Dicyclohexylphosphino-2',6'-diisopropoxybiphenyl ("Ruphos,", CAS [787618-22-8], 9.0 mg, 0.06 mmol) and was degassed with argon over a period of 5 min. To it then added chloro[2-(dicyclohexylphosphino)-3,6-dimethoxy-2',4',6'-triisopropyl-1,1'-biphenyl][2-(2-aminoethyl)phenyl]palladium(II) ("BrettPhos Pd G1", CAS [1148148-01-9], 10.0 mg, 0.03 mmol) and sodium tertbutoxide (72.0 mg, 0.75 mmol). The reaction mixture was irradiated at microwave at 110° C. with stirring for a period of 30 min. Reaction mixture was then concentrated followed by purification of crude by combiflash column chromatography (silica gel 15 gm), eluting with ethyl acetate/n-hexane 80:20 v/v) and this followed by reversed phase prep HPLC (YMC-Actus Triart C18 (250×20 mm, 5μ), flow 16 mL/min, eluting with acetonitrile/(water+20 mM ammonium bicarbonate), gradient 20:80 to 95:5) method to yield title compound as off-white solid (8.7 mg, 6%). MS (ES+) m/z 527.4 [M+H].

Example 174 and example 175

(1R,5S,8s)-N-(5-(3-Chloro-2-fluorophenoxy)-1-(2,2-difluoroethyl)-1H-1,2,4-triazol-3-yl)-3-(6-methylpyrimidin-4-yl)-3-azabicyclo[3.2.1]octan-8-amine (174) and (1R,5S,8s)-N-(5-(3-chloro-2-fluorophenoxy)-1-(2-fluorovinyl)-1H-1,2,4-triazol-3-yl)-3-(6-methylpyrimidin-4-yl)-3-azabicyclo[3.2.1]octan-8-amine (175, E/Z mixture)

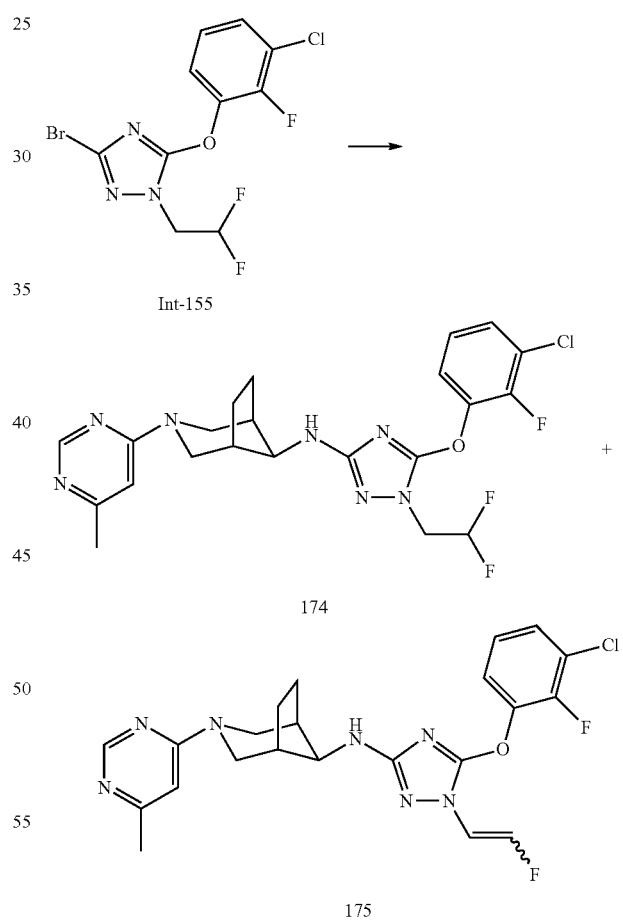

In an 8 mL microwave vial, (1R,5S,8s)-3-(6-methylpyrimidin-4-yl)-3-azabicyclo[3.2.1]octan-8-amine (Int-114, 121 mg, 552 μmol), 3-bromo-5-(3-chloro-2-fluorophenoxy)-1-(2,2-difluoroethyl)-1H-1,2,4-triazole (Int-155, 179 mg, 502 μmol), and sodium tert-butoxide (102 mg, 1.06 mmol) were suspended in 1,4-dioxane (7 mL). The flask was degassed thoroughly with Argon. 1,2,3,4,5-Pentaphenyl-1'-

(di-tert-butylphosphino)ferrocene ("Q-phos", CAS [312959-24-3], 57.1 mg, 80.3 µmol), and tris(dibenzylideneacetone)dipalladium (0) chloroform adduct (41.6 mg, 40.2 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 95:5 v/v), followed by preparative chiral HPLC (Reprosil chiral-NR, eluting n-heptane/ethanol, 70:30 v/v isocratic) to afford example 174 (68 mg, 27%) as white foam and example 175 (13 mg, 5%) as off-white foam. Example 174: HPLC (method LCMS_fastgradient) $t_R$=0.96 min. $^1$H NMR (CDCl$_3$, 300 MHz): δ1.49-1.58 (m, 2H), 1.77-1.85 (m, 2H), 2.36 (s, 3H), 2.41-2.48 (m, 2H), 3.04-3.12 (m, 2H), 3.71 (d, J=5.8 Hz, 1H), 3.98 (d, J=6.0 Hz, 1H), 4.06-4.18 (m, 2H), 4.32 (dt, J=4.4, 13.0 Hz, 2H), 6.18 (tt, J=4.4, 55.5 Hz, 1H), 6.34 (s, 1H), 7.09-7.17 (m, 1H), 7.29-7.36 (m, 2H), 8.51 (d, J=0.8 Hz, 1H). MS (ES+) m/z 494.6, 496.6 [M+H, Cl isotopes]. Example 175: HPLC (method LCMS_fastgradient) $t_R$=0.96 min. $^1$H NMR (CDCl$_3$, 300 MHz): δ1.50-1.59 (m, 2H), 1.78-1.86 (m, 2H), 2.36 (s, 3H), 2.44-2.51 (m, 2H), 3.04-3.13 (m, 2H), 3.79 (d, J=5.8 Hz, 1H), 4.06 (d, J=5.8 Hz, 1H), 4.07-4.18 (m, 2H), 6.18 & 6.28 (2d, J=4.2 Hz, 1H), 6.34 (s, 3H), 6.39 & 6.64 (2d, J=4.2 Hz, 1H), 7.10-7.18 (m, 1H), 7.29-7.39 (m, 2H), 8.51 (s, 1H). MS (ES+) m/z 474.6, 476.6 [M+H, Cl isotopes].

Example 176

(1R,5S,8s)-N-(5-(2-Chlorophenoxy)-1-(2-fluoroethyl)-1H-1,2,4-triazol-3-yl)-3-(6-methylpyrimidin-4-yl)-3-azabicyclo[3.2.1]octan-8-amine

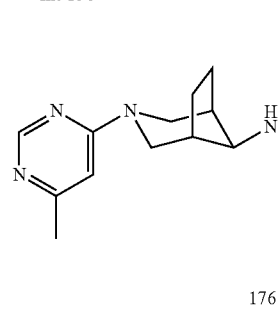

Int-156

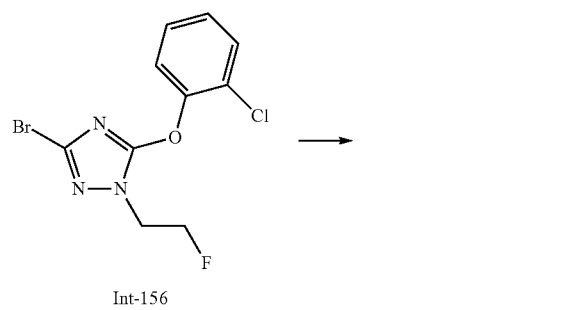

176

In an 8 mL microwave vial, (1R,5S,8s)-3-(6-methylpyrimidin-4-yl)-3-azabicyclo[3.2.1]octan-8-amine (Int-114, 147 mg, 674 µmol), 3-bromo-5-(2-chlorophenoxy)-1-(2-fluoroethyl)-1H-1,2,4-triazole (Int-156, 180 mg, 562 µmol), and sodium tert-butoxide (108 mg, 1.12 mmol) were suspended in 1,4-dioxane (5.4 mL). The flask was degassed thoroughly with Argon. 1,2,3,4,5-Pentaphenyl-1'-(di-tert-butylphosphino)ferrocene ("Q-phos", CAS [312959-24-3], 63.9 mg, 89.8 µmol), and tris(dibenzylideneacetone)dipalladium (0) chloroform adduct (46.5 mg, 44.9 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 90:10 v/v), followed by preparative chiral HPLC (Reprosil chiral-NR, eluting n-heptane/ethanol, 70:30 v/v isocratic) to afford the title compound as white foam (97 mg, 37%). HPLC (method LCMS_fastgradient) $t_R$=0.87 min. $^1$H NMR (CDCl$_3$, 300 MHz): δ1.48-1.58 (m, 2H), 1.76-1.87 (m, 2H), 2.37 (s, 3H), 2.42-2.49 (m, 2H), 3.05-3.13 (m, 2H), 3.74 (d, J=6.0 Hz, 1H), 3.96 (d, J=5.8 Hz, 1H), 4.05-4.19 (m, 2H), 4.30 (td, J=4.9, 24.2 Hz, 2H), 4.81 (td, J=4.9, 46.7 Hz, 2H), 6.34 (s, 1H), 7.18-7.25 (m, 1H), 7.32 (ddd, J=1.6, 7.4, 8.1 Hz, 1H), 7.42 (dd, J=1.7, 8.2 Hz, 1H), 7.47 (dd, J=1.6, 8.1 Hz, 1H), 8.50 (d, J=0.6 Hz, 1H). MS (ES+) m/z 458.6, 460.6 [M+H, Cl isotopes].

Example 177 and example 178

(1R,5S,8s)-N-(5-(3-Chloro-2-fluorophenoxy)-1-(2-fluoroethyl)-1H-1,2,4-triazol-3-yl)-3-(6-methylpyrimidin-4-yl)-3-azabicyclo[3.2.1]octan-8-amine (177) and (1R,5S,8s)-N-(5-(3-chloro-2-fluorophenoxy)-1-vinyl-1H-1,2,4-triazol-3-yl)-3-(6-methylpyrimidin-4-yl)-3-azabicyclo[3.2.1]octan-8-amine (178)

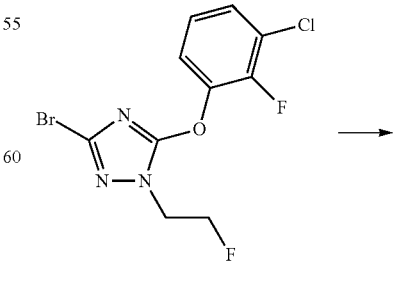

Int-157

Example 179

(1R,5S,8s)-N-(5-(2-Chloro-3-fluorophenoxy)-1-isopropyl-1H-1,2,4-triazol-3-yl)-3-(6-methylpyrimidin-4-yl)-3-azabicyclo[3.2.1]octan-8-amine

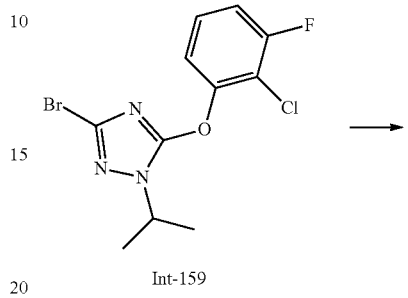

Int-159

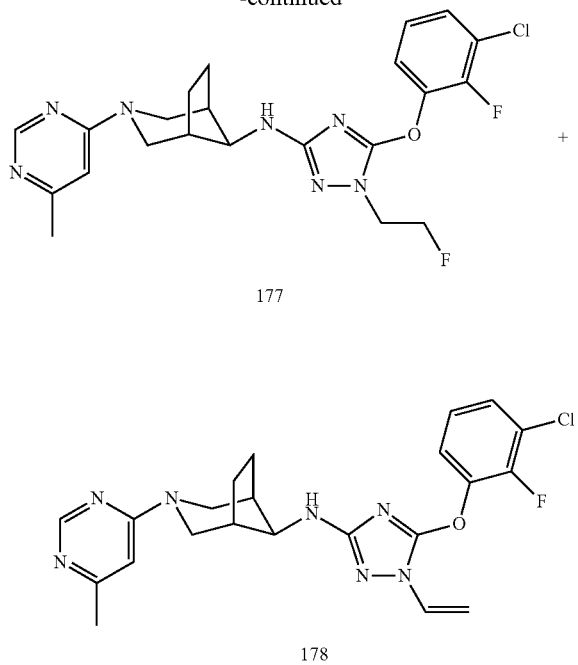

177

178

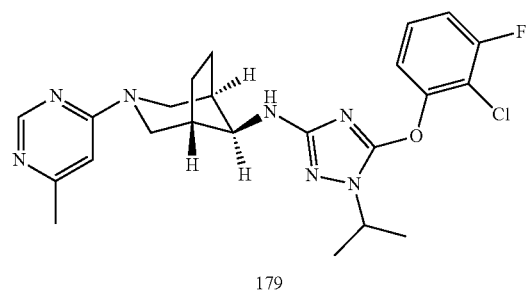

179

In an 8 mL microwave vial, (1R,5S,8s)-3-(6-methylpyrimidin-4-yl)-3-azabicyclo[3.2.1]octan-8-amine (Int-114, 139 mg, 638 µmol), and 3-bromo-5-(3-chloro-2-fluorophenoxy)-1-(2-fluoroethyl)-1H-1,2,4-triazole (Int-157, 180 mg, 532 µmol) were suspended in 1,4-dioxane (5.4 mL). The flask was degassed thoroughly with Argon. 1,2,3,4,5-Pentaphenyl-1'-(di-tert-butylphosphino)ferrocene ("Q-phos", CAS [312959-24-3], 60.5 mg, 85.1 µmol), tris(dibenzylideneacetone)dipalladium (0) chloroform adduct (44.0 mg, 42.5 µmol), and sodium tert-butoxide (102 mg, 1.06 mmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 90:10 v/v), followed by preparative chiral HPLC (Reprosil chiral-NR, eluting n-heptane/ethanol, 70:30 v/v isocratic) to yield example 177 (70 mg, 28%) as white foam and example 178 (10 mg, 4%) as off-white foam. Example 177: HPLC (method LCMS_fastgradient) $t_R$=0.90 min. $^1$H NMR (CDCl$_3$, 300 MHz): δ1.49-1.59 (m, 2H), 1.78-1.86 (m, 2H), 2.36 (s, 3H), 2.42-2.48 (m, 2H), 3.05-3.12 (m, 2H), 3.74 (d, J=6.0 Hz, 1H), 3.95 (d, J=6.0 Hz, 1H), 4.05-4.18 (m, 2H), 4.27 (td, J=4.9, 24.6 Hz, 2H), 4.79 (td, J=4.9, 46.7 Hz, 2H), 6.34 (s, 1H), 7.08-7.15 (m, 1H), 7.27-7.36 (m, 2H), 8.51 (d, J=0.8 Hz, 1H). MS (ES+) m/z 476.6, 478.6 [M+H, Cl isotopes]. Example 178: HPLC (method LCMS_fastgradient) $t_R$=1.01 min. $^1$H NMR (CDCl$_3$, 300 MHz): δ 1.50-1.61 (m, 2H), 1.78-1.87 (m, 2H), 2.38 (s, 3H), 2.47-2.53 (m, 2H), 3.07-3.14 (m, 2H), 3.81 (d, J=6.0 Hz, 1H), 4.06 (d, J=6.0 Hz, 1H), 4.08-4.19 (m, 2H), 4.85 (d, J=8.7 Hz, 1H), 5.51 (d, J=15.5 Hz, 1H), 6.98 (dd, J=8.9, 15.3 Hz, 1H), 7.10-7.17 (m, 1H), 7.30-7.38 (m, 2H), 8.51 (s, 1H). MS (ES+) m/z 456.1, 458.0 [M+H, Cl isotopes].

In a 10 mL flask, (1R,5S,8s)-3-(6-methylpyrimidin-4-yl)-3-azabicyclo[3.2.1]octan-8-amine (Int-114, 78.3 mg, 359 µmol), 3-bromo-5-(2-chloro-3-fluorophenoxy)-1-(propan-2-yl)-1H-1,2,4-triazole (Int-159, 100 mg, 299 µmol), and sodium tert-butoxide (86.2 mg, 897 µmol) were charged. The flask was evacuated and backfilled with argon, Then, 2-methyltetrahydrofuran (5 mL), di-tert-butyl(2',4',6'-triisopropylbiphenyl-2-yl)phosphine ("tBuXPhos", CAS [564483-19-8], 7.6 mg, 18 µmol), and tris(dibenzylideneacetone)dipalladium (0) chloroform adduct (9.3 mg, 9.0 µmol) were added subsequently. The flask was degassed thoroughly with Argon and sealed. The reaction mixture was stirred at 80° C. for 1 h. After that, water (30 mL) was added and the mixture was extracted with ethyl acetate (2×50 mL). The combined organic extracts were washed with water (30 mL) and brine (30 mL), dried (sodium sulfate) and concentrated in vacuo. The resulting crude product was purified by column chromatography (silica gel, 12 g, eluting with dichloromethane/methanol, gradient 100:0 to 90:10 v/v) to afford the title compound as an off-white foam (65 mg, 46%). HPLC (method LCMS_fastgradient) $t_R$=1.00 min. $^1$H NMR (CDCl$_3$, 300 MHz): δ 1.49-1.58 (m, 2H), 1.50 (d, J=6.6 Hz, 6H), 1.79-1.88 (m, 2H), 2.36 (s, 3H), 2.42-2.49 (m, 2H), 3.05-3.14 (m, 2H), 3.76 (d, J=6.0 Hz, 1H), 3.88 (d, J=6.0 Hz, 1H), 4.03-4.17 (m, 2H), 4.54 (hept, J=6.7 Hz, 1H), 6.34 (s, 1H), 7.03-7.11 (m, 1H), 7.23-7.33 (m, 2H), 8.51 (d, J=0.8 Hz, 1H). MS (ES+) m/z 472.6, 474.6 [M+H, Cl isotopes].

Example 180

(1R,5S,8s)-N-(5-(3-Chloro-5-fluorophenoxy)-1-(propan-2-yl)-1H-1,2,4-triazol-3-yl)-3-(3-methyl-1,2,4-oxadiazol-5-yl)-3-azabicyclo[3.2.1]octan-8-amine

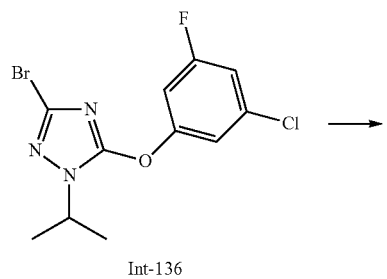

Int-136

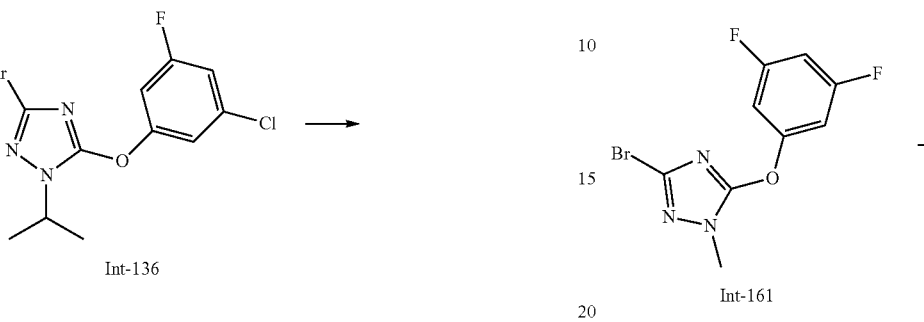

180

To a solution of (1R,5S,8s)-3-(3-methyl-1,2,4-oxadiazol-5-yl)-3-azabicyclo[3.2.1]octan-8-amine (Int-102, 134 mg, 646 µmol) and 5-(3-chloro-5-fluorophenoxy)-3-bromo-1-(propan-2-yl)-1H-1,2,4-triazole (Int-136, 180 mg, 538 µmol) in dry 1,4-dioxane (5.4 mL) in microwave tube was added 1,2,3,4,5-pentaphenyl-1'-(di-tert-butylphosphino)ferrocene ("Q-phos", CAS 312959-24-3, 61.2 mg, 86.1 µmol). The reaction mixture was degassed with argon in a microwave tube over a period of 15 min. To it then added tris(dibenzylideneacetone)dipalladium-chloroform adduct ("Pd$_2$(dba)$_3$.CHCl$_3$", CAS 52522-40-4, 44.6 mg, 43 µmol) and sodium tertbutoxide (103 mg, 1.08 mmol). The reaction mixture was irradiated at 120° C. for 20 min in microwave. Reaction mixture was filtered and the filtrate was concentrated to get the crude which was purified by column chromatography (silica gel, 12 g, eluting with dichloromethane/methanol, gradient 100:0 to 90:10 v/v) followed by reversed phase prep HPLC (YMC Triart C18 5µ 250×20 mm, flow 16 mL/min, eluting with acetonitrile/(water+20 mM ammonium bicarbonate), gradient 40:60 to 95:5) to yield the title compound as white foam (45 mg, 18%). HPLC (method LCMS_fastgradient) $t_R$=1.42 min. $^1$H NMR (CDCl$_3$, 300 MHz): 1.45 (d, J=6.6 Hz, 6H), 1.58-1.66 (m, 2H), 1.86-1.94 (m, 2H), 2.22 (s, 3H), 2.40-2.46 (m, 2H), 3.32-3.39 (m, 2H), 3.75 (d, J=6.2 Hz, 1H), 3.85-3.93 (m, 2H), 4.43 (hept, J=6.6 Hz, 1H), 6.93-7.01 (m, 2H), 7.11-7.14 (m, 1H). MS (ES+) m/z 462.6, 464.6 [M+H, Cl isotopes].

Example 181

(1R,5S,8s)-N-(5-(3,5-Difluorophenoxy)-1-isopropyl-1H-1,2,4-triazol-3-yl)-3-(6-methylpyrimidin-4-yl)-3-azabicyclo[3.2.1]octan-8-amine

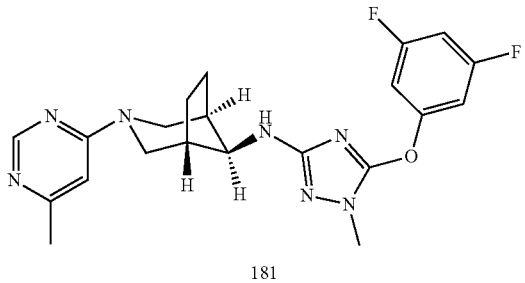

Int-161

181

In a vial under Argon, 3-bromo-5-(3,5-difluorophenoxy)-1-methyl-1H-1,2,4-triazole (Int-161, 50 mg, 172 µmol) was suspended in 2-methyltetrahydrofuran (1.5 mL) and (1R,5S,8s)-3-(6-methylpyrimidin-4-yl)-3-azabicyclo[3.2.1]octan-8-amine hydrochloride (Int-114, 52.7 mg, 207 µmol) was added followed by sodium tert-butoxide (49.7 mg, 517 µmol). The suspension was carefully degassed during 2 min and tris(dibenzylideneacetone)dipalladium (0) chloroform adduct (5.35 mg, 5.17 µmol) followed by 2-di-tert-butylphosphino-2',4',6'-triisopropylbiphenyl (tBuXPhos, CAS [564483-19-8]) (4.39 mg, 10.3 µmol) were added. The vial was closed under Argon and heated to 80° C. during 2 hours. The reaction mixture was poured into 15 mL H2O and extracted with EtOAc (3×15 mL). The organic layers were dried over MgSO4 and concentrated in vacuo. The crude material was purified by flash chromatography (silica gel, eluting with dichloromethane/methanol, gradient 100:0 to 90:10) to afford the title compound (42.3 mg, 57.4% yield) as a white solid. MS (ES+) m/z 428.2 [M+H].

Example 182

(1S,5R.8s)-N-[5-(3-Chloro-5-fluorophenoxy)-1-methyl-1,2,4-triazol-3-yl]-3-(6-methylpyrimidin-4-yl)-3-azabicyclo[3.2.1]octan-8-amine

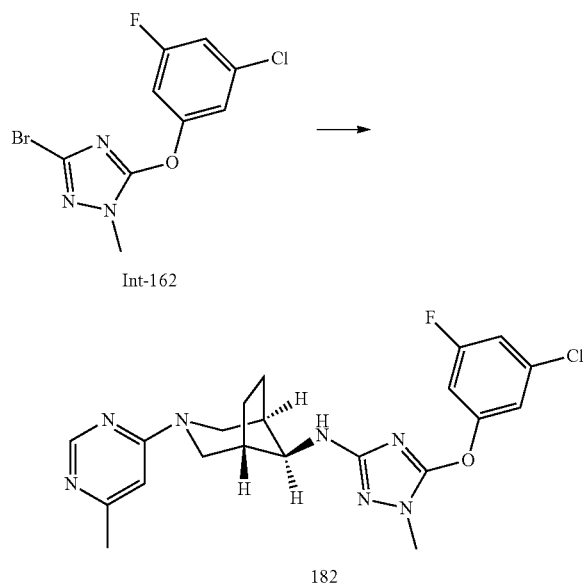

The title compound was prepared in analogy to example 181, from 3-bromo-5-(3-chloro-5-fluorophenoxy)-1-methyl-1H-1,2,4-triazole (Int-162, 50 mg, 163 µmol,) and (1R,5S,8s)-3-(6-methylpyrimidin-4-yl)-3-azabicyclo[3.2.1]octan-8-amine (Int-114, 42.7 mg, 196 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 2 hours. The title compound was isolated as an off-white solid (13.8 mg, 19.1% yield). MS (ES+) m/z: 444.2 [(M+H)+].

Example 183

(1R,5S,8s)-N-[5-(3-Chloro-5-fluorophenoxy)-1-methyl-1,2,4-triazol-3-yl]-3-(6-methoxypyridazin-4-yl)-3-azabicyclo[3.2.1]octan-8-amine

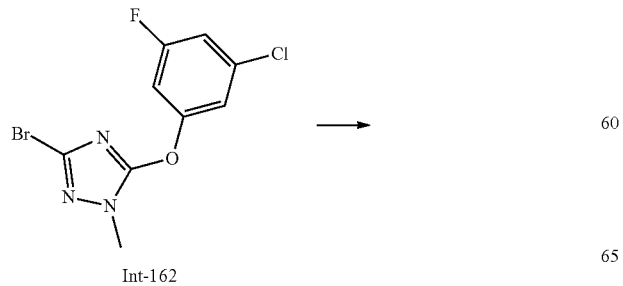

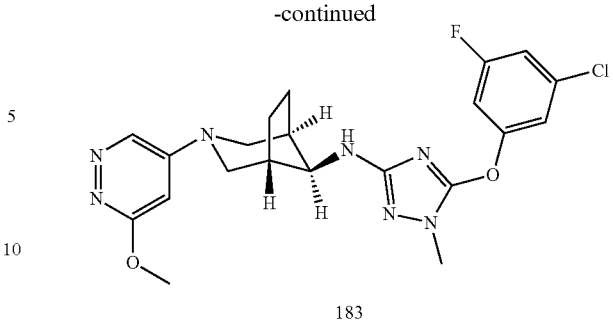

In a vial under Argon, 3-bromo-5-(3-chloro-5-fluorophenoxy)-1-methyl-1H-1,2,4-triazole (Int-162, 40 mg, 130 µmol) was suspended in 2-methyltetrahydrofuran (1.5 ml) and (1R,5S,8s)-3-(6-Methoxypyridazin-4-yl)-3-azabicyclo[3.2.1]octan-8-amine (Int-128, 36.7 mg, 157 µmol) was added followed by sodium tert-butoxide (37.6 mg, 391 µmol). The suspension was carefully degassed during 2 min and tris(dibenzylideneacetone)dipalladium (0) chloroform adduct (4.05 mg, 3.91 µmol) followed by 2-di-tert-butylphosphino-2',4',6'-triisopropylbiphenyl (tBuXPhos, CAS [564483-19-8]) (3.32 mg, 7.83 µmol) were added. The vial was closed under Argon and heated to 80° C. during 30 min. The reaction mixture was poured into water and extracted with EtOAc (3×15 ml). The organic layers were dried over MgSO4 and concentrated in vacuo. The crude material was purified by column chromatography (silica gel, eluting with dichloromethane/methanol, gradient 100:0 to 94:6). The title compound was isolated as a white solid (34.5 mg, 57.5% yield). MS (ES+) m/z 460.2 [M+H].

Example 184

(1R,5S,8s)-N-[5-(3-Chloro-5-fluorophenoxy)-1-methyl-1,2,4-triazol-3-yl]-3-(2-methoxypyridin-4-yl)-3-azabicyclo[3.2.1]octan-8-amine

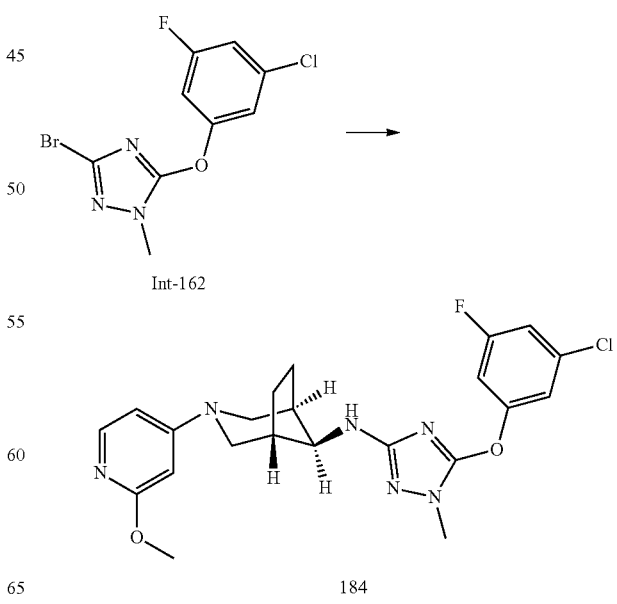

In a vial, 3-bromo-5-(3-chloro-5-fluorophenoxy)-1-methyl-1H-1,2,4-triazole (Int-162, 40 mg, 130 µmol) was suspended in 2-methyltetrahydrofuran (1.5 ml) and (1R,5S,8s)-3-(2-methoxy-4-pyridyl)-3-azabicyclo[3.2.1]octan-8-amine (Int-111, 36.5 mg, 157 µmol) was added followed by sodium tert-butoxide (37.6 mg, 391 µmol). The suspension was carefully degassed during 2 min and tris(dibenzylideneacetone)dipalladium (0) chloroform adduct (4.05 mg, 3.91 µmol) followed by 2-di-tert-butylphosphino-2',4',6'-triisopropylbiphenyl (tBuXPhos, CAS [564483-19-8]) (3.32 mg, 7.83 µmol) were added. The vial was closed under Argon and heated to 80° C. during 30 min. The reaction mixture was poured into water and extracted with EtOAc (3×15 ml). The organic layers were dried over MgSO4 and concentrated in vacuo. The crude material was purified by column chromatography (silica gel, eluting with dichloromethane/methanol, gradient 100:0 to 94:6). The title compound was isolated as a white solid. (30.5 mg, 50.9% yield). MS (ES+) m/z 459.2[M+H].

Example 185

(1R,5S,8s)-N-(5-(4-Chlorophenoxy)-1-methyl-1H-1,2,4-triazol-3-yl)-3-(6-methylpyrimidin-4-yl)-3-azabicyclo[3.2.1]octan-8-amine

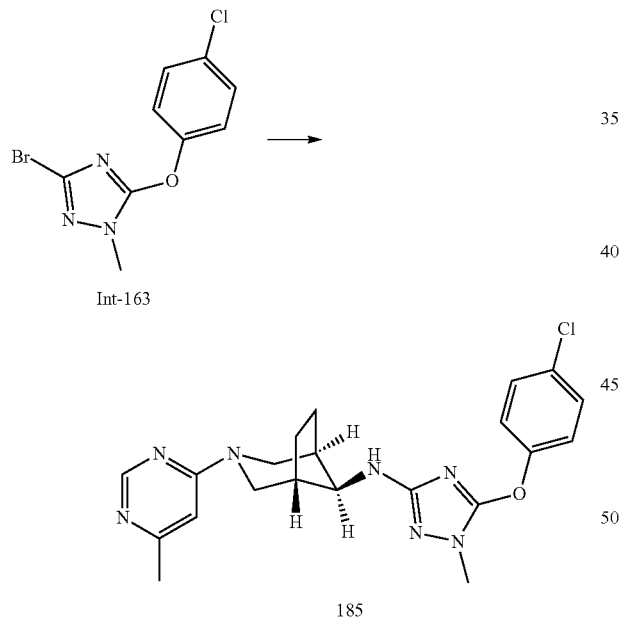

The title compound was prepared in analogy to example 181, from 3-bromo-5-(4-chlorophenoxy)-1-methyl-1H-1,2,4-triazole (Int-163, 40 mg, 139 µmol) and (1R,5S,8s)-3-(6-methylpyrimidin-4-yl)-3-azabicyclo[3.2.1]octan-8-amine (Int-114, 36.3 mg, 166 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 min. The title compound was isolated as an off-white solid (40.3 mg, 68.3% yield). MS (ES+) m/z: 426.2 [(M+H)+].

Example 186

(1R,5S,8s)-N-[5-(3-Chloro-4-fluorophenoxy)-1-methyl-1,2,4-triazol-3-yl]-3-(6-methylpyrimidin-4-yl)-3-azabicyclo[3.2.1]octan-8-amine

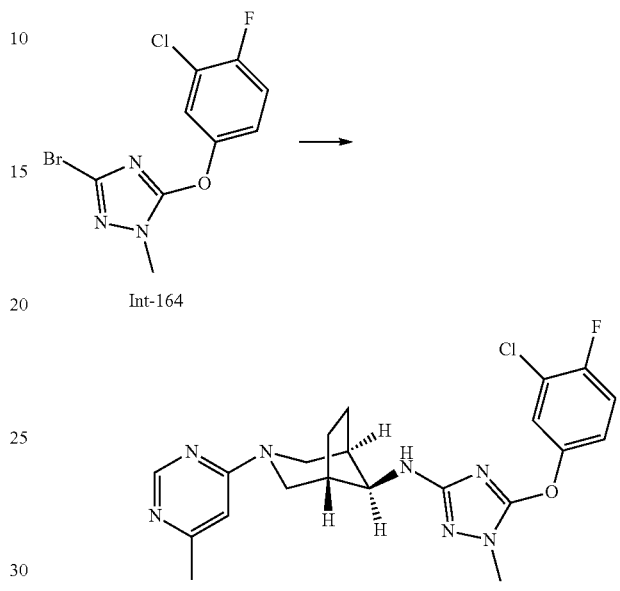

The title compound was prepared in analogy to example 181, from 3-bromo-5-(3-chloro-4-fluorophenoxy)-1-methyl-1,2,4-triazole (Int-164, 50 mg, 163 µmol) and (1R,5S,8s)-3-(6-methylpyrimidin-4-yl)-3-azabicyclo[3.2.1]octan-8-amine (Int-114, 49.9 mg, 196 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 min. The title compound was isolated as a white solid (39.7 mg, 54.8% yield). MS (ES+) m/z: 444.2 [(M+H)+].

Example 187

(1R,5S,8s)-N-[5-(3-Chloro-4-fluorophenoxy)-1-methyl-1,2,4-triazol-3-yl]-3-(3-methyl-1,2,4-oxadiazol-5-yl)-3-azabicyclo[3.2.1]octan-8-amine

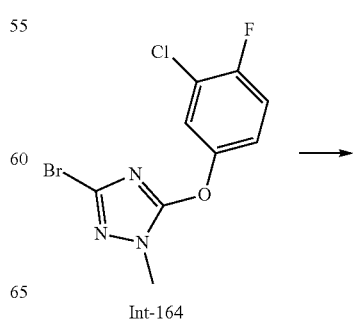

-continued

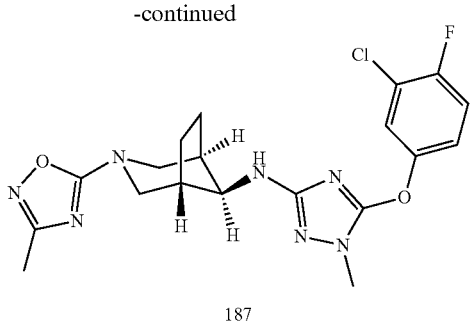

187

In a microwave-vial, 3-bromo-5-(3-chloro-4-fluorophenoxy)-1-methyl-1,2,4-triazole (Int-164, 50 mg, 163 µmol) was suspended in 1,4-dioxane (1.5 ml). (1R,5S,8s)-3-(3-methyl-1,2,4-oxadiazol-5-yl)-3-azabicyclo[3.2.1]octan-8-amine (Int-102, 40.8 mg, 196 µmol, Eq: 1.2) was added followed by sodium tert-butoxide (31.4 mg, 326 µmol) were added. The suspension was carefully degassed during 2 min and tris(dibenzylideneacetone)dipalladium (0) chloroform adduct (13.5 mg, 13 µmol) followed 1,2,3,4,5-pentaphenyl-1'-(di-tert-butylphosphino) ferrocene (Q-Phos, CAS [312959-24-3]) (18.5 mg, 26.1 µmol) were added. The vial was capped and heated in the microwave at 120° C. for 30 min. The reaction mixture was poured into 15 mL H2O and extracted with EtOAc (3×15 mL). The organic layers were dried over MgSO4 and concentrated in vacuo. The crude material was purified by flash chromatography (silica gel, eluting with 0% to 10% MeOH in DCM) to afford the title compound (16.1 mg, 22.7% yield) as a white solid. MS (ES+) m/z 434.2 [M+H].

Example 188

(1R,5S,8s)-N-[5-(3-Chloro-2-fluorophenoxy)-1-methyl-1,2,4-triazol-3-yl]-3-(6-methylpyrimidin-4-yl)-3-azabicyclo[3.2.1]octan-8-amine

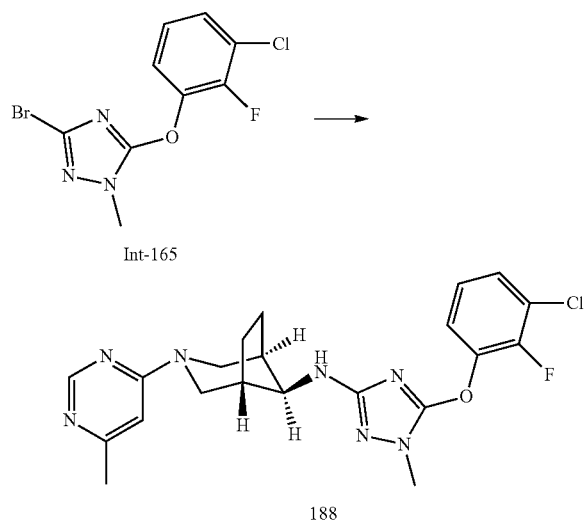

The title compound was prepared in analogy to example 181, from 3-bromo-5-(3-chloro-2-fluorophenoxy)-1-methyl-1,2,4-triazole (Int-165, 40 mg, 130 µmol) and (1R,5S,8s)-3-(6-methylpyrimidin-4-yl)-3-azabicyclo[3.2.1]octan-8-amine (Int-114, 34.2 mg, 157 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 min. The compound was isolated as a yellow solid (41.9 mg, 72.3% yield). MS (ES+) m/z: 444.2 [(M+H)+].

Example 189

(1S,5R.8s)-N-[5-(2-Chloro-3-fluorophenoxy)-1-methyl-1,2,4-triazol-3-yl]-3-(6-methylpyrimidin-4-yl)-3-azabicyclo[3.2.1]octan-8-amine

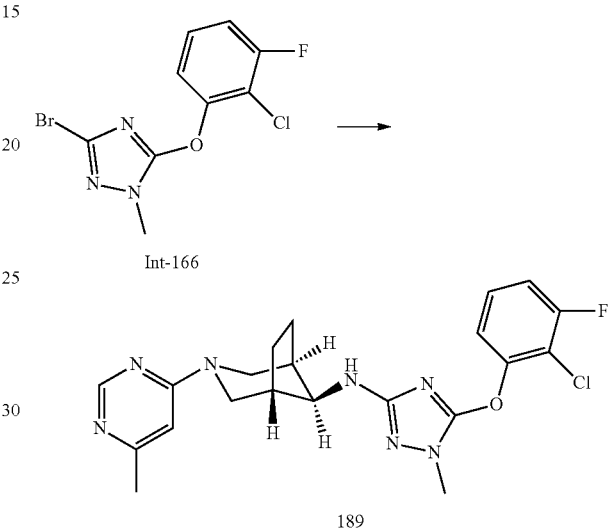

The title compound was prepared in analogy to example 181, 3-bromo-5-(2-chloro-3-fluorophenoxy)-1-methyl-1,2,4-triazole (Int-166, 40 mg, 130 µmol) and (1R,5S,8s)-3-(6-methylpyrimidin-4-yl)-3-azabicyclo[3.2.1]octan-8-amine (Int-114, 34.2 mg, 157 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 min. The compound was isolated as an off-white solid (9.4 mg, 16.2% yield). MS (ES+) m/z: 444.2 [(M+H)+].

Example 190

(1R,5S,8s)-N-[5-(3-Chloro-5-fluorophenoxy)-1-ethyl-1,2,4-triazol-3-yl]-3-(6-methylpyrimidin-4-yl)-3-azabicyclo[3.2.1]octan-8-amine

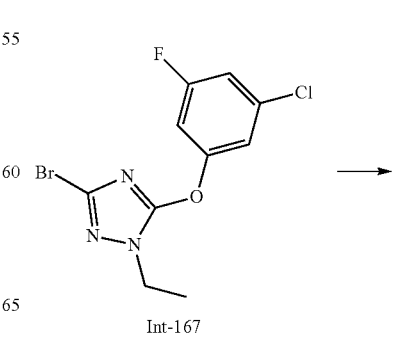

Int-167

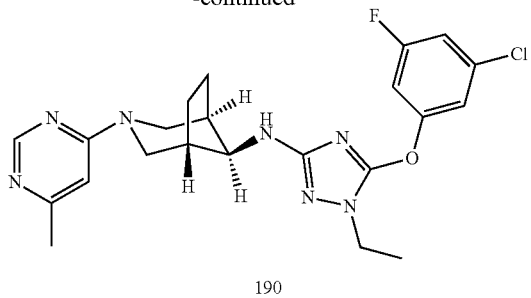

190

The title compound was prepared in analogy to example 181, from 3-bromo-5-(3-chloro-5-fluorophenoxy)-1-ethyl-1,2,4-triazole (Int-167, 40 mg, 125 μmol) and (1R,5S,8s)-3-(6-methylpyrimidin-4-yl)-3-azabicyclo[3.2.1]octan-8-amine (Int-114, 32.7 mg, 150 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (27.9 mg, 48.8% yield). MS (ES+) m/z: 458.2 [(M+H)$^+$].

Example 191

(1R,5S,8s)-N-[5-(3,5-Difluorophenoxy)-1-ethyl-1,2,4-triazol-3-yl]-3-(6-methylpyrimidin-4-yl)-3-azabicyclo[3.2.1]octan-8-amine

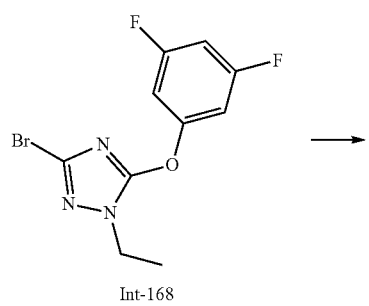

Int-168

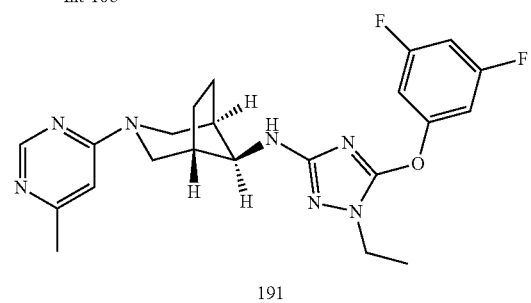

191

The title compound was prepared in analogy to example 181, from 3-bromo-5-(3,5-difluorophenoxy)-1-ethyl-1,2,4-triazole (Int-168, 40 mg, 132 μmol) and (1R,5S,8s)-3-(6-methylpyrimidin-4-yl)-3-azabicyclo[3.2.1]octan-8-amine (Int-114, 34.5 mg, 158 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (38.6 mg, 66.5% yield). MS (ES+) m/z: 442.3 [(M+H)$^+$].

Example 192

(1R,5S,8s)-N-(5-(2-Chlorophenoxy)-1-ethyl-1H-1,2,4-triazol-3-yl)-3-(6-methylpyrimidin-4-yl)-3-azabicyclo[3.2.1]octan-8-amine

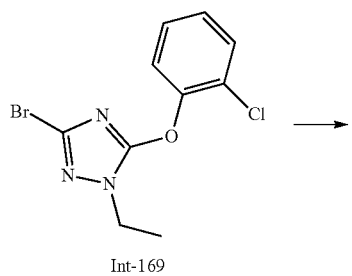

Int-169

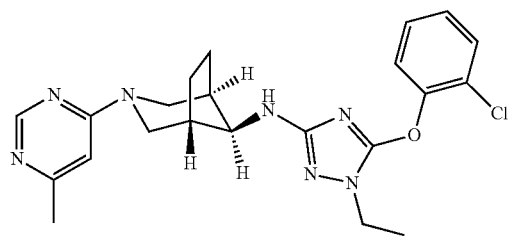

192

The title compound was prepared in analogy to example 181, from 3-bromo-5-(2-chlorophenoxy)-1-ethyl-1H-1,2,4-triazole (Int-169, 40 mg, 132 μmol) and (1R,5S,8s)-3-(6-methylpyrimidin-4-yl)-3-azabicyclo[3.2.1]octan-8-amine (Int-114, 34.5 mg, 158 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid ((41.8 mg, 71.9% yield). MS (ES+) m/z: 440.1 [(M+H)$^+$].

Example 193

(1R,5S)—N-[5-(3-Chloro-4-fluorophenoxy)-1-ethyl-1,2,4-triazol-3-yl]-3-(6-methylpyrimidin-4-yl)-3-azabicyclo[3.2.1]octan-8-amine

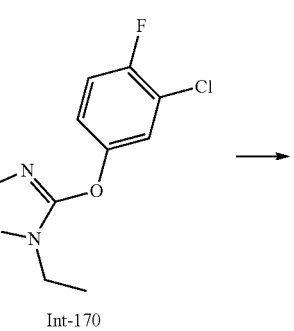

Int-170

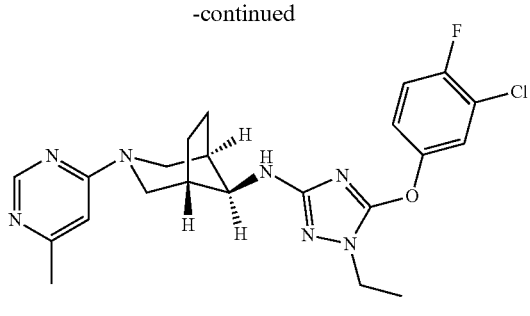

193

The title compound was prepared in analogy to example 181, from 3-bromo-5-(3-chloro-4-fluorophenoxy)-1-ethyl-1,2,4-triazole (Int-170, 40 mg, 125 µmol) and (1R,5S,8s)-3-(6-methylpyrimidin-4-yl)-3-azabicyclo[3.2.1]octan-8-amine (Int-114, 32.7 mg, 150 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (33.6 mg, 58.8% yield). MS (ES+) m/z: 458.2 [(M+H)+].

Example 194

(1R,5S,8s)-N-(5-(3-Chloro-4-fluorophenoxy)-1-ethyl-1H-1,2,4-triazol-3-yl)-3-(6-methoxypyridazin-4-yl)-3-azabicyclo[3.2.1]octan-8-amine

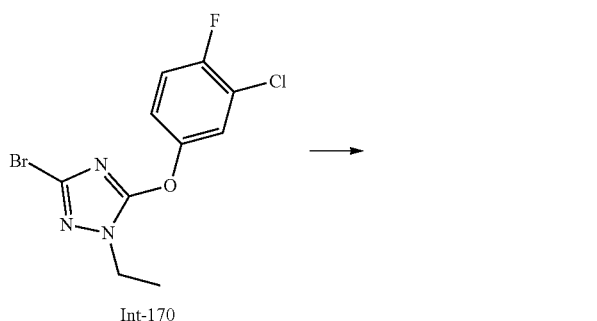

194

The title compound was prepared in analogy to example 183, from 3-bromo-5-(3-chloro-4-fluorophenoxy)-1-ethyl-1,2,4-triazole (Int-170, 40 mg, 125 µmol) and (1R,5S,8s)-3-(6-Methoxypyridazin-4-yl)-3-azabicyclo[3.2.1]octan-8-amine (Int-128, 35.1 mg, 150 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (28 mg, 47.3% yield). MS (ES+) m/z: 474.2 [(M+H)+].

Example 195

(1R,5S,8s)-N-(5-(3-Chloro-4-fluorophenoxy)-1-ethyl-1H-1,2,4-triazol-3-yl)-3-(2-methoxypyridin-4-yl)-3-azabicyclo[3.2.1]octan-8-amine

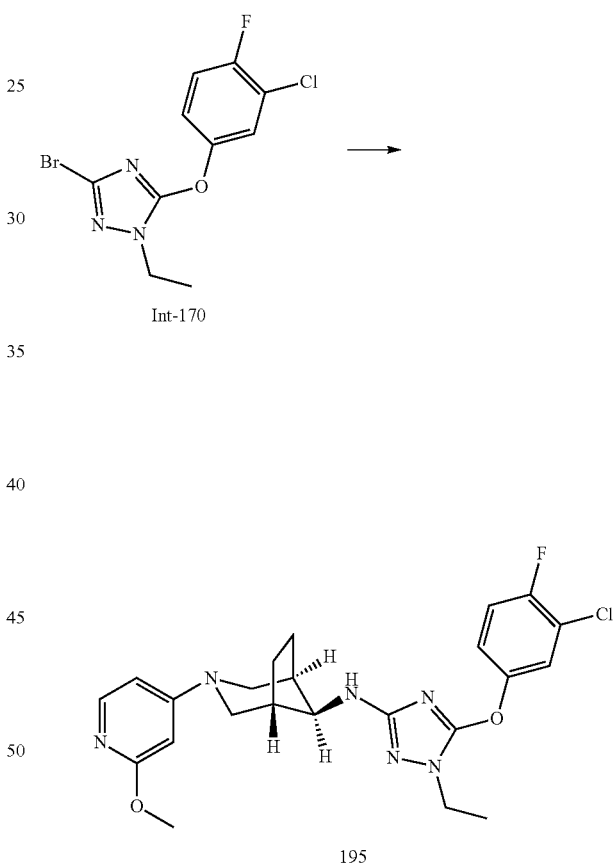

195

The title compound was prepared in analogy to example 184, from 3-bromo-5-(3-chloro-4-fluorophenoxy)-1-ethyl-1,2,4-triazole (Int-170, 40 mg, 125 µmol) and (1R,5S,8s)-3-(2-Methoxy-4-pyridyl)-3-azabicyclo[3.2.1]octan-8-amine (Int-111, 34.9 mg, 150 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a light brown solid (27.1 mg, 45.9% yield). MS (ES+) m/z: 473.2 [(M+H)+].

Example 196

(1R,5S,8s)-N-[5-(3-Chloro-5-fluorophenoxy)-1-propyl-1,2,4-triazol-3-yl]-3-(6-methylpyrimidin-4-yl)-3-azabicyclo[3.2.1]octan-8-amine

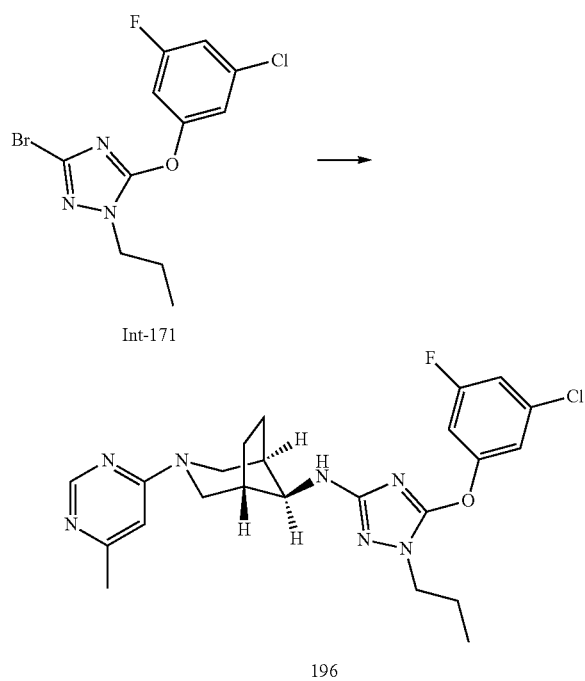

Int-171

196

The title compound was prepared in analogy to example 181, from 3-Bromo-5-(3-chloro-5-fluorophenoxy)-1-propyl-1,2,4-triazole (Int-171, 40 mg, 120 µmol) and (1R,5S,8s)-3-(6-methylpyrimidin-4-yl)-3-azabicyclo[3.2.1]octan-8-amine (Int-114, 31.3 mg, 143 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (30.5 mg, 54.1% yield). MS (ES+) m/z: 472.2 [(M+H)$^+$].

Example 197

(1R,5S,8s)-N-[5-(3,5-Difluorophenoxy)-1-propyl-1,2,4-triazol-3-yl]-3-(6-methylpyrimidin-4-yl)-3-azabicyclo[3.2.1]octan-8-amine

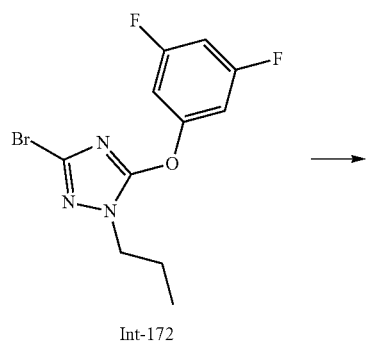

Int-172

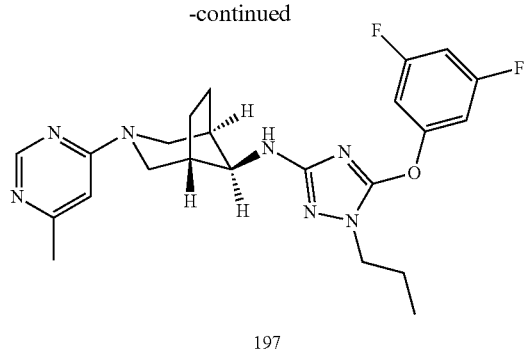

197

The title compound was prepared in analogy to example 181, from 3-bromo-5-(3,5-difluorophenoxy)-1-propyl-1,2,4-triazole (Int-172, 40 mg, 126 µmol) and (1R,5S,8s)-3-(6-methylpyrimidin-4-yl)-3-azabicyclo[3.2.1]octan-8-amine (Int-114, (32.9 mg, 151 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (29.5 mg, 51.5% yield). MS (ES+) m/z: 456.3 [(M+H)$^+$].

Example 198

(1R,5S,8s)-N-(5-(2-Chlorophenoxy)-1-propyl-1H-1,2,4-triazol-3-yl)-3-(6-methylpyrimidin-4-yl)-3-azabicyclo[3.2.1]octan-8-amine

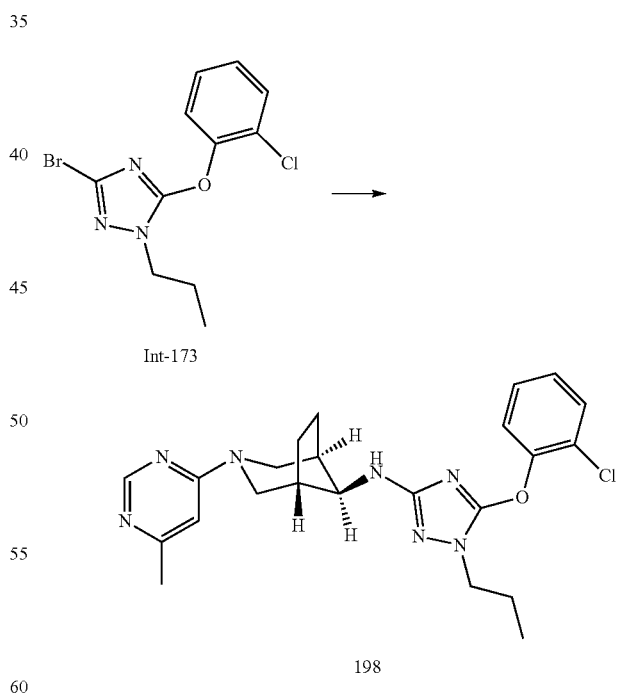

The title compound was prepared in analogy to example 181, from 3-bromo-5-(2-chlorophenoxy)-1-propyl-1H-1,2,4-triazole (Int-173, 40 mg, 126 µmol) and (1R,5S,8s)-3-(6-methylpyrimidin-4-yl)-3-azabicyclo[3.2.1]octan-8-amine (Int-114, (32.9 mg, 151 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a light yellow solid (28.8 mg, 50.2% yield). MS (ES+) m/z: 454.1 [(M+H)+].

Example 199

(1R,5S,8s)-N-[5-(3-Chloro-4-fluorophenoxy)-1-propyl-1,2,4-triazol-3-yl]-3-(6-methylpyrimidin-4-yl)-3-azabicyclo[3.2.1]octan-8-amine Example 200

(1R,5S,8s)-N-(5-(3-Chloro-4-fluorophenoxy)-1-propyl-1H-1,2,4-triazol-3-yl)-3-(6-methoxypyridazin-4-yl)-3-azabicyclo[3.2.1]octan-8-amine

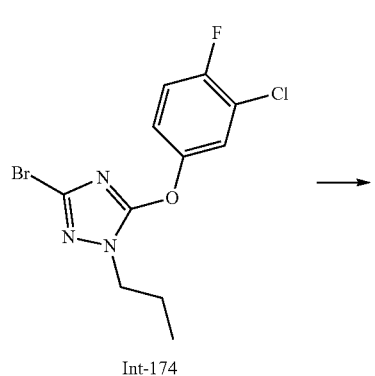

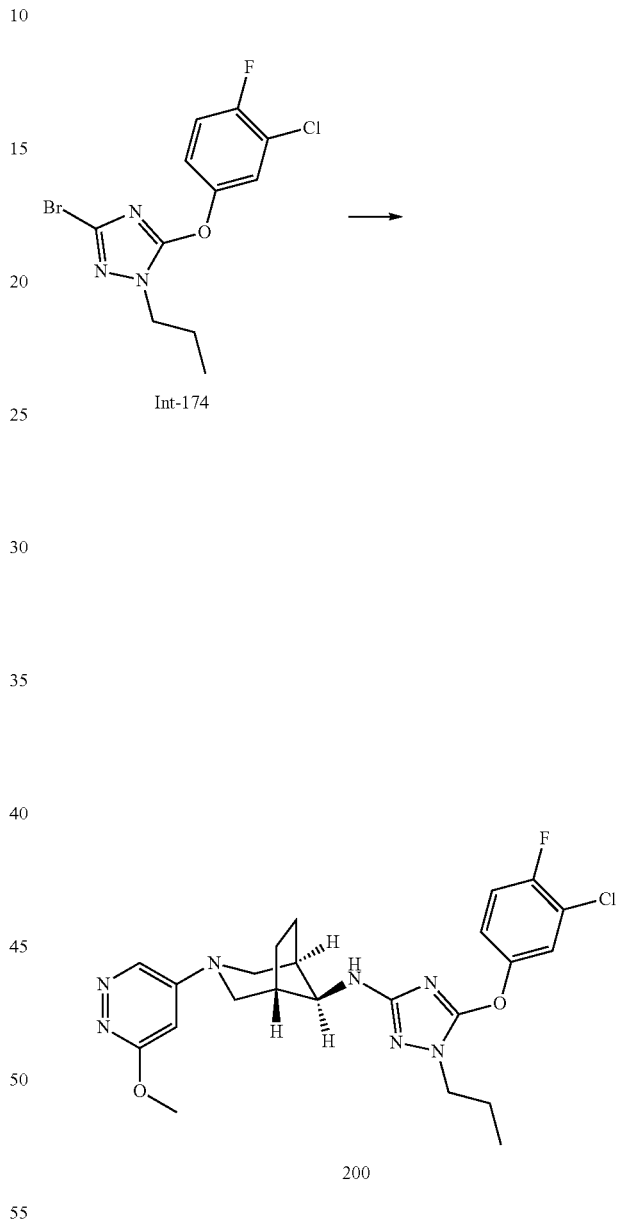

The title compound was prepared in analogy to example 181, from 3-bromo-5-(3-chloro-4-fluorophenoxy)-1-propyl-1,2,4-triazole (Int-174, 40 mg, 120 µmol) and (1R,5S,8s)-3-(6-methylpyrimidin-4-yl)-3-azabicyclo[3.2.1]octan-8-amine (Int-114, 31.3 mg, 143 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a yellow solid (29.5 mg, 52.3% yield). MS (ES+) m/z: 472.2 [(M+H)+].

The title compound was prepared in analogy to example 183, from 3-bromo-5-(3-chloro-4-fluorophenoxy)-1-propyl-1,2,4-triazole (Int-174, 40 mg, 120 µmol) and (1R,5S,8s)-3-(6-Methoxypyridazin-4-yl)-3-azabicyclo[3.2.1]octan-8-amine (Int-128, 33.6 mg, 143 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (30.1 mg, 51.6% yield). MS (ES+) m/z: 489.2 [(M+H)+].

Example 201

(1R,5S,8s)-N-(5-(3-Chloro-4-fluorophenoxy)-1-propyl-1H-1,2,4-triazol-3-yl)-3-(2-methoxypyridin-4-yl)-3-azabicyclo[3.2.1]octan-8-amine

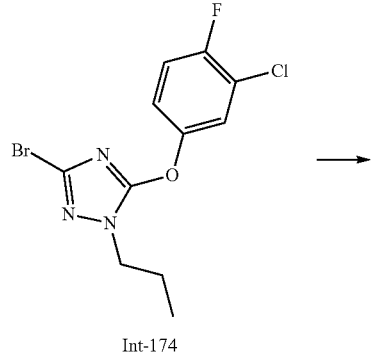

Int-174

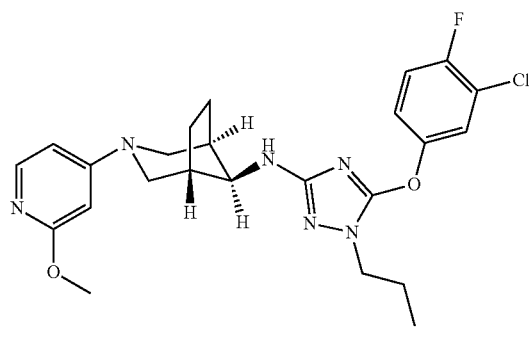

201

The title compound was prepared in analogy to example 184, from 3-bromo-5-(3-chloro-4-fluorophenoxy)-1-propyl-1,2,4-triazole (Int-174, 40 mg, 120 µmol) and (1R,5S,8s)-3-(2-Methoxy-4-pyridyl)-3-azabicyclo[3.2.1]octan-8-amine (Int-111, 33.5 mg, 143 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a yellow solid (27.7 mg, 47.6% yield). MS (ES+) m/z: 487.2 [(M+H)⁺].

Example 202

(1R,5S,8s)-N-(5-(3-Chloro-4-fluorophenoxy)-1-propyl-1H-1,2,4-triazol-3-yl)-3-(5-methyl-1,3,4-oxadiazol-2-yl)-3-azabicyclo[3.2.1]octan-8-amine

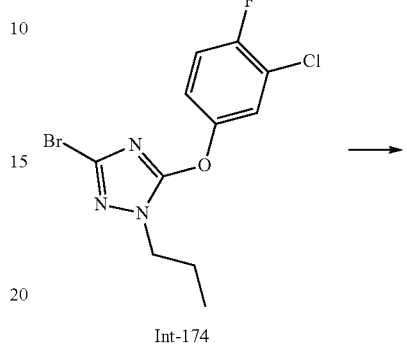

Int-174

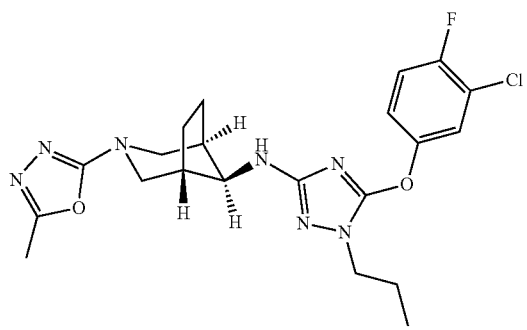

202

In a vial, 3-bromo-5-(3-chloro-4-fluorophenoxy)-1-propyl-1,2,4-triazole (Int-174, 40 mg, 120 µmol) was suspend in 2-methyltetrahydrofuran (1.5 ml) and (1R,5S,8s)-3-(5-methyl-1,3,4-oxadiazol-2-yl)-3-azabicyclo[3.2.1]octan-8-amine (Int-105, 29.9 mg, 143 µmol) was added followed by sodium tert-butoxide (34.5 mg, 359 µmol). The suspension was carefully degassed during 2 min and tris(dibenzylideneacetone)dipalladium (0) chloroform adduct (3.71 mg, 3.59 µmol) followed by 2-di-tert-butylphosphino-2',4',6'-triisopropylbiphenyl (tBuXPhos, CAS [564483-19-8]) ((3.05 mg, 7.17 µmol) were added. The vial was closed under Argon and heated to 80° C. during 30 min. The reaction mixture was poured into water and extracted with EtOAc (3×15 ml). The organic layers were dried over MgSO4 and concentrated in vacuo. The crude material was purified by column chromatography (silica gel, eluting with dichloromethane/methanol, gradient 100:0 to 93:7). The compound was isolated as a white solid (11.1 mg, 20% yield). MS (ES+) m/z 462.2 [M+H].

Example 203

(1R,5S,8s)-N-[5-(3-Chloro-5-fluorophenoxy)-1-(2-methylpropyl)-1,2,4-triazol-3-yl]-3-(6-methylpyrimidin-4-yl)-3-azabicyclo[3.2.1]octan-8-amine

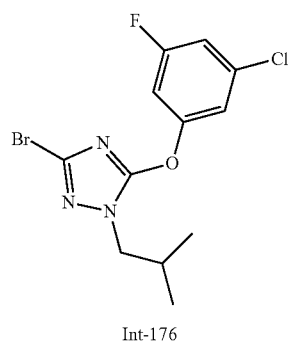

Int-176

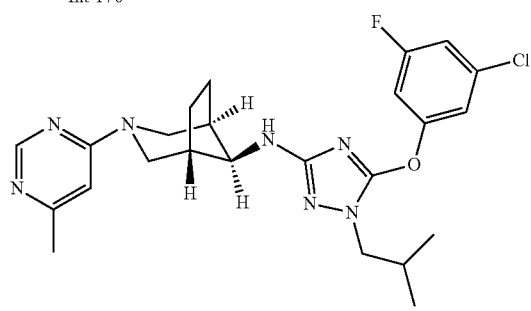

203

The title compound was prepared in analogy to example 181, from 3-bromo-5-(3-chloro-5-fluorophenoxy)-1-(2-methylpropyl)-1,2,4-triazole (Int-176, 40 mg, 115 µmol) and (1R,5S,8s)-3-(6-methylpyrimidin-4-yl)-3-azabicyclo[3.2.1]octan-8-amine (Int-114, 30.1 mg, 138 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (31 mg, 55.6% yield). MS (ES+) m/z: 486.2 [(M+H)$^+$].

Example 204

(1R,5S,8s)-N-(5-(2-Chlorophenoxy)-1-isobutyl-1H-1,2,4-triazol-3-yl)-3-(6-methylpyrimidin-4-yl)-3-azabicyclo[3.2.1]octan-8-amine

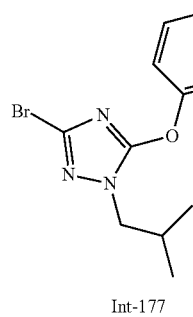

Int-177

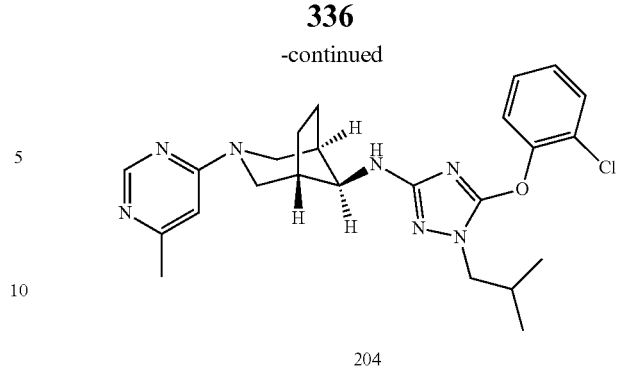

204

The title compound was prepared in analogy to example 181, from 3-bromo-5-(2-chlorophenoxy)-1-isobutyl-1H-1,2,4-triazole (Int-177, 40 mg, 121 µmol) and (1R,5S,8s)-3-(6-methylpyrimidin-4-yl)-3-azabicyclo[3.2.1]octan-8-amine (Int-114, 31.7 mg, 145 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (31.4 mg, 55.5% yield). MS (ES+) m/z: 468.1 [(M+H)$^+$].

Example 205

(1R,5S,8s)-N-(5-(3-Chloro-4-fluorophenoxy)-1-isobutyl-1H-1,2,4-triazol-3-yl)-3-(6-methylpyrimidin-4-yl)-3-azabicyclo[3.2.1]octan-8-amine

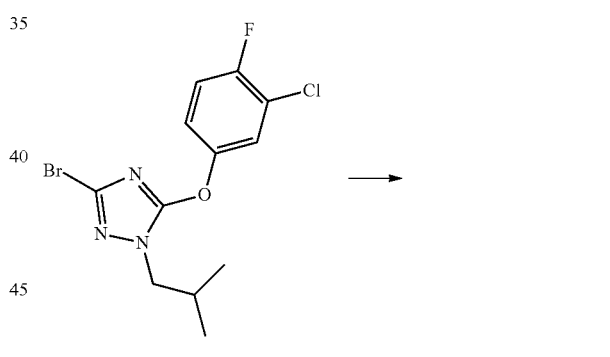

Int-178

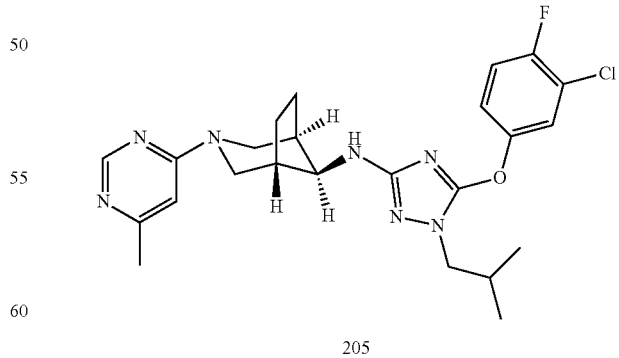

205

The title compound was prepared in analogy to example 181, from 3-bromo-5-(3-chloro-4-fluorophenoxy)-1-isobutyl-1H-1,2,4-triazole (Int-178, 40 mg, 115 µmol) and (1R,5S,8s)-3-(6-methylpyrimidin-4-yl)-3-azabicyclo[3.2.1]

octan-8-amine (Int-114, 30.1 mg, 138 µmol) with sodium tert-butoxide, tris(dibenzylideneacetone)dipalladium (0) chloroform adduct and 2-di-tert-butylphosphino-2',4',6'-tri-isopropylbiphenyl (tBuXPhos, CAS [564483-19-8]). The reaction was heated to 80° C. during 30 minutes. The compound was isolated as an off-white solid (28.7 mg, 51.5% yield). MS (ES+) m/z: 486.2 [(M+H)+].

Example 206

(1R,5S,8s)-N-(5-(3-Chloro-4-fluorophenoxy)-1-isobutyl-1H-1,2,4-triazol-3-yl)-3-(6-methoxy-pyridazin-4-yl)-3-azabicyclo[3.2.1]octan-8-amine

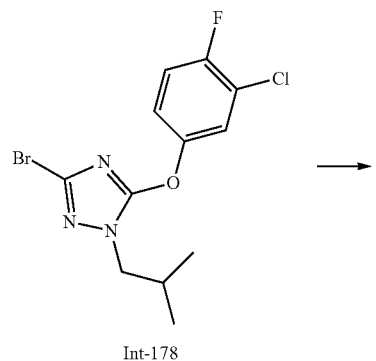

Int-178

Example 207

(1R,5S,8s)-N-(5-(3-Chloro-4-fluorophenoxy)-1-isobutyl-1H-1,2,4-triazol-3-yl)-3-(2-methoxypyridin-4-yl)-3-azabicyclo[3.2.1]octan-8-amine

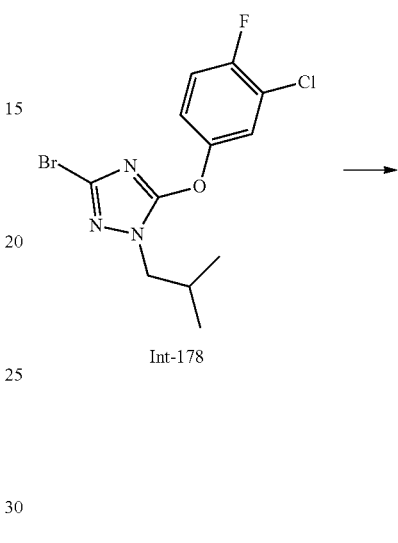

206

The title compound was prepared in analogy to example 183, from 3-bromo-5-(3-chloro-4-fluorophenoxy)-1-isobutyl-1H-1,2,4-triazole (Int-178, 40 mg, 115 µmol) and (1R,5S,8s)-3-(6-Methoxypyridazin-4-yl)-3-azabicyclo[3.2.1]octan-8-amine (Int-128, 32.3 mg, 138 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (23.6 mg, 41% yield). MS (ES+) m/z: 502.3 [(M+H)+].

The title compound was prepared in analogy to example 184, from 3-bromo-5-(3-chloro-4-fluorophenoxy)-1-isobutyl-1H-1,2,4-triazole (Int-178, 40 mg, 115 µmol) and (1R,5S,8s)-3-(2-Methoxy-4-pyridyl)-3-azabicyclo[3.2.1]octan-8-amine (Int-111, 32.1 mg, 138 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a light brown oil (20.8 mg, 36.2% yield). MS (ES+) m/z: 501.2 [(M+H)+].

339
Example 208

(1R,5S,8s)-N-[5-(3-Chloro-5-fluorophenoxy)-1-[(3-methyloxetan-3-yl)methyl]-1,2,4-triazol-3-yl]-3-(6-methylpyrimidin-4-yl)-3-azabicyclo[3.2.1]octan-8-amine

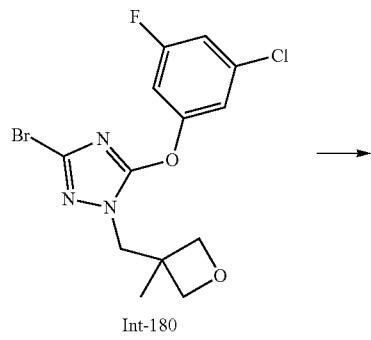

Int-180

340
Example 209

(1R,5S,8s)-N-[5-(3-Chloro-4-fluorophenoxy)-1-[(3-methyloxetan-3-yl)methyl]-1,2,4-triazol-3-yl]-3-(6-methylpyrimidin-4-yl)-3-azabicyclo[3.2.1]octan-8-amine

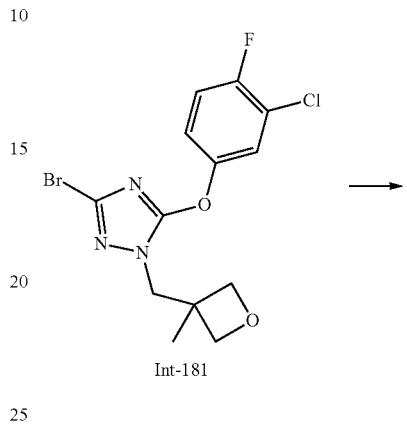

Int-181

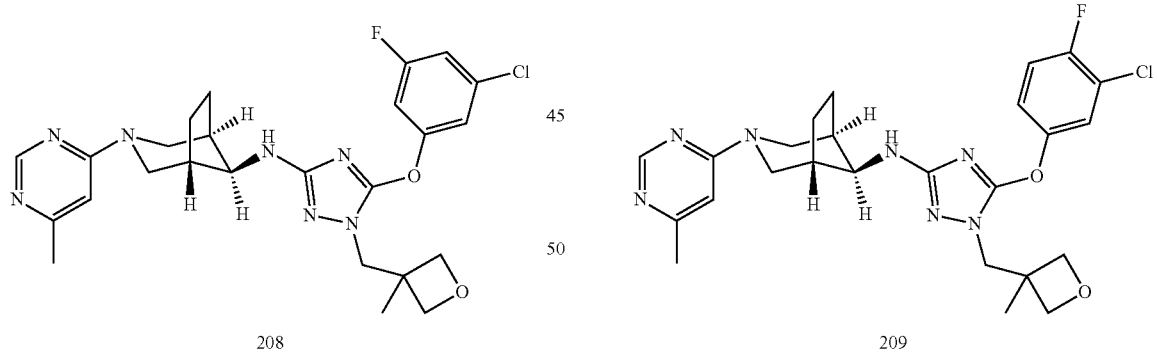

208

209

The title compound was prepared in analogy to example 181, from 3-bromo-5-(3-chloro-5-fluorophenoxy)-1-isobutyl-1H-1,2,4-triazole (Int-180, 40 mg, 106 μmol) and (1R,5S,8s)-3-(6-methylpyrimidin-4-yl)-3-azabicyclo[3.2.1]octan-8-amine (Int-114, 27.8 mg, 127 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (25.7 mg, 47.1% yield). MS (ES+) m/z: 514.2 [(M+H)⁺].

The title compound was prepared in analogy to example 181, from 3-bromo-5-(3-chloro-4-fluorophenoxy)-1-[(3-methyloxetan-3-yl)methyl]-1,2,4-triazole (Int-181, 50 mg, 133 μmol) and (1R,5S,8s)-3-(6-methylpyrimidin-4-yl)-3-azabicyclo[3.2.1]octan-8-amine (Int-114, 34.8 mg, 159 μmol) with sodium tert-butoxide, tris(dibenzylideneacetone) dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The title compound was isolated as an off-white solid (34.3 mg, 3% yield). MS (ES+) m/z: 514.2 [(M+H)⁺].

Example 210

(1R,5S,8s)-N-[5-(3-Chloro-5-fluorophenoxy)-1-[2-methoxypropyl]-1,2,4-triazol-3-yl]-3-(6-methylpyrimidin-4-yl)-3-azabicyclo[3.2.1]octan-8-amine

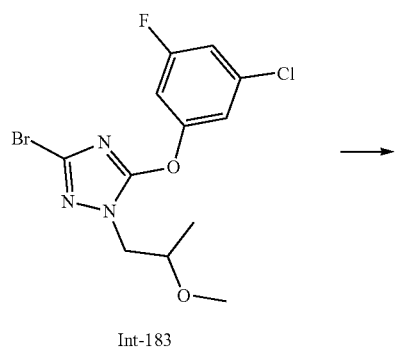

Int-183

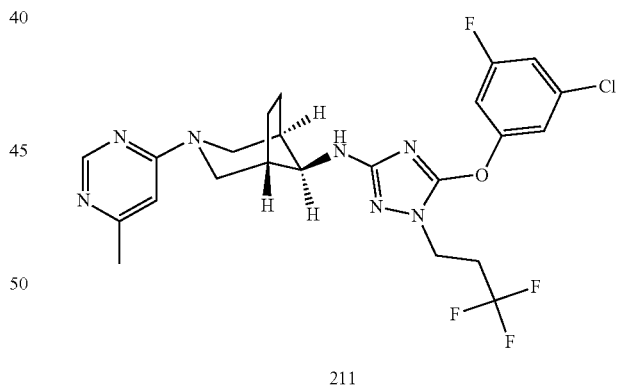

210

The title compound was prepared in analogy to example 181, from 3-bromo-5-(3-chloro-5-fluorophenoxy)-1-(2-methoxypropyl)-1,2,4-triazole (Int-183, 27.5 mg, 75.4 µmol) and (1R,5S,8s)-3-(6-methylpyrimidin-4-yl)-3-azabicyclo[3.2.1]octan-8-amine (Int-114, 19.8 mg, 90.5 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The title compound was isolated as a light yellow solid (24.2 mg, 63.9% yield). MS (ES+) m/z: 502.2 [(M+H)$^+$].

Example 211

(1R,5S,8s)-N-[5-(3-Chloro-5-fluorophenoxy)-1-(3,3,3-trifluoropropyl)-1,2,4-triazol-3-yl]-3-(6-methylpyrimidin-4-yl)-3-azabicyclo[3.2.1]octan-8-amine

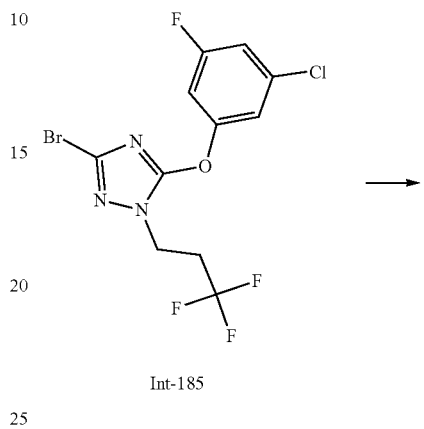

Int-185

211

The title compound was prepared in analogy to example 181, 3-bromo-5-(3-chloro-5-fluorophenoxy)-1-(3,3,3-trifluoropropyl)-1,2,4-triazole (Int-185, 40 mg, 103 µmol) and (1R,5S,8s)-3-(6-methylpyrimidin-4-yl)-3-azabicyclo[3.2.1]octan-8-amine (Int-114, 27 mg, 124 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The title compound was isolated as an off-white solid (32.9 mg, 60.8% yield). MS (ES+) m/z: 526.2 [(M+H)$^+$].

Example 212

(1R,5S,8s)-N-(5-(3-Chloro-5-fluorophenoxy)-1-((3,3-difluorocyclobutyl)methyl)-1H-1,2,4-triazol-3-yl)-3-(6-methylpyrimidin-4-yl)-3-azabicyclo[3.2.1]octan-8-amine

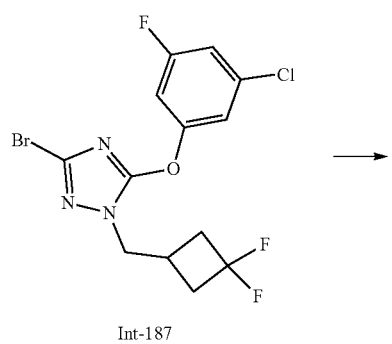

Int-187

Example 213

(1R,5S,8s)-N-(5-(3-Chloro-4-fluorophenoxy)-1-((3,3-difluorocyclobutyl)methyl)-1H-1,2,4-triazol-3-yl)-3-(6-methylpyrimidin-4-yl)-3-azabicyclo[3.2.1]octan-8-amine

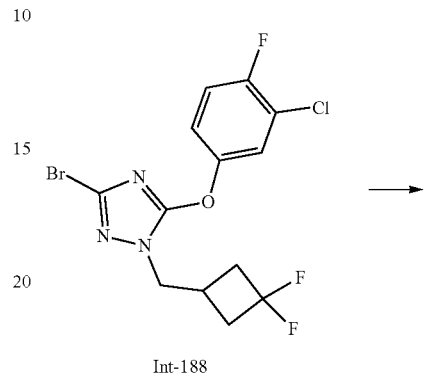

Int-188

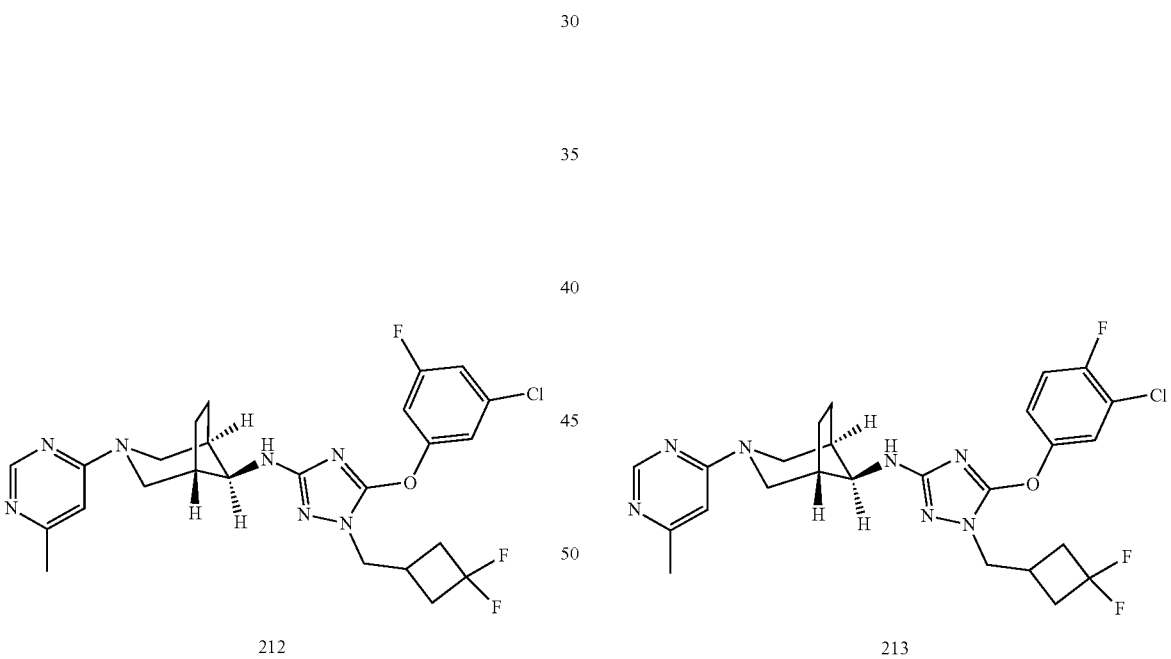

212

213

The title compound was prepared in analogy to example 181, 3-bromo-5-(3-chloro-5-fluorophenoxy)-1-((3,3-difluorocyclobutyl)methyl)-1H-1,2,4-triazole (Int-187, 40 mg, 101 µmol) and (1R,5S,8s)-3-(6-methylpyrimidin-4-yl)-3-azabicyclo[3.2.1]octan-8-amine (Int-114, 26.4 mg, 121 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The title compound was isolated as a white solid (16.3 mg, 30.3% yield). MS (ES+) m/z: 534.3 [(M+H)$^+$].

The title compound was prepared in analogy to example 181, 3-bromo-5-(3-chloro-4-fluorophenoxy)-1-((3,3-difluorocyclobutyl)methyl)-1H-1,2,4-triazole (Int-188, 40 mg, 101 µmol) and (1R,5S,8s)-3-(6-methylpyrimidin-4-yl)-3-azabicyclo[3.2.1]octan-8-amine (Int-114, 26.4 mg, 121 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (11.5 mg, 21.4% yield). MS (ES+) m/z: 534.3 [(M+H)$^+$].

Example 214

(1R,5S,8s)-N-(5-(3-Chloro-4-fluorophenoxy)-1-((3,3-difluorocyclobutyl)methyl)-1H-1,2,4-triazol-3-yl)-3-(6-methoxypyridazin-4-yl)-3-azabicyclo[3.2.1]octan-8-amine

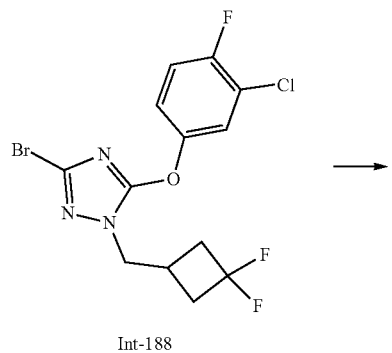

Int-188

Example 215

(1R,5S,8s)-N-(5-(3-Chloro-4-fluorophenoxy)-1-((3,3-difluorocyclobutyl)methyl)-1H-1,2,4-triazol-3-yl)-3-(2-methoxypyridin-4-yl)-3-azabicyclo[3.2.1]octan-8-amine

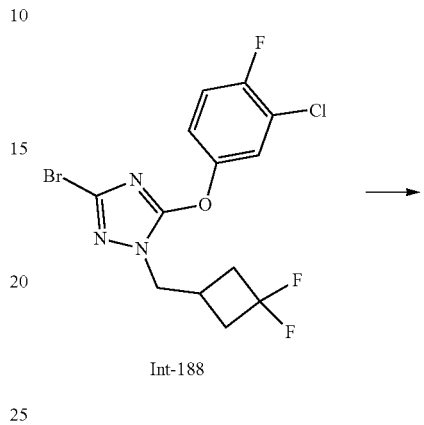

Int-188

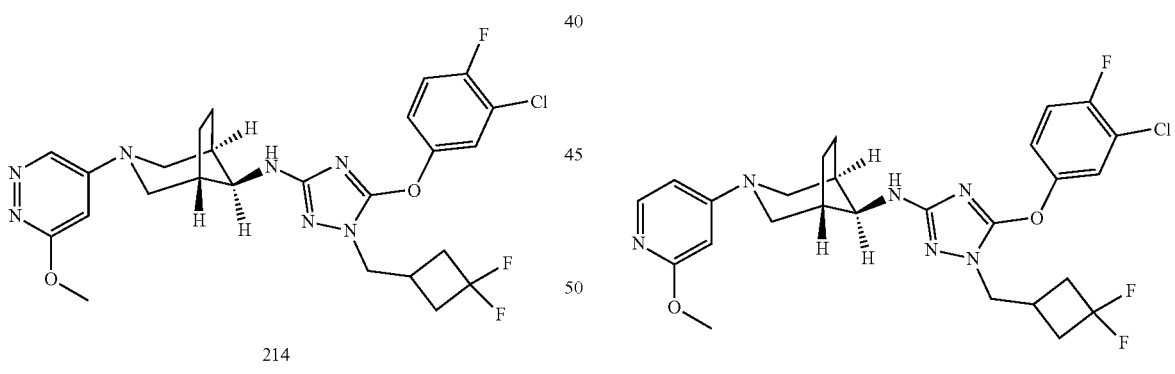

214

215

The title compound was prepared in analogy to example 183, from 3-bromo-5-(3-chloro-4-fluorophenoxy)-1-((3,3-difluorocyclobutyl)methyl)-1H-1,2,4-triazole (Int-188, 50 mg, 126 µmol) and (1R,5S,8s)-3-(6-Methoxypyridazin-4-yl)-3-azabicyclo[3.2.1]octan-8-amine (Int-128, 35.4 mg, 151 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (15.9 mg, 22.9% yield). MS (ES+) m/z: 550.3 [(M+H)$^+$].

The title compound was prepared in analogy to example 184, from 3-bromo-5-(3-chloro-4-fluorophenoxy)-1-((3,3-difluorocyclobutyl)methyl)-1H-1,2,4-triazole (Int-188, 30 mg, 75.6 µmol) and (1R,5S,8s)-3-(2-Methoxy-4-pyridyl)-3-azabicyclo[3.2.1]octan-8-amine (Int-111, 21.2 mg, 90.8 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (18.5 mg, 44.5% yield). MS (ES+) m/z: 549.2 [(M+H)$^+$].

Example 216

(1R,5S,8s)-N-[5-(3-Chloro-5-fluorophenoxy)-1-(oxetan-3-yl)-1,2,4-triazol-3-yl]-3-(6-methylpyrimidin-4-yl)-3-azabicyclo[3.2.1]octan-8-amine

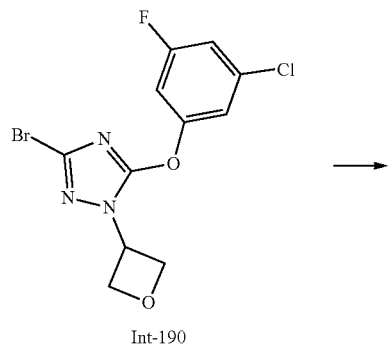

Int-190

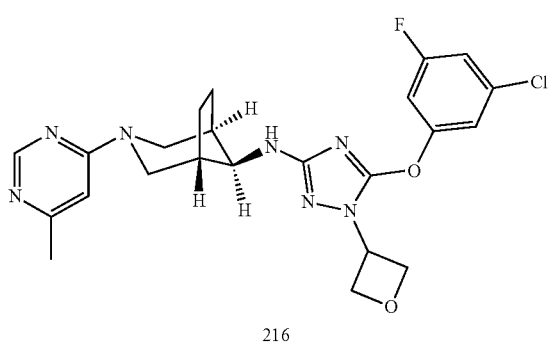

216

The title compound was prepared in analogy to example 181, 3-bromo-5-(3-chloro-5-fluorophenoxy)-1-(oxetan-3-yl)-1,2,4-triazole (Int-190, 30 mg, 86.1 μmol) and (1R,5S,8s)-3-(6-methylpyrimidin-4-yl)-3-azabicyclo[3.2.1]octan-8-amine (Int-114, 22.5 mg, 103 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (20.7 mg, 49.5% yield). MS (ES+) m/z: 486.3 [(M+H)$^+$].

Example 217

(1R,5S,8s)-N-[5-(3-Chloro-4-fluorophenoxy)-1-(oxetan-3-yl)-1,2,4-triazol-3-yl]-3-(6-methylpyrimidin-4-yl)-3-azabicyclo[3.2.1]octan-8-amine

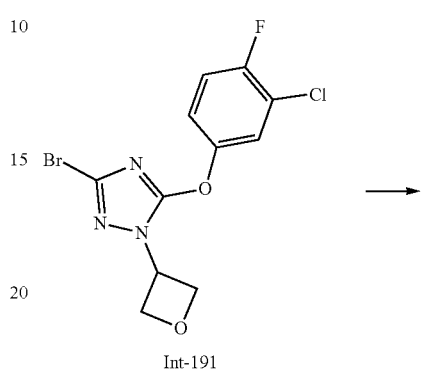

Int-191

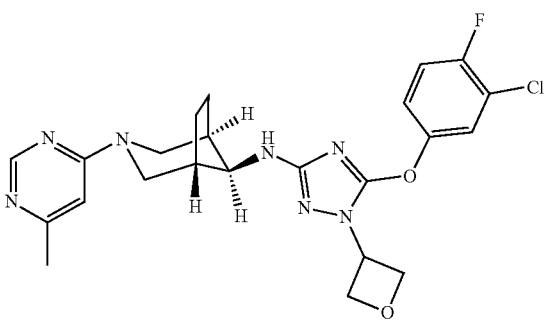

217

The title compound was prepared in analogy to example 181, 3-bromo-5-(3-chloro-4-fluorophenoxy)-1-(oxetan-3-yl)-1,2,4-triazole (Int-191, 30 mg, 86.1 μmol) and (1R,5S,8s)-3-(6-methylpyrimidin-4-yl)-3-azabicyclo[3.2.1]octan-8-amine (Int-114, 22.5 mg, 103 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (22.3 mg, 53.3% yield). MS (ES+) m/z: 486.3 [(M+H)$^+$].

Example 218

(1R,5S,8s)-N-[5-(3-Chloro-5-fluorophenoxy)-1-(oxolan-3-yl)-1,2,4-triazol-3-yl]-3-(6-methylpyrimidin-4-yl)-3-azabicyclo[3.2.1]octan-8-amine

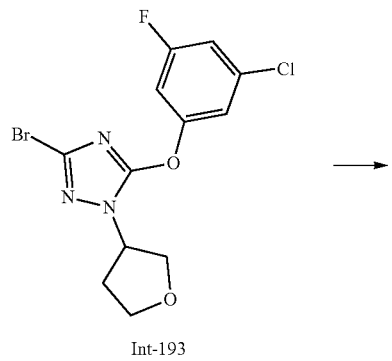

Int-193

→

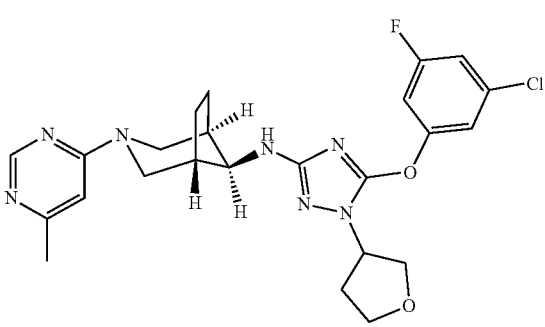

218

The title compound was prepared in analogy to example 181, 3-bromo-5-(3-chloro-5-fluorophenoxy)-1-(oxolan-3-yl)-1,2,4-triazole (Int-193, 40 mg, 110 µmol) and (1R,5S,8s)-3-(6-methylpyrimidin-4-yl)-3-azabicyclo[3.2.1]octan-8-amine (Int-114, 28.9 mg, 132 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The title compound was isolated as an off-white solid (19.4 mg, 35.2% yield). MS (ES+) m/z: 500.2 [(M+H)+].

Example 219

(1R,5S,8s)-N-[5-(3-Chloro-4-fluorophenoxy)-1-(oxolan-3-yl)-1,2,4-triazol-3-yl]-3-(6-methylpyrimidin-4-yl)-3-azabicyclo[3.2.1]octan-8-amine

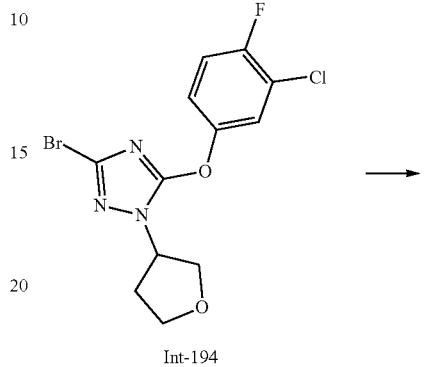

Int-194

→

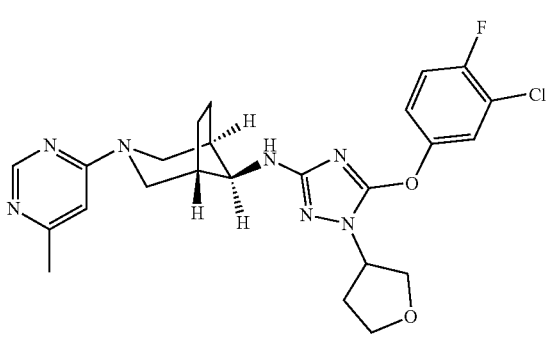

219

The title compound was prepared in analogy to example 181, 3-bromo-5-(3-chloro-4-fluorophenoxy)-1-(oxolan-3-yl)-1,2,4-triazole (Int-194, 40 mg, 110 µmol) and (1R,5S,8s)-3-(6-methylpyrimidin-4-yl)-3-azabicyclo[3.2.1]octan-8-amine (Int-114, 28.9 mg, 132 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The title compound was isolated as an off-white solid (18.6 mg, 33.7% yield). MS (ES+) m/z: 500.3 [(M+H)+].

Example 220

(1R,5S,8s)-N-(5-(3-Chloro-5-fluorophenoxy)-1-cyclobutyl-1H-1,2,4-triazol-3-yl)-3-(6-methylpyrimidin-4-yl)-3-azabicyclo[3.2.1]octan-8-amine

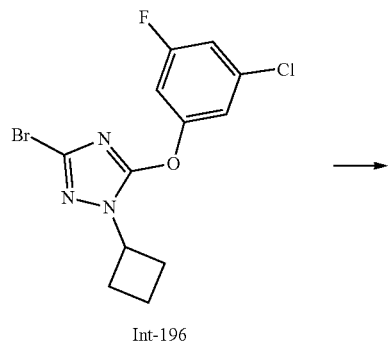

Int-196

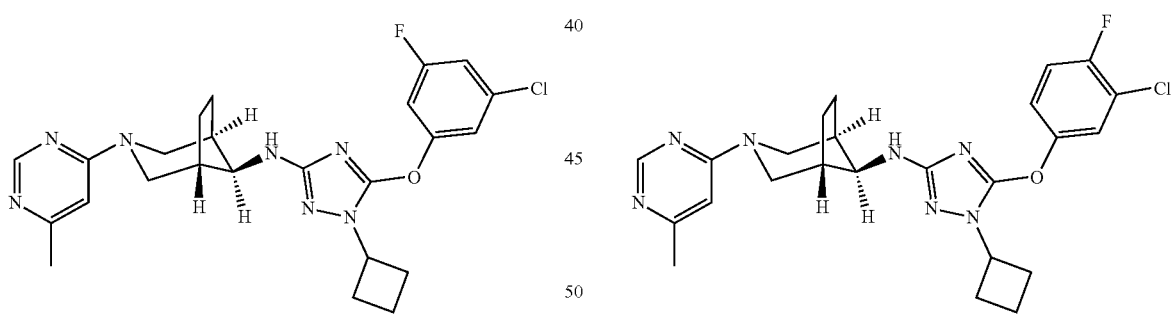

220

The title compound was prepared in analogy to example 181, 3-bromo-5-(3-chloro-5-fluorophenoxy)-1-cyclobutyl-1H-1,2,4-triazole (Int-196, 40 mg, 115 µmol) and (1R,5S,8s)-3-(6-methylpyrimidin-4-yl)-3-azabicyclo[3.2.1]octan-8-amine (Int-114, 33.3 mg, 346 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (14.2 mg, 25.4% yield). MS (ES+) m/z: 484.3 [(M+H)+].

Example 221

(1R,5S,8s)-N-(5-(3-Chloro-4-fluorophenoxy)-1-cyclobutyl-1H-1,2,4-triazol-3-yl)-3-(6-methylpyrimidin-4-yl)-3-azabicyclo[3.2.1]octan-8-amine

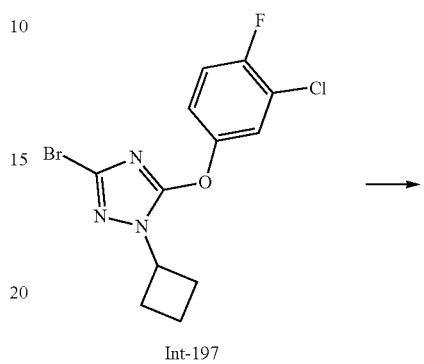

Int-197

221

The title compound was prepared in analogy to example 181, 3-bromo-5-(3-chloro-4-fluorophenoxy)-1-cyclobutyl-1H-1,2,4-triazole (Int-197, 40 mg, 115 µmol) and (1R,5S,8s)-3-(6-methylpyrimidin-4-yl)-3-azabicyclo[3.2.1]octan-8-amine (Int-114, 33.3 mg, 346 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (10.3 mg, 18.4% yield). MS (ES+) m/z: 484.3 [(M+H)+].

353

Example 222

(1R,5S,8s)-N-[5-(3-Chloro-5-fluorophenoxy)-1-(1,1,1,3,3,3-hexadeuteriopropan-2-yl)-1,2,4-triazol-3-yl]-3-(6-methylpyrimidin-4-yl)-3-azabicyclo[3.2.1]octan-8-amine

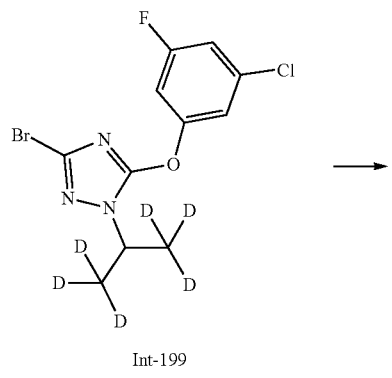

Int-199

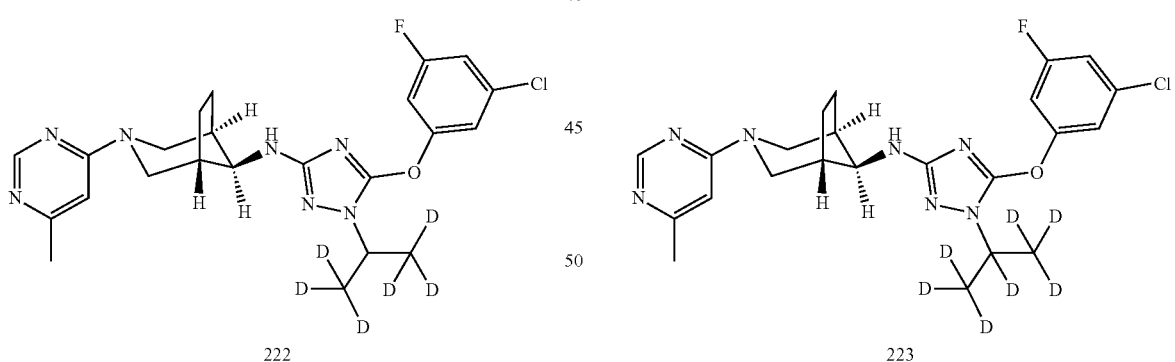

222

The title compound was prepared in analogy to example 181, 3-bromo-5-(3-chloro-5-fluorophenoxy)-1-(1,1,1,3,3,3-hexadeuteriopropan-2-yl)-1,2,4-triazole (Int-199, 40 mg, 117 µmol) and (1R,5S,8s)-3-(6-methylpyrimidin-4-yl)-3-azabicyclo[3.2.1]octan-8-amine (Int-114, 30.8 mg, 141 µmol) with sodium tert-butoxide, tris(dibenzylideneacetone) dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The title compound was isolated as a light yellow solid (24.7 mg, 44% yield). MS (ES+) m/z: 478.2 [(M+H)+].

354

Example 223

(1R,5S,8s)-N-[5-(3-Chloro-5-fluorophenoxy)-1-(1,1,1,2,3,3,3-heptadeuteriopropan-2-yl)-1,2,4-triazol-3-yl]-3-(6-methylpyrimidin-4-yl)-3-azabicyclo[3.2.1]octan-8-amine

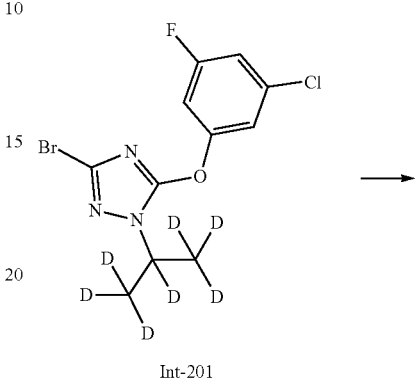

Int-201

223

The title compound was prepared in analogy to example 181, 3-bromo-5-(3-chloro-5-fluorophenoxy)-1-(1,1,1,2,3,3,3-heptadeuteriopropan-2-yl)-1,2,4-triazole (Int-201, 40 mg, 117 µmol) and (1R,5S,8s)-3-(6-methylpyrimidin-4-yl)-3-azabicyclo[3.2.1]octan-8-amine (Int-114, 30.7 mg, 141 µmol) with sodium tert-butoxide, tris(dibenzylideneacetone) dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a light yellow solid (15.8 mg, 28.2% yield). MS (ES+) m/z: 479.4 [(M+H)+].

Example 224

(1R,5S,8s)-N-[5-(3-Chloro-4-fluorophenoxy)-1-(1,1,1,2,3,3,3-heptadeuteriopropan-2-yl)-1,2,4-triazol-3-yl]-3-(6-methylpyrimidin-4-yl)-3-azabicyclo[3.2.1]octan-8-amine

Example 225

(1R,5S,8s)-N-[5-(3-Chloro-4-fluorophenoxy)-1-(1,1,1,2,3,3,3-heptadeuteriopropan-2-yl)-1,2,4-triazol-3-yl]-3-(6-methoxypyridazin-4-yl)-3-azabicyclo[3.2.1]octan-8-amine

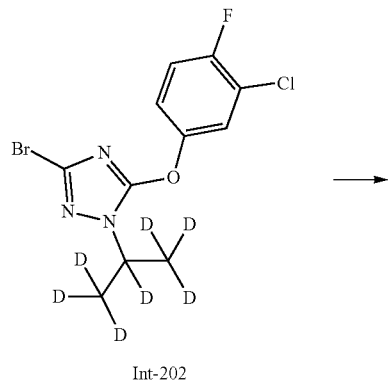
Int-202

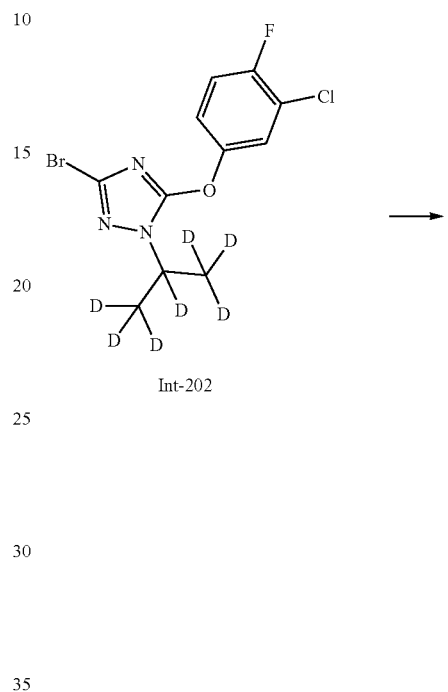
Int-202

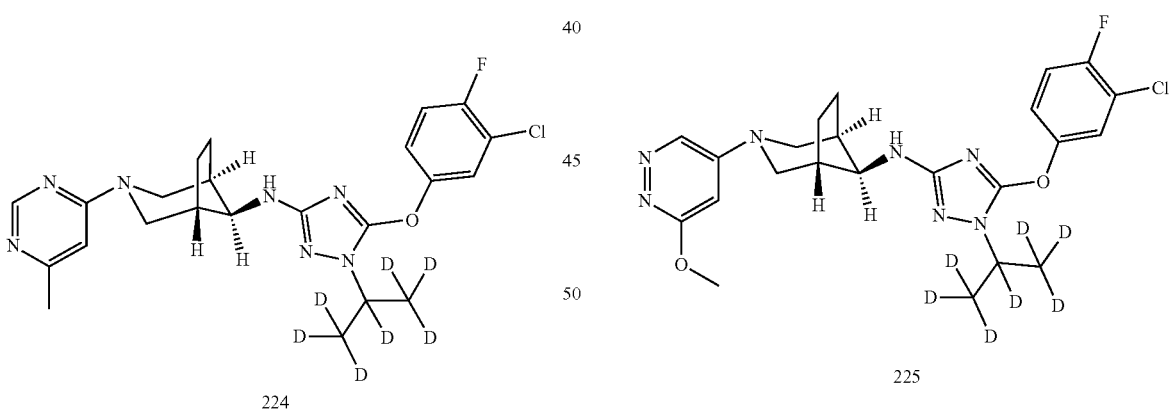

224

225

The title compound was prepared in analogy to example 181, 3-bromo-5-(3-chloro-4-fluorophenoxy)-1-(1,1,1,2,3,3,3-heptadeuteriopropan-2-yl)-1,2,4-triazole (Int-202, 40 mg, 117 μmol) and (1R,5S,8s)-3-(6-methylpyrimidin-4-yl)-3-azabicyclo[3.2.1]octan-8-amine (Int-114, 30.7 mg, 141 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (22.1 mg, 39.4% yield). MS (ES+) m/z: 479.3 [(M+H)⁺].

The title compound was prepared in analogy to example 183, from 3-bromo-5-(3-chloro-4-fluorophenoxy)-1-(1,1,1,2,3,3,3-heptadeuteriopropan-2-yl)-1,2,4-triazole (Int-202, 40 mg, 117 μmol) and (1R,5S,8s)-3-(6-methoxypyridazin-4-yl)-3-azabicyclo[3.2.1]octan-8-amine (Int-128, 32.9 mg, 141 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (10.1 mg, 17.4% yield). MS (ES+) m/z: 495.3 [(M+H)⁺].

Example 226

(1R,5S,8s)-N-[5-(3-Chloro-4-fluorophenoxy)-1-(1,1,1,2,3,3,3-heptadeuteriopropan-2-yl)-1,2,4-triazol-3-yl]-3-(2-methoxypyridin-4-yl)-3-azabicyclo[3.2.1]octan-8-amine

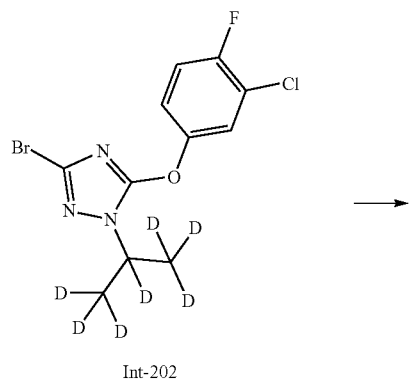

Int-202

Example 227

(1R,5S,8s)-N-[5-(3-Chloro-4-fluorophenoxy)-1-(1,1,1,2,3,3,3-heptadeuteriopropan-2-yl)-1,2,4-triazol-3-yl]-3-(5-methyl-1,3,4-oxadiazol-2-yl)-3-azabicyclo[3.2.1]octan-8-amine

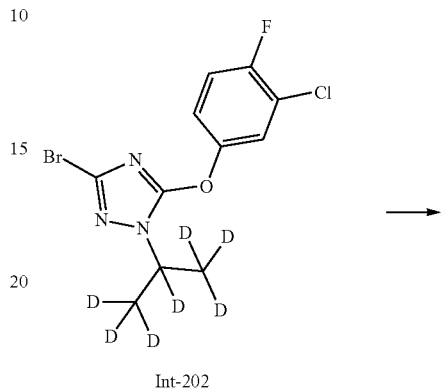

Int-202

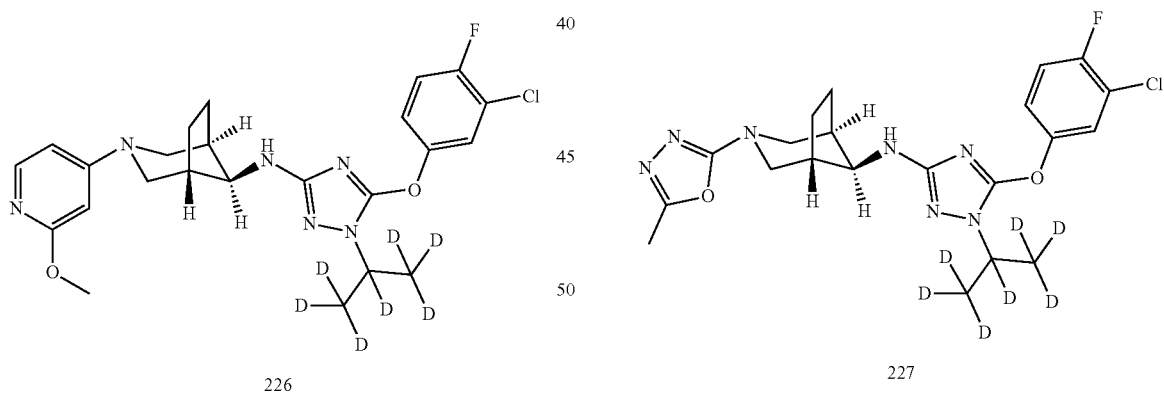

226

227

The title compound was prepared in analogy to example 184, from 3-bromo-5-(3-chloro-4-fluorophenoxy)-1-(1,1,1,2,3,3,3-heptadeuteriopropan-2-yl)-1,2,4-triazole (Int-202, 40 mg, 117 µmol) and (1R,5S,8s)-3-(2-methoxy-4-pyridyl)-3-azabicyclo[3.2.1]octan-8-amine (Int-111, 32.8 mg, 141 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (30.5 mg, 52.7% yield). MS (ES+) m/z: 494.3 [(M+H)$^+$].

The title compound was prepared in analogy to example 202, from 3-bromo-5-(3-chloro-4-fluorophenoxy)-1-(1,1,1,2,3,3,3-heptadeuteriopropan-2-yl)-1,2,4-triazole (Int-202, 40 mg, 117 µmol) and (1R,5S,8s)-3-(5-methyl-1,3,4-oxadiazol-2-yl)-3-azabicyclo[3.2.1]octan-8-amine (Int-105, 29.3 mg, 141 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (20.5 mg, 37.3% yield). MS (ES+) m/z: 469.1 [(M+H)$^+$].

Example 228

(1R,5S,8s)-N-[5-(3-Chloro-4-fluorophenoxy)-1-(1,1,1,2,3,3,3-heptadeuteriopropan-2-yl)-1,2,4-triazol-3-yl]-3-(3-methyl-1,2,4-oxadiazol-5-yl)-3-azabicyclo[3.2.1]octan-8-amine

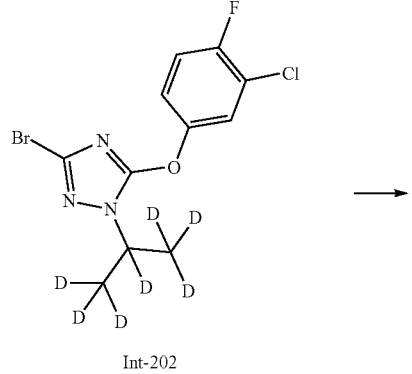

Int-202

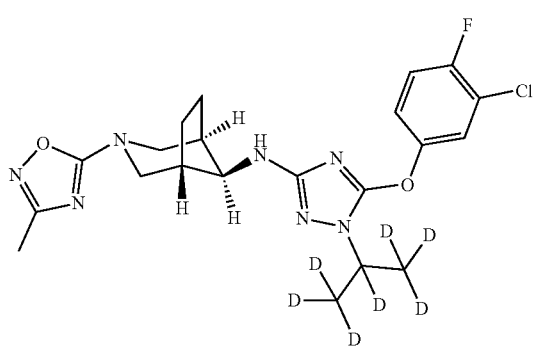

228

The title compound was prepared in analogy to example 187, from 3-bromo-5-(3-chloro-4-fluorophenoxy)-1-(1,1,1,2,3,3,3-heptadeuteriopropan-2-yl)-1,2,4-triazole (Int-202, 60 mg, 176 µmol) and (1R,5S,8s)-3-(3-methyl-1,2,4-oxadiazol-5-yl)-3-azabicyclo[3.2.1]octan-8-amine (Int-102, 43.9 mg, 211 µmol) with sodium tert-butoxide, tris(dibenzylideneacetone)dipalladium (0) chloroform adduct and 1,2,3,4,5-pentaphenyl-1'-(di-tert-butylphosphino)ferrocene (Q-Phos, CAS [312959-24-3]). The reaction was heated in a microwave to 120° C. during 30 minutes. The compound was isolated as a light brown solid (9.2 mg, 11.2% yield). MS (ES+) m/z: 469.3 [(M+H)+].

Example 229

(1R,5S,8s)-N-[5-(3-Chloro-5-fluorophenoxy)-1-(trideuteriomethyl)-1,2,4-triazol-3-yl]-3-(6-methylpyrimidin-4-yl)-3-azabicyclo[3.2.1]octan-8-amine

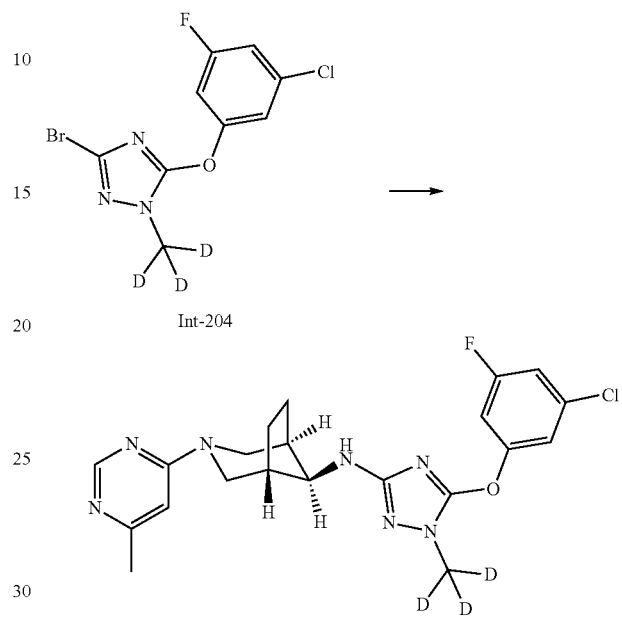

Int-204

229

The title compound was prepared in analogy to example 181, 3-bromo-5-(3-chloro-5-fluorophenoxy)-1-(trideuteriomethyl)-1,2,4-triazole (Int-204, 40 mg, 129 µmol) and (1R,5S,8s)-3-(6-methylpyrimidin-4-yl)-3-azabicyclo[3.2.1] octan-8-amine (Int-114, 33.9 mg, 155 µmol) with sodium tert-butoxide, tris(dibenzylideneacetone)dipalladium (0) chloroform adduct and 2-di-tert-butylphosphino-2',4',6'-tri-isopropylbiphenyl (tBuXPhos, CAS [564483-19-8]). The reaction was heated to 80° C. during 30 minutes. The compound was isolated as a white solid (25.4 mg, 44% yield). MS (ES+) m/z: 447.2 [(M+H)+].

Example 230

(1R,5S,8s)-N-[5-(3-Chloro-4-fluorophenoxy)-1-(trideuteriomethyl)-1,2,4-triazol-3-yl]-3-(6-methylpyrimidin-4-yl)-3-azabicyclo[3.2.1]octan-8-amine

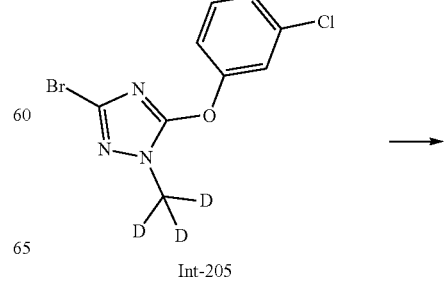

Int-205

-continued

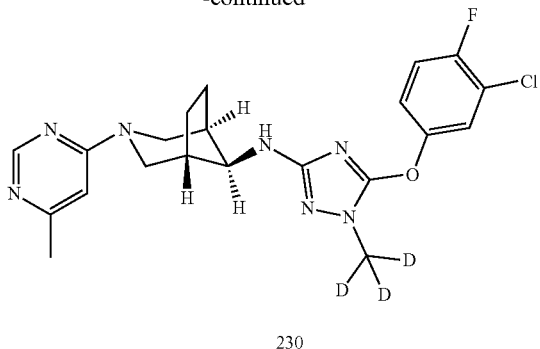

230

The title compound was prepared in analogy to example 181, 3-bromo-5-(3-chloro-4-fluorophenoxy)-1-(trideuteriomethyl)-1,2,4-triazole (Int-205, 40 mg, 129 μmol) and (1R,5S,8s)-3-(6-methylpyrimidin-4-yl)-3-azabicyclo[3.2.1]octan-8-amine (Int-114, 33.9 mg, 155 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (16.6 mg, 28.7% yield). MS (ES+) m/z: 447.2 [(M+H)$^+$].

Example 231

(1R,5S,8s)-N-[5-(3-Chloro-4-fluorophenoxy)-1-(trideuteriomethyl)-1,2,4-triazol-3-yl]-3-(6-methoxypyridazin-4-yl)-3-azabicyclo[3.2.1]octan-8-amine

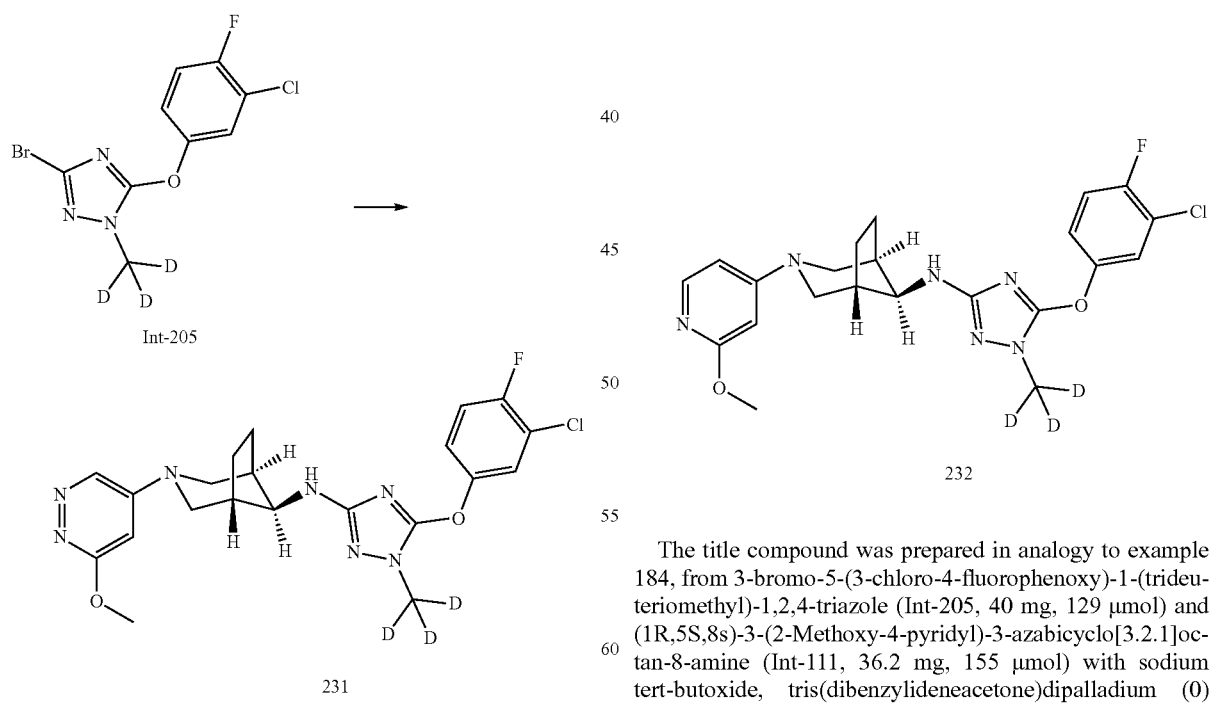

231

The title compound was prepared in analogy to example 183, from 3-bromo-5-(3-chloro-4-fluorophenoxy)-1-(trideuteriomethyl)-1,2,4-triazole (Int-205, 40 mg, 129 μmol) and (1R,5S,8s)-3-(6-methoxypyridazin-4-yl)-3-azabicyclo[3.2.1]octan-8-amine (Int-128, 36.3 mg, 155 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (13.3 mg, 22.2% yield). MS (ES+) m/z: 463.2 [(M+H)$^+$].

Example 232

(1R,5S,8s)-N-[5-(3-Chloro-4-fluorophenoxy)-1-(trideuteriomethyl)-1,2,4-triazol-3-yl]-3-(2-methoxypyridin-4-yl)-3-azabicyclo[3.2.1]octan-8-amine

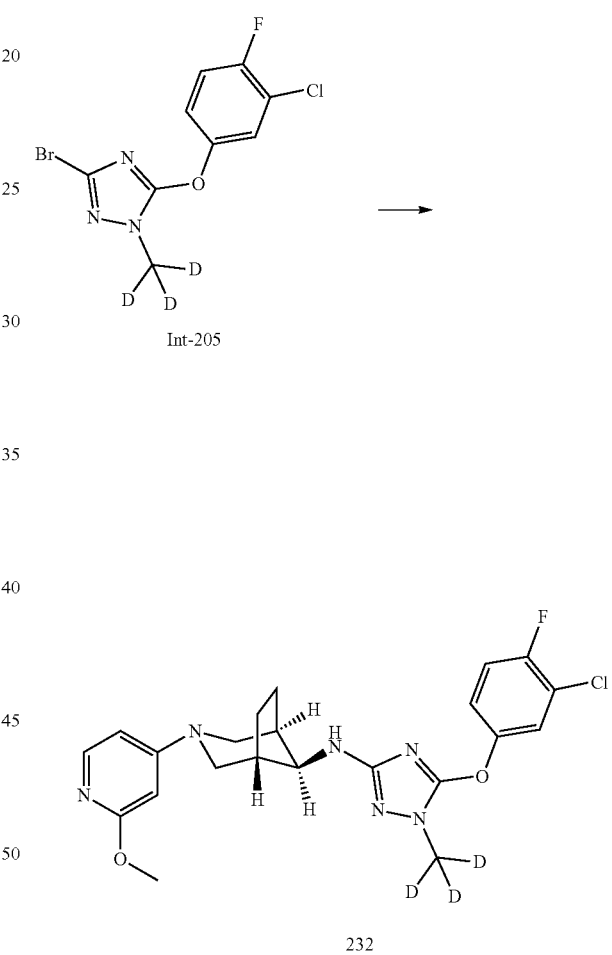

232

The title compound was prepared in analogy to example 184, from 3-bromo-5-(3-chloro-4-fluorophenoxy)-1-(trideuteriomethyl)-1,2,4-triazole (Int-205, 40 mg, 129 μmol) and (1R,5S,8s)-3-(2-Methoxy-4-pyridyl)-3-azabicyclo[3.2.1]octan-8-amine (Int-111, 36.2 mg, 155 μmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (31.8 mg, 53.3% yield). MS (ES+) m/z: 463.2 [(M+H)$^+$].

Example 233

(1R,5S,8s)-N-[5-(3-Chloro-5-fluorophenoxy)-1-(1,1,2,2,2-pentadeuterioethyl)-1,2,4-triazol-3-yl]-3-(6-methylpyrimidin-4-yl)-3-azabicyclo[3.2.1]octan-8-amine

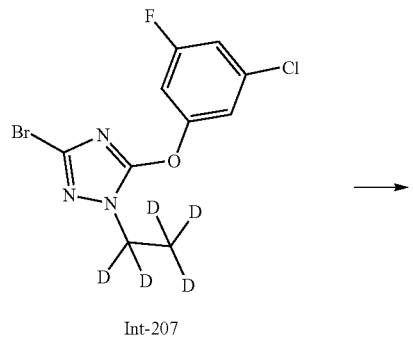

Int-207

Example 234

(1R,5S,8s)-N-[5-(3-Chloro-4-fluorophenoxy)-1-(1,1,2,2,2-pentadeuterioethyl)-1,2,4-triazol-3-yl]-3-(6-methylpyrimidin-4-yl)-3-azabicyclo[3.2.1]octan-8-amine

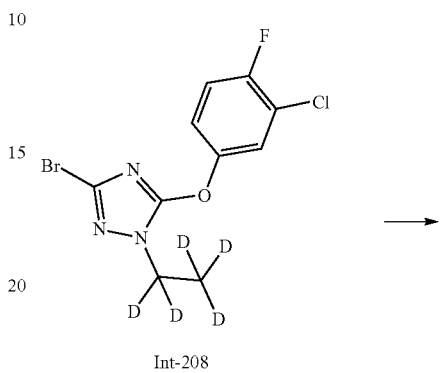

Int-208

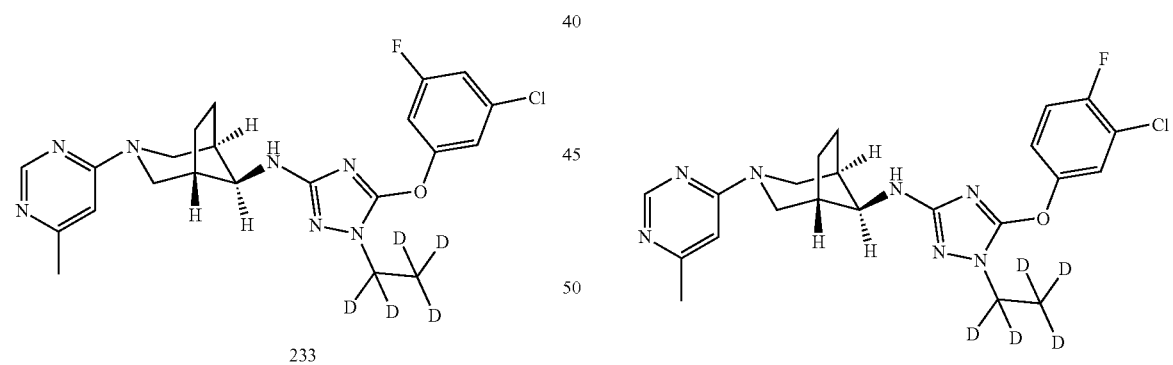

233

234

The title compound was prepared in analogy to example 181, 3-bromo-5-(3-chloro-5-fluorophenoxy)-1-(1,1,2,2,2-pentadeuterioethyl)-1,2,4-triazole (Int-207, 40 mg, 123 µmol) and (1R,5S,8s)-3-(6-methylpyrimidin-4-yl)-3-azabicyclo[3.2.1]octan-8-amine (Int-114, 32.2 mg, 147 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an light yellow solid (15.3 mg, 26.9% yield). MS (ES+) m/z: 463.3 [(M+H)+].

The title compound was prepared in analogy to example 181, 3-bromo-5-(3-chloro-4-fluorophenoxy)-1-(1,1,2,2,2-pentadeuterioethyl)-1,2,4-triazole (Int-208, 40 mg, 123 µmol) and (1R,5S,8s)-3-(6-methylpyrimidin-4-yl)-3-azabicyclo[3.2.1]octan-8-amine (Int-114, 32.2 mg, 147 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an off-white solid (13.1 mg, 23% yield). MS (ES+) m/z: 463.3 [(M+H)+].

Example 235

(1R,5S,8s)-N-[5-(3-Chloro-4-fluorophenoxy)-1-(1,1,2,2,2-pentadeuterioethyl)-1,2,4-triazol-3-yl]-3-(6-methoxypyridazin-4-yl)-3-azabicyclo[3.2.1]octan-8-amine

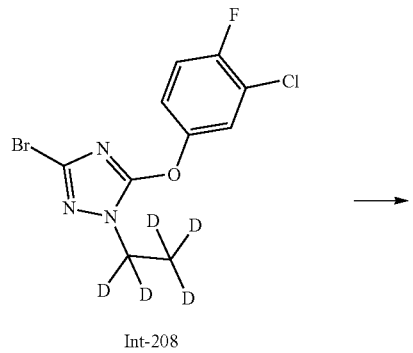

Int-208

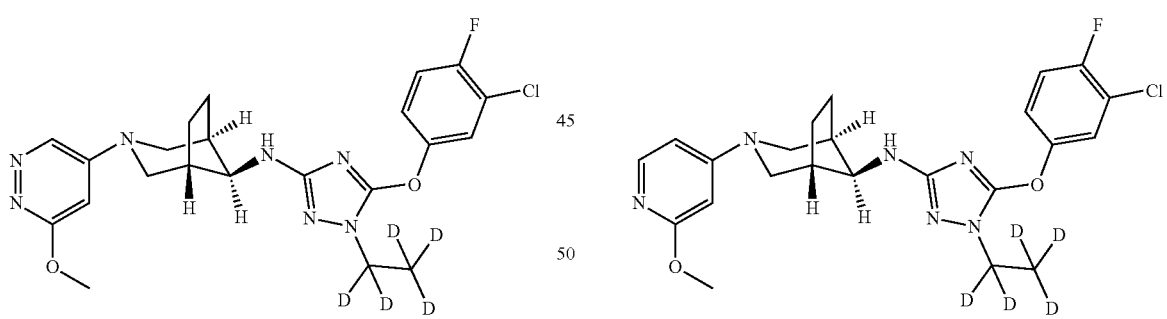

235

The title compound was prepared in analogy to example 183, from 3-bromo-5-(3-chloro-4-fluorophenoxy)-1-(1,1,2,2,2-pentadeuterioethyl)-1,2,4-triazole (Int-208, 30 mg, 92.1 µmol) and (1R,5S,8s)-3-(6-methoxypyridazin-4-yl)-3-azabicyclo[3.2.1]octan-8-amine (Int-128, 25.9 mg, 111 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as an white solid (8.9 mg, 20.2% yield). MS (ES+) m/z: 479.3 [(M+H)+].

Example 236

(1R,5S,8s)-N-[5-(3-Chloro-4-fluorophenoxy)-1-(1,1,2,2,2-pentadeuterioethyl)-1,2,4-triazol-3-yl]-3-(2-methoxypyridin-4-yl)-3-azabicyclo[3.2.1]octan-8-amine

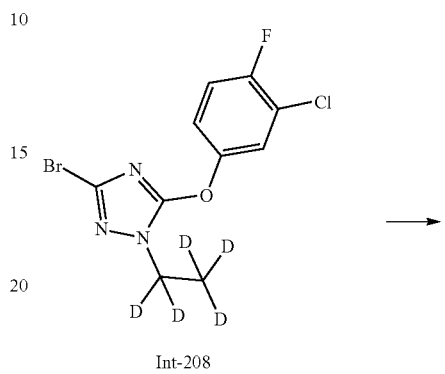

Int-208

236

The title compound was prepared in analogy to example 184, from 3-bromo-5-(3-chloro-4-fluorophenoxy)-1-(1,1,2,2,2-pentadeuterioethyl)-1,2,4-triazole (Int-208, 30 mg, 92.1 µmol) and (1R,5S,8s)-3-(2-Methoxy-4-pyridyl)-3-azabicyclo[3.2.1]octan-8-amine (Int-111, 25.8 mg, 111 µmol) with sodium tert-butoxide, tris(dibenzylideneacetone)dipalladium (0) chloroform adduct and 2-di-tert-butylphosphino-2',4',6'-triisopropylbiphenyl (tBuXPhos, CAS [564483-19-8]). The reaction was heated to 80° C. during 30 minutes. The compound was isolated as a white solid (22.3 mg, 50.6% yield). MS (ES+) m/z: 478.3 [(M+H)+].

Example 237

(1R,5S,8s)-N-(5-(3-Chloro-5-fluorophenoxy)-1-(2,2,2-trifluoroethyl)-1H-1,2,4-triazol-3-yl)-3-(6-methylpyrimidin-4-yl)-3-azabicyclo[3.2.1]octan-8-amine

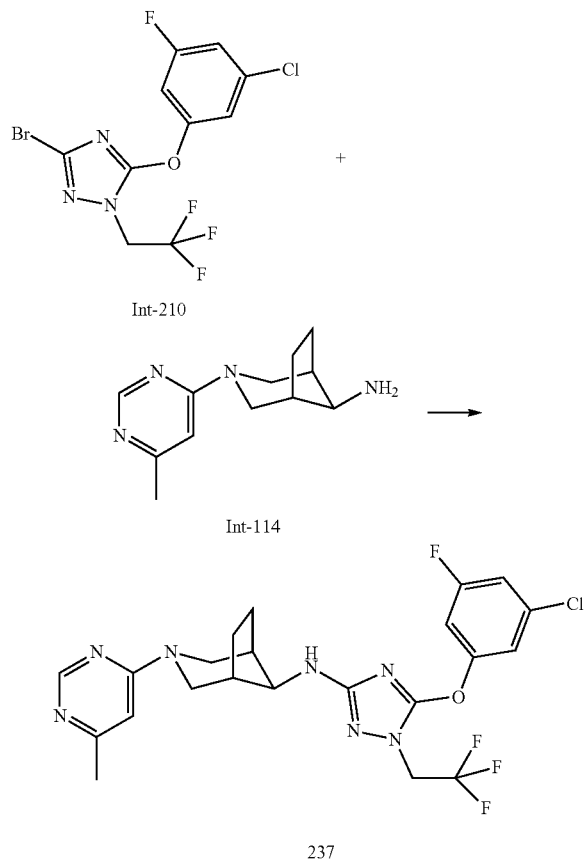

In an 8 mL microwave vial, (1R,5S,8s)-3-(6-methylpyrimidin-4-yl)-3-azabicyclo[3.2.1]octan-8-amine (Int-114, 124 mg, 567 µmol), 3-bromo-5-(3-chloro-5-fluorophenoxy)-1-(2,2,2-trifluoroethyl)-1H-1,2,4-triazole (Int-210, 177 mg, 473 µmol), and sodium tert-butoxide (114 mg, 1.2 mmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 53.7 mg, 75.6 µmol), and tris(dibenzylideneacetone)dipalladium (0) chloroform adduct (39.1 mg, 37.8 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100×30 mm×5 µm, eluting with acetonitrile/(water+0.1% triethylamine), gradient 20:80 to 98:2 v/v) to yield the title compound as white foam (82 mg, 34%). HPLC (method LCMS_fastgradient) $t_R$=0.99 min. $^1$H NMR (CDCl$_3$, 300 MHz): δ1.50-1.61 (m, 2H), 1.78-1.90 (m, 2H), 2.37 (s, 3H), 2.42-2.51 (m, 2H), 3.04-3.14 (m, 2H), 3.75 (d, J=6.0 Hz, 1H), 4.04 (d, J=6.0 Hz, 1H), 4.06-4.22 (m, 2H), 4.51 (q, J=8.2 Hz, 2H), 6.35 (s, 1H), 6.99-7.08 (m, 2H), 7.16-7.20 (m, 1H), 8.51 (s, 1H). MS (ES+) m/z 512.1, 514.0 [M+H, Cl isotopes].

Example 238

(1R,5S,8s)-N-(5-(3-Chloro-5-fluorophenoxy)-1-(2,2,2-trifluoroethyl)-1H-1,2,4-triazol-3-yl)-3-(2-methoxypyridin-4-yl)-3-azabicyclo[3.2.1]octan-8-amine

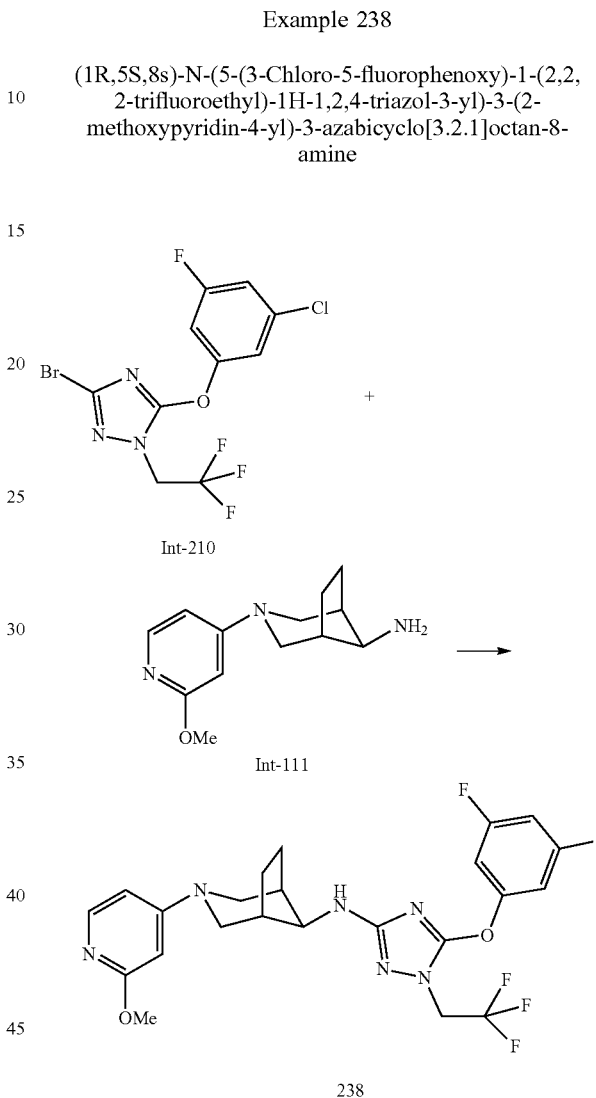

In an 8 mL microwave vial, (1R,5S,8s)-3-(2-methoxypyridin-4-yl)-3-azabicyclo[3.2.1]octan-8-amine (Int-111, 135 mg, 577 µmol), 3-bromo-5-(3-chloro-5-fluorophenoxy)-1-(2,2,2-trifluoroethyl)-1H-1,2,4-triazole (Int-210, 180 mg, 481 µmol), and sodium tert-butoxide (92 mg, 961 µmol) were suspended in 1,4-dioxane (5 mL). The flask was degassed thoroughly with Argon. 1,2,3,4,5-Pentaphenyl-1'-(di-tert-butylphosphino)ferrocene ("Q-phos", CAS [312959-24-3], 54.7 mg, 77 µmol), and tris(dibenzylideneacetone)dipalladium (0) chloroform adduct (40 mg, 38 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were washed with water (2×20 mL), dried (sodium sulfate) and concentrated in vacuo. The resulting crude product was purified by column chromatography (silica gel, 12 g, eluting with dichloromethane/methanol, gradient 100:0 to 95:5 v/v), followed by preparative HPLC (YMC-Actus Triart C18, 100×30 mm×5 µm, eluting with acetonitrile/(water+0.1% triethylamine), gradient 20:80 to 98:2 v/v) to yield the title compound as a white foam (30 mg, 11%). HPLC (method LCMS_fastgradient) $t_R$=1.07 min. $^1$H NMR (CDCl$_3$, 300 MHz): δ 1.59-1.67 (m, 2H), 1.82-1.91 (m, 2H), 2.44-2.51 (m, 2H), 3.02-3.10 (m, 2H), 3.59 (dd, J=3.2, 11.9 Hz, 2H), 3.70 (d, J=5.8 Hz, 1H), 3.90 (s, 3H), 4.04 (d, J=5.8 Hz, 1H), 4.51 (q, J=8.2 Hz, 2H), 6.00 (d, J=2.2 Hz, 1H), 6.35 (dd, J=2.4, 6.2 Hz, 1H), 6.99-7.07 (m, 2H), 7.17-7.20 (m, 1H), 7.87 (d, J=6.2 Hz, 1H). MS (ES+) m/z 527.1, 529.0 [M+H, Cl isotopes].

Example 239

(1R,5S,8s)-N-(5-(3-Chlorophenoxy)-1-(2-fluoroethyl)-1H-1,2,4-triazol-3-yl)-3-(6-methylpyrimidin-4-yl)-3-azabicyclo[3.2.1]octan-8-amine

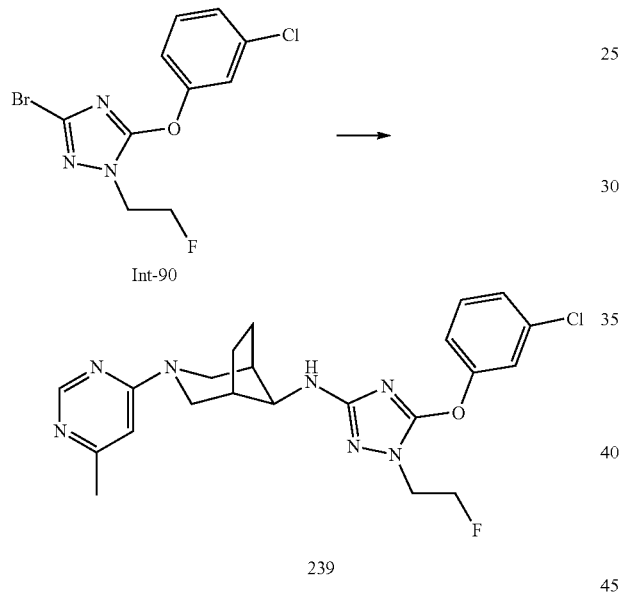

In a 20 mL microwave vial, (1R,5S,8s)-3-(6-methylpyrimidin-4-yl)-3-azabicyclo[3.2.1]octan-8-amine (Int-114, 131 mg, 599 µmol), 3-bromo-5-(3-chlorophenoxy)-1-(2-fluoroethyl)-1H-1,2,4-triazole (Int-90, 160 mg, 499 µmol), and sodium tert-butoxide (96 mg, 1.0 mmol) were suspended in 1,4-dioxane (12 mL). The flask was degassed thoroughly with Argon. 1,2,3,4,5-Pentaphenyl-1'-(di-tert-butylphosphino)ferrocene ("Q-phos", CAS [312959-24-3], 57 mg, 80 µmol), and tris(dibenzylideneacetone)dipalladium (0) chloroform adduct (41 mg, 40 µmol) were added subsequently. The vial was again degassed thoroughly with Argon and sealed. The reaction mixture was heated under microwave irradiation at 110° C. for 30 min. After that, water (30 mL) was added and the mixture was extracted with ethyl acetate (2×50 mL). The combined organic extracts were dried (sodium sulfate) and concentrated in vacuo. The resulting crude product was purified by column chromatography (silica gel, 12 g, eluting with dichloromethane/methanol, gradient 100:0 to 90:10 v/v), followed by preparative chiral HPLC (Reprosil chiral-NR, eluting n-heptane/ethanol, 70:30 v/v isocratic) to afford the title compound as white foam (65 mg, 28%). HPLC (method LCMS_fastgradient) $t_R$=0.93 min. $^1$H NMR (CDCl$_3$, 300 MHz): δ1.50-1.59 (m, 2H), 1.79-1.89 (m, 2H), 2.36 (s, 3H), 2.43-2.50 (m, 2H), 3.05-3.14 (m, 2H), 3.75 (d, J=6.0 Hz, 1H), 3.99 (d, J=6.0 Hz, 1H), 4.06-4.19 (m, 2H), 4.23 (td, J=4.8, 24.8 Hz, 2H), 4.77 (td, J=4.8, 46.7 Hz, 2H), 6.34 (s, 1H), 7.15-7.24 (m, 2H), 7.29-7.36 (m, 2H), 8.51 (d, J=0.8 Hz, 1H). MS (ES+) m/z 458.6, 460.6 [M+H, Cl isotopes].

The invention claimed is:
1. A compound of formula I,

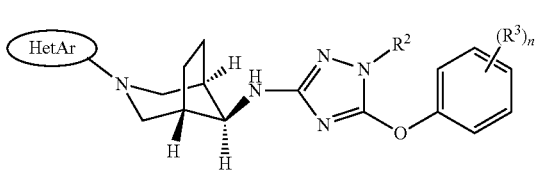

wherein:
HetAr is a five or six membered heteroaryl group, selected from:

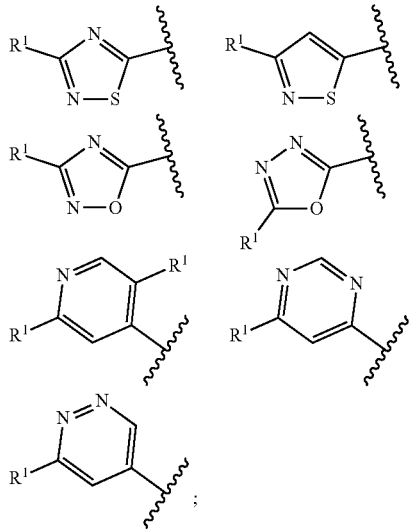

and

;

wherein:
R$^1$ is hydrogen, halogen, lower alkyl, lower alkoxy or lower alkyl substituted by halogen, and may be the same or different if two R$^1$ occur;
R$^2$ is selected from: lower alkyl or a mono- or poly-deuterated derivative thereof, lower alkyl substituted by halogen or lower alkoxy, lower alkenyl unsubstituted or substituted by halogen, cycloalkyl or CH$_2$-cycloalkyl unsubstituted or substituted by halogen, and heterocycloalkyl or CH$_2$-heterocycloalkyl unsubstituted or substituted by lower alkyl;
R$^3$ is halogen, lower alkyl, lower alkyl substituted by halogen, lower alkoxy substituted by halogen, or S(O)$_2$-lower alkyl; and
n is 1, 2 or 3, wherein if n is >1, then R$^3$ may be the same or different;
or a pharmaceutically acceptable acid addition salt, a racemic mixture or a corresponding enantiomer r an optical isomer or stereoisomer thereof.

2. A compound of formula I according to claim 1, wherein:
HetAr is

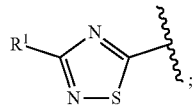

or a pharmaceutically acceptable acid addition salt, a racemic mixture or a corresponding enantiomer or an optical isomer or stereoisomer thereof.

3. A compound according to claim 2, which compound is:
(1R,5S,8s)-N-(5-(2-Chlorophenoxy)-1-(propan-2-yl)-1H-1,2,4-triazol-3-yl)-3-(3-methyl-1,2,4-thiadiazol-5-yl)-3-azabicyclo[3.2.1]octan-8-amine.

4. A compound according to claim 1, wherein:
HetAr is

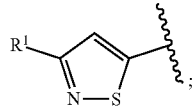

or a pharmaceutically acceptable acid addition salt, a racemic mixture or a corresponding enantiomer r an optical isomer or stereoisomer thereof.

5. A compound according to claim 4, selected from:
(1R,5S,8s)-N-(5-(2-Chlorophenoxy)-1-(propan-2-yl)-1H-1,2,4-triazol-3-yl)-3-(3-methylisothiazol-5-yl)-3-azabicyclo[3.2.1]octan-8-amine;
(1R,5S,8s)-N-(5-(3-Fluorophenoxy)-1-(propan-2-yl)-1H-1,2,4-triazol-3-yl)-3-(3-methylisothiazol-5-yl)-3-azabicyclo[3.2.1]octan-8-amine;
(1R,5S,8s)-N-(5-(4-Fluoro-3-(trifluoromethyl)phenoxy)-1-(propan-2-yl)-1H-1,2,4-triazol-3-yl)-3-(3-methylisothiazol-5-yl)-3-azabicyclo[3.2.1]octan-8-amine;
(1R,5S,8s)-N-(1-(Propan-2-yl)-5-(2-(trifluoromethoxy)phenoxy)-1H-1,2,4-triazol-3-yl)-3-(3-methylisothiazol-5-yl)-3-azabicyclo[3.2.1]octan-8-amine;
(1R,5S,8s)-N-(5-(2-Fluorophenoxy)-1-(propan-2-yl)-1H-1,2,4-triazol-3-yl)-3-(3-methylisothiazol-5-yl)-3-azabicyclo[3.2.1]octan-8-amine;
(1R,5S,8s)-3-(3-Methyl-1,2-thiazol-5-yl)-N-[1-(propan-2-yl)-5-[4-(trifluoromethoxy)phenoxy]-1H-1,2,4-triazol-3-yl]-3-azabicyclo[3.2.1]octan-8-amine;
(1R,5S,8s)-N-[5-(4-Fluorophenoxy)-1-(propan-2-yl)-1H-1,2,4-triazol-3-yl]-3-(3-methyl-1,2-thiazol-5-yl)-3-azabicyclo[3.2.1]octan-8-amine;
(1R,5S,8s)-N-{5-[3-Fluoro-5-(trifluoromethyl)phenoxy]-1-(propan-2-yl)-1H-1,2,4-triazol-3-yl}-3-(3-methyl-1,2-thiazol-5-yl)-3-azabicyclo[3.2.1]octan-8-amine;
(1R,5S,8s)-3-(3-Methyl-1,2-thiazol-5-yl)-N-[1-(propan-2-yl)-5-[3-(trifluoromethyl)phenoxy]-1H-1,2,4-triazol-3-yl]-3-azabicyclo[3.2.1]octan-8-amine;
(1R,5S,8s)-N-[5-(3,5-Difluorophenoxy)-1-(propan-2-yl)-1H-1,2,4-triazol-3-yl]-3-(3-methyl-1,2-thiazol-5-yl)-3-azabicyclo[3.2.1]octan-8-amine;
(1R,5S,8s)-N-[5-(4-Methanesulfonylphenoxy)-1-(propan-2-yl)-1H-1,2,4-triazol-3-yl]-3-(3-methyl-1,2-thiazol-5-yl)-3-azabicyclo[3.2.1]octan-8-amine; and
(1R,5S,8s)-N-[5-(3-Methanesulfonylphenoxy)-1-(propan-2-yl)-1H-1,2,4-triazol-3-yl]-3-(3-methyl-1,2-thiazol-5-yl)-3-azabicyclo[3.2.1]octan-8-amine.

6. A compound according to claim 1, wherein:
HetAr is

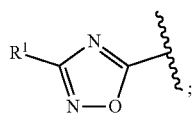

or a pharmaceutically acceptable acid addition salt, a racemic mixture or a corresponding enantiomer or an optical isomer or stereoisomer thereof.

7. A compound according to claim 6, selected from:
(1R, 5S, 8s)-N-{5-[4-Fluoro-3-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine;
(1R, 5S, 8s)-N-(1-(Propan-2-yl)-5-(2-(trifluoromethoxy)phenoxy)-ill-1,2,4-triazol-3-yl)-3-(3-methyl-1,2,4-oxadiazol-5-yl)-3-azabicyclo[3.2.1]octan-8-amine;
(1R,5S,8s)-3-(3-Methyl-1,2,4-oxadiazol-5-yl)-N-[1-(propan-2-yl)-5-[3-(trifluoromethoxy)phenoxy]-1H-1,2,4-triazol-3-yl]-3-azabicyclo[3.2.1]octan-8-amine;
(1R,5,8s)-3-(3-Methyl-1,2,4-oxadiazol-5-yl)-N-[4-(propan-2-yl)-5-[4-(trifluoromethoxy)phenoxy]-1H-1,2,4-triazol-3-yl]-3-azabicyclo[3.2.1]octan-8-amine;
(1R,5S,8s)-N-[5-(3-Fluorophenoxy)-1-(propan-2-yl)-1H-1,2,4-triazol-3-yl]-3-(3-methyl-1,2,4-oxadiazol-5-yl)-3-azabicyclo[3.2.1]octan-8-amine;
(1R,5S,8s)-3-(3-Methyl-1,2,4-oxadiazol-5-yl)-N-[1-(propan-2-yl)-5-[3-(trifluoromethyl)phenoxy]-1H-1,2,4-triazol-3-yl]-3-azabicyclo[3.2.1]octan-8-amine;
(1R,5S,8s)-N-(5-(3-Fluorophenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine;
(1R,5S,8s)-N-(5-(4-Fluoro-3-(trifluoromethyl)phenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine;
(1R,5S,8s)-N-(5-(4-Fluoro-3-(trifluoromethyl)phenoxy)-1-methyl-1H-1,2,4-triazol-3-yl)-3-(3-methyl-1,2,4-oxadiazol-5-yl)-3-azabicyclo[3.2.1]octan-8-amine;
(1R,5S,8s)-3-(3-Methyl-1,2,4-oxadiazol-5-yl)-N-[1-(propan-2-yl)-5-[2-fluoro-3-(trifluoromethyl)phenoxy]-1H-1,2,4-triazol-3-yl]-3-azabicyclo[3.2.1]octan-8-amine;
(1R,5S,8s)-N-{5-[2-Fluoro-5-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine;
(1R,5S,8s)-N-{5-[3-Fluoro-4-(trifluoromethoxy)phenoxy]-1-(propan-2-yl)-1H-1,2,4-triazol-3-yl}-3-(3-methyl-1,2,4-oxadiazol-5-yl)-3-azabicyclo[3.2.1]octan-8-amine;
(1R,5S,8s)-3-(3-Methyl-1,2,4-oxadiazol-5-yl)-N-(1-(2,2,2-trifluoroethyl)-5-(3-(trifluoromethyl)phenoxy)-1H-1,2,4-triazol-3-yl)-3-azabicyclo[3.2.1]octan-8-amine;
(1R,5S,8s)-3-(3-Methyl-1,2,4-oxadiazol-5-yl)-N-(1-(2,2,2-trifluoroethyl)-5-(4-(trifluoromethyl)phenoxy)-1H-1,2,4-triazol-3-yl)-3-azabicyclo[3.2.1]octan-8-amine;
(1R,5S,8s)-3-(3-Methyl-1,2,4-oxadiazol-5-yl)-N-{5-[3-methyl-5-(trifluoromethyl)phenoxy]-1-(propan-2-yl)-1H-1,2,4-triazol-3-yl}-3-azabicyclo[3.2.1]octan-8-amine;

(1R,5S,8s)-N-{5-[4-Fluoro-3-methyl-5-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine;
(1R,5S,8s)-N-{5-[3-Chloro-5-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine;
(1R,5S,8s)-N-(5-(3-Chlorophenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine;
(1R,5S,8s)-N-{5-[4-Methyl-3-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine;
(1R,5S,8s)-N-{5-[4-Chloro-3-(trifluoromethyl)phenoxy]-1-(propan-2-yl)-1H-1,2,4-triazol-3-yl}-3-(3-methyl-1,2,4-oxadiazol-5-yl)-3-azabicyclo[3.2.1]octan-8-amine;
(1R,5S,8s)-N-[1-(Propan-2-yl)-5-[4-(trifluoromethoxy)-3-(trifluoromethyl)phenoxy]-1,2,4-triazol-3-yl]-3-(3-methyl-1,2,4-oxadiazol-5-yl)-3-azabicyclo[3.2.1]octan-8-amine;
(1R,5S,8s)(1R,5S,8s)-N-[5-[3,5-Bis(trifluoromethyl)phenoxy]-1-(propan-2-yl)-1H-1,2,4-triazol-3-yl]-3-(3-methyl-1,2,4-oxadiazol-5-yl)-3-azabicyclo[3.2.1]octan-8-amine;
(1R,5S,8s)-N-[5-(3-Chlorophenoxy)-1-(propan-2-yl)-1H-1,2,4-triazol-3-yl]-3-(3-methyl-1,2,4-oxadiazol-5-yl)-3-azabicyclo[3.2.1]octan-8-amine;
(1R,5S,8s)-N-[5-(3-Chloro-4-methylphenoxy)-1-(propan-2-yl)-1H-1,2,4-triazol-3-yl]-3-(3-methyl-1,2,4-oxadiazol-5-yl)-3-azabicyclo[3.2.1]octan-8-amine;
(1R,5S,8s)-N-[5-(3-Chloro-2-methylphenoxy)-1-(propan-2-yl)-1H-1,2,4-triazol-3-yl]-3-(3-methyl-1,2,4-oxadiazol-5-yl)-3-azabicyclo[3.2.1]octan-8-amine;
(1R,5S,8s)-N-[5-(3-Chloro-5-methylphenoxy)-1-(propan-2-yl)-1H-1,2,4-triazol-3-yl]-3-(3-methyl-1,2,4-oxadiazol-5-yl)-3-azabicyclo[3.2.1]octan-8-amine;
(1R,5S,8s)-N-(5-(3-Chloro-5-fluorophenoxy)-1-(propan-2-yl)-1H-1,2,4-triazol-3-yl)-3-(3-methyl-1,2,4-oxadiazol-5-yl)-3-azabicyclo[3.2.1]octan-8-amine;
(1R,5S,8s)-N-[5-(3-Chloro-4-fluorophenoxy)-1-methyl-1,2,4-triazol-3-yl]-3-(3-methyl-1,2,4-oxadiazol-5-yl)-3-azabicyclo[3.2.1]octan-8-amine; and
(1R,5S,8s)-N-[5-(3-Chloro-4-fluorophenoxy)-1-(1,1,1,2,3,3,3-heptadeuteriopropan-2-yl)-1,2,4-triazol-3-yl]-3-(3-methyl-1,2,4-oxadiazol-5-yl)-3-azabicyclo[3.2.1]octan-8-amine.

8. A compound according to claim 1, wherein:
HetAr is

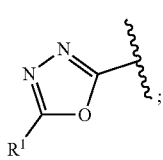

or a pharmaceutically acceptable acid addition salt, a racemic mixture or a corresponding enantiomer r an optical isomer or stereoisomer thereof.

9. A compound according to claim 8, selected from:
(1R,5S,8s)-N-(5-(3-Fluorophenoxy)-1-(2,2,2-trifluoroethyl)-1H-1,2,4-triazol-3-yl)-3-(5-methyl-1,3,4-oxadiazol-2-yl)-3-azabicyclo[3.2.1]octan-8-amine;
(1R,5S,8s)-N-(5-(4-Fluoro-3-(trifluoromethyl)phenoxy)-1-(2,2,2-trifluoroethyl)-1H-1,2,4-triazol-3-yl)-3-(5-methyl-1,3,4-oxadiazol-2-yl)-3-azabicyclo[3.2.1]octan-8-amine;
(1R,5S,8s)-N-(5-(3-Chlorophenoxy)-1-(2,2,2-trifluoroethyl)-1H-1,2,4-triazol-3-yl)-3-(5-methyl-1,3,4-oxadiazol-2-yl)-3-azabicyclo[3.2.1]octan-8-amine;
(1R,5S,8s)-3-(5-Methyl-1,3,4-oxadiazol-2-yl)-N-(1-(2,2,2-trifluoroethyl)-5-(4-(trifluoromethyl)phenoxy)-1H-1,2,4-triazol-3-yl)-3-azabicyclo[3.2.1]octan-8-amine;
(1R,5S,8s)-3-(5-Methyl-1,3,4-oxadiazol-2-yl)-N-(1-(2,2,2-trifluoroethyl)-5-(3-(trifluoromethoxy)phenoxy)-1H-1,2,4-triazol-3-yl)-3-azabicyclo[3.2.1]octan-8-amine;
(1R,5S,8s)-3-(5-Methyl-1,3,4-oxadiazol-2-yl)-N-(1-(2,2,2-trifluoroethyl)-5-(3-(trifluoromethyl)phenoxy)-1H-1,2,4-triazol-3-yl)-3-azabicyclo[3.2.1]octan-8-amine;
(1R,5S,8s)-3-(5-Methyl-1,3,4-oxadiazol-2-yl)-N-[1-(propan-2-yl)-5-[4-(trifluoromethoxy)phenoxy]-1H-1,2,4-triazol-3-yl]-3-azabicyclo[3.2.1]octan-8-amine;
(1R,5S,8s)-3-(5-Methyl-1,3,4-oxadiazol-2-yl)-N-[1-(propan-2-yl)-5-[3-(trifluoromethyl)phenoxy]-1H-1,2,4-triazol-3-yl]-3-azabicyclo[3.2.1]octan-8-amine;
(1R,5S,8s)-3-(5-Methyl-1,3,4-oxadiazol-2-yl)-N-[1-(propan-2-yl)-5-[4-fluoro-3-(trifluoromethyl)phenoxy]-1H-1,2,4-triazol-3-yl]-3-azabicyclo[3.2.1]octan-8-amine;
(1R,5S,8s)-N-(5-(3-Chlorophenoxy)-1-(2,2,3,3,3-pentafluoropropyl)-1H-1,2,4-triazol-3-yl)-3-(5-methyl-1,3,4-oxadiazol-2-yl)-3-azabicyclo[3.2.1]octan-8-amine;
(1R,5S,8s)-3-(3-Methyl-1,2,4-oxadiazol-5-yl)-N-[1-(propan-2-yl)-5-[2-fluoro-5-(trifluoromethyl)phenoxy]-1H-1,2,4-triazol-3-yl]-3-azabicyclo[3.2.1]octan-8-amine;
(1R,5S,8s)-N-{5-[2-Fluoro-3-(trifluoromethyl)phenoxy]-1-(propan-2-yl)-1H-1,2,4-triazol-3-yl}-3-(5-methyl-1,3,4-oxadiazol-2-yl)-3-azabicyclo[3.2.1]octan-8-amine;
(1R,5S,8s)-3-(5-Methyl-1,3,4-oxadiazol-2-yl)-N-{5-[4-methyl-3-(trifluoromethyl)phenoxy]-1-(propan-2-yl)-1H-1,2,4-triazol-3-yl}-3-azabicyclo[3.2.1]octan-8-amine;
(1R,5S,8s)-3-(5-Methyl-1,3,4-oxadiazol-2-yl)-N-{5-[3-methyl-5-(trifluoromethyl)phenoxy]-1-(propan-2-yl)-1H-1,2,4-triazol-3-yl}-3-azabicyclo[3.2.1]octan-8-amine;
(1R,5S,8s)-3-(5-Methyl-1,3,4-oxadiazol-2-yl)-N-[1-(propan-2-yl)-5-[4-(trifluoromethoxy)-3-(trifluoromethyl)phenoxy]-1H-1,2,4-triazol-3-yl]-3-azabicyclo[3.2.1]octan-8-amine;
(1R,5S,8s)-N-{5-[3, 5-Bis(trifluoromethyl)phenoxy]-1-(propan-2-yl)-1H-1,2,4-triazol-3-yl}-3-(5-methyl-1,3,4-oxadiazol-2-yl)-3-azabicyclo[3.2.1]octan-8-amine;
(1R,5S,8s)-N-(5-(3-Chloro-5-methylphenoxy)-1-methyl-1H-1,2,4-triazol-3-yl)-3-(5-methyl-1,3,4-oxadiazol-2-yl)-3-azabicyclo[3.2.1]octan-8-amine;
(1R,5S,8s)-N-(5-(3-Chlorophenoxy)-1-ethyl-1H-1,2,4-triazol-3-yl)-3-(5-methyl-1,3,4-oxadiazol-2-yl)-3-azabicyclo[3.2.1]octan-8-amine;
(1R,5S,8s)-N-(5-(3-Chlorophenoxy)-1-propyl-1H-1,2,4-triazol-3-yl)-3-(5-methyl-1,3,4-oxadiazol-2-yl)-3-azabicyclo[3.2.1]octan-8-amine;
(1R,5S,8s)-N-[5-(3-Chlorophenoxy)-1-(propan-2-yl)-1H-1,2,4-triazol-3-yl]-3-(5-methyl-1,3,4-oxadiazol-2-yl)-3-azabicyclo[3.2.1]octan-8-amine;
(1R,5S,8s)-N-(5-(3-Chloro-5-fluorophenoxy)-1-(propan-2-yl)-1H-1,2,4-triazol-3-yl)-3-(5-methyl-1,3,4-oxadiazol-2-yl)-3-azabicyclo[3.2.1]octan-8-amine;

(1R,5S,8s)-N-(5-(3-Chloro-4-fluorophenoxy)-1-propyl-1H-1,2,4-triazol-3-yl)-3-(5-methyl-1,3,4-oxadiazol-2-yl)-3-azabicyclo[3.2.1]octan-8-amine; and (1R,5S,8s)-N-[5-(3-Chloro-4-fluorophenoxy)-1-(1,1,1,2,3,3,3-heptadeuteriopropan-2-yl)-1,2,4-triazol-3-yl]-3-(5-methyl-1,3,4-oxadiazol-2-yl)-3-azabicyclo[3.2.1]octan-8-amine.

10. A compound according to claim 1,
wherein:
HetAr is or a pharmaceutically acceptable acid addition salt, a racemic mixture or a corresponding enantiomer or an optical isomer or stereoisomer thereof.

11. A compound according to claim 10, selected from:

(1R,5S,8s)-N-{5-[4-Fluoro-3-(trifluoromethyl)phenoxy]-1-(propan-2-yl)-11H-1,2,4-triazol-3-yl}-3-[2-(trifluoromethyl)pyridin-4-yl]-3-azabicyclo[3.2.1]octan-8-amine;

(1R,5S,8s)-N-[5-(3,5-Difluorophenoxy)-1-(propan-2-yl)-1H-1,2,4-triazol-3-yl]-3-[2-(trifluoromethyl)pyridin-4-yl]-3-azabicyclo[3.2.1]octan-8-amine;

(1R,5S,8s)-N-(5-(2-Fluorophenoxy)-1-(2,2,2-trifluoroethyl)-1H-1,2,4-triazol-3-yl)-3-(2-[trifluoromethyl]pyridin-4-yl)-3-azabicyclo[3.2.1]octan-8-amine;

(1R,5S,8s)-N-[1-(Propan-2-yl)-5-[3-(trifluoromethyl)phenoxy]-1H-1,2,4-triazol-3-yl]-3-[2-(trifluoromethyl)pyridin-4-yl]-3-azabicyclo[3.2.1]octan-8-amine;

(1R,5S,8s)-N-[5-(3-Fluorophenoxy)-1-(propan-2-yl)-11H-1,2,4-triazol-3-yl]-3-[2-(trifluoromethyl)pyridin-4-yl]-3-azabicyclo[3.2.1]octan-8-amine;

(1R,5S,8s)-N-(5-(3-Fluorophenoxy)-1-(2,2,2-trifluoroethyl)-1H-1,2,4-triazol-3-yl)-3-(2-(trifluoromethyl)pyridin-4-yl)-3-azabicyclo[3.2.1]octan-8-amine;

(1R,5S,8s)-N-(5-(3-Fluorophenoxy)-1-methyl-1H-1,2,4-triazol-3-yl)-3-(2-(trifluoromethyl)pyridin-4-yl)-3-azabicyclo[3.2.1]octan-8-amine;

(1R,5S,8s)-3-(2-Chloropyridin-4-yl)-N-(5-(4-fluoro-3-(trifluoromethyl)phenoxy)-1-methyl-1H-1,2,4-triazol-3-yl)-3-azabicyclo[3.2.1]octan-8-amine;

(1R,5S,8s)-3-(2-Chloropyridin-4-yl)-N-(5-(3-fluorophenoxy)-1-(2,2,2-trifluoroethyl)-1H-1,2,4-triazol-3-yl)-3-azabicyclo[3.2.1]octan-8-amine;

(1R,5S,8s)-N-(5-(3-Chlorophenoxy)-1-methyl-1H-1,2,4-triazol-3-yl)-3-(5-fluoro-2-methylpyridin-4-yl)-3-azabicyclo[3.2.1]octan-8-amine;

(1R,5S,8s)-N-(5-(3-Chlorophenoxy)-1-methyl-1H-1,2,4-triazol-3-yl)-3-(2-methoxypyridin-4-yl)-3-azabicyclo[3.2.1]octan-8-amine;

(1R,5S,8s)-N-(5-(3-Chlorophenoxy)-1-methyl-1H-1,2,4-triazol-3-yl)-3-(2-chloropyridin-4-yl)-3-azabicyclo[3.2.1]octan-8-amine;

(1R,5S,8s)-N-(5-(3-Chlorophenoxy)-1-ethyl-1H-1,2,4-triazol-3-yl)-3-(2-methoxypyridin-4-yl)-3-azabicyclo[3.2.1]octan-8-amine;

(1R,5S,8s)-N-(5-(3-Chlorophenoxy)-1-(2,2,2-trifluoroethyl)-1H-1,2,4-triazol-3-yl)-3-(2-methoxypyridin-4-yl)-3-azabicyclo[3.2.1]octan-8-amine;

(1R,5S,8s)-N-(5-(3-Chlorophenoxy)-1-ethyl-1H-1,2,4-triazol-3-yl)-3-(2-chloropyridin-4-yl)-3-azabicyclo[3.2.1]octan-8-amine;

(1R,5S,8s)-N-(5-(3-Chlorophenoxy)-1-propyl-1H-1,2,4-triazol-3-yl)-3-(2-methoxypyridin-4-yl)-3-azabicyclo[3.2.1]octan-8-amine;

(1R,5S,8s)-N-(5-(3-Chlorophenoxy)-1-propyl-1H-1,2,4-triazol-3-yl)-3-(2-chloropyridin-4-yl)-3-azabicyclo[3.2.1]octan-8-amine;

(1R,5S,8s)-N-(5-(3-Chloro-5-methylphenoxy)-1-methyl-1H-1,2,4-triazol-3-yl)-3-(2-chloropyridin-4-yl)-3-azabicyclo[3.2.1]octan-8-amine;

(1R,5S,8s)-N-(5-(3-Fluoro-5-methylphenoxy)-1-methyl-1H-1,2,4-triazol-3-yl)-3-(2-chloropyridin-4-yl)-3-azabicyclo[3.2.1]octan-8-amine;

(1R,5S,8s)-N-[5-(3-Chlorophenoxy)-1-(propan-2-yl)-1H-1,2,4-triazol-3-yl]-3-(2-methoxy-4-pyridyl)-3-azabicyclo[3.2.1]octan-8-amine;

(1R,5S,8s)-N-[5-(3,4-Difluorophenoxy)-1-(propan-2-yl)-1H-1,2,4-triazol-3-yl]-3-(2-methoxypyridin-4-yl)-3-azabicyclo[3.2.1]octan-8-amine;

(1R,5S,8s)-N-(5-(3,4-Difluorophenoxy)-1-(2,2,2-trifluoroethyl)-1H-1,2,4-triazol-3-yl)-3-(2-methoxypyridin-4-yl)-3-azabicyclo[3.2.1]octan-8-amine;

(1R,5S,8s)-N-(5-(3-Fluorophenoxy)-1-(propan-2-yl)-1H-1,2,4-triazol-3-yl)-3-(2-methoxypyridin-4-yl)-3-azabicyclo[3.2.1]octan-8-amine;

(1R,5S,8s)-N-(5-(2,3-Difluorophenoxy)-1-(propan-2-yl)-1H-1,2,4-triazol-3-yl)-3-(2-methoxypyridin-4-yl)-3-azabicyclo[3.2.1]octan-8-amine;

(1R,5S,8s)-N-(5-(3,5-Difluorophenoxy)-1-(propan-2-yl)-1H-1,2,4-triazol-3-yl)-3-(2-methoxypyridin-4-yl)-3-azabicyclo[3.2.1]octan-8-amine;

(1R,5S,8s)-N-(5-(3-Chloro-4-fluorophenoxy)-1-(propan-2-yl)-1H-1,2,4-triazol-3-yl)-3-(2-methoxypyridin-4-yl)-3-azabicyclo[3.2.1]octan-8-amine;

(1R,5S,8s)-N-(5-(3,5-Difluorophenoxy)-1-(2,2,2-trifluoroethyl)-1H-1,2,4-triazol-3-yl)-3-(2-methoxypyridin-4-yl)-3-azabicyclo[3.2.1]octan-8-amine;

(1R,5S,8s)-N-(5-(2,3-Difluorophenoxy)-1-(2,2,2-trifluoroethyl)-1H-1,2,4-triazol-3-yl)-3-(2-methoxypyridin-4-yl)-3-azabicyclo[3.2.1]octan-8-amine;

(1R,5S,8s)-N-(5-(3-Chloro-4-fluorophenoxy)-1-(2,2,2-trifluoroethyl)-1H-1,2,4-triazol-3-yl)-3-(2-methoxypyridin-4-yl)-3-azabicyclo[3.2.1]octan-8-amine;

(1R,5S,8s)-N-[5-(3-Chloro-5-fluorophenoxy)-1-(propan-2-yl)-1H-1,2,4-triazol-3-yl]-3-(2-methoxypyridin-4-yl)-3-azabicyclo[3.2.1]octan-8-amine;

(1R,5S,8s)-N-(5-(3-Fluorophenoxy)-1-(2,2,2-trifluoroethyl)-1H-1,2,4-triazol-3-yl)-3-(2-methoxypyridin-4-yl)-3-azabicyclo[3.2.1]octan-8-amine;

(1R,5S)—N-[5-(3-Chloro-2-fluoro-phenoxy)-1-isopropyl-1,2,4-triazol-3-yl]-3-(2-methoxy-4-pyridyl)-3-azabicyclo[3.2.1]octan-8-amine;

(1R,5S,8s)-N-[5-(2-Chlorophenoxy)-1-(propan-2-yl)-1H-1,2,4-triazol-3-yl]-3-(2-methoxypyridin-4-yl)-3-azabicyclo[3.2.1]octan-8-amine;

(1R,5S,8s)-N-(5-(2-Chlorophenoxy)-1-(2,2,2-trifluoroethyl)-1H-1,2,4-triazol-3-yl)-3-(2-methoxypyridin-4-yl)-3-azabicyclo[3.2.1]octan-8-amine;

(1R,5S,8s)-N-[5-(3-Chloro-2-fluoro-phenoxy)-1-(2,2,2-trifluoroethyl)-1,2,4-triazol-3-yl]-3-(2-methoxy-4-pyridyl)-3-azabicyclo[3.2.1]octan-8-amine;

(1R,5S,8s)-N-[5-(3-Chloro-5-fluorophenoxy)-1-methyl-1,2,4-triazol-3-yl]-3-(2-methoxypyridin-4-yl)-3-azabicyclo[3.2.1]octan-8-amine;

(1R,5S,8s)-N-(5-(3-Chloro-4-fluorophenoxy)-1-ethyl-1H-1,2,4-triazol-3-yl)-3-(2-methoxypyridin-4-yl)-3-azabicyclo[3.2.1]octan-8-amine;
(1R,5S,8s)-N-(5-(3-Chloro-4-fluorophenoxy)-1-propyl-1H-1,2,4-triazol-3-yl)-3-(2-methoxypyridin-4-yl)-3-azabicyclo[3.2.1]octan-8-amine;
(1R,5S,8s)-N-(5-(3-Chloro-4-fluorophenoxy)-1-isobutyl-1H-1,2,4-triazol-3-yl)-3-(2-methoxypyridin-4-yl)-3-azabicyclo[3.2.1]octan-8-amine;
(1R,5S,8s)-N-(5-(3-Chloro-4-fluorophenoxy)-1-((3,3-difluorocyclobutyl)methyl)-1H-1,2,4-triazol-3-yl)-3-(2-methoxypyridin-4-yl)-3-azabicyclo[3.2.1]octan-8-amine;
(1R,5S,8s)-N-[5-(3-Chloro-4-fluorophenoxy)-1-(1,1,1,2,3,3,3-heptadeuteriopropan-2-yl)-1,2,4-triazol-3-yl]-3-(2-methoxypyridin-4-yl)-3-azabicyclo[3.2.1]octan-8-amine;
(1R,5S,8s)-N-[5-(3-Chloro-4-fluorophenoxy)-1-(trideuteriomethyl)-1,2,4-triazol-3-yl]-3-(2-methoxypyridin-4-yl)-3-azabicyclo[3.2.1]octan-8-amine;
(1R,5S,8s)-N-[5-(3-Chloro-4-fluorophenoxy)-1-(1,1,2,2,2-pentadeuterioethyl)-1,2,4-triazol-3-yl]-3-(2-methoxypyridin-4-yl)-3-azabicyclo[3.2.1]octan-8-amine; and
(1R,5S,8s)-N-(5-(3-Chloro-5-fluorophenoxy)-1-(2,2,2-trifluoroethyl)-1H-1,2,4-triazol-3-yl)-3-(2-methoxypyridin-4-yl)-3-azabicyclo[3.2.1]octan-8-amine.

12. A compound according to claim 1, wherein:
HetAr is

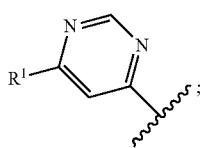

or a pharmaceutically acceptable acid addition salt, a racemic mixture or a corresponding enantiomer or an optical isomer stereoisomer thereof.

13. A compound according to claim 12, selected from:
(1R,5S,8s)-N-(5-(4-Fluoro-3-(trifluoromethyl)phenoxy)-1-methyl-1H-1,2,4-triazol-3-yl)-3-(6-methylpyrimidin-4-yl)-3-azabicyclo[3.2.1]octan-8-amine;
(1R,5S,8s)-N-(5-(4-Fluoro-3-(trifluoromethyl)phenoxy)-1-(2,2,2-trifluoroethyl)-1H-1,2,4-triazol-3-yl)-3-(6-methylpyrimidin-4-yl)-3-azabicyclo[3.2.1]octan-8-amine;
((1R,5S,8s)-N-(5-(3-Fluorophenoxy)-1-(2,2,2-trifluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chlorophenoxy)-1-methyl-1H-1,2,4-triazol-3-yl)-3-(6-methylpyrimidin-4-yl)-3-azabicyclo[3.2.1]octan-8-amine;
(1R,5S,8s)-N-(1-Methyl-5-(3-(trifluoromethoxy)phenoxy)-1H-1,2,4-triazol-3-yl)-3-(6-methylpyrimidin-4-yl)-3-azabicyclo[3.2.1]octan-8-amine;
(1R,5S,8s)-N-(5-(3-Chlorophenoxy)-1-(2,2,2-trifluoroethyl)-1H-1,2,4-triazol-3-yl)-3-(3-methyl-1,2,4-oxadiazol-5-yl)-3-azabicyclo[3.2.1]octan-8-amine;
(1R,5S,8s)-3-(6-Chloropyrimidin-4-yl)-N-[1-(propan-2-yl)-5-[3-(trifluoromethyl)phenoxy]-1H-1,2,4-triazol-3-yl]-3-azabicyclo[3.2.1]octan-8-amine;
(1R,5S,8s)-N-(5-(3-Chlorophenoxy)-1-methyl-1H-1,2,4-triazol-3-yl)-3-(6-methoxypyrimidin-4-yl)-3-azabicyclo[3.2.1]octan-8-amine;
(1R,5S,8s)-N-[5-(3-Chlorophenoxy)-1-(propan-2-yl)-1H-1,2,4-triazol-3-yl]-3-(6-chloropyrimidin-4-yl)-3-azabicyclo[3.2.1]octan-8-amine;
(1R,5S,8s)-3-(6-Chloropyrimidin-4-yl)-N-[5-(3-fluorophenoxy)-1-(propan-2-yl)-1H-1,2,4-triazol-3-yl]-3-azabicyclo[3.2.1]octan-8-amine;
(1R,5S,8s)-N-(5-(3-Chlorophenoxy)-1-ethyl-1H-1,2,4-triazol-3-yl)-3-(6-methylpyrimidin-4-yl)-3-azabicyclo[3.2.1]octan-8-amine;
(1R,5S,8s)-N-(5-(3-Chlorophenoxy)-1-ethyl-1H-1,2,4-triazol-3-yl)-3-(6-chloropyrimidin-4-yl)-3-azabicyclo[3.2.1]octan-8-amine;
(1R,5S,8s)-N-(5-(3-Chlorophenoxy)-1-propyl-1H-1,2,4-triazol-3-yl)-3-(6-methylpyrimidin-4-yl)-3-azabicyclo[3.2.1]octan-8-amine;
(1R,5S,8s)-N-(5-(3-Chlorophenoxy)-1-(2,2,2-trifluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chlorophenoxy)-1-propyl-1H-1,2,4-triazol-3-yl)-3-(6-chloropyrimidin-4-yl)-3-azabicyclo[3.2.1]octan-8-amine;
(1R,5S,8s)-N-(5-(3-Chlorophenoxy)-1-(2,2,2-trifluoroethyl)-1H-1,2,4-triazol-3-yl)-3-(6-chloropyrimidin-4-yl)-3-azabicyclo[3.2.1]octan-8-amine;
(1R,5S,8s)-N-(5-(3-Fluoro-5-methylphenoxy)-1-methyl-1H-1,2,4-triazol-3-yl)-3-(6-chloropyrimidin-4-yl)-3-azabicyclo[3.2.1]octan-8-amine;
(1R,5S,8s)-N-(5-(3-Chloro-5-methylphenoxy)-1-methyl-1H-1,2,4-triazol-3-yl)-3-(6-methylpyrimidin-4-yl)-3-azabicyclo[3.2.1]octan-8-amine;
(1R,5S,8s)-N-(5-(3-Fluoro-5-methylphenoxy)-1-methyl-1H-1,2,4-triazol-3-yl)-3-(6-methylpyrimidin-4-yl)-3-azabicyclo[3.2.1]octan-8-amine;
(1R,5S,8s)-N-[5-(3-Chlorophenoxy)-1-(propan-2-yl)-1H-1,2,4-triazol-3-yl]-3-(6-methylpyrimidin-4-yl)-3-azabicyclo[3.2.1]octan-8-amine;
(1R,5S,8s)-N-(1-Cyclopropyl-5-(3,4-difluorophenoxy)-1H-1,2,4-triazol-3-yl)-3-(6-methylpyrimidin-4-yl)-3-azabicyclo[3.2.1]octan-8-amine;
(1R,5S,8s)-N-[5-(3,4-Difluorophenoxy)-1-(propan-2-yl)-1H-1,2,4-triazol-3-yl]-3-(6-methylpyrimidin-4-yl)-3-azabicyclo[3.2.1]octan-8-amine;
(1R,5S,8s)-N-(5-(3,4-Difluorophenoxy)-1-(2,2,2-trifluoroethyl)-1H-1,2,4-triazol-3-yl)-3-(6-methylpyrimidin-4-yl)-3-azabicyclo[3.2.1]octan-8-amine;
(1R,5S,8s)-N-[5-(3,5-Difluorophenoxy)-1-(propan-2-yl)-1H-1,2,4-triazol-3-yl]-3-(6-methylpyrimidin-4-yl)-3-azabicyclo[3.2.1]octan-8-amine;
(1R,5S,8s)-N-[5-(2,3-Difluorophenoxy)-1-(propan-2-yl)-1H-1,2,4-triazol-3-yl]-3-(6-methylpyrimidin-4-yl)-3-azabicyclo[3.2.1]octan-8-amine;
(1R,5S,8s)-N-(5-(3-Chloro-4-fluorophenoxy)-1-isopropyl-1H-1,2,4-triazol-3-yl)-3-(6-methylpyrimidin-4-yl)-3-azabicyclo[3.2.1]octan-8-amine;
(1R,5S,8s)-N-[5-(4-Fluorophenoxy)-1-(propan-2-yl)-1H-1,2,4-triazol-3-yl]-3-(6-methylpyrimidin-4-yl)-3-azabicyclo[3.2.1]octan-8-amine;
(1R,5S,8s)-N-[5-(3-Fluorophenoxy)-1-(propan-2-yl)-1H-1,2,4-triazol-3-yl]-3-(6-methylpyrimidin-4-yl)-3-azabicyclo[3.2.1]octan-8-amine;
(1R,5S,8s)-N-[5-(3-Chloro-5-fluorophenoxy)-1-(propan-2-yl)-1H-1,2,4-triazol-3-yl]-3-(6-methylpyrimidin-4-yl)-3-azabicyclo[3.2.1]octan-8-amine;

(1R,5S,8s)-N-(5-(3,5-Difluorophenoxy)-1-(2,2,2-trifluoroethyl)-1H-1,2,4-triazol-3-yl)-3-(6-methylpyrimidin-4-yl)-3-azabicyclo[3.2.1]octan-8-amine;
(1R,5S)—N-[5-(5-Chloro-2-fluoro-phenoxy)-1-isopropyl-1,2,4-triazol-3-yl]-3-(6-methylpyrimidin-4-yl)-3-azabicyclo[3.2.1]octan-8-amine;
(1R,5S,8s)-N-[5-(3-Chloro-2-fluoro-phenoxy)-1-isopropyl-1,2,4-triazol-3-yl]-3-(6-methylpyrimidin-4-yl)-3-azabicyclo[3.2.1]octan-8-amine;
(1R,5S,8s)-N-(5-(2,3-Difluorophenoxy)-1-(2,2,2-trifluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-4-fluorophenoxy)-1-(2,2,2-trifluoroethyl)-1H-1,2,4-triazol-3-yl)-3-(6-methylpyrimidin-4-yl)-3-azabicyclo[3.2.1]octan-8-amine;
(1R,5S,8s)-N-[5-(2-Chlorophenoxy)-1-(propan-2-yl)-1H-1,2,4-triazol-3-yl]-3-(6-methylpyrimidin-4-yl)-3-azabicyclo[3.2.1]octan-8-amine;
(1R,5S,8s)-N-(5-(3-Chloro-4-fluorophenoxy)-1-(2,2-difluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-4-fluorophenoxy)-1-(2-fluorovinyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-5-fluorophenoxy)-1-(2,2-difluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-5-fluorophenoxy)-1-(2-fluorovinyl)-1H-1,2,4-triazol-3-yl)-3-(6-methylpyrimidin-4-yl)-3-azabicyclo[3.2.1]octan-8-amine;
(1R,5S,8s)-N-(5-(3,5-Difluorophenoxy)-1-(2,2-difluoroethyl)-1H-1,2,4-triazol-3-yl)-3-(6-methylpyrimidin-4-yl)-3-azabicyclo[3.2.1]octan-8-amine;
(1R,5S,8s)-N-(5-(3,5-Difluorophenoxy)-1-(2-fluorovinyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-4-fluorophenoxy)-1-(2-fluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-4-fluorophenoxy)-1-vinyl-1H-1,2,4-triazol-3-yl)-3-(6-methylpyrimidin-4-yl)-3-azabicyclo[3.2.1]octan-8-amine;
(1R,5S,8s)-N-(5-(3-Chloro-5-fluorophenoxy)-1-(2-fluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-5-fluorophenoxy)-1-vinyl-1H-1,2,4-triazol-3-yl)-3-(6-methylpyrimidin-4-yl)-3-azabicyclo[3.2.1]octan-8-amine;
(1R,5S,8s)-N-(5-(3-Chloro-5-fluorophenoxy)-1-(2-methoxyethyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-4-fluorophenoxy)-1-(2-methoxyethyl)-1H-1,2,4-triazol-3-yl)-3-(6-methylpyrimidin-4-yl)-3-azabicyclo[3.2.1]octan-8-amine;
(1R,5S,8s)-N-(5-(3-Chlorophenoxy)-1-(2,2-difluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chlorophenoxy)-1-(2-fluorovinyl)-1H-1,2,4-triazol-3-yl)-3-(6-methylpyrimidin-4-yl)-3-azabicyclo[3.2.1]octan-8-amine;
(1R,5S,8s)-N-(5-(3,5-Difluorophenoxy)-1-(2-fluoroethyl)-1H-1,2,4-triazol-3-yl)-3-(6-methylpyrimidin-4-yl)-3-azabicyclo[3.2.1]octan-8-amine;
(1R,5S,8s)-N-(5-(3,5-Difluorophenoxy)-1-vinyl-1H-1,2,4-triazol-3-yl)-3-(6-methylpyrimidin-4-yl)-3-azabicyclo[3.2.1]octan-8-amine;
(1R,5S,8s)-N-(5-(2-Chlorophenoxy)-1-(2,2,2-trifluoroethyl)-1H-1,2,4-triazol-3-yl)-3-(6-methylpyrimidin-4-yl)-3-azabicyclo[3.2.1]octan-8-amine;
(1R,5S)—N-[5-(3-Chloro-2-fluoro-phenoxy)-1-(2,2,2-trifluoroethyl)-1,2,4-triazol-3-yl]-3-(6-methylpyrimidin-4-yl)-3-azabicyclo[3.2.1]octan-8-amine;
(1R,5S,8s)-N-(5-(2-Chlorophenoxy)-1-(2,2-difluoroethyl)-1H-1,2,4-triazol-3-yl)-3-(6-methylpyrimidin-4-yl)-3-azabicyclo[3.2.1]octan-8-amine;
(1R,5S,8s)-N-(5-(2-Chlorophenoxy)-1-(2-fluorovinyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-5-fluorophenoxy)-1-(methoxymethyl)-1H-1,2,4-triazol-3-yl)-3-(6-methylpyrimidin-4-yl)-3-azabicyclo[3.2.1]octan-8-amine;
(1R,5S,8s)-N-[5-(4-Chlorophenoxy)-1-(propan-2-yl)-1H-1,2,4-triazol-3-yl]-3-(6-methylpyrimidin-4-yl)-3-azabicyclo[3.2.1]octan-8-amine;
(1R,5S,8s)-N-(5-(3-Chloro-2-fluorophenoxy)-1-(2,2-difluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-2-fluorophenoxy)-1-(2-fluorovinyl)-1H-1,2,4-triazol-3-yl)-3-(6-methylpyrimidin-4-yl)-3-azabicyclo[3.2.1]octan-8-amine;
(1R,5S,8s)-N-(5-(2-Chlorophenoxy)-1-(2-fluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-2-fluorophenoxy)-1-(2-fluoroethyl)-1H-1,2,4-triazol-3-yl)-3-(6-methylpyrimidin-4-yl)-3-azabicyclo[3.2.1]octan-8-amine;
(1R,5S,8s)-N-(5-(3-Chloro-2-fluorophenoxy)-1-vinyl-1H-1,2,4-triazol-3-yl)-3-(6-methylpyrimidin-4-yl)-3-azabicyclo[3.2.1]octan-8-amine;
(1R,5S,8s)-N-(5-(2-Chloro-3-fluorophenoxy)-1-isopropyl-1H-1,2,4-triazol-3-yl)-3-(6-methylpyrimidin-4-yl)-3-azabicyclo[3.2.1]octan-8-amine;
(1R,5S,8s)-N-(5-(3,5-Difluorophenoxy)-1-isopropyl-1H-1,2,4-triazol-3-yl)-3-(6-methylpyrimidin-4-yl)-3-azabicyclo[3.2.1]octan-8-amine;
(1S,5R,8s)-N-[5-(3-Chloro-5-fluorophenoxy)-1-methyl-1,2,4-triazol-3-yl]-3-(6-methylpyrimidin-4-yl)-3-azabicyclo[3.2.1]octan-8-amine;
(1R,5S,8s)-N-(5-(4-Chlorophenoxy)-1-methyl-1H-1,2,4-triazol-3-yl)-3-(6-methylpyrimidin-4-yl)-3-azabicyclo[3.2.1]octan-8-amine;
(1R,5S,8s)-N-[5-(3-Chloro-4-fluorophenoxy)-1-methyl-1,2,4-triazol-3-yl]-3-(6-methylpyrimidin-4-yl)-3-azabicyclo[3.2.1]octan-8-amine;
(1S,5R.8s)-N-[5-(3-Chloro-2-fluorophenoxy)-1-methyl-1,2,4-triazol-3-yl]-3-(6-methylpyrimidin-4-yl)-3-azabicyclo[3.2.1]octan-8-amine;
(1S,5R.8s)-N-[5-(2-Chloro-3-fluorophenoxy)-1-methyl-1,2,4-triazol-3-yl]-3-(6-methylpyrimidin-4-yl)-3-azabicyclo[3.2.1]octan-8-amine;
(1R,5S,8s)-N-[5-(3-Chloro-5-fluorophenoxy)-1-ethyl-1,2,4-triazol-3-yl]-3-(6-methylpyrimidin-4-yl)-3-azabicyclo[3.2.1]octan-8-amine;
(1R,5S,8s)-N-[5-(3,5-Difluorophenoxy)-1-ethyl-1,2,4-triazol-3-yl]-3-(6-methylpyrimidin-4-yl)-3-azabicyclo[3.2.1]octan-8-amine;
(1R,5S,8s)-N-(5-(2-Chlorophenoxy)-1-ethyl-1H-1,2,4-triazol-3-yl)-3-(6-methylpyrimidin-4-yl)-3-azabicyclo[3.2.1]octan-8-amine;
(1R,5S)—N-[5-(3-Chloro-4-fluorophenoxy)-1-ethyl-1,2,4-triazol-3-yl]-3-(6-methylpyrimidin-4-yl)-3-azabicyclo[3.2.1]octan-8-amine;

(1R,5S,8s)-N-[5-(3-Chloro-5-fluorophenoxy)-1-propyl-1,2,4-triazol-3-yl]-3-(6-methylpyrimidin-4-yl)-3-azabicyclo[3.2.1]octan-8-amine;

(1R,5S,8s)-N-[5-(3,5-Difluorophenoxy)-1-propyl-1,2,4-triazol-3-yl]-3-(6-methylpyrimidin-4-yl)-3-azabicyclo[3.2.1]octan-8-amine;

(1R,5S,8s)-N-(5-(2-Chlorophenoxy)-1-propyl-1H-1,2,4-triazol-3-yl)-3-(6-methylpyrimidin-4-yl)-3-azabicyclo[3.2.1]octan-8-amine;

(1R,5S,8s)-N-[5-(3-Chloro-4-fluorophenoxy)-1-propyl-1,2,4-triazol-3-yl]-3-(6-methylpyrimidin-4-yl)-3-azabicyclo[3.2.1]octan-8-amine;

(1R,5S,8s)-N-[5-(3-Chloro-5-fluorophenoxy)-1-(2-methylpropyl)-1,2,4-triazol-3-yl]-3-(6-methylpyrimidin-4-yl)-3-azabicyclo[3.2.1]octan-8-amine;

(1R,5S,8s)-N-(5-(2-Chlorophenoxy)-1-isobutyl-1H-1,2,4-triazol-3-yl)-3-(6-methylpyrimidin-4-yl)-3-azabicyclo[3.2.1]octan-8-amine;

(1R,5S,8s)-N-(5-(3-Chloro-4-fluorophenoxy)-1-isobutyl-1H-1,2,4-triazol-3-yl)-3-(6-methylpyrimidin-4-yl)-3-azabicyclo[3.2.1]octan-8-amine;

(1R,5S,8s)-N-[5-(3-Chloro-5-fluorophenoxy)-1-[(3-methyloxetan-3-yl)methyl]-1,2,4-triazol-3-yl]-3-(6-methylpyrimidin-4-yl)-3-azabicyclo[3.2.1]octan-8-amine;

(1R,5S,8s)-N-[5-(3-Chloro-4-fluorophenoxy)-1-[(3-methyloxetan-3-yl)methyl]-1,2,4-triazol-3-yl]-3-(6-methylpyrimidin-4-yl)-3-azabicyclo[3.2.1]octan-8-amine;

(1R,5S,8s)-N-[5-(3-Chloro-5-fluorophenoxy)-1-[2-methoxypropyl]-1,2,4-triazol-3-yl]-3-(6-methylpyrimidin-4-yl)-3-azabicyclo[3.2.1]octan-8-amine;

(1R,5S,8s)-N-[5-(3-Chloro-5-fluorophenoxy)-1-(3,3,3-trifluoropropyl)-1,2,4-triazol-3-yl]-3-(6-methylpyrimidin-4-yl)-3-azabicyclo[3.2.1]octan-8-amine;

(1R,5S,8s)-N-(5-(3-Chloro-5-fluorophenoxy)-1-((3,3-difluorocyclobutyl)methyl)-1H-1,2,4-triazol-3-yl)-3-(6-methylpyrimidin-4-yl)-3-azabicyclo[3.2.1]octan-8-amine;

(1R,5S,8s)-N-(5-(3-Chloro-4-fluorophenoxy)-1-((3,3-difluorocyclobutyl)methyl)-1H-1,2,4-triazol-3-yl)-3-(6-methylpyrimidin-4-yl)-3-azabicyclo[3.2.1]octan-8-amine;

(1R,5S,8s)-N-[5-(3-Chloro-5-fluorophenoxy)-1-(oxetan-3-yl)-1,2,4-triazol-3-yl]-3-(6-methylpyrimidin-4-yl)-3-azabicyclo[3.2.1]octan-8-amine;

(1R,5S,8s)-N-[5-(3-Chloro-4-fluorophenoxy)-1-(oxetan-3-yl)-1,2,4-triazol-3-yl]-3-(6-methylpyrimidin-4-yl)-3-azabicyclo[3.2.1]octan-8-amine;

(1R,5S,8s)-N-[5-(3-Chloro-5-fluorophenoxy)-1-(oxolan-3-yl)-1,2,4-triazol-3-yl]-3-(6-methylpyrimidin-4-yl)-3-azabicyclo[3.2.1]octan-8-amine;

(1R,5S,8s)-N-[5-(3-Chloro-4-fluorophenoxy)-1-(oxolan-3-yl)-1,2,4-triazol-3-yl]-3-(6-methylpyrimidin-4-yl)-3-azabicyclo[3.2.1]octan-8-amine;

(1R,5S,8s)-N-(5-(3-Chloro-5-fluorophenoxy)-1-cyclobutyl-1H-1,2,4-triazol-3-yl)-3-(6-methylpyrimidin-4-yl)-3-azabicyclo[3.2.1]octan-8-amine;

(1R,5S,8s)-N-(5-(3-Chloro-4-fluorophenoxy)-1-cyclobutyl-1H-1,2,4-triazol-3-yl)-3-(6-methylpyrimidin-4-yl)-3-azabicyclo[3.2.1]octan-8-amine;

(1R,5S,8s)-N-[5-(3-Chloro-5-fluorophenoxy)-1-(1,1,3,3,3-hexadeuteriopropan-2-yl)-1,2,4-triazol-3-yl]-3-(6-methylpyrimidin-4-yl)-3-azabicyclo[3.2.1]octan-8-amine;

(1R,5S,8s)-N-[5-(3-Chloro-5-fluorophenoxy)-1-(1,1,1,2,3,3,3-heptadeuteriopropan-2-yl)-1,2,4-triazol-3-yl]-3-(6-methylpyrimidin-4-yl)-3-azabicyclo[3.2.1]octan-8-amine;

(1R,5S,8s)-N-[5-(3-Chloro-4-fluorophenoxy)-1-(1,1,1,2,3,3,3-heptadeuteriopropan-2-yl)-1,2,4-triazol-3-yl]-3-(6-methylpyrimidin-4-yl)-3-azabicyclo[3.2.1]octan-8-amine;

(1R,5S,8s)-N-[5-(3-Chloro-5-fluorophenoxy)-1-(trideuteriomethyl)-1,2,4-triazol-3-yl]-3-(6-methylpyrimidin-4-yl)-3-azabicyclo[3.2.1]octan-8-amine;

(1R,5S,8s)-N-[5-(3-Chloro-4-fluorophenoxy)-1-(trideuteriomethyl)-1,2,4-triazol-3-yl]-3-(6-methylpyrimidin-4-yl)-3-azabicyclo[3.2.1]octan-8-amine;

(1R,5S,8s)-N-[5-(3-Chloro-5-fluorophenoxy)-1-(1,1,2,2,2-pentadeuterioethyl)-1,2,4-triazol-3-yl]-3-(6-methylpyrimidin-4-yl)-3-azabicyclo[3.2.1]octan-8-amine;

(1R,5S,8s)-N-[5-(3-Chloro-4-fluorophenoxy)-1-(1,1,2,2,2-pentadeuterioethyl)-1,2,4-triazol-3-yl]-3-(6-methylpyrimidin-4-yl)-3-azabicyclo[3.2.1]octan-8-amine;

(1R,5S,8s)-N-(5-(3-Chloro-5-fluorophenoxy)-1-(2,2,2-trifluoroethyl)-1H-1,2,4-triazol-3-yl)-3-(6-methylpyrimidin-4-yl)-3-azabicyclo[3.2.1]octan-8-amine; and (1R,5S,8s)-N-(5-(3-Chlorophenoxy)-1-(2-fluoroethyl)-1H-1,2,4-triazol-3-yl)-3-(6-methylpyrimidin-4-yl)-3-azabicyclo[3.2.1]octan-8-amine.

14. A compound according to claim 1, wherein HetAr is or a pharmaceutically acceptable acid addition salt, a racemic mixture or a corresponding enantiomer or an optical isomer or stereoisomer thereof.

15. A compound according to claim 14, selected from:

(1R,5S,8s)-N-(5-(3-Chlorophenoxy)-1-methyl-1H-1,2,4-triazol-3-yl)-3-(6-chloropyridazin-4-yl)-3-azabicyclo[3.2.1]octan-8-amine;

(1R,5S,8s)-N-(5-(3-Chloro-5-methylphenoxy)-1-methyl-1H-1,2,4-triazol-3-yl)-3-(6-chloropyridazin-4-yl)-3-azabicyclo[3.2.1]octan-8-amine;

(1R,5S,8s)-N-(5-(3-Chlorophenoxy)-1-ethyl-1H-1,2,4-triazol-3-yl)-3-(6-methoxypyridazin-4-yl)-3-azabicyclo[3.2.1]octan-8-amine;

(1R,5S,8s)-N-(5-(3-Chlorophenoxy)-1-propyl-1H-1,2,4-triazol-3-yl)-3-(6-methoxypyridazin-4-yl)-3-azabicyclo[3.2.1]octan-8-amine;

(1R,5S,8s)-N-(5-(3-Chlorophenoxy)-1-propyl-1H-1,2,4-triazol-3-yl)-3-(6-chloropyridazin-4-yl)-3-azabicyclo[3.2.1]octan-8-amine;

(1R,5S,8s)-N-(5-(3-Chloro-5-methylphenoxy)-1-methyl-1H-1,2,4-triazol-3-yl)-3-(6-methoxypyridazin-4-yl)-3-azabicyclo[3.2.1]octan-8-amine;

(1R,5S,8s)-N-(5-(3-Chlorophenoxy)-1-methyl-1H-1,2,4-triazol-3-yl)-3-(6-methoxypyridazin-4-yl)-3-azabicyclo[3.2.1]octan-8-amine;

(1R,5S,8s)-N-(5-(3-Chlorophenoxy)-1-ethyl-1H-1,2,4-triazol-3-yl)-3-(6-chloropyridazin-4-yl)-3-azabicyclo[3.2.1]octan-8-amine;

(1R,5S,8s)-N-(5-(3-Chlorophenoxy)-1-(2,2,2-trifluoro-ethyl)-1H-1,2,4-triazol-3-yl)-3-(6-chloropyridazin-4-yl)-3-azabicyclo[3.2.1]octan-8-amine;
(1R,5S,8s)-N-(5-(3-Fluoro-5-methylphenoxy)-1-methyl-1H-1,2,4-triazol-3-yl)-3-(6-chloropyridazin-4-yl)-3-azabicyclo[3.2.1]octan-8-amine;
(1R,5S,8s)-N-(5-(3-Chlorophenoxy)-1-(2,2-difluoro-ethyl)-1H-1,2,4-triazol-3-yl)-3-(6-chloropyridazin-4-yl)-3-azabicyclo[3.2.1]octan-8-amine;
(1R,5S,8s)-N-(5-(3-Chlorophenoxy)-1-(2-fluoroethyl)-1H-1,2,4-triazol-3-yl)-3-(6-chloropyridazin-4-yl)-3-azabicyclo[3.2.1]octan-8-amine;
(1R,5S,8s)-N-(5-(3-Chlorophenoxy)-1-(2,2-difluoro-ethyl)-1H-1,2,4-triazol-3-yl)-3-(6-methoxypyridazin-4-yl)-3-azabicyclo[3.2.1]octan-8-amine;
(1R,5S,8s)-N-(5-(3-Chlorophenoxy)-1-(2-fluoroethyl)-1H-1,2,4-triazol-3-yl)-3-(6-methoxypyridazin-4-yl)-3-azabicyclo[3.2.1]octan-8-amine;
(1R,5S,8s)-N-[5-(3,4-Difluorophenoxy)-1-(propan-2-yl)-1H-1,2,4-triazol-3-yl]-3-(6-methoxypyridazin-4-yl)-3-azabicyclo[3.2.1]octan-8-amine;
(1R,5S,8s)-N-[5-(3-Fluorophenoxy)-1-(propan-2-yl)-1H-1,2,4-triazol-3-yl]-3-(6-methoxypyridazin-4-yl)-3-azabicyclo[3.2.1]octan-8-amine;
(1R,5S,8s)-N-(5-(2,3-Difluorophenoxy)-1-(propan-2-yl)-1H-1,2,4-triazol-3-yl)-3-(6-methoxypyridazin-4-yl)-3-azabicyclo[3.2.1]octan-8-amine;
(1R,5S,8s)-N-(5-(3,5-Difluorophenoxy)-1-(propan-2-yl)-1H-1,2,4-triazol-3-yl)-3-(6-methoxypyridazin-4-yl)-3-azabicyclo[3.2.1]octan-8-amine;
(1R,5S,8s)-N-(5-(3-Chloro-4-fluorophenoxy)-1-(propan-2-yl)-1H-1,2,4-triazol-3-yl)-3-(6-methoxypyridazin-4-yl)-3-azabicyclo[3.2.1]octan-8-amine;
(1R,5S,8s)-N-[5-(3-Chloro-5-fluorophenoxy)-1-(propan-2-yl)-1H-1,2,4-triazol-3-yl]-3-(6-methoxypyridazin-4-yl)-3-azabicyclo[3.2.1]octan-8-amine;
(1R,5S)—N-[5-(3-Chloro-2-fluoro-phenoxy)-1-isopropyl-1,2,4-triazol-3-yl]-3-(6-methoxypyridazin-4-yl)-3-azabicyclo[3.2.1]octan-8-amine;
(1R,5S,8s)-N-[5-(3-Chloro-5-fluorophenoxy)-1-methyl-1,2,4-triazol-3-yl]-3-(6-methoxypyridazin-4-yl)-3-azabicyclo[3.2.1]octan-8-amine;
(1R,5S,8s)-N-(5-(3-Chloro-4-fluorophenoxy)-1-ethyl-1H-1,2,4-triazol-3-yl)-3-(6-methoxypyridazin-4-yl)-3-azabicyclo[3.2.1]octan-8-amine;
(1R,5S,8s)-N-(5-(3-Chloro-4-fluorophenoxy)-1-propyl-1H-1,2,4-triazol-3-yl)-3-(6-methoxypyridazin-4-yl)-3-azabicyclo[3.2.1]octan-8-amine;
(1R,5S,8s)-N-(5-(3-Chloro-4-fluorophenoxy)-1-isobutyl-1H-1,2,4-triazol-3-yl)-3-(6-methoxypyridazin-4-yl)-3-azabicyclo[3.2.1]octan-8-amine;
(1R,5S,8s)-N-(5-(3-Chloro-4-fluorophenoxy)-1-((3,3-difluorocyclobutyl)methyl)-1H-1,2,4-triazol-3-yl)-3-(6-methoxypyridazin-4-yl)-3-azabicyclo[3.2.1]octan-8-amine;
(1R,5S,8s)-N-[5-(3-Chloro-4-fluorophenoxy)-1-(1,1,1,2,3,3,3-heptadeuteriopropan-2-yl)-1,2,4-triazol-3-yl]-3-(6-methoxypyridazin-4-yl)-3-azabicyclo[3.2.1]octan-8-amine;
(1R,5S,8s)-N-[5-(3-Chloro-4-fluorophenoxy)-1-(trideuteriomethyl)-1,2,4-triazol-3-yl]-3-(6-methoxypyridazin-4-yl)-3-azabicyclo[3.2.1]octan-8-amine; and
(1R,5S,8s)-N-[5-(3-Chloro-4-fluorophenoxy)-1-(1,1,2,2,2-pentadeuterioethyl)-1,2,4-triazol-3-yl]-3-(6-methoxypyridazin-4-yl)-3-azabicyclo[3.2.1]octan-8-amine.

16. A process for preparing the compound of formula I according to claim 1, which process comprises:
a) reacting a compound of formula II

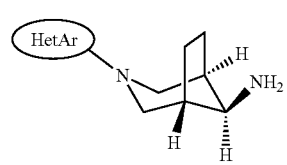

with a compound of formula III

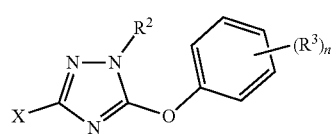

to produce the compound of formula I,
wherein X is halogen, and, optionally converting the compound obtained into a pharmaceutically acceptable acid addition salt thereof;
or
b) reacting a compound of formula VI

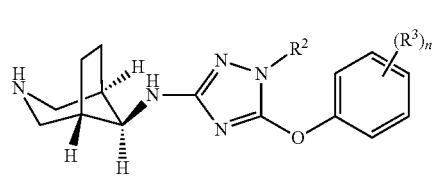

with a compound of formula HetAr-X
to produce the compound of formula
wherein X is halogen,
and
optionally converting the compound obtained into a pharmaceutically acceptable acid addition salt thereof.

17. A compound prepared by the process of claim 16.

18. A medicament containing a compound recited in claim 1 and one or more pharmaceutically inert carriers.

19. A method for treating one or more of Alzheimer's disease, cerebral amyloid angiopathy, hereditary cerebral hemorrhage with amyloidosis, Dutch-type (HCHWA-D), multi-infarct dementia, or dementia pugilistica, which method comprises:
administering an effective amount of a compound of claim 1.

* * * * *